US012372536B2

(12) United States Patent
Arch et al.

(10) Patent No.: US 12,372,536 B2
(45) Date of Patent: Jul. 29, 2025

(54) TUMOR NECROSIS FACTOR-LIKE LIGAND 1A SPECIFIC ANTIBODIES AND COMPOSITIONS AND USES THEREOF

(71) Applicants: Pfizer Inc., New York, NY (US); Bristol-Myers Squibb Company, Princeton, NJ (US)

(72) Inventors: Robert Arch, St. Louis, MO (US); Jun Zhang, Beijing (CN); Michelle Mader, Arlington, MA (US); Tetsuya Ishino, Boston, MA (US); Joel Bard, Newton, MA (US); William Finlay, Dublin (IE); Orla Cunningham, Dublin (IE); Ciara Reilly, Dublin (IE); Peter Brams, Sacramento, CA (US); Brigitte Devaux, Palo Alto, CA (US); Haichun Huang, Fremont, CA (US); Karla Henning, Milpitas, CA (US)

(73) Assignees: Pfizer Inc., New York, NY (US); Bristol-Myers Squibb Company, Princeton, NJ (US)

( * ) Notice: Subject to any disclaimer, the term of this patent is extended or adjusted under 35 U.S.C. 154(b) by 141 days.

(21) Appl. No.: 17/815,802

(22) Filed: Jul. 28, 2022

(65) Prior Publication Data

US 2022/0390463 A1 Dec. 8, 2022

Related U.S. Application Data

(62) Division of application No. 16/422,256, filed on May 24, 2019, now Pat. No. 11,474,112, which is a division of application No. 15/601,617, filed on May 22, 2017, now abandoned, which is a division of application No. 14/539,845, filed on Nov. 12, 2014, now Pat. No. 9,683,998.

(60) Provisional application No. 61/912,374, filed on Dec. 5, 2013, provisional application No. 61/903,836, filed on Nov. 13, 2013.

(51) Int. Cl.
*G01N 33/68* (2006.01)
*C07K 16/28* (2006.01)

(52) U.S. Cl.
CPC ..... *G01N 33/6863* (2013.01); *C07K 16/2875* (2013.01); *C07K 2317/56* (2013.01); *C07K 2317/565* (2013.01); *C07K 2317/76* (2013.01); *C07K 2317/90* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,521,422 B1 | 2/2003 | Hsu et al. | |
| 7,597,886 B2 | 10/2009 | Yu et al. | |
| 9,683,998 B2 | 6/2017 | Arch et al. | |
| 2011/0217310 A1 | 9/2011 | Siegel et al. | |
| 2012/0114654 A1 | 5/2012 | Classon et al. | |
| 2012/0263718 A1 | 10/2012 | Siegel et al. | |
| 2018/0052175 A1 | 2/2018 | Arch et al. | |
| 2019/0331694 A1 | 10/2019 | Arch et al. | |

FOREIGN PATENT DOCUMENTS

| | | | |
|---|---|---|---|
| CN | 101903402 A | 12/2010 | |
| CN | 103261228 A | 8/2013 | |
| JP | 2011-502522 A | 1/2011 | |
| TW | 201233796 A1 | 8/2012 | |
| WO | 2006/127900 A2 | 11/2006 | |
| WO | 2009/064854 A2 | 5/2009 | |
| WO | WO-2009064854 A3 * | 7/2009 | ................ A61P 1/00 |
| WO | WO-2012064682 A1 * | 5/2012 | ........... A61K 39/395 |
| WO | 2012/161856 A1 | 11/2012 | |
| WO | WO-2013044298 A1 * | 4/2013 | ................ A61P 1/00 |

OTHER PUBLICATIONS

Clarke (MAbs. May 2018/Jun. 10(4):664-677. Epub Mar. 5, 2018.) (Year: 2018).*
Ma (Modern Drug Discovery 2004, 7(6)) (Year: 2004).*
Steinman et al (Nat Med. Jan. 6, 2012;18(1):59-65) (Year: 2012).*
Blumberg et al (Nat Med.; 18(1): 35-41) (Year: 2015).*
Abaza M-S I. et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin", Journal of Protein Chemistry 11(5):433-444 (1992).
Bamias G. et al., "Differential Expression of the TL1A/DcR3 System of TNF/TNFR-Like Proteins in Large vs. Small Intestinal Croh's Disease", Dig. Liver Dis. 44(1):30-36 (Jan. 2012).
Bamias G. et al., "Expression, Localization, and Functional Activity of TL1A, a Novel Th1-Polarizing Cytokine in Inflammatory Bowel Disease", J Immunol. 171(9):4868-4874 (Nov. 1, 2003).
Bamias G. et al., "Role of TL1A and its Receptor DR3 in Two Models of Chronic Murine Ileitis", Proc Natl Acad Sci USA 103(22):8441-8446 (May 30, 2006).
Barrett JC et al., "Genome-Wide Association Defines More Than 30 Distinct Susceptibility Loci for Crohn's Disease", Nat Genet. 40(8):955-962 (Aug. 2008).

(Continued)

*Primary Examiner* — Brian Gangle
*Assistant Examiner* — Andrea K McCollum
(74) *Attorney, Agent, or Firm* — Scully, Scott, Murphy & Presser, P.C.

(57) ABSTRACT

The present invention provides antibodies, or antigen-binding fragment thereof, which specifically bind to tumor necrosis factor (TNF)-like ligand (TL1A). The invention further provides a method of obtaining such antibodies and nucleic acids encoding the same. The invention further relates to compositions and therapeutic methods for use of these antibodies for the treatment and/or prevention of TL1A mediated diseases, disorders or conditions.

30 Claims, 45 Drawing Sheets

Specification includes a Sequence Listing.

(56) References Cited

OTHER PUBLICATIONS

Brown M. et al., "Tolerance of Single, But Not Multiple, Amino Acid Replacements in Antibody VH CDR 2: A Means of Minimizing B Cell Wastage from Somatic Hypermutation?", Journal Immunology156(9):3285-3291 (May 1, 1996).
Caldas C. et al., "Humanization of the Anti-CD18 Antibody 6.7: An Unexpected Effect of a Framework Residue in Binding to Antigen", Molecular Immunology 39:941-952 (2003).
Casadevall A. et al., "Immunoglobulin Isotype Influences Affinity and Specificity", PNAS 109(31):12272-12273 (Jul. 31, 2012).
Du J. et al., "Molecular Basis of Recognition of Human Osteopontin by 23C3, a Potential Therapeutic Antibody for Treatment of Rheumatoid Arthritis", J. Mol. Biol. 382:835-842 (2008).
Hsu H. et al., "The Tale of TL1A in Inflammation", Mucosal Immunol. 4(4):368-370 (Jul. 2011).
Jostins L. et al., "Host-Microbe Interactions Have Shaped the Genetic Architecture of Inflammatory Bowel Disease", Nature 491(7422:119-124 (Nov. 1, 2012).
Kakuta Y. et al., "TNFSF15 Transcripts from Risk Haplotype for Crohn's Disease are Overexpressed in Stimulated T Cells", Hum Mol Genet. 18(6):1089-1098 (Mar. 15, 2009).
Kamada N. et al., "TL1A Produced by Lamina Propria Macrophages Induces Th1 and Th17 Immune Responses in Cooperation With IL-23 in Patients With Crohn's Disease", Inflamm Bowel Dis. 16(4):568-575 (Apr. 2010).
Kunik V. et al., Structural Consensus Among Antibodies Defines the Antigen Binding Site, PLoS Computational Biology 8(2)P:e1002388 (Feb. 2012).
Mariuzza R.A. et al., "The Structural Basis of Antigen-Antibody Recognition", Ann. Rev. Biophys. Chem. 16:139-159 (1987).
Meylan F. et al., "TL1A and DR3, a TNF Family Ligand-Receptor Pair that Promotes Lymphocyte Costimulation, Mucosal Hyperplasia, and Autoimmune Inflammation", Immunol Rev. 244(1):188-196 (Nov. 2011).
Meylan F. et al., "The TNF-Family Receptor DR3 is Essential for Diverse T Cell-Mediated Inflammatory Diseases", Immunity 29(1):79-89 (Jul. 18, 2008).
Migone TS et al., "TL1A is a TNF-Like Ligand for DR3 and TR6/DcR3 and Functions as a T Cell Costimulator", Immunity 16(3):479-492 (Mar. 2002).
Papadakis KA et al., "Dominant Role for TL1A/DR3 Pathway in IL-12 Plus IL-18-Induced IFN-Gamma Production by Peripheral Blood and Mucosal CCR9+ T Lymphocytes", J Immunol 174(8):4985-4990 (Apr. 15, 2005).
Papadakis KA et al., "TL1A Synergizes With IL-12 and IL-18 to Enhance IFN-Gamma Production in Human T Cells and NK Cells", J Immunol. 172(11):7002-7007 (Jun. 1, 2004).
Pappu BP et al., "TL1A-DR3 Interaction Regulates Th17 Cell Function and Th17-Mediated Autoimmune Disease", J Exp Med. 205(5):1049-1062 (May 12, 2008).
Prehn JL et al., "Potential Role for TL1A, the New TNF-Family Member and Potent Costimulator of IFN-Gamma, in Mucosal Inflammation", Clin Immunol. 112(1):66-77 (Jul. 2004).
Shih DQ et al., "Microbial Induction of Inflammatory Bowel Disease Associated Gene TL1A (TNFSF15) in Antigen Presenting Cells", Eur J Immunol. 39(11):3239-3250 (Nov. 2009).
Takedatsu H. et al., "TL1A (TNFSF15) Regulates the Development of Chronic Colitis by Modulating Both B-Helper 1 and T-Helper 17 Activation", Gastroenterology 135(2):552-567 (Aug. 2008).
Taraban VY et al., "Sustained TL1A Expression Modulates Effector and Regulatory T-Cell Responses and Drives Intestinal Goblet Cell Hyperplasia", Mucosal Immunol. 4(2):186-196 (Mar. 2011).
Vajdos FF et al., "Comprehensive Functional Maps of the Antigen-Binding Site of an Anti-ErbB2 Antibody Obtained with Shotgun Scanning Mutagenesis", J Mol Biol. 320(2):415-428 (Jul. 5, 2002).
Winkler K. et al., "Changing the Antigen Binding Specificity by Single Point Mutations of an Anti-p24 (HIV-1) Antibody", The Journal of Immunology 165:4505-4514 (2000).
Yamazaki K. et al., "A Genome-Wide Association Study Identifies 2 Susceptibility Loci for Crohn's Disease in a Japanese Population", Gastroenterology 144(4):781-788 (Apr. 2013).
Yamazaki K. et al., "Single Nucleotide Polymorphisms in TNFSF15 Confer Susceptibility to Crohn's Disease", Hum Mol Genet. 14(22):3499-3506 (Nov. 15, 2005).
Japanese Notice of Reasons for Rejection dated Nov. 27, 2018 received in Japanese Patent Application No. 2016-530124, together with an English-language translation.
Russian Office Action dated Dec. 25, 2018 received in Russian Patent Application No. 2016116168, together with an English-language translation.
Chinese Office Action dated Jan. 14, 2019 received in Chinese Application for Invention No. 201480062129.3, together with an English-language translation.
Israeli Office Action dated Feb. 21, 2019 received in Israeli Patent Application No. 245001, together with an English-language translation.
Indonesian Office Action dated Feb. 19, 2019 received in Indonesian Patent Application No. P00201603804, together with an English-language translation.
Taiwanese Office Action and Search Report dated Oct. 9, 2018 received in Taiwanese Patent Application No. 103139333, together with an English-language translation.
Australian Examination Report dated May 24, 2019 received in Australian Application No. 2014348676.
Taiwanese Office Action dated May 28, 2019 received in Taiwanese Application No. 103139333, together with an English-language translation.
European Communication dated Aug. 8, 2019 received in European Application No. 14 833 301.6.
Japanese Decision of Rejection dated Oct. 23, 2019 received in Japanese Patent Application No. 2016-530124, together with an English-language translation.
Chinese Office Action dated Nov. 1, 2019 received in Chinese Patent Application No. 201480062129.3, together with an English-language translation.
Indonesian Office Action dated Nov. 4, 2019 received in Indonesian Patent Application No. P00201603804, together with an English-language translation.
Mexican Office Action dated Nov. 7, 2019 received in Mexican Patent Application No. MX/a/2016/006232, together with an English-language translation.
English-language translation of Saudi Examination Report dated Feb. 3, 2020 received in Saudi Patent Application No. 516371109.
Argentine Office Action dated Feb. 18, 2020 received in Argentine Patent Application No. 20140104255.
Philippines Examination Report dated Jun. 29, 2020 received in Philippine Patent Application No. 1/2016/500878.
Israeli Office Action dated Jun. 29, 2020 received in Israeli Patent Application No. 245001.
Chinese Office Action dated Aug. 20, 2020 received in Chinese Application No. 201480062129.3, together with an English-language translation.
Indian Examination Report dated Sep. 2, 2020 received in Indian Application No. 201617015428, together with an English-language translation.
Brazilian Office Action dated Sep. 15, 2020 received in Brazilian Patent Application No. BR112016009797-1, together with an English-language translation.
Philippines Subsequent Substantive Examination Report dated Oct. 26, 2020 received in Philippines Patent Application No. 1/2016/500878, English-language translation only.
Zhan, C., et al., "Biochemical and Structural Characterization of the Human TL1A Ectodomain", Biochemistry, 2009, pp. 7636-7645, vol. 48, No. 32.
Peruvian Office Action dated Jun. 30, 2021 received in Peru Application No. 000625-2016/DIN, together with an English-language translation.
Korean Office Action dated Aug. 19, 2021 received in Korean Application No. 10-2016-7015236, together with an English-language translation.

(56) References Cited

OTHER PUBLICATIONS

New Zealand Examination Report dated Dec. 15, 2021 received in New Zealand Application No. 719092.
New Zealand Examination Report dated Mar. 30, 2022 received in New Zealand Application No. 719092.
Brazilian Unfavorable Opinion dated Jun. 1, 2023 received in Brazilian Application No. 112016009797-1, together with an Informal English-language translation.
Malaysian Substantive Examination Report dated Oct. 27, 2020 received in Malaysian Patent Application No. PI 2016701698, English-language translation only.
Mexican Office Action dated Nov. 10, 2020 received in Mexican Patent Application No. MX/a/2016/006232, together with an English-language translation.
English-language translation of Saudi Arabia Examination Report dated Nov. 23, 2020 received in Saudi Arabia Patent Application No. 516371109.
Taiwanese Office Action dated Oct. 19, 2020 received in Taiwanese Patent Application No. 103139333, together with an English-language translation.
European Examination Report dated Apr. 4, 2022 received in European Application No. 14 833 301.6.
Korean Notice of Preliminary Rejection dated Feb. 17, 2021 received in Korean Patent Application No. 10-2016-7015236, together with an English-language translation.
Japanese Notice of Reasons for Rejection dated Mar. 23, 2021 received in Japanese Patent Application No. 2020-028964, together with an English-language translation.
Peruvian Office Action dated Feb. 19, 2021 received in Peruvian Application No. 000625-2016, together with an English-language translation.
Canadian Office Action dated Apr. 9, 2021 received in Canadian Application No. 3,056,647.
Mexican Office Action dated Mar. 26, 2021 received in Mexican Application No. MX/a/2016/006232, together with an English-language translation.

* cited by examiner

FIG. 1A

9B3 VH1 QVQLVESGGGVVQPGRSLRLSCAAS*GFTFSNYALH*WVRQAPGKGLE WVALISYDGSDKYYADSVKGRFAISRDNSKNTLYLQMNSLRAEDTAVY YCARDREYCTYSSCSYDAFDIWGQGTMVTVSS SEQ ID NO: 3

9B3 VH2 QVQLVESGGGVVQPGRSLRLSCAAS*GFTFSSFAMH*WVRQAPGKGLE WVALIPFDGSSNYYADSVKGRFTISRDNSKNTLYLQMNSLRAEDTAVY YCARDRNYYGSGSFSFDAFDIWGQGTLVTVSS SEQ ID NO: 5

9B3 VL DIQMTQSPSSLSASVGDRVTITCRASQGISSWLAWYQQKPEKAPKSLI YAASSLQSGVPSRFSGSGSGTDFTLTISSLQPEDYATYYCQQYNSYPY TFGQGTKLEIK SEQ ID NO: 1

15A9 VH QVQLVQSGAEVKKPGASLKVSCKAS*GYPFTNYGIS*WVRQAPGQGLE WMGWISTYNGNTHYAQKLQGRVTMTTDTSTTTAYMDLRSLRSDDTA VYYCARENYYGSGSYRGGMDVWGQGTTVTVSS SEQ ID NO: 24

15A9 VL EIVLTQSPATLSLSPGERATLSCRASQSVSSYLAWYQQKPGQAPRLLI YDASNRATGIPARFSGSGSGTDFTLTISSLEPEDFAVYYCQQRSNWP WTFGQGTKVEIK SEQ ID NO: 22

15C11 VH QVQLVQSGAEVKKPGASVKVSCKAS*GYSFTTYGIS*WVRQAPGQGLE WMGWISTYNGNTHYAQKLQGRVTMTTDTSTRTAYMELRSLRSDDTA VYYCARENYYGSGSYRGGMDVWGQGTTVTVSS SEQ ID NO: 38

15C11 VL EIVLTQSPATLSLSPGERATLSCRASQSVSSYLAWYQQKPGQAPRLLI YDASNRATGIPARFSGSGSGTDFTLTISSLEPEDFAVYYCQQRSNWP WT SEQ ID NO: 36

22F9 VH QVQLVQSGAEVKKPGASVKVSCKAS*GYTFTSYAMH*WVRQAPGQRLE WMGWINAGNGNTKYSQKFQGRVTITRDTSASTAYMELSSLRSEDTAV YYCARGYSSAWFDAFDIWGQGTMVTVSS SEQ ID NO: 52

22F9 VL AIQLTQSPSSLSASVGDRVTITCRASQGISSALAWYQQKPGKAPKLLIY DASSLESGVPSRFSGSGSGTDFTLTISSLQPEDFATYYCQQFNSYPLT FGGGTKVEIK SEQ ID NO: 50

FIG. 1B

26B11 VH1 QVQLVESGGGVVQPGRSLRLSCAAS*GFTFSNYALH*WVRQAPGKGLEW
VALISYDGSDKYYADSVKGRFAISRDNSKNTLYLQMNSLRAEDTAVYYC
ARDREYCTYSSCSYDAFDIWGQGTMVTVSS SEQ ID NO: 66

26B11 VH2 QVQLVESGGGVVQPGRSLRLSCAAS*GFTFSSFAMH*WVRQAPGKGLE
WVALIPFDGSSNYYADSVKGRFTISRDNSKNTLYLQMNSLRAEDTAVYY
CARDRNYYGSGSFSFDAFDIWGQGTLVTVSS SEQ ID NO: 68

26B11 VH MDX QVQLVESGGGVVQPGRSLRLSCEAS*GFTFSNYAIH*WVRQAPGKGLEW
VALIPYDGSNNYYAASVKGRFTISRDNSKNTLYLQMNSLRAEDTAVYYC
ARDRNYYGSGSFSFDAFDIWGQGTMVTVSS SEQ ID NO: 70

26B11 VL DIQMTQSPSSLSASVGDRVTITCRASQGISNWLAWYQQKPEKAPKSLIY
AASSLQSGVPSRFSGSGSGTDFTLTISSLQPEDFATYYCQQYNSYPYTF
GQGTKLEIK SEQ ID NO: 64

7D4 VH QVQLVQSGAEVKKPGASVKVSCKAS*GYTFTSYGIN*WVRQAPGQGLEW
MGWISTYNGNTNSAQKLQGRVTMTTDTSTSTAYMELRSLRSDDTAVYY
CARAHSSSWFDAFDIWGQGTMVTVSS SEQ ID NO: 90

7D4 VL AIQLTQSPSSLSASVGDRVTITCRASQGISSALAWYQQKPGKAPKLLIYD
ASSLESGVPSRFSGSGSGTDFTLTISSLQPEDFATYYCQQFNSYPLTFG
GGTKVEIK SEQ ID NO: 88

1D1 VH QVQLVQSGAEVKKPGASVKVSCKAS*GYSFTYYGIS*WVRQAPGQGLEW
MGWISTYNGNTNYARMLQGRVTMTTDTSTRTAYMELRSLRSDDTAVYY
CARENYYGSGSYRGGMDVWGQGTTVTVSS SEQ ID NO: 104

1D1 VL EIVLTQSPATLSLSPGERATLSCRASQSVSSYLAWYQQKPGQAPRLLIY
DASNRATGIPARFSGSGSGTDFTLTISSLEPEDFAVYYCQQRSNWPWTF
GQGTKVEIK SEQ ID NO: 102

FIG. 1C

1D1 D5 VH QVQLVQSGAEVKKPGASVKVSCKASGYSFTYYGISWVRQAPGQGLEWMGWISTYNGNTNYARMLQGRVTMTTDTSTRTAYMELRSLRSDDTAVYYCARENYYGSGAFRGGMDGWGQGTTVTVSS SEQ ID NO: 116

1D1 D18 VH QVQLVQSGAEVKKPGASVKVSCKASGYSFTYYGISWVRQAPGQGLEWMGWISTYNGNTHYARMLQGRVTMTTDTSTRTAYMELRSLRSDDTAVYYCARENYYGSGSYRGGMDVWGQGTTVTVSS SEQ ID NO: 118

1D1 D21 VH QVQLVQSGAEVKKPGASVKVSCKASGYSFTYYGISWVRQAPGQGLEWMGWISTYNGKTHYARMLQGRVTMTTDTSTRTAYMELRSLRSDDTAVYYCARENYYGSGSYRGGMDVWGQGTTVTVSS SEQ ID NO: 120

1D1 D24 VH QVQLVQSGAEVKKPGASVKVSCKASGYSFTYYGISWVRQAPGQGLEWMGWISPYNGNTHYARMLQGRVTMTTDTSTRTAYMELRSLRSDDTAVYYCARENYYGSGSYRGGMDVWGQGTTVTVSS SEQ ID NO: 122

1D1 D25 VH QVQLVQSGAEVKKPGASVKVSCKASGYSFTYYGISWVRQAPGQGLEWMGWISTYNGATHYARMLQGRVTMTTDTSTRTAYMELRSLRSDDTAVYYCARENYYGSGSYRGGMDVWGQGTTVTVSS SEQ ID NO: 124

1D1 D28 VH QVQLVQSGAEVKKPGASVKVSCKASGYSFTYYGISWVRQAPGQGLEWMGWISTYNGKTHYARMHQGRVTMTTDTSTRTAYMELRSLRSDDTAVYYCARENYYGSGSYRGGMDVWGQGTTVTVSS SEQ ID NO: 126

1D1 D29 VH QVQLVQSGAEVKKPGASVKVSCKASGYSFTYYGISWVRQAPGQGLEWMGWISSYNGNTHYARMLQGRVTMTTDTSTRTAYMELRSLRSDDTAVYYCARENYYGSGSYRGGMDVWGQGTTVTVSS SEQ ID NO: 128

1D1 D31 VH QVQLVQSGAEVKKPGASVKVSCKASGYSFTYYGISWVRQAPGQGLEWMGWISTYNGNKHYARMLQGRVTMTTDTSTRTAYMELRSLRSDDTAVYYCARENYYGSGSYRGGMDVWGQGTTVTVSS SEQ ID NO: 130

1D1 D37 VH QVQLVQSGAEVKKPGASVKVSCKASGYSFTYYGISWVRQAPGQGLEWMGWISTYNGGTHYARMLQGRVTMTTDTSTRTAYMELRSLRSDDTAVYYCARENYYGSGSYRGGMDVWGQGTTVTVSS SEQ ID NO: 132

FIG. 1D

1D1 D38 VH QVQLVQSGAEVKKPGASVKVSCKAS*GYSFTYYGIS*WVRQAPGQGLEW
MGWISTYNGVTHYARMLQGRVTMTTDTSTRTAYMELRSLRSDDTAVY
YCARENYYGSGSYRGGMDVWGQGTTVTVSS SEQ ID NO: 134

1D1 D39 VH QVQLVQSGAEVKKPGASVKVSCKAS*GYSFTYYGIS*WVRQAPGQGLEW
MGWISTYNGNTNYARMLQGRVTMTTDTSTRTAYMELRSLRSDDTAVY
YCARENYYGSGAYRGGMDAWGQGTTVTVSS SEQ ID NO: 136

1D1 DH3 VH QVQLVQSGAEVKKPGASVKVSCKAS*GYSFTYYGIS*WVRQAPGQGLEW
MGWISTYNGNTHYAQMLQGRVTMTTDTSTRTAYMELRSLRSDDTAVY
YCARENYYGSGSYRGGMDVWGQGTTVTVSS SEQ ID NO: 138

1D1 DH8 VH QVQLVQSGAEVKKPGASVKVSCKAS*GYSFTYYGIS*WVRQAPGQGLEW
MGWISAYNGNTHYARMLQGRVTMTTDTSTRTAYMELRSLRSDDTAVY
YCARENYYGSGSYRGGMDVWGQGTTVTVSS SEQ ID NO: 140

1D1 DH9 VH QVQLVQSGAEVKKPGASVKVSCKAS*GYSFTYYGIS*WVRQAPGQGLEW
MGWISPYNGKTHYARMLQGRVTMTTDTSTRTAYMELRSLRSDDTAVY
YCARENYYGSGSYRGGMDVWGQGTTVTVSS SEQ ID NO: 142

1D1 DH10 VH QVQLVQSGAEVKKPGASVKVSCKAS*GYSFTYYGIS*WVRQAPGQGLEW
MGWISTYNGNTNYARMLQGRVTMTTDTSTRTAYMELRSLRSDDTAVY
YCARENYYGSGAYRGGMDVWGQGTTVTVSS SEQ ID NO: 144

FIG. 1E

1D1 1.1 VH QVQLVQSGAEVKKPGASVKVSCKAS*GYDFTYYGIS*WVRQAPGQGLE WMGWISTYNGNTNYARMLQGRVTMTTDTSTRTAYMELRSLRSDDTAV YYCARENYYGSGSYRGGMDVWGQGTTVTVSS SEQ ID NO: 146

1D1 1.2 VH QVQLVQSGAEVKKPGASVKVSCKAS*GYNFTYYGIS*WVRQAPGQGLE WMGWISTYNGNTNYARMLQGRVTMTTDTSTRTAYMELRSLRSDDTAV YYCARENYYGSGSYRGGMDVWGQGTTVTVSS SEQ ID NO: 148

1D1 1.3 VH QVQLVQSGAEVKKPGASVKVSCKAS*GYQFTYYGIS*WVRQAPGQGLE WMGWISTYNGNTNYARMLQGRVTMTTDTSTRTAYMELRSLRSDDTAV YYCARENYYGSGSYRGGMDVWGQGTTVTVSS SEQ ID NO: 150

1D1 1.4 VH QVQLVQSGAEVKKPGASVKVSCKAS*GYSFTHYGIS*WVRQAPGQGLE WMGWISTYNGNTNYARMLQGRVTMTTDTSTRTAYMELRSLRSDDTAV YYCARENYYGSGSYRGGMDVWGQGTTVTVSS SEQ ID NO: 152

1D1 1.5 VH QVQLVQSGAEVKKPGASVKVSCKAS*GYNFRYYGIS*WVRQAPGQGLE WMGWISTYNGNTNYARMLQGRVTMTTDTSTRTAYMELRSLRSDDTAV YYCARENYYGSGSYRGGMDVWGQGTTVTVSS SEQ ID NO: 154

1D1 1.6 VH QVQLVQSGAEVKKPGASVKVSCKAS*GYNFTHYGIS*WVRQAPGQGLE WMGWISTYNGNTNYARMLQGRVTMTTDTSTRTAYMELRSLRSDDTAV YYCARENYYGSGSYRGGMDVWGQGTTVTVSS SEQ ID NO: 156

1D1 1.7 VH QVQLVQSGAEVKKPGASVKVSCKAS*GYSFTYYGIS*WVRQAPGQGLEW MGWISTYNGKTNYARMLQGRVTMTTDTSTRTAYMELRSLRSDDTAVY YCARENYYGSGSYRGGMDVWGQGTTVTVSS SEQ ID NO: 158

1D1 1.8 VH QVQLVQSGAEVKKPGASVKVSCKAS*GYSFRYYGIS*WVRQAPGQGLE WMGWISTYNGNTHYARMLQGRVTMTTDTSTRTAYMELRSLRSDDTAV YYCARENYYGSGSYRGGMDVWGQGTTVTVSS SEQ ID NO: 160

1D1 1.9 VH QVQLVQSGAEVKKPGASVKVSCKAS*GYSFTYYGIS*WVRQAPGQGLEW MGWISTYNGNTHYARMLQGRVTMTTDTSTRTAYMELRSLRSDDTAVY YCARENYYGSGAYRGGMDVWGQGTTVTVSS SEQ ID NO: 162

FIG. 1F

1D1 1.10 VH QVQLVQSGAEVKKPGASVKVSCKAS*GYSFTYYGIS*WVRQAPGQGLEW
MGWISPYNGKTHYARMLQGRVTMTTDTSTRTAYMELRSLRSDDTAVY
YCARENYYGSGAYRGGMDVWGQGTTVTVSS SEQ ID NO: 164

1D1 1.11 VH QVQLVQSGAEVKKPGASVKVSCKAS*GYSFRYYGIS*WVRQAPGQGLE
WMGWISTYNGNTHYARMLQGRVTMTTDTSTRTAYMELRSLRSDDTAV
YYCARENYYGSGAYRGGMDVWGQGTTVTVSS SEQ ID NO: 166

1D1 1.12 VH QVQLVQSGAEVKKPGASVKVSCKAS*GYNFTYYGIS*WVRQAPGQGLE
WMGWISPYNGKTHYARMLQGRVTMTTDTSTRTAYMELRSLRSDDTAV
YYCARENYYGSGAYRGGMDVWGQGTTVTVSS SEQ ID NO: 168

1D1 1.13 VH QVQLVQSGAEVKKPGASVKVSCKAS*GYSFTHYGIS*WVRQAPGQGLE
WMGWISPYNGKTHYARMLQGRVTMTTDTSTRTAYMELRSLRSDDTAV
YYCARENYYGSGAYRGGMDVWGQGTTVTVSS SEQ ID NO: 170

1D1 1.14 VH QVQLVQSGAEVKKPGASVKVSCKAS*GYNFTHYGIS*WVRQAPGQGLE
WMGWISPYNGKTHYARMLQGRVTMTTDTSTRTAYMELRSLRSDDTAV
YYCARENYYGSGAYRGGMDVWGQGTTVTVSS SEQ ID NO: 172

1D1 1.15 VH QVQLVQSGAEVKKPGASVKVSCKAS*GYSFTYYGIS*WVRQAPGQGLEW
MGWISPYNGGTHYAQMLQGRVTMTTDTSTRTAYMELRSLRSDDTAVY
YCARENYYGSGAYRGGMDAWGQGTTVTVSS SEQ ID NO: 174

1D1 1.16 VH QVQLVQSGAEVKKPGASVKVSCKAS*GYSFTYYGIS*WVRQAPGQGLEW
MGWISPYNGVTHYAQMLQGRVTMTTDTSTRTAYMELRSLRSDDTAVY
YCARENYYGSGAYRGGMDAWGQGTTVTVSS SEQ ID NO: 176

1D1 1.17 VH QVQLVQSGAEVKKPGASVKVSCKAS*GYSFTYYGIS*WVRQAPGQGLEW
MGWISPYNGATHYAQMLQGRVTMTTDTSTRTAYMELRSLRSDDTAVY
YCARENYYGSGAYRGGMDAWGQGTTVTVSS SEQ ID NO: 178

1D1 1.18 VH QVQLVQSGAEVKKPGASVKVSCKAS*GYSFTYYGIS*WVRQAPGQGLEW
MGWISPYNGNKHYAQMLQGRVTMTTDTSTRTAYMELRSLRSDDTAVY
YCARENYYGSGAYRGGMDAWGQGTTVTVSS SEQ ID NO: 180

FIG. 1G

1D1 1.19 VH QVQLVQSGAEVKKPGASVKVSCKASGYSFTYYGISWVRQAPGQGLEW
MGWISTYNGGTHYARMLQGRVTMTTDTSTRTAYMELRSLRSDDTAVY
YCARENYYGSGAYRGGMDAWGQGTTVTVSS SEQ ID NO: 182

1D1 1.20 VH QVQLVQSGAEVKKPGASVKVSCKASGYSFTYYGISWVRQAPGQGLEW
MGWISPYNGNTHYARMLQGRVTMTTDTSTRTAYMELRSLRSDDTAVY
YCARENYYGSGAYRGGMDAWGQGTTVTVSS SEQ ID NO: 184

1D1 1.21 VH QVQLVQSGAEVKKPGASVKVSCKASGYSFTYYGISWVRQAPGQGLEW
MGWISTYNGNTHYAQMLQGRVTMTTDTSTRTAYMELRSLRSDDTAVY
YCARENYYGSGAYRGGMDAWGQGTTVTVSS SEQ ID NO: 186

1D1 1.22 VH QVQLVQSGAEVKKPGASVKVSCKASGYSFTYYGISWVRQAPGQGLEW
MGWISTYNGVTHYARMLQGRVTMTTDTSTRTAYMELRSLRSDDTAVY
YCARENYYGSGAYRGGMDAWGQGTTVTVSS SEQ ID NO: 188

1D1 1.23 VH QVQLVQSGAEVKKPGASVKVSCKASGYSFTYYGISWVRQAPGQGLEW
MGWISTYNGATHYARMLQGRVTMTTDTSTRTAYMELRSLRSDDTAVY
YCARENYYGSGAYRGGMDAWGQGTTVTVSS SEQ ID NO: 190

1D1 1.24 VH QVQLVQSGAEVKKPGASVKVSCKASGYSFTYYGISWVRQAPGQGLEW
MGWISTYNGNKHYARMLQGRVTMTTDTSTRTAYMELRSLRSDDTAVY
YCARENYYGSGAYRGGMDAWGQGTTVTVSS SEQ ID NO: 192

1D1 1.25 VH QVQLVQSGAEVKKPGASVKVSCKASGYSFTYYGISWVRQAPGQGLEW
MGWISTYNGKTHYARMHQGRVTMTTDTSTRTAYMELRSLRSDDTAVY
YCARENYYGSGAYRGGMDAWGQGTTVTVSS SEQ ID NO: 194

1D1 1.26 VH QVQLVQSGAEVKKPGASVKVSCKASGYSFTYYGISWVRQAPGQGLEW
MGWISTYNGNTHYARMLQGRVTMTTDTSTRTAYMELRSLRSDDTAVY
YCARENYYGSGAYRGGMDAWGQGTTVTVSS SEQ ID NO: 196

FIG. 1H

1D1 1.27 VH QVQLVQSGAEVKKPGASVKVSCKAS*GYDFTYYGIS*WVRQAPGQGLE
WMGWISTYNGNTHYARMLQGRVTMTTDTSTRTAYMELRSLRSDDTAV
YYCARENYYGSGSYRGGMDVWGQGTTVTVSS SEQ ID NO: 198

1D1 1.28 VH QVQLVQSGAEVKKPGASVKVSCKAS*GYDFTYYGIS*WVRQAPGQGLE
WMGWISTYNGNKHYARMLQGRVTMTTDTSTRTAYMELRSLRSDDTAV
YYCARENYYGSGSYRGGMDVWGQGTTVTVSS SEQ ID NO: 205

1D1 1.29 VH QVQLVQSGAEVKKPGASVKVSCKAS*GYDFTYYGIS*WVRQAPGQGLE
WMGWISTYNGGTHYARMLQGRVTMTTDTSTRTAYMELRSLRSDDTAV
YYCARENYYGSGSYRGGMDVWGQGTTVTVSS SEQ ID NO: 212

1D1 1.30 VH QVQLVQSGAEVKKPGASVKVSCKAS*GYDFTYYGIS*WVRQAPGQGLE
WMGWISTYNGVTHYARMLQGRVTMTTDTSTRTAYMELRSLRSDDTAV
YYCARENYYGSGSYRGGMDVWGQGTTVTVSS SEQ ID NO: 219

1D1 1.31 VH QVQLVQSGAEVKKPGASVKVSCKAS*GYDFTYYGIS*WVRQAPGQGLE
WMGWISTYNGNTHYARMLQGRVTMTTDTSTRTAYMELRSLRSDDTAV
YYCARENYYGSGAYRGGMDVWGQGTTVTVSS SEQ ID NO: 226

1D1 1.32 VH QVQLVQSGAEVKKPGASVKVSCKAS*GYDFTYYGIS*WVRQAPGQGLE
WMGWISTYNGGTHYARMLQGRVTMTTDTSTRTAYMELRSLRSDDTAV
YYCARENYYGSGAYRGGMDAWGQGTTVTVSS SEQ ID NO: 233

1D1 1.33 VH QVQLVQSGAEVKKPGASVKVSCKAS*GYDFTYYGIS*WVRQAPGQGLE
WMGWISTYNGVTHYARMLQGRVTMTTDTSTRTAYMELRSLRSDDTAV
YYCARENYYGSGAYRGGMDAWGQGTTVTVSS SEQ ID NO: 240

1D1 1.34 VH QVQLVQSGAEVKKPGASVKVSCKAS*GYDFTYYGIS*WVRQAPGQGLE
WMGWISTYNGKTHYARMHQGRVTMTTDTSTRTAYMELRSLRSDDTAV
YYCARENYYGSGAYRGGMDAWGQGTTVTVSS SEQ ID NO: 247

FIG. 1I-1

Alignment of Light Chain Variable Domains:

```
26B11    1 DIQMTQSPSSLSASVGDRVTITCRASQGISNWLAWYQQKPEKAP 44
7D4      1 AIQLTQSPSSLSASVGDRVTITCRASQGISSALAWYQQKPGKAP 44
1D1      1 EIVLTQSPATLSLSPGERATLSCRASQSVSSYLAWYQQKPGQAP 44

26B11   45 KSLIYAASSLQSGVPSRFSGSGSGTDFTLTISSLQPE 81
7D4     45 KLLIYDASSLESGVPSRFSGSGSGTDFTLTISSLQPE 81
1D1     45 RLLIYDASNRATGIPARFSGSGSGTDFTLTISSLEPE 81

26B11   82 DFATYYCQQYNSYPYTFGQGTKLEIK 107  (SEQ ID NO: 66)
7D4     82 DFATYYCQQFNSYPLTFGGGTKVEIK 107  (SEQ ID NO: 88)
1D1     82 DFAVYYCQQRSNWPWTFGQGTKVEIK 107  (SEQ ID NO: 102)
```

FIG. 1I-2

Alignment of Heavy Chain Variable Domains:

```
1D1     1 QVQLVQSGAEVKKPGASVKVSCKASGYSFTYYGISWVRQAPGQGL 45
7D4     1 QVQLVQSGAEVKKPGASVKVSCKASGYTFTSYGINWVRQAPGQGL 45
26B11   1 QVQLVESGGGVVQPGRSLRLSCAASGFTFSSFAMHWVRQAPGKGL 45

1D1    46 EWMGWISTYNGNTNYARMLQGRVTMTTDTSTRTAYM 80
7D4    46 EWMGWISTYNGNTNSAQKLQGRVTMTTDTSTSTAYM 80
26B11  46 EWVALIPFDGSSNYYADSVKGRFTISRDNSKNTLYL 80

1D1    81 ELRSLRSDDTAVYYCARENYYGSG..SYRGGMDVWGQGTTVTVSS 113
                                                    (SEQ ID NO: 104)
7D4    81 ELRSLRSDDTAVYYCARAHSS.....SWFDAFDIWGQGTMVTVSS 113
                                                    (SEQ ID NO: 90)
26B11  81 QMNSLRAEDTAVYYCARDRNYYGSGSFSFDAFDIWGQGTLVTVSS 113
                                                    (SEQ ID NO: 68)
```

FIG. 1J

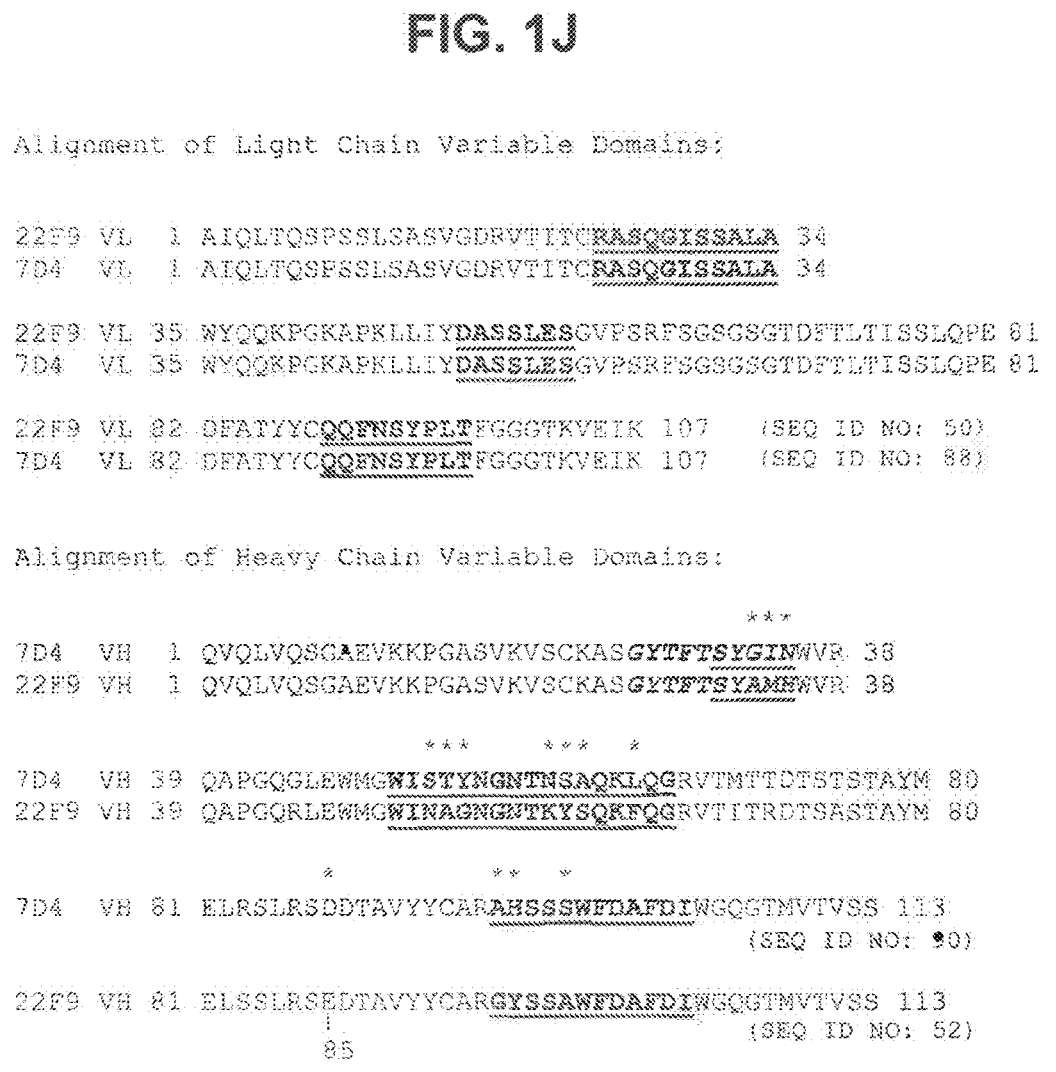

Alignment of Light Chain Variable Domains:

22F9 VL 1 AIQLTQSPSSLSASVGDRVTITCRASQGISSALA 34
7D4 VL 1 AIQLTQSPSSLSASVGDRVTITCRASQGISSALA 34

22F9 VL 35 WYQQKPGKAPKLLIYDASSLESGVPSRFSGSGSGTDFTLTISSLQPE 81
7D4 VL 35 WYQQKPGKAPKLLIYDASSLESGVPSRFSGSGSGTDFTLTISSLQPE 81

22F9 VL 82 DFATYYCQQFNSYPLTFGGGTKVEIK 107 (SEQ ID NO: 50)
7D4 VL 82 DFATYYCQQFNSYPLTFGGGTKVEIK 107 (SEQ ID NO: 88)

Alignment of Heavy Chain Variable Domains:

***
7D4 VH 1 QVQLVQSGAEVKKPGASVKVSCKAS*GYTFTSYGIN*WVR 38
22F9 VH 1 QVQLVQSGAEVKKPGASVKVSCKAS*GYTFTSYAMH*WVR 38

* * *
7D4 VH 39 QAPGQGLEWMGWISTYNGNTNSAQKLQGRVTMTTDTSTSTAYM 80
22F9 VH 39 QAPGQRLEWMGWINAGNGNTKYSQKFQGRVTITRDTSASTAYM 80

* ** *
7D4 VH 81 ELRSLRSDDTAVYYCARAHSSSWFDAFDIWGQGTMVTVSS 113
(SEQ ID NO: 90)

22F9 VH 81 ELSSLRSEDTAVYYCARGYSSAWFDAFDIWGQGTMVTVSS 113
(SEQ ID NO: 52)
85

FIG. 1K

Alignment of Light Chain Variable Domains:

```
                                             *
26B11 VL   1 DIQMTQSPSSLSASVGDRVTITCRASQGISNWLA 34
9B3   VL   1 DIQMTQSPSSLSASVGDRVTITCRASQGISSWLA 34

26B11 VL  35 WYQQKPEKAPKSLIYAASSLQSGVPSRFSGSGSGTDFTLTISSLQPE 81
9B3   VL  35 WYQQKPEKAPKSLIYAASSLQSGVPSRFSGSGSGTDFTLTISSLQPE 81

              *
26B11 VL  82 DFATYYCQQYNSYPYTFGQGTKLEIK 107  (SEQ ID NO: 64)
9B3   VL  82 DYATYYCQQYNSYPYTFGQGTKLEIK 107  (SEQ ID NO: 1)
              |
              83
```

Alignment of Heavy Chain Variable Domains VH1 and VH2 of antibodies 9B3 and 26B11, and MDX-VH of 26B11(9B3 and 26B11 produce multiple functional heavy chains which have the same sequences)

```
                                                        ** *
9B3/26B11 VH1   1 QVQLVESGGGVVQPGRSLRLSCAASGFTFSNYALHWVR 38
9B3/26B11 VH2   1 QVQLVESGGGVVQPGRSLRLSCAASGFTFSSFAMHWVR 38
26B11     MDX   1 QVQLVESGGGVVQPGRSLRLSCEASGFTFSNYAIHWVR 38

                                 **   **        *
9B3/26B11 VH1  39 QAPGKGLEWVALISYDGSDKYYADSVKGRFAISRDNSKNTLYL 80
9B3/26B11 VH2  39 QAPGKGLEWVALIPFDGSSNYYADSVKGRFTISRDNSKNTLYL 80
26B11     MDX  39 QAPGKGLEWVALIPYDGSNNYYAASVKGRFTISRDNSKNTLYL 80
                                                |
                                                68

                                     *  **** * *          *
9B3/26B11 VH1 81 QMNSLRAEDTAVYYCARDREYCTYSSCSYDAFDIWGQGTMVTVSS 113
                                                        (SEQ ID NOS: 3/66)

9B3/26B11 VH2 81 QMNSLRAEDTAVYYCARDRNYYGSGSFSFDAFDIWGQGTLVTVSS 113
                                                        (SEQ ID NOS: 5/68)

26B11     MDX 81 QMNSLRAEDTAVYYCARDRNYYGSGSFSFDAFDIWGQGTMVTVSS 113
                                                          |
                                                         108
                                                       (SEQ ID NO: 70)
```

FIG. 1L

Alignment of Light Chain Variable Domains:

```
15C11    1 EIVLTQSPATLSLSPGERATLSCRASQSVSSYLA 34
1D1      1 EIVLTQSPATLSLSPGERATLSCRASQSVSSYLA 34
15A9     1 EIVLTQSPATLSLSPGERATLSCRASQSVSSYLA 34

15C11   35 WYQQKPGQAPRLLIYDASNRATGIPARFSGSGSGTDFTLTISSL 78
1D1     35 WYQQKPGQAPRLLIYDASNRATGIPARFSGSGSGTDFTLTISSL 78
15A9    35 WYQQKPGQAPRLLIYDASNRATGIPARFSGSGSGTDFTLTISSL 78

15C11   79 EPEDFAVYYCQQRSNWPWTFGQGTKVEIK 107 (SEQ ID NO: 36)
1D1     79 EPEDFAVYYCQQRSNWPWTFGQGTKVEIK 107 (SEQ ID NO: 102)
15A9    79 EPEDFAVYYCQQRSNWPWTFGQGTKVEIK 107 (SEQ ID NO: 22)
```

Alignment of Heavy Chain Variable Domains:

```
                                          *   *
15A9     1 QVQLVQSGAEVKKPGASLKVSCKASGYPFTNYGIS 35
15C11    1 QVQLVQSGAEVKKPGASVKVSCKASGYSFTTYGIS
1D1      1 QVQLVQSGAEVKKPGASVKVSCKASGYSFTYYGIS 35

                                                **            *
15A9    36 WVRQAPGQGLEWMGWISTYNGNTHYAQKLQGRVTMTTDTSTTTAYM 80
15C11   36 WVRQAPGQGLEWMGWISTYNGNTHYAQKLQGRVTMTTDTSTRTAYM 80
1D1     36 WVRQAPGQGLEWMGWISTYNGNTNYARMLQGRVTMTTDTSTRTAYM 80
                                                              |
                                                              76
           *
15A9    81 DLRSLRSDDTAVYYCARENYYGSGSYRGGMDVWGQGTTVTVSS 113
                                                  (SEQ ID NO: 24)
15C11   81 ELRSLRSDDTAVYYCARENYYGSGSYRGGMDVWGQGTTVTVSS 113
                                                  (SEQ ID NO: 39)
1D1     81 ELRSLRSDDTAVYYCARENYYGSGSYRGGMDVWGQGTTVTVSS 113
           |                                      (SEQ ID NO: 104)
           81
```

FIG. 1M-1

Percentage identity of variable heavy domains for 1D1 and variants (1D1 variants share the same light chain as parent antibody 1D1)

| | 1D1 | 1.27 | 1.28 | 1.29 | 1.30 | 1.31 | 1.32 | 1.33 | 1.34 |
|---|---|---|---|---|---|---|---|---|---|
| 1D1 | 100 | 98.4 | 97.6 | 97.6 | 97.6 | 97.6 | 96.0 | 96.0 | 95.2 |
| 1.27 | 98.4 | 100 | 99.2 | 99.2 | 99.2 | 99.2 | 97.6 | 97.6 | 96.8 |
| 1.28 | 97.6 | 99.2 | 100 | 98.4 | 98.4 | 98.4 | 96.8 | 96.8 | 96.0 |
| 1.29 | 97.6 | 99.2 | 98.4 | 100 | 99.2 | 98.4 | 98.4 | 97.6 | 96.8 |
| 1.30 | 97.6 | 99.2 | 98.4 | 99.2 | 100 | 98.4 | 97.6 | 98.4 | 96.8 |
| 1.31 | 97.6 | 99.2 | 98.4 | 98.4 | 98.4 | 100 | 98.4 | 98.4 | 97.6 |
| 1.32 | 96.0 | 97.6 | 96.8 | 98.4 | 97.6 | 98.4 | 100 | 99.2 | 98.4 |
| 1.33 | 96.0 | 97.6 | 96.8 | 97.6 | 98.4 | 98.4 | 99.2 | 100 | 98.4 |
| 1.34 | 95.2 | 96.8 | 96.0 | 96.8 | 96.8 | 97.6 | 98.4 | 98.4 | 100 |

FIG. 1M-2

Variable Light Chain % identity of TL1A antibodies

| | 1D1 | 15A9 | 15C11 | 9B3 | 26B11 | 7D4 | 22F9 |
|---|---|---|---|---|---|---|---|
| 1D1 | 100 | 100 | 100 | 68.2 | 68.2 | 72.9 | 72.9 |
| 15A9 | 100 | 100 | 100 | 68.2 | 68.2 | 72.9 | 72.9 |
| 15C11 | 100 | 100 | 100 | 68.2 | 68.2 | 72.9 | 72.9 |
| 9B3 | 68.2 | 68.2 | 68.2 | 100 | 96.1 | 88.8 | 88.8 |
| 26B11 | 68.2 | 68.2 | 68.2 | 96.1 | 100 | 88.8 | 88.8 |
| 7D4 | 72.9 | 72.9 | 72.9 | 88.8 | 88.8 | 100 | 100 |
| 22F9 | 72.9 | 72.9 | 72.9 | 88.8 | 88.8 | 100 | 100 |

FIG. 1M-3

Variable heavy chain % identity of TL1A antibodies

| | 1D1 | 15A9 | 15C11 | 9B3/ 26B11 VH1 | 9B3/ 26B11 VH2 | 26B11 MDX | 7D4 | 22F9 |
|---|---|---|---|---|---|---|---|---|
| 1D1 | 100 | 93.5 | 96.8 | 56.6 | 57.0 | 59.4 | 86.0 | 75.2 |
| 15A9 | 93.5 | 100 | 96.0 | 56.1 | 55.6 | 58.9 | 85.1 | 75.2 |
| 15C11 | 96.8 | 96.0 | 100 | 54.5 | 54.8 | 57.3 | 86.8 | 76.9 |
| 9B3/26B11 VH1 | 56.6 | 56.1 | 54.5 | 100 | 87.3 | 88.9 | 59.2 | 60.3 |
| 9B3/26B11 VH2 | 57.0 | 55.6 | 54.8 | 87.3 | 100 | 93.7 | 59.2 | 61.2 |
| 26B11 MDX | 59.4 | 58.9 | 57.3 | 88.9 | 93.7 | 100 | 61.7 | 62.0 |
| 7D4 | 86.0 | 85.1 | 86.8 | 59.2 | 59.2 | 61.7 | 100 | 84.3 |
| 22F9 | 75.2 | 75.2 | 76.9 | 60.3 | 61.2 | 62.0 | 84.3 | 100 |

Epitope Binning with Murine TL1A

FIG. 18A

| | 1D1 | CDHR H1 | | | | | | CDR H2 | | | | | | |
|---|---|---|---|---|---|---|---|---|---|---|---|---|---|---|
| | | H S25 | H G26 | H Y27 | H S28 | H T30 | H Y31 | H W50 | H S52 | H Y53 | H N54 | H N56 | H T57 | H N58 |
| TL1A | total | 0 | 23.5 | 20.2 | 57.7 | 33.2 | 99 | 28.4 | 5.5 | 152.7 | 58.1 | 48.2 | 0.7 | 13.1 |
| A K113 | 25 | | | | 18.8 | 42.1 | | | | | | | | |
| A T115 | 12.7 | | | | 28.6 | | | | | | | | | |
| A Y118 | 118 | 15.5 | 48.8 | 50.4 | 36.8 | | | | | | | | | |
| A P121 | 7 | | | | | | 14.6 | | | | | | | |
| A T122 | 43.7 | | | | 28 | | 59.2 | | | | | | | |
| A Q123 | 16.9 | | | | | | 43.5 | | | | | | | |
| A M147 | 0.2 | | | | | | | | | 17.6w | | | | |
| A F148 | 5.5 | | | | | | | | | 28.3 | | | | |
| A S149 | 39.1 | | | | | | | | | 71.6h | | | | |
| A Q151 | 38.8 | | | | | | | | | | | | | |
| B V31 | 11.8 | | | | | | | | | | | | | |
| B V32 | 16.3 | | | | | | | | | | | | | |
| B R33 | 93.4 | | | | | | | | | | | | | |
| B E50 | 20.4 | | | | | | | | | | | | | |
| B H51 | 12.2 | | | | | | | | | | 12.7 | 26.6 | | |
| B E52 | 111 | | | | | | | 36.2 | 15.8 | | 22.4h | 33.1 | 6.4 | 34.8h |
| B L53 | 118 | | | | | | | 33.4 | | | 5.9 | | | |
| B G54 | 51.3 | | | | | | | | 9.5 | 21.9 | 4.5 | | | |
| B L55 | 53.4 | | | | | 21.4 | 35.6 | | | 62.7w | | | | |
| B A56 | 11.9 | | | | | | | | | 18.7 | 18.8h | | | |
| B F57 | 26.3 | | | | | | | | | 30.7 | 30.2 | | | |
| B T58 | 20.1 | | | | | | | | | | | 33.2 | | |
| B E91 | 6 | | | | | | | | | | | | | |
| B Y168 | 15.6 | | | | | | | | | | | | | |
| B T169 | 33 | | | | | | | | | | | | | |
| B K170 | 46 | | | | | | | | | | | | | |
| B E171 | 49 | | | | | | 22.4 | | | | | | | |

Figure 18B:
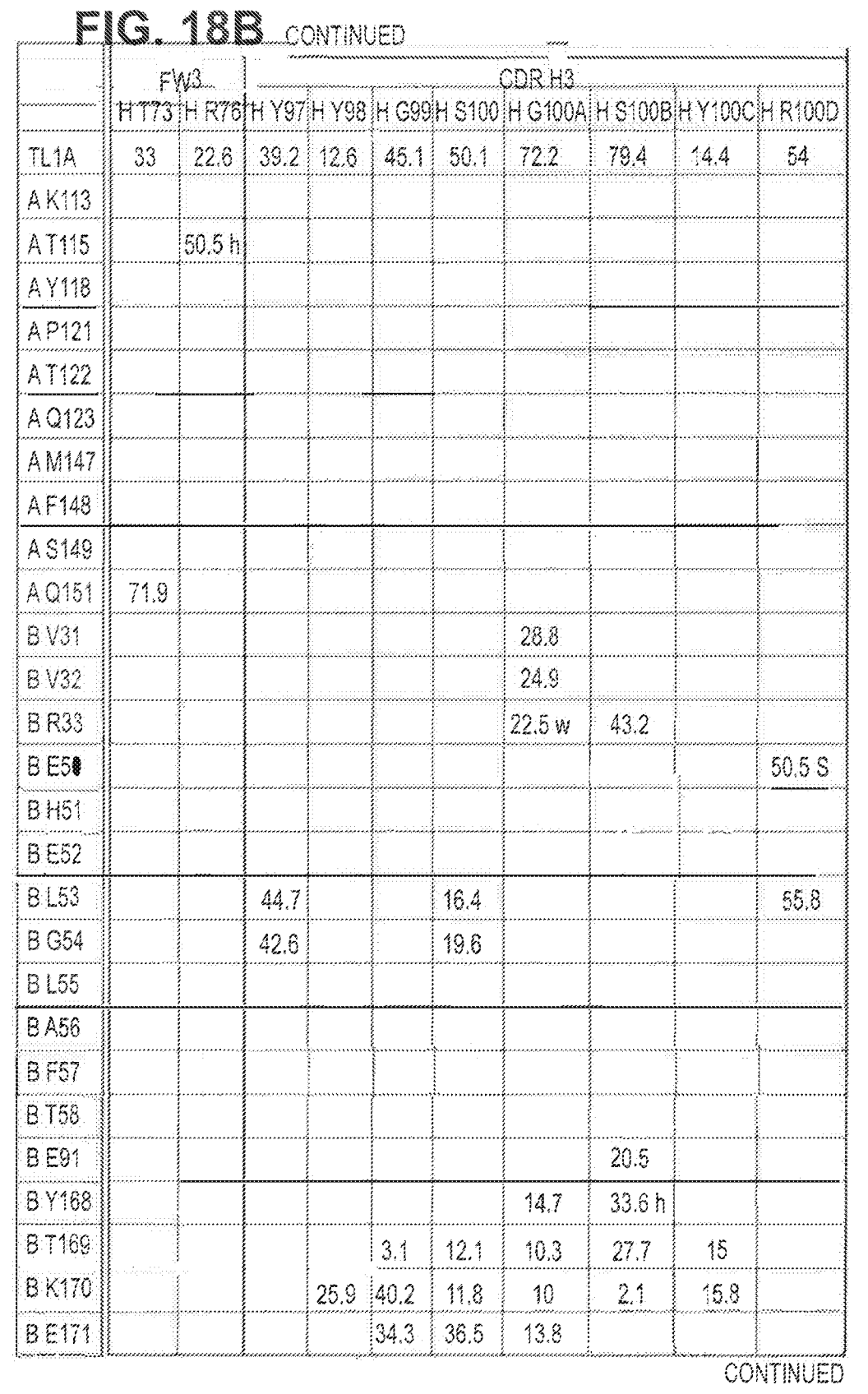

| | FW3 | | CDR H3 | | | | | | | |
|---|---|---|---|---|---|---|---|---|---|---|
| | H T73 | H R76 | H Y97 | H Y98 | H G99 | H S100 | H G100A | H S100B | H Y100C | H R100D |
| TL1A | 33 | 22.6 | 39.2 | 12.6 | 45.1 | 50.1 | 72.2 | 79.4 | 14.4 | 54 |
| A K113 | | | | | | | | | | |
| A T115 | | 50.5 h | | | | | | | | |
| A Y118 | | | | | | | | | | |
| A P121 | | | | | | | | | | |
| A T122 | | | | | | | | | | |
| A Q123 | | | | | | | | | | |
| A M147 | | | | | | | | | | |
| A F148 | | | | | | | | | | |
| A S149 | | | | | | | | | | |
| A Q151 | 71.9 | | | | | | | | | |
| B V31 | | | | | | | 28.8 | | | |
| B V32 | | | | | | | 24.9 | | | |
| B R33 | | | | | | | 22.5 w | 43.2 | | |
| B E50 | | | | | | | | | | 50.5 S |
| B H51 | | | | | | | | | | |
| B E52 | | | | | | | | | | |
| B L53 | | | 44.7 | | | 16.4 | | | | 55.8 |
| B G54 | | | 42.6 | | | 19.6 | | | | |
| B L55 | | | | | | | | | | |
| B A56 | | | | | | | | | | |
| B F57 | | | | | | | | | | |
| B T58 | | | | | | | | | | |
| B E91 | | | | | | | | 20.5 | | |
| B Y168 | | | | | | | 14.7 | 33.6 h | | |
| B T169 | | | | | 3.1 | 12.1 | 10.3 | 27.7 | 15 | |
| B K170 | | | | 25.9 | 40.2 | 11.8 | 10 | 2.1 | 15.8 | |
| B E171 | | | | | 34.3 | 36.5 | 13.8 | | | |

| | L1 | | | CDR L3 | |
|---|---|---|---|---|---|
| | L S30 | L S31 | L Y32 | L W94 | L W96 |
| TL1A | 9.6 | 15.5 | 29.7 | 26.1 | 6.4 |
| A K113 | | | | | |
| A T115 | | | | | |
| A Y118 | | | | | |
| A P121 | | | | | |
| A T122 | | | | | |
| A Q123 | | | | | |
| A M147 | | | | | |
| A F148 | | | | | |
| A S149 | | | | | |
| A Q151 | | | | | |
| B V31 | | | | | |
| B V32 | | | 7.4 | | |
| B R33 | 23.2 | 34.7 h | 56.8 w | | |
| B E50 | | | | | |
| B H51 | | | | | |
| B E52 | | | | 42.7 h | |
| B L53 | | | | 21.2 | 27 |
| B G54 | | | | | |
| B L55 | | | | | |
| B A56 | | | | | |
| B F57 | | | | | |
| B T58 | | | | | |
| B E91 | | | | | |
| B Y168 | | | | | |
| B T169 | | | | | |
| B K170 | | | | | |
| B E171 | | | | | |

FIG. 19A

| | 1.31 | CDHR H1 | | | | | CDR H2 | | | | | |
|---|---|---|---|---|---|---|---|---|---|---|---|---|
| TL1A | | H G26 | H Y27 | H D28 | H T30 | H Y31 | H W50 | H S52 | H Y53 | H N54 | H N56 | H H58 |
| | total | 32.8 | 18 | 76.3 | 34.1 | 88.1 | 25.2 | 9.6 | 151.1 | 50.5 | 35.1 | 11.1 |
| A K113 | 17.7 | | | 29.3 S | 18 | | | | | | | |
| A S117 | 41.9 | 24.5 | 7.7 | | | | | | | | | |
| A Y118 | 48.9 | 15.2 | 37.3 | 54.2 | | | | | | | | |
| A P119 | 14.2 | 28.8 | | | | | | | | | | |
| A T122 | 43.9 | | | 37.4 h | | 50.2 | | | | | | |
| A Q123 | 16.5 | | | | | 42.2 | | | 7.8 | | | |
| A M147 | 0 | | | | | | | | 32.7 | | | |
| A F148 | 6.1 | | | | | | | | 71.8 h | | | |
| A S149 | 35.4 | | | | | | | | | | | |
| A Q151 | 49.3 | | | 6.6 | 41.6 | | | | | | | |
| B V31 | 13.1 | | | | | | | | | | | |
| B V32 | 11.7 | | | | | | | | | | | |
| B R33 | 31.6 | | | | | | | | | | | |
| B E50 | 19.6 | | | | | | | | | | | |
| B H51 | 6.4 | | | | | | | | | 14.1 | | |
| B E52 | 110.9 | | | | | | 33.3 | 16.2 | | 25.8 h | 56.3 | 33.3 S |
| L53 | 113.8 | | | | | | 33.1 | | | | | |
| B G54 | 51.3 | | | | | | | 12 | 23.2 | 4.1 | | |
| B L55 | 56.3 | | | | 21.8 | 38.9 | | | 57.8 | | | |
| B A56 | 10.7 | | | | | | | | 20.2 | 17.3 h | | |
| B F57 | 26.4 | | | | | | | | 30.2 | 31 | | |
| B Y168 | 25.6 | | | | | | | | | | | |
| B T169 | 43.6 | | | | | | | | | | | |
| B K170 | 15.2 | | | | | | | | | | | |
| B E171 | 51.2 | | | | | 26.4 | | | | | | |
| B D172 | 0 | | | | | | | | | | | |

| | FW3 | | CDR H3 | | | | | | |
|---|---|---|---|---|---|---|---|---|---|
| TL1A | H T73 | H R76 | H Y97 | H G99 | H S100 | H G100A | H I S 10 0B | H Y100C | H R100D |
| | 24.7 | 24 | 36 | 38.5 | 48.2 | 68 | 46.9 | 8.4 | 41.7 |
| A K113 | | | | | | | | | |
| A S117 | | 44.5 | | | | | | | |
| A Y118 | | | | | | | | | |
| A P119 | | | | | | | | | |
| A T122 | | | | | | | | | |
| A Q123 | | | | | | | | | |
| A M147 | | | | | | | | | |
| A F148 | | | | | | | | | |
| A S149 | | | | | | | | | |
| A Q151 | 47.2 | | | | | | | | |
| B V31 | | | | | | 32 | | | |
| B V32 | | | | | | 27.6 | | | |
| B R33 | | | | | | 13.2 | | | |
| B E50 | | | | | | | | | 42.0 S |
| B H51 | | | | | | | | | |
| B E52 | | | | | | | | | |
| B L53 | | | 43 | | 16 | | | | 46.3 |
| B G54 | | | 40.9 | | 19.8 | | | | |
| B L55 | | | | | | | | | |
| B A56 | | | | | | | | | |
| B F57 | | | | | | | | | |
| B Y168 | | | | | 1.7 | 15.9 | 43.2 h | | |
| B T169 | | | | 5 | 14.5 h | 10.6 | 28.8 h | 21.7 | |
| B K170 | | | | 25.6 | 7.1 | 8.2 | 2.8 | | |
| B E171 | | | | 30.9 h | 36.9 | 14.3 | | | |
| B D172 | | | | 5.9 | | | | | |

| | L1 | CDR L3 | |
|---|---|---|---|
| TL1A | L Y32 | L W94 | L W96 |
| | 20.9 | 26.3 | 8.1 |
| A K113 | | | |
| A S117 | | | |
| A Y118 | | | |
| A P119 | | | |
| A T122 | | | |
| A Q123 | | | |
| A M147 | | | |
| A F148 | | | |
| A S149 | | | |
| A Q151 | | | |
| B V31 | | | |
| B V32 | | | |
| B R33 | 45.5 | | |
| B E50 | | | |
| B H51 | | | |
| B E52 | | 40.2 h | |
| B L53 | | 22.5 | 30.2 |
| B G54 | | | |
| B L55 | | | |
| B A56 | | | |
| B F57 | | | |
| B Y168 | | | |
| B T169 | | | |
| B K170 | | | |
| B E171 | | | |
| B D172 | | | |

FIG. 23A

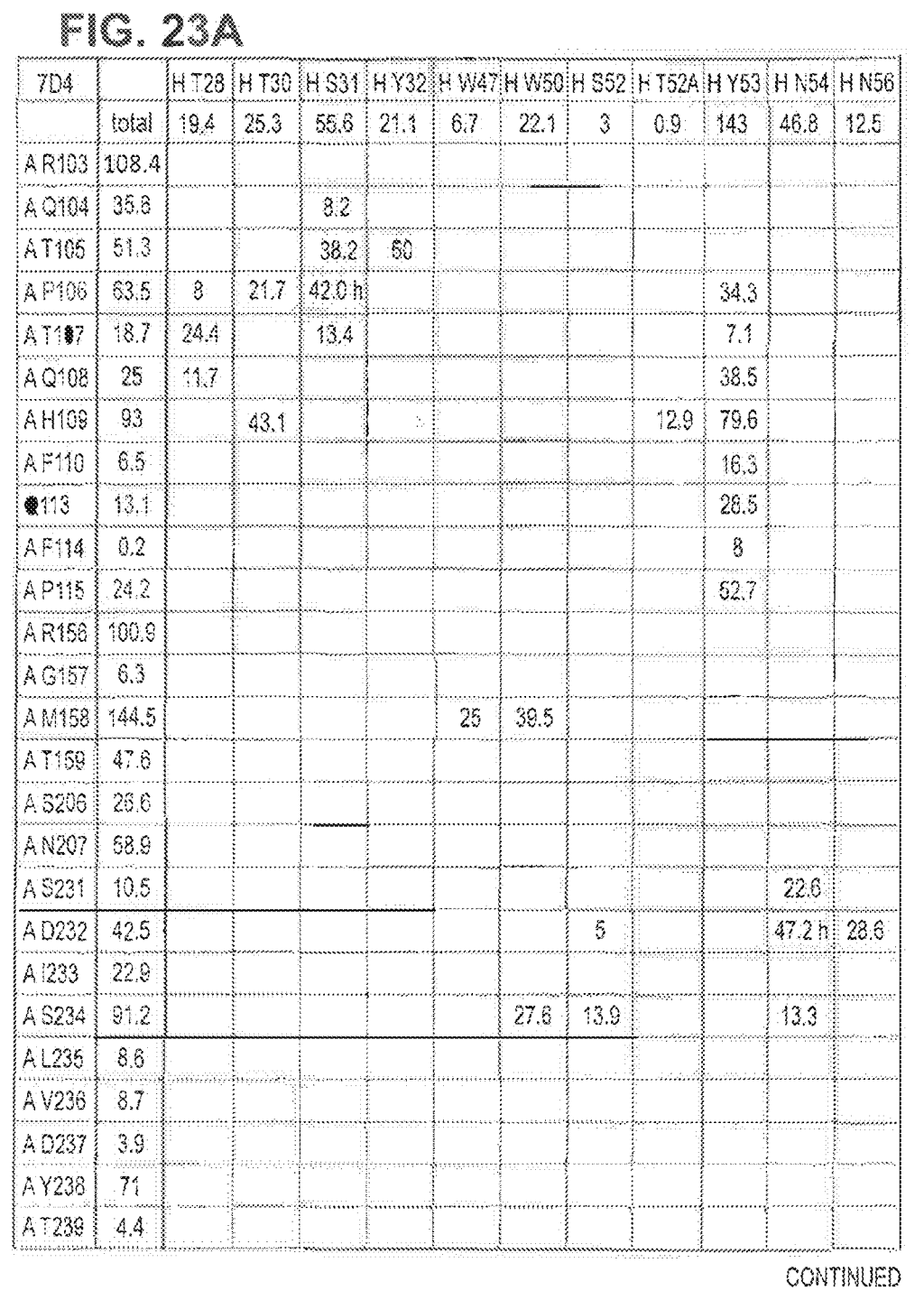

| 7D4 | | H T28 | H T30 | H S31 | H Y32 | H W47 | H W50 | H S52 | H T52A | H Y53 | H N54 | H N56 |
|---|---|---|---|---|---|---|---|---|---|---|---|---|
| | total | 19.4 | 25.3 | 55.6 | 21.1 | 6.7 | 22.1 | 3 | 0.9 | 143 | 46.8 | 12.5 |
| A R103 | 108.4 | | | | | | | | | | | |
| A Q104 | 35.8 | | | 8.2 | | | | | | | | |
| A T105 | 51.3 | | | 38.2 | 60 | | | | | | | |
| A P106 | 63.5 | 8 | 21.7 | 42.0 h | | | | | | 34.3 | | |
| A T1[illegible]7 | 18.7 | 24.4 | | 13.4 | | | | | | 7.1 | | |
| A Q108 | 25 | 11.7 | | | | | | | | 38.5 | | |
| A H109 | 93 | | 43.1 | | | | | | 12.9 | 79.6 | | |
| A F110 | 6.5 | | | | | | | | | 16.3 | | |
| [illegible]113 | 13.1 | | | | | | | | | 28.5 | | |
| A F114 | 0.2 | | | | | | | | | 8 | | |
| A P115 | 24.2 | | | | | | | | | 52.7 | | |
| A R156 | 100.9 | | | | | | | | | | | |
| A G157 | 6.3 | | | | | | | | | | | |
| A M158 | 144.5 | | | | | 25 | 39.5 | | | | | |
| A T159 | 47.6 | | | | | | | | | | | |
| A S206 | 26.6 | | | | | | | | | | | |
| A N207 | 58.9 | | | | | | | | | | | |
| A S231 | 10.5 | | | | | | | | | | 22.6 | |
| A D232 | 42.5 | | | | | | | 5 | | | 47.2 h | 28.6 |
| A I233 | 22.9 | | | | | | | | | | | |
| A S234 | 91.2 | | | | | | 27.6 | 13.9 | | | 13.3 | |
| A L235 | 8.6 | | | | | | | | | | | |
| A V236 | 8.7 | | | | | | | | | | | |
| A D237 | 3.9 | | | | | | | | | | | |
| A Y238 | 71 | | | | | | | | | | | |
| A T239 | 4.4 | | | | | | | | | | | |

| 7D4 | H N58 | H Q61 | H Q64 | H T73 | H H96 | H S97 | H S98 | H S99 | H W100 | H F100A | H D100B |
|---|---|---|---|---|---|---|---|---|---|---|---|
| | 53.8 | 16.8 | 5.1 | 13.3 | 15.2 | 38.7 | 67.4 | 28.5 | 90.7 | 106.9 | 18.1 |
| A R103 | | | | | | 41.9 | 30 | | | | 28.2 S |
| A Q104 | | | | | | | 28.8 | 31.8 h | | | |
| A T105 | | | | | | | 11.4 | 4.4 | | | |
| A P106 | | | | | | | | 17.3 | | | |
| A T107 | | | | | | | | | | | |
| A Q108 | | | | | | | | | | | |
| A H109 | | | | 27.6 | | | | | | | |
| A F110 | | | | | | | | | | | |
| Q113 | | | | | | | | | | | |
| A F114 | | | | | | | | | | | |
| A P115 | | | | | | | | | | | |
| A R156 | | | | | | | | | 35.0 h | 52 | |
| A G157 | | | | | | | | | 29.1 | | |
| A M158 | 52.6 | | | | | | | | 66.2 | | |
| A T159 | 51.7 | 14 | 10 | | | | | | | | |
| A S206 | | 22.2 | | | | | | | | | |
| A N207 | | | | | | | | | 13.6 | | |
| A S231 | | | | | | | | | | | |
| A D232 | | | | | | | | | | | |
| A I233 | | | | | | | 39.4 | 13.1 | | | |
| A S234 | | | | | | | 27 | 26.3 | 23.5 | 10.8 | |
| A L235 | | | | | | | | 3.7 | 21 | 15.3 | |
| A V236 | | | | | | | | 11 | | 19.4 | |
| A D237 | | | | | | | | | | 27.1 | |
| A Y238 | | | | | | 9.5 | | 19.3 | | 37.1 h | 23.6 |
| A T239 | | | | | | | | | | 15.9 | |

| 7D4 | L Y49 | L D50 | L F91 | L N92 | L S93 | L Y94 |
|---|---|---|---|---|---|---|
| | 3.8 | 24.7 | 6.4 | 28.5 | 13 | 71.9 |
| A R103 | 22.1 S | 40.2 S | 9.7 | | | |
| A Q104 | | | | | | |
| A T105 | | | | | | |
| A P106 | | | | | | |
| A T107 | | | | | | |
| A Q108 | | | | | | |
| A H109 | | | | | | |
| A F110 | | | | | | |
| Q113 | | | | | | |
| A F114 | | | | | | |
| A P115 | | | | | | |
| A R156 | | | 13.3 | 64.8 h | 7.6 | |
| A G157 | | | | | | |
| A M158 | | | | | | 51.3 |
| A T159 | | | | | | 21.5 |
| A S206 | | | | | | 33.5 |
| A N207 | | | | | 37.4 | 46.7 h |
| A S231 | | | | | | |
| A D232 | | | | | | |
| A I233 | | | | | | |
| A S234 | | | | | | |
| A L235 | | | | | | |
| A V236 | | | | | | |
| A D237 | | | | | | |
| A Y238 | | | 10.7 | 16 | | |
| A T239 | | | | | | |

FIG. 24A

| 26B11 | | H A33 | H L50 | H P52 | H F52A | H D53 | H S55 | H Y58 | H R96 | H N97 | H Y99 | H S100A |
|---|---|---|---|---|---|---|---|---|---|---|---|---|
| | total | 2.4 | 6.7 | 4.3 | 9.6 | 30.4 | 26.6 | 29.4 | 25.6 | 14.2 | 6 | 32.9 |
| D T105 | 23.2 | | | | | | | | | | 16.2 | |
| D P106 | 40.9 | | | | | 10.9 | | | | | | |
| D T107 | 31.6 | | | | | 22.9 | 35.1 | | | | | |
| D Q108 | 172.9 | 13.9 | | 26.3 | 45.2 h | 29.1h | 18.6 | | | 16.5 w | | |
| D H109 | 61.3 | | | | | | | | | | | |
| D F110 | 150.9 | | 18.1 | | | | | 47 | | | | |
| D K111 | 126.4 | | | | | | | | | 5.4 | | |
| D N112 | 54 | | | | | | | | | | | |
| D Q113 | 15.8 | | | | | | | 24.7 | | | | |
| D G169 | 6.7 | | | | | | | | | | | 17.7 |
| D R170 | 0 | | | | | | | | | | | |
| D P171 | 77.3 | | | | | | | | 30.7 h | 17.8 | | 41.4 |
| D N172 | 66.5 | | | | | | | | 12.7 | 13.9 h | | |
| D K173 | 68.8 | | | | | | | | 7.2 | | | |
| D P174 | 20.8 | | | | | | | | | | | |
| D D175 | 80 | | | | | | | | | | | |
| D S176 | 13.3 | | | | | | | | | | | |
| D S234 | 29.4 | | | | | | | | | | | |

| 26B11 | H G100B | H S100C | H F100D | H S100E | H F100F | H D100G | L S30 | L N31 | L W32 | L Y49 | L A50 | L S53 |
|---|---|---|---|---|---|---|---|---|---|---|---|---|
| | 29 | 32.2 | 102.9 | 56.5 | 66 | 9 | 15.9 | 45 | 73.6 | 31.4 | 17.6 | 15.8 |
| D T105 | | | 30.3 | | | | | | | | | |
| D P106 | | | 68.6 | | | | | | | | | |
| D T107 | | | 19.3 | | | | | | | | | |
| D Q108 | | | 34.1 h | 11.1 | 37.2 | | | | | | | |
| D H109 | | | 33 | 46.6 | 38.0 h | | | | | | | |
| D F110 | | | | 8.8 | 47.2 | | | | | | | |
| D K111 | | 0.5 | | 33.1 h | 29.0 w | 20.3 S | | | 50 | | | |
| D N112 | | | | | | | | | | | | |
| D Q113 | | | | | | | | | | | | |
| D G169 | | | | | | | | | | | | |
| D R170 | | 6.5 | | | | | | | | | | |
| D P171 | 11.6 | 16.6 | | | | 4.7 | | | | 9 | | |
| D N172 | | 24.6 h | | 12.5 h | | 16.4 w | | | 26.9 | 6.2 | 12 | |
| D K173 | | | | | | | | 16.7h | 14.1 | 46.5 h | 24.1 | 33 |
| D P174 | | | | | | | | 17.9 | 35.2 | | | |
| D D175 | | | | | | | | 48.4 | | | 1.3 | |
| D S176 | | | | | | | 29 | 4.2 | | | | |
| D S234 | 44.5 | 16.7 | | | | | | | | | | |

| 26B11 | L<br>G66 | L<br>S67 | L<br>Y91 | L<br>N92 | L<br>S93 | L<br>Y94 | L<br>Y96 | H<br>D95 |
|---|---|---|---|---|---|---|---|---|
| | 13.4 | 16.3 | 11.2 | 43 | 28.3 | 35.6 | 11.4 | 0 |
| D T105 | | | | | | | | |
| D P106 | | | | | | | | |
| D T107 | | | | | | | | |
| D Q108 | | | | | | | | 13.3 w |
| D H109 | | | | 1.4 | | | | |
| D F110 | | | | 8.7 | 10.3 | 20.7 | 51.8 | 29.5 |
| D K111 | | | | 40.1 w | 28.3 | | | 2.3 |
| D N112 | | | | | 41.6 h | | 41 | 27.1 w |
| D Q113 | | | | | | | | 5.6 |
| D G169 | | | | | | | | |
| D R170 | | | | | | | | |
| D P171 | | | | 2.3 | | | | |
| D N172 | | | | 9.8 w | | | | |
| D K173 | | | | | | | | |
| D P174 | | | | | | | | |
| D D175 | 41.0 w | 41.2 | | | | | | |
| D S176 | | | | | | | | |
| D S234 | | | | | | | | |

TUMOR NECROSIS FACTOR-LIKE LIGAND 1A SPECIFIC ANTIBODIES AND COMPOSITIONS AND USES THEREOF

RELATED APPLICATIONS

This application is a divisional application of U.S. patent application Ser. No. 16/422,256, filed May 24, 2019, which is a divisional application of U.S. patent application Ser. No. 15/601,617, filed May 22, 2017, now abandoned, which is a divisional application of U.S. patent application Ser. No. 14/539,845, dated Nov. 12, 2014, now U.S. Pat. No. 9,683, 998, which claims the benefit of U.S. provisional applications 61/903,836, filed Nov. 13, 2013, and 61/912,374, filed Dec. 5, 2013, which are incorporated by reference in their entireties.

SEQUENCE INFORMATION

The sequence listing in XML, named as 36790ABC_SequenceListing.xml of 622 KB, created on Jul. 25, 2022, and submitted to the United States Patent and Trademark Office via Patent Center, is incorporated herein by reference.

FIELD OF THE INVENTION

The present invention relates to antibodies, e.g., full length antibodies and antigen binding fragments thereof, that specifically bind tumor necrosis factor (TNF)-like ligand 1A (TL1A). The invention further relates to compositions comprising antibodies to TL1A, and methods of using the antibodies as a medicament. The TL1A antibodies are useful for treating and preventing diseases and disorders mediated by TL1A.

BACKGROUND OF THE INVENTION

Tumor necrosis factor (TNF)-like ligand 1A (TL1A) is a member of the TNF family of cytokines also known as TNFSF15. TL1A is the only known ligand for its receptor Death Receptor 3 (DR3) also known as TNFRSF25. TL1A expression on antigen presenting cells (monocytes, macrophages, dendritic cells) and DR3 expression on effector cells (T cells, NK and NKT cells) is highly dependent on pro-inflammatory conditions (Migone et al, 2002, Immunity 16(3):479-492; Prehn et al, 2004, Clin. Immunol. 112(1): 66-77; Shih et al, 2009, Eur J Immunol 39(11):3239-3250). In vivo and in vitro evidence support a co-stimulatory role for the TL1A/DR3 pathway on T cells and in enhancing effector cell functions, inflammatory cell expansion and cytokine secretion. Further, this pathway has been implicated in the regulation of pathogenic Th1, Th2, and Th17 T-helper responses, and of NK and NK-T cell responses, in immune-mediated diseases (Papadakis et al, 2004, J Immunol 172(11):7002-7007; Prehn et al, 2004, Clin. Immunol. 112(1):66-77; Papadakis et al, 2005, J Immunol 174(8): 4985-4990; Pappu et al, 2008, J Exp Med 205(5):1049-1062; Takedatsu et al, 2008, Gastroenterology 135(2):552-567).

Studies of DR3 or TL1A gene-deficient mice or mice treated with anti-TL1A antibodies demonstrate a role for this pathway in a number of autoimmune disease models, such as IBD, asthma, multiple sclerosis, and arthritis (see Meylan et al., 2008, Immunity 29(1):79-89.; Pappu et al, 2008; Hsu and Viney, 2011, Mucosal Immun. 4(4):368-370).

Moreover, significant literature from studies involving nonclinical species and humans implicates TL1A most prominently in the pathophysiology of inflammatory bowel disease (IBD), such as, ulcerative colitis (UC) and Crohn's Disease (CD). That is, numerous genome-wide association studies have linked several polymorphisms of the TL1A gene to UC and CD in patient populations of Japanese, European, and Asian origin (Yamazaki et al, 2005. Hum Mol Genet 14(22):3499-3506.; Barrett et al, 2008, Nat Genet 40(8):955-962; Kakuta et al, 2009, Hum Mol Genet 18(6): 1089-1098; Jostins et al, 2012, Nature 491(7422):119-124.; Yamazaki et al, 2013, Gastroenterology 144(4):781-788).

Additionally, human inflamed IBD tissues show high levels of TL1A and DR3 expression and several independent laboratories have demonstrated that antibody blockade of TL1A prevents or attenuates established gut inflammation in a number of murine IBD models (Bamias et al, 2003, J Immunol 171(9):4868-4874; Prehn et al, 2004; Bamias et al, 2006, Proc Natl Acad Sci USA 103(22):8441-8446.; Takedatsu et al, 2008, Gastroenterology 135(2):552-567; Shih et al, 2009; Kamada et al, 2010, Inflamm Bowel Dis 16(4): 568-575; Meylan et al, 2011, Immunol Rev 244(1):188-196; Taraban et al, 2011, Mucosal Immunol 4(2):186-196; Bamias et al, 2012, Dig Liver Dis. 44(1):30-36).

Although the exact cause of IBD, e.g., CD and UC, remains unclear, inhibition of pro-inflammatory cytokines and adhesion molecules have been shown to provide some therapeutic benefit. However, despite current medical therapy, most CD patients may ultimately require surgery, and, over time, repeated resections can result in short gut syndrome, ultimately committing the patient to life-long parenteral nutrition and its associated complications. Thus, there is a long-felt unmet need for more robust therapies for CD patients. Further, there is a long-felt unment need for novel therapeutics to treat or ameliorate IBD, including UC and CD, as well as to treat other TL1A-mediated diseases and conditions. The present invention meets these needs.

SUMMARY OF THE INVENTION

Disclosed are isolated antibodies, or antigen-binding fragments thereof, that specifically bind tumor necrosis factor-like ligand 1A (TL1A), as well as associated reagents, compositions and methods.

E1. According to a first aspect of the invention, there is provided, an isolated antibody or antigen-binding fragment thereof, that specifically binds tumor necrosis factor-like ligand 1A (TL1A).

Described below are a number of embodiments (E) of this first aspect of the invention where, for convenience E1 is identical thereto.

E2. The antibody or antigen-binding fragment thereof according to E1, wherein the antibody or antigen-binding fragment thereof binds human TL1A with an affinity of about 4 nM or less.

E3. The antibody or antigen-binding fragment thereof according to any one of E1-E2, wherein the antibody or antigen-binding fragment thereof binds human TL1A with an affinity of about 1 nM or less.

E4. The antibody or antigen-binding fragment thereof according to any one of E1-E3, wherein the antibody or antigen-binding fragment thereof binds human TL1A with an affinity of about 500 pM or less.

E5. The antibody or antigen-binding fragment thereof according to any one of E1-E4, wherein the antibody or antigen-binding fragment thereof binds human TL1A with an affinity of about 250 pM or less.

E6. The antibody or antigen-binding fragment thereof according to any one of E1-E5, wherein the antibody or antigen-binding fragment thereof binds human TL1A with an affinity of about 100 pM or less.

E7. The antibody or antigen-binding fragment thereof according to any one of E1-E6, wherein the antibody or antigen-binding fragment thereof binds human TL1A with an affinity of about 50 pM or less.

E8. The antibody or antigen-binding fragment thereof according to any one of E1-E7, wherein the antibody or antigen-binding fragment thereof binds human TL1A with an affinity of about 25 pM or less.

E9. The antibody or antigen-binding fragment thereof according to any one of E1-E8, wherein the antibody or antigen-binding fragment thereof binds human TL1A with an affinity of about 10 pM or less.

E10. The antibody or antigen-binding fragment thereof according to any one of E1-E9, wherein the antibody or antigen-binding fragment thereof binds human TL1A with an affinity of about 5 pM or less.

E11. The antibody or antigen-binding fragment thereof according to any one of E1-E9, wherein the antibody or antigen-binding fragment thereof binds human TL1A with an affinity of about 2 pM or less.

E12. The antibody or antigen-binding fragment thereof according to any one of E1-E11, wherein the antibody or antibody binding-fragment thereof has lower affinity for a human homolog of TL1A than it does for human TL1A, and said human homolog of TL1A is TNFSF6.

E13. The antibody or antigen-binding fragment thereof according to any one of E1-E12, wherein the antibody or antibody binding-fragment thereof has lower affinity for a human homolog of TL1A than it does for human TL1A, and said human homolog of TL1A is TNFSF10.

E14. The antibody or antigen-binding fragment thereof according to any one of E1-E13, wherein the antibody or antibody binding-fragment thereof has lower affinity for a human homolog of TL1A than it does for human TL1A, and said human homolog of TL1A is TNFSF14.

E15. The antibody or antigen-binding fragment thereof according to any one of E1-E14, wherein the antibody or antibody binding-fragment thereof has lower affinity for a human homolog of TL1A than it does for human TL1A, and said human homolog of TL1A is TNF-β.

E16. The antibody or antigen-binding fragment thereof according to any one of E1-E15, wherein the antibody or antibody binding-fragment thereof has lower affinity for a human homolog of TL1A than it does for human TL1A, and said human homolog of TL1A is TNF-α.

E17. The antibody or antigen-binding fragment thereof according to any one of E1-E16, wherein the antibody or antibody binding-fragment thereof has lower affinity for a human homolog of TL1A than it does for human TL1A, and said human homolog of TL1A is Lymphotoxin α2-β1.

E18. The antibody or antigen-binding fragment thereof according to any one of E1-E19, wherein the antibody or antibody binding-fragment thereof has lower affinity for a human homolog of TL1A than it does for human TL1A, and said human homolog of TL1A is Lymphotoxin α1-β2.

E19. The antibody or antigen-binding fragment thereof according to any one of E1-E20, wherein the antibody or antigen-binding fragment thereof has lower affinity for a human homolog of TL1A than it does for human TL1A, and said human homolog of TL1A is selected from the group consisting of: TNFSF6, TNFSF10, TNFSF14, TNF-β, TNF-α, Lymphotoxin α2-β1, and Lymphotoxin α1-β2.

E20. The antibody or antigen-binding fragment thereof according to any one of E12-E19, wherein the antibody or antigen-binding fragment thereof has an affinity for the human homolog of TL1A of a value selected from the group consisting of about 1 μM or greater, about 3 μM or greater, about 10 μM or greater, about 30 μM or greater, and about 100 μM or greater.

E21. The antibody or antigen-binding fragment thereof according to any one of E12-E20, wherein the antibody or antigen-binding fragment thereof has an affinity for the human homolog of TL1A of about 1 μM or greater.

E22. The antibody or antigen-binding fragment thereof according to any one of E12-E20, wherein the antibody or antigen-binding fragment thereof has an affinity for the human homolog of TL1A of about 3 μM or greater.

E23. The antibody or antigen-binding fragment thereof according to any one of E12-E22, wherein the antibody or antigen-binding fragment thereof has an affinity for the human homolog of TL1A of about 10 μM or greater.

E24. The antibody or antigen-binding fragment thereof according to any one of E12-E23, wherein the antibody or antigen-binding fragment thereof has an affinity for the human homolog of TL1A of about 100 μM or greater.

E25. The antibody or antigen-binding fragment thereof according to any one of E12-E24, wherein the antibody or antigen-binding fragment thereof has an affinity for the human homolog of TL1A of about 1 mM or greater.

E26. The antibody or antigen-binding fragment thereof according to any one of E12-E25, wherein the antibody or antigen-binding fragment thereof has an affinity for the human homolog of TL1A of about 1 μM or greater.

E27. The antibody or antigen-binding fragment thereof according to any one of E1-E26, wherein, the antibody or antigen-binding fragment thereof has an affinity for murine TL1A of about 10 nM or less.

E28. The antibody or antigen-binding fragment thereof according to any one of E1-E27, wherein, the antibody or antigen-binding fragment thereof has an affinity for murine TL1A of about 3 nM or less.

E29. The antibody or antigen-binding fragment thereof according to any one of E1-E28, wherein, the antibody or antigen-binding fragment thereof has an affinity for murine TL1A of about 1 nM or less.

E30. The antibody or antigen-binding fragment thereof according to any one of E1-E29, wherein, the antibody or antigen-binding fragment thereof has an affinity for murine TL1A of about 300 pM or less.

E31. The antibody or antigen-binding fragment thereof according to any one of E1-E30, wherein, the antibody or antigen-binding fragment thereof has an affinity for murine TL1A of about 100 pM or less.

E32. The antibody or antigen-binding fragment thereof according to any one of E1-E31, wherein the antibody or antigen-binding fragment thereof has an affinity for the human TL1A of about 100 pM or less, an affinity for the murine TL1A of about 300 pM or less, and an affinity for human TNF-α of about 1 μM or greater.

E33. The antibody or antigen-binding fragment thereof according to any one of E1-E32, wherein the affinity for human TL1A of the antibody or antigen-binding fragment thereof is measured by surface plasmon resonance (SPR).

E34. The antibody or antigen-binding fragment thereof according to any one of E1-E33, wherein the affinity is the KD value as measured by SPR.

E35. The antibody or antigen-binding fragment thereof according to any one of E1-E34, wherein the SPR uses a captured antibody, and solution phase target.

E36. The antibody or antigen-binding fragment thereof according to E35, wherein the captured antibody is immobilized onto a sensor chip using an anti-isotype antibody or antigen binding portion thereof.

E37. The antibody or antigen-binding fragment thereof according to E36, wherein the anti-isotype antibody or antigen binding portion thereof is immobilized onto the sensor chip to a density of between about 4,000 and about 13,000 response units.

E38. The antibody or antigen-binding fragment thereof according to any one of E33-E37, wherein the SPR measurement is substantially conducted according to the protocol set out in Example 8.

E39. The antibody or antigen-binding fragment thereof according to E33 or E34, wherein the SPR uses a captured target, and solution phase antibody.

E40. The antibody or antigen-binding fragment thereof according to any one of E33-E39, wherein the SPR measurement is conducted using a Biacore T100 or T200 instrument.

E41. The antibody or antigen-binding fragment thereof according to any one of E1-E32, wherein the affinity for human TL1A of the antibody or antigen-binding fragment thereof is measured by solution-based kinetic exclusion assay (KinExA)

E42. The antibody or antigen-binding fragment thereof according to E41, wherein the affinity is the KD value as measured by solution-based kinetic exclusion assay (KinExA).

E43. The antibody or antigen-binding fragment thereof according to any one of E41-E42, wherein the KinExA uses a captured target on a solid phase, and a solution phase antibody.

E44. The antibody or antigen-binding fragment thereof according to E43, wherein the antibody and target are pre-incubated in solution long enough to reach equilibrium.

E45. The antibody or antigen-binding fragment thereof according to E44, wherein the level of unbound antibody is measured after the antibody and target have reached equilibrium.

E46. The antibody or antigen-binding fragment thereof according to any one of E41-E45, wherein the KinExA measurement is conducted using a KinExA 3200 instrument (Sapidyne).

E47. The antibody or antigen-binding fragment thereof according to any one of E1-E46, wherein the antibody or antigen-binding fragment thereof is a humanized antibody.

E48. The antibody or antigen-binding fragment thereof according to any one of E1-E46, wherein the antibody or antigen-binding fragment thereof is a chimeric antibody.

E49. The antibody or antigen-binding fragment thereof according to any one of E1-E48, wherein the antibody or antigen-binding fragment thereof comprising an Fc domain having diminished effector function.

E50. The antibody or antigen-binding fragment thereof according to any one of E1-E49, wherein the antibody or antigen-binding fragment comprises a constant region which has reduced or abolished effector functions.

E51. The antibody or antigen-binding fragment thereof according to E50, wherein the antibody or antigen-binding fragment does not bind a Fcγ receptor.

E52. The antibody or antigen-binding fragment thereof according to E50-E51, wherein the antibody or antigen binding portion thereof comprises an effector domain that comprises an amino acid sequence at least about 90% homologous to the CH2 sequence from human IgG.

E53. The antibody or antigen-binding fragment thereof according to E52, wherein the IgG is selectedfrom the group consisting of IgG1, IgG2, and IgG4.

E54. The antibody or antigen-binding fragment thereof according to any one of E1-E53, wherein the antibody or antibody binding portion thereof comprises a human IgG1 CH2 domain, wherein the CH2 domain comprises one or more deletions at positions selected from the group consisting of 234, 235, and 237 (numbered with respect to the EU numbering system), or at positions 241, 242 and 244 of SEQ ID NO:228.

E55. The antibody or antigen-binding fragment thereof according to any one of E1-E54, wherein the antibody or antibody binding portion thereof comprises a human IgG1 CH2 domain, wherein the CH2 domain comprises one or more substitutions at positions corresponding to the positions selected from the group consisting of: 234, 235, and 237 (numbered with respect to the EU numbering system (see Kabat et al "Sequences of proteins of immunological interest". Bethesda, US Department of Health and Human Services, NIH, 1991), or at positions 241, 242 and 244 of SEQ ID NO:228.

E56. The antibody or antigen-binding fragment thereof according to E55, wherein the substitutions may comprise any amino acid selected from the group consisting of serine, alanine, and proline.

E57. The antibody or antigen-binding fragment thereof according to any one of E1-E56, wherein the antibody or antibody binding portion thereof comprises at least one of the residues selected from the group consisting of L241A, L242A, and G244A, according to the numbering of SEQ ID NO:228.

E58. The antibody or antigen-binding fragment thereof according to any one of E1-E57, wherein the antibody or antibody binding portion thereof comprises each of the following residues L241A, L242A, and G244A, according to the numbering of SEQ ID NO: 228.

E59. The antibody or antigen-binding fragment thereof according to any one of E1-E58, wherein the antibody or antibody binding portion thereof comprises the amino acid sequence of SEQ ID NO:257.

E60. The antibody or antigen-binding fragment thereof according to any one of E1-E59, wherein the antibody or antibody binding portion thereof has a solubility of at least about 10 mg/ml.

E61. The antibody or antigen-binding fragment thereof according to any one of E1-E60, wherein the antibody or antibody binding portion thereof has a solubility in aqueous solution selected from the group consisting of at least about about 20 mg/ml, at least about 30 mg/ml, at least about 40 mg/ml, at least about 50 mg/ml, at least about 60 mg/ml, at least about 70 mg/ml, at least about 80 mg/ml, at least about 90 mg/ml, at least about 100 mg/ml, at least about 125 mg/ml, at least about 150 mg/ml, at least about 175 mg/ml, and at least about 200 mg/ml.

E62. The antibody or antigen-binding fragment thereof according to E61, wherein the aqueous solution has a pH between about pH 5.0 and about pH 8.0, E63. The antibody or antigen-binding fragment thereof according to E61-E62, wherein the aqueous solution has a pH between about pH 6.0 and about pH 7.0.

E64. The antibody or antigen-binding fragment thereof according to E61-E63, wherein the aqueous solution comprises an ionic strength that is about equivalent to saline buffer, for example, PBS.

E65. The antibody or antigen-binding fragment thereof according to E1-E64, whereinthe antibody or antigen-binding fragment has a thermal stability with a melting temperature (Tm) of about 60° C. or greater, as measured by Differential Scanning Calorimetry.

E66. The antibody or antigen-binding fragment thereof according to E1-E65, whereinthe antibody or antigen-binding fragment has a thermal stability with a melting temperature (Tm) selected from the group consisting of about 60° C. or greater, about65° C. or greater, about 70° C. or greater, and about 75° C. or greater, as measured by Differential Scanning Calorimetry.

E67. The antibody or antigen-binding fragment thereof according to E1-E66, whereinthe antibody or antigen-binding fragment has a T1%, or the temperature at which the protein was 1% unfolded, of at least about 37° C.

E68. The antibody or antigen-binding fragment thereof according to E1-E67, whereinthe antibody or antigen-binding fragment has a T1%, or the temperature at which the protein was 1% unfolded selected from the group consisting of at least about 37° C., at least about 40° C., at least about 45° C., at least about 50° C., or at least about 55° C.

E69. The antibody or antigen-binding fragment thereof according to any one of E1-E68, wherein the antibody or antigen-binding fragment thereof competes for binding to TLA1 with or binds the same TL1A epitope as the antibody selected from the group consisting of 1D1 1.31, 26B11, 9B3, 7D4, 22F9, 15A9, and 15C11, as defined herein.

E70. The antibody or antigen-binding fragment thereof according to any one of E1-E69, wherein the antibody or antigen-binding fragment thereof comprises a heavy chain variable region (VH) comprising:
- a. a VH complementarity determining region one (CDR-H1) comprising the amino acid sequence of SEQ ID NO:374;
- b. a VH complementarity determining region two (CDR-H2) comprising the amino acid sequence of SEQ ID NO: 377; and
- c. a VH complementarity determining region three (CDR-H3) comprising the amino acid sequence of SEQ ID NO: 380.

E71. The antibody or antigen-binding fragment thereof according to any one of E1-E70, wherein the antibody or antigen-binding fragment thereof comprises a heavy chain variable region (VH) comprising:
- a. a VH complementarity determining region one (CDR-H1) comprising the amino acid sequence of SEQ ID NO: 375.
- b. a VH complementarity determining region two (CDR-H2) comprising the amino acid sequence of SEQ ID NO: 378; and
- c. a VH complementarity determining region three (CDR-H3) comprising the amino acid sequence of SEQ ID NO: 381.

E72. The antibody or antigen-binding fragment thereof according to any one of E1-E71, wherein the antibody or antigen-binding fragment thereof comprises a heavy chain variable region (VH) comprising:
- a. a VH complementarity determining region one (CDR-H1) comprising the amino acid sequence of SEQ ID NO: 376.
- b. a a VH complementarity determining region two (CDR-H2) comprising the amino acid sequence of SEQ ID NO: 379; and
- c. a VH complementarity determining region three (CDR-H3) comprising the amino acid sequence of SEQ ID NO: 382.

E73. The antibody or antigen-binding fragment thereof according to any one of E1-E72, wherein the antibody or antigen-binding fragment thereof comprises a light chain variable region (VL) comprising an amino acid sequence at least 90% identical to the amino acid sequence selected from the group consisting of SEQ ID NOs: 102, 1, 22, 36, 50, 64, 88.

E74. The antibody or antigen-binding fragment thereof according to any one of E1-E73, wherein the antibody or antigen-binding fragment thereof comprises a light chain variable region (VL) comprising an amino acid sequence at least 90% identical to the amino acid sequence of SEQ ID NO: 102.

E75. The antibody or antigen-binding fragment thereof according to any one of E1-E74, wherein the antibody or antigen-binding fragment thereof comprises a light chain variable region (VL) comprising an amino acid sequence selected from the group consisting of SEQ ID NOs: 102, 1, 22, 36, 50, 64, 88.

E76. The antibody or antigen-binding fragment thereof according to any one of E1-E75, wherein the antibody or antigen-binding fragment thereof comprises a light chain variable region (VL) comprising the amino acid sequence of SEQ ID NO: 102.

E77. The antibody or antigen-binding fragment thereof according to any one of E1-E76, comprising a heavy chain variable region (VH) comprising an amino acid sequence selected from the group consisting of SEQ ID NOs: 226, 3, 5, 24, 38, 52, 66, 68, 70, 90, 104, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 205, 212, 219, 233, 240, and 247.

E78. The antibody or antigen-binding fragment thereof according to any one of E1-E77, comprising a heavy chain variable region (VH) comprising the amino acid sequence of SEQ ID NO: 226.

E79. The antibody or antigen-binding fragment thereof according to any one of E1-E78, wherein the antibody or antigen-binding fragment thereof comprises a VL comprising a CDR-L1 having the amino acid sequence of SEQ ID NO:110, a CDR-L2 having the amino acid sequence of SEQ ID NO:111, and a CDR-L3 having the amino acid sequence of SEQ ID NO:112.

E80. The antibody or antigen-binding fragment thereof according to any one of E1-E79, wherein the antibody or antigen-binding fragment thereof comprises a light chain variable region (VL) comprising the amino acid sequence of SEQ ID NO:102.

E81. The antibody or antigen-binding fragment thereof according to any one of E1-E80, wherein the antibody or antigen-binding fragment thereof comprises a VL encoded by the nucleic acid sequence of SEQ ID NO:103.

E82. The antibody or antigen-binding fragment thereof according to any one of E1-E81, wherein the antibody or antigen-binding fragment thereof comprises a light chain variable region (VL) comprising an amino acid sequence at least about 90% identical to an amino acid sequence selected from the group consisting of SEQ ID NOs:1, 50, 88, and 64.

E83. The antibody or antigen-binding fragment thereof according to any one of E1-E82, wherein the antibody or antigen-binding fragment thereof comprises a VL comprising a CDR-L1 having the amino acid sequence of SEQ ID NO:13, a CDR-L2 having the amino acid sequence of SEQ ID NO:14, and a CDR-L3 having the amino acid sequence of SEQ ID NO:15.

E84. The antibody or antigen-binding fragment thereof according to any one of E1-E83, wherein the antibody or antigen-binding fragment thereof comprises a light chain variable region (VL) comprising the amino acid sequence of SEQ ID NO:1.

E85. The antibody or antigen-binding fragment thereof according to any one of E1-E84, wherein the antibody or antigen-binding fragment thereof comprises a VL encoded by the nucleic acid sequence of SEQ ID NO:2.

E86. The antibody or antigen-binding fragment thereof according to any one of E1-E85, wherein the antibody or antigen-binding fragment thereof comprises a VL comprising a CDR-L1 having the amino acid sequence of SEQ ID NO:58, a CDR-L2 having the amino acid sequence of SEQ ID NO:59, and a CDR-L3 having the amino acid sequence of SEQ ID NO:60.

E87. The antibody or antigen-binding fragment thereof according to E86, wherein the antibody or antigen-binding fragment comprises a light chain variable region (VL) comprising the amino acid sequence of SEQ ID NO:50.

E88. The antibody or antigen-binding fragment thereof according to any one of E86-E87, wherein the antibody or antigen-binding fragment comprises a VL encoded by the nucleic acid sequence of SEQ ID NO:51.

E89. The antibody or antigen-binding fragment thereof according to any one of E1-E85, wherein the antibody or antigen-binding fragment thereof comprises a VL comprising a CDR-L1 having the amino acid sequence of SEQ ID NO:76, a CDR-L2 having the amino acid sequence of SEQ ID NO:77, and a CDR-L3 having the amino acid sequence of SEQ ID NO:78.

E90. The antibody or antigen-binding fragment thereof according to E89, wherein the antibody or antigen-binding fragment comprises a light chain variable region (VL) comprising the amino acid sequence of SEQ ID NO:64.

E91. The antibody or antigen-binding fragment thereof according to any one of E89-E90, wherein the antibody or antigen-binding fragment comprises a VL encoded by the nucleic acid sequence of SEQ ID NO:89.

E92. The antibody or antigen-binding fragment thereof according to any one of E1-E91, wherein the antibody or antigen-binding fragment thereof comprises a T or R at position 76, as determined by Kabat numbering of the VH.

E93. The antibody or antigen-binding fragment thereof according to any one of E1-E92, wherein the antibody or antigen-binding fragment thereof comprises a D or E at position 81, as determined by Kabat numbering of the VH.

E94. The antibody or antigen-binding fragment thereof according to any one of E1-E93, wherein the antibody or antigen-binding fragment thereof comprises:

a. a VH comprising:
   i. a CDR-H1 comprising the amino acid sequence of SEQ ID NO:202;
   ii. a CDR-H2 comprising an amino acid sequence selected from SEQ ID NO: 203, 210, 217, 224, 231, 238, 245, or 252;
   iii. a CDR-H3 comprising an amino acid sequence selected from SEQ ID NO: 232, 204, 211, 218, 225, 239, 246, or 253; and b. a VL comprising a CDR-L1 having the amino acid sequence of SEQ ID NO:110, a CDR-L2 having the amino acid sequence of SEQ ID NO:111, and a CDR-L3 having the amino acid sequence of SEQ ID NO:112.

E95. The antibody or antigen-binding fragment thereof according to any one of E1-E94, wherein the antibody or antigen-binding fragment thereof comprises a VH comprising the CDR-H1 amino acid sequence of SEQ ID NO:230, the CDR-H2 amino acid sequence of SEQ NO:231, the CDR-H3 amino acid sequence of SEQ ID NO:232, and a VL comprising the CDR-L1 amino acid sequence of SEQ ID NO:110, the CDR-L2 amino acid sequence of SEQ ID NO:111, and the CDR-L3 amino acid sequence of SEQ ID NO:112.

E96. The antibody or antigen-binding fragment thereof according to any one of E1-E95, wherein the antibody or antigen-binding fragment thereof comprises a VH comprising the CDR-H1, CDR-H2, and CDR-H3 of the VH amino acid sequence of SEQ ID NO:226, and a VL comprising the CDR-L1, CDR-L2, and CDR-L3 of the VL amino acid sequence of SEQ ID NO:102;

E97. The antibody or antigen-binding fragment thereof according to any one of E1-E96, wherein the antibody or antigen-binding fragment thereof comprises a VH comprising the amino acid sequence of SEQ ID NO:226 and a VL comprising the amino acid sequence of SEQ ID NO:102;

E.98. The antibody or antigen-binding fragment thereof according to any one of E1-E97, wherein the antibody or antigen-binding fragment thereof comprises a heavy chain comprising the amino acid sequence of SEQ ID NO:228 and a light chain (LC) comprising the amino acid sequence of SEQ ID NO:106;

E99. The antibody or antigen-binding fragment thereof according to any one of E1-E98, wherein the antibody or antigen-binding fragment thereof comprises a VH comprising the CDR-H1, CDR-H2, and CDR-H3 of a VH encoded by the nucleic acid sequence of SEQ ID NO:227, and a VL comprising the CDR-L1, CDR-L2, and CDR-L3 of a VL encoded by the nucleic acid sequence of SEQ ID NO:103;

E100. The antibody or antigen-binding fragment thereof according to any one of E1-E99, comprising a VH encoded by a nucleic acid encoding the amino acid sequence of SEQ ID NO:226 and a VL encoded by a nucleic acid encoding the amino acid sequence of SEQ ID NO:102; or the antibody or antigen-binding fragment thereof according to any one of E1-E99, wherein the antibody or antigen-binding fragment thereof comprises a VH encoded by the nucleic acid sequence of SEQ ID NO:227, and a VL encoded by the nucleic acid sequence of SEQ ID NO:103; and E101. The antibody or antigen-binding fragment thereof according to any one of E1-E100, wherein the antibody or antigen-binding fragment thereof comprises a heavy chain encoded by the nucleic acid sequence of SEQ ID NO:229, and a light chain encoded by the nucleic acid sequence of SEQ ID NO:107.

E102. The antibody or antigen-binding fragment thereof according to any one of E1-E101, wherein the antibody or antigen-binding fragment thereof comprises a VH encoded by the nucleic acid sequence of the insert of the vector deposited as 1 D1 1.31 VH having ATCC accession number PTA-120639.

E103. The antibody or antigen-binding fragment thereof according to any one of E1-E102, wherein the antibody or antigen-binding fragment thereof comprises a VL encoded by the nucleic acid sequence of the insert of the vector deposited as 1 D1 1.31 VL having ATCC accession number PTA-120640.

E104. The antibody or antigen-binding fragment thereof according to any one of E1-E102, wherein the antibody or antigen-binding fragment thereof comprises a VH encoded by the nucleic acid sequence of the insert of the vector deposited as 1 D1 1.31 VH having ATCC accession number PTA-120639 and a VL encoded by the nucleic acid sequence of the insert of the vector deposited as 1 D1 1.31 VL having ATCC accession number PTA-120640.

E105. An isolated antibody or antigen-binding fragment thereof that binds tumor necrosis factor-like ligand 1A (TL1A), wherein the antibody binds to an epitope on TL1A, the epitope comprising at least one amino acid selected from the group consisting of T30, V31, V32, R33, Q34, T35, P36, T37, Q38, H39, F40, K41, N42, Q43, F44, P45, E50, H51, E52, L53, G54, L55, A56, F57, T58, R86, G87, M88, T89, E91, G99, R100, P101, N102, K103, P104, D105, S106, S136, N137, F139, S161, D162, I163, S164, L165, V166, D167, Y168, T169, K170, E171, D172, N42, F44, K103, P104, D105, S106, K113, T115, S117, Y118, P119, E120, P121, T122, Q123, M147, F148, S149, and Q151, according to the numbering of the amino acid sequence of TL1A as set forth in SEQ ID NO:254.

E106. The antibody or antigen-binding fragment thereof of E1-E105, wherein the antibody binds to a homomultimer of TL1A, the homomultimer comprising at least a first and a second TL1A monomer, wherein the antibody binds to a first epitope on the first TL1A monomer, wherein the first epitope comprises at least one amino acid selected from the group consisting of N42, F44, K103, P104, D105, S106, K113, T115, S117, Y118, P119, E120, P121, T122, Q123, M147, F148, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of T30, V31, V32, R33, Q34, T35, P36, T37, Q38, H39, F40, K41, N42, Q43, F44, P45, E50, H51, E52, L53, G54, L55, A56, F57, T58, R86, G87, M88, T89, E91, G99, R100, P101, N102, K103, P104, D105, S106, S136, N137, F139, S161, D162, I163, S164, L165, V166, D167, Y168, T169, K170, E171, and D172, according to the numbering of the amino acid sequence of TL1A as set forth in SEQ ID NO:254.

E107. The antibody or antigen-binding fragment thereof of E1-E106, wherein the antibody binds to an epitope on TL1A comprising at least one amino acid selected from the group consisting of V31, V32, R33, T35, P36, T37, Q38, H39, F40, Q43, E50, H51, E52, L53, G54, L55, A56, F57, R86, G87, M88, S136, N137, S164, L165, Y168, T169, K170, E171, K113, S117, Y118, P119, T122, Q123, M147, F148, S149, and Q151, according to the numbering of the amino acid sequence of TL1A as set forth in SEQ ID NO:254.

E108. The antibody or antigen-binding fragment thereof of E1-E107, wherein the antibody binds to a homomultimer of TL1A, and wherein the homomultimer comprising at least a first and second TL1A monomer, wherein the antibody binds to a first epitope on the first TL1A monomer, wherein the first epitope comprises at least one amino acid selected from the group consisting of K113, S117, Y118, P119, T122, Q123, M147, F148, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, T35, P36, T37, Q38, H39, F40, Q43, E50, H51, E52, L53, G54, L55, A56, F57, R86, G87, M88, S136, N137, S164, L165, Y168, T169, K170, and E171, according to the numbering of the amino acid sequence of TL1A as set forth in SEQ ID NO:254.

E109. The antibody or antigen-binding fragment thereof of E1-E110, wherein the antibody binds to an epitope on TL1A comprising at least one amino acid selected from the group consisting of V31, V32, R33, E50, L53, G54, S164, Y168, T169, K170, E171, Y118, and Q151, according to the numbering of the amino acid sequence of TL1A as set forth in SEQ ID NO:254.

E110. The antibody or antigen-binding fragment thereof of E1-E109, wherein the antibody binds to a homomultimer of TL1A, wherein the homomultimer comprising at least a first and second TL1A monomer, wherein the antibody binds to a first epitope on the first TL1A monomer, wherein the first epitope comprises at least one amino acid selected from the group consisting of Y118 and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, E50, L53, G54, S164, Y168, T169, K170, and E171, according to the numbering of the amino acid sequence of TL1A as set forth in SEQ ID NO:254.

E111. The antibody or antigen-binding fragment thereof of E1-E110, wherein the antibody binds to an epitope on TL1A comprising at least one TL1A amino acid selected from the group consisting of R33, Y168, and T169, according to the numbering of the amino acid sequence of TL1A as set forth in SEQ ID NO:254.

E112. The antibody or antigen-binding fragment thereof of E1-E111, In another embodiment, the antibody or antigen-binding fragment specifically binds TL1A wherein the antibody binds to an epitope on TL1A comprising at least one amino acid selected from the group consisting of V31, V32, R33, E50, H51, E52, L53, G54, L55, A56, F57, Y168, T169, K170, E171, K113, Y118, T122, Q123, M147, F148, S149, and Q151, according to the numbering of the amino acid sequence of TL1A as set forth in SEQ ID NO:254.

E113. The antibody or antigen-binding fragment thereof of E1-E112, wherein the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, T122, Q123, M147, F148, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, E50, H51, E52, L53, G54, L55, A56, F57, Y168, T169, K170, E171, according to the numbering of the amino acid sequence of TL1A as set forth in SEQ ID NO:254.

E114. The antibody or antigen-binding fragment thereof of E1-E113, wherein the antibody binding to TL1A causes a non-zero change in buried surface area due to interaction of the antibody with a TL1A amino acid selected from the group consisting of R33, Q34, T35, P36, T37, Q38, H39, F40, K41, N42, P45, E50, L53, G54, L55, F57, T58, R86, M88, T89, P101, N102, K103, P104, D105, S136, N137, D162, I163, S164, Y168, T169, K170, E171, N42, K103, P104, D105, K113, S117, Y118, T122, S149, and Q151, according to the numbering of the amino acid sequence of TL1A as set forth in SEQ ID NO:254.

E115. The antibody or antigen-binding fragment thereof of E1-E114, wherein the antibody or antigen-binding fragment thereof binds to a homomultimer of TL1A comprising at least a first and second TL1A monomer, wherein the antibody binding to the first epitope on the first TL1A monomer causes a non-zero change in buried surface area due to interaction of the antibody with a TL1A amino acid selected from the group consisting of N42, K103, P104, D105, K113, S117, Y118, T122, S149, and Q151, according to the numbering of the amino acid sequence of TL1A as set forth in SEQ ID NO:254, and the antibody binding to the second epitope on the second TL1A monomer causes a non-zero change in buried surface area due to interaction of the antibody with a TL1A amino acid selected from the group consisting of R33, Q34, T35, P36, T37, Q38, H39, F40, K41, N42, P45, E50, L53, G54, L55, F57, T58, R86, M88, T89, P101, N102, K103, P104, D105, S136, N137, D162, 1163, S164, Y168, T169, K170, and E171, according to the numbering of the amino acid sequence of TL1A as set forth in SEQ ID NO:254.

E116. The antibody or antigen-binding fragment thereof of E1-E115, wherein the antibody binding to TL1A causes a non-zero change in buried surface area due to interaction of the antibody with a TL1A amino acid selected from the group consisting of R33, T35, P36, Q38, H39, F40, K41, N42, L53, G54, L55, R86, M88, P101, N102, K103, D105, N137, S164, Y168, E171, N42, K103, D105, and Y118, according to the numbering of the amino acid sequence of TL1A as set forth in SEQ ID NO:254.

E117. The antibody or antigen-binding fragment thereof of E1-E116, wherein the antibody binds to a homomultimer of TL1A comprising at least a first and second TL1A monomer, wherein the antibody binding to the first epitope on the first TL1A monomer causes a non-zero change in buried surface area due to interaction of the antibody with a TL1A amino acid selected from the group consisting of N42, K103, D105, and Y118, according to the numbering of the amino acid sequence of TL1A as set forth in SEQ ID NO:254, and the antibody binding to the second epitope on the second TL1A monomer causes a non-zero change in buried surface area due to interaction of the antibody with a TL1A amino acid selected from the group consisting of R33, T35, P36, Q38, H39, F40, K41, N42, L53, G54, L55, R86, M88, P101, N102, K103, D105, N137, S164, Y168, and E171, according to the numbering of the amino acid sequence of TL1A as set forth in SEQ ID NO:254.

E118. The antibody or antigen-binding fragment thereof of E1-E117, wherein the antibody binding to TL1A causes a non-zero change in buried surface area due to interaction of the antibody with a TL1A amino acid selected from the group consisting of R33, Q38, F40, K41, L53, R86, M88, and Y118, according to the numbering of the amino acid sequence of TL1A as set forth in SEQ ID NO:254.

E119. The antibody or antigen-binding fragment thereof of E1-E118, wherein the antibody binds to a homomultimer of TL1A comprising at least a first and second TL1A monomer, wherein the antibody binding to the first epitope on the first TL1A monomer causes a non-zero change in buried surface area due to interaction with the antibody at Y118 according to the numbering of the amino acid sequence of TL1A as set forth in SEQ ID NO:254, and the antibody binding to the second epitope on the second TL1A monomer causes a non-zero change in buried surface area due to interaction of the antibody with a TL1A amino acid selected from the group consisting of R33, Q38, F40, K41, L53, R86, and M88, according to the numbering of the amino acid sequence of TL1A as set forth in SEQ ID NO:254.

E120. The antibody or antigen-binding fragment thereof of E1-E119, wherein one or more amino acid residues of the antibody participates in a hydrogen bond with one or more amino acid residues in TL1A selected from the group consisting of A56, D232, E171, E52, H109, K111, K173, N112, N172, N207, P106, P171, Q104, Q108, R156, R33, S149, T122, T169, Y118, Y168, and Y238, according to the numbering of the amino acid sequence of TL1A as set forth in SEQ ID NO:254.

E121. The antibody or antigen-binding fragment thereof of E1-E120, wherein one or more amino acid residues of the antibody participates in a hydrogen bond with one or more amino acid residues in TL1A selected from the group consisting of Q108, H109, K111, N112, P171, N172, and K173, according to the numbering of the amino acid sequence of TL1A as set forth in SEQ ID NO:254.

E122. The antibody or antigen-binding fragment thereof of E1-E121, wherein one or more amino acid residues of the antibody participates in a hydrogen bond with one or more amino acid residues in TL1A selected from the group consisting of Q104, P106, R156, N207, D232, and Y238, according to the numbering of the amino acid sequence of TL1A as set forth in SEQ ID NO:254.

E123. The antibody or antigen-binding fragment thereof of E1-E122, wherein one or more amino acid residues of the antibody participates in a hydrogen bond with one or more amino acid residues in TL1A selected from the group consisting of T122, S149, E52, A56, Y168, T169, and E171, according to the numbering of the amino acid sequence of TL1A as set forth in SEQ ID NO:254.

E124. The antibody or antigen-binding fragment thereof of E1-E123, wherein one or more amino acid residues of the antibody participates in a hydrogen bond with one or more amino acid residues in TL1A selected from the group consisting of Y118, S149, R33, E52, A56, and Y168, according to the numbering of the amino acid sequence of TL1A as set forth in SEQ ID NO:254.

E125. The antibody or antigen-binding fragment thereof of E1-E124, wherein one or more amino acid residues of the antibody participates in a salt bridge with one or more TL1A amino acid residues selected from the group consisting of R33, K41, E50, E52, and K113, according to the numbering of the amino acid sequence of TL1A as set forth in SEQ ID NO:254.

E126. The antibody or antigen-binding fragment thereof of E1-E125, wherein the antibody or antigen-binding fragment described herein binds to TL1A and participates in a water-mediated hydrogen bond with one or more residues of TL1A that is selected from the group consisting of R33, Q38, K41, N42, L55, N102, D105, and M147, according to the numbering of the amino acid sequence of TL1A as set forth in SEQ ID NO:254.

E127. The antibody or antigen-binding fragment thereof of E1-E126, wherein the antibody or antigen-binding fragment described herein binds to TL1A when one or more amino acid residues of the antibody participates in a hydrogen bond with one or more residues in TL1A, participates in a water-mediated hydrogen bond with one or more reisdues of TL1A, participates in a salt bridge with one or more residues in TL1, has a non-zero change in buried surface area due to interaction with TL1A, or when a heavy atom from one or more residues of the antibody is within a distance of 4 Å from a heavy atom in TL1A.

E128. A pharmaceutical composition comprising the antibody, or antigen-binding fragment thereof according to any one of E1-E127, and further comprising a pharmaceutically acceptable carrier or excipient.

E129. A method of preventing, ameliorating or treating a disease, disorder or condition mediated by TL1A, comprising administering to a subject in need thereof an effective amount of the antibody or antigen-binding fragment thereof according to any one of E1-E127, or the pharmaceutical composition according to E128.

E130. The antibody or antigen-binding fragment thereof according to any one of E1-E127, or a pharmaceutical composition according to E128, for use in the prevention, amelioration or treatment of a disease, disorder or condition mediated by TL1A.

E131. Use of an antibody, or antigen-binding fragment thereof according to any one of E1-E127 in the manufacture of a medicament for the prevention, amelioration or treatment of a disease, disorder or condition mediated by TL1A.

E132. The use according to E131, wherein the disease, disorder or condition is selected from the group consisting of: inflammatory bowel disease (IBD), Crohn's disease, ulcerative colitis, asthma, allergies, diabetes mellitus, arthritis, rheumatoid arthritis, juvenile rheumatoid arthritis, osteoarthritis, psoriatic arthritis, ankylosing spondylitis, multiple sclerosis, transplant rejection, graft-versus-host disease (GVHD), spondyloarthropathy, primary sclerosing cholangitis, primary biliary cirrhosis, atherosclerosis, bladder syndrome/intersticial cystitis, Urinary bowel disfunction, sepsis, uveitis, encephalomyelitis, myasthenia gravis, systemic lupus erythematosus, cutaneous lupus erythematosus, autoimmune thyroiditis, atopic dermatitis, eczematous dermatitis, psoriasis, Sjogren's syndrome, scleroderma, and vasculitis.

E133. A method of detecting TL1A in a sample, tissue, or cell, comprising providing the sample, tissue contacting or cell with the antibody or antigen-binding fragment thereof according to E1-E127, and detecting said antibody.

E134. An isolated nucleic acid encoding the antibody, or antigen-binding fragment thereof that specifically binds TL1A according to E1-E127.

E135. The isolated nucleic acid according to E134, wherein the nucleic acid is selected from the group consisting of:

a. the nucleic acid sequence of SEQ ID NO:103;
b. the nucleic acid sequence of SEQ ID NO: 105;
c. the nucleic acid sequence of SEQ ID NO:107;
d. the nucleic acid sequence of SEQ ID NO:109;
e. the nucleic acid sequence of SEQ ID NO:103 and 105;
f. the nucleic acid sequence of SEQ ID NO:107 and 109;
g. the nucleic acid sequence of the insert of the vector deposited as 1D1 1.31 VH having ATCC accession number PTA-120639;
h. the nucleic acid sequence of the insert of the vector deposited as 1D1 1.31 VL having ATCC accession number PTA-120640;
i. the nucleic acid sequence of the insert of the vector deposited as 1D1 1.31 VH having ATCC accession number PTA-120639 and the nucleic acid sequence of the insert of the vector deposited as 1 D1 1.31 VL having ATCC accession number PTA-120640;
j. the nucleic acid sequence of SEQ ID NO:227;
k. the nucleic acid sequence of SEQ ID NO: 229;
l. the nucleic acid sequence of SEQ ID NO:227 and 103;
m. the nucleic acid sequence of SEQ ID NO:229 and 107;
n. the nucleic acid sequence of SEQ ID NO:199;
o. the nucleic acid sequence of SEQ ID NO: 201;
p. the nucleic acid sequence of SEQ ID NO:199 and 103;
q. the nucleic acid sequence of SEQ ID NO:201 and 107;
r. the nucleic acid sequence of SEQ ID NO:206;
s. the nucleic acid sequence of SEQ ID NO: 208;
t. the nucleic acid sequence of SEQ ID NO:206 and 103;
u. the nucleic acid sequence of SEQ ID NO:208 and 107;
v. the nucleic acid sequence of SEQ ID NO:213;
w. the nucleic acid sequence of SEQ ID NO: 215;
x. the nucleic acid sequence of SEQ ID NO:213 and 103;
y. the nucleic acid sequence of SEQ ID NO:215 and 107;
z. the nucleic acid sequence of SEQ ID NO:220;
aa. the nucleic acid sequence of SEQ ID NO: 222;
bb. the nucleic acid sequence of SEQ ID NO:220 and 103;
cc. the nucleic acid sequence of SEQ ID NO:222 and 107;
dd. the nucleic acid sequence of SEQ ID NO:234;
ee. the nucleic acid sequence of SEQ ID NO: 236;
ff. the nucleic acid sequence of SEQ ID NO:234 and 103;
gg. the nucleic acid sequence of SEQ ID NO:236 and 107;
hh. the nucleic acid sequence of SEQ ID NO:241;
ii. the nucleic acid sequence of SEQ ID NO: 243;
jj. the nucleic acid sequence of SEQ ID NO:241 and 103;
kk. the nucleic acid sequence of SEQ ID NO:243 and 107;
ll. the nucleic acid sequence of SEQ ID NO:248;
mm. the nucleic acid sequence of SEQ ID NO: 250;
nn. the nucleic acid sequence of SEQ ID NO:248 and 103;
oo. the nucleic acid sequence of SEQ ID NO:250 and 107;
pp. the nucleic acid sequence of SEQ ID NO:65;
qq. the nucleic acid sequence of SEQ ID NO: 67;
rr. the nucleic acid sequence of SEQ ID NO:69;
ss. the nucleic acid sequence of SEQ ID NO: 71;
tt. the nucleic acid sequence of SEQ ID NO:73;
uu. the nucleic acid sequence of SEQ ID NO:75;
vv. the nucleic acid sequence of SEQ ID NO:67 and 65;
ww. the nucleic acid sequence of SEQ ID NO:69 and 65;
xx. the nucleic acid sequence of SEQ ID NO:71 and 65;
yy. the nucleic acid sequence of SEQ ID NO:73 and 75;
zz. the nucleic acid sequence of SEQ ID NO:2;
aaa. the nucleic acid sequence of SEQ ID NO: 4;
bbb. the nucleic acid sequence of SEQ ID NO:6;
ccc. the nucleic acid sequence of SEQ ID NO:8;
ddd. the nucleic acid sequence of SEQ ID NO:10;
eee. the nucleic acid sequence of SEQ ID NO:12;
fff. the nucleic acid sequence of SEQ ID NO:4 and 2;
ggg. the nucleic acid sequence of SEQ ID NO:6 and 2;
hhh. the nucleic acid sequence of SEQ ID NO:10 and 8;
iii. the nucleic acid sequence of SEQ ID NO:12 and 8;
jjj. the nucleic acid encoding the amino acid sequence of SEQ ID NO:102; and
kkk. the nucleic acid encoding the amino acid sequence of SEQ ID NO: 226.

E136. A vector comprising the nucleic acid according to E134 or E135.

E137. A host cell comprising the vector according to E136.

E138. The host cell according to E137, selected from the group consisting of a bacterial cell, a fungal cell, an insect cell, avian cell, a plant cell or a mammalian cell.

E139. A method of producing an antibody, or antigen-binding fragment thereof, that specifically binds TL1A, comprising culturing the host cell according to E137 or E138 and growing the cells under conditions wherein the antibody is expressed, and further comprising isolating the antibody.

E140. An isolated antibody, or antigen-binding fragment thereof, that specifically binds tumor necrosis factor-like ligand 1A (TL1A) and comprises:

a) a heavy chain variable region (VH) comprising:

i) a VH complementarity determining region one (CDR-H1) comprising the amino acid sequence $GYX_1FX_2X_3YGIS$, wherein $X_1$ is S, D, Q, N or P; $X_2$ is T or R; and $X_3$ is Y or H (SEQ ID NO: 384);

ii) a CDR-H2 comprising the amino acid sequence $WISX_4YNGX_5X_6X_7YAX_8MX_9QG$, wherein $X_4$ is T, P, S, or A; $X_5$ is K, A, G, N, or V; $X_6$ is T or K; $X_7$ is N or H; $X_8$ is R or Q; and $X_9$ is L or H (SEQ ID NO: 385); and iii) a CDR-H3 comprising the amino acid sequence $ENYYGSGX_9X_{10}RGGMDX_{11}$, wherein $X_9$ is S or A; $X_{10}$ is Y or F; and $X_{11}$ is V, G, or A (SEQ ID NO: 382);

b) a VH comprising:

i) a CDR-H1 comprising the amino acid sequence $GYX_1FX_2X_3YGIS$, wherein $X_1$ is S, D, Q, N or P; $X_2$ is T or R; and $X_3$ is Y or H (SEQ ID NO: 384);

ii) a CDR-H2 comprising the amino acid sequence $WISX_4YNGX_5X_6X_7YAX_8MX_9QG$, wherein $X_4$ is T, P, S, or A; $X_5$ is K, A, G, N, or V; $X_6$ is T or K; $X_7$ is N or H; $X_8$ is R or Q; and $X_9$ is L or H (SEQ ID NO: 385);

iii) a CDR-H3 comprising the amino acid sequence $ENYYGSGX_9X_{10}RGGMDX_{11}$, wherein $X_9$ is S or A; $X_{10}$ is Y or F; and $X_{11}$ is V, G, or A (SEQ ID NO: 382); and a light chain variable region (VL) comprising an amino acid sequence at least 90% identical to the amino acid sequence of SEQ ID NO:102;

c) a VH comprising:

a CDR-H1 comprising the amino acid sequence $GYX_1FX_2X_3YGIS$, wherein $X_1$ is S, D, Q, N or P; $X_2$ is T or R; and $X_3$ is Y or H (SEQ ID NO: 384);

ii) a CDR-H2 comprising the amino acid sequence $WISX_4YNGX_5X_6X_7YAX_8MX_9QG$, wherein $X_4$ is T, P, S, or A; $X_5$ is K, A, G, N, or V; $X_6$ is T or K; $X_7$ is N or H; $X_8$ is R or Q; and $X_9$ is L or H (SEQ ID NO: 385);

iii) a CDR-H3 comprising the amino acid sequence $ENYYGSGX_9X_{10}RGGMDX_{11}$, wherein $X_9$ is S or A; $X_{10}$ is Y or F; and $X_{11}$ is V, G, or A (SEQ ID NO: 382);

iv) a T or R at position H76, as determined by Kabat numbering of the VH;

v) a D or E at position H81, as determined by Kabat numbering of the VH; and a VL comprising a CDR-L1 having the amino acid sequence of SEQ ID NO:110, a CDR-L2 having the amino acid sequence of SEQ ID NO:111, and a CDR-L3 having the amino acid sequence of SEQ ID NO:112;

d) a VH comprising:

i) a CDR-H1 comprising the amino acid sequence of SEQ ID NO:202;

ii) a CDR-H2 comprising the acid sequence selected from SEQ ID NO: 203, 210, 217, 224, 231, 238, 245, or 252;

iii) a CDR-H2 comprising the amino acid sequence selected from SEQ ID NO:204, 211, 218, 225, 232, 239, 246, or 253; and a VL comprising a CDR-L1 having the amino acid sequence of SEQ ID NO:110, a CDR-L2 having the amino acid sequence of SEQ ID NO:111, and a CDR-L3 having the amino acid sequence of SEQ ID NO:112;

e) a VH comprising the CDR-H1 amino acid sequence of SEQ ID NO:113, the CDR-H2 amino acid sequence of SEQ NO:114, the CDR-H3 amino acid sequence of SEQ ID NO:115, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

f) a VH comprising the CDR-H1, CDR-H2, and CDR-H3 of the VH amino acid sequence of SEQ ID NO:104, and a VL comprising the CDR-L1, CDR-L2, and CDR-L3 of the VL amino acid sequence of SEQ ID NO:102;

g) a VH comprising the amino acid sequence of SEQ ID NO:104 and a VL comprising the amino acid sequence of SEQ ID NO:102;

h) a heavy chain comprising the amino acid sequence of SEQ ID NO:108 and a light chain (LC) comprising the amino acid sequence of SEQ ID NO:106;

i) a VH comprising the CDR-H1, CDR-H2, and CDR-H3 encoded by the nucleic acid sequence of SEQ ID NO:105, and a VL comprising the CDR-L1, CDR-L2, and CDR-L3 encoded by the nucleic acid sequence of SEQ ID NO:103;

j) a VH encoded by the nucleic acid sequence of SEQ ID NO:105, and a VL encoded by the nucleic acid sequence of SEQ ID NO:103;

k) a heavy chain encoded by the nucleic acid sequence of SEQ ID NO:109, and a light chain encoded by the nucleic acid sequence of SEQ ID NO:107;

l) a VH comprising the CDR-H1 amino acid sequence of SEQ ID NO:230, the CDR-H2 amino acid sequence of SEQ NO:231, the CDR-H3 amino acid sequence of SEQ ID NO:232, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

m) a VH comprising the CDR-H1, CDR-H2, and CDR-H3 of the VH amino acid sequence of SEQ ID NO:226, and a VL comprising the CDR-L1, CDR-L2, and CDR-L3 of the VL amino acid sequence of SEQ ID NO:102;

n) a VH comprising the amino acid sequence of SEQ ID NO:226 and a VL comprising the amino acid sequence of SEQ ID NO:102;

o) a heavy chain comprising the amino acid sequence of SEQ ID NO:228 and a light chain (LC) comprising the amino acid sequence of SEQ ID NO:106;

p) a VH comprising the CDR-H1, CDR-H2, and CDR-H3 encoded by the nucleic acid sequence of SEQ ID NO:227, and a VL comprising the CDR-L1, CDR-L2, and CDR-L3 encoded by the nucleic acid sequence of SEQ ID NO:103;

q) a VH encoded by the nucleic acid sequence of SEQ ID NO:227, and a VL encoded by the nucleic acid sequence of SEQ ID NO:103;

r) a heavy chain encoded by the nucleic acid sequence of SEQ ID NO:229, and a light chain encoded by the nucleic acid sequence of SEQ ID NO:107;

s) a VH comprising the CDR-H1 amino acid sequence of SEQ ID NO:202, the CDR-H2 amino acid sequence of SEQ NO:203, the CDR-H3 amino acid sequence of SEQ ID NO:204, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

t) a VH comprising the CDR-H1, CDR-H2, and CDR-H3 of the VH amino acid sequence of SEQ ID NO:198, and a VL comprising the CDR-L1, CDR-L2, and CDR-L3 of the VL amino acid sequence of SEQ ID NO:102;

u) a VH comprising the amino acid sequence of SEQ ID NO:198 and a VL comprising the amino acid sequence of SEQ ID NO:102;

v) a heavy chain comprising the amino acid sequence of SEQ ID NO:200 and a light chain (LC) comprising the amino acid sequence of SEQ ID NO:106;

w) a VH comprising the CDR-H1, CDR-H2, and CDR-H3 encoded by the nucleic acid sequence of SEQ ID NO:199, and a VL comprising the CDR-L1, CDR-L2, and CDR-L3 encoded by the nucleic acid sequence of SEQ ID NO:103;

x) a VH encoded by the nucleic acid sequence of SEQ ID NO:199, and a VL encoded by the nucleic acid sequence of SEQ ID NO:103;

y) a heavy chain encoded by the nucleic acid sequence of SEQ ID NO:201, and a light chain encoded by the nucleic acid sequence of SEQ ID NO:107;

z) a VH comprising the CDR-H1 amino acid sequence of SEQ ID NO:209, the CDR-H2 amino acid sequence of SEQ NO:210, the CDR-H3 amino acid sequence of SEQ ID NO:211, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

aa) a VH comprising the CDR-H1, CDR-H2, and CDR-H3 of the VH amino acid sequence of SEQ ID NO:205, and a VL comprising the CDR-L1, CDR-L2, and CDR-L3 of the VL amino acid sequence of SEQ ID NO:102;

bb) a VH comprising the amino acid sequence of SEQ ID NO:205 and a VL comprising the amino acid sequence of SEQ ID NO:102;

cc) a heavy chain comprising the amino acid sequence of SEQ ID NO:207 and a light chain (LC) comprising the amino acid sequence of SEQ ID NO:106;

dd) a VH comprising the CDR-H1, CDR-H2, and CDR-H3 encoded by the nucleic acid sequence of SEQ ID NO:206, and a VL comprising the CDR-L1, CDR-L2, and CDR-L3 encoded by the nucleic acid sequence of SEQ ID NO:103;

ee) a VH encoded by the nucleic acid sequence of SEQ ID NO:206, and a VL encoded by the nucleic acid sequence of SEQ ID NO:103;

ff) a heavy chain encoded by the nucleic acid sequence of SEQ ID NO:208, and a light chain encoded by the nucleic acid sequence of SEQ ID NO:107;

gg) a VH comprising the CDR-H1 amino acid sequence of SEQ ID NO:216, the CDR-H2 amino acid sequence of SEQ NO:217, the CDR-H3 amino acid sequence of SEQ ID NO:218, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

hh) a VH comprising the CDR-H1, CDR-H2, and CDR-H3 of the VH amino acid sequence of SEQ ID NO:212, and a VL comprising the CDR-L1, CDR-L2, and CDR-L3 of the VL amino acid sequence of SEQ ID NO:102;

ii) a VH comprising the amino acid sequence of SEQ ID NO:212 and a VL comprising the amino acid sequence of SEQ ID NO:102;

jj) a heavy chain comprising the amino acid sequence of SEQ ID NO:214 and a light chain (LC) comprising the amino acid sequence of SEQ ID NO:106;

kk) a VH comprising the CDR-H1, CDR-H2, and CDR-H3 encoded by the nucleic acid sequence of SEQ ID NO:213, and a VL comprising the CDR-L1, CDR-L2, and CDR-L3 encoded by the nucleic acid sequence of SEQ ID NO:103;

ll) a VH encoded by the nucleic acid sequence of SEQ ID NO:213, and a VL encoded by the nucleic acid sequence of SEQ ID NO:103;

mm) a heavy chain encoded by the nucleic acid sequence of SEQ ID NO:215, and a light chain encoded by the nucleic acid sequence of SEQ ID NO:107;

nn) a VH comprising the CDR-H1 amino acid sequence of SEQ ID NO:223, the CDR-H2 amino acid sequence of SEQ NO:224, the CDR-H3 amino acid sequence of SEQ ID NO:225, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

oo) a VH comprising the CDR-H1, CDR-H2, and CDR-H3 of the VH amino acid sequence of SEQ ID NO:219, and a VL comprising the CDR-L1, CDR-L2, and CDR-L3 of the VL amino acid sequence of SEQ ID NO:102;

pp) a VH comprising the amino acid sequence of SEQ ID NO:219 and a VL comprising the amino acid sequence of SEQ ID NO:102;

qq) a heavy chain comprising the amino acid sequence of SEQ ID NO:221 and a light chain (LC) comprising the amino acid sequence of SEQ ID NO:106;

rr) a VH comprising the CDR-H1, CDR-H2, and CDR-H3 encoded by the nucleic acid sequence of SEQ ID NO:220, and a VL comprising the CDR-L1, CDR-L2, and CDR-L3 encoded by the nucleic acid sequence of SEQ ID NO:103;

ss) a VH encoded by the nucleic acid sequence of SEQ ID NO:220, and a VL encoded by the nucleic acid sequence of SEQ ID NO:103;

tt) a heavy chain encoded by the nucleic acid sequence of SEQ ID NO:222, and a light chain encoded by the nucleic acid sequence of SEQ ID NO:107;

uu) a VH comprising the CDR-H1 amino acid sequence of SEQ ID NO:237, the CDR-H2 amino acid sequence of SEQ NO:238, the CDR-H3 amino acid sequence of SEQ ID NO:239, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

vv) a VH comprising the CDR-H1, CDR-H2, and CDR-H3 of the VH amino acid sequence of SEQ ID NO:233, and a VL comprising the CDR-L1, CDR-L2, and CDR-L3 of the VL amino acid sequence of SEQ ID NO:102;

ww) a VH comprising the amino acid sequence of SEQ ID NO:233 and a VL comprising the amino acid sequence of SEQ ID NO:102;

xx) a heavy chain comprising the amino acid sequence of SEQ ID NO:235 and a light chain (LC) comprising the amino acid sequence of SEQ ID NO:106;

yy) a VH comprising the CDR-H1, CDR-H2, and CDR-H3 encoded by the nucleic acid sequence of SEQ ID NO:234, and a VL comprising the CDR-L1, CDR-L2, and CDR-L3 encoded by the nucleic acid sequence of SEQ ID NO:103;

zz) a VH encoded by the nucleic acid sequence of SEQ ID NO:234, and a VL encoded by the nucleic acid sequence of SEQ ID NO:103;

aaa) a heavy chain encoded by the nucleic acid sequence of SEQ ID NO:236, and a light chain encoded by the nucleic acid sequence of SEQ ID NO:107;

bbb) a VH comprising the CDR-H1 amino acid sequence of SEQ ID NO:244, the CDR-H2 amino acid sequence of SEQ NO:245, the CDR-H3 amino acid sequence of SEQ ID NO:246, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

ccc) a VH comprising the CDR-H1, CDR-H2, and CDR-H3 of the VH amino acid sequence of SEQ ID NO:240, and a VL comprising the CDR-L1, CDR-L2, and CDR-L3 of the VL amino acid sequence of SEQ ID NO:102;

ddd) a VH comprising the amino acid sequence of SEQ ID NO:240 and a VL comprising the amino acid sequence of SEQ ID NO:102;

eee) a heavy chain comprising the amino acid sequence of SEQ ID NO:242 and a light chain (LC) comprising the amino acid sequence of SEQ ID NO:106;

fff) a VH comprising the CDR-H1, CDR-H2, and CDR-H3 encoded by the nucleic acid sequence of SEQ ID NO:241, and a VL comprising the CDR-L1, CDR-L2, and CDR-L3 encoded by the nucleic acid sequence of SEQ ID NO:103;

ggg) a VH encoded by the nucleic acid sequence of SEQ ID NO:241, and a VL encoded by the nucleic acid sequence of SEQ ID NO:103;

hhh) a heavy chain encoded by the nucleic acid sequence of SEQ ID NO:243, and a light chain encoded by the nucleic acid sequence of SEQ ID NO:107;

iii) a VH comprising the CDR-H1 amino acid sequence of SEQ ID NO:251, the CDR-H2 amino acid sequence of SEQ NO:252, the CDR-H3 amino acid sequence of SEQ ID NO:253, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

jjj) a VH comprising the CDR-H1, CDR-H2, and CDR-H3 of the VH amino acid sequence of SEQ ID NO:247, and a VL comprising the CDR-L1, CDR-L2, and CDR-L3 of the VL amino acid sequence of SEQ ID NO:102;

kkk) a VH comprising the amino acid sequence of SEQ ID NO:247 and a VL comprising the amino acid sequence of SEQ ID NO:102;

lll) a heavy chain comprising the amino acid sequence of SEQ ID NO:249 and a light chain (LC) comprising the amino acid sequence of SEQ ID NO:106;

mmm) a VH comprising the CDR-H1, CDR-H2, and CDR-H3 encoded by the nucleic acid sequence of SEQ ID NO:248, and a VL comprising the CDR-L1, CDR-L2, and CDR-L3 encoded by the nucleic acid sequence of SEQ ID NO:103;

nnn) a VH encoded by the nucleic acid sequence of SEQ ID NO:248, and a VL encoded by the nucleic acid sequence of SEQ ID NO:103;

ooo) a heavy chain encoded by the nucleic acid sequence of SEQ ID NO:250, and a light chain encoded by the nucleic acid sequence of SEQ ID NO:107;

ppp) a VH encoded by the nucleic acid sequence of the insert of the vector deposited as 1D1 1.31 VH having ATCC accession number PTA-120639 and a VL encoded by the nucleic acid sequence of the insert of the vector deposited as 1D1 1.31 VL having ATCC accession number PTA-120640;

qqq) a VL encoded by a nucleic acid encoding the amino acid sequence of SEQ ID NO:102; and rrr) a VH encoded by a nucleic acid encoding the amino acid sequence of SEQ ID NO:226.

E141. The isolated antibody or antigen-binding fragment thereof according to any of E1-E127, or E140, wherein the antibody comprises:

a) a VH comprising:

i) a CDR-H1 comprising the amino acid sequence GYTFTSY$X_1X_2X_3$, wherein $X_1$ is G or A; $X_2$ is I or M; and $X_3$ is N or H (SEQ ID NO: 386);

ii) a CDR-H2 comprising the amino acid sequence WI$X_4X_5X_6$NGNT$X_7X_8X_9$QK$X_{10}$QG, wherein $X_4$ is S or N; $X_5$ is T or A; $X_6$ is Y or G; $X_7$ is N or K; $X_8$ is S or Y; and $X_9$ is A or S; $X_{10}$ is L or F (SEQ ID NO: 387);

iii) a CDR-H3 comprising the amino acid sequence $X_{11}X_{12}$SS$X_{13}$WFDAFDI wherein $X_{11}$ is A or G; $X_{12}$ is H or Y; and $X_{13}$ is S or A (SEQ ID NO: 388);

iv) a D or an E at position H85, as determined by Kabat numbering of the VH; and a VL comprising a CDR-L1 having the amino acid sequence of SEQ ID NO:96, a CDR-L2 having the amino acid sequence of SEQ ID NO:97, and a CDR-L3 having the amino acid sequence of SEQ ID NO:98;

b) a VH comprising SEQ ID NO:52 or SEQ ID NO:90, and a VL comprising SEQ ID NO:50;

c) a VH comprising the CDR-H1 amino acid sequence of SEQ ID NO:99, the CDR-H2 amino acid sequence of SEQ NO:100, the CDR-H3 amino acid sequence of SEQ ID NO:101, and a VL comprising the CDR-L1 amino acid sequence of SEQ ID NO:96, the CDR-L2 amino acid sequence of SEQ ID NO:97, and the CDR-L3 amino acid sequence of SEQ ID NO:98;

d) a VH comprising the CDR-H1, CDR-H2, and CDR-H3 of the VH amino acid sequence of SEQ ID NO:90, and a VL comprising the CDR-L1, CDR-L2, and CDR-L3 of the VL amino acid sequence of SEQ ID NO:88;

e) a VH comprising the amino acid sequence of SEQ ID NO:90 and a VL comprising the amino acid sequence of SEQ ID NO:88;

f) a heavy chain comprising the amino acid sequence of SEQ ID NO:94 and a light chain (LC) comprising the amino acid sequence of SEQ ID NO:92;

g) a VH comprising the CDR-H1, CDR-H2, and CDR-H3 encoded by the nucleic acid sequence of SEQ ID NO:91, and a VL comprising the CDR-L1, CDR-L2, and CDR-L3 encoded by the nucleic acid sequence of SEQ ID NO:89;

h) a VH encoded by the nucleic acid sequence of SEQ ID NO:91, and a VL encoded by the nucleic acid sequence of SEQ ID NO:89;

i) a heavy chain encoded by the nucleic acid sequence of SEQ ID NO:95, and a light chain encoded by the nucleic acid sequence of SEQ ID NO:93;

j) a VH comprising the CDR-H1 amino acid sequence of SEQ ID NO:61, the CDR-H2 amino acid sequence of SEQ NO:62, the CDR-H3 amino acid sequence of SEQ ID NO:63, and a VL comprising the CDR-L1 amino acid sequence of SEQ ID NO:58, the CDR-L2 amino acid sequence of SEQ ID NO:59, and the CDR-L3 amino acid sequence of SEQ ID NO:60;

k) a VH comprising the CDR-H1, CDR-H2, and CDR-H3 of the VH amino acid sequence of SEQ ID NO:52, and a VL comprising the CDR-L1, CDR-L2, and CDR-L3 of the VL amino acid sequence of SEQ ID NO:50;

l) a VH comprising the amino acid sequence of SEQ ID NO:52 and a VL comprising the amino acid sequence of SEQ ID NO:50;

m) a heavy chain comprising the amino acid sequence of SEQ ID NO:56 and a light chain (LC) comprising the amino acid sequence of SEQ ID NO:54;

n) a VH comprising the CDR-H1, CDR-H2, and CDR-H3 encoded by the nucleic acid sequence of SEQ ID NO:53, and a VL comprising the CDR-L1, CDR-L2, and CDR-L3 encoded by the nucleic acid sequence of SEQ ID NO:51;

o) a VH encoded by the nucleic acid sequence of SEQ ID NO:53, and a VL encoded by the nucleic acid sequence of SEQ ID NO:51; or p) a heavy chain encoded by the nucleic acid sequence of SEQ ID NO:57, and a light chain encoded by the nucleic acid sequence of SEQ ID NO:55.

E142. The isolated antibody or antigen-binding fragment thereof according to any of E1-E127, E140 or E141, comprising:

a) a VH comprising:

i) a CDR-H1 comprising the amino acid sequence GFTFS$X_1X_2$A$X_3$H, wherein $X_1$ is N or S; $X_2$ is Y or F; and $X_3$ is L, M, or I (SEQ ID NO: 389);

ii) a CDR-H2 comprising the amino acid sequence LI$X_4X_5$DGS$X_6X_7$YYADSVKG, wherein $X_4$ is S or P; $X_5$ is Y or F; $X_6$ is D,S, or N; $X_7$ is K or N (SEQ ID NO: 390);

iii) a CDR-H3 comprising the amino acid sequence DR$X_8$Y$X_9X_{10}X_{11}X_{12}$S$X_{13}$S$X_{14}$DAFDI wherein $X_8$ is E or N; $X_9$ is C or Y; $X_{10}$ is T or G; $X_{11}$ is Y or S; $X_{12}$ is S or G; $X_{13}$ is C or F; $X_{14}$ is Y or F (SEQ ID NO: 391);

iv) an A or T at position H85, as determined by Kabat numbering of the VH;

v) a M or L at position 108, as determined by Kabat numbering of the VH; and a VL comprising a CDR-L1 having the amino acid sequence of SEQ ID NO:76, a CDR-L2 having the amino acid sequence of SEQ ID NO:77, and a CDR-L3 having the amino acid sequence of SEQ ID NO:78; and a F or Y at position L83, as determined by Kabat numbering of the VL.

b) a VH comprising SEQ ID NO:66, 68 or 70, and a VL comprising SEQ ID NO:1 or 64;

c) a VH comprising i) the CDR-H1 amino acid sequence of SEQ ID NO:79, the CDR-H2 amino acid sequence of SEQ NO:80, and the CDR-H3 amino acid sequence of SEQ ID NO:81;

ii) the CDR-H1 amino acid sequence of SEQ ID NO:82, the CDR-H2 amino acid sequence of SEQ NO:83, and the CDR-H3 amino acid sequence of SEQ ID NO:84; or iii) the CDR-H1 amino acid sequence of SEQ ID NO:85, the CDR-H2 amino acid sequence of SEQ NO:86, and the CDR-H3 amino acid sequence of SEQ ID NO:87; and a VL comprising the CDR-L1 amino acid sequence of SEQ ID NO:76, the CDR-L2 amino acid sequence of SEQ ID NO:77, and the CDR-L3 amino acid sequence of SEQ ID NO:78;

d) a VH comprising the CDR-H1, CDR-H2, and CDR-H3 of the VH amino acid sequence of SEQ ID NO:66, and a VL comprising the CDR-L1, CDR-L2, and CDR-L3 of the VL amino acid sequence of SEQ ID NO:64;

e) a VH comprising the CDR-H1, CDR-H2, and CDR-H3 of the VH amino acid sequence of SEQ ID NO:68, and a VL comprising the CDR-L1, CDR-L2, and CDR-L3 of the VL amino acid sequence of SEQ ID NO:64;

f) a VH comprising the CDR-H1, CDR-H2, and CDR-H3 of the VH amino acid sequence of SEQ ID NO:70, and a VL comprising the CDR-L1, CDR-L2, and CDR-L3 of the VL amino acid sequence of SEQ ID NO:64;

g) a VH comprising the amino acid sequence of SEQ ID NO:66 and a VL comprising the amino acid sequence of SEQ ID NO:64;

h) a VH comprising the amino acid sequence of SEQ ID NO:68 and a VL comprising the amino acid sequence of SEQ ID NO:64;

i) a VH comprising the amino acid sequence of SEQ ID NO:70 and a VL comprising the amino acid sequence of SEQ ID NO:64;

j) a heavy chain comprising the amino acid sequence of SEQ ID NO:74 and a light chain (LC) comprising the amino acid sequence of SEQ ID NO:72;

k) a VH comprising the CDR-H1, CDR-H2, and CDR-H3 encoded by the nucleic acid sequence of SEQ ID NO:67, and a VL comprising the CDR-L1, CDR-L2, and CDR-L3 encoded by the nucleic acid sequence of SEQ ID NO:65;

l) a VH comprising the CDR-H1, CDR-H2, and CDR-H3 encoded by the nucleic acid sequence of SEQ ID NO:69, and a VL comprising the CDR-L1, CDR-L2, and CDR-L3 encoded by the nucleic acid sequence of SEQ ID NO:65;

m) a VH comprising the CDR-H1, CDR-H2, and CDR-H3 encoded by the nucleic acid sequence of SEQ ID NO:71, and a VL comprising the CDR-L1, CDR-L2, and CDR-L3 encoded by the nucleic acid sequence of SEQ ID NO:65;

n) a VH encoded by the nucleic acid sequence of SEQ ID NO:67, and a VL encoded by the nucleic acid sequence of SEQ ID NO:65;

o) a VH encoded by the nucleic acid sequence of SEQ ID NO:69, and a VL encoded by the nucleic acid sequence of SEQ ID NO:65;

p) a VH encoded by the nucleic acid sequence of SEQ ID NO:71, and a VL encoded by the nucleic acid sequence of SEQ ID NO:65;

q) a heavy chain encoded by the nucleic acid sequence of SEQ ID NO:75, and a light chain encoded by the nucleic acid sequence of SEQ ID NO:73;

r)) a VH comprising the CDR-H1 amino acid sequence of SEQ ID NO:16, the CDR-H2 amino acid sequence of SEQ NO:17, the CDR-H3 amino acid sequence of SEQ ID NO:18, and a VL comprising the CDR-L1 amino acid sequence of SEQ ID NO:13, the CDR-L2 amino acid sequence of SEQ ID NO:14, and the CDR-L3 amino acid sequence of SEQ ID NO:15;

s) a VH comprising the CDR-H1 amino acid sequence of SEQ ID NO:19, the CDR-H2 amino acid sequence of SEQ NO:20, the CDR-H3 amino acid sequence of SEQ ID NO:21, and a VL comprising the CDR-L1 amino acid sequence of SEQ ID NO:13, the CDR-L2 amino acid sequence of SEQ ID NO:14, and the CDR-L3 amino acid sequence of SEQ ID NO:15;

t) a VH comprising the CDR-H1, CDR-H2, and CDR-H3 of the VH amino acid sequence of SEQ ID NO:3, and a VL comprising the CDR-L1, CDR-L2, and CDR-L3 of the VL amino acid sequence of SEQ ID NO:1;

u) a VH comprising the CDR-H1, CDR-H2, and CDR-H3 of the VH amino acid sequence of SEQ ID NO:5, and a VL comprising the CDR-L1, CDR-L2, and CDR-L3 of the VL amino acid sequence of SEQ ID NO:1;

v) a VH comprising the amino acid sequence of SEQ ID NO:3 and a VL comprising the amino acid sequence of SEQ ID NO:1;

w) a VH comprising the amino acid sequence of SEQ ID NO:5 and a VL comprising the amino acid sequence of SEQ ID NO:1;

x) a heavy chain comprising the amino acid sequence of SEQ ID NO:9 and a light chain (LC) comprising the amino acid sequence of SEQ ID NO:7;

y) a heavy chain comprising the amino acid sequence of SEQ ID NO:11 and a light chain (LC) comprising the amino acid sequence of SEQ ID NO:7;

z) a VH comprising the CDR-H1, CDR-H2, and CDR-H3 encoded by the nucleic acid sequence of SEQ ID NO:4, and a VL comprising the CDR-L1, CDR-L2, and CDR-L3 encoded by the nucleic acid sequence of SEQ ID NO:2;

aa) a VH comprising the CDR-H1, CDR-H2, and CDR-H3 encoded by the nucleic acid sequence of SEQ ID NO:6, and a VL comprising the CDR-L1, CDR-L2, and CDR-L3 encoded by the nucleic acid sequence of SEQ ID NO:2;

bb) a VH encoded by the nucleic acid sequence of SEQ ID NO:4, and a VL encoded by the nucleic acid sequence of SEQ ID NO:2;

cc) a VH encoded by the nucleic acid sequence of SEQ ID NO:6, and a VL encoded by the nucleic acid sequence of SEQ ID NO:2;

dd) a heavy chain encoded by the nucleic acid sequence of SEQ ID NO:10, and a light chain encoded by the nucleic acid sequence of SEQ ID NO:8; or ee) a heavy chain encoded by the nucleic acid sequence of SEQ ID NO:12, and a light chain encoded by the nucleic acid sequence of SEQ ID NO:8.

E143. A isolated antibody, or antigen-binding fragment thereof, that comprises a VH sequence at least 84% identical to the VH sequence of SEQ ID NO:90.

E144. The antibody or antigen-binding fragment thereof according to E143, further comprising a VL sequence that is at least 95% identical to the VL of SEQ ID NO:88.

E145. An isolated antibody, or antigen-binding fragment thereof, that comprises a VH sequence at least 87% identical to the VH sequence of SEQ ID NO:68.

E146. An isolated antibody, or antigen-binding fragment thereof, that comprises a VL sequence at least 98% identical to the VL sequence of SEQ ID NO:64.

E147. An isolated antibody, or antigen-binding fragment thereof, that binds TL1A, wherein the antibody competes with the antibody or antigen-binding fragment thereof according any of E1-E120, or E133-E139 for binding to TL1A.

E148. The antibody or antigen-binding fragment thereof according to any of E1-E127, or E140-E147, having a paratope that comprises:

a) one or more heavy chain variable domain residues selected from Gly26, Tyr27, Ser28, Thr30, Tyr31, Trp50, Tyr53, Asn54, Asn56, Asn58, Thr73, Arg76, Tyr97, Gly99, Ser100, Gly100A, Ser100B, and Arg100D, based on Kabat numbering with respect to the sequence of SEQ ID NO:104, and one or more light chain variable domain residues selected from Tyr32 and Trp94, based on Kabat numbering with respect to the sequence of SEQ ID NO:102; or b) one or more heavy chain variable domain residues Gly26, Asp28, Thr30, Tyr31, Trp50, Tyr53, Asn54, Asn56, His58, Thr73, Arg76, Tyr97, Gly99, Ser100, Gly100A, Ser100B, Arg100D, based on Kabat numbering with respect to the sequence of SEQ ID NO:104, one or more light chain variable domain residues Tyr32 and Trp94 based on Kabat numbering with respect to the sequence of SEQ ID NO:102.

E149. The antibody or antigen-binding fragment thereof according to any of E1-E127, or E140-E148, wherein the antibody binds to human TL1A with a KD ranging from 4 nM to 1 pM.

E150. The antibody or antigen-binding fragment thereof according to any of E1-E127, or E140-E149, wherein wherein the antibody or antigen-binding fragment binds to human TL1A with a KD of less than 2 nM.

E151. The antibody or antigen-binding fragment thereof according to any of E1-E127, or E140-E150, wherein the antibody binds to human TL1A with a KD less than 1 nM.

E152. The antibody or antigen-binding fragment thereof according to any of E1-E127, or E140-E151, wherein:

a) the antibody binds to at least one TL1A amino acid selected from the group consisting of K113, T115, S117, Y118, P119, P121, T122, 0123, M147, F148, S149, Q151, V31, V32, R33, E50, H51, E52, L53, G54, L55, A56, F57, T58, E91, Y168, T169, K170, and E171, according to the numbering of the amino acid sequence of TL1A as set forth in SEQ ID NO:254;

b) the antibody binds to a homomultimer of TL1A, the homomultimer comprising at least a first and a second TL1A monomer, wherein the antibody binds to a first epitope on the first TL1A monomer, wherein the first epitope comprises at least one amino acid selected from the group consisting of K113, T115, S117, Y118, P119, P121, T122, Q123, M147, F148, S149, and Q151 according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, E50, H51, E52, L53, G54, L55, A56, F57, T58, E91, Y168, T169, K170, and E171, according to the numbering of the amino acid sequence of TL1A as set forth in SEQ ID NO:254;

c) the antibody binds to at least one TL1A amino acid selected from the group consisting of K113, Y118, T122, 0123, M147, F148, S149, Q151, V31, V32, R33, E50, H51, E52, L53, G54, L55, A56, F57, Y168, T169, K170, and E171, according to the numbering of the amino acid sequence of TL1A as set forth in SEQ ID NO:254;

d) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, T122, Q123, M147, F148, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, E50, H51, E52, L53, G54, L55, A56, F57, Y168, T169, K170, and E171, according to the numbering of the amino acid sequence of TL1A as set forth in SEQ ID NO:254;

e) the antibody binds to at least one TL1A amino acid selected from the group consisting of K113, Y118, T122, M147, S149, Q151, V32, R33, E50, H51, E52, L53, G54, L55, A56, F57, Y168, T169, K170, and E171, according to the numbering of the amino acid sequence of TL1A as set forth in SEQ ID NO:254.

f) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, T122, M147, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of V32, R33, E50, H51, E52, L53, G54, L55, A56, F57, Y168, T169, K170, and E171, according to the numbering of the amino acid sequence of TL1A as set forth in SEQ ID NO:254;

g) the antibody binds to at least one TL1A amino acid selected from the group consisting of K113, Y118, T122, M147, S149, Q151, R33, E50, E52, L53, G54, L55, A56, F57, Y168, T169, K170, and E171, according to the numbering of the amino acid sequence of TL1A as set forth in SEQ ID NO:254;

h) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, T122, M147, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of R33, E50, E52, L53, G54, L55, A56, F57, Y168, T169, K170, and E171, according to the numbering of the amino acid sequence of TL1A as set forth in SEQ ID NO:254;

i) the antibody binds to at least one TL1A amino acid selected from the group consisting of K113, Y118, T122, M147, S149, Q151, R33, E50, E52, L53, G54, L55, A56, F57, Y168, T169, and E171, according to the numbering of the amino acid sequence of TL1A as set forth in SEQ ID NO:254;

j) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, T122, M147, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of R33, E50, E52, L53, G54, L55, A56, F57, Y168, T169, and E171, according to the numbering of the amino acid sequence of TL1A as set forth in SEQ ID NO:254;

k) the antibody binds to at least one TL1A amino acid selected from the group consisting of K113, Y118, T122, S149, R33, E50, E52, L53, A56, F57, Y168, T169, and E171, according to the numbering of the amino acid sequence of TL1A as set forth in SEQ ID NO:254;

l) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, T122, and S149, according to the numbering of the amino acid sequence of TL1A as set forth in SEQ ID NO:254, and the antibody binds to a second epitope on the second TL1A monomer, wherein the second epitope comprises at least one amino acid selected from the group consisting of R33, E50, E52, L53, A56, F57, Y168, T169, and E171, according to the numbering of the amino acid sequence of TL1A as set forth in SEQ ID NO:254;

m) the antibody binds to at least one TL1A amino acid selected from the group consisting of residues 117-123 of SEQ ID NO:254 and residues 50-58 of SEQ ID NO:254;

n) the antibody binds to a homomultimer of TL1A comprising at least a first and second TL1A monomer, wherein the antibody binds to a first epitope on the first TL1A monomer, the first epitope comprising at least one amino acid from residues 117-123 of SEQ ID NO:254, and the antibody binds to a second epitope on the second monomer, the second epitope comprising at least one amino acid from residues 50-58 of SEQ ID NO:254;

o) the antibody binds to at least one TL1A amino acid selected from the group consisting of K113, Y118, T122, S149, E50, E52, L53, A56, Y168, T169 and E171 of SEQ ID NO:254;

p) the antibody binds to a homomultimer of TL1A comprising at least a first and second TL1A monomer, wherein the antibody binds to a first epitope on the first TL1A monomer, the first epitope comprising at least one amino acid selected from the group consisting of K113, Y118, T122, and S149 according to the numbering of the amino acid sequence of TL1A as set forth in SEQ ID NO:254, and the antibody binds to a second epitope on the second monomer, the second epitope comprising at least one amino acid selected from the group consisting of E50, E52, L53, A56, Y168, T169 and E171 according to the numbering of the amino acid sequence of TL1A as set forth in SEQ ID NO:254;

q) the antibody binds to at least one TL1A amino acid selected from the group consisting of K113, Y118, T122, S149, E50, E52, A56, and Y168 of SEQ ID NO:254;

r) the antibody binds to a homomultimer of TL1A comprising at least a first and second TL1A monomer, wherein the antibody binds to a first epitope on the first TL1A monomer, the first epitope comprising at least one amino acid selected from the group consisting of K113, Y118, T122, and S149 according to the numbering of the amino acid sequence of TL1A as set forth in SEQ ID NO:254, and the antibody binds to a second epitope on the second monomer, the second epitope comprising at least one amino acid selected from the group consisting of E50, E52, A56, and Y168 according to the number of SEQ ID NO:254;

s) the antibody binds to at least one TL1A amino acid selected from the group consisting of K113, T115, Y118, P121, T122, Q123, M147, F148, S149, Q151, V31, V32, R33, E50, H51, E52, L53, G54, L55, A56, F57, T58, E91, Y168, T169, K170, and E171, according to the numbering of the amino acid sequence of TL1A as set forth in SEQ ID NO:254;

t) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, T115, Y118, P121, T122, Q123, M147, F148, S149, and Q151 according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, E50, H51, E52, L53, G54, L55, A56, F57, T58, E91, Y168, T169, K170, and E171, according to the numbering of the amino acid sequence of TL1A as set forth in SEQ ID NO:254;

u) the antibody binds to at least one TL1A amino acid selected from the group consisting of Y118, M147, S149, R33, E50, E52, L55, A56, and Y168, according to the numbering of the amino acid sequence of TL1A as set forth in SEQ ID NO:254;

v) the antibody binds to a homomultimer of TL1A comprising at least a first and second TL1A monomer, wherein the antibody binds to a first epitope on the first TL1A monomer, wherein the first epitope comprises at least one amino acid selected from the group consisting of Y118, M147, and S149, according to the numbering of the amino acid sequence of TL1A as set forth in SEQ ID NO:254, and the antibody binds to a second epitope on the second TL1A monomer, wherein the second epitope comprises at least one amino acid selected from the group consisting of R33, E50, E52, L55, A56, and Y168, according to the numbering of the amino acid sequence of TL1A as set forth in SEQ ID NO:254;

w) the antibody binds to at least one TL1A amino acid selected from the group consisting of K113, Y118, T122, S149, Q151, R33, E50, E52, L53, G54, L55, A56, F57, T58, Y168, T169, K170, and E171, according to the numbering of the amino acid sequence of TL1A as set forth in SEQ ID NO:254;

x) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, T122, S149, and Q151 according to the numbering of the amino acid sequence of TL1A as set forth in SEQ ID NO:254, and the antibody binds to a second epitope on the second TL1A monomer, wherein the second epitope comprises at least one amino acid selected from the group consisting of R33, E50, E52, L53, G54, L55, A56, F57, T58, Y168, T169, K170, and E171, according to the numbering of the amino acid sequence of TL1A as set forth in SEQ ID NO:254;

y) the antibody binds to at least one TL1A amino acid selected from the group consisting of Y118, E50, E52, and L53, according to the numbering of the amino acid sequence of TL1A as set forth in SEQ ID NO:254;

z) the antibody binds to a homomultimer of TL1A comprising at least a first and second TL1A monomer, wherein the antibody binds to a first epitope on the first TL1A monomer, wherein the first epitope comprises at least Y118 according to the numbering of the amino acid sequence of TL1A as set forth in SEQ ID NO:254, and the antibody binds to a second epitope on the second TL1A monomer, wherein the second epitope comprises at least one amino acid selected from the group consisting of E50, E52, L53, according to the numbering of the amino acid sequence of TL1A as set forth in SEQ ID NO:254;

aa) the antibody binds to at least one TL1A amino acid selected from the group consisting of K113, S117, Y118, P119, T122, Q123, M147, F148, S149, Q151, V31, V32, R33, E50, H51, E52, L53, G54, L55, A56, F57, Y168, T169, K170, and E171, according to the numbering of the amino acid sequence of TL1A as set forth in SEQ ID NO:254;

bb) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, S117, Y118, P119, T122, Q123, M147, F148, S149, and Q151 according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, E50, H51, E52, L53, G54, L55, A56, F57, Y168, T169, K170, and E171, according to the numbering of the amino acid sequence of TL1A as set forth in SEQ ID NO:254;

bb) the antibody binds to at least one TL1A amino acid selected from the group consisting of K113, T122, S149, E50, E52, A56, Y168, T169, and E171, according to the numbering of the amino acid sequence of TL1A as set forth in SEQ ID NO:254;

cc) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, T122, and S149, according to the numbering of the amino acid sequence of TL1A as set forth in SEQ ID NO:254, and the antibody binds to a second epitope on the second TL1A monomer, wherein the second epitope comprises at least one amino acid selected from the group consisting of E50, E52, A56, Y168, T169, and E171, according to the numbering of the amino acid sequence of TL1A as set forth in SEQ ID NO:254;

dd) the antibody binds to at least one TL1A amino acid selected from the group consisting of K113, S117, Y118, T122, S149, Q151, R33, E50, E52, L53, G54, L55, A56, F57, Y168, T169, and E171, according to the numbering of the amino acid sequence of TL1A as set forth in SEQ ID NO:254;

ee) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, S117, Y118, T122, S149, and Q151 according to the numbering of the amino acid sequence of TL1A as set forth in SEQ ID NO:254, and the antibody binds to a second epitope on the second TL1A monomer, wherein the second epitope comprises at least one amino acid selected from the group consisting of R33, E50, E52, L53, G54, L55, A56, F57, Y168, T169, and E171, according to the numbering of the amino acid sequence of TL1A as set forth in SEQ ID NO:254;

ff) the antibody binds to at least one TL1A amino acid selected from the group consisting of K113, Y118, T122, E50, E52, and L53, according to the numbering of the amino acid sequence of TL1A as set forth in SEQ ID NO:254;

gg) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, and T122, according to the numbering of the amino acid sequence of TL1A as set forth in SEQ ID NO:254, and the antibody binds to a second epitope on the second TL1A monomer, wherein the second epitope comprises at least one amino acid selected from the group consisting of E50, E52, and L53, according to the numbering of the amino acid sequence of TL1A as set forth in SEQ ID NO:254;

hh) the antibody binds to at least one TL1A amino acid selected from the group consisting of K113, Y118, T122, F148, S149, Q151, V31, V32, R33, E50, E52, L53, G54, L55, A56, F57, E91, Y168, T169, K170, and E171, according to the numbering of the amino acid sequence of TL1A as set forth in SEQ ID NO:254;

ii) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, T122, F148, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, E50, E52, L53, G54, L55, A56, F57, E91, Y168, T169, K170, and E171, according to the numbering of the amino acid sequence of TL1A as set forth in SEQ ID NO:254;

jj) the antibody binds to at least one TL1A amino acid selected from the group consisting of K113, Y118, P119, T122, 0123, F148, S149, V31, V32, E50, E52, L53, G54, L55, A56, Y168, T169, K170, and E171, according to the numbering of the amino acid sequence of TL1A as set forth in SEQ ID NO:254;

kk) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, P119, T122, Q123, F148, and S149, according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, E50, E52, L53, G54, L55, A56, Y168, T169, K170, and E171, according to the numbering of the amino acid sequence of TL1A as set forth in SEQ ID NO:254;

ll) the antibody binds to at least one TL1A amino acid selected from the group consisting of K113, Y118, P119, T122, Q123, F148, S149, Q151, V31, V32, R33, E50, E52, L53, G54, L55, A56, F57, E91, Y168, T169, K170, and E171, according to the numbering of the amino acid sequence of TL1A as set forth in SEQ ID NO:254;

mm) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, P119, T122, Q123, F148, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, E50, E52, L53, G54, L55, A56, F57, E91, Y168, T169, K170, and E171, according to the numbering of the amino acid sequence of TL1A as set forth in SEQ ID NO:254;

nn) the antibody binds to at least one TL1A amino acid selected from the group consisting of K113, Y118, T122, F148, S149, V31, V32, E50, E52, L53, G54, L55, A56, Y168, T169, K170, and E171, according to the numbering of the amino acid sequence of TL1A as set forth in SEQ ID NO:254; or oo) the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, T122, F148, and S149, according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, E50, E52, L53, G54, L55, A56, Y168, T169, K170, and E171, according to the numbering of the amino acid sequence of TL1A as set forth in SEQ ID NO:254.

E153. The antibody or antigen-binding fragment thereof according to any of E1-E127, or E140-E152, wherein the antibody binds to TL1A when one or more amino acid residues of the antibody participates in a hydrogen bond with one or more residues in TL1A, participates in a water-mediated hydrogen bond with one or more reisdues of TL1A, participates in a salt bridge with one or more residues in TL1A, has a non-zero change in buried surface area due to interaction with TL1A, or when a heavy atom from one or more residues of the antibody is within a distance of 4 Å from a heavy atom in TL1A.

E154. An isolated nucleic acid encoding the antibody, or antigen-binding fragment thereof, according to any of E1-E127, or E140-E153.

E155. The isolated nucleic acid encoding an antibody, or antigen-binding fragment thereof according to E154, wherein said nucleic acid comprises the nucleic acid sequence selected from the group consisting of:

a) the nucleic acid sequence of SEQ ID NO:103;
b) the nucleic acid sequence of SEQ ID NO: 105;
c) the nucleic acid sequence of SEQ ID NO:107;
d) the nucleic acid sequence of SEQ ID NO:109;
e) the nucleic acid sequence of SEQ ID NO:103 and 105;
f) the nucleic acid sequence of SEQ ID NO:107 and 109;
g) the nucleic acid sequence of the insert of the vector deposited as 1D1 1.31 VH having ATCC accession number PTA-120639;
h) the nucleic acid sequence of the insert of the vector deposited as 1D1 1.31 VL having ATCC accession number PTA-120640;
i) the nucleic acid sequence of the insert of the vector deposited as 1D1 1.31 VH having ATCC accession number PTA-120639 and the nucleic acid sequence of the insert of the vector deposited as 1D1 1.31 VL having ATCC accession number PTA-120640;
j) the nucleic acid sequence of SEQ ID NO:227;
k) the nucleic acid sequence of SEQ ID NO: 229;
l) the nucleic acid sequence of SEQ ID NO:227 and 103;
m) the nucleic acid sequence of SEQ ID NO:229 and 107;
n) the nucleic acid sequence of SEQ ID NO:199;
o) the nucleic acid sequence of SEQ ID NO: 201;
p) the nucleic acid sequence of SEQ ID NO:199 and 103;
q) the nucleic acid sequence of SEQ ID NO:201 and 107;
r) the nucleic acid sequence of SEQ ID NO:206;
s) the nucleic acid sequence of SEQ ID NO: 208;
t) the nucleic acid sequence of SEQ ID NO:206 and 103;
u) the nucleic acid sequence of SEQ ID NO:208 and 107;
v) the nucleic acid sequence of SEQ ID NO:213;
w) the nucleic acid sequence of SEQ ID NO: 215;
x) the nucleic acid sequence of SEQ ID NO:213 and 103;
y) the nucleic acid sequence of SEQ ID NO:215 and 107;
z) the nucleic acid sequence of SEQ ID NO:220;
aa) the nucleic acid sequence of SEQ ID NO: 222;
bb) the nucleic acid sequence of SEQ ID NO:220 and 103;
c) the nucleic acid sequence of SEQ ID NO:222 and 107;
dd) the nucleic acid sequence of SEQ ID NO:234;
ee) the nucleic acid sequence of SEQ ID NO: 236;
ff) the nucleic acid sequence of SEQ ID NO:234 and 103;
gg) the nucleic acid sequence of SEQ ID NO:236 and 107;
hh) the nucleic acid sequence of SEQ ID NO:241;
ii) the nucleic acid sequence of SEQ ID NO: 243;
jj) the nucleic acid sequence of SEQ ID NO:241 and 103;
kk) the nucleic acid sequence of SEQ ID NO:243 and 107;
ll) the nucleic acid sequence of SEQ ID NO:248;
mm) the nucleic acid sequence of SEQ ID NO: 250;
nn) the nucleic acid sequence of SEQ ID NO:248 and 103; or
oo) the nucleic acid sequence of SEQ ID NO:250 and 107.

E156. The isolated nucleic acid encoding an antibody, or antigen-binding fragment thereof according to E154 or E155, wherein said nucleic acid comprises:
a) the nucleic acid sequence of SEQ ID NO:89;
b) the nucleic acid sequence of SEQ ID NO: 91;
c) the nucleic acid sequence of SEQ ID NO:93;
d) the nucleic acid sequence of SEQ ID NO:95;
e) the nucleic acid sequence of SEQ ID NO:89 and 91;
f) the nucleic acid sequence of SEQ ID NO:93 and 95;
j) the nucleic acid sequence of SEQ ID NO:53;
k) the nucleic acid sequence of SEQ ID NO: 57;
l) the nucleic acid sequence of SEQ ID NO:53 and 89;
m) the nucleic acid sequence of SEQ ID NO:57 and 93;
n) a nucleic acid encoding the amino acid sequence of SEQ ID NO:102; or
o) a nucleic acid encoding the amino acid sequence of SEQ ID NO:226.

E157. The isolated nucleic acid encoding an antibody, or antigen-binding fragment thereof according to any of E154-E156, wherein said nucleic acid comprises:
a) the nucleic acid sequence of SEQ ID NO:65;
b) the nucleic acid sequence of SEQ ID NO: 67;
c) the nucleic acid sequence of SEQ ID NO:69;
d) the nucleic acid sequence of SEQ ID NO: 71;
e) the nucleic acid sequence of SEQ ID NO:73;
f) the nucleic acid sequence of SEQ ID NO:75;
g) the nucleic acid sequence of SEQ ID NO:67 and 65;
h) the nucleic acid sequence of SEQ ID NO:69 and 65;
i) the nucleic acid sequence of SEQ ID NO:71 and 65;
j) the nucleic acid sequence of SEQ ID NO:73 and 75;
k) the nucleic acid sequence of SEQ ID NO:2;
l) the nucleic acid sequence of SEQ ID NO: 4;
m) the nucleic acid sequence of SEQ ID NO:6;
n) the nucleic acid sequence of SEQ ID NO:8;
o) the nucleic acid sequence of SEQ ID NO:10;
p) the nucleic acid sequence of SEQ ID NO:12;
q) the nucleic acid sequence of SEQ ID NO:4 and 2;
r) the nucleic acid sequence of SEQ ID NO:6 and 2;
s) the nucleic acid sequence of SEQ ID NO:10 and 8; or
t) the nucleic acid sequence of SEQ ID NO:12 and 8.

E158. A vector comprising the nucleic acid according to any of E154-157.

E159. A host cell comprising the nucleic acid according to any of E154-157 or the vector of E158.

E160. The host cell of E159, wherein the cell is a bacterial cell or a mammalian cell.

E161. A method of producing an antibody, or antigen-binding fragment thereof, that specifically binds TL1A, said method comprising culturing the host cell according to E159 or E160 under conditions wherein said antibody is expressed, and further comprising isolating said antibody.

E162. A pharmaceutical composition comprising an antibody or antigen-binding fragment thereof according to any one of E1-E127, and E140-E153, and a pharmaceutically acceptable carrier or excipient.

E163. A method for preventing or treating a disease, disorder or condition mediated by TL1A, said method comprising administering to a subject in need thereof an effective amount of the antibody or antigen-binding fragment thereof according to any one of E1-E120, and E133-E145, or the pharmaceutical composition of E154.

E164. The antibody or antigen-binding fragment thereof according according to any one of E1-E127, and E140-E153, or the pharmaceutical composition of E162 for use in preventing or treating a disease, disorder or condition mediated by TL1A.

E165. Use of an antibody or antigen binding fragment thereof according to any one of E1-E127, and E140-E153, in the manufacture of a medicament for treating a disease, disorder or condition mediated by TL1A.

E166. The method according to E163, the antibody or pharmaceutical composition according to E162, or the use according to E165, wherein the disease, disorder or condition is at least one selected from the group consisting of: inflammatory bowel disease (IBD), Crohn's disease, ulcerative colitis, asthma, allergies, diabetes mellitus, arthritis, rheumatoid arthritis, juvenile rheumatoid arthritis, osteoarthritis, psoriatic arthritis, ankylosing spondylitis, multiple sclerosis, transplant rejection, graft-versus-host disease (GVHD), spondyloarthropathy, primary sclerosing cholangitis, primary biliary cirrhosis, atherosclerosis, bladder syndrome/intersticial cystitis, Urinary bowel disfunction, sepsis, uveitis, encephalomyelitis, myasthenia gravis, systemic lupus erythematosus, cutaneous lupus erythematosus, autoimmune thyroiditis, atopic dermatitis, eczematous dermatitis, psoriasis, Sjogren's syndrome, scleroderma, and vasculitis.

E159 A method of detecting TL1A in a sample, tissue, or cell using the antibody or antigen-binding fragment thereof according to any one of E1-E127, and E140-E153, comprising contacting the sample, tissue or cell with the antibody and detecting the antibody.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiment(s) which are presently preferred. It should be understood, however, that the invention is not limited to the precise arrangements and instrumentalities shown.

In the drawings:

FIGS. 1A, 1B, 1C, 1D, 1E, 1F, 1G, and 1H depict amino acid sequences of various anti-TL1A antibodies of the invention. Throughout FIGS. 1A, 1B, 1C, 1D, 1E, 1F, 1G, 1H, 1I-1, 1I-2, 1J, 1K, 1L, 1M-1, 1M-2, and 1M-3, the VH domain CDR H1 regions, as defined by AntibodyM, are set out in bold and italicized. The CDR regions, as defined by Kabat, are underlined. Specifically, FIG. 1A depicts the VH and VL region amino acid sequences of antibodies 9B3, 15A9, 15C11, and 22F9. FIG. 16 depicts the VH and VL region amino acid sequences of antibodies 26B11, 7D4, and 1D1. FIG. 1C and FIG. 1D depict the VH region amino acid sequences of a series of 1D1 antibodies that were affinity matured through phage display and were designated 1D1 D5, 1D1 D18, 1D1 D21, 1D1 D24, 1D1 D25, 1D1 D28, 1D1 D29, 1D1 D31, 1D1 D37, 1D1 D38, 1D1 D39, 1D1 DH3, 1D1 DH8, 1D1 DH9, and 1D1 DH10. FIGS. 1E, 1F, 1G, and FIG. 1H depict the VH region amino acid sequences of 1D1 antibodies that were affinity matured through co-crystal structure and phage display analysis and designated 1D1 1.1 through 1D1 1.34. For affinity matured antibodies in FIGS. 1C, 1D, 1E, 1F, 1G and 1H, the VL regions have the same amino acid sequence as parental antibody 1D1 VL region. FIG. 1I-1 depicts an alignment of the amino acid sequences of the VL regions of 26B1, 7D4, and 1D1, and FIG. 1I-2 shows the sequence alignment of the VH regions of parental antibodies 1D1, 7D4, and 26B11. Each of these antibodies represents a different epitope-binding antibody bin/group. FIG. 1J depicts an alignment of the amino acid sequences from antibodies 7D4 and 22F9, which share an epitope binding bin. FIG. 1K depicts an alignment of the amino acid sequences between antibodies 26B11 and 9B3, which share an epitope binding bin. FIG. 1L depicts an alignment of the amino acid sequences of antibody 1D1 and antibodies 15A9 and 15C11, which share an epitope-binding bin. FIG. 1M-1 shows a table depicting the percent amino acid sequence identity shared between the VH domains of 1D1 and various 1D1 variant anti-TL1A antibodies. FIG. 1M-2 shows a table depicting the percent amino acid sequence identity between the VL domains of various anti-TL1A antibodies (1D1, 15A9, 15C11, 9B3, 26B11, 7D4 and 22F9). FIG. 1M-3 shows a table depicting the percent amino acid sequence identity between the VH domains of various anti-TL1A antibodies (1D1, 15A9, 15C11, 9B3/26B11 VH1, 9B3/26B11 VH2, 26B11 MDX, 7D4 and 22F9).

FIG. 2 depicts a Venn diagram showing anti-TL1A antibodies according to epitope bins. Antibodies within the same circle compete for binding to human TL1A while antibodies in separate circles do not compete for binding on human TL1A.

FIG. 3 depicts another Venn diagram of anti-TL1A antibodies showing antibodies according to epitope bins. Antibodies within the same circle compete for binding to human TL1A while antibodies in separate circles do not compete for binding on human TL1A.

FIG. 14A depicts a graph demonstrating constitutive expression of DR3 on TF-1 cells after overnight culture without GM-CSF. Constitutive expression of DR3 on TF-1 cells was demonstrated by staining with a commercial biotinylated-anti-DR3 antibody followed by staining with streptavidin-PE. After staining, DR3 expression was examined by flow cytometry analysis. Cell counts are plotted against mean fluorescence intensity (MFI) as a measure of DR3 expression which is demonstrated by the increase in MFI in the cells stained with the DR3 antibody (light gray) as compared to the streptavidin-PE control cells (dark gray). FIG. 14B depicts a graph illustrating TL1A dose-dependent activation of NFκB activity in TF-1-NFκB-luciferase cells. TF-1-NFκB-luciferase cells were stimulated with the indicated pM concentrations of TL1A for 6 hours at 37° C. NFκB activity was measured by expression of luciferase activity (light units). Relative light units were measured by a luminometer and plotted against TL1A concentrations. FIG. 14C depicts a representative graph demonstrating dose dependent inhibition of NFκB activation by antibody 1D1 1.31 activity in TF-1-NFκB-luciferase cells in response to TL1A stimulation. TF-1-NFκB-luciferase cells were stimulated by 150 pM TL1A in the presence of the indicated concentrations of 1D1 1.31 for 6 hours at 37° C. NFκB activity was measured by expression of luciferase activity. Relative light units were measured by a luminometer and plotted against 1D1 1.31 concentrations. FIG. 14D depicts a graph illustrating TL1A dose-dependent activation of NFκB activity in TF-1-NFκB-luciferase cells in the presence or absence of 3 nM isotype control antibody. TF-1-NFκB-luciferase cells were stimulated with the indicated concentrations of TL1A and with or without 3 nM isotype control antibody for 6 hours at 37° C. NFκB activity was measured by expression of luciferase activity. Relative light units were measured by a luminometer and plotted against TL1A concentrations. FIG. 14E depicts a graph illustration anti-tetanus toxoid isotype control antibody dose-dependent inhibition of NFκB activation in TF-1-NRκB-luciferase cells in response TL1A stimulation. TF-1-NFκB-luciferase cells were stimulated by 150 pM TL1A in the presence of the indicated concentrations of isotype control antibody for 6 hours at 37° C. NFκB activity was measured by expression of luciferase activity. Relative light units were measured by a luminometer and plotted against 1D1 1.31 antibody concentrations.

FIG. 15A depicts a graph illustrating TL1A dose-dependent activation of caspase activity in TF-1 cells. TF-1 cells were stimulated with the indicated concentrations of TL1A for 6 hours at 37° C. in the presence of cycloheximide. Caspase activity was measured by luciferin activity released upon cleavage of the caspase-specific substrate. Relative light units were measured by a luminometer and plotted against TL1A concentrations. The data shown demonstrate an EC50 of about 94.17. FIG. 15B depicts a graph illustrating dose-dependent inhibition of caspase activity by antibody 1D1 1.31 in TF-1 cells in response to TL1A stimulation. TF-1 cells were stimulated by 87 pM TL1A in the presence of the indicated concentrations of 1D1 1.31 for 6 hours at 37° C. in the presence of cycloheximide. Caspase activity was measured by luciferin activity released upon cleavage of the caspase-specific substrate. Relative light units were measured by a luminometer and plotted against 1D1 1.31 concentrations. The data shown demonstrate an IC50 about 54.26 for Ab 1D1 1.31.

FIG. 16A depicts a graph illustrating inhibition of IFN gamma secretion upon immune complex (IC) and IL-12 and IL-18 stimulation of human peripheral blood by 1D1 1.31. Human peripheral blood treated with 0.5 ng/mL recombinant human IL-12 and 5 ng/mL recombinant human IL-18 was stimulated by immune complex coated plates for 24 hours at 37° C. (to upregulate DR3 on NK/NKT cells and TL1A on monocytes, respectively) in the absence or presence of the indicated 1D1 1.31 or isotype control antibody concentrations. Plasma was prepared from these samples and IFNγ was measured in the plasma samples by a quantitative immune-ligand binding assay using a Mesoscale (MSD) kit. FIG. 16B depicts a graph showing 1D1 1.31 decrease on 1D1-1.31-free soluble TL1A (sTL1A) upon IC and IL-12 and IL-18 stimulation of human peripheral blood. Human peripheral blood treated with 0.5 ng/mL recombinant human IL-12 and 5 ng/mL recombinant human IL-18 was stimulated by immune complex coated plates for 24 hours at 37° C. (to upregulate DR3 on NK/NKT cells and TL1A on monocytes, respectively) in the absence or presence of the indicated 1D1 1.31 or isotype control antibody concentrations. Plasma was prepared from these samples and 1D1 1.31-free sTL1A was measured in the plasma samples by a quantitative immunoligand binding assay using Mesoscale (MSD).

FIG. 17A depicts antibody 1D1 1.31 inhibition of IFN gamma production upon IC and IL-12 and IL-18 stimulation of cynomolgus monkey peripheral blood. Cynomolgus monkey peripheral blood treated with 1 ng/mL recombinant human IL-12 and 10 ng/mL recombinant human IL-18 was stimulated by immune complex coated plates for 24 hours at 37° C. (to upregulate DR3 on NK/NKT cells and TL1A on monocytes, respectively) in the absence or presence of the indicated 1D1 1.31 or isotype control antibody concentrations. Plasma was prepared from these samples and IFNγ was measured in the plasma samples by a quantitative immune-ligand binding assay using a Mesoscale (MSD) kit. FIG. 17B depicts a graph illustrating the decrease on antibody 1D1-1.31-free soluble TL1A under IC and IL-12 and IL-8 stimulation of cynomolgus monkey blood. Cynomolgus monkey peripheral blood treated with 1 ng/mL recombinant human IL-12 and 10 ng/mL recombinant human IL-18 was stimulated by immune complex coated plates for 24 hours at 37° C. (to upregulate DR3 on NK/NKT cells and TL1A on monocytes, respectively) in the absence or presence of the indicated 1D1 1.31 or isotype control antibody concentrations. Plasma was prepared from these samples and 1D1 1.31-free sTL1A was measured in the plasma samples by a quantitative immunoligand binding assay using a Mesoscale (MSD) kit.

FIGS. 18A, 18B, and 18C show a chart summarizing the normalized surface area (Å$^2$) buried due to interactions between pairs of 1D1 antibody residues and TL1A residues. FIG. 184A is part one of the chart; FIG. 18B is part two of the chart; and FIG. 18C is part three of the chart. The 1D1 residues are designated by chain (H for heavy chain, or L for light chain), single letter amino acid code, and residue number. The TL1A residues are designated by TL1A monomer/chain (A or B), single letter amino acid code, and residue number. Pairs that form a hydrogen bond are indicated with an 'h'. Pairs that form a salt bridge are indicated with an 'S'. Pairs that jointly coordinate a water molecule are indicated with a 'w'.

FIGS. 19A, 19B, and 19C show a chart summarizing the normalized surface area (Å$^2$) buried due to interactions between pairs of 1D1 1.31 antibody residues and TL1A residues. FIG. 19A is part one of the chart; FIG. 19B is part two of the chart; and FIG. 19C is part three of the chart. The 1D1 1.31 residues are designated by chain (H for heavy chain, or L for light chain), single letter amino acid code, and residue number. The TL1A residues are designated by TL1A monomer/chain (A or B), single letter amino acid code, and residue number. Pairs that form a hydrogen bond are indicated with an 'h'. Pairs that form a salt bridge are indicated with an 'S'. Pairs that jointly coordinate a water molecule are indicated with a 'w'.

FIGS. 23A, 23B, and 23C shows a chart summarizing the normalized surface area ($Å^2$) buried due to interactions between pairs of 7D4 antibody residues and TL1A residues. FIG. 23A is part one of the chart; FIG. 23B is part two of the chart; and FIG. 23C is part three of the chart. The 7D4 residues are designated by chain (H for heavy chain, or L for light chain), single letter amino acid code, and residue number. The TL1A residues are designated by TL1A monomer/chain (A or B), single letter amino acid code, and residue number. Pairs that form a hydrogen bond are indicated with an 'h'. Pairs that form a salt bridge are indicated with an 'S'. Pairs that jointly coordinate a water molecule are indicated with a 'w'.

FIGS. 24A, 24B, and 24C shows a chart summarizing the normalized surface area ($Å^2$) buried due to interactions between pairs of 26B11 antibody residues and TL1A residues. FIG. 24A is part one of the chart; FIG. 24B is part two of the chart; and FIG. 24C is part three of the chart. The 26B11 residues are designated by chain (H for heavy chain, or L for light chain), single letter amino acid code, and residue number. The TL1A residues are designated by TL1A monomer/chain (A or B), single letter amino acid code, and residue number. Pairs that form a hydrogen bond are indicated with an 'h'. Pairs that form a salt bridge are indicated with an 'S'. Pairs that jointly coordinate a water molecule are indicated with a 'w'.

DETAILED DESCRIPTION OF THE INVENTION

Figure 2:
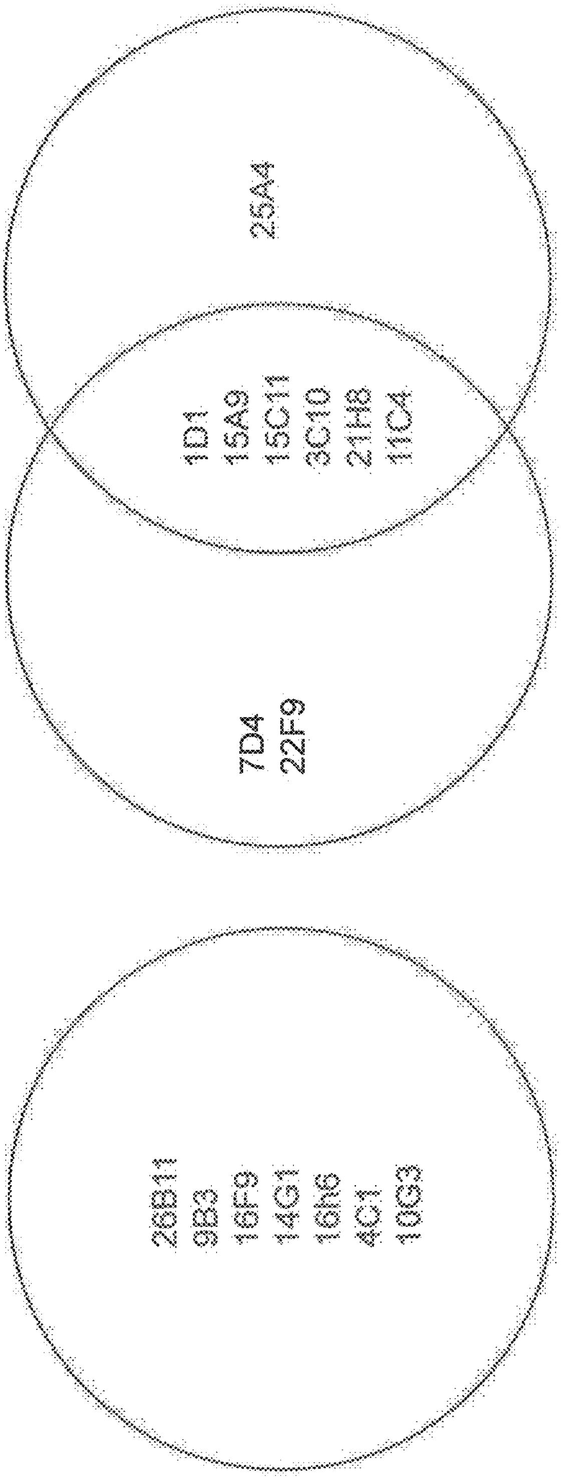

Disclosed herein are antibodies that specifically bind to TL1A and further, antibodies that inhibit its binding to DR3. Methods of making TL1A antibodies, compositions comprising these antibodies, and methods of using these antibodies are provided. TL1A antibodies can be used in the prevention, treatment, and/or amelioration of diseases, disorders or conditions caused by and/or associated with TL1A, such as immune-related or inflammatory diseases. Such diseases, disorders or conditions include, but are not limited to, IBD, including UC and CD, asthma, multiple sclerosis, psoriasis, and rheumatoid arthritis, among others as would be appreciated by one skilled in the art provided with the teachings disclosed herein.

General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, NY (2001); Ausubel et al., Current Protocols in Molecular Biology, John Wiley & Sons, NY (2002); Harlow and Lane Using Antibodies: A Laboratory Manual, Cold Spring Harbor Laboratory Press, Cold Spring Harbor, NY (1998); Coligan et al., Short Protocols in Protein Science, John Wiley & Sons, NY (2003); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Definitions

The following terms, unless otherwise indicated, shall be understood to have the following meanings: the term "isolated molecule" (where the molecule is, for example, a polypeptide, a polynucleotide, or an antibody or fragment thereof) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, "substantially pure" means an object species is the predominant species present (i.e., on a molar basis it is more abundant than any other individual species in the composition), and preferably a substantially purified fraction is a composition wherein the object species (e.g., a glycoprotein, including an antibody or receptor) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', $F(ab')_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody or antigen-binding fragment thereof of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$ and $IgA_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

The terms "antigen-binding portion" or "antigen-binding fragment" of an antibody (or simply "antibody portion"), as used interchangeably herein, refers to one or more fragments of an antibody that retain the ability to specifically bind to an antigen (e.g., TL1A). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. Science 242:423-426 (1988) and Huston et al. Proc. Natl. Acad. Sci. USA 85:5879-5883 (1988)). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. Proc. Natl. Acad. Sci. USA 90:6444-6448 (1993); Poljak et al., 1994, Structure 2:1121-1123).

Antibodies may be derived from any mammal, including, but not limited to, humans, monkeys, pigs, horses, rabbits, dogs, cats, mice, etc., or other animals such as birds (e.g. chickens), fish (e.g., sharks) and camelids (e.g., llamas).

A "variable region" of an antibody refers to the variable region of the antibody light chain (VL) or the variable region of the antibody heavy chain (VH), either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J. Mol. Biol. 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As outlined elsewhere herein, certain positions of the antibody molecule can be altered. By "position" as used herein is meant a location in the sequence of a protein. Positions may be numbered sequentially, or according to an established format, for example the EU index and Kabat index can be used to number amino acid residues of an antibody. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', $F(ab')_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody or vice versa. The term also encompasses an antibody comprising a V region from one individual from one species (e.g., a first mouse) and a constant region from another individual from the same species (e.g., a second mouse).

The terms "antigen" and "Ag" refers to the molecular entity used for immunization of an immunocompetent vertebrate to produce the antibody (Ab) that recognizes the Ag or to screen an expression library (e.g., phage, yeast or ribosome display library, among others). Herein, Ag is termed more broadly and is generally intended to include target molecules that are specifically recognized by the Ab, thus including fragments or mimics of the molecule used in an immunization process for raising the Ab or in library screening for selecting the Ab. Thus, for antibodies of the invention binding to TL1A, full-length TL1A from mammalian species (e.g., human, monkey, mouse and rat TL1A), including monomers and multimers, such as dimers, trimers, etc. thereof, as well as truncated and other variants of TL1A, are referred to as an antigen.

Generally, the term "epitope" refers to the area or region of an antigen to which an antibody specifically binds, e.g., an area or region comprising a contact residue that interacts with the antibody. Thus, the term "epitope" refers to that portion of a molecule capable of being recognized by and bound by an antibody at one or more of the antibody's antigen-binding regions. Typically, an epitope is defined in the context of a molecular interaction between an antibody, or antigen-binding fragment thereof, and its corresponding antigen. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to TL1A, e.g., the antibodies compete for binding to the antigen.

As used herein, the terms "wild-type amino acid," "wild-type IgG," "wild-type antibody," or "wild-type mAb," refer to a sequence of amino or nucleic acids that occurs naturally within a certain population (e.g., human, mouse, rats, cell, etc.).

The term "antagonist antibody" refers to an antibody that binds to a target and prevents or reduces the biological effect of that target. In some embodiments, the term can denote an antibody that prevents the target to which it is bound from performing a biological function, e.g., binding to its cognate receptors.

As used herein, an "anti-TL1A antagonist antibody" refers to an antibody that is able to inhibit TL1A biological activity, or the activity of a homopolymer comprising TL1A, such as a homodimer or a homotrimer) and/or downstream event(s) mediated by TL1A, including, but not limited to, binding to its receptors, including DR3, and mediating signaling thereby. TL1A antagonist antibodies encompass antibodies that block, antagonize, suppress or reduce (to any degree, including significantly) TL1A biological activity, including downstream events mediated by TL1A, such as, DR3 binding and downstream signaling. For purposes of the present invention, it will be explicitly understood that the term "anti-TL1A antibody" (interchangeably termed "antagonist TL1A antibody", "antagonist anti-TL1A antibody", "anti-TL1A antagonist antibody",) encompasses all the previously identified terms, titles, and functional states and characteristics whereby the TL1A itself, a TL1A biological activity (including but not limited to its ability to bind a receptor), or the consequences of the biological activity, are substantially nullified, decreased, or neutralized in any meaningful degree. In some embodiments, an anti-TL1A antibody binds TL1A and prevents its binding and signalling through DR3. In some embodiments, the antagonist ability is characterized and/or described via a cell-based assay, such as an NFκB inhibition assay or caspase inhibition assay as disclosed herein. In some embodiments, the antagonist ability is described in terms of an $IC_{50}$ or $EC_{50}$ value. In some embodiments, the TL1A antibody or antigen-binding fragment thereof of the disclosure is considered to block, antagonize, suppress or reduce TL1A activity if it reduces a TL1A activity by 5%, 10%, 15%, 20%, 25%, 30%, 35%, 40%, 45%, 50%, 55%, 60%, 65%, 70%, 75%, 80%, 85%, 90%, 95% or more relative to the TL1A activity in the absence of the antibody.

As known in the art, a "constant region" of an antibody refers to the constant region of the antibody light chain or the constant region of the antibody heavy chain, either alone or in combination.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

The term "bind", in the context of an antigen binding protein of the invention (e.g., an antibody, or antigen-binding fragment thereof) binding an amino acid on the antigen or binding an epitope comprising an amino acid on the antigen, means an amino acid residue of the antigen that participates in an electrostatic interaction with the antigen binding protein, participates in a hydrogen bond with the antigen binding protein, or participates in a water-mediated hydrogen bond with the antigen binding protein, or participates in a salt bridge with the antigen binding protein, or it has a non-zero change in buried surface area due to interaction with the antigen binding protein, and/or a heavy atom of the antigen amino acid residue is located within 4 Å of a heavy atom of a residue of the antigen binding protein.

The term "compete", as used herein with regard to an antibody, means that a first antibody, or an antigen-binding portion thereof, binds to an epitope in a manner sufficiently similar to the binding of a second antibody, an antigen-binding portion thereof, or a ligand that is not an antibody such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

"Contact residue" as used herein with respect to an antibody or the antigen specifically bound thereby, refers to an amino acid residue present on an antibody/antigen comprising at least one heavy atom (i.e., not hydrogen) that is within 4 Å or less of a heavy atom of an amino acid residue present on the cognate antibody/antigen.

As used herein, an antibody "interacts with"TL1A when the equilibrium dissociation constant (KD) is equal to or less than 5 nM, preferably less than 1nM, preferably less than 100 pM, preferably less than about 50 pM, more preferably less than about 20 pM, most preferably less than about 10 pM, more preferably less than about 5 pM, yet more preferably less than about 2 pM. The term "dissociation constant" is sometimes used interchangeably with "equilibrium dissociation constant", and refers to the value obtained in a titration measurement at equilibrium, or by dividing the dissociation rate constant (koff) by the association rate constant (kon). The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB a GE Healthcare company, Uppsala, Sweden). Additionally, a KinExA® (Kinetic Exclusion Assay) assay, available from Sapidyne Instruments (Boise, Id.) can also be used. In one embodiment, the dissociation constant is measured using surface plasmon resonance (SPR) method (Biacore). In certain embodiments, the affinity is the KD value as measured by SPR. In still other cases, the SPR uses a captured antibody, and solution phase target. In some embodiments, the captured antibody is immobilized onto a sensor chip using an anti-isotype antibody or antigen binding portion thereof. For example, the anti-isotype antibody or antigen binding portion thereof can be immobilized onto the sensor chip to a density of between about 4,000 and about 13,000 response units. SPR measurement can also be performed, for example, as substantially conducted according to the protocol set out in Example 8. In some cases, the SPR uses a captured target, and solution phase antibody. In some embodiments, the SPR measurement is conducted using a Biacore T100 or T200 instrument. In another embodiment, the dissociation constant is measured using solution-based kinetic exclusion assay (KinExA). In other embodiments, the affinity of the antibody or antigen-binding fragment thereof for human TL1A is measured by solution-based kinetic exclusion assay (KinExA). For example, in some cases, the affinity is the KD value as measured by solution-based kinetic exclusion assay (KinExA). In other cases, the KinExA uses a captured target on a solid phase, and a solution phase antibody. In still other cases, the antibody and target are pre-incubated in solution long enough to reach equilibrium. In one embodiment, the level of unbound antibody is measured after the antibody and target have reached equilibrium. In a particular embodiment, the KinExA measurement is conducted using a KinExA 3200 instrument (Sapidyne). In one embodiment, the antibody interacts with TL1A when the KD ranges from about 20 pM to about 1 pM, as measured by KinExA. In one embodiment, the antibody interacts with TL1A with a $K_D$ of about 1.38 pM as measured by KinExA.

A number of methodologies are available for the measurement of binding affinity of an antibody to its antigens, one such methodology is KinExA™. The Kinetic Exclusion Assay (KinExA™) is a general purpose immunoassay platform (basically a flow spectrofluorimeter) that is capable of measuring equilibrium dissociation constants, and association and dissociation rate constants for antigen/antibody interactions. Since KinExA™ is performed after equilibrium has been obtained it is an advantageous technique to use for measuring the KD of high affinity interactions where the off-rate of the interaction may be very slow. The use of KinExA™ is particularly appropriate in this case where the affinity of antibody and antigen are higher than can be accurately predicted by surface plasmon resonance analysis. The KinExA™ methodology can be conducted generally as described in Drake et al (2004) Analytical Biochemistry 328, 35-43, which is incorporated herein by reference in its entirety, and also as detailed in the Examples section. The term "surface plasmon resonance", as used herein, refers to an optical phenomenon that allows for the analysis of real-time biospecific interactions by detection of alterations in protein concentrations within a biosensor matrix, for example using the BIACORE™ system.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. Also, an antibody "specifically binds" or "preferentially binds" to a target if it binds with greater affinity, avidity, more readily, and/or with greater duration to that target in a sample than it binds to other substances present in the sample. For example, an antibody that specifically or preferentially binds to a TL1A epitope is an antibody that binds this epitope with greater affinity, avidity, more readily, and/or with greater duration than it binds to other TL1A epitopes or non-TL1A epitopes. It is also understood by reading this definition, for example, that an antibody (or moiety or epitope) which specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specific binding" or "preferential binding" includes a compound, e.g., a protein, a nucleic acid, an antibody, and the like, which recognizes and binds to a specific molecule, but does not substantially recognize or bind other molecules in a sample. For instance, an antibody or a peptide receptor which recognizes and binds to a cognate ligand or binding partner (e.g., an anti-TL1A antibody that binds TL1A) in a sample, but does not substantially recognize or bind other molecules in the sample, specifically binds to that cognate ligand or binding partner. Thus, under designated assay conditions, the specified binding moiety (e.g., an antibody or an antigen-binding portion thereof or a receptor or a ligand binding portion thereof) binds preferentially to a particular target molecule and does not bind in a significant amount to other components present in a test sample.

A variety of assay formats may be used to select an antibody or peptide that specifically binds a molecule of interest. For example, solid-phase ELISA immunoassay, immunoprecipitation, Biacore™ (GE Healthcare, Piscataway, NJ), KinExA, fluorescence-activated cell sorting (FACS), Octet™ (ForteBio, Inc., Menlo Park, CA) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice the background signal or noise, more typically more than 10 times background, even more typically, more than 50 times background, more typically, more than 100 times background, yet more typically, more than 500 times background, even more typically, more than 1000 times background, and even more typically, mora than 10,000 times background. Also, an antibody is said to "specifically bind" an antigen when the equilibrium dissociation constant (KD) is ≤1 μM, preferably ≤100 nM, more preferably ≤10 nM, even more preferably, yet more preferably, ≤1 nM, even more preferably, ≤100 pM, yet more preferably, 10 pM, and even more preferably, ≤1 pM.

The term "binding affinity" is herein used as a measure of the strength of a non-covalent interaction between two molecules, e.g., and antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the dissociation constant ($K_D$). In turn, $K_D$ can be determined by measurement of the kinetics of complex formation and dissociation using, e.g., the surface plasmon resonance (SPR) method (Biacore). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D=k_d/k_a$. The value of the dissociation constant can be determined directly by well-known methods, and can be computed even for complex mixtures by methods such as those, for example, set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein. The binding kinetics and binding affinity of the antibody also can be assessed by standard assays known in the art, such as Surface Plasmon Resonance (SPR), e.g. by using a Biacore™ system, or KinExA.

A competitive binding assay can be conducted in which the binding of the antibody to the antigen is compared to the binding of the target by another ligand of that target, such as another antibody or a soluble receptor that otherwise binds the target. The concentration at which 50% inhibition occurs is known as the $K_i$. Under ideal conditions, the $K_i$ is equivalent to $K_D$. The $\kappa_i$ value will never be less than the $K_D$, so measurement of K can conveniently be substituted to provide an upper limit for $K_D$.

Following the above definition, binding affinities associated with different molecular interactions, e.g., comparison of the binding affinity of different antibodies for a given antigen, may be compared by comparison of the $K_D$ values for the individual antibody/antigen complexes. $K_D$ values for antibodies or other binding partners can be determined using methods well established in the art. One method for determining the $K_D$ is by using surface plasmon resonance, typically using a biosensor system such as a Biacore® system.

Similarly, the specificity of an interaction may be assessed by determination and comparison of the $K_D$ value for the interaction of interest, e.g., a specific interaction between an antibody and an antigen, with the $K_D$ value of an interaction not of interest, e.g., a control antibody known not to bind TL1A.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1\times10^{-6}$M or more, more preferably $1\times10^{-5}$ M or more, more preferably $1\times10^{-4}$ M or more, more preferably $1\times10^{-3}$ M or more, even more preferably $1\times10^{-2}$ M or more. An antibody or antigen-binding fragment thereof of the invention is preferably capable of binding to its target with an affinity that is at least two-fold, 10-fold, 50-fold, 100-fold 200-fold, 500-fold, 1, 000-fold or 10,000-fold or greater than its affinity for binding to another non-TL1A molecule.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as described in Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain or antigen-binding portion thereof) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected and/or transformed in vivo with a polynucleotide of this invention.

As used herein, "treatment" is an approach for obtaining beneficial or desired clinical results. For purposes of this invention, beneficial or desired clinical results include, but are not limited to, one or more of the following: improved survival rate (reduced mortality), reduction in inflammatory response to the disease, reduction in the amount of tissue fibrosis, improvement in the appearance of the disease lesions, limitation of the pathological lesions to focal sites, decreased extent of damage from the disease, decreased duration of the disease, and/or reduction in the number, extent, or duration of symptoms related to the disease. The term includes the administration of the compounds or agents of the present invention to prevent or delay the onset of the symptoms, complications, or biochemical indicia of a disease, alleviating the symptoms or arresting or inhibiting further development of the disease, condition, or disorder.

Treatment may be prophylactic (to prevent or delay the onset of the disease, or to prevent the manifestation of clinical or subclinical symptoms thereof) or therapeutic suppression or alleviation of symptoms after the manifestation of the disease.

"Ameliorating" means a lessening or improvement of one or more symptoms as compared to not administering a TL1A antibody. "Ameliorating" also includes shortening or reduction in duration of a symptom.

As used herein, an "effective dosage" or "effective amount" of drug, compound, or pharmaceutical composition is an amount sufficient to affect any one or more beneficial or desired results. In more specific aspects, an effective amount prevents, alleviates or ameliorates symptoms of disease or infection, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a TL1A mediated disease, disorder or condition, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats. In some embodiments, the individual is considered to be at risk for a disease, disorder or condition mediated by or associated with TL1A binding to its receptor and signaling mediated thereby.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, PA, 1990; and Remington, The Science and Practice of Pharmacy 20th Ed. Mack Publishing, 2000).

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g. within the 95% confidence interval for the mean) or within 10 percent of the indicated value, whichever is greater. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

It is understood that wherever embodiments are described herein with the language "comprising," otherwise analogous embodiments described in terms of "consisting of" and/or "consisting essentially of" are also provided. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control.

Exemplary methods and materials are described herein, although methods and materials similar or equivalent to those described herein can also be used in the practice or testing of the present invention. The materials, methods, and examples are illustrative only and not intended to be limiting.

TL1A Antibodies

The present invention relates to antibodies that bind to TL1A. The antibodies preferably specifically bind to TL1A. In particular, the invention relates to antibodies that bind to TL1A and that modulate its activity. For example, an antibody or antigen-binding fragment thereof of the invention may have the ability to decrease or inhibit binding of TL1A to its receptor DR3 and thereby to reduce or inhibit downstream receptor signaling. The invention also relates to compositions comprising such antibodies as well as uses for such antibodies, including therapeutic and pharmaceutical uses.

By the term "TL1A" is meant any naturally occurring form of TL1A, whether monomeric or multimeric, including dimers, trimers, etc., which may be derived from any suitable organism. As used herein, "TL1A" refers to a mammalian TL1A, such as human, rat or mouse, as well as non-human primate, bovine, ovine, or porcine TL1A. Preferably, the TL1A is human (see, e.g., Genbank Accession Number NP_005109, SEQ ID NO:258). The term "TL1A" also encompasses fragments, variants, isoforms, and other homologs of such TL1A molecules. Variant TL1A molecules will generally be characterized by having the same type of activity as naturally occurring TL1A, such as the ability to bind DR3, and the ability to induce receptor-mediated activity.

The TL1A may be in homomultimeric form. The homomultimer may comprise two, three, four, five, six or more TL1A monomer units. In some aspects, the homomultimer may be a homodimer or homotrimer. In some aspects, there are 3 TL1A monomers in the homomultimer, and the TL1A homomultimer is a homotrimer. In some aspects, there are 2 TL1A monomers in the TL1A homomultimer, and the homomultimer is a homodimer.

The TL1A may comprise one or more, two or more, three or more, four or more, five or more, six or more, seven or more, eight or more, nine or more, ten or more, twelve or more or fifteen or more surface accessible residues of TL1A. Where the TL1A comprises a homomultimeric form of TL1A, the target may comprise one or more, two or more, three or more, four or more, five or more, six or more, seven or more, eight or more, nine or more, ten or more, twelve or more, or fifteen or more surface accessible residues of a first subunit of TL1A, and one or more, two or more, three or more, four or more, five or more, six or more, seven or more, eight or more, nine or more, ten or more, twelve or more, or fifteen or more surface accessible residues of a second subunit of TL1A.

The target molecule may comprise a known epitope from TL1A.

The antibody or antigen-binding fragment thereof of the invention specifically binds TL1A and inhibits its interaction with DR3, thereby inhibiting TL1A activity. By the terms "TL1A mediated activity," "TL1A mediated effect," "TL1A activity," "TL1A biological activity" or "TL1A function," as used interchangeably herein, is meant any activity mediated by TL1A interaction with a cognate receptor including, but not limited to, TL1A binding to DR3, through binding of DR3, activation of downstream expression/secretion of cytokines, especially pro-inflammatory cytokines, such as INFγ, IL-6, TNF-α, IL-17, IL-22, IL-4, IL-5, IL-13, IL-25, and other cytokines that well known to persons killed in the art, any other activity of TL1A either known in the art or to be elucidated in the future.

Thus, the methods of the invention use the TL1A antibody or antigen-binding fragment thereof of the invention that blocks, suppresses or reduces (e.g., significantly reduces) TL1A activity, including downstream events mediated by TL1A binding to its receptor, DR3. A TL1A antibody or antigen-binding fragment thereof of the invention can exhibit any one or more of the following characteristics: (a) specifically bind to TL1A; (b) block TL1A interaction with its receptor DR3; (c)block, suppress or reduce downstream signaling events that are activated by DR3; and (d) block suppress or reduce any other TL1A activity of TL1A-mediated activity.

In one embodiment, the disclosure provides any of the following, or compositions (including pharmaceutical compositions) comprising, an antibody having a light chain sequence, or a portion thereof, and a heavy chain, or a portion thereof, derived from any of the following antibodies: 1D1, 1D1 1.27, 1D1 1.28, 1D1 1.29, 1D1 1.30, 1D1 1.31, 1D1 1.32, 1D1 1.33, 1D1 1.34, 15A9, 15C11, 7D4, 22F9, 9B3, 2B11.

The antibodies useful in the present invention can encompass monoclonal antibodies, polyclonal antibodies, antibody fragments (e.g., Fab, Fab', $F(ab')_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the TL1A antibody is a monoclonal antibody. In some embodiments, the antibody is a chimeric, humanized or human antibody. In a particular embodiment, the antibody is a human antibody.

In some cases, antibodies of the present invention are defined by the complementarity determining regions ("CDRs"). In certain cases, the CDRs are in a human variable domain. In another embodiment, the CDRs are within a humanized variable domain. In still other embodiments, the CDRs are within a chimeric variable domain. The antibody or antigen-binding fragment thereof according to the present invention includes an antibody or antigen-binding fragment thereof of any class, such as IgG, IgA, IgE or IgM (or sub-class thereof). In one embodiment, the antibody is an IgG, including any of the major subclasses (e.g., $IgG_1$, $IgG_2$, $IgG_3$, $IgG_4$). In one embodiment, the antibody is of the subtype $IgG_1$. In another embodiment, the antibody is of the subtype $IgG_2$. In other cases, the antibody can be of the $IgG_3$ subtype. In still other cases, the antibody can be $IgG_4$. In other cases, the antibody can be an IgA antibody, including any of its subtypes. In one embodiment, the antibody is $IgA_1$. In another embodiment, the antibody is $IgA_2$.

In one embodiment, the antibody or antigen-binding fragment thereof according to the present invention comprises a variable region which comprises framework regions, wherein the framework regions are selected from the group consisting of IgG, IgA, IgM IgE and IgD framework regions. In another embodiment, the antibody or antigen-binding fragment thereof according to the present invention comprises a variable region which comprises framework regions, wherein the framework regions are selected from the group consisting of $IgG_1$, $IgG_2$, $IgG_3$, $IgG_4$ framework regions. In still another embodiment, the antibody or antigen-binding fragment thereof according to the present invention comprises a variable region which comprises framework regions, wherein the framework regions are selected from the group consisting of a human, humanized and chimeric framework region.

The TL1A antibodies of the invention may be made by any method known in the art. General techniques for production of human and mouse antibodies are known in the art and/or are described herein.

Methods known in the art can be employed to detect and/or measure a reduction, amelioration, or neutralization in TL1A activity mediated by the antibodies or antigen binding fragments described herein. In some embodiments, a TL1A antibody is identified by incubating a candidate agent (e.g., DR3) with TL1A and monitoring binding and/or attendant reduction or inhibition of a biological activity of TL1A. The binding assay may be performed with, e.g., purified TL1A polypeptide(s), or with cells naturally expressing various receptors, or transfected to express, TL1A receptors. In one embodiment, the binding assay is a competitive binding assay, where the ability of a candidate antibody to compete with a known TL1A antibody for TL1A binding is evaluated. The assay may be performed in various formats, including the ELISA format. In some embodiments, a TL1A antibody is identified by incubating a candidate antibody with TL1A and monitoring binding. In some embodiments, a TL1A antibody is identified by incubating a candidate antibody (e.g., a human anti-TL1A antibody) with TL1A and monitoring the binding of a second TL1A antibody to TL1A to assess whether one antibody competes for binding of TL1A with the second antibody.

In addition, the activity of a candidate TL1A antibody can be measured by bioassays known to test the targeted biological activities. In some embodiments, an in vitro cell assay is used to further characterize a candidate TL1A antibody. For example, bioassays can be used to screen candidates directly. Some of the methods for identifying and characterizing TL1A antibody are described in detail in the Examples.

As discussed above, the TL1A antibodies of the invention exhibit one or more of the following characteristics: (a) specifically bind to TL1A; (b) block TL1A interaction with its receptor, DR3, and (c) attenuate or block downstream signaling events. Preferably, a TL1A antibody or antigen-binding fragment thereof of the invention has at least one of these features, more preferably, the antibody has two or more of these features. More preferably, the antibodies have all of the features.

TL1A Epitopes

TL1A antibodies may be characterized using additional methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, New York, 1999. In an additional example, epitope mapping can be used to determine the sequence to which TL1A antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with TL1A antibody. In another example, the epitope to which the TL1A antibody binds can be determined in a systematic screening by using overlapping peptides derived from the TL1A sequence and determining binding by the antibody. According to the gene fragment expression assays, the open reading frame encoding TL1A can be fragmented either randomly or by specific genetic constructions and the reactivity of the expressed fragments of TL1A with the antibody to be tested is determined. The gene fragments may, for example, be produced by PCR and then transcribed and translated into protein in vitro, in the presence of radioactive amino acids. The binding of the antibody to the radioactively labeled TL1A fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant TL1A in which various residues of the TL1A polypeptide have been replaced with alanine. By assessing binding of the antibody to the mutant TL1A, the importance of the particular TL1A residues to antibody binding can be assessed.

Yet another method which can be used to characterize a TL1A antibody is to use competition assays with other antibodies known to bind to the same antigen, i.e., various fragments on TL1A, to determine if the TL1A antibody binds to the same epitope as other antibodies. Competition assays are well known to those of skill in the art.

Further, the epitope for a given antibody/antigen binding pair can be defined and characterized at different levels of detail using a variety of experimental and computational epitope mapping methods. The experimental methods include mutagenesis, X-ray crystallography, Nuclear Magnetic Resonance (NMR) spectroscopy, hydrogen/deuterium exchange Mass Spectrometry (H/D-MS) and various competition binding methods well-known in the art. As each method relies on a unique principle, the description of an epitope is intimately linked to the method by which it has been determined. Thus, the epitope for a given antibody/antigen pair will be defined differently depending on the epitope mapping method employed.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level the epitope can be characterized by the spatial coordinates defining the atomic contacts between the Ag and Ab. At a further less detailed level the epitope can be characterized by the amino acid residues that it comprises as defined by a specific criterium, e.g., by distance between atoms (e.g.,heavy, i.e., non-hydrogen atoms) in the Ab and the Ag. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag (e.g. using alanine scanning).

In the context of an X-ray derived crystal structure defined by spatial coordinates of a complex between an antibody, e.g., a Fab fragment, and its Ag, the term epitope is herein, unless otherwise specified or contradicted by context, specifically defined as TL1A residues characterized by having a heavy atom (i.e. a non-hydrogen atom) within a distance of 4 Å from a heavy atom in the Ab. Alternatively, a given TL1A amino acid residue is considered to be part of an epitope if it participates in a hydrogen bond with the antibody or with a water molecule that is also hydrogen bonded to the antibody (water-mediated hydrogen bonding) or it participates in a salt bridge to a residue on the antibody, or if it has a non-zero change in buried surface area due to interaction with the antibody. Alternatively, a given TL1A amino acid residue is considered to be part of an epitope if it participates in a hydrogen bond with the antibody, or if it is hydrogen bonded with a water molecule that is also hydrogen bonded to the antibody (water-mediated hydrogen bonding), or if it participates in a salt bridge with a residue on the antibody, or if it has a non-zero change in buried surface area due to interaction with the antibody. Thus, an amino acid on the antibody is considered to "bind" an amino acid on TL1A if at least one of these conditions is satisfied, e.g., the TL1A amino acid residue has a heavy atom within 4 Å from a heavy atom on an amino acid residue of the antibody, the TL1A amino acid residue participates in a hydrogen bond with an amino acid residue of the antibody, the TL1A amino acid residue is hydrogen bonded with a water molecule where the same water molecule is also hydrogen bonded with an amino acid residue of the antibody, the TL1A amino acid residue participates in a salt bridge with an amino acid residue of the antibody, and the TL1A amino acid residue has a non-zero change in buried surface area due to interaction with the antibody.

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described at the amino acid level, e.g., determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

Epitopes characterized by competition binding are said to be overlapping if the binding of the corresponding antibodies are mutually exclusive, i.e., binding of one antibody excludes simultaneous or consecutive binding of the other antibody. The epitopes are said to be separate (unique) if the antigen is able to accommodate binding of both corresponding antibodies simultaneously.

The definition of the term "paratope" is derived from the above definition of "epitope" by reversing the perspective. Thus, the term "paratope" refers to the area or region on the antibody which specifically binds an antigen, i.e., the amino acid residues on the antibody which make contact with the antigen (TL1A) as "contact" is defined elsewhere herein.

In the context of an X-ray derived crystal structure defined by spatial coordinates of a complex between an antibody, e.g., a Fab fragment or two Fab fragments, and its antigen, the term paratope is herein, unless otherwise specified or contradicted by context, specifically defined as antigen residues characterized by having a heavy atom (i.e., a non-hydrogen atom) within a distance of 4 Å from a heavy atom in TL1A. Alternatively or additionally, a given TL1A amino acid residue is considered to be part of an epitope if it participates in a hydrogen bond with the antibody or with a water molecule that is also hydrogen bonded to the antibody (water-mediated hydrogen bonding) or if it participates in a salt bridge to a residue on the antibody, or if it has a non-zero change in buried surface area due to interaction with the antibody. Any amino acids according to the foregoing are said to "contact" each other.

The epitope and paratope for a given antibody/antigen pair may be identified by routine methods. For example, the general location of an epitope may be determined by assessing the ability of an antibody to bind to different fragments or variant TL1A polypeptides. The specific amino acids within TL1A that make contact with an antibody (epitope) and the specific amino acids in an antibody that make contact with TL1A (paratope) may also be determined using routine methods, such as those described in the examples. For example, the antibody and target molecule may be combined and the antibody/antigen complex may be crystallized. The crystal structure of the complex may be determined and used to identify specific sites of interaction between the antibody and its target.

An antibody or antigen-binding fragment thereof according to the current invention may bind to the same epitope or domain of TL1A as the antibodies of the invention that are specifically disclosed herein. For example, other yet unidentified antibodies of the invention may be identified by comparing their binding to TL1A with that of any of the following monoclonal antibodies: 1D1, 1D1 1.27, 1D1 1.28, 1D1 1.29, 1D1 1.30, 1D1 1.31, 1D1 1.32, 1D1 1.33, 1D1 1.34, 15A9, 15C11, 7D4, 22F9, 9B3, 2B11, and variants thereof; or by comparing the function of yet unidentified antibodies with that of the antibodies described herein; and/or by comparing the epitope/contact residues on TL1A of yet unidentified antibodies with those of the antibodies of the invention. Analyses and assays that may be used for the purpose of such identification include assays assessing the competition for binding of TL1A between the antibody or antigen-binding fragment thereof of interest and DR3, in biological activity assays as described in Examples 10-14, and in analysis of the crystal structure of the antibody.

As disclosed herein, such a crystal structure analysis was carried out for the interaction between the 1D1 parental antibody and TL1A, and variant antibody 1D1 1.31 and TL1A. This analysis is described in more detail in the examples. The binding epitope of antibody 1D1 and TL1A, and antibody 1D1 1.31 and TL1A, were mapped as also described in further detail in the examples.

Disclosed herein are also detailed interactions between TL1A and its natural ligand, DR3. As such, antibodies which "contact" TL1A at the same amino acid residues as DR3 would be expected to interfere with the interaction between TL1A and DR3. As such, in some embodiments, a TL1A epitope bound by the antibody or antigen-binding fragment thereof of the present invention encompasses one or more of the TL1A residues selected from T30 (T100), V31 (V101), V32 (V102), R33 (R103), E50 (E120), L53 (L123), G54 (G124), R86 (R156), G87 (G157), M88 (M158), S136 (S206), N137 (N207), F139 (F209), S164 (S234), L165 (L235), Y168 (Y238), T169 (T239), K170 (K240), E171 (E241), N42 (N112), F44 (F114), K103 (K173), P104 (P174), D105 (D175), S106 (S176), S117 (S187), Y118 (Y188), P119 (P189), E120 (E190), Q151 (Q221), according to the numbering of the amino acid sequence of TL1A as set forth in SEQ ID NO:254 [numbering of SEQ ID NO: 258 in parenthesis].

As shown in Table 42, which displays the amino acids of TL1A that interact with the ligand DR3 and antibodies 1D1 1.31, 1D1, 26B11 and 7B4, several antibodies described herein interact with the same amino acids as those which interact with the ligand DR3. Therefore, in a particular embodiment, a TL1A epitope bound by the antibody encompasses one or more of the TL1A residues selected from the group consisting of: V31 (V101), V32 (V102), R33 (R103), E50 (E120), L53 (L123), G54 (G124), R86 (R156), G87 (G157), M88 (M158), S136 (S206), N137 (N207), S164 (S234), L165 (L235), Y168 (Y238), T169 (T239), K170 (K240), E171 (E241), S117 (S187), Y118 (Y188), P119 (P189), and Q151 (Q221), according to the numbering of the amino acid sequence of TL1A as set forth in SEQ ID NO:254 [numbering of SEQ ID NO: 258 in parenthesis].

Figure 5:
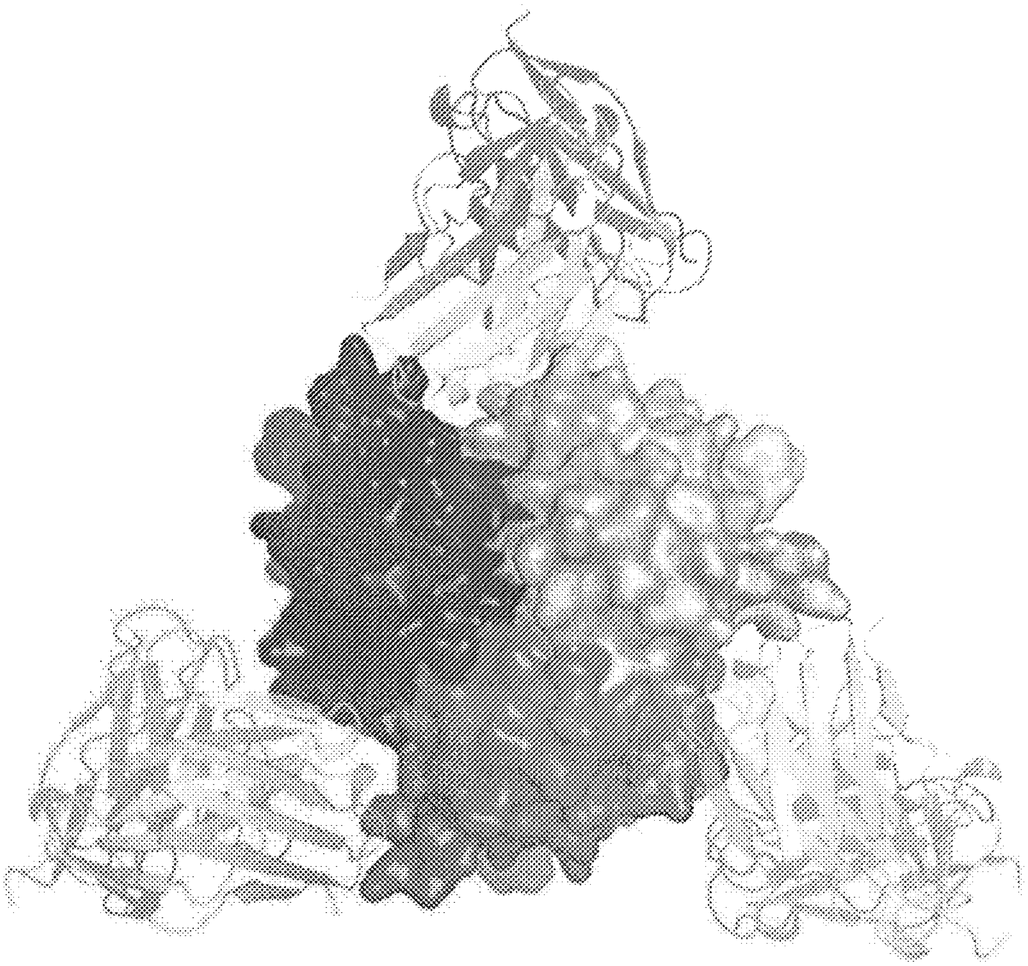
FIG. 5 depicts the co-crystal structure of three 1D1 scFv molecules (ribbon) bound to three TL1A monomers (surface model with TL1A molecules shown as light gray, dark gray, and black). The heavy chain of 1D1 is closer to the viewer with the light chain behind it.

As depicted in FIG. 5, in some embodiments, TL1A antibodies 1D1 and 1D1 1.31 bind to a TL1A homotrimer between two TL1A monomers. Accordingly, a single 1D1 or 1D1 1.31 may bind to two TL1A monomers simultaneously, and a single antibody is unlikely to bind to all of the epitope residues on a single TL1A monomer. Alternatively, it is possible that one TL1A antibody or antigen-binding fragment thereof of the invention may bind some of the epitopes on a TL1A protein, while another TL1A antibody binds the other epitopes.

Thus, in some embodiments, the TL1A epitope bound by the antibody or antigen-binding fragment thereof of the invention encompasses one or more of the TL1A residues selected from K113, T115, S117, Y118, P119, P121, T122, Q123, M147, F148, S149, Q151, V31, V32, R33, E50, H51, E52, L53, G54, L55, A56, F57, T58, E91, Y168, T169, K170, and E171, according to the numbering of the amino acid sequence of TL1A as set forth in SEQ ID NO:254. Given the geometry of the binding of antibodies 1D1 and 1D1 1.31 to TL1A between two TL1A monomers, some of the binding residues are found on the first monomer (also called monomer A of chain A of TL1A), and other binding residues are found on the second monomer (also called monomer B or chain B or TL1A). In particular, one or more of the TL1A binding epitope residues on monomer A are selected from K113, T115, S117, Y118, P119, P121, T122, Q123, M147, F148, S149, and Q151, and one or more TL1A binding epitope residues on monomer B are selected from V31, V32, R33, E50, H51, E52, L53, G54, L55, A56, F57, T58, E91, Y168, T169, K170, and E171. In some embodiment, the epitopes found on monomer A are bound by one TL1A antibody, while the epitopes found on monomer B are bound another TL1A antibody.

In another embodiment, a TL1A antibody or antigen-binding fragment thereof of the disclosure binds to an epitope on TL1A comprising one or more of the TL1A residues selected from K113, Y118, T122, Q123, M147, F148, S149, Q151, V31, V32, R33, E50, H51, E52, L53, G54, L55, A56, F57, Y168, T169, K170, and E171, according to the numbering of the amino acid sequence of TL1A as set forth in SEQ ID NO:254), wherein one or more of the TL1A binding epitope residues on monomer A are selected from the group consisting of K113, Y118, T122, Q123, M147, F148, S149, Q151, according to the numbering of the amino acid sequence of TL1A as set forth in SEQ ID NO:254, and wherein one or more of the TL1A binding epitope residues on monomer B are selected from the group consisting of V31, V32, R33, E50, H51, E52, L53, G54, L55, A56, F57,Y168, T169, K170, and E171, according to the numbering of the amino acid sequence of TL1A as set forth in SEQ ID NO:254.

In a further embodiment, the TL1A epitope may comprise amino acid residues selected from the group consisting of K113, Y118, T122, M147, S149, Q151, V32, R33, E50, H51, E52, L53, G54, L55, A56, F57, Y168, T169, K170, and E171, according to the numbering of the amino acid sequence of TL1A as set forth in SEQ ID NO:254; wherein one or more of the TL1A binding epitope residues on monomer A are selected from the group consisting of K113, Y118, T122, M147, S149, and Q151, according to the numbering of the amino acid sequence of TL1A as set forth in SEQ ID NO:254, and wherein one or more of the TL1A binding epitope residues on monomer B are selected from the group consisting of V32, R33, E50, H51, E52, L53, G54, L55, A56, F57, Y168, T169, K170, and E171, according to the numbering of the amino acid sequence of TL1A as set forth in SEQ ID NO:254, wherein the residues are involved in electrostatic interactions between a TL1A antibody or antigen-binding fragment thereof of the invention and TL1A, or the buried surface area surrounding the residue is greater than 20 Å$^2$ when bound to a TL1A antibody or antigen-binding fragment thereof of the invention.

In another embodiment, the TL1A epitope may comprise amino acid residues selected from the group consisting of K113, Y118, T122, S149, R33, E50, E52, L53, A56, F57, Y168, T169, and E171, according to the numbering of the amino acid sequence of TL1A as set forth in SEQ ID NO:254; wherein one or more of the TL1A binding epitope residues on monomer A are selected from the group consisting of K113, Y118, T122, and S149, according to the numbering of the amino acid sequence of TL1A as set forth in SEQ ID NO:254, and wherein one or more of the TL1A binding epitope residues on monomer B are selected from the group consisting of R33, E50, E52, L53, A56, F57, Y168, T169, and E171, according to the numbering of the amino acid sequence of TL1A as set forth in SEQ ID NO:254, wherein the residues are involved in electrostatic interactions between a TL1A antibody or antigen-binding fragment thereof of the invention and TL1A, or the buried surface area surrounding the residue is greater than 40 Å$^2$ when bound to a TL1A antibody or antigen-binding fragment thereof of the invention.

In some embodiments, the TL1A epitope bound by the TL1A antibodies of the present disclosure are selected from the group consisting of one or more amino acid residues 117-123 of SEQ ID NO:254 and residues 50-158 of SEQ ID NO:254, wherein one or more of the residues on monomer A are selected from from residues 117-123 of SEQ ID NO:254, and one or more of the residues on monomer B are selected from residues 50-58 of SEQ ID NO:254.

In another embodiment, a TL1A antibody or antigen-binding fragment thereof of the disclosure binds to an epitope on TL1A comprising one or more of the TL1A residues selected from K113, Y118, T122, S149, E50, E52, L53, A56, Y168, T169 and E171, according to the numbering of the amino acid sequence of TL1A as set forth in SEQ ID NO:254, wherein one or more of the TL1A binding epitope residues on monomer A are selected from the group consisting of K113, Y118, T122, and S149, according to the numbering of the amino acid sequence of TL1A as set forth in SEQ ID NO:254, and wherein one or more of the TL1A binding epitope residues on monomer B are selected from the group consisting of E50, E52, L53, A56, Y168, T169 and E171, according to the numbering of the amino acid sequence of TL1A as set forth in SEQ ID NO:254.

In a further embodiment, a TL1A antibody or antigen-binding fragment thereof of the disclosure binds to an epitope on TL1A comprising one or more of the TL1A residues selected from K113, Y118, T122, S149, E50, E52, A56, and Y168, according to the numbering of the amino acid sequence of TL1A as set forth in SEQ ID NO:254, wherein one or more of the TL1A binding epitope residues on monomer A are selected from the group consisting of K113, Y118, T122, and S149, according to the numbering of the amino acid sequence of TL1A as set forth in SEQ ID NO:254, and wherein one or more of the TL1A binding epitope residues on monomer B are selected from the group consisting of E50, E52, A56, and Y168, according to the numbering of the amino acid sequence of TL1A as set forth in SEQ ID NO:254.

In another embodiment, a TL1A antibody or antigen-binding fragment thereof of the disclosure binds to an epitope on TL1A comprising one or more of the TL1A residues selected from K113, Y118, P119, T122, Q123, F148, S149, Q151, V31, V32, R33, E50, E52, L53, G54, L55, A56, F57, E91, Y168, T169, K170, and E171, according to the numbering of the amino acid sequence of TL1A as set forth in SEQ ID NO:254, wherein one or more of the TL1A binding epitope residues on monomer A are selected from the group consisting of K113, Y118, P119, T122, Q123, F148, S149, and Q151, according to the numbering of the amino acid sequence of TL1A as set forth in SEQ ID NO:254, and wherein one or more of the TL1A binding epitope residues on monomer B are selected from the group consisting of V31, V32, R33, E50, E52, L53, G54, L55, A56, F57, E91, Y168, T169, K170, and E171, according to the numbering of the amino acid sequence of TL1A as set forth in SEQ ID NO:254, wherein a heavy atom of the residues is found within 3.8 Å of a heavy atom of an amino acid residue of antibody 1D1 1.31 when bound TL1A is found with 1D1.

In some embodiments, a TL1A antibody or antigen-binding fragment thereof of the disclosure binds to an epitope on TL1A comprising one or more of the TL1A residues selected from K113, Y118, T122, F148, S149, V31, V32, E50, E52, L53, G54, L55, A56, Y168, T169, K170, and E171, according to the numbering of the amino acid sequence of TL1A as set forth in SEQ ID NO:254, wherein one or more of the TL1A binding epitope residues on monomer A are selected from the group consisting of K113, Y118, T122, F148, and S149, according to the numbering of the amino acid sequence of TL1A as set forth in SEQ ID NO:254, and wherein one or more of the TL1A binding epitope residues on monomer B are selected from the group consisting of V31, V32, E50, E52, L53, G54, L55, A56, Y168, T169, K170, and E171, according to the numbering of the amino acid sequence of TL1A as set forth in SEQ ID NO:254, wherein the TL1A epitope residues are found within 3.8 Å of residues the TL1A antibody when the TL1A antibody is bound to TL1A.

In another embodiment, the antibody 1D1 binds to an epitope on TL1A comprising one or more of the TL1A residues selected from K113, T115, Y118, P121, T122, Q123, M147, F148, S149, Q151, V31, V32, R33, E50, H51, E52, L53, G54, L55, A56, F57, T58, E91, Y168, T169, K170, and E171, according to the numbering of the amino acid sequence of TL1A as set forth in SEQ ID NO:254, wherein one or more of the TL1A binding epitope residues on monomer A are selected from the group consisting of K113, T115, Y118, P121, T122, Q123, M147, F148, S149, and Q151 according to the numbering of the amino acid sequence of TL1A as set forth in SEQ ID NO:254, and wherein one or more of the TL1A binding epitope residues on monomer B are selected from the group consisting of V31, V32, R33, E50, H51, E52, L53, G54, L55, A56, F57, T58, E91, Y168, T169, K170, and E171, according to the numbering of the amino acid sequence of TL1A as set forth in SEQ ID NO:254.

In a further embodiment, the antibody 1D1 binds to an epitope on TL1A comprising one or more of the TL1A residues selected from Y118, M147, S149, R33, E50, E52, L55, A56, and Y168, according to the numbering of the amino acid sequence of TL1A as set forth in SEQ ID NO:254, wherein one or more of the TL1A binding epitope residues on monomer A are selected from the group consisting of Y118, M147, and S149 according to the numbering of the amino acid sequence of TL1A as set forth in SEQ ID NO:254, and wherein one or more of the TL1A binding epitope residues on monomer B are selected from the group consisting of R33, E50, E52, L55, A56, and Y168 according to the numbering of the amino acid sequence of TL1A as set forth in SEQ ID NO:254; wherein the epitopes are involved in electrostatic interactions between antibody 1 D1 and TL1A.

In a further embodiment, the antibody 1D1 binds to an epitope on TL1A comprising one or more of the TL1A residues selected from K113, Y118, T122, S149, Q151, R33, E50, E52, L53, G54, L55, A56, F57, T58, Y168, T169, K170, and E171, according to the numbering of the amino acid sequence of TL1A as set forth in SEQ ID NO:254, wherein one or more of the TL1A binding epitope residues on monomer A are selected from the group consisting of K113, Y118, T122, S149, and Q151 according to the numbering of the amino acid sequence of TL1A as set forth in SEQ ID NO:254, and wherein one or more of the TL1A binding epitope residues on monomer B are selected from the group consisting of R33, E50, E52, L53, G54, L55, A56, F57, T58, Y168, T169, and E171 according to the numbering of the amino acid sequence of TL1A as set forth in SEQ ID NO:254; wherein the epitopes are involved in electrostatic interactions between antibody 1D1 and TL1A or the buried surface area surrounding the residue is greater than 20 $Å^2$ when bound to a TL1A antibody or antigen-binding fragment thereof of the invention.

In some embodiments, the antibody 1D1 binds to an epitope on TL1A comprising one or more of the TL1A residues selected from Y118, E50, E52, and L53, according to the numbering of the amino acid sequence of TL1A as set forth in SEQ ID NO:254, wherein Y118 is found on monomer A, and wherein one or more of the TL1A binding epitope residues on monomer B are selected from the group consisting of E50, E52, L53 according to the numbering of the amino acid sequence of TL1A as set forth in SEQ ID NO:254; wherein the epitopes are involved in salt bridge interactions between antibody 1 D1 and TL1A or the buried surface area surrounding the residue is greater than 100 $Å^2$ when bound to a TL1A antibody or antigen-binding fragment thereof of the invention.

In yet another embodiment, the antibody 1D1 binds to an epitope on TL1A comprising one or more of the TL1A residues selected from K113, Y118, T122, F148, S149, Q151, V31, V32, R33, E50, E52, L53, G54, L55, A56, F57, E91, Y168, T169, K170, and E171, according to the numbering of the amino acid sequence of TL1A as set forth in SEQ ID NO:254, wherein one or more of the TL1A binding epitope residues on monomer A are selected from the group consisting of K113, Y118, T122, F148, S149, and Q151 according to the numbering of the amino acid sequence of TL1A as set forth in SEQ ID NO:254, and wherein one or more of the TL1A binding epitope residues on monomer B are selected from the group consisting of V31, V32, R33, E50, E52, L53, G54, L55, A56, F57, E91, Y168, T169, K170, and E171 according to the numbering of the amino acid sequence of TL1A as set forth in SEQ ID NO:254; wherein the residues are found within 3.8 A of antibody 1D1 when bound TL1A is found with 1D1.

In another embodiment, the antibody 1D1 1.31 binds to an epitope on TL1A comprising one or more of the TL1A residues selected from K113, S117, Y118, P119, T122, Q123, M147, F148, S149, Q151, V31, V32, R33, E50, H51, E52, L53, G54, L55, A56, F57, Y168, T169, K170, and E171, according to the numbering of the amino acid sequence of TL1A as set forth in SEQ ID NO:254, wherein one or more of the TL1A binding epitope residues on monomer A are selected from the group consisting of K113, S117, Y118, P119, T122, Q123, M147, F148, S149, and Q151 according to the numbering of the amino acid sequence of TL1A as set forth in SEQ ID NO:254, and wherein one or more of the TL1A binding epitope residues on monomer B are selected from the group consisting of V31, V32, R33, E50, H51, E52, L53, G54, L55, A56, F57, Y168, T169, K170, and E171, according to the numbering of the amino acid sequence of TL1A as set forth in SEQ ID NO:254.

In a further embodiment, the antibody 1D1 1.31 binds to an epitope on TL1A comprising one or more of the TL1A residues selected from K113, T122, S149, E50, E52, A56, Y168, T169, and E171, according to the numbering of the amino acid sequence of TL1A as set forth in SEQ ID NO:254, wherein one or more of the TL1A binding epitope residues on monomer A are selected from the group consisting of K113, T122, and S149 according to the numbering of the amino acid sequence of TL1A as set forth in SEQ ID NO:254, and wherein one or more of the TL1A binding epitope residues on monomer B are selected from the group consisting of E50, E52, A56, Y168, T169, and E171 according to the numbering of the amino acid sequence of TL1A as set forth in SEQ ID NO:254; wherein the epitopes are involved in electrostatic interactions between antibody 1D1 1.31 and TL1A.

In a further embodiment, the antibody 1D1 1.31 binds to an epitope on TL1A comprising one or more of the TL1A residues selected from K113, S117, Y118, T122, S149, Q151, R33, E50, E52, L53, G54, L55, A56, F57, Y168, T169, and E171, according to the numbering of the amino acid sequence of TL1A as set forth in SEQ ID NO:254, wherein one or more of the TL1A binding epitope residues on monomer A are selected from the group consisting of K113, S117, Y118, T122, S149, and Q151 according to the numbering of the amino acid sequence of TL1A as set forth in SEQ ID NO:254, and wherein one or more of the TL1A binding epitope residues on monomer B are selected from the group consisting of R33, E50, E52, L53, G54, L55, A56, F57, Y168, T169, and E171 according to the numbering of the amino acid sequence of TL1A as set forth in SEQ ID NO:254; wherein the epitopes are involved in electrostatic interactions between antibody 1D1 1.31 and TL1A or the buried surface area surrounding the residue is greater than 20 $Å^2$ when bound to antibody 1D1 1.31.

In some embodiments, the antibody 1D1 1.31 binds to an epitope on TL1A comprising one or more of the TL1A residues selected from K113, Y118, T122, E50, E52, and L53, according to the numbering of the amino acid sequence of TL1A as set forth in SEQ ID NO:254, wherein one or more of the TL1A binding epitope residues on monomer A are selected from the group consisting of K113, Y118, and T122, and wherein one or more of the TL1A binding epitope residues on monomer B are selected from the group consisting of E50, E52, L53 according to the numbering of the amino acid sequence of TL1A as set forth in SEQ ID NO:254; wherein the epitopes are involved in salt bridge interactions between antibody 1D1 and TL1A or the buried surface area surrounding the residue is greater than 100 $Å^2$ when bound to a TL1A antibody or antigen-binding fragment thereof of the invention.

In yet another embodiment, the antibody 1D1 1.31 binds to an epitope on TL1A comprising one or more of the TL1A residues selected from K113, Y118, P119, T122, Q123, F148, S149, V31, V32, E50, E52, L53, G54, L55, A56, Y168, T169, K170, and E171, according to the numbering of the amino acid sequence of TL1A as set forth in SEQ ID NO:254, wherein one or more of the TL1A binding epitope residues on monomer A are selected from the group consisting of K113, Y118, P119, T122, Q123, F148, and S149 according to the numbering of the amino acid sequence of TL1A as set forth in SEQ ID NO:254, and wherein one or more of the TL1A binding epitope residues on monomer B are selected from the group consisting of V31, V32, E50, E52, L53, G54, L55, A56, Y168, T169, K170, and E171 according to the numbering of the amino acid sequence of TL1A as set forth in SEQ ID NO:254; wherein the residues are found within 3.8 Å of antibody 1D1 1.31 when bound TL1A is found with 1D1.

In a further embodiment, the antibody 1D1 comprises a paratope encompassing one or more heavy chain variable domain residues selected from Gly26, Tyr27, Ser28, Thr30, Tyr31, Trp50, Tyr53, Asn54, Asn56, Asn58, Thr73, Arg76, Tyr97, Gly99, Ser100, Gly100A, Ser100B, and Arg100D, based on Kabat numbering with respect to the sequence of SEQ ID NO:104, and one or more light chain variable domain residues selected from Tyr32 and Trp94 based on Kabat numbering with respect to the sequence of SEQ ID NO:102.

In yet another embodiment, the antibody 1D1 1.31 comprises a paratope encompassing one or more heavy chain variable domain residues selected from Gly26, Asp28, Thr30, Tyr31, Trp50, Tyr53, Asn54, Asn56, His58, Thr73, Arg76, Tyr97, Gly99, Ser100, Glyl00A, Ser100B, and Arg100D, based on Kabat numbering with respect to the sequence of SEQ ID NO:104, and one or more light chain variable domain residues selected from Tyr32 and Trp94 based on Kabat numbering with respect to the sequence of SEQ ID NO:102.

An antibody or antigen-binding fragment thereof of the invention may have the ability to compete or cross-compete with another antibody or antigen-binding fragment thereof of the invention for binding to TL1A as described herein. For example, an antibody or antigen-binding fragment thereof of the invention may compete or cross-compete with antibodies described herein for binding to TL1A, or to a suitable fragment or variant of TL1A that is bound by the antibodies disclosed herein.

That is, if a first antibody competes with a second antibody for binding to TL1A, but it does not compete where the second antibody is first bound to TL1A, it is still deemed to compete with the second antibody (also referred to as unidirectional competition). Where an antibody competes with another antibody regardless of which antibody is first bound to TL1A, then the antibody cross-competes for binding to TL1A with the other antibody. Such competing or cross-competing antibodies can be identified based on their ability to compete/cross-compete with a known antibody or antigen-binding fragment thereof of the invention in standard binding assays. For example, SPR e.g. by using a Biacore™ system, ELISA assays or flow cytometry may be used to demonstrate competition/cross-competition. Such competition/cross-competition may suggest that the two antibodies bind to identical, overlapping or similar epitopes.

An antibody or antigen-binding fragment thereof of the invention may therefore be identified by a method that comprises a binding assay which assesses whether or not a test antibody is able to compete/cross-compete with a reference antibody or antigen-binding fragment thereof of the invention (e.g., 1D1, 1D1 variants, 7D4, 9B3, and 26B11, among others) for a binding site on the target molecule. Methods for carrying out competitive binding assays are disclosed herein and/or are well known in the art. For example they may involve binding a reference antibody or antigen-binding fragment thereof of the invention to a target molecule using conditions under which the antibody can bind to the target molecule. The antibody/target complex may then be exposed to a test/second antibody and the extent to which the test antibody is able to displace the reference antibody or antigen-binding fragment thereof of the invention from antibody/target complexes may be assessed. An alternative method may involve contacting a test antibody with a target molecule under conditions that allow for antibody binding, then adding a reference antibody or antigen-binding fragment thereof of the invention that is capable of binding that target molecule and assessing the extent to which the reference antibody or antigen-binding fragment thereof of the invention is able to displace the test antibody from antibody/target complexes or to simultaneously bind to the target (i.e., non-competing antibody).

The ability of a test antibody to inhibit the binding of a reference antibody or antigen-binding fragment thereof of the invention to the target demonstrates that the test antibody can compete with a reference antibody or antigen-binding fragment thereof of the invention for binding to the target and thus that the test antibody binds to the same, or substantially the same, epitope or region on the TL1A protein as the reference antibody or antigen-binding fragment thereof of the invention. A test antibody that is identified as competing with a reference antibody or antigen-binding fragment thereof of the invention in such a method is also an antibody or antigen-binding fragment thereof of the present invention. The fact that the test antibody can bind TL1A in the same region as a reference antibody or antigen-binding fragment thereof of the invention and can compete with the reference antibody or antigen-binding fragment thereof of the invention suggests that the test antibody may act as a ligand at the same binding site as the antibody or antigen-binding fragment thereof of the invention and that the test antibody may therefore mimic the action of the reference antibody and is, thus, an antibody or antigen-binding fragment thereof of the invention. This can be confirmed by comparing the activity of TL1A in the presence of the test antibody wih the activity of TL1A in the presence of the reference antibody under otherwise identical conditions, using an assay as more fullydescribed elsewhere herein.

The reference antibody or antigen-binding fragment thereof of the invention may be an antibody as described herein, such as 1D1, 1D1 1.27, 1D1 1.28, 1D1 1.29, 1D1 1.30, 1D1 1.31, 1D1 1.32, 1D1 1.33, 1D1 1.34, 15A9, 15C11, 7D4, 22F9, 9B3, 2B11, or any variant, or fragment thereof, as described herein that retains the ability to bind to TL1A. An antibody or antigen-binding fragment thereof of the invention may bind to the same epitope as the reference antibodies described herein or any variant or fragment thereof as described herein that retains the ability to bind to TL1A.

As stated previously elsewhere herein, specific binding may be assessed with reference to binding of the antibody to a molecule that is not the target. This comparison may be made by comparing the ability of an antibody to bind to the target and to another molecule. This comparison may be made as described above in an assessment of $K_D$ or $K_i$. The other molecule used in such a comparison may be any molecule that is not the target molecule. Preferably, the other molecule is not identical to the target molecule. Preferably the target molecule is not a fragment of the target molecule.

The $K_D$ of an antibody or antigen-binding fragment thereof of the current invention may be less than 50 nM, such as less than 10 nM, such as less than 5 nM, such as less than 1 nM, such as less than 750 pM, such as less than 500 pM, such as less than 100 pM, such as less than 50 pM, such as less than 25 pM, such as less than 20 pM, such as less than 10pM, such as less than 9 pM, such as less than 9 pM, such as less than 7 pM, such as less than 6 pM, such as less than 5 pM, such as less than 4 pM, such as less than 3 pM, such as less than 2 pM, such as less than 1pM,such as between 20 pM and 1 pM.

In other embodiments, the binding affinity ($K_D$) of TL1A antibody to TL1A can be about 0.001 to about 250 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, about 2 pM, or about 1 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, about 2 pM, or about 1pM. In some embodiments, the $K_D$ of a TL1A antibody ranges from about 70 pM to about 1 pM. In some embodiments, the $K_D$ of a TL1A antibody for human TL1A ranges from about 30 pM to about 2 pM. In some embodiments, the binding affinity of a TL1A antibody or antigen-binding fragment thereof of the invention is about 69 pM, about 28 pM, about 25 pM, about 15 pM, about 13 pM, about 10 pM, about 4 pM, and about 2 pM.

The other molecule used to determine specific binding may be unrelated in structure or function to the target. For example, the other molecule may be an unrelated material or accompanying material in the environment.

The other molecule used to determine specific binding may be another molecule involved in the same in vivo pathway as the target molecule, i.e., TL1A. By ensuring that the antibody or antigen-binding fragment thereof of the invention has specificity for TL1A over another such molecule, unwanted in vivo cross-reactivity may be avoided.

The antibody or antigen-binding fragment thereof of the invention may retain the ability to bind to some molecules that are related to the target molecule.

Alternatively, the antibody or antigen-binding fragment thereof of the invention may have specificity for a particular target molecule. For example, it may bind to one target molecule as described herein, but may not bind, or may bind with significantly reduced affinity to a different target molecule as described herein. For example, a full length mature human TL1A may be used as the target, but the antibody that binds to that target may be unable to bind to or may bind with lesser affinity to, e.g. other TL1A proteins from other species, such as other mammalian TL1A.

An antibody or antigen-binding fragment thereof of the invention may bind to TL1A and in doing so may inhibit an activity of TL1A.

Polypeptide or antibody "fragments" or "portions" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

An antibody or antigen-binding fragment thereof of the invention may be, or may comprise, a fragment of, any one of antibodies 1D1, 1D1 1.27, 1D1 1.28, 1D1 1.29, 1D1 1.30, 1D1 1.31, 1D1 1.32, 1D1 1.33, 1D1 1.34, 15A9, 15C11, 7D4, 22F9, 9B3, 2B11, or a variant thereof. The antibody or antigen-binding fragment thereof of the invention may be or may comprise an antigen binding portion of this antibody or a variant thereof. For example, the antibody or antigen-binding fragment thereof of the invention may be a Fab fragment of this antibody or a variant thereof or may be a single chain antibody derived from this antibody or a variant thereof.

A variant antibody may comprise 1, 2, 3, 4, 5, up to 10, up to 20, up to 30 or more amino acid substitutions and/or deletions and/or insertions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" shown below, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The invention also provides methods of generating, selecting, and making TL1A antibodies. The antibodies of this invention can be made by procedures known in the art. In some embodiments, antibodies may be made recombinantly and expressed using any method known in the art.

In some embodiments, antibodies may be prepared and selected by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from human donors can be constructed and antibodies to a diverse array of antigens (including self-antigens) can be isolated essentially following the techniques described by Mark et al., 1991, J. Mol. Biol. 222:581-597, or Griffith et al., 1993, EMBO J. 12:725-734. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., 1992,Bio/Technol. 10:779-783). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

In some embodiments, antibodies may be made using hybridoma technology. It is contemplated that any mammalian subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the TL1A monoclonal antibodies of the subject invention. The hybridomas or other immortalized B-cells are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for TL1A, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a TL1A polypeptide, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups, can yield a population of antibodies (e.g., monoclonal antibodies).

If desired, the TL1A antibody (monoclonal or polyclonal) of interest may be sequenced and the polynucleotide sequence may then be cloned into a vector for expression or propagation. The sequence encoding the antibody or antigen-binding fragment thereof of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In some embodiments, the polynucleotide sequence may be used for genetic manipulation to humanize the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, CA) and HuMAb-Mouse® and TC Mouse™ from Medarex, Inc. (Princeton, NJ).

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., domain, single chain, etc. are known in the art.

Immunoassays and flow cytometry sorting techniques such as fluorescence activated cell sorting (FACS) can also be employed to isolate antibodies that are specific for TL1A.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, chimeric or hybrid antibodies are prepared that have the binding specificity of a TL1A antibody herein.

Antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In some embodiments, a polynucleotide comprises a sequence encoding the heavy chain and/or the light chain variable regions of TL1A antibody or antigen-binding fragment thereof of the present disclosure. The sequence encoding the antibody or antigen-binding fragment thereof of interest may be maintained in a vector in a host cell and the host cell can then be expanded and frozen for future use. Vectors (including expression vectors) and host cells are further described herein.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18.

The CDR may be heavy chain variable region (VH) CDR3 and/or light chain variable region (VL) CDR3. The CDR may be one or more of VH CDR1, VH CDR2, VH CDR3, VL CDR1, VL CDR2, and/or VL CDR3. The CDR may be a Kabat CDR, a Chothia CDR, an extended CDR, an AbM CDR, a contact CDR, or a conformational CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore, Kinexa™ biosensor analysis, and selection using any method known in the art for selection, including phage display, yeast display, and ribosome display.

To express the TL1A antibodies of the present invention, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The invention encompasses modifications to the variable regions shown in FIG. 1A-L and the CDRs indicated in FIG. 1A-L. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to TL1A. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody or antigen-binding fragment thereof of an enzyme or a polypeptide which increases the half-life of the antibody in the blood circulation.

The antibodies may also be modified, e.g., in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the KD of the antibody for TL1A, to increase or decrease koff, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of a TL1A antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments, the antibody comprises a modified constant region that has increased or decreased binding affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., Immunology 86:319-324, 1995; Lund et al., J. Immunology 157: 4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Application No. PCT/GB99/01441; and/or UK Patent Application No. 9809951.8.

In some embodiments, an antibody constant region can be modified to avoid interaction with Fc gamma receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In some embodiments, the constant region is modified as described in Eur. J. Immunol., 1999, 29:2613-2624; PCT Application No. PCT/GB99/01441; and/or UK Patent Application No. 9809951.8. In such embodiments, the Fc can be human $IgG_2$ or human $IgG_4$. The Fc can be human $IgG_2$ containing the mutation A330P331 to S330S331 ($IgG_{2\Delta a}$), in which the amino acid residues are numbered with reference to the wild type $IgG_2$ sequence. Eur. J. Immunol., 1999, 29:2613-2624. In some embodiments, the antibody comprises a constant region of $IgG_4$ comprising the following mutations (Armour et al., 2003, Molecular Immunology 40 585-593): E233F234L235 to P233V234A235 ($IgG_{4\Delta c}$), in which the numbering is with reference to wild type $IgG_4$. In yet another embodiment, the Fc is human $IgG_4$ E233F234L235 to P233V234A235 with deletion G236 ($IgG_{4\Delta b}$). In another embodiment, the Fc is any human $IgG_4$ Fc ($IgG_4$, $IgG_{4\Delta b}$ or $IgG_{4\Delta c}$) containing hinge stabilizing mutation S228 to P228 (Aalberse et al., 2002, Immunology 105, 9-19).

In some embodiments, the antibody comprises a human heavy chain $IgG_2$ constant region comprising the following mutations: A330P331 to S330S331 (amino acid numbering with reference to the wild type $IgG_2$ sequence). Eur. J. Immunol., 1999, 29:2613-2624. In still other embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The disclosure also provides an antibody constant domain that may be further modified. It is known that variants of the Fc region, e.g., amino acid substitutions, insertions, and/or additions and/or deletions, enhance or diminish effector function. See, e.g., Presta et al, 2002, Biochem. Soc. Trans. 30:487-490; Strohl, 2009, Curr. Opin. Biotechnol. 20(6): 685-691; U.S. Pat. Nos. 5,624,821, 5,648,260, 5,885,573, 6,737,056, 7,317,091; PCT publication Nos. WO 99/58572, WO 00/42072, WO 04/029207, WO 2006/105338, WO 2008/022152, WO 2008/150494, WO 2010/033736; U.S. Patent Application Publication Nos. 2004/0132101, 2006/0024298, 2006/0121032, 2006/0235208, 2007/0148170; Armour et al., 1999, Eur. J. Immunol. 29(8):2613-2624 (reduced ADCC and CDC); Shields et al., 2001, J. Biol. Chem. 276(9):6591-6604 (reduced ADCC and CDC); Idusogie et al., 2000, J. Immunol. 164(8):4178-4184 (increased ADCC and CDC); Steurer et al., 1995, J. Immunol. 155(3): 1165-1174 (reduced ADCC and CDC); Idusogie et al., 2001, J. Immunol. 166(4):2571-2575 (increased ADCC and CDC); Lazar et al., 2006, Proc. Natl. Acad. Sci. USA 103(11): 4005-4010 (increased ADCC); Ryan et al., 2007, Mol. Cancer. Ther., 6: 3009-3018 (increased ADCC); Richards et al., 2008, Mol. Cancer Ther. 7(8):2517-2527.

In some embodiments, the antibody comprises a modified constant region that has increased binding affinity for FcRn and/or an increased serum half-life as compared with the unmodified antibody.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836).

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of a TL1A antibody or antigen-binding fragment thereof of the invention can be cleaved or otherwise removed. In various embodiments of the invention, the heavy and light chains of the antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. An example of a linking peptide is $(GGGGS)_3$ (SEQ ID NO: 383), which bridges approximately 3.5 nm between the carboxy terminus of one variable region and the amino terminus of the other variable region. Linkers of other sequences have been designed and used (Bird et al., 1988, supra). Linkers can in turn be modified for additional functions, such as attachment of drugs or attachment to solid supports. The single chain antibody may be monovalent, if only a single VH and VL are used, bivalent, if two VH and VL are used, or polyvalent, if more than two VH and VL are used. Bispecific or polyvalent antibodies may be generated that bind specifically to TL1A and to another molecule. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies, are also encompassed. Diabodies are bivalent, bispecific antibodies in which VH and VL are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad Sci. USA 90:6444-6448; Poljak, R. J., et al., 1994, Structure 2:1121-1123).

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

The invention also encompasses fusion proteins comprising one or more fragments or regions from the antibodies disclosed herein. In some embodiments, a fusion antibody may be made that comprises all or a portion of a TL1A antibody or antigen-binding fragment thereof of the invention linked to another polypeptide. In another embodiment, only the variable domains of the TL1A antibody are linked to the polypeptide. In another embodiment, the VH domain of a TL1A antibody is linked to a first polypeptide, while the VL domain of a TL1A antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In some embodiments, a fusion polypeptide is provided that comprises at least 10 contiguous amino acids of the variable light chain region shown in SEQ ID NOs: 1, 22, 36, 50, 64, 88, or 102 and/or at least 10 amino acids of the variable heavy chain region shown in SEQ ID NOs:3, 5, 24, 38, 52, 66, 68, 67, 198, 205, 212, 219, 226, 233, 240,or 247. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises one or more CDR(s). In still other embodiments, the fusion polypeptide comprises VH CDR3 and/or VL CDR3. For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag (SEQ ID NO: 392). Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

In other embodiments, other modified antibodies may be prepared using nucleic acid molecules encoding a TL1A antibody. For instance, "Kappa bodies" (Ill et al., 1997, Protein Eng. 10:949-57), "Minibodies" (Martin et al., 1994, EMBO J. 13:5303-9), "Diabodies" (Holliger et al., supra), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121:210). For example, bispecific antibodies or antigen-binding fragments can be produced by fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. Traditionally, the recombinant production of bispecific antibodies was based on the coexpression of two immunoglobulin heavy chain-light chain pairs, with the two heavy chains having different specificities (Millstein and Cuello, 1983, Nature 305, 537-539). In addition, bispecific antibodies may be formed as "diabodies" or "Janusins." In some embodiments, the bispecific antibody binds to two different epitopes of TL1A. In some embodiments, the modified antibodies described above are prepared using one or more of the variable domains or CDR regions from a TL1A antibody provided herein.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the TL1A binding and/or antagonist embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

An antibody or polypeptide of this invention may be linked to a labeling agent such as a fluorescent molecule, a radioactive molecule or any others labels known in the art. Labels are known in the art which generally provide (either directly or indirectly) a signal.

As described in greater detail in Example 1, this application discloses multiple TL1A antibodies that may be characterized as belonging to one of three different epitope "bins." That is, antibodies which are grouped together in one epitope bin compete with each other for binding to TL1A. More specifically, antibody 1D1, its affinity optimized variants, and antibodies 15A9 and 15C11, each compete for binding to TL1A and thus are grouped together into a first epitope bin. Antibodies 7D4 and 22F9 also compete with each other for binding to TL1A, but bind to a different epitope than the other antibodies disclosed herein, and hence are grouped in a second epitope bin. Antibodies 26B11 and 9B3 compete with each other for binding to TL1A, but also bind to a different epitope than the other antibodies disclosed herein and therefore, they are grouped into a third epitope bin. Details of the antibodies within each epitope bin are provided below.

The amino acid sequences of the light chain variable domain (VL) heavy chain variable domains (VH), full length light chain (LC), and full length heavy chain (HC) of the TL1A antibodies disclosed herein are summarized in Table 2 by sequence identification number. The nucleic acid sequences encoding the VL,VH, LC, and HC of these antibodies are summarized in Table 3 by sequence identification number. These sequences designated by the sequence identification numbers provided in Tables 2 and 3 are set forth in the Sequence Listing Table (Table 40).

TABLE 2

Amino Acid Sequence SEQ ID NOs of TL1A Antibodies

| | Region | | | |
|---|---|---|---|---|
| Antibody | VL | VH | LC | HC |
| 1D1 | 102 | 104 | 106 | 108 |
| 1.27 | 102 | 198 | 106 | 200 |
| 1.28 | 102 | 205 | 106 | 207 |
| 1.29 | 102 | 212 | 106 | 214 |
| 1.30 | 102 | 219 | 106 | 221 |
| 1.31 | 102 | 226 | 106 | 228 |
| 1.32 | 102 | 233 | 106 | 235 |
| 1.33 | 102 | 240 | 106 | 242 |
| 1.34 | 102 | 247 | 106 | 249 |
| 15A9 | 22 | 24 | 26 | 28 |
| 15C11 | 36 | 38 | 40 | 42 |
| 7D4 | 88 | 90 | 92 | 94 |
| 22F9 | 50 | 52 | 54 | 56 |
| 26B11 | 64 | 66 or 68 or 70 | 72 | 74 |
| 9B3 | 1 | 3 or 5 | 7 | 9 or 11 |

TABLE 3

Nucleic Acid Sequence SEQ ID NOs of TL1A Antibodies

| | Nucleic Acid SEQ ID NOs. | | | |
|---|---|---|---|---|
| Antibody | VL | VH | LC | HC |
| 1D1 | 103 | 105 | 107 | 109 |
| 1.27 | 103 | 199 | 107 | 201 |
| 1.28 | 103 | 206 | 107 | 208 |
| 1.29 | 103 | 213 | 107 | 215 |
| 1.30 | 103 | 220 | 107 | 222 |
| 1.31 | 103 | 227 | 107 | 229 |
| 1.32 | 103 | 234 | 107 | 236 |
| 1.33 | 103 | 241 | 107 | 243 |
| 1.34 | 103 | 248 | 107 | 250 |
| 15A9 | 23 | 25 | 27 | 29 |
| 15C11 | 37 | 39 | 41 | 43 |
| 7D4 | 89 | 91 | 93 | 95 |
| 22F9 | 51 | 53 | 55 | 57 |
| 26B11 | 65 | 67 or 69 or 71 | 73 | 75 |
| 9B3 | 2 | 4 or 6 | 8 | 10 or 12 |

TABLE 3A

Alignment of CDR-H1 Sequences

| SEQ ID NO: | DESCRIPTION | Epitope Bin | 1 | 2 | 3 | 4 | 5 | 6 | 7 | 8 | 9 | 10 |
|---|---|---|---|---|---|---|---|---|---|---|---|---|
| 16 | 9B3 CDR-VH1 | 1 | G | F | T | F | S | N | Y | A | L | H |
| 19 | 9B3 CDR-VH2 | 1 | G | F | T | F | S | S | F | A | M | H |
| 79 | 26B11 CDR-VH1 | 1 | G | F | T | F | S | N | Y | A | L | H |
| 82 | 26B11 CDR-VH2 | 1 | G | F | T | F | S | S | F | A | M | H |

TABLE 3A-continued

Alignment of CDR-H1 Sequences

| SEQ ID NO: | DESCRIPTION | Epitope Bin | 1 | 2 | 3 | 4 | 5 | 6 | 7 | 8 | 9 | 10 |
|---|---|---|---|---|---|---|---|---|---|---|---|---|
| 85 | 26B11 CDR-VH-MDX | 1 | G | F | T | F | S | N | Y | A | I | H |
| 33 | 15A9 CDR | 2B | G | Y | P | F | T | N | Y | G | I | S |
| 47 | 15C11 CDR | 2B | G | Y | S | F | T | T | Y | G | I | S |
| 61 | 22F9 CDR | 2A | G | Y | T | F | T | S | Y | A | M | H |
| 99 | 7D4 CDR | 2A | G | Y | T | F | T | S | Y | G | I | N |
| 113 | 1D1 CDR | 2B | G | Y | S | F | T | Y | Y | G | I | S |
| 263 | 1D1 D5 VH | 2B | G | Y | S | F | T | Y | Y | G | I | S |
| 266 | 1D1 D18 VH | 2B | G | Y | S | F | T | Y | Y | G | I | S |
| 269 | 1D1 D21 VH | 2B | G | Y | S | F | T | Y | Y | G | I | S |
| 272 | 1D1 D24 VH | 2B | G | Y | S | F | T | Y | Y | G | I | S |
| 275 | 1D1 D25 VH | 2B | G | Y | S | F | T | Y | Y | G | I | S |
| 278 | 1D1 D28 VH | 2B | G | Y | S | F | T | Y | Y | G | I | S |
| 281 | 1D1 D29 VH | 2B | G | Y | S | F | T | Y | Y | G | I | S |
| 284 | 1D1 D31 VH | 2B | G | Y | S | F | T | Y | Y | G | I | S |
| 287 | 1D1 D37 VH | 2B | G | Y | S | F | T | Y | Y | G | I | S |
| 290 | 1D1 D38 VH | 2B | G | Y | S | F | T | Y | Y | G | I | S |
| 293 | 1D1 D39 VH | 2B | G | Y | S | F | T | Y | Y | G | I | S |
| 296 | 1D1 DH3 VH | 2B | G | Y | S | F | T | Y | Y | G | I | S |
| 299 | 1D1 DH8 VH | 2B | G | Y | S | F | T | Y | Y | G | I | S |
| 302 | 1D1 DH9 VH | 2B | G | Y | S | F | T | Y | Y | G | I | S |
| 305 | 1D1DH10 VH | 2B | G | Y | S | F | T | Y | Y | G | I | S |
| 308 | 1D1 1.1 | 2B | G | Y | D | F | T | Y | Y | G | I | S |
| 311 | 1D1 1.3 | 2B | G | Y | Q | F | T | Y | Y | G | I | S |
| 314 | 1D1 1.4 | 2B | G | Y | S | F | T | H | Y | G | I | S |
| 317 | 1D1 1.5 | 2B | G | Y | N | F | R | Y | Y | G | I | S |
| 320 | 1D1 1.7 | 2B | G | Y | S | F | T | Y | Y | G | I | S |
| 323 | 1D1 1.8 | 2B | G | Y | S | F | R | Y | Y | G | I | S |
| 326 | 1D1 1.9 | 2B | G | Y | S | F | T | Y | Y | G | I | S |
| 329 | 1D1 1.10 | 2B | G | Y | S | F | T | Y | Y | G | I | S |
| 332 | 1D1 1.11 | 2B | G | Y | S | F | R | Y | Y | G | I | S |
| 335 | 1D1 1.13 | 2B | G | Y | S | F | T | H | Y | G | I | S |
| 338 | 1D1 1.15 | 2B | G | Y | S | F | T | Y | Y | G | I | S |
| 341 | 1D1 1.16 | 2B | G | Y | S | F | T | Y | Y | G | I | S |
| 344 | 1D1 1.17 | 2B | G | Y | S | F | T | Y | Y | G | I | S |
| 347 | 1D1 1.18 | 2B | G | Y | S | F | T | Y | Y | G | I | S |
| 350 | 1D1 1.19 | 2B | G | Y | S | F | T | Y | Y | G | I | S |
| 353 | 1D1 1.20 | 2B | G | Y | S | F | T | Y | Y | G | I | S |
| 356 | 1D1 1.21 | 2B | G | Y | S | F | T | Y | Y | G | I | S |
| 359 | 1D1 1.22 | 2B | G | Y | S | F | T | Y | Y | G | I | S |
| 362 | 1D1 1.23 | 2B | G | Y | S | F | T | Y | Y | G | I | S |
| 365 | 1D1 1.24 | 2B | G | Y | S | F | T | Y | Y | G | I | S |
| 368 | 1D1 1.25 | 2B | G | Y | S | F | T | Y | Y | G | I | S |
| 371 | 1D1 1.26 | 2B | G | Y | S | F | T | Y | Y | G | I | S |
| 202 | 1D1 1.27 CDR | 2B | G | Y | D | F | T | Y | Y | G | I | S |
| 209 | 1D1 1.28 CDR | 2B | G | Y | D | F | T | Y | Y | G | I | S |
| 216 | 1D1 1.29 CDR | 2B | G | Y | D | F | T | Y | Y | G | I | S |
| 223 | 1D1 1.30 CDR | 2B | G | Y | D | F | T | Y | Y | G | I | S |
| 230 | 1D1 1.31 CDR | 2B | G | Y | D | F | T | Y | Y | G | I | S |
| 237 | 1D1 1.32 CDR | 2B | G | Y | D | F | T | Y | Y | G | I | S |
| 244 | 1D1 1.33 CDR | 2B | G | Y | D | F | T | Y | Y | G | I | S |
| 251 | 1D1 1.34 CDR | 2B | G | Y | D | F | T | Y | Y | G | I | S |
| Consensus CH1 sequence of antibodies across epitope bins 1, 2A and 2B (SEQ ID NO: 374) | | | G | F<br>Y | T<br>P<br>S<br>D<br>Q<br>N | F | S<br>T<br>R | N<br>S<br>T<br>Y<br>H | Y<br>F | A<br>G | L<br>M<br>I | H<br>S<br>N |
| Consensus CH1 sequence of antibodies across epitope bins 2A and 2B (SEQ ID NO: 375) | | | G | Y | P<br>S<br>T<br>D<br>Q<br>N | F | T<br>R | N<br>T<br>S<br>Y<br>H | Y | A<br>G | I<br>M | S<br>H<br>N |
| Consensus CH1 sequence of antibodies in epitope bin 2B (SEQ ID NO: 376) | | | G | Y | P<br>S<br>D<br>Q<br>N | F | T<br>R | N<br>T<br>Y<br>H | Y | G | I | S |

TABLE 3B

Alignment of CDR-H2 Sequences

| SEQ ID NO: | Epitope Bin | DESCRIPTION | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|
| 17 | 1 | 9B3CDR-H2-VH1 | L | I | S | Y | D | G | S | D | K | Y | Y | A | D | S | V | K | G |
| 20 | 1 | 9B3CDR-H2-VH2 | L | I | P | F | D | G | S | S | N | Y | Y | A | D | S | V | K | G |
| 80 | 1 | 26B11 CDR-H2-VH1 | L | I | S | Y | D | G | S | D | K | Y | Y | A | D | S | V | K | G |
| 83 | 1 | 26B11 CDR-H2-VH2 | L | I | P | F | D | G | S | S | N | Y | Y | A | D | S | V | K | G |
| 86 | 1 | 26B11 CDR-H2-VH-MDX | L | I | P | Y | D | G | S | N | N | Y | Y | A | A | S | V | K | G |
| 62 | 2A | 22F9 CDR-H2 | W | I | N | A | G | N | G | N | T | K | Y | S | Q | K | F | Q | G |
| 100 | 2A | 7D4 CDR-H2 | W | I | S | T | Y | N | G | N | T | N | S | A | Q | K | L | Q | G |
| 34 | 2B | 15A9 CDR-H2 | W | I | S | T | Y | N | G | N | T | H | Y | A | Q | K | L | Q | G |
| 48 | 2B | 15C11 CDR-H2 | W | I | S | T | Y | N | G | N | T | H | Y | A | Q | K | L | Q | G |
| 114 | 2B | 1D1 CDR-H2 | W | I | S | T | Y | N | G | N | T | N | Y | A | R | M | L | Q | G |
| 203 | 2B | 1D1 1.27 CDR-H2 | W | I | S | T | Y | N | G | N | T | H | Y | A | R | M | L | 0 | G |
| 210 | 2B | 1D1 1.28 CDR-H2 | W | I | S | T | Y | N | G | N | K | H | Y | A | R | M | L | Q | G |
| 217 | 2B | 1D1 1.29 CDR-H2 | W | I | S | T | Y | N | G | G | T | H | Y | A | R | M | L | Q | G |
| 224 | 2B | 1D1 1.30 CDR-H2 | W | I | S | T | Y | N | G | V | T | H | Y | A | R | M | L | Q | G |
| 231 | 2B | 1D1 1.31 CDR-H2 | W | I | S | T | Y | N | G | N | T | H | Y | A | R | M | L | Q | G |
| 238 | 2B | 1D1 1.32 CDR-H2 | W | I | S | T | Y | N | G | G | T | H | Y | A | R | M | L | 0 | G |
| 245 | 2B | 1D1 1.33 CDR-H2 | W | I | S | T | Y | N | G | V | T | H | Y | A | R | M | L | Q | G |
| 252 | 2B | 1D1 1.34 CDR-H2 | W | I | S | T | Y | N | G | K | T | H | Y | A | R | M | H | Q | G |
| 114 | 2B | 1D1 Parental VH | W | I | S | T | Y | N | G | N | T | N | Y | A | R | M | L | Q | G |
| 264 | 2B | 1D1 D5 VH | W | I | S | T | Y | N | G | N | T | N | Y | A | R | M | L | Q | G |
| 267 | 2B | 1D1 D18 VH | W | I | S | T | Y | N | G | N | T | H | Y | A | R | M | L | Q | G |
| 270 | 2B | 1D1 D21 VH | W | I | S | T | Y | N | G | K | T | H | Y | A | R | M | L | Q | G |
| 273 | 2B | 1D1 D24 VH | W | I | S | P | Y | N | G | N | T | H | Y | A | R | M | L | Q | G |
| 276 | 2B | 1D1 D25 VH | W | I | S | T | Y | N | G | A | T | H | Y | A | R | M | L | Q | G |
| 279 | 2B | 1D1 D28 VH | W | I | S | T | Y | N | G | K | T | H | Y | A | R | M | H | Q | G |
| 282 | 2B | 1D1 D29 VH | W | I | S | S | Y | N | G | N | T | H | Y | A | R | M | L | Q | G |
| 285 | 2B | 1D1 D31 VH | W | I | S | T | Y | N | G | N | K | H | Y | A | R | M | L | Q | G |
| 288 | 2B | 1D1 D37 VH | W | I | S | T | Y | N | G | G | T | H | Y | A | R | M | L | Q | G |
| 291 | 2B | 1D1 D38 VH | W | I | S | T | Y | N | G | V | T | H | Y | A | R | M | L | Q | G |
| 294 | 2B | 1D1 D39 VH | W | I | S | T | Y | N | G | N | T | N | Y | A | R | M | L | Q | G |
| 297 | 2B | 1D1 DH3 VH | W | I | S | T | Y | N | G | N | T | H | Y | A | Q | M | L | Q | G |
| 300 | 2B | 1D1 DH8 VH | W | I | S | A | Y | N | G | N | T | H | Y | A | R | M | L | Q | G |
| 303 | 2B | 1D1 DH9 VH | W | I | S | P | Y | N | G | K | T | H | Y | A | R | M | L | Q | G |
| 306 | 2B | 1D1 DH10 VH | W | I | S | T | Y | N | G | N | T | N | Y | A | R | M | L | Q | G |
| 309 | 2B | 1D1 1.1 | W | I | S | T | Y | N | G | N | T | N | Y | A | R | M | L | Q | G |
| 312 | 2B | 1D1 1.3 | W | I | S | T | Y | N | G | N | T | N | Y | A | R | M | L | Q | G |
| 315 | 2B | 1D1 1.4 | W | I | S | T | Y | N | G | N | T | N | Y | A | R | M | L | Q | G |

TABLE 3B-continued

Alignment of CDR-H2 Sequences

| SEQ ID NO: | Epitope Bin | DESCRIPTION | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|
| 318 | 2B | 1D1 1.5 | W | I | S | T | Y | N | G | N | T | N | Y | A | R | M | L | Q | G |
| 321 | 2B | 1D1 1.7 | W | I | S | T | Y | N | G | K | T | N | Y | A | R | M | L | Q | G |
| 324 | 2B | 1D1 1.8 | W | I | S | T | Y | N | G | N | T | H | Y | A | R | M | L | Q | G |
| 327 | 2B | 1D1 1.9 | W | I | S | T | Y | N | G | N | T | H | Y | A | R | M | L | Q | G |
| 330 | 2B | 1D1 1.10 | W | I | S | P | Y | N | G | K | T | H | Y | A | R | M | L | Q | G |
| 333 | 2B | 1D1 1.11 | W | I | S | T | Y | N | G | N | T | H | Y | A | R | M | L | Q | G |
| 336 | 2B | 1D1 1.13 | W | I | S | P | Y | N | G | K | T | H | Y | A | R | M | L | Q | G |
| 339 | 2B | 1D1 1.15 | W | I | S | P | Y | N | G | G | T | H | Y | A | Q | M | L | Q | G |
| 342 | 2B | 1D1 1.16 | W | I | S | P | Y | N | G | V | T | H | Y | A | Q | M | L | Q | G |
| 345 | 2B | 1D1 1.17 | W | I | S | P | Y | N | G | A | T | H | Y | A | Q | M | L | Q | G |
| 348 | 2B | 1D1 1.18 | W | I | S | P | Y | N | G | N | K | H | Y | A | Q | M | L | Q | G |
| 351 | 2B | 1D1 1.19 | W | I | S | T | Y | N | G | G | T | H | Y | A | R | M | L | Q | G |
| 354 | 2B | 1D1 1.20 | W | I | S | P | Y | N | G | N | T | H | Y | A | R | M | L | Q | G |
| 357 | 2B | 1D1 1.21 | W | I | S | T | Y | N | G | N | T | H | Y | A | Q | M | L | Q | G |
| 360 | 2B | 1D1 1.22 | W | I | S | T | Y | N | G | V | T | H | Y | A | R | M | L | Q | G |
| 363 | 2B | 1D1 1.23 | W | I | S | T | Y | N | G | A | T | H | Y | A | R | M | L | Q | G |
| 366 | 2B | 1D1 1.24 | W | I | S | T | Y | N | G | N | K | H | Y | A | R | M | L | Q | G |
| 369 | 2B | 1D1 1.25 | W | I | S | T | Y | N | G | K | T | H | Y | A | R | M | H | Q | G |
| 372 | 2B | 1D1 1.26 | W | I | S | T | Y | N | G | N | T | H | Y | A | R | M | L | Q | G |
| 203 | 2B | 1D1 1.27 | W | I | S | T | Y | N | G | N | T | H | Y | A | R | M | L | Q | G |
| 210 | 2B | 1D1 1.28 | W | I | S | T | Y | N | G | N | K | H | Y | A | R | M | L | Q | G |
| 217 | 2B | 1D1 1.29 | W | I | S | T | Y | N | G | G | T | H | Y | A | R | M | L | Q | G |
| 224 | 2B | 1D1 1.30 | W | I | S | T | Y | N | G | V | T | H | Y | A | R | M | L | Q | G |
| 231 | 2B | 1D1 1.31 | W | I | S | T | Y | N | G | N | T | H | Y | A | R | M | L | Q | G |
| 238 | 2B | 1D1 1.32 | W | I | S | T | Y | N | G | G | T | H | Y | A | R | M | L | Q | G |
| 245 | 2B | 1D1 1.33 | W | I | S | T | Y | N | G | V | T | H | Y | A | R | M | L | Q | G |
| 252 | 2B | 1D1 1.34 | W | I | S | T | Y | N | G | K | T | H | Y | A | R | M | H | Q | G |
| Consensus CH2 sequence of antibodies across epitope bins 1, 2A and 2B (SEQ ID NO: 377) | | | L<br>W | I | S<br>P<br>N | Y<br>F<br>A<br>T<br>P<br>S | D<br>G<br>Y | G<br>N | S<br>G | D<br>S<br>N<br>G<br>V<br>K<br>A | K<br>N<br>T | Y<br>K<br>N<br>H | Y<br>S | A<br>S | D<br>A<br>Q<br>R | S<br>K<br>M | V<br>F<br>L<br>H | K<br>Q | G |
| Consensus CH2 sequence of antibodies across epitope bins 2A and 2B (SEQ ID NO: 378) | | | W | I | N<br>S | A<br>T<br>P<br>S | G<br>Y | N | G | N<br>G<br>V<br>K<br>A | T<br>K | K<br>N<br>H | Y<br>S | S<br>A | Q<br>R | K<br>M | F<br>L<br>H | Q | G |
| Consensus CH2 sequence of antibodies in epitope bin 2B (SEQ ID NO: 379) | | | W | I | S | T<br>P<br>S<br>A | Y | N | G | N<br>G<br>V<br>K<br>A | T<br>K | H<br>N | Y | A | Q<br>R | K<br>M | L<br>H | Q | G |

TABLE 3C

Alignment of CDR-H3 Sequences

| SEQ ID NO: | DESCRIPTION | Epitope Bin | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|
| 18 | 9B3 CDR-H3-VH1 | 1 | H | R | E | Y | C | T | Y | S | S | C | S | Y | D | A | F | D | I |
| 21 | 9B3 CDR-H3-VH2 | 1 | D | R | N | Y | Y | G | S | G | S | F | S | F | D | A | F | D | I |
| 81 | 26B11 CDR-H3-VH1 | 1 | D | R | E | Y | C | T | Y | S | S | C | S | Y | D | A | F | D | I |
| 84 | 26B11 CDR-H3-VH2 | 1 | D | R | N | Y | Y | G | S | G | S | F | S | F | D | A | F | D | I |
| 87 | 26B11 CDR-H3-VH-MDX | 1 | D | R | N | Y | Y | G | S | G | S | F | S | F | D | A | F | D | I |
| 35 | 15A9 CDR-H3 | 2B | E | N | Y | Y | G | S | G | S | Y | R | G | G | M | D | V | . | . |
| 49 | 15C11 CDR-H3 | 2B | E | N | Y | Y | G | S | G | S | Y | R | G | G | M | D | V | . | . |
| 63 | 22F9 CDR-H3 | 2A | . | . | . | G | Y | S | S | A | W | F | D | A | F | D | I | . | . |
| 101 | 7D4 CDR-H3 | 2A | . | . | . | A | H | S | S | S | W | F | D | A | F | D | I | . | . |
| 115 | 1D1 CDR-H3 | 2B | E | N | Y | Y | G | S | G | S | Y | R | G | G | M | D | V | . | . |
| 204 | 1D1 1.27 CDR-H3 | 2B | E | N | Y | Y | G | S | G | S | Y | R | G | G | M | D | V | . | . |
| 211 | 1D1 1.28 CDR-H3 | 2B | E | N | Y | Y | G | S | G | S | Y | R | G | G | M | D | V | . | . |
| 218 | 1D1 1.29 CDR-H3 | 2B | E | N | Y | Y | G | S | G | S | Y | R | G | G | M | D | V | . | . |
| 225 | 1D1 1.30 CDR-H3 | 2B | E | N | Y | Y | G | S | G | S | Y | R | G | G | M | D | V | . | . |
| 232 | 1D1 1.31 CDR-H3 | 2B | E | N | Y | Y | G | S | G | A | Y | R | G | G | M | D | V | . | . |
| 239 | 1D1 1.32 CDR-H3 | 2B | E | N | Y | Y | G | S | G | A | Y | R | G | G | M | D | A | . | . |
| 246 | 1D1 1.33 CDR-H3 | 2B | E | N | Y | Y | G | S | G | A | Y | R | G | G | M | D | A | . | . |
| 253 | 1D1 1.34 CDR-H3 | 2B | E | N | Y | Y | G | S | G | A | Y | R | G | G | M | D | A | . | . |
| 265 | 1D1 D5 VH | 2B | E | N | Y | Y | G | S | G | A | F | R | G | G | M | D | G | . | . |
| 268 | 1D1 D18 VH | 2B | E | N | Y | Y | G | S | G | S | Y | R | G | G | M | D | V | . | . |
| 271 | 1D1 D21 VH | 2B | E | N | Y | Y | G | S | G | S | Y | R | G | G | M | D | V | . | . |
| 274 | 1D1 D24 VH | 2B | E | N | Y | Y | G | S | G | S | Y | R | G | G | M | D | V | . | . |
| 277 | 1D1 D25 VH | 2B | E | N | Y | Y | G | S | G | S | Y | R | G | G | M | D | V | . | . |
| 280 | 1D1 D28 VH | 2B | E | N | Y | Y | G | S | G | S | Y | R | G | G | M | D | V | . | . |
| 283 | 1D1 D29 VH | 2B | E | N | Y | Y | G | S | G | S | Y | R | G | G | M | D | V | . | . |
| 286 | 1D1 D31 VH | 2B | E | N | Y | Y | G | S | G | S | Y | R | G | G | M | D | V | . | . |
| 289 | 1D1 D37 VH | 2B | E | N | Y | Y | G | S | G | S | Y | R | G | G | M | D | V | . | . |
| 292 | 1D1 D38 VH | 2B | E | N | Y | Y | G | S | G | S | Y | R | G | G | M | D | V | . | . |
| 295 | 1D1 D39 VH | 2B | E | N | Y | Y | G | S | G | A | Y | R | G | G | M | D | A | . | . |
| 298 | 1D1 DH3 VH | 2B | E | N | Y | Y | G | S | G | S | Y | R | G | G | M | D | V | . | . |
| 301 | 1D1 DH8 VH | 2B | E | N | Y | Y | G | S | G | S | Y | R | G | G | M | D | V | . | . |
| 304 | 1D1 DH9 VH | 2B | E | N | Y | Y | G | S | G | S | Y | R | G | G | M | D | V | . | . |
| 307 | 1D1 DH10 VH | 2B | E | N | Y | Y | G | S | G | A | Y | R | G | G | M | D | V | . | . |
| 310 | 1D1 1.1 | 2B | E | N | Y | Y | G | S | G | S | Y | R | G | G | M | D | V | . | . |
| 313 | 1D1 1.3 | 2B | E | N | Y | Y | G | S | G | S | Y | R | G | G | M | D | V | . | . |
| 316 | 1D1 1.4 | 2B | E | N | Y | Y | G | S | G | S | Y | R | G | G | M | D | V | . | . |
| 319 | 1D1 1.5 | 2B | E | N | Y | Y | G | S | G | S | Y | R | G | G | M | D | V | . | . |

TABLE 3C-continued

Alignment of CDR-H3 Sequences

| SEQ ID NO: | DESCRIPTION | Epitope Bin | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|
| 322 | 1D1 1.7 | 2B | E | N | Y | Y | G | S | G | S | Y | R | G | G | M | D | V | . | . |
| 325 | 1D1 1.8 | 2B | E | N | Y | Y | G | S | G | S | Y | R | G | G | M | D | V | . | . |
| 328 | 1D1 1.9 | 2B | E | N | Y | Y | G | S | G | A | Y | R | G | G | M | D | V | . | . |
| 331 | 1D1 1.10 | 2B | E | N | Y | Y | G | S | G | A | Y | R | G | G | M | D | V | . | . |
| 334 | 1D1 1.11 | 2B | E | N | Y | Y | G | S | G | A | Y | R | G | G | M | D | V | . | . |
| 337 | 1D1 1.13 | 2B | E | N | Y | Y | G | S | G | A | Y | R | G | G | M | D | V | . | . |
| 340 | 1D1 1.15 | 2B | E | N | Y | Y | G | S | G | A | Y | R | G | G | M | D | A | . | . |
| 343 | 1D1 1.16 | 2B | E | N | Y | Y | G | S | G | A | Y | R | G | G | M | D | A | . | . |
| 346 | 1D1 1.17 | 2B | E | N | Y | Y | G | S | G | A | Y | R | G | G | M | D | A | . | . |
| 349 | 1D1 1.18 | 2B | E | N | Y | Y | G | S | G | A | Y | R | G | G | M | D | A | . | . |
| 352 | 1D1 1.19 | 2B | E | N | Y | Y | G | S | G | A | Y | R | G | G | M | D | A | . | . |
| 355 | 1D1 1.20 | 2B | E | N | Y | Y | G | S | G | A | Y | R | G | G | M | D | A | . | . |
| 358 | 1D1 1.21 | 2B | E | N | Y | Y | G | S | G | A | Y | R | G | G | M | D | A | . | . |
| 361 | 1D1 1.22 | 2B | E | N | Y | Y | G | S | G | A | Y | R | G | G | M | D | A | . | . |
| 364 | 1D1 1.23 | 2B | E | N | Y | Y | G | S | G | A | Y | R | G | G | M | D | A | . | . |
| 367 | 1D1 1.24 | 2B | E | N | Y | Y | G | S | G | A | Y | R | G | G | M | D | A | . | . |
| 370 | 1D1 1.25 | 2B | E | N | Y | Y | G | S | G | A | Y | R | G | G | M | D | A | . | . |
| 373 | 1D1 1.26 | 2B | E | N | Y | Y | G | S | G | A | Y | R | G | G | M | D | A | . | . |
| 204 | 1D1 1.27 | 2B | E | N | Y | Y | G | S | G | S | Y | R | G | G | M | D | V | . | . |
| 211 | 1D1 1.28 | 2B | E | N | Y | Y | G | S | G | S | Y | R | G | G | M | D | V | . | . |
| 218 | 1D1 1.29 | 2B | E | N | Y | Y | G | S | G | S | Y | R | G | G | M | D | V | . | . |
| 225 | 1D1 1.30 | 2B | E | N | Y | Y | G | S | G | S | Y | R | G | G | M | D | V | . | . |
| 232 | 1D1 1.31 | 2B | E | N | Y | Y | G | S | G | A | Y | R | G | G | M | D | V | . | . |
| 239 | 1D1 1.32 | 2B | E | N | Y | Y | G | S | G | A | Y | R | G | G | M | D | A | . | . |
| 246 | 1D1 1.33 | 2B | E | N | Y | Y | G | S | G | A | Y | R | G | G | M | D | A | . | . |
| 253 | 1D1 1.34 | 2B | E | N | Y | Y | G | S | G | A | Y | R | G | G | M | D | A | . | . |
| | Consensus CH3 sequence of | | . | . | . | Y | C | T | Y | S | S | C | S | Y | D | A | F | . | . |
| | antibodies across epitope | | D | R | E | G | Y | G | S | G | Y | F | G | F | M | D | V | D | I |
| | bins 1, 2A and 2B | | E | N | N | A | G | S | G | A | W | R | D | G | F | | I | | |
| | (SEQ ID NO: 380) | | | | Y | | H | | | | F | | | A | | | A | | |
| | | | | | | | | | | | | | | | | | G | | |
| | Consensus CH3 sequence of | | . | . | . | Y | G | S | G | S | Y | R | G | G | M | D | V | | |
| | antibodies across epitope | | E | N | Y | G | Y | | S | A | W | F | D | A | F | | I | | |
| | bins 2A and 2B | | | | | A | H | | | | F | | | | | | A | | |
| | (SEQ ID NO: 381) | | | | | | | | | | | | | | | | G | | |
| | Consensus CH3 sequence of | | E | N | Y | Y | G | S | G | S | Y | R | G | G | M | D | V | | |
| | antibodies in epitope bin | | | | | | | | | A | F | | | | | | A | | |
| | 2B (SEQ ID NO: 382) | | | | | | | | | | | | | | | | G | | |

Antibody 1 D1 and Variants Thereof

In one embodiment, the antibody or antigen-binding fragment thereof comprises comprises a VH comprising: i) a CDR-H1 comprising the amino acid sequence of SEQ ID NO: 374; ii) a CDR-H2 comprising the amino acid sequence of SEQ ID NO: 377; and iii) a CDR-H3 comprising the amino acid sequence of SEQ ID NO: 380. The antibody or antigen-binding fragment thereof according to this embodiment can also comprise a VL comprising an amino acid sequence at least 90%, 91%, 92%, 93%, 94%, 95%, 96%, 97%, 98%, 99%, or 100% identical to the VL sequence comprising the amino acid sequence selected from the group consisting of SEQ ID NOs:1, 22, 36, 50, 64, 88 and 102.

In one embodiment, the antibody or antigen-binding fragment thereof comprises comprises a VH comprising: i) a CDR-H1 comprising the amino acid sequence of SEQ ID NO: 375; ii) a CDR-H2 comprising the amino acid sequence of SEQ ID NO: 378; and iii) a CDR-H3 comprising the amino acid sequence of SEQ ID NO: 381. The antibody or antigen-binding fragment thereof according to this embodiment can also comprise a VL comprising an amino acid sequence at least 90%, 91%, 92%, 93%, 94%, 95%, 96%, 97%, 98%, 99%, or 100% identical to the VL sequence comprising the amino acid sequence selected from the group consisting of SEQ ID NOs: 50, 64, and 102.

In one embodiment, the antibody or antigen-binding fragment thereof comprises comprises a VH comprising: i) a CDR-H1 comprising the amino acid sequence of SEQ ID NO: 376; ii) a CDR-H2 comprising the amino acid sequence of SEQ ID NO: 379; and iii) a CDR-H3 comprising the amino acid sequence of SEQ ID NO: 382. The antibody or antigen-binding fragment thereof according to this embodiment can also comprise a VL comprising an amino acid sequence at least 90%, 91%, 92%, 93%, 94%, 95%, 96%, 97%, 98%, 99%, or 100% identical to the VL sequence of SEQ ID NO: 102.

In one embodiment, the antibody or antigen-binding fragment thereof of the invention comprises a VH comprising: i) a CDR-H1 comprising the amino acid sequence $GYX_1FX_2X_3YGIS$, wherein $X_1$ is S, D, Q, N or P; $X_2$ is T or R; and $X_3$ is Y or H (SEQ ID NO: 384); ii) a CDR-H2 comprising the amino acid sequence $WISX_4YNGX_5X_6X_7YAX_8MX_9QG$, wherein $X_4$ is T, P, S, or A; $X_5$ is K, A, G, N, or V; $X_6$ is T or K; $X_7$ is N or H; $X_8$ is R or Q; and $X_9$ is L or H (SEQ ID NO: 385); and iii) a CDR-H3 comprising the amino acid sequence $ENYYGSGX_9X_{10}RGGMDX_{11}$, wherein $X_9$ is S or A; $X_{10}$ is Y or F; and $X_{11}$ is V, G, or A (SEQ ID NO: 382).

An antibody or antigen-binding fragment thereof of the invention may comprise a VL comprising an amino acid sequence at least 90%, 91%, 92%, 93%, 94%, 95%, 96%, 97%, 98%, or 99% identical to the amino acid sequence of SEQ ID NO:102.

In another embodiment, an antibody or antigen-binding fragment thereof of the invention may comprise a VH comprising: a CDR-H1 comprising the amino acid sequence $GYX_1FX_2X_3YGIS$, wherein $X_1$ is S, D, Q, N or P; $X_2$ is T or R; and $X_3$ is Y or H (SEQ ID NO: 384); ii) a CDR-H2 comprising the amino acid sequence $WISX_4YNGX_5X_6X_7YAX_8MX_9QG$, wherein $X_4$ is T, P, S, or A; $X_5$ is K, A, G, N, or V; $X_6$ is T or K; $X_7$ is N or H; $X_8$ is R or Q; and $X_9$ is L or H (SEQ ID NO: 385); iii) a CDR-H3 comprising the amino acid sequence $ENYYGSGX_9X_{10}RGGMDX_{11}$, wherein $X_9$ is S or A; $X_{10}$ is Y or F; and $X_{11}$ is V, G, or A (SEQ ID NO: 382); iv) a T or R at position H76, as determined by Kabat numbering of the VH; v) a D or E at position H81, as determined by Kabat numbering of the VH; and a VL comprising a CDR-L1 having the amino acid sequence of SEQ ID NO:110, a CDR-L2 having the amino acid sequence of SEQ ID NO:111, and a CDR-L3 having the amino acid sequence of SEQ ID NO:112.

In a further embodiment, an antibody or antigen-binding fragment thereof of the invention may comprise a VH comprising: i) a CDR-H1 comprising the amino acid sequence of SEQ ID NO:202; ii) a CDR-H2 comprising the acid sequence selected from SEQ ID NO: 203, 210, 217, 224, 231, 238, 245, or 252; iii) a CDR-H2 comprising the amino acid sequence selected from SEQ ID NO:204, 211, 218, 225, 232, 239, 246, or 253; and a VL comprising a CDR-L1 having the amino acid sequence of SEQ ID NO:110, a CDR-L2 having the amino acid sequence of SEQ ID NO:111, and a CDR-L3 having the amino acid sequence of SEQ ID NO:112.

An antibody or antigen-binding fragment thereof of the invention may comprise both:

a) a VH comprising the amino acid sequence of SEQ ID NO:104 and a VL comprising the amino acid sequence of SEQ ID NO:102; or b) a VH comprising the amino acid sequence of SEQ ID NO:198 and a VL comprising the amino acid sequence of SEQ ID NO:102; or c) a VH comprising the amino acid sequence of SEQ ID NO:205 and a VL comprising the amino acid sequence of SEQ ID NO:102; or d) a VH comprising the amino acid sequence of SEQ ID NO:212 and a VL comprising the amino acid sequence of SEQ ID NO:102; or e) a VH comprising the amino acid sequence of SEQ ID NO:219 and a VL comprising the amino acid sequence of SEQ ID NO:102; or f) a VH comprising the amino acid sequence of SEQ ID NO:226 and a VL comprising the amino acid sequence of SEQ ID NO:102; or g) a VH comprising the amino acid sequence of SEQ ID NO:233 and a VL comprising the amino acid sequence of SEQ ID NO:102; or h) a VH comprising the amino acid sequence of SEQ ID NO:240 and a VL comprising the amino acid sequence of SEQ ID NO:102; or i) a VH comprising the amino acid sequence of SEQ ID NO:247 and a VL comprising the amino acid sequence of SEQ ID NO:102; or j) a VH comprising the amino acid sequence of SEQ ID NO:24 and a VL comprising the amino acid sequence of SEQ ID NO:22; or k) a VH comprising the amino acid sequence of SEQ ID NO:38 and a VL comprising the amino acid sequence of SEQ ID NO:36.

In one aspect, the antibody comprises a VL comprising the sequence of SEQ ID NO:102, SEQ ID NO:22, or SEQ ID NO:36. In another aspect, the antibody comprises a VH comprising the amino acid sequence of SEQ ID NO:106, SEQ ID NO:198, SEQ ID NO:205, SEQ ID NO:205, SEQ ID NO:212, SEQ ID NO:219, SEQ ID NO:226, SEQ ID NO:233, SEQ ID NO:240, SEQ ID NO:247, SEQ ID NO: 24, or SEQ ID NO:38. In another aspect, the antibody comprises a variant of these sequences, wherein such variants can include both conservative and non-conservative substitutions, deletions, and/or additions, and typically include peptides that share at least 60%, at least 65%, at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific sequences disclosed herein.

For example, in one aspect, the disclosure provides an isolated antibody or antigen-binding portion thereof that comprises a VH chain amino acid sequence as set forth in SEQ ID NO:106, SEQ ID NO:198, SEQ ID NO:205, SEQ ID NO:205, SEQ ID NO:212, SEQ ID NO:219, SEQ ID NO:226, SEQ ID NO:233, SEQ ID NO:240, SEQ ID NO:247, SEQ ID NO: 24, or SEQ ID NO:38, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:106, SEQ ID NO:198, SEQ ID NO:205, SEQ ID NO:205, SEQ ID NO:212, SEQ ID NO:219, SEQ ID NO:226, SEQ ID NO:233, SEQ ID NO:240, SEQ ID NO:247, SEQ ID NO: 24, or SEQ ID NO:38. In a further aspect, said variant shares at least 65%, at least 75%, at least 85%, at least 90%, at least 95%, at least 96%, at least 97%, at least 98%, or at least 99% sequence identity with SEQ ID NO:106, SEQ ID NO:198, SEQ ID NO:205, SEQ ID NO:205, SEQ ID NO:212, SEQ ID NO:219, SEQ ID NO:226, SEQ ID NO:233, SEQ ID NO:240, SEQ ID NO:247, SEQ ID NO: 24, or SEQ ID NO:38, and wherein said antibody or antigen-binding portion specifically binds TL1A.

In a further aspect, the disclosure provides an isolated antibody or antigen-binding portion thereof that comprises a $V_L$ chain amino acid sequence as set forth in SEQ ID NO:102, SEQ ID NO:22, or SEQ ID NO:36 or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:102, SEQ ID NO:22, or SEQ ID NO:36. In a further aspect, said variant shares at least 65%, at least 75%, at least 85%, at least 90%, at least 95%, at least 96%, at least 97%, at least 98%, or at least 99% sequence identity with SEQ ID NO:102, SEQ ID NO:22, or SEQ ID NO:36, and wherein said antibody or antigen-binding portion specifically binds TL1A.

An antibody or antigen-binding fragment thereof of the invention may comprise a heavy chain comprising a VH comprising the amino acid sequence of SEQ ID NO:106, SEQ ID NO:198, SEQ ID NO:205, SEQ ID NO:205, SEQ ID NO:212, SEQ ID NO:219, SEQ ID NO:226, SEQ ID NO:233, SEQ ID NO:240, SEQ ID NO:247, SEQ ID NO: 24, or SEQ ID NO:38, wherein the antibody further comprises a heavy chain constant domain. As more fully set forth elsewhere herein, the antibody heavy chain constant domain can be selected from an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). For a Fab fragment heavy chain gene, the VH-encoding DNA can be operatively linked to another DNA molecule encoding only the heavy chain CH1 constant region. The CH1 heavy chain constant region may be derived from any of the heavy chain genes.

In one aspect, the antibody may comprise a heavy chain comprising a VH selected from a VH comprising the amino acid sequence of SEQ ID NO:106, SEQ ID NO:198, SEQ ID NO:205, SEQ ID NO:205, SEQ ID NO:212, SEQ ID NO:219, SEQ ID NO:226, SEQ ID NO:233, SEQ ID NO:240, SEQ ID NO:247, SEQ ID NO: 24, or SEQ ID NO:38 and further comprising a human wild type IgG1 constant domain comprising the amino acid sequence of SEQ ID NO:256. In another aspect, the IgG1 constant domain comprises a triple mutation decreasing or abolishing Fc effector function (hIgG1-3m; SEQ ID NO:257). In one aspect, the antibody or antigen-binding fragment thereof of the invention may comprise a heavy chain comprising a VH comprising the sequence of SEQ ID NO:106, SEQ ID NO:198, SEQ ID NO:205, SEQ ID NO:205, SEQ ID NO:212, SEQ ID NO:219, SEQ ID NO:226, SEQ ID NO:233, SEQ ID NO:240, SEQ ID NO:247, SEQ ID NO: 24, or SEQ ID NO:38 and further comprising a human IgG1-3m constant domain such that the full-length heavy chain amino acid sequence comprises SEQ ID NO. 108, SEQ ID NO:200, SEQ ID NO:207, SEQ ID NO:214, SEQ ID NO:221, SEQ ID NO:228, SEQ ID NO:235, SEQ ID NO: 242, SEQ ID NO:249, SEQ ID NO:28, or SEQ ID NO:42.

In a further aspect, the disclosure provides an isolated antibody or antigen-binding portion thereof that comprises a full-length heavy chain comprising the amino acid sequence as set forth in SEQ ID NO. 108, SEQ ID NO:200, SEQ ID NO:207, SEQ ID NO:214, SEQ ID NO:221, SEQ ID NO:228, SEQ ID NO:235, SEQ ID NO: 242, SEQ ID NO:249, SEQ ID NO:28, or SEQ ID NO:42, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO. 108, SEQ ID NO:200, SEQ ID NO:207, SEQ ID NO:214, SEQ ID NO:221, SEQ ID NO:228, SEQ ID NO:235, SEQ ID NO: 242, SEQ ID NO:249, SEQ ID NO:28, or SEQ ID NO:42. In a further aspect, said variant shares at least 65%, at least 75%, at least 85%, at least 90%, at least 95%, at least 96%, at least 97%, at least 98%, or at least 99% sequence identity with SEQ ID NO. 108, SEQ ID NO:200, SEQ ID NO:207, SEQ ID NO:214, SEQ ID NO:221, SEQ ID NO:228, SEQ ID NO:235, SEQ ID NO: 242, SEQ ID NO:249, SEQ ID NO:28, or SEQ ID NO:42, and wherein said antibody or antigen-binding portion specifically binds TL1A.

An antibody or antigen-binding fragment thereof of the invention may comprise a light chain comprising a VL comprising the amino acid sequence of SEQ ID NO:102, SEQ ID NO:22, or SEQ ID NO:36, wherein the antibody further comprises a light chain constant domain. As more fully set forth elsewhere herein, the antibody light chain constant domain can be selected from a Cκ or Cμ constant region, preferably, a Cκ constant region.

In one aspect, the antibody may comprise a light chain comprising a VL selected from a VL comprising the amino acid sequence of SEQ ID NO:102, SEQ ID NO:22, or SEQ ID NO:36 and further comprising a human wild type CA constant domain comprising the amino acid sequence of SEQ ID NO:255, such that the full-length light chain amino acid sequence comprises SEQ ID NO:106, SEQ ID NO:26, or SEQ ID NO:40.

In a further aspect, the disclosure provides an isolated antibody or antigen-binding portion thereof that comprises a full-length light chain comprising the amino acid sequence as set forth in SEQ ID NO:106, SEQ ID NO:26, or SEQ ID NO:40, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:106, SEQ ID NO:26, or SEQ ID NO:40. In a further aspect, said variant shares at least 65%, at least 75%, at least 85%, at least 90%, at least 95%, at least 96%, at least 97%, at least 98%, or at least 99% sequence identity with SEQ ID NO:106, SEQ ID NO:26, or SEQ ID NO:40, and wherein said antibody or antigen-binding portion specifically binds TL1A.

The invention encompasses an antibody, or antigen-binding fragment thereof, comprising the three CDRs of the heavy chain variable domain amino acid sequence encoded by the polynucleotide insert of the vector deposited with the ATCC on Oct. 17. 2013, as 1D1 1.31 VH (ATCC Acc. No. PTA-120639). In one aspect, the antibody, or antigen-binding fragment thereof, of the invention comprises the VH domain amino acid sequence encoded by the polynucleotide insert of the vector deposited with the ATCC as 1D1 1.31VH (ATCC Acc. No. PTA-120639).

The invention encompasses an antibody, or antigen-binding fragment thereof, comprising the three CDRs of the light chain variable domain amino acid sequence encoded by the polynucleotide insert of the vector deposited with the ATCC on Oct. 17, 2013, as 1D1 1.31 VL (ATCC Acc. No. PTA-120640). In one aspect, the antibody, or antigen-binding fragment thereof, of the invention comprises the VL domain amino acid sequence encoded by the polynucleotide insert of the vector deposited with the ATCC as 1D1 1.31 VL (ATCC Acc. No. PTA-120640).

The invention encompasses an antibody, or antigen-binding fragment thereof, comprising the three CDRs of the light chain variable domain amino acid sequence encoded by the polynucleotide insert of the vector deposited with the ATCC on Oct. 17, 2013, as 1D1 1.31 VL (ATCC Acc. No. PTA-120640), and the three CDRs of the heavy chain variable domain amino acid sequence encoded by the polynucleotide insert of the vector deposited with the ATCC as 1D1 1.31 VH (ATCC Acc. No. PTA-120639).

The invention encompasses an antibody, or antigen-binding fragment thereof, comprising the light chain variable domain amino acid sequence encoded by the polynucleotide insert of the vector deposited with the ATCC on Oct. 17, 2013, as 1D1 1.31 VL (ATCC Acc. No. PTA-120640), and the heavy chain variable domain amino acid sequence encoded by the polynucleotide insert of the vector deposited with the ATCC as 1D1 1.31 VH (ATCC Acc. No. PTA-120639).

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

An antibody or antigen-binding fragment thereof of the invention may comprise a fragment of one of the VL or VH amino acid sequences shown in FIG. 1A-L. For example, an antibody or antigen-binding fragment thereof of the invention may comprise a fragment of at least 7, at least 8, at least 9, at least 10, at least 12, at least 15, at least 18, at least 20 or at least 25 consecutive amino acids from a VH comprising SEQ ID NO:106, SEQ ID NO:198, SEQ ID NO:205, SEQ ID NO:205, SEQ ID NO:212, SEQ ID NO:219, SEQ ID NO:226, SEQ ID NO:233, SEQ ID NO:240, SEQ ID NO:247, SEQ ID NO: 24, or SEQ ID NO:38, or from a VL comprising SEQ ID NO:102, SEQ ID NO:22, or SEQ ID NO:36. Such a fragment will preferably retain one or more of the functions discussed above, such as the ability to bind to TL1A.

A suitable fragment or variant of any of these VH or VL sequences will retain the ability to bind to TL1A. It will preferably retain the ability to specifically bind to TL1A. It will preferably retain the ability to specifically bind to the same or similar epitope or region of the TL1A molecule as the antibody from which it is derived. It will preferably retain one or more additional functions of the antibody from which it is derived, such as the ability to inhibit TL1A binding to its receptor, among others.

A suitable fragment or variant VL sequence will preferably retain the amino acids at positions Tyr32 and Trp94 based on Kabat numbering with respect to the sequence of SEQ ID NO:102. A suitable fragment or variant VH sequence will preferably retain the amino acids at positions Gly26, Tyr27, Ser28, Thr30, Tyr31, Trp50, Tyr53, Asn54, Asn56, Asn58, Thr73, Arg76, Tyr97, Gly99, Ser100, Gly100A, Ser100B, Arg100D, based on Kabat numbering with respect to the sequence of SEQ ID NO:104, or those at positions Gly26, Asp28, Thr30, Tyr31, Trp50, Tyr53, Asn54, Asn56, His58, Thr73, Arg76, Tyr97, Gly99, Ser100, Gly100A, Ser100B, Arg100D, based on Kabat numbering with respect to the sequence of SEQ ID NO:104. As identified in the Examples, these are the residues in the 1D1 and 1D1 1.31 light and heavy chain variable domain sequences that have a buried surface (BSA) of 20 $Å^2$ or greater, or are involved in electrostatic interactions when the antibodies are bound to TL1A.

An antibody or antigen-binding fragment thereof of the invention may comprise a CDR region from the specific antibody identified herein such as a CDR region from within SEQ ID NO:106, SEQ ID NO:198, SEQ ID NO:205, SEQ ID NO:205, SEQ ID NO:212, SEQ ID NO:219, SEQ ID NO:226, SEQ ID NO:233, SEQ ID NO:240, SEQ ID NO:247, SEQ ID NO: 24, SEQ ID NO:38, SEQ ID NO:102, SEQ ID NO:22, or SEQ ID NO:36. Such an antibody will preferably retain the ability to bind to TL1A as described herein.

For example, the CDR sequences of the antibodies of the invention are shown in FIG. 1A-L, Table 8, Table 11, and the Sequence Listing Table (Table 40), using both the Kabat definition and AntibodyM definitions.

In one aspect, the disclosure provides an isolated antibody or antigen-binding portion thereof that comprises a) a VH comprising: i) a CDR-H1 comprising the amino acid sequence of SEQ ID NO:202; ii) a CDR-H2 comprising the acid sequence selected from SEQ ID NO: 203, 210, 217, 224, 231, 238, 245, or 252; iii) a CDR-H2 comprising the amino acid sequence selected from SEQ ID NO:204, 211, 218, 225, 232, 239, 246, or 253; and a VL comprising a CDR-L1 having the amino acid sequence of SEQ ID NO:110, a CDR-L2 having the amino acid sequence of SEQ ID NO:111, and a CDR-L3 having the amino acid sequence of SEQ ID NO:112;

b) a VH comprising the CDR-H1 amino acid sequence of SEQ ID NO:113, the CDR-H2 amino acid sequence of SEQ NO:114, the CDR-H3 amino acid sequence of SEQ ID NO:115, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

c) a VH comprising the CDR-H1 amino acid sequence of SEQ ID NO:202, the CDR-H2 amino acid sequence of SEQ NO:203, the CDR-H3 amino acid sequence of SEQ ID NO:204, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

d) a VH comprising the CDR-H1 amino acid sequence of SEQ ID NO:209, the CDR-H2 amino acid sequence of SEQ NO:210, the CDR-H3 amino acid sequence of SEQ ID NO:211, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

e) a VH comprising the CDR-H1 amino acid sequence of SEQ ID NO:216, the CDR-H2 amino acid sequence of SEQ NO:217, the CDR-H3 amino acid sequence of SEQ ID NO:218, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

f) a VH comprising the CDR-H1 amino acid sequence of SEQ ID NO:223, the CDR-H2 amino acid sequence of SEQ NO:224, the CDR-H3 amino acid sequence of SEQ ID NO:225, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

g) a VH comprising the CDR-H1 amino acid sequence of SEQ ID NO:230, the CDR-H2 amino acid sequence of SEQ NO:231, the CDR-H3 amino acid sequence of SEQ ID NO:232, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

h) a VH comprising the CDR-H1 amino acid sequence of SEQ ID NO:237, the CDR-H2 amino acid sequence of SEQ NO:238, the CDR-H3 amino acid sequence of SEQ ID NO:239, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

i) a VH comprising the CDR-H1 amino acid sequence of SEQ ID NO:244, the CDR-H2 amino acid sequence of SEQ NO:245, the CDR-H3 amino acid sequence of SEQ ID NO:246, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

j) a VH comprising the CDR-H1 amino acid sequence of SEQ ID NO:251, the CDR-H2 amino acid sequence of SEQ NO:252, the CDR-H3 amino acid sequence of SEQ ID NO:253, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

k) a VH comprising the CDR-H1 amino acid sequence of SEQ ID NO:33, the CDR-H2 amino acid sequence of SEQ NO:34, the CDR-H3 amino acid sequence of SEQ ID NO:35, and a VL comprising the CDR-L1 amino acid sequence of SEQ ID NO:30, the CDR-L2 amino acid sequence of SEQ ID NO:31, and the CDR-L3 amino acid sequence of SEQ ID NO:32; or l) a VH comprising the CDR-H1 amino acid sequence of SEQ ID NO:47, the CDR-H2 amino acid sequence of SEQ NO:48, the CDR-H3 amino acid sequence of SEQ ID NO:49, and a VL comprising the CDR-L1 amino acid sequence of SEQ ID NO:44, the CDR-L2 amino acid sequence of SEQ ID NO:45, and the CDR-L3 amino acid sequence of SEQ ID NO:46.

In one aspect, the disclosure provides an antibody variant comprising 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the CDRs listed above. In a further aspect, the variant shares at least 65%, at least 75%, at least 85%, at least 90%, at least 95%, at least 96%, at least 97%, at least 98%, or at least 99% sequence identity with the CDR sequences listed above, and wherein the antibody, or antigen-binding portion thereof, specifically binds TL1A.

Antibody 7D4, 22F9, and Variants Thereof

An antibody or antigen-binding fragment thereof of the invention may comprise a VH comprising: i) a CDR-H1 comprising the amino acid sequence GYTFTSY$X_1X_2X_3$, wherein $X_1$ is G or A; $X_2$ is I or M; and $X_3$ is N or H (SEQ ID NO: 386); ii) a CDR-H2 comprising the amino acid sequence WI$X_4X_5X_6$NGNT$X_7X_8X_9$QK$X_{10}$QG, wherein $X_4$ is S or N; $X_5$ is T or A; $X_6$ is Y or G; $X_7$ is N or K; $X_8$ is S or Y; and $X_9$ is A or S; $X_{10}$ is L or F (SEQ ID NO: 387); iii) a CDR-H3 comprising the amino acid sequence $X_{11}X_{12}$SS$X_{13}$WFDAFDI wherein $X_{11}$ is A or G; $X_{12}$ is H or Y; and $X_{13}$ is S or A (SEQ ID NO: 388); iv) a D or an E at position H85, as determined by Kabat numbering of the VH; and a VL comprising a CDR-L1 having the amino acid sequence of SEQ ID NO:96, a CDR-L2 having the amino acid sequence of SEQ ID NO:97, and a CDR-L3 having the amino acid sequence of SEQ ID NO:98.

In a further embodiment, an antibody or antigen-binding fragment thereof of the invention may comprise a VH comprising SEQ ID NO:52 or 90, and a VL comprising SEQ ID NO:50.

An antibody or antigen-binding fragment thereof of the invention may comprise both:

a) a VH comprising the amino acid sequence of SEQ ID NO:90 and a VL comprising the amino acid sequence of SEQ ID NO:88; or b) a VH comprising the amino acid sequence of SEQ ID NO:52 and a VL comprising the amino acid sequence of SEQ ID NO:50.

In one aspect, the antibody comprises a VL comprising the sequence of SEQ ID NO:88 or SEQ ID NO:50. In another aspect, the antibody comprises a variant of these sequences, wherein such variants can include both conservative and non-conservative substitutions, deletions, and/or additions, and typically include peptides that share at least 60%, at least 65%, at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific sequences disclosed herein.

For example, in one aspect, the disclosure provides an isolated antibody or antigen-binding portion thereof comprising a VL chain amino acid sequence as set forth in SEQ ID NO:88 or SEQ ID NO:50, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:88 or SEQ ID NO:50. In a further aspect, said variant shares at least 65%, at least 75%, at least 85%, at least 90%, at least 95%, at least 96%, at least 97%, at least 98%, or at least 99% sequence identity with SEQ ID NO:88 or SEQ ID NO:50, and wherein said antibody or antigen-binding portion specifically binds TL1A.

In a further aspect, the disclosure provides an isolated antibody or antigen-binding portion thereof comprising a VH chain amino acid sequence as set forth in SEQ ID NO:90 or SEQ ID NO:52, or a variant thereof. In one aspect, the antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:90 or SEQ ID NO:52. In a further aspect, the variant shares at least 65%, at least 75%, at least 85%, at least 90%, at least 95%, at least 96%, at least 97%, at least 98%, or at least 99% sequence identity with SEQ ID NO:90 or SEQ ID NO:52, and wherein the antibody or antigen-binding portion specifically binds TL1A.

An antibody or antigen-binding fragment thereof of the invention may comprise a heavy chain comprising a VH comprising the amino acid sequence of SEQ ID NO:90 or SEQ ID NO:52, wherein the antibody further comprises a heavy chain constant domain. As more fully set forth elsewhere herein, the antibody heavy chain constant domain can be selected from an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). For a Fab fragment heavy chain gene, the VH-encoding DNA can be operatively linked to another DNA molecule encoding only the heavy chain CH1 constant region. The CH1 heavy chain constant region may be derived from any of the heavy chain genes.

In one aspect, the antibody may comprise a heavy chain comprising a VH selected from a VH comprising the amino acid sequence of SEQ ID NO:90 or SEQ ID NO:52 and further comprising a human wild type IgG1 constant domain comprising the amino acid sequence of SEQ ID NO:256. In another aspect, the IgG1 constant domain comprises a triple mutation decreasing or abolishing Fc effector function (hIgG1-3m; SEQ ID NO:257). In one aspect, the antibody or antigen-binding fragment thereof of the invention may comprise a heavy chain comprising a VH comprising the sequence of SEQ ID NO:90 or SEQ ID NO:52, and further comprising a human IgG1-3m constant domain such that the full-length heavy chain amino acid sequence comprises SEQ ID NO. 94 or SEQ ID NO:56.

In a further aspect, the disclosure provides an isolated antibody or antigen-binding portion thereof comprising a full-length heavy chain comprising the amino acid sequence as set forth in SEQ ID NO. 94 or SEQ ID NO:56, or a variant thereof. In one aspect, the antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO. 94 or SEQ ID NO:56. In a further aspect, the variant shares at least 65%, at least 75%, at least 85%, at least 90%, at least 95%, at least 96%, at least 97%, at least 98%, or at least 99% sequence identity with SEQ ID NO. 94 or SEQ ID NO:56, and wherein theantibody or antigen-binding portion specifically binds TL1A.

An antibody or antigen-binding fragment thereof of the invention may comprise a light chain comprising a VL comprising the amino acid sequence of SEQ ID NO:88 or SEQ ID NO:50, wherein the antibody further comprises a light chain constant domain. As more fully set forth elsewhere herein, the antibody light chain constant domain can be selected from a CK or CA constant region, preferably, a CK constant region.

In one aspect, the antibody may comprise a light chain comprising a VL selected from a VL comprising the amino acid sequence of SEQ ID NO:88 or SEQ ID NO:50, and further comprising a human wild type CA constant domain comprising the amino acid sequence of SEQ ID NO:255, such that the full-length light chain amino acid sequence comprises SEQ ID NO:92 or SEQ ID NO:54.

In a further aspect, the disclosure provides an isolated antibody or antigen-binding portion thereof comprising a full-length light chain comprising the amino acid sequence as set forth in SEQ ID NO:92 or SEQ ID NO:54, or a variant thereof. In one aspect, the antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:92 or SEQ ID NO:54. In a further aspect, the variant shares at least 65%, at least 75%, at least 85%, at least 90%, at least 95%, at least 96%, at least 97%, at least 98%, or at least 99% sequence identity with SEQ ID NO:92 or SEQ ID NO:54, and wherein the antibody or antigen-binding portion specifically binds TL1A.

An antibody or antigen-binding fragment thereof of the invention may comprise a fragment of one of the VL or VH amino acid sequences shown in FIG. 1A-L. For example, an antibody or antigen-binding fragment thereof of the invention may comprise a fragment of at least 7, at least 8, at least 9, at least 10, at least 12, at least 15, at least 18, at least 20 or at least 25 consecutive amino acids from a VH comprising SEQ ID NO:90 or SEQ ID NO:52, or from a VL comprising SEQ ID NO:88, or SEQ ID NO:50. Such a fragment will preferably retain one or more of the functions discussed above, such as the ability to bind to TL1A, the ability to inhibit TL1A binding to its receptor DR3, the ability to inhibit TL1A signaling via its receptor, among others.

A suitable fragment or variant of any of these VH or VL sequences will retain the ability to bind to TL1A. It will preferably retain the ability to specifically bind to TL1A. It will preferably retain the ability to specifically bind to the same or similar epitope or region of the TL1A molecule as the antibody from which it is derived. It will preferably retain one or more additional functions of the antibody from which it is derived, such as the ability to inhibit TL1A binding to its receptor (e.g., DR3), the ability to inhibit TL1A signaling by its receptor, among others.

An antibody or antigen-binding fragment thereof of the invention may comprise a CDR region from the specific antibody identified herein such as a CDR region from within SEQ ID NO: 88, SEQ ID NO:50, SEQ ID NO:90, or SEQ ID NO:50. Such an antibody will preferably retain the ability to bind to TL1A as described herein.

For example, the CDR sequences of the antibodies of the invention are shown in FIG. 1A-L and in the Sequence Listing Table (Table 40), using both the Kabat definition and AntibodyM definitions.

In one aspect, the disclosure provides an isolated antibody or antigen-binding portion thereof comprising:

a) a VH comprising the CDR-H1 amino acid sequence of SEQ ID NO:99, the CDR-H2 amino acid sequence of SEQ NO:100, the CDR-H3 amino acid sequence of SEQ ID NO:101, and a VL comprising the CDR-L1 amino acid sequence of SEQ ID NO:96, the CDR-L2 amino acid sequence of SEQ ID NO:97, and the CDR-L3 amino acid sequence of SEQ ID NO:98; or b) a VH comprising the CDR-H1 amino acid sequence of SEQ ID NO:61, the CDR-H2 amino acid sequence of SEQ NO:62, the CDR-H3 amino acid sequence of SEQ ID NO:63, and a VL comprising the CDR-L1 amino acid sequence of SEQ ID NO:58, the CDR-L2 amino acid sequence of SEQ ID NO:59, and the CDR-L3 amino acid sequence of SEQ ID NO:60.

In one aspect, the disclosure provides an antibody variant comprising 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the CDRs listed above as SEQ ID NOS:96-101 or SEQ ID NOS: 58-63. In a further aspect, the variant shares at least 65%, at least 75%, at least 85%, at least 90%, at least 95%, at least 96%, at least 97%, at least 98%, or at least 99% sequence identity with the CDR sequences listed above, and wherein the antibody or antigen-binding portion specifically binds TL1A.

Antibody 26B11, 9B3, and Variants Thereof

An antibody or antigen-binding fragment thereof of the invention may comprise a VH comprising: i) a CDR-H1 comprising the amino acid sequence GFTFS$X_1X_2$A$X_3$H, wherein $X_1$ is N or S; $X_2$ is Y or F; and $X_3$ is L, M, or I (SEQ ID NO: 389); ii) a CDR-H2 comprising the amino acid sequence LI$X_4X_5$DGS$X_6X_7$YYADSVKG, wherein $X_4$ is S or P; $X_5$ is Y or F; $X_6$ is D,S, or N; $X_7$ is K or N (SEQ ID NO: 390); iii) a CDR-H3 comprising the amino acid sequence DR$X_8$Y$X_9X_{10}X_{11}X_{12}$S$X_{13}$S$X_{14}$DAFDI wherein $X_8$ is E or N; $X_9$ is C or Y; $X_{10}$ is T or G; $X_{11}$ is Y or S; $X_{12}$ is S or G; $X_{13}$ is C or F; $X_{14}$ is Y or F; iv) an A or T at position H85, as determined by Kabat numbering of the VH; v) a M or L at position 108, as determined by Kabat numbering of the VH; and a VL comprising a CDR-L1 having the amino acid sequence of SEQ ID NO:76, a CDR-L2 having the amino acid sequence of SEQ ID NO:77, and a CDR-L3 having the amino acid sequence of SEQ ID NO:78; and a F or Y at position L83, as determined by Kabat numbering of the VL.

In a further embodiment, an antibody or antigen-binding fragment thereof of the invention may comprise a VH comprising SEQ ID NO:66, 68 or 70, and a VL comprising SEQ ID NO:1 or 64.

An antibody or antigen-binding fragment thereof of the invention may comprise both:

a) a VH comprising the amino acid sequence of SEQ ID NO:66 and a VL comprising the amino acid sequence of SEQ ID NO:64; or b) a VH comprising the amino acid sequence of SEQ ID NO:68 and a VL comprising the amino acid sequence of SEQ ID NO:64, or c) a VH comprising the amino acid sequence of SEQ ID NO:70 and a VL comprising the amino acid sequence of SEQ ID NO:64, or d) a VH comprising the amino acid sequence of SEQ ID NO:3 and a VL comprising the amino acid sequence of SEQ ID NO:1; or e) a VH comprising the amino acid sequence of SEQ ID NO:5 and a VL comprising the amino acid sequence of SEQ ID NO:1.

In one aspect, the antibody comprises a VL comprising the sequence of SEQ ID NO:64 or SEQ ID NO:1. In another aspect, the antibody comprises a variant of these sequences, wherein such variants can include both conservative and non-conservative substitutions, deletions, and/or additions, and typically include peptides that share at least 60%, at least 65%, at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific sequences disclosed herein.

For example, in one aspect, the disclosure provides an isolated antibody or antigen-binding portion thereof that comprises a VL chain amino acid sequence as set forth in SEQ ID NO:64 or SEQ ID NO:1, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:64 or SEQ ID NO:1. In a further aspect, said variant shares at least 65%, at least 75%, at least 85%, at least 90%, at least 95%, at least 96%, at least 97%, at least 98%, or at least 99% sequence identity with SEQ ID NO:64 or SEQ ID NO:1, and wherein said antibody or antigen-binding portion specifically binds TL1A.

In a further aspect, the disclosure provides an isolated antibody or antigen-binding portion thereof that comprises a $V_H$ chain amino acid sequence as set forth in SEQ ID NO:66, SEQ ID NO: 68 or SEQ ID NO:70, SEQ ID NO:3, or SEQ ID NO:5 or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:66, SEQ ID NO: 68 or SEQ ID NO:70, SEQ ID NO:3, or SEQ ID NO:5. In a further aspect, said variant shares at least 65%, at least 75%, at least 85%, at least 90%, at least 95%, at least 96%, at least 97%, at least 98%, or at least 99% sequence identity with SEQ ID NO:66, SEQ ID NO: 68 or SEQ ID NO:70, SEQ ID NO:3, or SEQ ID NO:5, and wherein said antibody or antigen-binding portion specifically binds TL1A.

An antibody or antigen-binding fragment thereof of the invention may comprise a heavy chain comprising a VH comprising the amino acid sequence of SEQ ID NO:66, SEQ ID NO: 68 or SEQ ID NO:70, SEQ ID NO:3, or SEQ ID NO:5, wherein the antibody further comprises a heavy chain constant domain. As more fully set forth elsewhere herein, the antibody heavy chain constant domain can be selected from an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). For a Fab fragment heavy chain gene, the VH-encoding DNA can be operatively linked to another DNA molecule encoding only the heavy chain CH1 constant region. The CH1 heavy chain constant region may be derived from any of the heavy chain genes.

In one aspect, the antibody may comprise a heavy chain comprising a VH selected from a VH comprising the amino acid sequence of SEQ ID NO:66, SEQ ID NO: 68 or SEQ ID NO:70, SEQ ID NO:3, or SEQ ID NO:5 and further comprising a human wild type IgG1 constant domain comprising the amino acid sequence of SEQ ID NO:256. In another aspect, the IgG1 constant domain comprises a triple mutation decreasing or abolishing Fc effector function (hIgG1-3m; SEQ ID NO:257). In one aspect, the antibody or antigen-binding fragment thereof of the invention may comprise a heavy chain comprising a VH comprising the sequence of SEQ ID NO:66, SEQ ID NO: 68 or SEQ ID NO:70, SEQ ID NO:3, or SEQ ID NO:5, and further comprising a human IgG1-3m constant domain such that the full-length heavy chain amino acid sequence comprises SEQ ID NO. 74, SEQ ID NO:9 or SEQ ID NO:11.

In a further aspect, the disclosure provides an isolated antibody or antigen-binding portion thereof that comprises a full-length heavy chain comprising the amino acid sequence as set forth in SEQ ID NO. 74, SEQ ID NO:9 or SEQ ID NO:11, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO. 74, SEQ ID NO:9 or SEQ ID NO:11. In a further aspect, said variant shares at least 65%, at least 75%, at least 85%, at least 90%, at least 95%, at least 96%, at least 97%, at least 98%, or at least 99% sequence identity with SEQ ID NO. 74, SEQ ID NO:9 or SEQ ID NO:11, and wherein said antibody or antigen-binding portion specifically binds TL1A.

An antibody or antigen-binding fragment thereof of the invention may comprise a light chain comprising a VL comprising the amino acid sequence of SEQ ID NO:64 or SEQ ID NO:1, wherein the antibody further comprises a light chain constant domain. As more fully set forth elsewhere herein, the antibody light chain constant domain can be selected from a Cκ or Cλ constant region, preferably, a Cκ constant region.

In one aspect, the antibody may comprise a light chain comprising a VL selected from a VL comprising the amino acid sequence of SEQ ID NO:64 or SEQ ID NO:1, and further comprising a human wild type Cλ constant domain comprising the amino acid sequence of SEQ ID NO:255, such that the full-length light chain amino acid sequence comprises SEQ ID NO:72 or SEQ ID NO:7.

In a further aspect, the disclosure provides an isolated antibody or antigen-binding portion thereof that comprises a full-length light chain comprising the amino acid sequence as set forth in SEQ ID NO:72 or SEQ ID NO:7, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:72 or SEQ ID NO:7. In a further aspect, said variant shares at least 65%, at least 75%, at least 85%, at least 90%, at least 95%, at least 96%, at least 97%, at least 98%, or at least 99% sequence identity with SEQ ID NO:72 or SEQ ID NO:7, and wherein said antibody or antigen-binding portion specifically binds TL1A.

An antibody or antigen-binding fragment thereof of the invention may comprise a fragment of one of the VL or VH amino acid sequences shown in FIG. 1A-L. For example, an antibody or antigen-binding fragment thereof of the invention may comprise a fragment of at least 7, at least 8, at least 9, at least 10, at least 12, at least 15, at least 18, at least 20 or at least 25 consecutive amino acids from a VH comprising SEQ ID NO:66, SEQ ID NO: 68 or SEQ ID NO:70, SEQ ID NO:3, or SEQ ID NO:5, or from a VL comprising SEQ ID NO:72 or SEQ ID NO:7. Such a fragment will preferably retain one or more of the functions discussed above, such as the ability to bind to TL1A.

A suitable fragment or variant of any of these VH or VL sequences will retain the ability to bind to TL1A. It will preferably retain the ability to specifically bind to TL1A. It will preferably retain the ability to specifically bind to the same or similar epitope or region of the TL1A molecule as the antibody from which it is derived. It will preferably retain one or more additional functions of the antibody from which it is derived, such as the ability to inhibit TL1A binding to its receptor, among others.

An antibody or antigen-binding fragment thereof of the invention may comprise a CDR region from the specific antibody identified herein such as a CDR region from within SEQ ID NO:66, SEQ ID NO: 68 or SEQ ID NO:70, SEQ ID NO:3, SEQ ID NO:5, SEQ ID NO:64 or SEQ ID NO:1. Such an antibody will preferably retain the ability to bind to TL1A as described herein.

For example, the CDR sequences of the antibodies of the invention are shown in FIG. 1A-L and the Sequence Listing Table (Table 40), using both the Kabat definition and AntibodyM definitions.

In one aspect, the disclosure provides an isolated antibody or antigen-binding portion thereof comprising:

a) the CDR-H1 amino acid sequence of SEQ ID NO:79, the CDR-H2 amino acid sequence of SEQ NO:80, and the CDR-H3 amino acid sequence of SEQ ID NO:81, and a VL comprising the CDR-L1 amino acid sequence of SEQ ID NO:76, the CDR-L2 amino acid sequence of SEQ ID NO:77, and the CDR-L3 amino acid sequence of SEQ ID NO:78;

b) a VH comprising the CDR-H1 amino acid sequence of SEQ ID NO:82, the CDR-H2 amino acid sequence of SEQ NO:83, and the CDR-H3 amino acid sequence of SEQ ID NO:84, and a VL comprising the CDR-L1 amino acid sequence of SEQ ID NO:76, the CDR-L2 amino acid sequence of SEQ ID NO:77, and the CDR-L3 amino acid sequence of SEQ ID NO:78; or c) a VH comprising the CDR-H1 amino acid sequence of SEQ ID NO:85, the CDR-H2 amino acid sequence of SEQ NO:86, and the CDR-H3 amino acid sequence of SEQ ID NO:87, and a VL comprising the CDR-L1 amino acid sequence of SEQ ID NO:76, the CDR-L2 amino acid sequence of SEQ ID NO:77, and the CDR-L3 amino acid sequence of SEQ ID NO:78; or d) a VH comprising the CDR-H1 amino acid sequence of SEQ ID NO:16, the CDR-H2 amino acid sequence of SEQ NO:17, the CDR-H3 amino acid sequence of SEQ ID NO:18, and a VL comprising the CDR-L1 amino acid sequence of SEQ ID NO:13, the CDR-L2 amino acid sequence of SEQ ID NO:14, and the CDR-L3 amino acid sequence of SEQ ID NO:15; or e) a VH comprising the CDR-H1 amino acid sequence of SEQ ID NO:19, the CDR-H2 amino acid sequence of SEQ NO:20, the CDR-H3 amino acid sequence of SEQ ID NO:21, and a VL comprising the CDR-L1 amino acid sequence of SEQ ID NO:13, the CDR-L2 amino acid sequence of SEQ ID NO:14, and the CDR-L3 amino acid sequence of SEQ ID NO:15.

In one aspect, the disclosure provides an antibody variant comprising 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the CDRs listed above. In a further aspect, the variant shares at least 65%, at least 75%, at least 85%, at least 90%, at least 95%, at least 96%, at least 97%, at least 98%, or at least 99% sequence identity with the CDR sequences listed above, and wherein the antibody or antigen-binding portion specifically binds TL1A.

Polynucleotides, Vectors, and Host Cells

The invention also provides polynucleotides encoding any of the antibodies, including antibody fragments and modified antibodies described herein, such as, e.g., antibodies having impaired effector function. In another aspect, the invention provides a method of making any of the polynucleotides described herein. Polynucleotides can be made and expressed by procedures known in the art. Accordingly, the invention provides polynucleotides or compositions, including pharmaceutical compositions, comprising polynucleotides, encoding any of the following TL1A antibodies and antigen-binding fragments thereof: 1D1 VL (SEQ ID NO:102), 1D1 VH (SEQ ID NO:104), 1D1 LC (SEQ ID NO: 106), 1D1-hIgG1-3m-HC (SEQ ID NO:108), 1D1 1.27 VH (SEQ ID NO: 198), 1D1 1.27-hIgG1-3m-HC (SEQ ID NO:200), 1D1 1.28 VH (SEQ ID NO: 205), 1D1 1.28-hIgG1-3m-HC (SEQ ID NO:207), 1D1 1.29 VH (SEQ ID NO: 212), 1D1 1.29-hIgG1-3m-HC (SEQ ID NO:214), 1D1 1.30 VH (SEQ ID NO: 219), 1D1 1.30-hIgG1-3m-HC (SEQ ID NO:221), 1D1 1.31 VH (SEQ ID NO: 226), 1D1 1.31-hIgG1-3m-HC (SEQ ID NO:228), 1D1 1.32 VH (SEQ ID NO: 233), 1D1 1.32-hIgG1-3m-HC (SEQ ID NO:235), 1D1 1.33 VH (SEQ ID NO: 240), 1D1 1.33-hIgG1-3m-HC (SEQ ID NO:242), 1D1 1.34 VH (SEQ ID NO: 247), 1D1 1.34- hIgG1-3m-HC (SEQ ID NO:249), 15A9 VL (SEQ ID NO:22), 15A9 VH (SEQ ID NO:24), 15A9 LC (SEQ ID NO: 26), 1D1-hIgG1-3m-HC (SEQ ID NO:28), 15C11 VL (SEQ ID NO:36), 15C11 VH (SEQ ID NO:38), 15C11 LC (SEQ ID NO: 40), 15C11-hIgG1-3m-HC (SEQ ID NO:42), 7D4 VL (SEQ ID NO:88), 7D4 VH (SEQ ID NO:90), 7D4 LC (SEQ ID NO:92), 7D4-hIgG1-3m-HC (SEQ ID NO:94), 22F9 VL (SEQ ID NO:50), 22F9 VH (SEQ ID NO:52), 22F9 LC (SEQ ID NO:54), 22F9-hIgG1-3m-HC (SEQ ID NO:56), 26B11 VL (SEQ ID NO:64), 26B11 VH1 (SEQ ID NO:66), 26B11 VH2 (SEQ ID NO:68), 26B11 VH-MDX (SEQ ID NO:70), 26B11 LC (SEQ ID NO:72), 26B11-hIgG1-3m-HC (SEQ ID NO:74), 9B3 VL (SEQ ID NO:1), 9B3 VH1 (SEQ ID NO:3); 9B3 VH2 (SEQ ID NO:5), 9B3 LC (SEQ ID NO:7), 9B3-hIgG1-3m-HC1 (SEQ ID NO:9), 9B3-hIgG1-3m-HC2 (SEQ ID NO:11), or any fragment or part thereof having the ability to bind TL1A.

The invention provides polynucleotides, or compositions comprising the polynucleotides, encoding any of the following TL1A antibodies and antigen-binding fragments thereof or the invention, including: 1D1 VL (SEQ ID NO:102), 1D1 VH (SEQ ID NO:104), 1D1 LC (SEQ ID NO: 106), 1D1-hIgG1-3m-HC (SEQ ID NO:108), 1D1 1.27 VH (SEQ ID NO: 198), 1D1 1.27-hIgG1-3m-HC (SEQ ID NO:200), 1D1 1.28 VH (SEQ ID NO: 205), 1D1 1.28-hIgG1-3m-HC (SEQ ID NO:207), 1D1 1.29 VH (SEQ ID NO: 212), 1D1 1.29-hIgG1-3m-HC (SEQ ID NO:214), 1D1 1.30 VH (SEQ ID NO: 219), 1D1 1.30-hIgG1-3m-HC (SEQ ID NO:221), 1D1 1.31 VH (SEQ ID NO: 226), 1D1 1.31-hIgG1-3m-HC (SEQ ID NO:228), 1D1 1.32 VH (SEQ ID NO: 233), 1D1 1.32-hIgG1-3m-HC (SEQ ID NO:235), 1D1 1.33 VH (SEQ ID NO: 240), 1D1 1.33-hIgG1-3m-HC (SEQ ID NO:242), 1D1 1.34 VH (SEQ ID NO: 247), 1D1 1.34-hIgG1-3m-HC (SEQ ID NO:249), 15A9 VL (SEQ ID NO:22), 15A9 VH (SEQ ID NO:24), 15A9 LC (SEQ ID NO: 26), 1D1-hIgG1-3m-HC (SEQ ID NO:28), 15C11 VL (SEQ ID NO:36), 15C11 VH (SEQ ID NO:38), 15C11 LC (SEQ ID NO: 40), 15C11-hIgG1-3m-HC (SEQ ID NO:42), 7D4 VL (SEQ ID NO:88), 7D4 VH (SEQ ID NO:90), 7D4 LC (SEQ ID NO:92), 7D4-hIgG1-3m-HC (SEQ ID NO:94), 22F9 VL (SEQ ID NO:50), 22F9 VH (SEQ ID NO:52), 22F9 LC (SEQ ID NO:54), 22F9-hIgG1-3m-HC (SEQ ID NO:56), 26B11 VL (SEQ ID NO:64), 26B11 VH1 (SEQ ID NO:66), 26B11 VH2 (SEQ ID NO:68), 26B11 VH-MDX (SEQ ID NO:70), 26B11 LC (SEQ ID NO:72), 26B11-hIgG1-3m-HC (SEQ ID NO:74), 9B3 VL (SEQ ID NO:1), 9B3 VH1 (SEQ ID NO:3); 9B3 VH2 (SEQ ID NO:5), 9B3 LC (SEQ ID NO:7), 9B3-hIgG1-3m-HC1 (SEQ ID NO:9), 9B3-hIgG1-3m-HC2 (SEQ ID NO:11), or any fragment or part thereof having the ability to bind TL1A, wherein the sequence of the polynucleotide encompasses the sequence of SEQ ID NO:103 (encoding 1D1 VL), SEQ ID NO:105 (encoding 1D1 VH), SEQ ID NO:107 (encoding 1D1 LC), SEQ ID NO: 109 (encoding 1D1-hIgG1-3m-HC), SEQ ID NO:199 (encoding 1D1 1.27 VH), SEQ ID NO:201 (encoding 1D1 1.27-hIgG1-3m-HC), SEQ ID NO:206 (encoding 1D1 1.28 VH), SEQ ID NO: 208 (encoding 1D1 1.28-hIgG1-3m-HC), SEQ ID NO:213 (encoding 1D1 1.29 VH), SEQ ID NO: 215 (encoding 1D1 1.29-hIgG1-3m-HC), SEQ ID NO:220 (encoding 1D1 1.30 VH), SEQ ID NO: 222 (encoding 1D1 1.30-hIgG1-3m-HC), SEQ ID NO:227 (encoding 1D1 1.31 VH), SEQ ID NO: 229 (encoding 1D1 1.31-hIgG1-3m-HC), SEQ ID NO:234 (encoding 1D1 1.32 VH), SEQ ID NO: 236 (endoding 1D1 1.32-hIgG1-3m-HC), SEQ ID NO:241 (encoding 1D1 1.33 VH), SEQ ID NO: 243 (encoding 1D1 1.33-hIgG1-3m-HC), SEQ ID NO:248 (encoding 1D1 1.34 VH), SEQ ID NO: 250 (encoding 1D1 1.34-hIgG1-3m-HC), SEQ ID NO:23 (encoding 15A9 VL), SEQ ID NO:25 (encoding 15A9 VH), SEQ ID NO:27 (encoding 15A9 LC), SEQ ID NO: 29 (encoding 1D1-hIgG1-3m-HC), SEQ ID NO:37 (encoding 15C11 VL), SEQ ID NO:39 (encoding 15C11 VH), SEQ ID NO:41 (endoding 15C11 LC), SEQ ID NO: 43 (encoding 15C11-hIgG1-3m-HC), SEQ ID NO:89 (encoding 7D4 VL), SEQ ID NO:91 (encoding 7D4 VH, SEQ ID NO:93 (encoding 7D4 LC), SEQ ID NO:95 (encoding 7D4-hIgG1-3m-HC), SEQ ID NO:51 (encoding 22F9 VL), SEQ ID NO:53 (encoding 22F9 VH), SEQ ID NO:55 (encoding 22F9 LC), SEQ ID NO:57 (encoding 22F9-hIgG1-3m-HC), SEQ ID NO:65 (encoding 26B11 VL), SEQ ID NO:67 (encoding 26B11 VH1), SEQ ID NO:69 (encoding 26B11 VH2), SEQ ID NO:71 (encoding 26B11 VH-MDX), SEQ ID NO:73 (encoding 26B11 LC), SEQ ID NO:75 (encoding 26B11-hIgG1-3m-HC), SEQ ID NO:2 (encoding 9B3 VL), SEQ ID NO:4 (encoding 9B3 VH1), SEQ ID NO:6 (encoding 9B3 VH2), SEQ ID NO:8 (encoding 9B3 LC), SEQ ID NO:10 (encoding 9B3-hIgG1-3m-HC1), SEQ ID NO:12 (encoding 9B3-hIgG1-3m-HC2), or any fragment or part thereof having the ability to bind TL1A).

In one embodiment, the VH and VL domains, or antigen-binding fragment thereof, or full length HC or LC, are encoded by separate polynucleotides. Alternatively, both VH and VL, or antigen-binding fragment thereof, or HC and LC, are encoded by a single polynucleotide.

In another aspect, the invention provides polynucleotides and variants thereor encoding a TL1A antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid disclosed herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to TL1A is effected by an immunoassay or FACS. A cell overexpressing the antibody or protein of interest can be identified.

An expression vector can be used to direct expression of a TL1A antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Antibody Binding

The antibody or antigen-binding fragment thereof described herein selectively bind tumor necrosis factor-like ligand 1A (TL1A). In one embodiment, the antibody or antigen-binding fragment thereof bind the human tumor necrosis factor-like ligand 1A (hTL1A).

In certain cases, particularly when developing a therapeutic, it is advantageous for the antibody to cross-react with TL1A from other species that can be used as surrogate models of safety and/or efficacy. For example, in some cases, toxicity and/or efficacy of a therapeutic can be measured in a surrogate animal model of a particular disease. As such, in one embodiment, the antibody or antigen-binding fragment thereof binds the human tumor necrosis factor-like ligand 1A (hTL1A), as well as the tumor necrosis factor-like ligand 1A from at least one other mammal selected from the group consisting of a mouse, rat, dog, and a cynologous monkey. In a particular embodiment, the KD of the antibody for the tumor necrosis factor-like ligand 1A from at least one other mammal selected from the group consisting of a mouse, rat, dog, and a cynologous monkey is no greater than 30 fold higher, for example, no greater than 20 fold higher, no greater than 15 fold higher, or no greater than 10-fold higher, than the KD of the antibody for hTL1A. In still another embodiment, the antibody or antigen-binding fragment thereof has an affinity for the murine TL1A of 10 nM or less, for example, 3 nM or less, 1 nM or less, 300 pM or less, or 100 pM or less, as measured by SPR.

In another embodiment, the antibody or antigen-binding fragment thereof has an affinity for human TNF alpha of 1 μM or greater, for example, 3 μM or greater, 10 μM or greater, 30 μM or greater, 100 μM or greater, as measured by SPR.

In still another embodiment, the antibody or antigen-binding fragment thereof has an affinity for the murine TL1A of 10 nM or less, for example, 3 nM or less, 1 nM or less, 300 pM or less, or 100 pM or less, as measured by SPR. In a particular embodiment, the antibody or antigen-binding fragment there of has an affinity for the human TL1A of 100 pM or less, an affinity for the murine TL1A of 300 pM or less, as measured by SPR, and an affinity for human TNF alpha of 1 μM or greater.

In one embodiment, the antibody or antigen-binding fragment thereof has an affinity for human TL1A of 4 nM or less, for example, 1 nM or less, 500 pM or less, 250 pM or less, 100 pM or less, 50 pM or less, 25 pM or less, 10 pM or less, 5 pM or less, as measured by surface plasmon resonance (SPR).

In another embodiment, the antibody or antigen-binding fragment thereof has an affinity for human TNF alpha of 1 μM or greater, for example, 3 μM or greater, 10 μM or greater, 30 μM or greater, 100 μM or greater, as measured by SPR.

In still another embodiment, the antibody or antigen-binding fragment thereof competes with the antibody selected from the group consisting of 1D1 1.31, 26B11, 9B3, 7D4, 22F9, 15A9, and 15C11, as defined herein below.

In a particular embodiment, the antibody or antigen-binding fragment there of has an affinity for the human TL1A of 100 pM or less, an affinity for the murine TL1A of 300 pM or less, as measured by SPR, and an affinity for human TNF alpha of 1 μM or greater.

In certain cases, the binding of the antibody or antigen-binding fragment thereof to TL1A or any other protein can be measured using surface plasmon resonance (SPR). In certain embodiments, the affinity is the KD value as measured by SPR. In still other cases, the SPR uses a captured antibody, and solution phase target. In some embodiments, the captured antibody is immobilized onto a sensor chip using an anti-isotype antibody or antigen binding portion thereof. For example, the anti-isotype antibody or antigen binding portion thereof can be immobilized onto the sensor chip to a density of between about 4,000 and about 13,000 response units. SPR measurement can also be performed, for example, as substantially conducted according to the protocol set out in Example 8. In some cases, the SPR uses a captured target, and solution phase antibody. In some embodiments, the SPR measurement is conducted using a Biacore T100 or T200 instrument.

In other embodiments, the affinity of the antibody or antigen-binding fragment thereof for human TL1A is measured by solution-based kinetic exclusion assay (KinExA). For example, in some cases, the affinity is the KD value as measured by solution-based kinetic exclusion assay (KinExA). In other cases, the KinExA uses a captured target on a solid phase, and a solution phase antibody. In still other cases, the antibody and target are pre-incubated in solution long enough to reach equilibrium. In one embodiment, the level of unbound antibody is measured after the antibody and target have reached equilibrium. In a particular embodiment, the KinExA measurement is conducted using a KinExA 3200 instrument (Sapidyne).

Therapeutic Methods

Therapeutic methods involve administering to a subject in need of treatment a therapeutically effective amount, or effective amount, of a TL1A antibody, or antigen-binding portion, of the invention and are contemplated by the present disclosure. As used herein, a “therapeutically effective”, or “effective”, amount refers to an amount of an antibody or portion thereof that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents. One of ordinary skill in the art would be able to determine such amounts based on such factors as the subject’s size, the severity of the subject’s symptoms, and the particular composition or route of administration selected. The subject may be a human or non-human animal (e.g., rabbit, rat, mouse, monkey or other lower-order primate).

An antibody or antigen-binding portion of the invention might be co-administered with known medicaments, and in some instances the antibody might itself be modified. For example, an antibody could be conjugated to an immunotoxin or radioisotope to potentially further increase efficacy. Regarding co-administration with additional therapeutic agents, such agents can include a cytotoxic agent, a radiotoxic agent or an immunosuppressive agent. The antibody can be linked to the agent (as an immunocomplex) or can be administered separately from the agent. In the latter case (separate administration), the antibody can be administered before, after or concurrently with the agent or can be co-administered with other known therapies, e.g., an anti-cancer therapy, e.g., radiation. Co-administration of the TL1A antibodies, or antigen binding fragments thereof, of the present disclosure with a therapeutic agent provides two agents which operate via different mechanisms may provide a therapeutic and perhaps synergistic effect to human disease.

The antibodies and antigen-binding portions disclosed herein can be used as a therapeutic or a diagnostic tool in a variety of situations where TL1A is undesirably expressed or found as reviewed, for example, in Hsu and Viney, supra. Given the involvement of TL1A in flammatory pathways and in numerous diseases, disorders and conditions, many such diseases, disorders or conditions are particularly suitable for treatment with an antibody or antigen-binding portion of the present invention. Accordingly, the TL1A antibodies, or antigen binding fragments thereof, of this disclosure can used in the treatment or prevention of TL1A-mediated disorders. In addition, the invention provides for use of the TL1A antibodies, or antigen binding fragments thereof, of this disclosure in the manufacture of a medicament for use in treatment or prevention of TL1A-mediated disorders. In another embodiment, this application discloses TL1A antibodies, or antigen binding fragments thereof, for use in treatment of TL1A-mediated disorders. In a further embodiment, this application discloses pharmaceutical compositions comprising the TL1A antibodies, or antigen binding fragments thereof, of this disclosure for use in treating or prevening TL1A-mediated diseases. These TL1A-mediated diseases, disorders or conditions include, but are not limited to, inflammatory disorder such as IBD (including Crohn's disease and ulcerative colitis), asthma (including intrinsic asthma and allergic asthma), allergies (for example, atopic allergy), diabetes mellitus, arthritic disorders (including rheumatoid arthritis, juvenile rheumatoid arthritis, osteoarthritis, psoriatic arthritis, and ankylosing spondylitis), multiple sclerosis, transplant rejection, graft-versus-host disease (GVHD), spondyloarthropathy, primary sclerosing cholangitis, primary biliary cirrhosis, atherosclerosis, bladder syndrome/intersticial cystitis, Urinary bowel disfunction, sepsis, uveitis, encephalomyelitis, myasthenia gravis, systemic lupus erythematosus, cutaneous lupus erythematosus, autoimmune thyroiditis, dermatitis (including atopic dermatitis and eczematous dermatitis), psoriasis, Sjogren's syndrome, scleroderma, and vasculitis.

To treat any of the foregoing disorders, pharmaceutical compositions for use in accordance with the present disclosure may be formulated in a conventional manner using one or more pharmaceutically acceptable carriers or excipients and administered as more fully discussed below.

Determining a therapeutically effective amount of an antibody or antigen-binding portion according to the present disclosure will largely depend on particular patient characteristics, route of administration, and the nature of the disorder being treated and is more fully discussed below.

Administration and dosing of the antibody are more fully discussed elsewhere below.

Diagnostic Methods

The TL1A antibodies, or antigen binding portions thereof disclosed herein can be used for diagnostic testing and imaging. For example, the TL1A antibodies or antigen binding portions thereof can be used in an ELISA assay. The antibodies or antigen binding portions thereof can also be used as a radiolabeled monoclonal antibody. See, for example, Srivastava (ed.), Radiolabeled Monoclonal Antibodies For Imaging And Therapy, Plenum Press (1988); Chase, "Medical Applications of Radioisotopes," in Remington's Pharmaceutical Sciences, 18th Edition, Gennaro et al. (eds.), Mack Publishing Co., pp. 624-652 (1990); and Brown, "Clinical Use of Monoclonal Antibodies," in Biotechnology and Pharmacy, Pezzuto et al. (eds.), Chapman and Hall, pp. 227-249 (1993); Grossman, 1986, Urol. Clin. North Amer. 13:465-474; Unger et al., 1985, Invest. Radiol. 20:693-700; and Khaw et al., 1980, Science 209:295-297. This technique, also known as immunoscintigraphy, uses a gamma camera to detect the location of gamma-emitting radioisotopes conjugated to monoclonal antibodies. Diagnostic imaging can be used to diagnose cancer, autoimmune disease, infectious disease and/or cardiovascular disease. (See, e.g., Brown, supra.)

In one embodiment, the TL1A antibodies or antigen binding fragments thereof can be used to diagnose TL1A-related diseases, disorders, or conditions, including immune-related diseases. For example, the antibodies, or antigen binding fragments thereof, can be used to detect TL1A levels in patients, among other uses.

In addition to diagnosis, the TL1A antibodies or antigen binding fragments thereof can be used to monitor therapeutic responses, detect recurrences of a disease, and guide subsequent clinical decisions.

In some embodiments, for diagnostic and monitoring purposes, radioisotopes may be bound to antibody fragments either directly or indirectly by using an intermediary functional group. Such intermediary functional groups include, for example, DTPA (diethylenetriaminepentaacetic acid) and EDTA (ethylene diamine tetraacetic acid). The radiation dose delivered to the patient is typically maintained at as low a level as possible. This may be accomplished through the choice of isotope for the best combination of minimum half-life, minimum retention in the body, and minimum quantity of isotope which will permit detection and accurate measurement. Examples of radioisotopes which can be bound to antibodies and are appropriate for diagnostic imaging include $^{99}$mTc and $^{111}$ In.

Studies indicate that antibody fragments, particularly Fab and Fab', provide suitable tumor/background ratios. (See, e.g., Brown, supra.)

The TL1A antibody or antigen binding fragments thereof also can be labeled with paramagnetic ions for purposes of in vivo diagnosis. Elements which are particularly useful for Magnetic Resonance Imaging include Gd, Mn, Dy, and Fe ions.

The TL1A antibody or antigen binding fragments thereof can also detect the presence of TL1A in vitro. In such immunoassays, the antibody or antigen binding fragments thereof may be utilized in liquid phase or bound to a solid-phase carrier. For example, an intact antibody, or antigen-binding fragment thereof, can be attached to a polymer, such as aminodextran, in order to link the antibody component to an insoluble support such as a polymer-coated bead, plate, or tube.

Alternatively, the TL1A antibody or antigen binding fragments thereof can be used to detect the presence of particular antigens in tissue sections prepared from a histological specimen. Such in situ detection can be accomplished, for example, by applying a detectably-labeled TL1A antibody or antigen binding fragment thereof to the tissue sections. In situ detection can be used to determine the presence of a particular antigen and to determine the distribution of the antigen in the examined tissue. General techniques of in situ detection are well known to those of ordinary skill. (See, e.g., Ponder, "Cell Marking Techniques and Their Application," in Mammalian Development: A Practical Approach, Monk (ed.), IRL Press, pp. 115-138 (1987); Coligan et al., supra.)

Detectable labels such as enzymes, fluorescent compounds, electron transfer agents, and the like can be linked to a carrier by conventional methods well known to the art. These labeled carriers and the antibody conjugates prepared from them can be used for in vitro immunoassays and for in situ detection, much as an antibody conjugate can be prepared by direct attachment of the labels to antibody. The loading of the antibody conjugates with a plurality of labels can increase the sensitivity of immunoassays or histological procedures, where only a low extent of binding of the antibody, or antibody fragment, to target antigen is achieved.

Compositions

The invention also provides pharmaceutical compositions comprising an effective amount of a TL1A antibody described herein. Examples of such compositions, as well as how to formulate, are also described herein. In some embodiments, the composition comprises one or more TL1A antibodies. In other embodiments, the TL1A antibody recognizes TL1A. In other embodiments, the TL1A antibody is a human antibody. In other embodiments, the TL1A antibody is a humanized antibody. In some embodiments, the TL1A antibody comprises a constant region that is capable of triggering a desired immune response, such as antibody-mediated lysis or ADCC. In other embodiments, the TL1A antibody comprises a constant region that does not trigger an unwanted or undesirable immune response, such as antibody-mediated lysis or ADCC. In other embodiments, the TL1A antibody comprises one or more CDR(s) of the antibody (such as one, two, three, four, five, or, in some embodiments, all six CDRs).

It is understood that the compositions can comprise more than one TL1A antibody (e.g., a mixture of TL1A antibodies that recognize different epitopes of TL1A). Other exemplary compositions comprise more than one TL1A antibody that recognize the same epitope(s), or different species of TL1A antibodies that bind to different epitopes of TL1A. In some embodiments, the compositions comprise a mixture of TL1A antibodies that recognize different variants of TL1A.

In some cases, it is desirable to have an antibody or antigen-binding fragment with high solubility in aqueous solution or in pharmaceutical formulations. Therefore, in one embodiment, the antibody or antigen-binding fragment thereof according to the present invention has a solubility of at least about 10 mg/ml, for example, at least about about 20 mg/ml, at least about 30 mg/ml, at least about 40 mg/ml, at least about 50 mg/ml, at least about 60 mg/ml, at least about 70 mg/ml, at least about 80 mg/ml, at least about 90 mg/ml, at least about 100 mg/ml, at least about 125 mg/ml, at least about 150 mg/ml, at least about 175 mg/ml, and at least about 200 mg/ml, in aqueous solution. In certain cases, the aqueous solution is a solution with a pH of about 5.0-9.0. In other cases, the pH of the aqueous solution is between about pH 6.0 and pH 8.0.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The TL1A antibody and compositions thereof can also be used in conjunction with other agents that serve to enhance and/or complement the effectiveness of the agents.

The invention also provides compositions, including pharmaceutical compositions, comprising any of the polynucleotides of the invention. In some embodiments, the composition comprises an expression vector comprising a polynucleotide encoding the antibody as described herein. In other embodiments, the composition comprises an expression vector comprising a polynucleotide encoding any of the antibodies described herein. In still other embodiments, the composition comprises either or both of the polynucleotides comprising the sequence shown in SEQ ID NO: 103 and SEQ ID NO: 105, either or both of the polynucleotides shown in SEQ ID NO: 107 and SEQ ID NO: 109, either or both of the polynucleotides shown in SEQ ID NO:103 and SEQ ID NO:199, either or both of the polynucleotides shown in SEQ ID NO:107 and SEQ ID NO:201, either or both of the polynucleotides shown in SEQ ID NO:103 and SEQ ID NO:206, or either or both of the polynucleotides shown in SEQ ID NO:107 and SEQ ID NO:208, or either or both of the polynucleotides shown in SEQ ID NO:103 and SEQ ID NO:213, or either or both of the polynucleotides shown in SEQ ID NO:107 and SEQ ID NO:215, or either or both of the polynucleotides shown in SEQ ID NO:103 and SEQ ID NO:220, or either or both of the polynucleotides shown in SEQ ID NO:107 and SEQ ID NO:222, or either or both of the polynucleotides shown in SEQ ID NO:103 and SEQ ID NO:227, or either or both of the polynucleotides shown in SEQ ID NO:107 and SEQ ID NO:229, or either or both of the polynucleotides shown in SEQ ID NO:103 and SEQ ID NO:241, or either or both of the polynucleotides shown in SEQ ID NO:107 and SEQ ID NO:243, or either or both of the polynucleotides shown in SEQ ID NO:103 and SEQ ID NO:248, or either or both of the polynucleotides shown in SEQ ID NO:107 and SEQ ID NO:250, or either or both of the polynucleotides shown in SEQ ID NO:23 and SEQ ID NO:25, or either or both of the polynucleotides shown in SEQ ID NO:27 and SEQ ID NO:29, or either or both of the polynucleotides shown in SEQ ID NO:37 and SEQ ID NO:39, or either or both of the polynucleotides shown in SEQ ID NO:41 and SEQ ID NO:43, or either or both of the polynucleotides shown in SEQ ID NO:89 and SEQ ID NO:91, or either or both of the polynucleotides shown in SEQ ID NO:93 and SEQ ID NO:95, or either or both of the polynucleotides shown in SEQ ID NO:51 and SEQ ID NO:53, or either or both of the polynucleotides shown in SEQ ID NO:55 and SEQ ID NO:57, or either or both of the polynucleotides shown in SEQ ID NO:65 and SEQ ID NO:67, or either or both of the polynucleotides shown in SEQ ID NO:65 and SEQ ID NO:69, or either or both of the polynucleotides shown in SEQ ID NO:65 and SEQ ID NO:71, or either or both of the polynucleotides shown in SEQ ID NO:73 and SEQ ID NO:75, or either or both of the polynucleotides shown in SEQ ID NO:2 and SEQ ID NO:4, or either or both of the polynucleotides shown in SEQ ID NO:2 and SEQ ID NO:6, or either or both of the polynucleotides shown in SEQ ID NO:8 and SEQ ID NO:10, or either or both of the polynucleotides shown in SEQ ID NO:8 and SEQ ID NO:12.

In another aspect, the polynucleotide can encode the VH, VL and/or both VH and VL of the antibody or antigen-binding fragment thereof of the invention. That is, the composition comprises a single polynucleotide or more than one polynucleotide encoding the antibody, or antigen-binding portion thereof, or the invention.

Pharmaceutical compositions of the disclosure also can be administered in combination therapy, such as, combined with other agents. For example, the combination therapy can include TL1A antibody, or antigen binding fragment thereof, of the present disclosure combined with at least one other therapy wherein the therapy may be surgery, immunotherapy, chemotherapy, radiation treatment, or drug therapy.

The pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the present disclosure may be prepared, packaged, or sold in a formulation suitable for ophthalmic administration. Such formulations may, for example, be in the form of eye drops including, for example, a 0.1 1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences, Genaro, ed., Mack Publishing Co., Easton, PA (1985), which is incorporated herein by reference.

In one embodiment, the TL1A antibody, or antigen binding fragment thereof, is administered in an intravenous formulation as a sterile aqueous solution containing 5 mg/ml, or more preferably, about 10 mg/ml, or yet more preferably, about 15 mg/ml, or even more preferably, about 20 mg/ml of antibody, with sodium acetate, polysorbate 80, and sodium chloride at a pH ranging from about 5 to 6. Preferably, the intravenous formulation is a sterile aqueous solution containing 5 or 10 mg/ml of antibody, with 20 mM sodium acetate, 0.2 mg/ml polysorbate 80, and 140 mM sodium chloride at pH 5.5. Further, a solution comprising an antibody, or antigen binding fragment thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 100 mg TL1A antibody or antigen binding fragment of the present disclosure, 10 mM histidine, 5% sucrose, and 0.01% polysorbate 80 at pH 5.8. This composition may be provided as a lyophilized powder. When the powder is reconstituted at full volume, the composition retains the same formulation. Alternatively, the powder may be reconstituted at half volume, in which case the composition comprises 100 mg TL1A antibody or antigen binding fragment thereof of the present disclosure, 20 mM histidine, 10% sucrose, and 0.02% polysorbate 80 at pH 5.8.

In one embodiment, part of the dose is administered by an intraveneous bolus and the rest by infusion of the antibody-formulation. For example, a 0.01 mg/kg intravenous injection of the TL1A antibody, or antigen binding fragment thereof, may be given as a bolus, and the rest of the antibody dose may be administered by intravenous injection. A predetermined dose of the TL1A antibody, or antigen binding fragment thereof, may be administered, for example, over a period of an hour and a half to two hours to five hours.

With regard to a therapeutic agent, where the agent is, e.g., a small molecule, it can be present in a pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment the compositions of the disclosure are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food and Drug Administration (FDA) has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In another embodiment, endotoxin and pyrogen levels in the composition are less than about 10 EU/mg, or less than about 5 EU/mg, or less than about 1 EU/mg, or less than about 0.1 EU/mg, or less than about 0.01 EU/mg, or less than about 0.001 EU/mg.

In one embodiment, the disclosure comprises administering a composition wherein said administration is oral, parenteral, intramuscular, intranasal, vaginal, rectal, lingual, sublingual, buccal, intrabuccal, intravenous, cutaneous, subcutaneous or transdermal.

In another embodiment the disclosure further comprises administering a composition in combination with other therapies, such as surgery, chemotherapy, hormonal therapy, biological therapy, immunotherapy or radiation therapy.

In some aspects, the compositions and methods of the invention are specifically intended for use in combination with one or more of the products and classes selected from the group consisting of: analgesics such as acetaminophen, naproxen sodium, ibuprofen, tramadol, aspirin, celecoxib, valdecoxib, indomethacin, and other NSAIDs; COX-2 inhibitors; anti-inflammatory drugs; sulfasalazine, mesalamine, balsalazide, and olsalazine; and corticosteroids such as prednisone and budesonide; immunosuppressant drugs such as azathioprine, mercaptopurine, TNF blockers such as infliximab and adalimumab, methotrexate, and cyclosporine; antibiotics such as metronidazole and ciprofloxacin; anti-diarrheals such as loperamide; immunosuppressant drugs such as azathioprine, mercaptopurine, corticosteroids; immunosuppressants; Janus kinase-3 (Jak-3) inhibitors; and laxatives; antihistamines such as chlorpheniramine, desloratadine, levocetirizine, diphenhydramine, doxylamine succinate, triprolidine, clemastine, pheniramine, brompheniramine, dexbrompheniramine, loratadine, cetirizine and fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenaldine, picumast, tolpropamine, ramatroban, repirinast, suplatast tosylate aminoalkylethers, tazanolast, bromodiphenhydramine, tranilast, carbinoxamine, traxanox, chlorphenoxamine, diphenylpyaline, embramine, p-methyldiphenhydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, tritoqualine.

Dosing/Administration

To prepare pharmaceutical or sterile compositions including a TL1A antibody, or antigen binding fragment thereof of the disclosure, the antibody is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.),1993, Monoclonal Antibodies and Peptide Therapy in Autoimmune Diseases, Marcel Dekker, New York, N.Y.; Baert, et al., 2003, New Engl. J. Med. 348:601-608; Milgrom, et al., 1999, New Engl. J. Med. 341:1966-1973; Slamon, et al., 2001, New Engl. J. Med. 344:783-792; Beniaminovitz, et al., 2000, New Engl. J. Med. 342:613-619; Ghosh, et al., 2003, New Engl. J. Med. 348:24-32; Lipsky, et al., 2000, New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Compositions comprising TL1A antibodies or antigen binding fragments thereof, of the disclosure can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 μg/kg body weight, at least 0.2 μg/kg, at least 0.5 μg/kg, at least 1 μg/kg, at least 10 μg/kg, at least 100 μg/kg, at least 0.2 mg/kg, at least 1.0 mg/kg, at least 2.0 mg/kg, at least 10 mg/kg, at least 15 mg/kg, at least 20 mg/kg, at least 25 mg/kg, or at least 50 mg/kg (see, e.g., Yang, et al., 2003, New Engl. J. Med. 349:427-434; Herold, et al., 2002, New Engl. J. Med. 346:1692-1698; Liu, et al., 1999, J. Neurol. Neurosurg. Psych. 67:451-456; Portielji, et al., 2003, Cancer. Immunol. Immunother. 52: 133-144). The dose may be at least 15 μg, at least 20 μg, at least 25 μg, at least 30 μg, at least 35 μg, at least 40 μg, at least 45 μg, at least 50 μg, at least 55 μg, at least 60 μg, at least 65 μg, at least 70 μg, at least 75 μg, at least 80 μg, at least 85 μg, at least 90 μg, at least 95 μg, or at least 100 μg. The doses administered to a subject may number at least 1, 2, 3, 4, 5, 6, 7, 8, 9, 10, 11, or 12, or more.

For TL1A antibodies or antigen binding fragments thereof of the disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/'kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the TL1A antibody or antigen binding fragment thereof may be calculated using the patient's weight in kilograms (kg) multiplied by the dose to be administered in mg/kg. The dosage of the antibodies of the disclosure may be 150 μg/kg or less, 125 μg/kg or less, 100 μg/kg or less, 95 μg/kg or less, 90 μg/kg or less, 85 μ/kg or less, 80 μ/kg or less, 75 μ/kg or less, 70 μ/kg or less, 65 μ/kg or less, 60 μ/kg or less, 55 μ/kg or less, 50 μ/kg or less, 45 μ/kg or less, 40 μ/kg or less, 35 μ/kg or less, 30 μ/kg or less, 25 μ/kg or less, 20 μ/kg or less, 15 μ/kg or less, 10 μ/kg or less, 5 μ/kg or less, 2.5 μ/kg or less, 2 μ/kg or less, 1.5 μ/kg or less, 1 μ/kg or less, 0.5 μ/kg or less, or 0.1 μ/kg or less of a patient's body weight.

Unit dose of the TL1A antibodies or antigen binding fragments thereof of the disclosure may be 0.1 mg to 200 mg, 0.1 mg to 175 mg, 0.1 mg to 150 mg, 0.1 mg to 125 mg, 0.1 mg to 100mg, 0.1 mg to 75 mg, 0.1 mg to 50 mg, 0.1 mg to 30 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the TL1A antibodies or antigen binding fragments thereofof the disclosure may achieve a serum titer of at least 0.1 μg/ml, at least 0.5 μg/ml, at least 1 μg/ml, at least 2 μg/ml, at least 5 μg/ml, at least 6 μg/ml, at least 10 μg/ml, at least 15 μg/ml, at least 20 μg/ml, at least 25 μg/ml, at least 50 μg/ml, at least 100 μg/ml, at least 125 μg/ml, at least 150 v, at least 175 μg/ml, at least 200 μg/ml, at least 225 μg/ml, at least 250 μg/ml, at least 275 μg/ml, at least 300 μg/ml, at least 325 μg/ml, at least 350 μg/ml, at least 375 μg/ml/ml, or at least 400 μg/ml/ml in a subject. Alternatively, the dosage of the antibodies of the disclosure may achieve a serum titer of at least 0.1 μg/ml, at least 0.5 μg/ml, at least 1 μg/ml, at least, 2 μg/ml, at least 5 μg/ml, at least 6 μg/ml, at least 10 μg/ml, at least 15 μg/ml, at least 20 μg/ml, at least 25 μg/ml, at least 50 μg/ml, at least 100 μg/ml, at least 125 μg/ml, at least 150 μg/ml, at least 175 μg/ml, at least 200 μg/ml, at least 225 μg/ml, at least 250 μg/ml, at least 275 μg/ml, at least 300 μg/ml, at least 325 μg/ml, at least 350 μg/ml, at least 375 μg/ml, or at least 400 μg/ml in the subject.

Doses of TL1A antibodies, or antigen binding fragments thereof of the disclosure may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side effects (see, e.g., Maynard, et al., 1996, A Handbook of SOPs for Good Clinical Practice, Interpharm Press, Boca Raton, Fla.; Dent, 2001, Good Laboratory and Good Clinical Practice, Urch Publ, London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., 1983, Biopolymers 22:547-556; Langer, et al., 1981, J. Biomed. Mater. Res. 15: 167-277; Langer, 1982, Chem. Tech. 12:98-105; Epstein, et al., 1985, Proc. Natl. Acad. Sci. USA 82:3688-3692; Hwang, et al., 1980, Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985, 320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, the TL1A antibody, or antigen binding fragment thereof, or a composition of the disclosure is administered using Alkermes AIR™ pulmonary drug delivery technology (Alkermes, Inc., Cambridge, Mass.).

A composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasally, orally, vaginally, rectally, sublingually or topically.

If the TL1A antibodies, or antigen binding fragments thereof, of the disclosure are administered in a controlled release or sustained release system, a pump may be used to achieve controlled or sustained release (see Langer, supra; Sefton, 1987, CRC Crit. Ref. Biomed. Eng. 14:20; Buchwald et al., 1980, Surgery 88:501; Saudek et al., 1989, N. Engl. J. Med. 321:514).

Polymeric materials can be used to achieve controlled or sustained release of the therapies of the disclosure (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. ScL Rev. Macromol. Chem. 23:61; see also Levy et al, 1985, Science 11 225:190; During et al., 19Z9, Ann. Neurol. 25:351; Howard et al, 1989, J. Neurosurg. 71: 105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), polyvinyl alcohol), polyacrylamide, polyethylene glycol), polylactides (PLA), polyoeactide-coglycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, 1990, Science 249:1527-1533. Any technique known to one of skill in the art can be used to produce sustained release formulations comprising one or more antibodies of the disclosure or conjugates thereof. See, e.g., U.S. Pat. No. 4,526,938, International Patent Publication Nos. WO 91/05548, WO 96/20698, Ning et al., 1996, "Intratumoral Radioimmunotheraphy of a Human Colon Cancer Xenograft Using a Sustained-Release Gel," Radiotherapy and Oncology 59:179-189, Song et al., 1995, "Antibody Mediated Lung Targeting of Long-Circulating Emulsions," PDA Journal of Pharmaceutical Science and Technology 50:372-397, Cleek et ah, 1997, "Biodegradable Polymeric Carriers for a bFGF Antibody for Cardiovascular Application," Pro. MI. Symp. Control. Rel. Bioact. Mater. 24:853-854, and Lam et al., 1997, "Microencapsulation of Recombinant Humanized Monoclonal Antibody for Local Delivery," Proc. MI. Symp. Control Rel. Bioact. Mater. 24:759-160, each of which is incorporated herein by reference in their entirety.

If the TL1A antibody, or antigen binding fragment thereof, of the disclosure is administered topically, it can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising TL1A antibodies, or antigen binding fragments thereof, are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) Goodman and Gilman's The Pharmacological Basis of Therapeutics, 10 th ed., McGraw-Hill, New York, N.Y.; Poole and Peterson (eds.) (2001) Pharmacotherapeutics for Advanced Practice: A Practical Approach, Lippincott, Williams and Wilkins, Phila., Pa.; Chabner and Longo (eds.) (2001) Cancer Chemotherapy and Biotherapy, Lippincott, Williams and Wilkins, Phila., Pa.). An effective amount of therapeutic may decrease the symptoms by at least 10 percent; by at least 20 percent; at least about 30 percent; at least 40 percent, or at least 50 percent.

Additional therapies (e.g., prophylactic or therapeutic agents), which can be administered in combination with the TL1A antibodies, or antigen binding fragments of the disclosure, may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies of the disclosure. The two or more therapies may be administered within one same patient visit.

The TL1A antibodies, or antigen binding fragments thereof, of the disclosure and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In one embodiment, the TL1A antibodies of the invention can be co-administered with compositions for treating Crohn's Disease, including compositions for inhibition of pro-inflammatory cytokines and adhesion molecules, such as NSAIDs, 5-aminosalicylic acid, glucocorticoids/corticosteroids, 6-mercaptopurine, or TNF-α inhibitors, including adalimumab, infliximab, and others which are known to persons skilled in the art.

In certain embodiments, the TL1A antibodies, or antigen binding fragments thereof of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989, J. Clin. Pharmacol. 29:685). Exemplary targeting moieties include folate or biotin (see, e.g., U.S. Pat. No. 5,416,016); mannosides (Umezawa et al., Biochem. Biophys. Res. Commun. 153: 1038); antibodies (P. G. Bloeman et al., 1995, FEBS Lett. 357: 140; M. Owais et al., 1995, Antimicrob. Agents Chemother. 39: 180); surfactant protein A receptor (Briscoe et al. (1995) Am. J. Physiol. 1233: 134); pI20 (Schreier et al. (1994) J. Biol. Chem. 269:9090); see also K. Keinanen; M. L. Laukkanen, 1994, FEBS Lett. 346:123; Killion; Fidler, 1994; Immunomethods 4:273.

The disclosure provides protocols for the administration of pharmaceutical composition comprising TL1A antibodies, or antigen binding fragments thereof, of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising TL1A antibodies, or antigen binding fragments thereof, of the disclosure are administered to a subject in a sequence and within a time interval such that the antibodies of the disclosure or conjugates thereof can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Kits

The invention also provides kits comprising any or all of the antibodies described herein. Kits of the invention include one or more containers comprising a TL1A antibody described herein and instructions for use in accordance with any of the methods of the invention described herein. Generally, these instructions comprise a description of administration of the antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing an applicator, e.g., single and multi-chambered pre-filled syringes (e.g., liquid syringes and lyosyringes),are included.

The instructions relating to the use of a TL1A antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a TL1A antibody or antigen-binding fragment thereof of the invention. The container may further comprise a second pharmaceutically active agent.

Kits may optionally provide additional components such as buffers and interpretive information. Normally, the kit comprises a container and a label or package insert(s) on or associated with the container.

The invention also provides diagonistic kits comprising any or all of the antibodies described herein. The diagonistic kits are useful for, for example, detecting the presence of TL1A in a sample. In some embodiments, a diagnostic kit can be used to identify an individual with a latent disease, disorder or condition that may put them at risk of developing TL1A-mediated disease, disorder or condition. In some embodiments, a diagnostic kit can be used to detect the presence and/or level of TL1A in an individual suspected of having a TL1A mediated disease.

Diagnostic kits of the invention include one or more containers comprising a TL1A antibody described herein and instructions for use in accordance with any of the methods of the invention described herein. Generally, these instructions comprise a description of use of the TL1A antibody to detect the presence of TL1A in individuals at risk for, or suspected of having, a TL1A mediated disease. In some embodiments, an exemplary diagonistic kit can be configured to contain reagents such as, for example, a TL1A antibody, a negative control sample, a positive control sample, and directions for using the kit.

Biological Deposit

Representative materials of the present invention were deposited in the American Type Culture Collection, 10801 University Boulevard, Manassas, Va. 20110-2209, USA, on Oct. 17, 2013. Vector 1D1 1.31 VH having ATCC Accession No.PTA-120639 comprises a DNA insert encoding the heavy chain variable region of antibody 1D1 1.31, and vector 1D1 1.31 VL having ATCC Accession No. PTA-120640 comprises a DNA insert encoding the light chain variable region of antibody 1D1 1.31. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Equivalents

The foregoing written specification is considered to be sufficient to enable one skilled in the art to practice the disclosure. The foregoing description and Examples detail certain exemplary embodiments of the disclosure. It will be appreciated, however, that no matter how detailed the foregoing may appear in text, the disclosure may be practiced in many ways and the disclosure should be construed in accordance with the appended claims and any equivalents thereof.

All references cited herein, including patents, patent applications, papers, text books, and the like, and the references cited therein, to the extent that they are not already, are hereby incorporated herein by reference in their entirety.

Exemplary Embodiments

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1: Generation of anti-TL1A Antibodies

Recombinant soluble human and mouse TL1A protein were transiently expressed in HEK293 cells. TL1A protein was purified by HitrapNTA, Hitrap Q and Sephacryl-200 (all purchased from GE healthcare). The resulting purified protein solution was concentrated and stored below −80° C. The purity was confirmed by SDS-PAGE and analytical SEC.

Recombinant soluble human and mouse TL1A protein were used to immunize Medarex KM and Hco mice. Some mice received alternating human and mouse TL1A, while others received only human TL1A. In some cases, the mice were administered 3× 25 μg of recombinant human TL1A plus 1× 25 μg of recombinant mouse TL1A in Ribi adjuvant weekly, intraperitoneally and subcutaneously. Hybridomas produced by E-fusion protocol were made from mice that showed reactivity to TL1A by serum titer analysis. The subsequent hybridomas were screened for production of antibodies that bound TL1A but not TNF alpha. Those hybridomas that showed specific binding to TL1A were further screened for neutralizing antibodies.

Example 2: Epitope Binning of Anti-TL1A Antibodies by SPR

A pairwise binding strategy was employed to characterize the anti-TL1A antibodies by epitope binning using surface plasmon resonance. One antibody was directly immobilized via amine coupling onto a carboxymethylated dextran sensor chip surface (CM5) using a Biacore 2000 or 3000 instrument. Then, recombinant soluble human TL1A or murine TL1A diluted to 10 nM in 8.1 mM $Na_2HPO_4$, 1.47 mM $KH_2PO_4$, pH 7.2, 237 mM NaCI, 2.7 mM KCI, 3.4 mM EDTA and 0.01% tween 20 (PBS-NET) was injected for about 1 minutes at a flow rate of 10 μl/minute to achieve binding levels on the immobilized antibody or antigen-binding fragment thereof of at least 100 response units (RU). Next, the same antibody that was immobilized on the chip was injected at 30 nM for 5 minutes in order to saturate all of the potential binding sites on the trimeric TL1A. A repeat injection of antibody was performed to confirm this saturation. Finally, a second antibody in PBS-NET or PBS-NET alone as a control was injected at 30 nM for 5 minutes. If the second antibody bound to the TL1A saturated with the first antibody, this indicated that the second antibody bound a non-competiting epitope on TL1A as compared to the first antibody. If the second antibody could not bind to the saturated TL1A, this indicated that the two antibodies shared the same or competiting epitope on TL1A. This strategy was repeated for the top neutralizing antibodies. At the end of each cycle, the immobilized antibody surface was regenerated either by a 30-second pulse of 3 M $MgCl_2$ or by 0.1% TFA followed by two consecutive 15-second pulses of PBS-NET. All injections were performed at 25° C. at a collection rate of 10 Hz. All sensorgrams were double referenced by using both a control surface and buffer injections.

Figure 3:
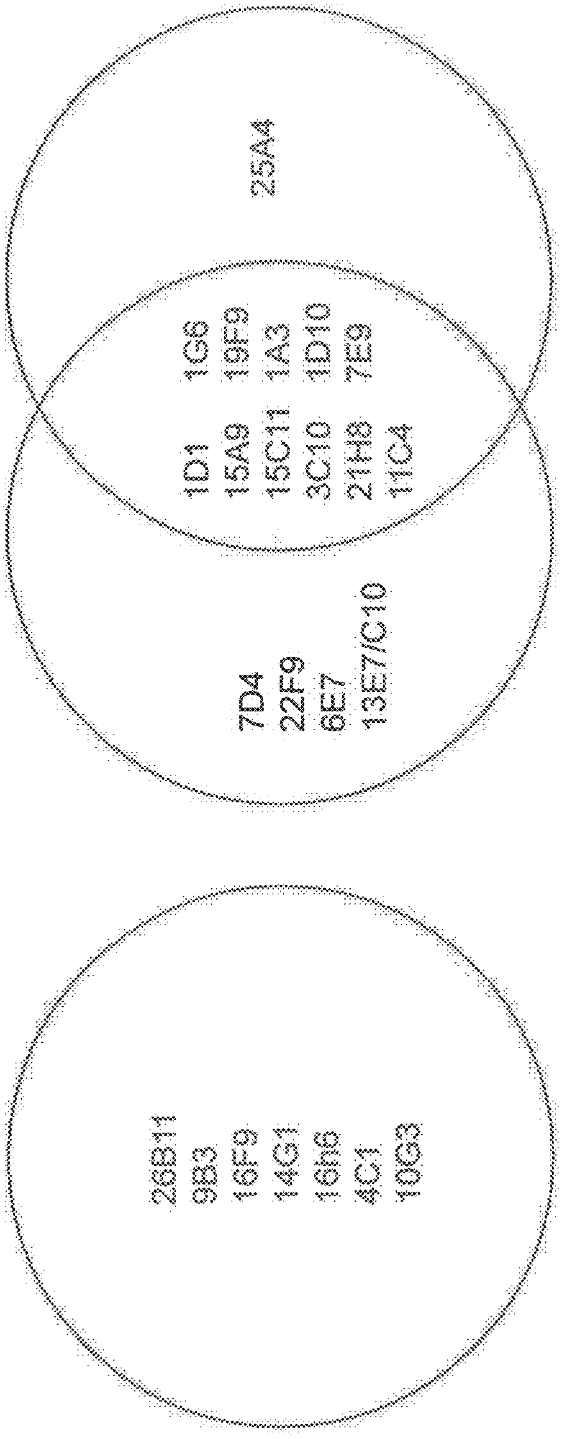

Epitope binning of the initial 15 neutralizing antibodies against human TL1A revealed at least two distinct epitopes (FIG. 2). Within the 2nd epitope bin, there appeared to be an overlapping epitope. Antibody 25A4 bound a non-competing epitope to 7D4 and 22F9, while it was shown have a competing epitope to 1D1. Subsequently, antibodies were compared against 1D1, 7D4 and 25A4 to determine its location within this second epitope bin (FIG. 3). Additionally, within the first epitope bin, antibodies 14G1, 4C1 and 10G3 each were compared against immobilized 16F9 to reconfirm their binning for binding to human TL1A. Each of these antibodies binds a competing epitope with 16F9, as do 26B11 and 9B3. Antibody 1D1 was used as a control for binding to 16F9 since these two antibodies bind human TL1A at non-competing epitopes.

Figure 4:
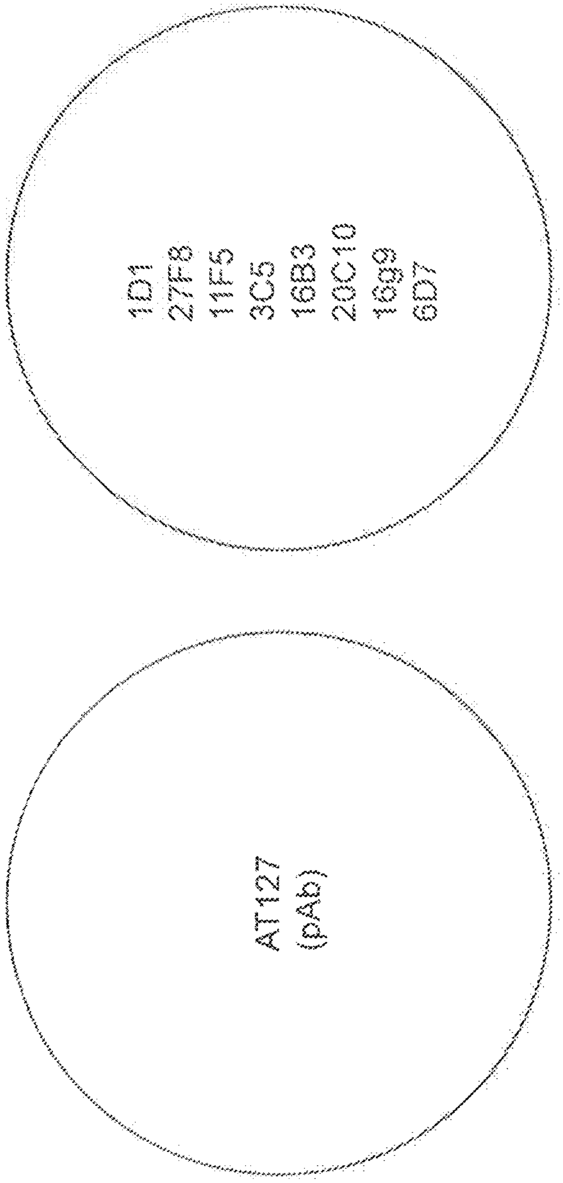
FIG. 4 depicts a Venn diagram of epitope bins of anti-TL1A antibodies. Antibodies within the same circle compete for binding to murine TL1A while antibodies in separate circles do not compete for binding on murine TL1A. The figure shows data demonstrating that polyclonal Ab AT127 does not compete with any of the antibodies in the other circle (1D1, 27F8, 11F5, 3C5, 16B3, 20C10, 16g9, and 6D7) and it also shows that all of the antibodies within the circle compete with each other for binding to murine TL1A.

Epitope binning against murine TL1A was conducted for eight of the anti-TL1A antibodies (which showed the ability to neutralize murine TL1A in the cell-based caspase assay) as well as a commercially available anti-TL1A polyclonal antibody AT127 (Enzo Life Sciences, Farmingdale, NY). All of the anti-TL1A antibodies, other than AT127, bound to murine TL1A at competiting epitopes. AT127 appeared to bind murine TL1A at a separate, nonoverlapping epitope (FIG. 4).

Example 3: Characterization of TL1A Binding Kinetics of Neutralizing Antibodies To characterize the binding kinetics of the anti-TL1A antibodies to TL1A by surface plasmon resonance, each anti-TL1A antibody was captured via directly immobilized anti-human IgG (GE Healthcare) onto a carboxymethylated dextran sensor chip surface (CM5) using a Biacore T100 or T200 instrument. Anti-human IgG was immobilized through amine coupling to densities of approximately 4,000-13,000 response units (RU). Each anti-TL1A antibody was diluted to 0.075-0.15 μg/ml in 8.1 mM $Na_2HPO_4$, 1.47 mM $KH_2PO_4$, pH 7.2, 237 mM NaCl, 2.7 mM KCl, 3.4 mM EDTA and 0.01% tween 20 (PBS-NET) and injected onto the anti-hlgG surface for about 1-2 minutes at a flow rate of 5 μl/minute to achieve low captured levels as low as 30 RU. After capture, the flow rate was increased to 100 μl/minute and various concentrations of recombinant soluble human TL1A, cynomologous monkey TL1A, or murine TL1A ranging from 0.195 nM to 100 nM in PBS-NET were injected for a 2-3 minute association and allowed to dissociate for up to 60 minutes. At the end of each cycle, the entire anti-human IgG (hlgG) surface was regenerated by a 30-second pulse of 3 M $MgCl_2$ followed by two consecutive 15-second pulses of PBS-NET. All injections were performed at 25° C. at a collection rate of 10 Hz. All sensorgrams were double referenced by using both a control surface and buffer injections. Rate constants were determined by fitting the data to a 1:1 model in Biacore T100, T200 evaluation software v1.0, or BIAevaluation software v4.1.1 and the equation $K_D=k_d/k_a$.

Initially, the binding of human and murine TL1A to select anti-TL1A antibodies, was measured in real time on a Biacore T100 instrument. All of the antibodies bound to human TL1A or murine TL1A with similar equilibrium dissociation constants ($K_D$). The determined $K_d$s also were comparable to those previously generated cell-based assay IC50s (data not shown).

For subsequent evaluation of TL1A binding in real time, antibodies 1D1, 26B11 and 7D4, which are representative of antibodies that bind to different epitopes of TL1A, were expressed as follows. Transient expression of recombinant anti-TL1A antibodies were assessed by co-transfection of heavy and light chain V-regions cloned into mammalian expression vectors. For example, to each 100 mm tissue culture dish (Corning 430176); 40 μl of TransIT (Mirus MIR2306) was added to 2 mls of room temperature Optimem (Invitrogen-Gibco 11058-021)+glutamine 2 mM final concentration. This mixture of Optimem and Trans-IT was vortexed and incubated at room temperature for 15 minutes. Maxiprep DNA was added (8 μg of heavy chain and 8 μg of light chain) to the mixture and incubated at room temperature for 15 minutes. This solution was then added to the p100 containing ~8 ml of growth media (DMEM+HI FBS+Penn+Strep+Glutamine). After 24 hours at 37° C., 10% $CO_2$, the cells were rinsed with R1CD1(serum free growth media), then 10 ml of R1CD1+PSG was added to each p100. Conditioned medium was harvested after 48 hours at 37° C., 10% $CO_2$, spun down to pellet cells and supernatant removed to a new tube. This was adjusted accordingly to accommodate more cells for larger expression runs.

Conditioned medium from transient transfection was quantitated by total human IgG-Fc-specific ELISA. Briefly, a flat bottom ELISA plate (Costar 3590) was coated overnight at room temperature with 100 μl each well of 1 μg/ml goat anti-human IgG in PBS (Pierce 31125). Plates were blocked with 100 μl/well of a 0.02% Casein Solution in PBS for a minimum of 3 hours or up to 24 hours at room temperature. If the plates were not used immediately they were stored for up to one month at 4° C. in storage buffer, 0,02% $NaN_3$ in PBS. Standard and samples were run in serial dilution series in assay buffer (0.5% bovine serum albumin+0.02%Tween-20 in PBS) with 100 μl added to the washed wells of the ELISA plate and incubated for 3 to 24 hours at room temperature. Goat anti-human IgG (Pierce 31413) was diluted 1:5000 in assay buffer and 100 μl was added to well after the plate was washed and allowed to incubate for 15 minutes at room temperature. The plate was washed and developed in 100 μl per well BioFX TMB (TMBW-0100-01) the reaction was stopped in 100 μl per well 0.18 N $H_2SO_4$ and the plate was read at 450 nm on Molecular Devices vMax plate reader. The unknowns were calculated from the linear range of the curve from the dilution series of the standard. Antibody 26B11 was used as quantitated conditioned medium in this experiment while 1D1, and 7D4 were protein A purified.

The anti-TL1A antibodies were captured onto immobilized anti-human Fc on a CM5 sensor chip on a Biacore T100 instrument. Human TL1A (0.4-100nM) or cynomolgus monkey TL1A (8-200 nM) were injected over captured anti-TL1A antibodies. Rate constants shown in the table were determined by fitting to a 1:1 Langmuir binding model in BiaEvaluation v4.1.1 (fit lines shown in red). Data shown are the average and standard deviation of at least 3 independent surfaces between 2 experiments. No nonspecific binding of recombinant solube human or cynomolgus TL1A to the immobilized anti-human Fc was observed.

Capture levels were kept intentionally low to allow conditions of 1:1 binding, avoid the impact of avidity, and to minimize rebinding during dissociation. At capture levels above 30 RU, slower off-rates had been observed to the antibodies which were likely due to these complications (data not shown).

For either human or cynomolgus TL1A, binding to anti-TL1A antibodies was dependent on the concentration of TL1A tested. At the highest cytokine concentrations, the dissociation phase was sometimes extended to 60 minutes to achieve at least a 5% decrease in binding signal. This is the minimum decrease recommended for accurately measuring relatively slow antigen dissociation rates (Katsamba, et al. Kinetic analysis of a high affinity antibody/antigen interaction performed by multiple Biacore users. Analytical Biochemistry 2006 May 15;352(2):208-21). When this condition was met, the association and dissociation rate constants between each species of TL1A and each antibody were calculated from the binding sensorgrams using a 1:1 Langmuir binding model. The Kd values for antibodies 1D1, 7D4, and 26B11 binding to human and cyno TL1A are summarized in Table 4.

TABLE 4

Kd values for antibodies 1D1, 7D4, and 26B11

| | Human TL1A | | | Cyno TL1A | | |
|---|---|---|---|---|---|---|
| Antibody | $k_a$ (1/Ms)1 × E + 05 | $k_d$(1/s) 1 × E−03 | $K_D$(nM) | $k_a$ (1/Ms)1 × E+05 | $k_d$(1/s) 1 × E−03 | $K_D$(nM) |
| 1D1 | 6 ± 2 | 1.8 ± 0. 2 | 3.1 ± 0.8 | 6 ± 1 | 4.1 ± 0.9 | 7 ± 1 |
| 7D4 | 4 ± 1 | 0.4 ± 0.1 | 0.9 ± 0.2 | 2.0 ± 0.5 | 1.4 ± 0.3 | 6.9 ± 0.9 |
| 26B11 | 1.7 ± 0.1 | 0.11 ± 0.04 | 0.6 ± 0.2 | 2.0 ± 0.9 | 6 ± 2 | 36 ± 12 |

Example 4: Anti-TL1A Antibody Sequences

Top neutralizing antibodies representing the various epitope bins were selected for sequencing. Sequences were obtained for anti-TL1A antibodies 1D1, 7D4, 26B11, 15C11, 15A9, 9B3 and 22F9 as follows. Anti-TL1A hybridomas of interest were selected to clone the variable domains. RNAs from the hybridomas were extracted and the variable region DNA sequences from the expressed antibodies were obtained via RT-PCR cloning. Generally, one to five million of the subcloned hybridoma cells were homogenized for total RNA isolation, run through QIAShredder with QIAGEN RNAeasy Mini kit, or cell numbers adjusted to use other Qiagen kit such as RNAeasy micro kit. First strand cDNA was then produced using superscript II or superscript III reverse transcriptase (Invitrogen). Double stranded cDNAs for variable regions of anti-TL1A IgGs were subsequently generated and amplified by PCR using primers specific for constant regions and 5' known cap, such as SMART IIa oligo. The resulting RT-PCR products were cloned into TOPO-Blunt cloning vector, zero blunt, topo TA or similar vector (Invitrogen) and sequenced by conventional methods.

Sequences are listed in the Sequence Listing Table (Table 40) and shown in FIG. 1A-L. For antibodies 9B3 and 26B11, multiple heavy chains were cloned from the hybridoma and are listed in the Sequence Listing Table (Table 40) and FIG. 1A-L. For 26B11, experiments were performed with constructs having the VH2 variable heavy chain domain (SEQ ID NO:74).

FIG. 1I depicts an alignment of the sequences of antibodies 1D1, 7D4, and 26B11, which are representative of the 3 epitope bins discuss above. FIG. 1J depicts an alignment of the VH and VL sequences from antibodies 7D4 and 22F9, which bind to competing TL1A epitopes. These antibodies have the same VL but different VH regions. Table 5 provides a summary of the amino acid differences between the VH domains of antibodies 7D4 and 22F9 FIG. 1K depicts an alignment of the sequences between antibodies 26B11 and 9B3, which bind to competing TL1A epitopes. These antibodies have different VL regions, but each produce multiple, identical VH regions (VH1, VH2). Antibody 26B11 also produces a third VH domain, named MDX-VH. Table 6 provides a summary of the amino acid differences between antibodies 26B11 and 9B3. FIG. 1L depicts an alignment of the sequences of antibody 1D1 and antibodies 15A9 and 15C11, which compete for binding to TL1A. These antibodies have the same VL, but each have different VH regions. Table 12 provides a summary of the amino acid differences between antibodies 1D1, 15A9, and 15C11 and the 1D1 affinity matured variants. FIG. 1M is a chart depicting the percentage sequence identity between various anti-TL1A antibodies.

TABLE 5

Summary of Amino Acid Differences in VH Domains of Antibodies 7D4 and 22F9. For CDR-H1, sequence is defined by AntibodyM, and Kabat-defined residues are in bold and italicized.

| CDR-H1 | | CDR-H2 | | CDR-H3 | | VH Domain | |
|---|---|---|---|---|---|---|---|
| Amino Acid Sequence in 22F9 (SEQ ID NO: 61) | Amino Acid Sequence in 7D4 (SEQ ID NO: 99) | Amino Acid Sequence in 22F9 (SEQ ID NO: 62) | Amino Acid Sequence in 7D4 (SEQ ID NO: 100) | Amino Acid Sequence in 22F9 (SEQ ID NO: 63) | Amino Acid Sequence in 7D4 (SEQ ID NO: 101) | Amino Acid Sequence in 22F9 | Amino Acid Sequence in 7D4 |
| G | G | W | W | G | A | D85 | E85 |
| Y | Y | I | I | Y | H | | |
| T | T | N | s | S | S | | |
| F | F | A | T | S | S | | |
| T | T | G | Y | A | S | | |
| ***S*** | ***S*** | N | N | W | W | | |
| ***Y*** | ***Y*** | G | G | F | F | | |
| ***A*** | ***G*** | N | N | D | D | | |
| ***M*** | ***I*** | T | T | A | A | | |
| ***H*** | ***N*** | K | N | F | F | | |
| | | Y | S | D | D | | |
| | | S | A | I | I | | |
| | | Q | Q | | | | |
| | | K | K | | | | |
| | | F | L | | | | |
| | | Q | Q | | | | |
| | | G | G | | | | |

TABLE 6

Summary of Amino Acid Differences in VH and VL Domains of Antibodies 9B3 and 26B11. For CDR-H1, sequence is defined by AntibodyM, and Kabat-defined residues are in bold and italicized.

| CDR-L1 | | VL Domain | | CDR-H1 | | |
|---|---|---|---|---|---|---|
| Amino Acid Sequence in 26B11 (SEQ ID NO: 76) | Amino Acid Sequence in 9B3 (SEQ ID NO: 13) | Amino Acid Sequence in 26B11 | Amino Acid Sequence in 9B3 | Amino Acid Sequence in 26B11 (SEQ ID NO: 79)/9B3 VH1 (SEQ ID NO: 16) | Amino Acid Sequence in 26B11 (SEQ ID NO: 82)/9B3 VH2 (SEQ ID NO: 19) | Amino Acid Sequence in 26B11 MDX (SEQ ID NO: 85) |
| R | R | 83F | 83Y | G | G | G |
| A | A | | | F | F | F |
| S | S | | | T | T | T |
| Q | Q | | | F | F | F |
| G | G | | | S | S | S |
| I | I | | | ***N*** | ***S*** | ***N*** |
| S | S | | | ***Y*** | ***F*** | ***Y*** |
| N | S | | | ***A*** | ***A*** | ***A*** |
| W | W | | | ***L*** | ***M*** | ***I*** |
| L | L | | | ***H*** | ***H*** | ***H*** |
| A | A | | | | | |

| CDR-H2 | | | CDR-H3 | | | VH Domain | | |
|---|---|---|---|---|---|---|---|---|
| Amino Acid Sequence in 26B11 (SEQ ID NO: 80)/9B3 VH1 (SEQ ID NO: 17) | Amino Acid Sequence in 26B11 (SEQ ID NO: 83)/9B3 VH2 (SEQ ID NO: 20) | Amino Acid Sequence in 26B11 MDX (SEQ ID NO: 86) | Amino Acid Sequence in 26B11 (SEQ ID NO: 81)/9B3 VH1 (SEQ ID NO: 18) | Amino Acid Sequence in 26B11 (SEQ ID NO: 84)/9B3 VH2 (SEQ ID NO: 21) | Amino Acid Sequence in 26B11 MDX (SEQ ID NO: 87) | Amino Acid in VH1 | Amino Acid in VH2 | Amino Acid in MDX |
| L | L | L | D | D | D | 68A | 68T | 68T |
| I | I | I | R | R | R | 108M | 108L | 108M |
| S | P | P | E | N | N | | | |
| Y | F | Y | Y | Y | Y | | | |
| D | D | D | C | Y | Y | | | |
| G | G | G | T | G | G | | | |
| S | S | S | Y | S | S | | | |
| D | S | N | S | G | G | | | |
| K | N | N | S | S | S | | | |
| Y | Y | Y | C | F | F | | | |
| Y | Y | Y | S | S | S | | | |
| A | A | A | Y | F | F | | | |
| D | D | A | D | D | D | | | |
| S | S | S | A | A | A | | | |

TABLE 6-continued

| Summary of Amino Acid Differences in VH and VL Domains of Antibodies 9B3 and 26B11. For CDR-H1, sequence is defined by AntibodyM, and Kabat-defined residues are in bold and italicized. | | | | | |
|---|---|---|---|---|---|
| V | V | V | F | F | F |
| K | K | K | D | D | D |
| G | G | G | I | I | I |

Example 5: Affinity Maturation of Anti-TL1A Antibody 1D1 via Phage Display Library a) Phage Library Design Three libraries were planned, each of which contained randomization in VHCDR1, VHCDR2 or VHCDR3 regions of 1D1 (also referred to herein as "Parental 1D1" or wild type 1D1 or WT 1D1). X-ray crystallography studies of 1D1 IgG bound to human TL1A trimer (see Example 6) indicated that the VL was not heavily involved in the binding interaction, therefore the VL region was not mutagenized. Two types of randomization were used, binary substitution with oligonucleotides supplied by Eurofins, and spiking mutagenesis with oligonucleotides supplied by IDT (Integrated DNA Technologies). In the binary substitution method, the wild-type amino acid was replaced with a codon which incorporates either the original wild-type amino acid or a closely related homolog. This mutagenesis allows subtle changes to be introduced. Spiking mutagenesis involves replacing the wild type amino acid with all other amino acids at a rate of 50%.

Several highly conserved amino acids were maintained throughout the library build—for example Y31, I51 and D101 were not mutated due to their conservation in human antibodies. The C-terminal end of the VHCDR2 loop was not mutated; keeping in mind previously generated data which pointed to the importance of these residues in binding function. Some possibly pivotal positions were only mutated by binary substitution. Others were subject to two methods of randomization; these positions were thought to have more potential to affect binding affinity.

The VHCDR3 was mutated most heavily, as traditionally this loop has the largest role in affinity determination. The entire loop (except D101) was mutated by both binary substitution and spiking mutagenesis. Two spiking mutagenesis oligos were used for the VHCDR3 due to its length.

b) Phage Library Build

Construction of the mutant libraries was performed. Primary and secondary (SOE) PCRs involved the use of Platinum® Taq DNA Polymerase High Fidelity (Invitrogen), according to the manufacturer's recommendations. SOE-PCR products were restriction digested, purified, and cloned into the pWRIL-1 vector in *E. coli* TG1. Total library sizes were calculated by plating serial dilutions of transformations onto 2YT agar/100 μg per millilitre of carbenicillin/2% (v/v) glucose (2YT-CG). Total cell populations from each electroporation were plated onto 22-cm bioassay dishes (Genetix) containing 2YT agar/100 μg per milliliter of carbenicillin/2% (v/v) glucose (2YT-CG), incubated overnight at 30° C., and finally harvested by scraping and resuspension in 2YT broth/20% (v/v) glycerol. Library aliquots were then frozen at −80° C.

c) Phage Library Rescue and Selections

Phage libraries were rescued and selections were carried out in two different styles, the first being a classical solution-phase method. In these selections the libraries were selected over three rounds, with a starting concentration of 3 nM biotinylated-hTL1A, ending with 50 pM in round three. Washes were increased from 12 in round one to 18 in round three. Also in round three, another branch containing an 'off-rate competition' step was included, where 50 nM excess unlabelled antigen was added for 30 min.

The second style of selection involved the same biotinylated antigen and beads as the first. The purpose of these selections is to drive forcefully towards high affinity in the first round, followed by a gentle recovery in the second round. Four branches of selection were completed, two of which contained 1 nM biotinylated hTL1A in round one, the remaining branches contained 100 pM biotinylated antigen in round one. The first round also contained an overnight 'off-rate competition' step, where 100 nM unlabelled antigen was added for 18 h. Stringent washing was also used in round one, with 13 washes being applied. The second round of selection involved four branches, two of which contained 1 nM biotinylated-recombinant soluble human TL1A, the remaining two contained 1 nM biotinylated-recombinant soluble murine TL1A. Ten washes were applied in round two.

d) Primary Screening—scFv Expression and Purification

For high-throughput screening, *E. coli* clones were plated on 2YT-CG agar in 22-cm bioassay trays (Genetix), picked into standard sterile 96-well plates containing 2YT-CG broth using a QPix II colony picker (Genetix), and grown in a Multitron multiplate incubator (Infors AG) at 600 rpm, 37° C., and 80% humidity overnight. Following growth, glycerol was added to a final concentration of 30% (v/v) and plates were stored at −80° C. or used to immediately inoculate 96-well deep-well plates containing 900 μl of 2YT-CG broth. These were grown at 37° C., 80% humidity, and 600 rpm for 5-6 h; expression was induced by addition of IPTG to a final concentration of 0.5 mM and incubation at 28° C. overnight. Cells were pelleted by centrifugation at 1260 g and resuspended in 150 μl of ice-cold periplasmic buffer [50 mM Tris-HCl, 1 mM ethylenediaminetetraacetic acid, and 20% sucrose (w/v), pH 8]. Osmotic shock was induced by addition of 150 μl/well of a 1:5 dilution of periplasmic buffer, and samples were placed on ice for 30 min. This was followed by centrifugation at 3220 g for 10 min, and the supernatant, consisting of the periplasmic fraction containing expressed scFv's, was recovered. High-throughput screening by ELISA or HTRF assay was carried out using crude periplasmic extracts in single-point analyses.

Small-scale, single-step scFv purifications were carried out for more detailed HTRF titration and caspase activity assay analysis. *E. coli* clones of interest were selected on the basis of performance in the binding ELISA and HTRF screening assay, and inoculated for small-scale protein expression and purification.

e) Binding ELISA

Maxisorp plates (Nunc) were coated with 1 μg/ml of human or murine TL1A in PBS overnight at 4° C. Wells were washed three times with 250 μl of PBS containing 0.02% (v/v) Tween-20, using a Zoomwasher liquid handling robot (Titertek), and blocked in 100 μl of PBS/3% (w/v) dried milk protein with 1% bovine serum albumin for 1 h. Crude periplasmic extracts (50%, v/v) were blocked in PBS/6% (w/v) dried milk protein with 2% bovine serum albumin for 1 h. The blocked periplasmic extracts (50%, v/v) were then incubated with an HRP-conjugated anti-c-myc antibody (Roche) at a final concentration of 1:2500 for 30 min prior to addition to the coated ELISA plate, which was incubated for a further 2 h. Following four washing cycles on the Zoomwasher, the reaction was developed using UltraTMB (Pierce) and stopped by a 1:1 addition of 0.18 M phosphoric acid. The plate was read in an EnVision Multiplate Reader at 450 nm. All data were plotted using Decision Site 8 (Spotfire) and Prism 5 (GraphPad) software.

f) High-throughput competition HTRF assay

A high-throughput competition HTRF assay was established in order to allow identification of affinity improved clones. The parental 1D1 antibody was labeled with europium cryptate using a cryptate labeling kit (CisBio) according to the manufacturer's instructions. The final reaction mix contained 6 nM biotinylated recombinant soluble human or murine TL1A, 1:1600 dilution of SA-XL665 (CisBio), 1:1000 dilution of the europium cryptate-labeled parental 1D1, and 10% (v/v) periplasmic extract containing scFv's of interest, prepared as described above, in a total reaction volume of 20 μl in HTRF Detection Buffer (Cisbio). Reagents were added sequentially on a MiniTrak Liquid Handling Platform (Perkin-Elmer) into 384-well low-volume black plates (Nunc). Reactions were allowed to proceed for 3 hours at room temperature, and plates were subsequently read on the EnVision Multilabel Plate Reader (Perkin-Elmer) with excitation at 340 nm and two emission readings at 615 nm (measuring input donor fluorescence from 1D1-europium cryptate) and 665 nm (measuring output acceptor fluorescence from SAXL665). All readings were expressed as the percentage of change in fluorescence, %ΔF, as described previously (Finlay et al., J. Mol Biol 388(3):541-58 (2009)). All data were plotted using Decision Site 8 (Spotfire) and Prism 5 (GraphPad) software.

g) Reformatting to IgG, and Expression and Purification

The selected clones were inoculated from their frozen stock and grown overnight at 250 rpm, 37° C. in single wells containing 150 μL 2YT media with 100 μg/mL carbenicillin. Next 0.5 μL of each of the overnight cultures were added to the PCR mixture. The forward primer read 5' CAACAGCTACAGGCGCGCACTCCCAGGTTCAGCTGGTG 3' (SEQ ID NO: 393) and the reverse primer 5' GACCGATGGGCCCTTGGTCGACGCTGAGGAGACGGT GAC 3' (SEQ ID NO: 394). All PCR reactions were then pooled and resolved on a 2% agarose gel. The approximately 400 bp band was excised and purified using a QIAquick gel extraction kit (Qiagen). The purified PCR products were then subject to a BssHII digest at 50° C. for 3 h, followed by deactivation at 80° C. for 20 min. Next, 0.6 μL of bovine serum albumin (100×) and 3 μL of SalI enzyme was added to the reaction and allowed to digest at 50° C. for a further 3 hours, followed by deactivation at 65° C. for 20 min. The bulk digestion was resolved on a 2% agarose gel, gel purified and then ligated into an expression vector engineered to include an effector function null mutation (also referred to as "triple mutant" or "3muf") in the Fc.

IgGs were transiently expressed in 30 ml HEK293 cells (Invitrogen) after standard transfection. Conditioned medium was harvested after 5 days at 37° C., 7% $CO_2$ and cells were removed by centrifugation. The resulting supernatant was filtered and purification was carried out using ProPlus 40 ul Resin tips with the MEA robot (both Phynexus Inc). Briefly, after tip equilibration in wash buffer (Phynexus), 1 ml of conditioned media was drawn through each tip at a flow rate of 0.5 ml/min, 6 times, to enable capture of the IgG by the ProA/G mixture resin, before being discarded. This step was repeated with all 30 ml of media, overnight. Following wash steps with two buffers (Phynexus Inc) the captured protein was eluted with 0.1 M glycine pH 2, and neutralised with 1 M Tris pH9. Purified proteins were buffer exchanged into PBS, concentration was determined by MicroBCA (Thermo), and purity by reducing SDS-PAGE.

h) Caspase Activity Assay

The purified scFvs identified after initial screening, and later the reformatted IgGs, were tested for their ability to neutralize TL1A-induced caspase activity in TF-1 cells (a human erythroleukaemia cell line), to ensure functionality had been maintained. On day one, TF-1 cells were seeded to a density of $3\times10^5$ cells/ml and incubated at 37° C., 5% $CO_2$. On day two, the stimuli mixture of cycloheximide (20 ug/ml) and hTL1A (125 ng/ml) was incubated with a 3-fold dilution series of scFv, starting at 40 nM, for 30 min at 37° C. TF-1 cells (50000 cells/well) were added to the stimuli-scFv mix. After 6 h incubation at 37° C., 100 μl/well Caspase-Glo 3/7 reagent (Promega) was added. The plate was incubated at room temperature for 15 min, after which it was read on the Envision Plate Reader (Perkin-Elmer) at 700 nm. Analysis was performed in duplicate, and data was plotted using Prism 5 (Graph Pad) software.

i) Biacore Analysis of IgGs

Biacore analysis was performed using T-200 biosensor, series S CM5 chips and approximately 4000 RU (response units) of an anti-human IgG (GE Healthcare), immobilized in 10 mM sodium acetate immobilization buffer at pH 5.0. Assay conditions were established to minimize the influence of mass transfer, avidity, and rebinding events, as described below. A blank immobilization was carried out on a separate flow cell for reference subtraction. The purified IgGs were diluted in running buffer (PBS, 300 mM sodium chloride, 3.2 mM ethylenediaminetetraacetic acid, 0.01% Tween20) and low levels (<30 RU) captured using a flow rate of 100 ul/min for 2 min, to reduce possible rebinding by the trimeric TL1A. TL1A was injected at a range of concentrations (0.4-33 nM) in running buffer, at a flow rate of 100 ul/min for 30 s, followed by two 30 sec regeneration steps with 3M magnesium chloride and running buffer. Reference-subtracted sensorgrams for each concentration were analyzed using Biacore T-200 evaluation software (v1.0).

k) Library QC Sequencing

Single colonies were sent for QC sequence analysis from each of the constructed 1D1 mutant scFv libraries (VHCDR1, VHCDR2, VHCDR3A and VHCDR3B). Analysis of the sequence results showed incorporation of all desired mutations at all of the positions targeted in the mutagenesis strategy.

I) Identification and Analysis of Affinity-Matured Variants

Clones were picked randomly from each branch of selection, and initially screened in a crude, single-point periprep format. The binding ELISA identified clones expressing TL1A-binding scFv enriched by the phage display selection process, with increasing numbers of binders observed from round one through to round three of both selection approaches. The HTRF assay measures the decrease in fluorescence observed upon binding of europium cryptate-labeled parental 1D1 IgG to recombinant soluble human/murine TL1A, in the presence of competing scFv antibodies. This allows the identification of clones that compete strongly for binding to the original epitope of 1D1, which has been shown to mediate biological potency in vivo. Similarly, an increase was observed in the number of competing clones retrieved after round 3 of selection. As the periprep concentration cannot be determined, in order to determine the effect of expression on the assay signal, those with %ΔF similar to or better than the parental 1D1 periprep, were taken forward for further analysis. From the classical selection, 800 clones were screened, and 270 were selected for confirmatory screening and sequence analysis, while from the second selection method, an additional 800 clones were screened, and 120 were taken forward.

m) Sequence Analysis

Sequence analysis of clones which were positive in the primary screen led to identification of 40 unique sequences from the classical selections, and an additional 13 unique sequences from the second selection, following removal of any clones with glycosylation motifs (NXS, NXT). Mutations were identified in all 3 VH CDRs. Heavy chain variable domain (VH) sequences for some of these variants are provided in the Sequence Listing Table (Table 40) and FIG. 1A-L.

All clones were subjected to further analysis as purified scFvs, in both the HTRF competition assay and caspase activity assay, indicating all clones could compete with the parental 1D1 for binding to TL1A and inhibit caspase activity in a concentration-dependent manner (data not shown). The scFvs were subsequently reformatted to IgG for further analysis, where similarly all hits showed the ability to compete with parental 1D1 in the HTRF assay and inhibit caspase activity. However, neither assay could be used to rank clones due to a probable stacking effect. As a final concentration of 2 nM TL1A was used in the caspase assay, it is believed the clones had passed the limit of detection of the assay and further optimization would be required in order to accurately rank the potency of each clone.

Biacore analysis of the IgGs showed a number of hits with a KD<2 nM, and 15 hits had a KD<1 nM (Table 7) The greatest affinity improvements, with gains of 2 to 6-fold in KD, were observed in clones with mutations in the VHCDR3 and VHCDR2, with all VHCDR3 variants including the Asn to His mutation. VHCDR3 variants all included a Serine (S) to Alanine (A) mutation at position 93. Sequences of the heavy chain variable domain (VH) of these variants are provided in Table 8, the Sequence Listing Table (Table 40), and FIG. 1A-L. These variants have the same light chain as the parental 1D1 antibody.

TABLE 7

Affinity Improvements in Anti-TL1A IgGs
Affinity Matured Via Phage Display

| Antibody Clone | ka (1/Ms) $\times 10^{+5}$ | kd (1/Ms) $\times 10^{-3}$ | Avg KD (nM) |
|---|---|---|---|
| 1D1 | 11.7 | 1.77 | 2 (±0.5) |
| D37 | 12.6 | 0.35 | 0.3258 (±0.03) |
| D24 | 20.44 | 0.806 | 0.3941 (±0.03) |
| DH3 | 24.91 | 1.017 | 0.4117 (±0.07) |
| D38 | 10.5 | 0.463 | 0.4399 (±0.046) |
| D39 | 7.84 | 0.355 | 0.4417 (±0.04) |
| D25 | 8.68 | 0.387 | 0.4530 (±0.08) |
| D31 | 8.221 | 0.42 | 0.518 (±0.06) |
| D28 | 10.89 | 0.568 | 0.527 (±0.08) |
| DH10 | 8.528 | 0.5 | 0.5885 (±0.04) |
| D5 | 7.765 | 0.478 | 0.6248 (±0.03) |
| D18 | 7.173 | 0.473 | 0.6624 (±0.06) |
| D29 | 10.13 | 0.712 | 0.705 (±0.08) |
| D21 | 7.452 | 0.52 | 0.7093 (±0.08) |
| DH9 | 10.35 | 0.866 | 0.84 (±0.1) |
| DH8 | 9.768 | 0.896 | 0.9245 (±0.137) |

TABLE 8

Sequences of VH CDRs of 1D1 Variants Affinity Matured via Phage Display. Mutated positions relative to 1D1 parental clone are underlined. For CDR-H1, sequence is defined by AntibodyM, and Kabat-defined residues are in bold and italicized.

| Clone Name | CDR-H1 | CDR-H2 | CDR-H3 |
|---|---|---|---|
| 1D1 Parental VH | GYSFT***YYGIS*** SEQ ID NO: 113 | WISTYNGNTNYARMLQG SEQ ID NO: 114 | ENYYGSGSYRGGMDV SEQ ID NO: 115 |
| 1D1 D5 VH | GYSFT***YYGIS*** SEQ ID NO: 263 | WISTYNGNTNYARMLQG SEQ ID NO: 264 | ENYYGSGAFRGGMDG SEQ ID NO: 265 |
| 1D1 D18 VH | GYSFT***YYGIS*** SEQ ID NO: 266 | WISTYNGNTHYARMLQG SEQ ID NO: 267 | ENYYGSGSYRGGMDV SEQ ID NO: 268 |
| 1D1 D21 VH | GYSFT***YYGIS*** SEQ ID NO: 269 | WISTYNGKTHYARMLQG SEQ ID NO: 270 | ENYYGSGSYRGGMDV SEQ ID NO: 271 |
| 1D1 D24 VH | GYSFT***YYGIS*** SEQ ID NO: 272 | WISPYNGNTHYARMLQG SEQ ID NO: 273 | ENYYGSGSYRGGMDV SEQ ID NO: 274 |

TABLE 8-continued

Sequences of VH CDRs of 1D1 Variants Affinity Matured via Phage Display. Mutated positions relative to 1D1 parental clone are underlined. For CDR-H1, sequence is defined by AntibodyM, and Kabat-defined residues are in bold and italicized.

| Clone Name | CDR-H1 | CDR-H2 | CDR-H3 |
|---|---|---|---|
| 1D1 D25 VH | GYSFT***YYGIS*** SEQ ID NO: 275 | WISTYNGATHYARMLQG SEQ ID NO: 276 | ENYYGSGSYRGGMDV SEQ ID NO: 277 |
| 1D1 D28 VH | GYSFT***YYGIS*** SEQ ID NO: 278 | WISTYNGKTHYARMHQG SEQ ID NO: 279 | ENYYGSGSYRGGMDV SEQ ID NO: 280 |
| 1D1 D29 VH | GYSFT***YYGIS*** SEQ ID NO: 281 | WISSYNGNTHYARMLQG SEQ ID NO: 282 | ENYYGSGSYRGGMDV SEQ ID NO: 283 |
| 1D1 D31 VH | GYSFT***YYGIS*** SEQ ID NO: 284 | WISTYNGNKHYARMLQG SEQ ID NO: 285 | ENYYGSGSYRGGMDV SEQ ID NO: 286 |
| 1D1 D37 VH | GYSFT***YYGIS*** SEQ ID NO: 287 | WISTYNGGTHYARMLQG SEQ ID NO: 288 | ENYYGSGSYRGGMDV SEQ ID NO: 289 |
| 1D1 D38 VH | GYSFT***YYGIS*** SEQ ID NO: 290 | WISTYNGVTHYARMLQG SEQ ID NO: 291 | ENYYGSGSYRGGMDV SEQ ID NO: 292 |
| 1D1 D39 VH | GYSFT***YYGIS*** SEQ ID NO: 293 | WISTYNGNTNYARMLQG SEQ ID NO: 294 | ENYYGSGAYRGGMDA SEQ ID NO: 295 |
| 1D1 DH3 VH | GYSFT***YYGIS*** SEQ ID NO: 296 | WISTYNGNTHYAQMLQG SEQ ID NO: 297 | ENYYGSGSYRGGMDV SEQ ID NO: 298 |
| 1D1 DH8 VH | GYSFT***YYGIS*** SEQ ID NO: 299 | WISAYNGNTHYARMLQG SEQ ID NO: 300 | ENYYGSGSYRGGMDV SEQ ID NO: 301 |
| 1D1 DH9 VH | GYSFT***YYGIS*** SEQ ID NO: 302 | WISPYNGKTHYARMLQG SEQ ID NO: 303 | ENYYGSGSYRGGMDV SEQ ID NO: 304 |
| 1D1 DH10 VH | GYSFT***YYGIS*** SEQ ID NO: 305 | WISTYNGNTNYARMLQG SEQ ID NO: 306 | ENYYGSGAYRGGMDV SEQ ID NO: 307 |

Clones were also tested for affinity to both murine and cyno TL1A with similar affinity gains observed (Table 9). Affinity gains were mostly derived from improvements in off-rate. Improvements in affinity were also observed when tested for cross-species reactivity against murine and cyno TL1A (Table 9).

TABLE 9

Affinity of Lead Anti-TL1A IgGs to Human, Murine, and Cyno TL1A

| Antibody Clone | Human TL1A KD pM | Murine TL1A KD pM | Cyno TL1A KD pM |
|---|---|---|---|
| 1D1 | 1436 | 1320 | 1670 |
| D37 | 305 | 786.6 | 334.9 |
| D24 | 931.6 | 803.9 | 942.5 |
| DH3 | 560.3 | 620.3 | 674.6 |
| D38 | 686.6 | 1294 | 610.8 |
| D39 | 441 | 612.6 | 395.5 |

Example 6: Crystal Structure Determination of Anti-TL1A Antibody 1D1

Wild-type human TL1A forms disulfide linked multimers that complicate purification and have, in the literature, led to lower resolution crystal structures. For this reason C95S/C135S double mutants were used for crystallization. The mutant TL1A was expressed in *E.coli* and purified using Ni chelation chromatography followed by ion exchange chromatography and a final size exclusion step.

Fab fragments from parental 1D1 IgG were prepared by digestion with papain. Initial attempts to grow crystals of the complex of TL1A with the 1D1 Fab were unsuccessful. Subsequently, 1D1 scFv-Fc was expressed in HEK cells. The scFv-Fc was purified from conditioned media by protein A capture and the scFv cleaved from the Fc using papain. The isolated scFv was partially cleaved at the linker between the VH and VL domains but the clipped material was still able to bind to TL1A. The complex of 1D1 scFv with TL1A formed cubic crystals in a solution of potassium thiocyanate and succinic acid.

Data was collected to 2.5 | at beamline 17-ID at the Advanced Photon Source. The structure was solved by molecular replacement using the published structure of TL1A (PDB code 2RJL) and an ensemble of variable domain structures. After rebuilding and refinement, the final Rfree value is 0.237 with Rwork of 0.199. The crystal structure has a single copy of the 1D1 scFv bound to a single TL1A monomer in the asymmetric unit. The trimer is generated by crystallographic symmetry from the threefold axis connecting opposite corners of the unit cell in the cubic space group P432 (FIG. 5). The antibody interacts with adjacent faces of two monomers binding in the same groove as seen for the decoy receptor DCR3 in its costructure with TL1A. By analogy with the structures of other TNF family members with their signaling receptors it is assumed that this antibody binding mode would lead to direct blocking of the signaling interaction with the DR3 receptor. Almost all of the paratope is contained within the heavy chain.

Example 7: Computational Design of an Affinity Enhanced Point Mutation

Using the crystal structure, the sequence tolerance protocol, adapted from Smith and Kortemme 2010, publicly available at the PlosOne website, was used to identify mutations that might improve the binding affinity of 1D1 for TL1A. This protocol evaluates a very large number of sequences relatively quickly using the Rosetta protein design software package from the University of Washington. A separate experiment was done for each of the heavy chain CDRs. Residues within a defined distance of the TL1A interface were allowed to vary.

Figure 6:
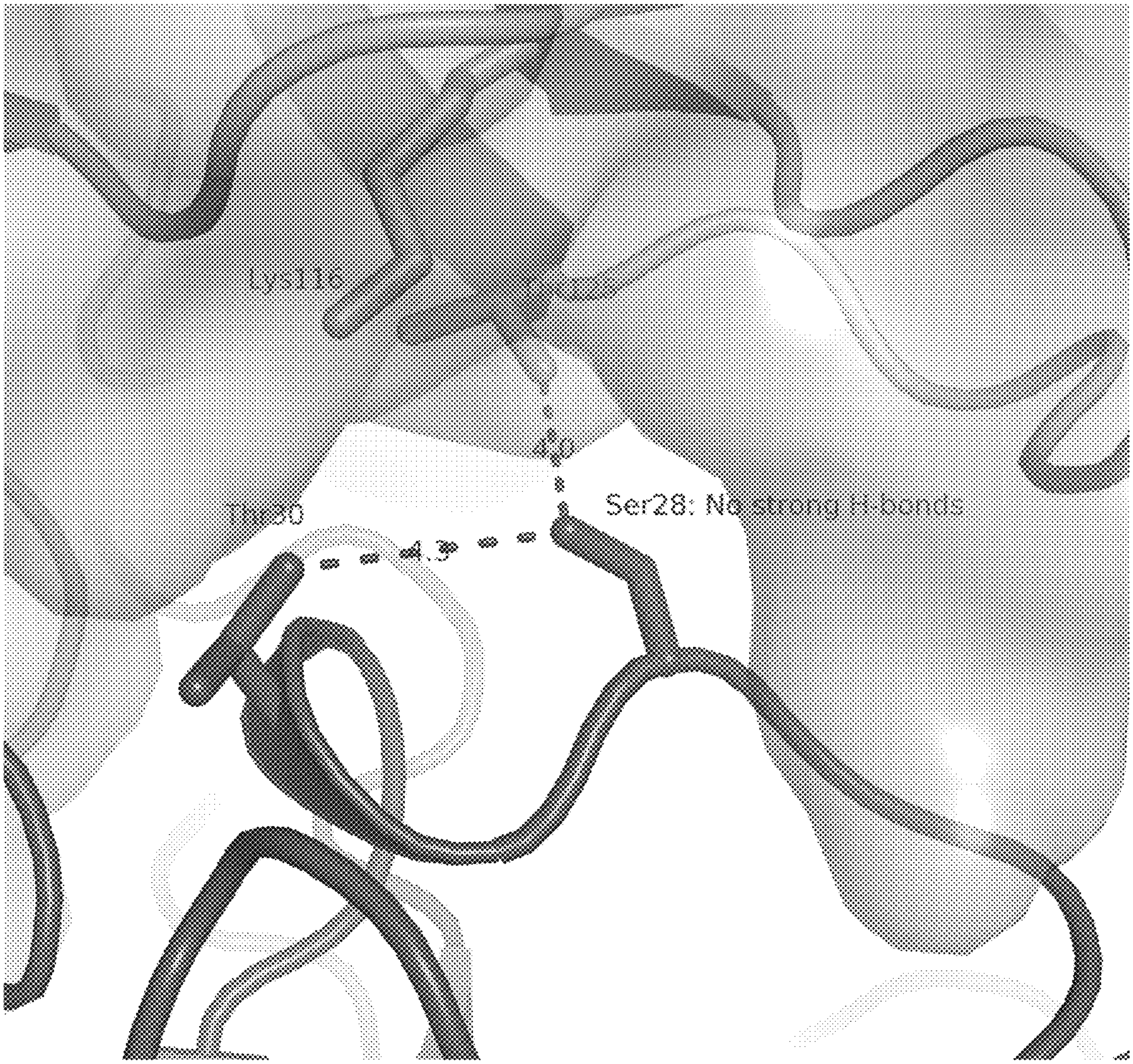
FIG. 6 depicts a magnified view of a selected region in CDRH1 (as defined by AbM) of 1D1 scFv, which illustrates that serine 28 residue of CDRH1 has no strong H-bond partners with any residues on TL1A.
Figure 7:
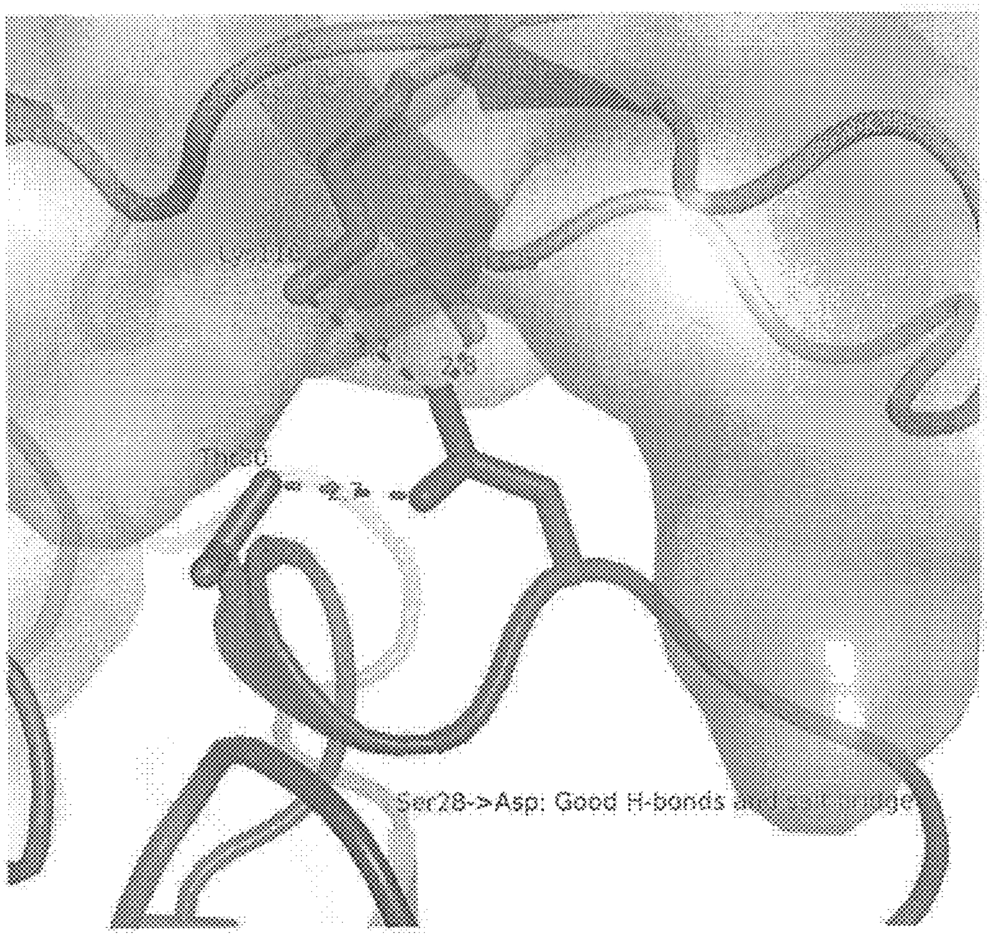
FIG. 7 depicts a magnified view of a selected region in CDRH1 (as defined by AbM) of 1D1 scFv as shown in FIG. 6. The diagram shows that the model indicates that substitution of serine 28 with aspartic acid provides opportunity for strong interactions (e.g., H-bonds and a salt bridge).

Since the contacting residues from CDRs 2 and 3 were well sampled in parallel phage display optimizations we focused on results from CDR H1. In particular, it was apparent that serine 28 in 1D1 was buried in the interface but did not make any strong hydrogen bonds (FIG. 6). The sequence tolerance protocol suggested substituting aspartic acid (FIG. 7), asparagines, or glutamine and also favored a tyrosine to histidine mutation at position 31. These options were examined further by modeling the mutations using the program SCWRL from the Fox Chase Cancer Center and using Macromodel from Schrodinger, Inc. to minimize and calculate a change in binding energy. These mutations (Table 10) were then made and the resulting proteins tested for binding.

TABLE 10

Mutations selected for testing for improvement in 1D1 binding

| Mutation | Predicted ddG | Kd (nM) |
|---|---|---|
| WT 1D1 (parental) | 0 | 2.3 |
| S28D | −6.7 | 0.42 |
| S28N | −10.2 | no binding (created glycosylation site) |
| S28Q | −10.0 | 6.8 |
| Y31H | −17.7 | 12.7 |

The modification of S28D was selected for combination with the best sequences from phage display optimization of CDRs H2 and H3 yielding variants with Kd<0.1 nM. These variants and their VH CDR sequences are listed in Table 11 (clones 1D1 1.1-1.14). To further try to improve the affinity, the beneficial mutations found in the phage display screen across CDRH2 and CDRH3 were combined to look for synergy, (clones 1D1 1.15-1.26). After all of these clones were analyzed, mutation S28D was added into the best CDRH2 and CDRH3 combinations, VH1.27-VH1.34. The heavy chain variable domain (VH) sequences for each of these variants is listed in Table 40 and in FIG. 1A-L. These variants have the same light chain as parental antibody 1 D1.

Table 12 provides a summary of the various amino acid substitutions in the VH regions of antibody1D1 as compared to the affinity matured variants from Table 8 and Table 11, as well as antibodies 15C11 and 15A9 which compete for binding to the same TL1A epitope as antibody 1D1 (see FIG. 1L).

TABLE 11

List of 1D1 Variants Affinity Matured Via Computational Design and Phage Display with improved affinity over 1D1. Mutated positions relative to 1D1 parental clone are underlined. For CDR-H1, sequence is defined by AntibodyM, and Kabat-defined residues are in bold and italicized.

| Clone Name | CDR-H1 | SEQ ID NO: | CDR-H2 | SEQ ID NO: | CDR-H3 | SEQ ID NO: |
|---|---|---|---|---|---|---|
| 1D1 | GYSFT***YYGIS*** | 113 | WISTYNGNTNYARMLQG | 114 | ENYYGSGSYRGGMDV | 115 |
| 1D1 1.1 | GYDFT***YYGIS*** | 308 | WISTYNGNTNYARMLQG | 309 | ENYYGSGSYRGGMDV | 310 |
| 1D1 1.3 | GYQFT***YYGIS*** | 311 | WISTYNGNTNYARMLQG | 312 | ENYYGSGSYRGGMDV | 313 |
| 1D1 1.4 | GYSFT***HYGIS*** | 314 | WISTYNGNTNYARMLQG | 315 | ENYYGSGSYRGGMDV | 316 |
| 1D1 1.5 | GYNFR***YYGIS*** | 317 | WISTYNGNTNYARMLQG | 318 | ENYYGSGSYRGGMDV | 319 |
| 1D1 1.7 | GYSFT***YYGIS*** | 320 | WISTYNGKTNYARMLQG | 321 | ENYYGSGSYRGGMDV | 322 |
| 1D1 1.8 | GYSFR***YYGIS*** | 323 | WISTYNGNTHYARMLQG | 324 | ENYYGSGSYRGGMDV | 325 |

TABLE 11-continued

List of 1D1 Variants Affinity Matured Via Computational Design and Phage Display with improved affinity over 1D1. Mutated positions relative to 1D1 parental clone are underlined. For CDR-H1, sequence is defined by AntibodyM, and Kabat-defined residues are in bold and italicized.

| Clone Name | CDR-H1 | SEQ ID NO: | CDR-H2 | SEQ ID NO: | CDR-H3 | SEQ ID NO: |
|---|---|---|---|---|---|---|
| 1D1 1.9 | GYSFT***YYGIS*** | 326 | WISTYNGNTHYARMLQG | 327 | ENYYGSGAYRGGMDV | 328 |
| 1D1 1.10 | GYSFT***YYGIS*** | 329 | WISPYNGKTHYARMLQG | 330 | ENYYGSGAYRGGMDV | 331 |
| 1D1 1.11 | GYSFR***YYGIS*** | 332 | WISTYNGNTHYARMLQG | 333 | ENYYGSGAYRGGMDV | 334 |
| 1D1 1.13 | GYSFT***HYGIS*** | 335 | WISPYNGKTHYARMLQG | 336 | ENYYGSGAYRGGMDV | 337 |
| 1D1 1.15 | GYSFT***YYGIS*** | 338 | WISPYNGGTHYAQMLQG | 339 | ENYYGSGAYRGGMDA | 340 |
| 1D1 1.16 | GYSFT***YYGIS*** | 341 | WISPYNGVTHYAQMLQG | 342 | ENYYGSGAYRGGMDA | 343 |
| 1D1 1.17 | GYSFT***YYGIS*** | 344 | WISPYNGATHYAQMLQG | 345 | ENYYGSGAYRGGMDA | 346 |
| 1D1 1.18 | GYSFT***YYGIS*** | 347 | WISPYNGNKHYAQMLQG | 348 | ENYYGSGAYRGGMDA | 349 |
| 1D1 1.19 | GYSFT***YYGIS*** | 350 | WISTYNGGTHYARMLQG | 351 | ENYYGSGAYRGGMDA | 352 |
| 1D1 1.20 | GYSFT***YYGIS*** | 353 | WISPYNGNTHYARMLQG | 354 | ENYYGSGAYRGGMDA | 355 |
| 1D1 1.21 | GYSFT***YYGIS*** | 356 | WISTYNGNTHYAQMLQG | 357 | ENYYGSGAYRGGMDA | 358 |
| 1D1 1.22 | GYSFT***YYGIS*** | 359 | WISTYNGVTHYARMLQG | 360 | ENYYGSGAYRGGMDA | 361 |
| 1D1 1.23 | GYSFT***YYGIS*** | 362 | WISTYNGATHYARMLQG | 363 | ENYYGSGAYRGGMDA | 364 |
| 1D1 1.24 | GYSFT***YYGIS*** | 365 | WISTYNGNKHYARMLOG | 366 | ENYYGSGAYRGGMDA | 367 |
| 1D1 1.25 | GYSFT***YYGIS*** | 368 | WISTYNGKTHYARMHQG | 369 | ENYYGSGAYRGGMDA | 370 |
| 1D1 1.26 | GYSFT***YYGIS*** | 371 | WISTYNGNTHYARMLQG | 372 | ENYYGSGAYRGGMDA | 373 |
| 1D1 1.27 | GYDFT***YYGIS*** | 202 | WISTYNGNTHYARMLQG | 203 | ENYYGSGSYRGGMDV | 204 |
| 1D1 1.28 | GYDFT***YYGIS*** | 209 | WISTYNGNKHYARMLOG | 210 | ENYYGSGSYRGGMDV | 211 |
| 1D1 1.29 | GYDFT***YYGIS*** | 216 | WISTYNGGTHYARMLQG | 217 | ENYYGSGSYRGGMDV | 218 |
| 1D1 1.30 | GYDFT***YYGIS*** | 223 | WISTYNGVTHYARMLQG | 224 | ENYYGSGSYRGGMDV | 225 |
| 1D1 1.31 | GYDFT***YYGIS*** | 230 | WISTYNGNTHYARMLQG | 231 | ENYYGSGAYRGGMDV | 232 |
| 1D1 1.32 | GYDFT***YYGIS*** | 237 | WISTYNGGTHYARMLQG | 238 | ENYYGSGAYRGGMDA | 239 |
| 1D1 1.33 | GYDFT***YYGIS*** | 244 | WISTYNGVTHYARMLQG | 245 | ENYYGSGAYRGGMDA | 246 |

TABLE 11-continued

List of 1D1 Variants Affinity Matured Via Computational Design and Phage Display with improved affinity over 1D1. Mutated positions relative to 1D1 parental clone are underlined. For CDR-H1, sequence is defined by AntibodyM, and Kabat-defined residues are in bold and italicized.

| Clone Name | CDR-H1 | SEQ ID NO: | CDR-H2 | SEQ ID NO: | CDR-H3 | SEQ ID NO: |
|---|---|---|---|---|---|---|
| 1D1 1.34 | GYDFT***YYGIS*** | 251 | WISTYNGKTHYARMHQG | 252 | ENYYGSGAYRGGMDA | 253 |

TABLE 12

Summary of Amino Acid Substitutions in 1D1 Variant Antibodies, and Antibodies 15C11 and 15A9 Relative to Parent 1D1 Antibody in VH and VH CDRs. For CDR-H1, sequence is defined by AntibodyM, and Kabat-defined residues are in bold and italicized.

| CDR-H1* | | CDR-H2 | | CDR-H3 | | VH Domain | |
|---|---|---|---|---|---|---|---|
| Amino Acid Sequence in 1D1 (SEQ ID NO: 113) | Variant Amino Acids (SEQ ID NO: 376) | Amino Acid Sequence in 1D1 (SEQ ID NO: 114) | Variant Amino Acids (SEQ ID NO: 379) | Amino Acid Sequence in 1D1 (SEQ ID NO: 115) | Variant Amino Acids (SEQ ID NO: 382) | Amino Acid Sequence in 1D1 | Variant Amino Acids |
| G | | W | | E | | 76R | 76T |
| Y | | I | | N | | 81E | 81D |
| S | D, Q, N, P | S | | Y | | | |
| F | | T | P, S, A | Y | | | |
| T | R | Y | | G | | | |
| ***Y*** | H, N, T | N | | S | | | |
| ***Y*** | | G | | G | | | |
| ***G*** | | N | K, A, G, V, | S | A | | |
| ***I*** | | T | K, | Y | F | | |
| ***S*** | | N | H | R | | | |
| | | Y | | G | | | |
| | | A | | G | | | |
| | | R | Q | M | | | |
| | | M | K | D | | | |
| | | L | H | V | G, A | | |
| | | Q | Q | | | | |
| | | G | G | | | | |

Example 8: Determining TL1A Binding by 1D1 and Top Affinity Optimized Clones Via Biacore/Kinexa To characterize the binding kinetics of various 1D1 variant anti-TL1A antibodies to soluble recombinant TL1A by surface plasmon resonance, each anti-TL1A antibody was expressed as an IgG1 antibody. Stable pool expression of antibodies recognizing TL1A (1D1 parental, 7D4 and 26B11) were established using a lipofectamine transfection protocol. CHO cells were grown to 80% confluence; 25 ugs of DNA for both heavy and light chains were added. Spent media was exchanged with R1+10%FBS repeated on a three/four day schedule while the pools were being established. The Pools were subsequently adapted to serum-free suspension. This material was purified by protein A and used as controls in the program.

The new clone variants for 1D1 were tested by small scale expression in 50 mL HEK 293 transient transfections. Small scale purification on Protein A resin using AKTA express system gave protein that could be run in early Biacore and cell based assays for screening. As clones were selected for further characterization, larger scale transient expression and stable cell line development was carried out.

The antibodies were captured via directly immobilized anti-human IgG (GE Healthcare) onto a carboxymethylated dextran sensor chip surface (CM5) using a Biacore T100 or T200 instrument. Anti-human IgG was immobilized through amine coupling to densities of approximately 4,000-13,000 response units (RU). The antibodies were diluted to 0.075-0.15 μg/ml in 8.1 mM $Na_2HPO_4$, 1.47 mM $KH_2PO_4$, pH 7.2, 237 mM NaCl, 2.7 mM KCl, 3.4 mM EDTA and 0.01% tween 20 (PBS-NET) and injected onto the anti-hlgG surface for about 1-2 minutes at a flow rate of 5 μl/minute to achieve low captured levels of less than 30 RU. After capture, the flow rate was increased to 100 μl/minute and various concentrations of recombinant soluble human TL1A (SEQ ID NO:254), recombinant soluble cynomologous monkey TL1A (SEQ ID NO:259), recombinant soluble mouse TL1A (SEQ ID NO:260), recombinant soluble rat TL1A (SEQ ID NO:261), or recombinant soluble rabbit TL1A (SEQ ID NO:262), ranging from 0.195 nM to 100 nM in PBS-NET were injected for an approximate 2-3 minute association and allowed to dissociate for ~3-60 minutes. At the end of each cycle, the entire anti-hlgG surface was regenerated by a 30-second pulse of 3 M $MgCl_2$ followed by two consecutive 15-second pulses of PBS-NET. Alternatively, the surface was regenerated with two 30-second pulses of an ionic solution containing 0.46 M KSCN, 1.83 M MgCl2, 0.92 M urea, and 1.83 M guanidine-HCl pH7.4, followed by a single 30-second pulse with PBS-NET. All injections were performed at 25° C. at a collection rate of 10 Hz. All sensorgrams were double referenced by using both a control surface and buffer injections. Rate constants were determined by fitting the data to a 1:1 model in Biacore T100, T200 evaluation software v1.0, or BIAevaluation software v4.1.1 and the equation $K_D=k_d/k_a$.

The equilibrium dissociation constant ($K_D$) of each anti-TL1A antibody for human TL1A was measured using a kinetic exclusion assay (KinExA) on a KinExA 3200 instrument (Sapidyne). This assay involves pre-incubating antibody: antigen mixtures in solution long enough to reach equilibrium before measuring the level of unbound antibody using a solid phase component. To prepare the solid phase, two hundred milligrams of polymethylmethacrylate beads (PMMA, Sapidyne) were coated with recombinant human TL1A at 30 ug/m1 in 1 ml of PBS pH7.4 and tumbled for two hours at room temperature. Beads were blocked for 1 hour with PBS plus 10 mg/ml bovine serum albumin (bovine serum albumin, Sigma) at room temperature before being diluted up to a total of 27 ml in PBS. For the in-solution component, each antibody was held at a constant concentration while human, cyno or mouse TL1A were titrated over a broad range from 240 fM-100 nM in PBS plus 1 mg/ml bovine serum albumin. The antibody concentration was held either near the estimated $K_D$ for the $K_D$ controlled curve or at a concentration 10-fold or more above the estimated $K_D$ for the antigen binding concentration (ABC)-controlled curve. For each titration series, a buffer sample and a sample of antibody alone were included. Each antibody: TL1A mixture was tumbled at room temperature for at least six hours to reach equilibrium and then each mixture was injected over the solid phase of TL1A-coated beads in the instrument flow cell. Only free, unoccupied antibody bound to the beads and was detected with 500 ul of 0.25 ug/ml or 1.5 ug/ml Alexa-647-goat-anti-human IgG (H+L) antibody (Jackson) delivered to the flow cell at 0.25 ml/min. Beads were replenished between each sample. Binding signals of detected free antibody were converted to percentage of free, unbound antibody as measured by the antibody only sample and plotted versus each concentration of TL1A. For each antibody, the $K_D$ and ABC controlled curves were fit simultaneously using n-Curve Analysis software v3.1.4 to fit the curves to the 'affinity, unknown ligand' model and measure an equilibrium $K_D$.

For evaluation of TL1A binding in real time, each antibody was captured via anti-IgG onto the Biacore sensor chip surfaces at low densities below 30 RU. Capture levels were kept intentionally low to allow conditions of 1:1 binding, avoid the impact of avidity, and to minimize rebinding during dissociation. At capture levels above 30 RU, slower off-rates had been observed for 1D1 which were likely due to these complications.

For all species of TL1A, binding to 1D1 and each of the affinity matured clones was dependent on the concentration of TL1A tested, as expected. At the highest cytokine concentrations, the dissociation phase was sometimes extended to 60 minutes to achieve at least a 5% decrease in binding signal. This is the minimum decrease recommended for accurately measuring relatively slow antigen dissociation rates. When this condition was met, the association and dissociation rate constants between each species of TL1A and each antibody were calculated from the binding sensorgrams using a 1:1 Langmuir binding model (Table 13-Table 17). For the affinity matured antibodies that did not meet this criteria when binding human TL1A, the off rates were too slow to measure and the $K_D$s were estimated to be less than 100 pM (Table 13).

TABLE 13

Binding Kinetics of anti-TL1A Antibodies to Human TL1A

| Antibody | $k_a$(1/Ms) 1 × E+05 | $k_d$(1/s) 1 × E−04 | $t_{1/2}$ (s) | $K_D$(pM) |
|---|---|---|---|---|
| 1D1 | 6 ± 2 | 18 ± 2 | 397 | 3112 ± 816 |
| 1D1 1.27 | | Too slow to measure | | <100 |
| 1D1 1.28 | | Too slow to measure | | <100 |
| 1D1 1.29 | | Too slow to measure | | <100 |
| 1D1 1.30 | | Too slow to measure | | <100 |
| 1D1 1.31 | | Too slow to measure | | <100 |
| 1D1 1.32 | | Too slow to measure | | <100 |
| 1D1 1.33 | | Too slow to measure | | <100 |
| 1D1 1.34 | | Too slow to measure | | <100 |

TABLE 14

Binding Kinetics of anti-TL1A Antibodies to Cynomolgus Monkey TL1A

| Antibody | $k_a$(1/Ms) 1 × E+05 | $k_d$(1/s) 1 × E−04 | $t_{1/2}$ (s) | $K_D$(pM) |
|---|---|---|---|---|
| 1D1 | 6 ± 1 | 41 ± 9 | 169 | 6694 ± 1094 |
| 1D1 1.27 | 3.9 ± 0.8 | 0.8 ± 0.2 | 8443 | 220 ± 87 |
| 1D1 1.28 | 3.8 ± 0.2 | 0.54 ± 0.05 | 12924 | 144 ± 21 |
| 1D1 1.29 | 4.9 ± 0.4 | 0.45 ± 0.004 | 15553 | 92 ± 14 |
| 1D1 1.30 | 4.1 ± 0.3 | 0.6 ± 0.1 | 11915 | 142 ± 21 |
| 1D1 1.31 | 4.5 ± 0.4 | 0.36 ± 0.07 | 19236 | 81 ± 23 |
| 1D1 1.32 | 4.6 ± 0.5 | 0.29 ± 0.05 | 23874 | 66 ± 17 |
| 1D1 1.33 | 3.6 ± 0.4 | 0.37 ± 0.05 | 18517 | 107 ± 28 |
| 1D1 1.34 | 4.4 ± 0.4 | 0.36 ± 0.05 | 19380 | 83 ± 18 |

TABLE 15

| Binding Kinetics of anti-TL1A Antibodies to Mouse TL1A | | | | |
|---|---|---|---|---|
| Antibody | $k_a$(1/Ms) 1 × E+05 | $k_d$(1/s) 1 × E−04 | $t_{1/2}$ (s) | $K_D$(pM) |
| 1D1 | 4.9 ± 0.9 | 36 ± 6 | 195 | 7286 ± 756 |
| 1D1 1.27 | 2.7 ± 0.5 | 4.3 ± 0.5 | 1616 | 1643 ± 547 |
| 1D1 1.28 | 2.1 ± 0.4 | 3.2 ± 0.5 | 2166 | 153 ± 430 |
| 1D1 1.29 | 2.6 ± 0.4 | 7 ± 1 | 947 | 2860 ± 812 |
| 1D1 1.30 | 1.4 ± 0.3 | 7 ± 2 | 1075 | 5253 ± 1964 |
| 1D1 1.31 | 2.7 ± 0.3 | 2.7 ± 0.06 | 2525 | 1059 ± 336 |
| 1D1 1.32 | 2.6 ± 0.4 | 2.3 ± 0.03 | 2971 | 906 ± 234 |
| 1D1 1.33 | 1.6 ± 0.1 | 2.9 ± 0.06 | 2342 | 1910 ± 485 |
| 1D1 1.34 | 2.5 ± 0.3 | 2.8 ± 0.6 | 2508 | 1109 ± 335 |

TABLE 16

| Binding Kinetics of anti-TL1A Antibodies to Rat TL1A | | | | |
|---|---|---|---|---|
| Antibody | $k_a$(1/Ms) 1 × E+05 | $k_d$(1/s) 1 × E−03 | $t_{1/2}$ (s) | $K_D$(pM) |
| 1D1 | 17.1 ± 3.2 | 13.4 ± 0.4 | 52 | 8141 ± 1775 |
| 1D1 1.27 | 6.7 ± 0.2 | 7.2 ± 0.4 | 96 | 10903 ± 1047 |
| 1D1 1.30 | 2.4 ± 0.1 | 9.8 ± 2.1 | 71 | 41890 ± 10820 |
| 1D1 1.31 | 5.4 ± 0.1 | 2.6 ± 0.1 | 263 | 4858 ± 249 |
| 1D1 1.32 | 5.8 ± 0.01 | 2.9 ± 0.1 | 237 | 5022 ± 95 |
| 1D1 1.34 | 4.1 ± 0.2 | 2.4 ± 0.01 | 286 | 5924 ± 306 |

TABLE 17

| Binding Kinetics of anti-TL1A Antibodies to Rabbit TL1A | | | | |
|---|---|---|---|---|
| Antibody | $k_a$(1/Ms) 1 × E+05 | $k_d$(1/s) 1 × E−04 | $t_{1/2}$ (s) | $K_D$(pM) |
| 1D1 | 6.1 ± 0.7 | 7.9 ± 0.24 | 877 | 1313 ± 191 |
| 1D1 1.27 | 3.0 ± 0.2 | 1.4 ± 0.02 | 4928 | 478 ± 31 |
| 1D1 1.31 | 3.2 ± 0.4 | 1.1 ± 0.04 | 6075 | 361 ± 31 |

Solution-based kinetic exclusion assays (KinExA) were carried out as an orthogonal technique to measure equilibrium $K_D$ values. Both a $K_D$-controlled and an ABC-controlled curve were generated for each affinity matured antibody with TL1A. Curves were generated as well for the parental 1D1 antibody and a Fab generated from the 1D1 antibody to use as comparators. N-curve analysis was performed using the “affinity, unknown ligand” model to determine the equilibrium $K_D$ for each antibody (Table 18). For the affinity matured antibodies with $K_D$s that could not be determined by surface plasmon resonance, measured equilibrium $K_D$s could distinguish these antibodies from the parental 1D1 antibody.

TABLE 18

| Equilibrium KD’s of 1D1 Variant Antibodies | | | |
|---|---|---|---|
| Antibody | Human TL1A KinExA $K_D$ (pM) | Cyno TL1A KinExA $K_D$ (pM) | Mouse TL1A KinExA $K_D$ (pM) |
| 1D1 | 84, 127 (n = 2) | 384 | 383 |
| 1D1 Fab | 3000 | N.D. | N.D. |
| 1D1 1.27 | 7.69 | N.D. | N.D. |
| 1D1 1.28 | 2.52 | N.D. | N.D. |
| 1D1 1.29 | 19.4 | N.D. | N.D. |
| 1D1 1.30 | 6.8 | N.D. | N.D. |
| 1D1 1.31 | 1.38, 3.6 (n = 2) | 3.5 | 95.3 |
| 1D11.32 | 6.15 | N.D. | N.D. |
| 1D11.33 | 10.6 | N.D. | N.D. |
| 1D11.34 | 1.16 | N.D. | N.D. |

Due to the homotrimeric composition of TL1A and the fact that KinExA $K_D$s are carried out in-solution, it is possible that the multivalent TL1A forms lattices structures with the bivalent antibodies. Therefore, the KinExA $K_D$ values likely include an avidity index. The avidity index of 1D1 antibody was determined due to the availability of the 1D1 Fab protein. The Fab of 1D1 bound human TL1A with an equilibrium $K_D$ of 3 nM (Table 18). The Fab is monovalent for human TL1A and accordingly, the KinExA $K_D$ agreed with the $K_D$ of 3.2±0.9 nM from the full length antibody under conditions of 1:1 binding on the Biacore sensor chip surface. There was not enough of the Fab to measure the $K_D$ to human TL1A by SPR. Compared to the 127 pM $K_D$ measured by KinExA, the avidity index for 1D1 is apparently 24. The avidity indices of the affinity matured antibodies are unknown and are not necessarily the same of the apparent 24-fold index for the parental 1D1 antibody.

Example 9: Crystal Structures of 7D4 Fab, 26B11 Fab, and 1D1 1.31 scFv, and DR3 with TL1A C95S/C135S double mutant TL1A was expressed in *E. coli* and purified as described in Example 6. The Fab fragment of antibody 7D4 was obtained by cleaving the full length IgG with papain and removing the Fc using a Protein A resin. The Fab was mixed with double mutant TL1A at a 1:1 molar ratio and the resulting complex was purified by SEC. Crystals of the complex formed in 100 mM Tris pH 8, 25% PEG 400.

Figure 8:
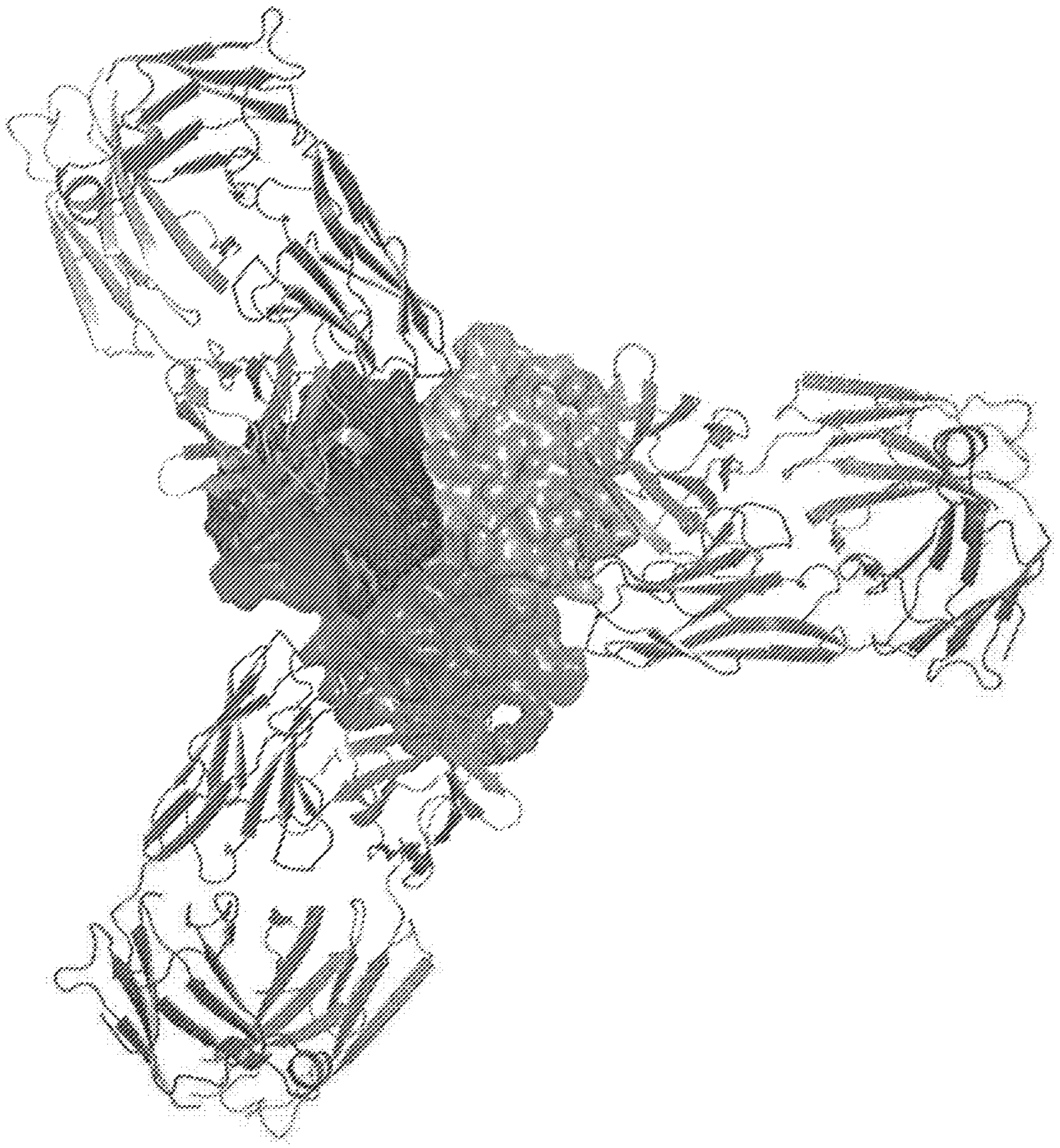
FIG. 8 depicts the crystal structure of Fab of anti-TL1A antibody 7D4 co-crystallized with human TL1A. Individual TL1A monomers are shown as surfaces in light gray, dark gray and black. 7D4 Fabs are shown as ribbons with the VL in dark gray and the VH in light gray.

Data was collected to 3.1 Å at beamline 17-ID at the Advanced Photon Source. The structure was solved by molecular replacement and refined to R/Rfree of 0.187/0.238 (FIG. 8). The crystal structure has a single copy of TL1A bound to a single 7D4 Fab fragment in the asymmetric unit in space group I213. As for 1D1, the biological trimer is generated by crystallographic symmetry. In contrast with 1D1, which interacts with the receptor-binding groove between adjacent TL1A monomers, the 7D4 epitope is almost entirely contained within a single TL1A monomer. Nevertheless, the epitope is sufficiently broad that 7D4 binding would be expected to interfere directly with receptor binding as is seen in the cell based neutralization assay.

Figure 9:
FIG. 9 depicts a model of the crystal structure of Fab of anti-TL1A antibody 26B11 co-crystallized with human TL1A. The model was formed by successive superposition of the crystal structure of a single complex on the structure of the TL1A trimer. Individual TL1A monomers are shown as surfaces with different shades of gray. 26B11 Fabs are shown as ribbons with the light chain in dark gray and the heavy chain in light gray.

For determination of the costructure of TL1A with 26B11, the same double mutant TL1A was combined with the Fab fragment of 26B11 and the resulting complex purified by SEC. Crystals were obtained in 16% PEG 3350, 250 mM ammonium nitrate and diffracted to 2.5 Å at beamline 17-ID at the Advanced Photon Source. The structure was refined to R/Rfree values of 0.177/0.224 (FIG. 9). The crystallographic asymmetric unit contains 2 copies of the complex. Surprisingly, the TL1A molecules in the crystal do not form the biologically active trimer. The low pH of the crystallization solution may have caused dissociation of the trimer. The complex elutes from a gel filtration column at a time consistent with the molecular weight of the 3:3 complex of 26B11 Fab and TL1A demonstrating that the antibody does not interfere with trimerization. Furthermore, if the TL1A in the 26B11 complex is superimposed on a structure of the TL1A trimer there are no clashes observed between individual copies of the 26B11 Fab. The 7D4 and 26B11 epitopes are overlapping, although according to the data in Example 2, these antibodies did not compete for binding to TL1A.

Figure 10:
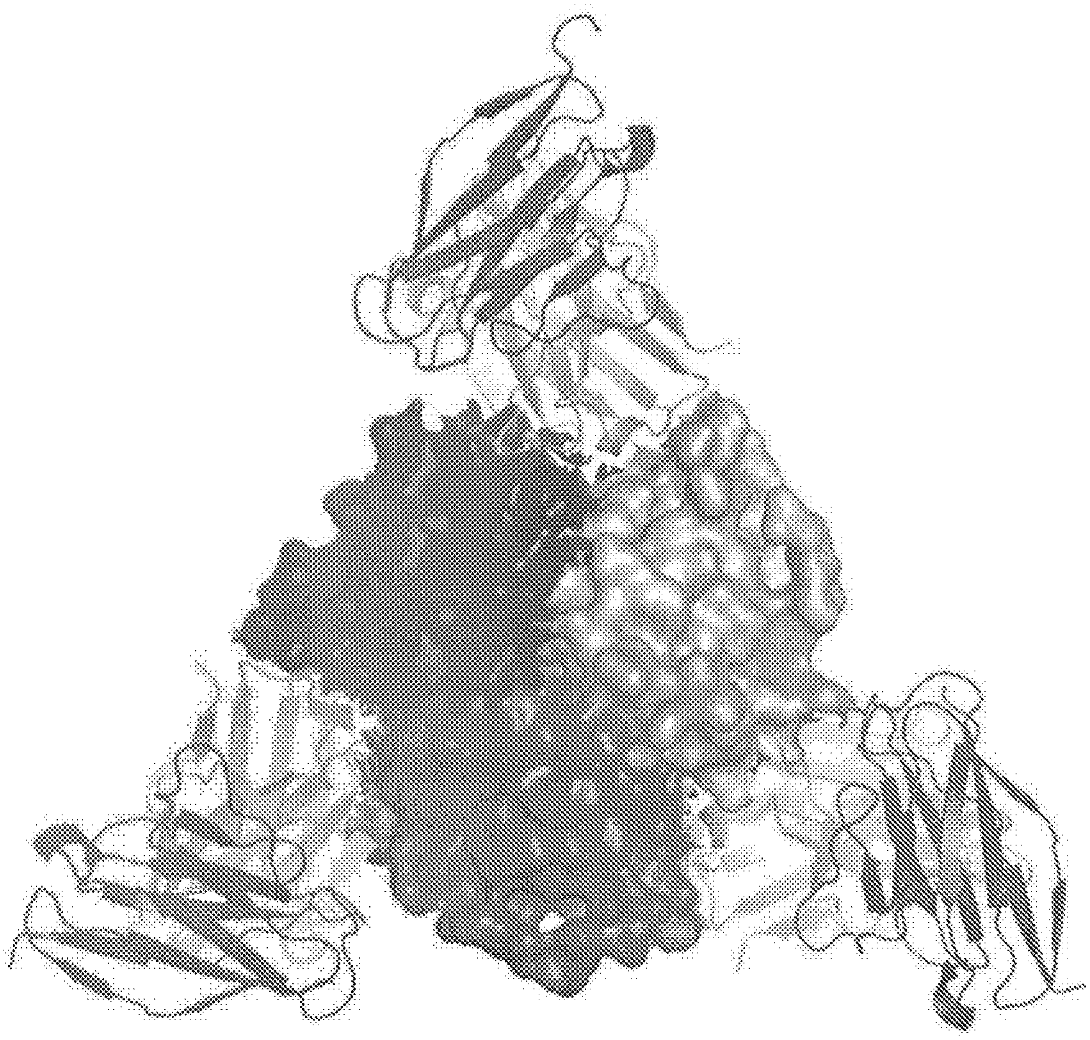
FIG. 10 depicts the crystal structure of the scFv of anti-TL1A antibody 1D1 1.31 co-crystallized with human TL1A. Individual TL1A monomers are each shown as surfaces in light gray, dark gray and black. The 1D1 1.31 scFv is shown in ribbons with the heavy chain in light gray and the light chain in dark gray.

For determination of the costructure of TL1A with 1D1 1.31, an scFv version of the affinity optimized antibody was expressed as an Fc fusion, cleaved with papain, and purified as for the parental 1D1 antibody. The purified scFv was mixed with double mutant TL1A and the complex was purified by SEC. Crystals were obtained in 1800 mM ammonium sulfate, 8.33333% dioxane, 100 mM MES pH 6.5 and diffracted to 3.2 Å on beamline 17-ID at the Advanced Photon Source (FIG. 10). The asymmetric unit contains a single copy of the full trimeric complex consisting of three TL1A monomers and three 1.31 scFv molecules.

The overall binding mode of 1D1 1.31 to TL1A is the same as that for parental 1D1. There are two sequence differences between 1D1 1.31 and 1D1 that were expected to be located within the interface with TL1A: histidine in 1D1 1.31 vs. asparagine in 1D1 at position H58, and aspartic acid in 1D1 1.31 vs. serine at position H28 (see FIG. 11). As expected, the histidine makes essentially the same interaction as the original asparagines with glutamic acid 55 of TL1A, but this interaction is stronger because the proximity of the glutamic acid would likely raise the pKa of the histidine to the point where it would carry a positive charge at physiological pH. The aspartic acid at position 28 shows the expected improved hydrogen bonding coordination and charge complimentarity relative to the parental serine (see FIG. 12). In addition, the crystal structure shows an altered conformation in the adjacent TL1A loop 118-121 relative to the conformation bound to 1D1. Tyrosine 121 of TL1A is in a different rotamer and backbone trajectory is altered. The Y121 side chain forms new hydrophobic interactions with 1D1 1.31 that may contribute to the increased affinity of this antibody. In the structure with 1D1, a water molecule occupies the position held by the Y121 side chain in the structure with 1D1 1.31. These differences are observed in all three copies of the complex but it cannot be ruled out that it is an effect of the different crystallization conditions rather than the sequence differences between 1D1 and 1D1 1.31.

Similarly, crystals of the TL1A:DR3 complex were obtained. The interaction between residues of TL1A and DR3, as well as the interaction between TL1A and antibodies 1D1, 1D1 1.31 (1.31), 7D4 and 26B11 are summarized in Table 42. As shown in Table 42, a number of amino acids, including T30, V31, V32, R33, Q34, T35, P36, T37, Q38, H39, F40, K41, N42, Q43, F44, P45, E50, H51, E52, L53, G54, L55, A56, F57, T58, R86, G87, M88, T89, E91, G99, R100, P101, N102, K103, P104, D105, S106, S136, N137, F139, S161, D162, I163, S164, L165, V166, D167, Y168, T169, K170, E171, D172, N42, F44, K103, P104, D105, S106, K113, T115, S117, Y118, P119, E120, P121, T122, 0123, M147, F148, S149, and Q151, according to the numbering of the amino acid sequence of TL1A as set forth in SEQ ID NO:254 interact with at least one of the 1D1, 1.31, 7D4, 26B11 antibodies or DR3; in some cases, the TL1A amino acid can reside within different subunits of the TL1A multimer, such that the antibody binds to a homomultimer of TL1A, the homomultimer comprising at least a first and a second TL1A monomer, wherein the antibody binds to a first epitope on the first TL1A monomer, wherein the first epitope comprises at least one amino acid selected from the group consisting of N42, F44, K103, P104, D105, S106, K113, T115, S117, Y118, P119, E120, P121, T122, Q123, M147, F148, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of T30, V31, V32, R33, Q34, T35, P36, T37, Q38, H39, F40, K41, N42, Q43, F44, P45, E50, H51, E52, L53, G54, L55, A56, F57, T58, R86, G87, M88, T89, E91, G99, R100, P101, N102, K103, P104, D105, S106, S136, N137, F139, S161, D162, 1163, S164, L165, V166, D167, Y168, T169, K170, E171, and D172, according to the numbering of the amino acid sequence of TL1A as set forth in SEQ ID NO:254.

Some of the amino acid residues of TL1A may be involved in interaction with more than one of antibodies 1D1, 1D1 1.31 (1.31), 7D4 and 26B11, or DR3. As shown in Table 42, amino acids V31, V32, R33, T35, P36, T37, Q38, H39, F40, Q43, E50, H51, E52, L53, G54, L55, A56, F57, R86, G87, M88, S136, N137, S164, L165, Y168, T169, K170, E171, K113, S117, Y118, P119, T122, Q123, M147, F148, S149, and Q151, according to the numbering of the amino acid sequence of TL1A as set forth in SEQ ID NO:254 interact with at least two of the 1D1, 1.31, 7D4, 26B11 antibodies or DR3. In some cases, the TL1A amino acid can reside within different subunits of the TL1A multimer, such that the antibody binds to a homomultimer of TL1A comprising at least a first and second TL1A monomer, wherein the antibody binds to a first epitope on the first TL1A monomer, wherein the first epitope comprises at least one amino acid selected from the group consisting of K113, S117, Y118, P119, T122, Q123, M147, F148, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, T35, P36, T37, Q38, H39, F40, Q43, E50, H51, E52, L53, G54, L55, A56, F57, R86, G87, M88, S136, N137, S164, L165, Y168, T169, K170, and E171, according to the numbering of the amino acid sequence of TL1A as set forth in SEQ ID NO:254.

Some of the amino acid residues of TL1A may be involved in interaction with more than two of antibodies 1D1, 1D1 1.31 (1.31), 7D4 and 26B11, or DR3, as shown in Table 42. Therefore, in one embodiment, the TL1A antibody or antigen-binding fragment thereof according to the present invention binds to one or more amino acids selected from the group consisting of V31, V32, R33, E50, L53, G54, S164, Y168, T169, K170, E171, Y118, and Q151, according to the numbering of the amino acid sequence of TL1A as set forth in SEQ ID NO:254 interact with at least three of the 1D1, 1.31, 7D4, 26B11 antibodies or DR3. In some cases, the TL1A antibody can interact with amino acids of TL1A reside within different subunits of the TL1A multimer, such that the antibody binds to a homomultimer of TL1A comprising at least a first and second TL1A monomer, wherein the antibody binds to a first epitope on the first TL1A monomer, wherein the first epitope comprises at least one amino acid selected from the group consisting of Y118 and Q151 according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, E50, L53, G54, S164, Y168, T169, K170, and E171, according to the numbering of the amino acid sequence of TL1A as set forth in SEQ ID NO:254.

Some amino acids of TL1A may be involved in interaction with more than three of antibodies 1D1, 1D1 1.31 (1.31), 7D4 and 26B11, or DR3, as shown in Table 42. As such, in one embodiment, the TL1A antibody or antigen-binding fragment thereof according to the present invention interacts with an amino acid of TL1A selected from the group consisting of R33, Y168, and T169, according to the numbering of the amino acid sequence of TL1A as set forth in SEQ ID NO:254.

In still other cases, the TL1A amino acid residue is involved interaction with 1D1 and 1D1 1.31 antibodies. As such, in certain embodiments, the TL1A antibody or antigen-binding fragment thereof according to the present invention binds to at least one TL1A amino acid selected from the group consisting of V31, V32, R33, E50, H51, E52, L53, G54, L55, A56, F57, Y168, T169, K170, E171, K113, Y118, T122, Q123, M147, F148, S149, and Q151, according to the numbering of the amino acid sequence of TL1A as set forth in SEQ ID NO:254. In other cases, the antibody can bind to amino acids within different subunits of the TL1A homomultimer. As such, in one embodiment, the TL1A antibody or antigen-binding fragment thereof according to the present invention binds to a homomultimer of TL1A comprising at least a first and second TL1A monomer, wherein the antibody binds to a first epitope on the first TL1A monomer, wherein the first epitope comprises at least one amino acid selected from the group consisting of K113, Y118, T122, Q123, M147, F148, S149, and Q151, according to the numbering of the amino acid sequence of TL1A as set forth in SEQ ID NO:254, and the antibody binds to a second epitope on the second TL1A monomer, wherein the second epitope comprises at least one amino acid selected from the group consisting of V31, V32, R33, E50, H51, E52, L53, G54, L55, A56, F57, Y168, T169, K170, E171, according to the numbering of the amino acid sequence of TL1A as set forth in SEQ ID NO:254.

In still other cases, the binding of the antibody to TL1A causes a non-zero change in buried surface area in an amino acid of TL1A. For example, there is an increase of at least 20 $Å^2$ in the buried surface area in the amino acids R33, Q34, T35, P36, T37, Q38, H39, F40, K41, N42, P45, E50, L53, G54, L55, F57, T58, R86, M88, T89, P101, N102, K103, P104, D105, S136, N137, D162, I163, S164, Y168, T169, K170, E171, N42, K103, P104, D105, K113, S117, Y118, T122, S149, and Q151, according to the numbering of the amino acid sequence of TL1A as set forth in SEQ ID NO:254. These amino acids can be present on different subunits of TL1A: for example, amino acids of N42, K103, P104, D105, K113, S117, Y118, T122, S149, and Q151 of a first TL1A subunit, and R33, Q34, T35, P36, T37, Q38, H39, F40, K41, N42, P45, E50, L53, G54, L55, F57, T58, R86, M88, T89, P101, N102, K103, P104, D105, S136, N137, D162, 1163, S164, Y168, T169, K170, and E171 of a second TL1A subunit, according to the numbering of SEQ ID NO: 254. In other cases, there is an increase of at least 50 $Å^2$ in the buried surface area in the amino acids R33, T35, P36, Q38, H39, F40, K41, N42, L53, G54, L55, R86, M88, P101, N102, K103, D105, N137, S164, Y168, E171, N42, K103, D105, and Y118, according to the numbering of the amino acid sequence of TL1A as set forth in SEQ ID NO:254. These amino acids can be present on different subunits of TL1A: for example, amino acids of N42, K103, D105, and Y118, of a first TL1A subunit, and R33, T35, P36, Q38, H39, F40, K41, N42, L53, G54, L55, R86, M88, P101, N102, K103, D105, N137, S164, Y168, and E171, according to the numbering of the amino acid sequence of TL1A as set forth in SEQ ID NO:254.1n other cases, there is an increase of at least 100 $Å^2$ in the buried surface area in the amino acids R33, Q38, F40, K41, L53, R86, M88, and Y118, according to the numbering of the amino acid sequence of TL1A as set forth in SEQ ID NO:254. These amino acids can be present on different subunits of TL1A: for example, amino acid Y118 of a first TL1A subunit, and R33, Q38, F40, K41, L53, R86, and M88, according to the numbering of the amino acid sequence of TL1A as set forth in SEQ ID NO:254.

A number of amino acid residues of TL1A, for example, amino acids A56, D232, E171, E52, H109, K111, K173, N112, N172, N207, P106, P171, Q104, Q108, R156, R33, S149, T122, T169, Y118, Y168, and Y238, according to the numbering of the amino acid sequence of TL1A as set forth in SEQ ID NO:254, are involved in hydrogen bonding with DR3 or the antibodies of the present invention. For example, as shown in Table 42, TL1A amino acids Q108, H109, K111, N112, P171, N172, and K173, according to the numbering of the amino acid sequence of TL1A as set forth in SEQ ID NO:254 are involved in hydrogen-bond formation with the antibody 26B11. For binding with antibody 7D4, Q104, P106, R156, N207, D232, and Y238, are shown to form hydrogen bonds. Amino acids Y118, S149, R33, E52, A56, and Y168, according to the numbering of the amino acid sequence of TL1A as set forth in SEQ ID NO:254 can form hydrogen bonds with the antibody 1D1. Amino acids T122, S149, E52, A56, Y168, T169, and E171, can form hydrogen bonds when TL1A is bound to 1.31.

In certain cases, the antibody or antigen-binding fragment thereof of the present invention binds to TL1A and participates with a water molecule that is also hydrogen bonded to one or more reisdues of TL1A that is selected from the group consisting of R33, Q38, K41, N42, L55, N102, D105, and M147, according to the numbering of the amino acid sequence of TL1A as set forth in SEQ ID NO:254.

Example 10: Binding of Anti-TL1A Antibodies to Human Monocyte Cell Surface TL1A This study demonstrates that TL1A is expressed on the surface of monocytes upon stimulation with immune complex and that antibody 1D1 1.31 binds to human monocyte cell surface TL1A. Antibody 1D1 1.31, expressed as a full length human IgG1 with effector function-null mutations in the heavy chain Fc (1D1 1.31-hIgG1-3mut) was produced in CHO cells. The isotype control antibody was an anti-tetanus toxoid (aTT) antibody which is also a human IgG1 antibody containing the same three effector function-null mutations as 1D1 1.31.

Peripheral blood mononuclear cells (PBMC) were isolated from 100 mL of human peripheral blood by first diluting whole blood 50:50 with phosphate buffered saline (PBS) and layering 25 mL of diluted blood over 15 mL Ficoll-Paque. Layered blood was centrifuged at 930×g for 30 minutes. Following centrifugation, the cellular interface containing PBMC was collected and washed twice with 10 mL sterile PBS. Cells were resuspended in 5 mL Pharm Lysing Buffer (BD Biosciences, San Jose, CA) and incubated at room temperature for 5 minutes to lyse the contaminating red blood cells. After incubation, cells were washed twice with RPMI 1640 medium containing 10% heat-inactivated fetal bovine serum (FBS), 10 mM HEPES, 10 units/mL penicillin/streptomycin, and 2 mM glutamine and resuspended in complete medium at a final concentration of $2\times10^6$ cells/mL.

Induction of TL1A on peripheral blood monocytes and staining with 1D1 1.31 was accomplished by plating 2 mL complete medium containing $4\times10^6$ PBMC into IC coated 12-well plates in the presence or absence of 1D1 1.31 and stimulating cells for 4 hours at 37° C. Induction was accomplished using IC formed by optimal concentrations of human IgG and mouse anti-human IgG. Plate-bound IC was prepared by incubating 500 μL of 0.5 mg/mL human IgG (Jackson ImmunoResearch Laboratories, West Grove, PA) in PBS per well of a 12-well plate for 1 hour at 37° C. Following incubation, plates were washed 3 times with PBS and incubated with mouse anti-human IgG (Jackson ImmunoResearch Laboratories, West Grove, PA) in PBS (20 μg/mL) for 1 hour. Coated plates were washed 3 times with PBS and stored in PBS prior to use.

Membrane-bound TL1A expression on human monocytes was demonstrated by staining with biotinylated 1D1 1.31 antibody. Following a 4-hour stimulation, cells were collected by using a cell lifter/scraper to detach adherent cells from the wells. Harvested cells were collected by centrifugation and resuspended in 100 μL BD Pharmingen™ Stain Buffer (FBS; BD Biosciences, San Jose, CA) and blocked with TruStain FcX (BioLegend™, BD San Diego, CA) on ice for 10 minutes. Anti-CD14 Pacific Blue (BD Pharmingen™, BD Biosciences, San Jose, CA) and 10 μg/mL biotinylated 1D1 1.31 or isotype control antibodies were added and cells were incubated on ice for 15 minutes. After incubation, cells were washed with 3 mL of stain buffer, centrifuged at 800×g for 5 minutes and resuspended in 400 μL of stain buffer containing phycoerythrin (PE)-streptavidin (a 1:1000 dilution of fluorescently-labeled streptavidin). After incubation, cells were washed twice, centrifuged, and resuspended in 400 μL of stain buffer. Membrane-bound TL1A expression was measured using the BD LSR-Fortessa™ instrument and demonstrated by the increase in mean fluorescence intensity (MFI) as compared to the biotinylated isotype control antibody.

Figure 13:
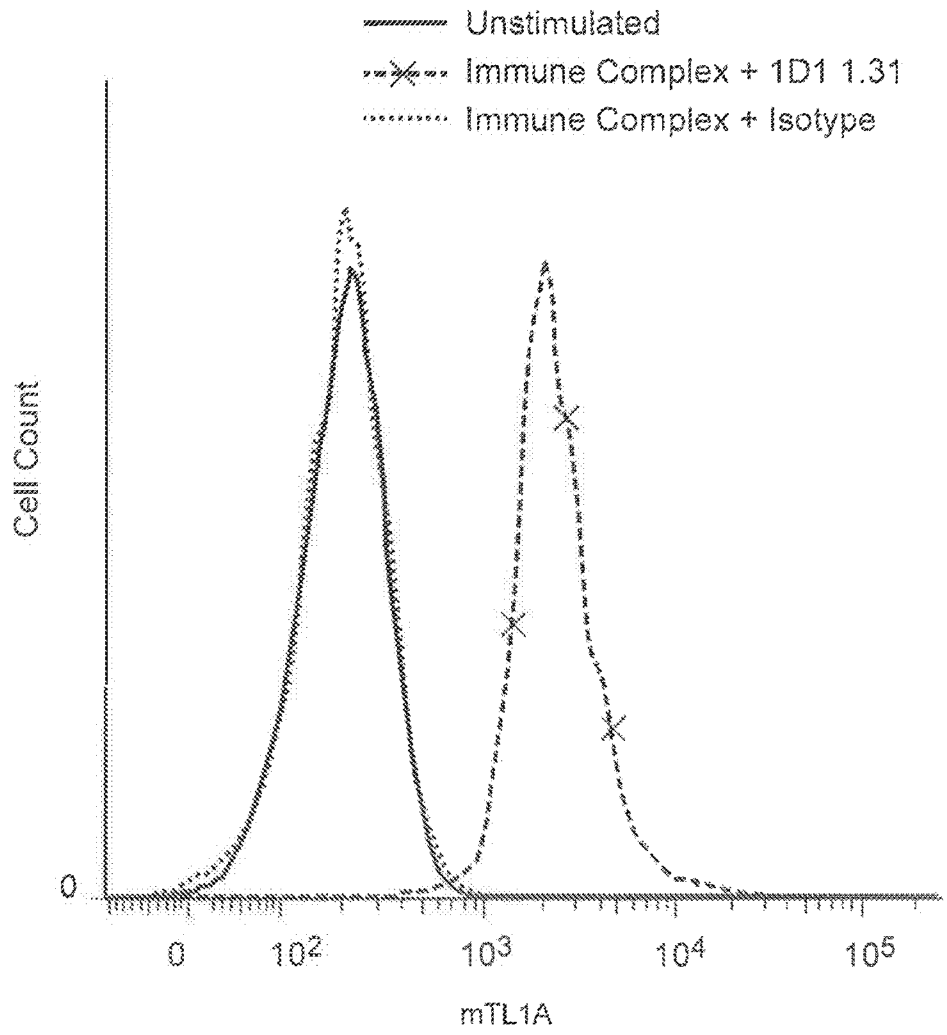
FIG. 13 is a graph depicting expression of membrane-bound TL1A (mTL1A) by monocytes in the presence and absence of anti-TL1A antibody 1D1 1.31. Human monocytes from whole blood were stimulated by plate-bound IC for 4 hours±1D1 1.31 and show a peak to the right of the overlapping peaks demonstrated by both isotype control (light gray) and unstimulated cells (dark gray). Membrane TL1A was detected using streptavidin PE and measured by flow cytometry such that amount of TL1A on cell surface is expressed along the x-axis ranging from 0 to $10^5$ mTL1A as increasing fluorescence signal.

The binding of 1D1 1.31 to membrane-bound TL1A was evaluated on stimulated human monocytes. Preliminary studies indicated resting peripheral blood monocytes do not constitutively express membrane-bound TL1A. Therefore, monocytes were induced to express endogenous TL1A following immune complex stimulation (via Fc receptor engagement) to demonstrate binding of 1D1 1.31 to monocyte cell surface TL1A. Prior in depth characterization of TL1A up-regulation kinetics demonstrated maximal expression at 4 hours post IC stimulation, the time point used in subsequent studies to demonstrate 1D1 1.31 binding to monocytes. IC coated plates induced TL1A expression on monocyte cell surface 4 hours post stimulation (FIG. 13). Cells treated with 1D1 1.31 had increased mean fluorescence intensity compared to the isotype treated and unstimulated control cells. The specificity of this binding was confirmed in competition assays using purified naked anti-TL1A antibodies at 1 and 10 μg/mL (data not shown). These results illustrate that antibody 1D1 1.31 is an anti-TL1A antibody that binds specifically to membrane-bound TL1A expressed on stimulated circulating monocytes.

Example 11: Inhibition of NFκB by Anti-TL1A Antibodies in TF-1 Cells

To evaluate the functional inhibitory potency and ability of antibody 1D1 1.31 to inhibit intracellular signaling of TL1A through DR3, the antibody was evaluated in TF-1 cells (an erythroblastoma cell line) which constitutively express DR3 and which were transduced with an NFκB-promotor-driven luciferase gene.

Antibody 1D1 1.31, expressed as a full length human IgG1 with effector function-null mutations in the heavy chain Fc (1D1 1.31-hIgG1-3mut) was produced in CHO cells. The isotype control antibody was an anti-tetanus toxoid (aTT) antibody which is also a human IgG1 antibody containing the same three effector function-null mutations as 1D1 1.31. Soluble TL1A (rsTL1A) was recombinantly produced.

TF-1 cells were obtained from the American Tissue Typing Collection (ATCC, Manassas, VA). TF-1 cells are derived from a human hematopoietic erythroblastoma cell line obtained from ATCC. The TF-1-NRκB-luciferase reporter cells were generated by infecting the TF-1 cells with the lentivirus pCignal Lenti NFκB-Luciferase reporter (Catalog No. CLS-013L; SA Biosciences, Valencia, CA). Briefly, 30,000 cells per well of a 24-well plate were seeded in 150 μL of RPMI 1640, 10% fetal bovine serum (FBS), and 2 ng/mL granulocyte macrophage-colony stimulating factor (GM-CSF). The following day they were infected with 50 μL (1X) and 100 μL (2X) of lentivirus pCignal Lenti NFκB-luciferase reporter in the presence of 6 μg/mL of polybrene. After 4 days, cells were expanded and exposed to 1 μg/mL of puromycin for selection of stable integrates. Selection continued until all mock-infected cells died. Activity of the reporter in stable pools was assessed by treating the TF-1-NFκB-Luc 1× and 2× cells with various TNF or TL1A concentrations. Cells (20,000 per 96 well in 100 μL of media without GM-CSF) were treated with the cytokines for 5 hours at 37° C., 5% CO2. D-luciferin substrate (1500 μg/mL) was then added and after 10 minutes incubation at 37° C., the luminescence signal was read in an EnVision Luminometer (PerkinElmer, Waltham, MA). The TF-1-NFκB-Luc 2X cells were selected for subsequent studies. TF-1 cells require either interleukin 13 (IL13) or GM-CSF for their long-term growth. Cells were grown in RPMI 1640 containing 10% heat-inactivated FBS, 10 mM HEPES, 1 mM sodium pyruvate, 2 ng/mL recombinant human GM-CSF and 1 μg/mL puromycin.

Constitutive expression of DR3 on TF-1 cells was demonstrated by staining with a commercial biotinylated-anti-DR3 antibody. Cells were grown overnight without GM-CSF as described in Section 5.4 for the TL1A-induced caspase activation assay. Cells were harvested and re-suspended in BD Pharmingen® Stain Buffer (FBS) at $1\times10^6$ cells/mL and incubated on ice for 15 minutes with 10 μg/mL of anti-DR3 antibody. After incubation, cells were washed with 3 mL of stain buffer, centrifuged at 800 g and re-suspended at $1\times10^6$ cells/mL in the same buffer with phycoerythrin (PE)-streptavidin, a 1:1000 dilution of fluorescently-labeled streptavidin. After incubation, the cells were washed, centrifuged and re-suspended in stain buffer at $1\times10^6$ cells/mL. DR3 expression was examined by flow cytometry analysis in a BD Biosciences LSRFortessa™ instrument (San Jose, CA). DR3 expression is demonstrated by the increase in mean fluorescence intensity (MFI) as compared to the streptavidin-PE control.

To determine the ability of rsTL1A to activate the transcription factor NFκB, luciferase activity was measured in response to rsTL1A in TF-1 cells transfected with a luciferase gene under the transcriptional control of NFκB. Two days before the experiment, TF-1 cells were cultured at a cell density of $0.3\times10^6$ cells/mL in TF-1 culture media containing puromycin but not GM-CSF. Solutions containing 2X each of the final concentrations of rsTL1A in 50 μL of TF-1 media without puromycin or GM-CSF were prepared in duplicate in 96-well plates (flat bottom for luminescence plates). The 8 rsTL1A concentrations were titrated down in 3 fold dilutions starting at 3986 pM (3968.3, 1322.8, 440.9, 147, 49, 16.3, 5.4, and 1.8 pM). This TL1A dose response experiment was also performed in the presence of a final concentration of 3 nM of the isotype control antibody. In this case, the same TL1A dose response solutions described above also contained 2X final concentration of isotype control antibody. The plates were then sealed with aluminum foil and placed overnight at 4° C. to reach equilibrium. The following day, plates were pre-warmed at 37° C. for 30 minutes, cells were harvested, washed once in phosphate buffered saline (PBS), re-suspended at $1\times10^6$ cells/mL in TF-1 media without puromycin or GM-CSF and 50,000 cells in 50 μL of cell suspension were added to 50 μL of pre-warmed TL1A solutions and incubated for 6 hours at 37° C. One hundred (100) μL of 2X final concentration of 150 μg/mL of Beetle luciferin were added to the 100 μL wells, mixed well and incubated at 37° C. for 30 minutes. Plates were read in a luminometer (EnVision, 1 second/well). Mean relative luminescence units (RLU) were plotted against log TL1A or log 1D1 1.31 concentrations.

EC50 and IC50 Determinations

TL1A activation curves or antibody inhibition curves were generated by plotting the luminescence values against the log of TL1A or antibody concentrations respectively. EC50 (for TL1A) or IC50 values (for 1D1 1.31) were determined from these graphs using GraphPad Prism® (version 5.02, GraphPad Software, Inc., San Diego, CA) nonlinear regression curve fits and a sigmoidal log of agonist (three parameters) or antagonist dose response (variable slope, four parameters) model (Equation 1 for TL1A agonist and Equation 2 for antagonist 1D1 1.31).

Log(agonist) vs. response (three parameters)

$$Y=\text{Bottom}+(\text{Top}-\text{Bottom})/(1+10\hat{}((\text{Log EC50}-X)) \qquad \text{Equation 1}$$

Log(inhibitor) vs. response-variable slope (four parameters)

$$Y=\text{Bottom}+(\text{Top}-\text{Bottom})/(1+10\hat{}((\text{Log IC50}-X)*\text{HillSlope})) \qquad \text{Equation 2}$$

Where Y is the luminescence value and X is agonist TL1A (Equation 1) or antagonist 1D1 1.31 (Equation 2) concentration, Top is the maximum Y value corresponding to the upper plateau of the sigmoidal curve, Bottom is the minimum Y value corresponding to the lower plateau of the sigmoidal curve, and Log EC50 or Log IC50 is the log of the concentration of the agonist or antagonist respectively at the inflection point midway between the maximum and minimum. The EC50 or IC50 values were summarized across experiments using means and standard deviations (STDEV).

Figure 14A:
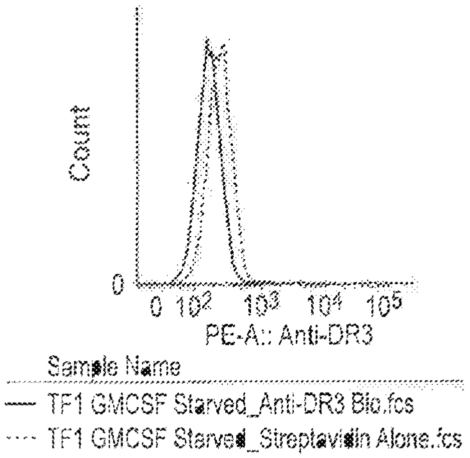
FIG. 14A, 14B, 14C, 14D, 14E depict graphs showing inhibition of NFκB inhibition by anti-TL1A antibodies. Specifically.

The potency and ability of 1D1 1.31 in inhibiting signaling of TL1A through DR3 was evaluated in an assay that measures NFκB activation in TF-1-NFκB-luciferase cells in response to TL1A stimulation. FIG. 14A demonstrates constitutive expression of DR3 on TF-1 cells after overnight culture without GM-CSF. Biotin-anti-DR3 antibody stained cells had increased mean fluorescence intensity than the cells treated only with the streptavidin secondary detection reagent. Biotin-TL1A also stained the cells while neither the biotin-DR3 antibody nor biotin-TL1A stained several other DR3-negative cells, demonstrating the specificity of the staining (not shown).

Figure 14B:
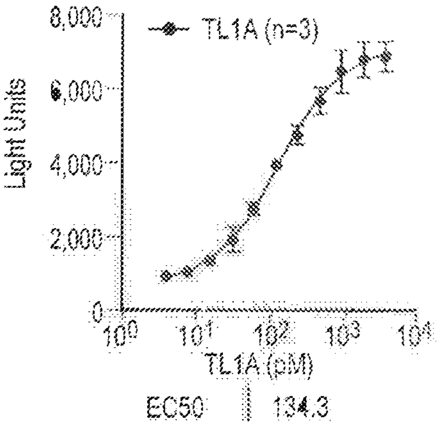
Figure 14C:
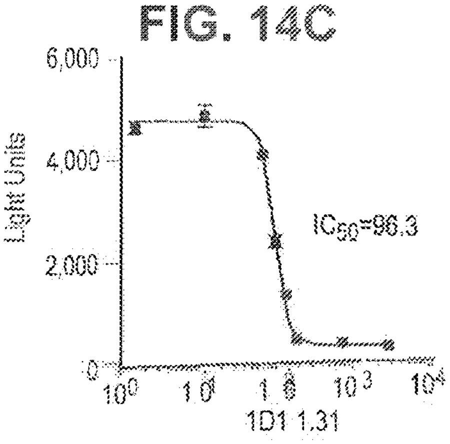

The ability of TL1A to activate NFκB-regulated gene transcription was evaluated in TF-1-NFκB-luciferase cells stimulated with TL1A. Recombinant human soluble TL1A dose-dependent increase in NFκB activity is illustrated for a representative experiment in FIG. 14B. TL1A stimulated NFκB activity in TF-1-NFκB-luciferase cells with a mean EC50 value of 149±38 pM (n=8). In this assay, relative light units (RLU) increased 10-15 fold over background at saturating TL1A concentrations. 1D1 1.31 dose dependent inhibition of NFκB activation by 150 pM TL1A in TF-1-NFκB-luciferase cells is shown for a representative experiment in FIG. 14C. 1D1 1.31 inhibited TL1A activation of NFκB with a mean IC50 value of 95±5.5 pM (n=4). These functional potency values are in agreement with the binding affinity of 1D1 1.31 for TL1A. In addition, similar potency values were calculated in other functional studies measuring the inhibition of the activation of caspase activity in TF-1 (see Example 12) or the production of IFNγ in response to IC, IL-12 and IL-18 stimulation in human whole blood (see Example 13).

Figure 14D:
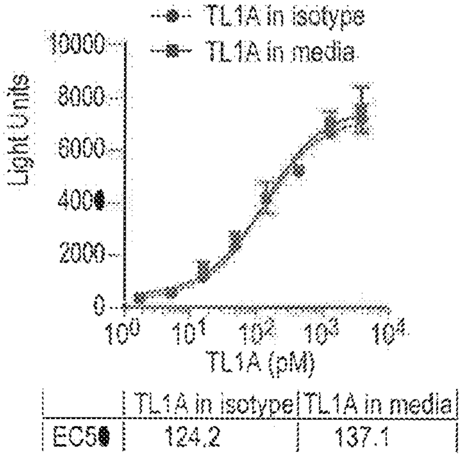
Figure 14E:
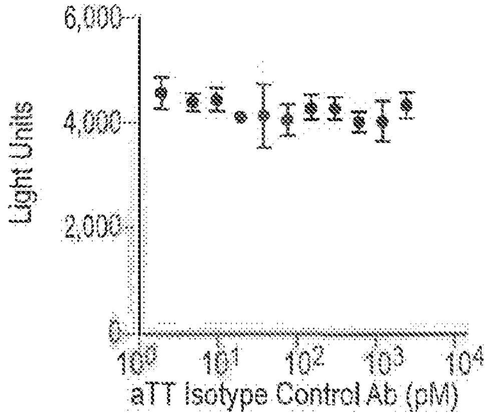

The isotype control antibody had no inhibitory effect on this assay as shown in FIG. 14D and FIG. 14E. Results are illustrated for a representative experiment FIG. 14D. The mean EC50 value for TL1A stimulation of NFκB activity in the absence of isotype control antibody was 103±27 pM (n=4) and in the presence of isotype control antibody was 110±18 pM (n=4). In addition, an isotype control antibody dose response experiment with up to 30 nM TL1A did not cause inhibition (illustrated in FIG. 14E). These experiments indicated that there was no inhibition attributed to the isotype antibody.

The studies described demonstrate the ability of 1D1 1.31 to potently block the downstream signaling of the TL1A/DR3 interaction leading to NFκB activation in TF-1-NFκB-luciferase cells. These experiments show that 1D1 1.31 is a potent antagonist of TL1A/DR3 signaling.

Example 12: Inhibition of Caspase Activation Response by Anti-TL1A Antibodies TL1A activates the NFκB pathway in TF-1 cells but is also able to induce apoptosis by activating the caspase pathway when the NFκB pathway is inhibited by protein synthesis inhibitors such as cycloheximide. The purpose of this study was to evaluate the neutralizing activity and potency of the anti-TL1A antibody 1 D1 1.31 in a caspase activation assay in TF-1 cells in response to stimulation by recombinant soluble human TL1A (rsTL1A).

TF-1 cells were derived from a human hematopoietic erythroblastoma cell line obtained from ATCC. TF-1 cells require either IL-13 or granulocyte macrophage-colony stimulating factor (GM-CSF) for their long-term growth. The TF-1 cells were grown in RPMI 1640 containing 10% heat-inactivated fetal bovine serum (FBS), 10 mM HEPES, 1 mM sodium pyruvate, and 2 ng/mL recombinant human GM-CSF.

Expression of DR3 in TF-1 Cells

Constitutive expression of DR3 on TF-1 cells was demonstrated by staining with a commercial biotinylated-anti-DR3 antibody (eBiosciences, San Diego, CA). Cells were grown overnight without GM-CSF as described below for the TL1A-induced caspase activation assay. Cells were harvested and re-suspended in BD Pharmingen™ Stain Buffer (FBS; BD Biosciences, San Jose, CA) at $1\times10^6$ cells/mL and incubated on ice for 15 minutes with 10 μg/mL of anti-DR3 antibody. After incubation, cells were washed with 3 mL of stain buffer, centrifuged at 800×g and re-suspended at $1\times10^6$ cells/mL in the same buffer with phycoerythrin (PE)-streptavidin, a 1:1000 dilution of fluorescently-labeled streptavidin. After incubation, the cells were washed, centrifuged and re-suspended in stain buffer at $1\times10^6$ cells/mL. DR3 expression was examined by flow cytometry analysis in a BD LSRFortessa™ instrument. DR3 expression is demonstrated by the increase in mean fluorescence intensity (MFI) as compared to the streptavidin-PE control.

Caspase Activation in TF-1 Cells by Recombinant Soluble TL1A

To determine the ability of rsTL1A to activate the apoptotic pathway, caspase activation in response to exogenous rsTL1A was evaluated in TF-1 cells treated with cycloheximide (CHX) to inhibit the signaling toward the NFκB pathway and allow caspase and apoptotic pathway activation. The day before the experiment TF-1 cells were cultured at a cell density of $0.3\times10^6$ cells/mL in TF-1 culture media containing 2 ng/mL of GM-CSF. Separately, solutions containing 2X each of the final concentrations of rsTL1A and CHX (2 nM final concentration) in 50 μof TF-1 media without GM-CSF were prepared in triplicate in 96 well plates (flat bottom for luminescence plates). The 12 rsTL1A concentrations were titrated down in 2 fold dilutions starting at 3986 pM (3986, 1984, 992, 496,248, 124, 62, 31, 15.5, 7.75, 3.88 and 1.94 pM). The following day, plates were pre-warmed at 37° C. for 30 minutes, cells were harvested, washed once in phosphate buffered saline (PBS), re-suspended at $0.6\times10^6$ cells/mL in TF-1 media without GM-CSF and 30,000 cells in 50 μL of cell suspension were added to 50 μL of pre-warmed TL1A/CHX solutions and incubated for 6 hours at 37° C. One hundred (100) μL of Caspase-Glo® 3/7 kit (Promega, Madison, WI) was added and incubated at room temperature for 15 minutes. Plates were read in an EnVision™ luminometer (1 second/well; PerkinElmer, Waltham, MA). Early steps in apoptosis involve activation of caspases including caspase-3 and -7. The CaspaseGlo® 3/7 Assay is a homogeneous luminescent assay that measures caspase-3 and -7 activities in purified enzyme preparations or cultures of adherent or suspension cells. The assay provides a luminogenic caspase-3/7 selective substrate, which contains the tetrapeptide sequence DEVD (SEQ ID NO: 395) (recognition sequence). This substrate is cleaved to release aminoluciferin, a substrate of luciferase used in the production of light. The Caspase-Glo® 3/7 Reagent is optimized for caspase activity, luciferase activity and cell lysis. Addition of the Caspase-Glo® 3/7 Reagent in an “add-mix-measure” format results in cell lysis, followed by caspase cleavage of the substrate and generation of a “glow-type” luminescent signal. The assay relies on the properties of a proprietary thermostable luciferase (Ultra-Glo Luciferase®, Promega) formulated to generate a stable signal across a wide range of assay conditions. The luminescence is proportional to the amount of caspase activity present.

Figure 15A:
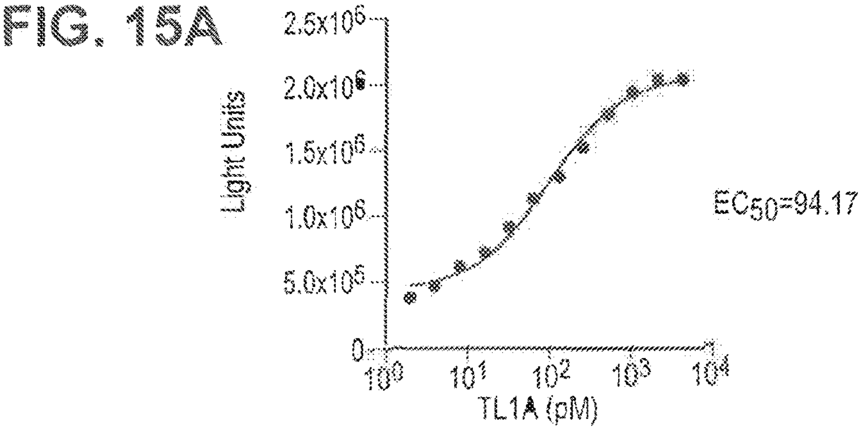
FIGS. 15A and 15B demonstrate inhibition of caspase activity in TF-1 cells by anti-TL1A antibodies.
Figure 15B:
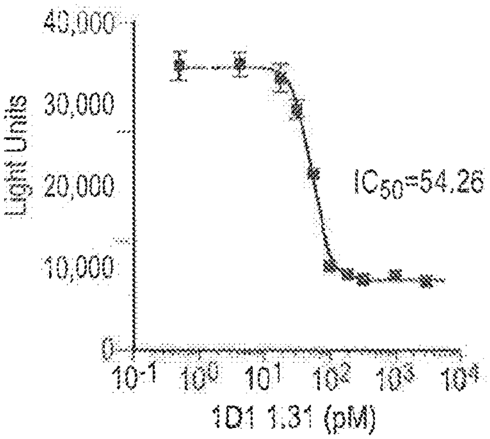

Antibody 1D1 1.31 Inhibition of Caspase Activation in TF-1 Cells by Recombinant Soluble TL1A Antibody 1D1 1.31 inhibition of caspase activation was evaluated in TF-1 cells in the presence of CHX. Briefly, the day before the experiment, TF-1 cells were cultured at $0.3\times10^6$ cells/mL in TF-1 culture media containing 2 ng/mL of GM-CSF. Separately, solutions containing 2X each of the final concentrations of antibody, CHX (20 μg/mL or 2 nM final concentration) and rsTL1A (5.5 ng/mL or 87 pM final concentration) in 50 μL of TF-1 media (without GM-CSF) were prepared in triplicate in a 96 well plate. The plates were then sealed with aluminum foil and placed overnight at 4° C. to reach equilibrium. The 10 or 12 point antibody concentrations were titrated down in 2 and/or 3 fold dilutions starting at 1, 2 or 3 nM depending on the experiment. For the representative experiment in FIG. 15B, concentrations were 3000, 1000, 333, 185, 103, 57, 31.8, 17.6, 4.1, and 0.5 pM. rsTL1A (87 pM) was calculated as the mean concentration which gives half of maximal response (EC50) in previous rsTL1A dose response caspase activation experiments (n=3) as described above. The following day, plates were pre-warmed at 37° C. for 30 minutes, cells were harvested, washed once in PBS, re-suspended at $0.6\times10^6$ cells/mL in TF-1 media without GM-CSF and 30,000 cells in 50 μL of cell suspension were added to 50 μL of pre-warmed antibody/TL1A/CHX solutions and incubated for 6 hours at 37° C. One hundred (100) μL of Caspase-Glo® 3/7 kit (Promega) was added and incubated at room temperature for 15 minutes. Plates were read in a luminometer (Envision, 1 sec/well). In parallel with the 1D1 1.31 inhibition dose response experiments, a rsTL1A dose response experiment was performed to calculate the EC50 for each particular experiment and to verify the approximate percent of maximal response corresponding to 87 pM, the concentration used to evaluate the inhibitory potency of the antibody.

EC50 and IC50 Determinations

Mean relative luminescence units (RLU) were plotted against log TL1A or log 1D1 1.31 concentrations. TL1A activation curves or antibody inhibition curves were generated by plotting the luminescence values against the log of TL1A or antibody concentrations respectively. EC50 (for TL1A) or IC50 values (for 1D1 1.31) were determined from these graphs using GraphPad Prism® (version 5.02, GraphPad Software, Inc., San Diego, CA) nonlinear regression curve fits and a sigmoidal log of agonist or antagonist dose response model (Equation 1 for TL1A agonist and Equation 2 for antagonist 1D1 1.31).

Log(agonist) vs. response (three parameters)

$$Y=\text{Bottom}+(\text{Top}-\text{Bottom})/(1+10\hat{}(\text{Log EC50}-X)) \qquad \text{Equation 1}$$

Log(inhibitor) vs. response-variable slope (four parameters)

$$Y=\text{Bottom}+(\text{Top}-\text{Bottom})/(1+10\hat{}((\text{Log IC50}-X)*\text{HillSlope})) \qquad \text{Equation 2}$$

Where Y is the luminescence value and X is agonist TL1A (Equation 1) or antagonist 1D1 1.31 (Equation 2) concentration, Top is the maximum Y value corresponding to the upper plateau of the sigmoidal curve, Bottom is the minimum Y value corresponding to the lower plateau of the sigmoidal curve, and Log EC50 or Log IC50 is the log of the concentration of the agonist or antagonist respectively at the inflection point midway between the maximum and minimum. The EC50 or IC50 values were summarized across experiments using means and standard deviations (STDEV).

The potency and ability of 1D1 1.31 in inhibiting signaling of TL1A through DR3 was evaluated in an assay that measures caspase activation in TF-1 cells in response to TL1A stimulation. DR3 was constitutively expressed on TF-1 cells at the time of performing the caspase activation experiment after overnight culture without GM-CSF. Biotin-anti-DR3 antibody treated cells had increased mean fluorescence intensity than the cells treated only with the streptavidin secondary detection reagent. Biotin-TL1A also stained the cells while neither the biotin-DR3 antibody nor biotin-TL1A stained several other DR3-negative cells, demonstrating the specificity of the staining (not shown).

TL1A-induced caspase activation was evaluated in TF-1 cells in the presence of CHX to block signaling through the NFκB pathway and consequently deviate to the downstream receptor signaling mechanism towards the apoptotic pathway via caspase activation. A dose-dependent increase in caspase activity via recombinant soluble TL1A (rsTL1A) is illustrated from a representative experiment in FIG. 15A TL1A stimulated caspase activity in TF-1 cells with a mean EC50 value of 90±7 pM (n=3). In this assay, RLU increased 3-5 fold over background at saturating TL1A concentrations. 1D1 1.31 dose dependent inhibition of caspase activation by 87 pM TL1A in TF-1 cells is shown from a representative experiment in FIG. 15B. 1D1 1.31 inhibited the TL1A-dependent increase in caspase activity with a mean IC50 value of 69±15 pM (n=3). These functional potency values are in agreement with the binding affinity of 1D1 1.31 for TL1A. In addition, similar potency values were calculated in other functional studies measuring the inhibition of the activation of NFκB in TF-1 cells or the production of IFNγ in response to immune complex (IC), IL-12 and IL-18 stimulation in human whole blood.

These studies demonstrate the ability of 1D1 1.31 to potently block the downstream signaling of the TL1A/DR3 interaction leading to caspase activation and apoptosis in TF-1 cells treated with CHX. These studies show that 1D1 1.31 is a potent antagonist of TL1A/DR3 signaling.

Example 13: Inhibition and Depletion of Cytokines by Anti-TL1A Antibodies In Human Whole Blood The purpose of this study was to evaluate the neutralizing activity and potency of the anti-TL1A antibody 1D1 1.31 in an assay in human peripheral blood that measures cytokine secretion under conditions of up-regulation and activation of membrane-expressed endogenous TL1A and DR3. In this assay, expression of the membrane-bound form of TL1A permits evaluation of inhibition of both forms of TL1A, the cell associated and the soluble form, as well as soluble TL1A target coverage in a physiologically relevant ex vivo human whole blood system.

For immune complex (IC) stimulation of human blood, IC plates were prepared the day before the experiment. Ninety-six well (96), flat bottom tissue culture plates were coated with 50 μL per well of 0.5 mg/mL or 0.25 mg/mL of human immunoglobulin G (hlgG) in phosphate buffered saline (PBS), and kept at 4° C. overnight. The next morning, the plates were washed three times with 150 μL PBS per well. After removal of PBS, 50 μL per well of 0.02 mg/mL or 0.08 mg/mL of mouse anti-human IgG in PBS were added and plates were incubated at 37° C. for 1 hour. Plates were then washed three times with 150 μL PBS per well prior to use.

For IC and IL-12 and IL-18 stimulation of human whole blood, approximately 10 mL of blood from healthy donors was collected in Na Heparin coated tubes. Blood samples were normally delivered at room temperature within one hour after the blood draw. IL-12 (0.5 ng/mL final concentration) and IL-18 (5 ng/mL final concentration) were mixed in with blood prior to addition of 190 μL of the blood/IL-12/IL-18 mixture to each well of the IC coated plates. To evaluate the inhibitory potency of 1D1 1.31, 12-concentration dose response curves were generated by adding 10 μL per well of a 20 X final concentration of 1D1 1.31 (or isotype control antibody) in 0.1% bovine serum albumin (bovine serum albumin) in PBS. 1D1 1.31 (or isotype control antibody) concentrations were 30000, 10000, 3333.33, 1111.11, 370.37, 123.45, 12.34, 1.234, 0.1234, 0. 01234, 0.001234 and 0.0001 pM; and 30000, 10000, 3333.3, 1111.11, 370.37, 37.037, 3.7 037, 0.3704, 0.037, 0.002, 9E-05 and 4.6E-06 pM. All conditions were done in triplicate but controls (no antibody) were repeated in 10-12 wells; no or single stimulation controls (only IC or only IL-12/IL-18) were also included in triplicate or more replicates. After 24 hours of culture at 37° C., 100 μL of 5% bovine serum albumin in PBS were added and mixed well with the 200 μL of blood cultures to dilute plasma (dilution factor: 1.5). One hundred fifty (150) μL per well of diluted plasma were harvested after the plates were centrifuged at 930×g (2000 rpm) for 15 minutes and further diluted 4 times in 5% bovine serum albumin in PBS for quantification of IFNγ and 1D1 1.31-free form of TL1A using MSD (Mesoscale Discovery, Rockville, MD)-based ligand-binding assays. IFNγ was measured using the MSD human IFNγ kit (Catalog No. K151AEB-1) following the manufacturer's instructions. Two assays were developed at PGRD for measuring sTL1A, one that measures only antibody unbound sTL1A and another one that measures total sTL1A (antibody bound and unbound). Briefly, to measure 1D1 1.31-free sTL1A, MSD blank plates (MSD, Catalog No. L15XA-6) were coated with 30 μL per well of 2 μg/mL in PBS of anti-TL1A clone No. 26B11 at 4° C. overnight. The following day, plates were washed three times with 150 μL per well of 0.1% Tween 20 in PBS, followed with 150 μL per well of blocking solution (5% bovine serum albumin in PBS), then the plates were incubated at room temperature for 1 hour with orbital shaking (1500 rpm). After the plates were washed as mentioned above, diluted plasma samples were added and incubated at 4° C. overnight. The following day, 0.25 μg/mL of Sulfo-tag labeled detection Ab (MSD anti-TL1A clone No. 1D1-VH-37 (1D1 D37); 30 μL per well; labeled as per manufacturer's instructions) were added after the plates had been washed, and were incubated at room temperature for 2 hours with orbital shaking (1500 rpm) followed by the same plate wash protocol mentioned above. TL1A standard curves were generated using recombinant human soluble TL1A. Plates were read following the manufacturer's procedure, standard curve and plasma concentration of the cytokine were calculated with the MSD software. A similar protocol but using non-competitive antibodies for both capture and detection was used to detect total TL1A (1 D1 1.31-free and -bound soluble TL1A).

Antibody 1D1 1.31 inhibition dose response curves were generated by plotting the concentrations of either IFNγ or soluble TL1A in pg/mL of plasma against the log of antibody concentrations. The 1D1 1.31 IC50 values were determined from these graphs using GraphPad Prism® (version 5.02, GraphPad Software, Inc, San Diego, CA) nonlinear regression curve fits and a sigmoidal log of antagonist dose response (variable slope, four parameters) model (Equation 1).

Log(inhibitor) vs. response-variable slope (four parameters)

$$Y=\text{Bottom}+(\text{Top}-\text{Bottom})/(1+10\hat{}((\text{Log IC50}-X)*\text{HillSlope})) \quad \text{Equation 1}$$

Where Y is the concentration of cytokine and X the antagonist 1D1 1.31 (Equation 1) concentration, Top is the maximum Y value corresponding to the upper plateau of the sigmoidal curve, Bottom is the minimum Y value corresponding to the lower plateau of the sigmoidal curve, and LogIC50 is the log of the concentration of the antagonist at the inflection point midway between the maximum and minimum. The IC50 values were summarized across experiments using means and standard deviations (STDEV).

The potency and ability of 1D1 1.31 to inhibit endogenous TL1A activation of DR3-expressing primary cells in human whole blood was evaluated in an assay that measures the release of IFNγ in response to stimulation by IC (which upregulates TL1A expression on monocytes) and IL-12 and IL-18 (which upregulate CD3 expression on NK and NKT cells).

Figure 16A:
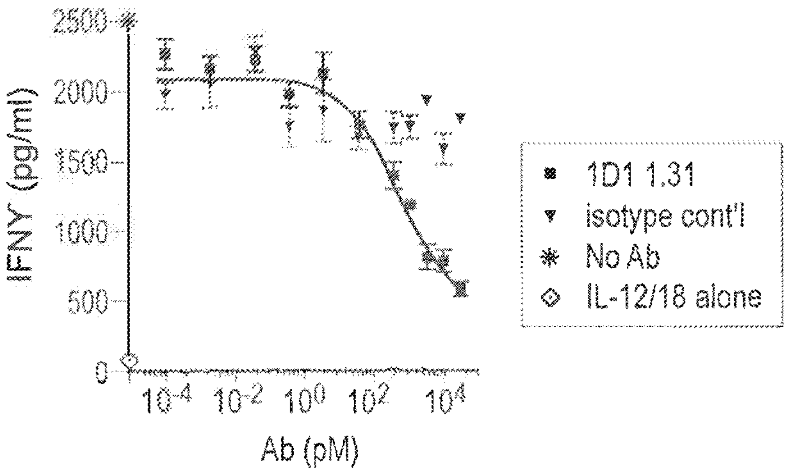
FIGS. 16A and 16B depict inhibition and depletion of cytokines by anti-TL1A antibodies in human whole blood.

Due to the lack of constitutive expression of TL1A and DR3 on peripheral blood leukocytes, and in order to measure downstream DR3 activation (such as IFNγ secretion) upon endogenous TL1A engagement, upregulation of expression of TL1A on monocytes and DR3 on responding NK or NKT is required. Optimal stimulatory conditions were derived from previous experiments demonstrating the kinetics of TL1A upregulation on monocytes by IC stimulation and the upregulation of DR3 on NK and NKT cells by the combination of the IL-12 and IL-18 cytokines. Single stimulation conditions (eg, only IC or only IL-12/IL-18) indicated that IC stimulation is sufficient for the levels of TL1A up-regulation achieved and that IL-12/IL-18 alone is sufficient to up-regulate DR3. However, it is likely that both stimuli synergize for optimal functional response beyond their effects on up-regulation of expression. Conditions were also optimized for cytokine production and TL1A-dependence of that production. Mean IFNγ concentrations following IC and IL-12 and IL-18 stimulation were 4089±2908 pg/mL (range 289-8946 pg/mL; mean 537 fold induction over un-stimulated blood; n=14; 8 unique donors). 1D1 1.31 dose-dependent inhibition of IFNγ production by whole blood stimulated by IC and IL-12 and IL-18 is shown for a representative experiment in FIG. 16A. At the highest saturating 1D1 1.31 concentrations, inhibition reached a maximum without achieving complete inhibition and suggesting partial inhibition of the response. This is not surprising given that many pro-inflammatory pathways lead to inflammatory cytokine production and that the stimulatory conditions used are not specific to the TL1A/DR3 pathway and are likely to activate other pathways in addition to the TL1A/DR3 pathway. The IFNγ response measured is likely contributed by TL1A-dependent and independent pathways. Nonetheless, under these conditions, the TL1A pathway seems to be a major contributor to the response as mean maximal inhibition of IFNγ secretion by 1D1 1.31 in this system was 62%±10% n=14; 8 unique donors; range 38-77%) suggesting that the TL1A-dependent response accounts for approximately an average of two thirds of the response and that TL1A-independent mechanisms also contribute to the total IFNγ production in this assay system. The potency of 1D1 1.31 was determined by calculating the IC50 for the TL1A-mediated response. 1D1 1.31 inhibits IFNγ □secretion by endogenous TL1A upregulated in whole blood by IC with an IC50 of 277±125 pM (n=11; 8 unique donors).

Figure 16B:
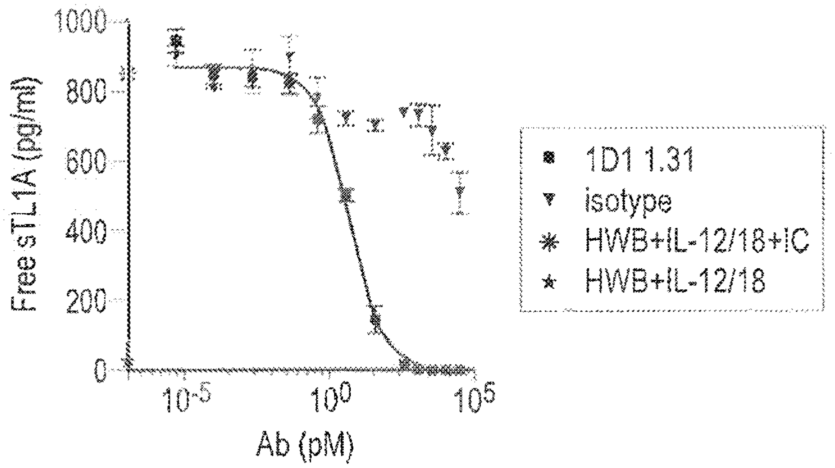

In the same human peripheral blood assay in which 1D1 1.31 was evaluated for its suppression on IFNγ levels in response to IC and IL-12 and IL-18 stimulation, 1D1 1.31 was also evaluated for its effect on sTL1A plasma levels. IC and IL-12/IL-18 stimulation of human whole blood resulted in endogenous soluble TL1A elevations to mean values of 940±293 pg/mL (FIG. 16B; range 535-1409 pg/mL; mean 50 fold induction over unstimulated blood; n=8, 5 unique donors). These increases of sTL1A at 24 hours likely reflect proteolytic cleavage from monocyte membrane TL1A which was shown to be maximally and transiently expressed on monocytes at earlier time points upon IC stimulation. 1D1 1.31 binding to soluble TL1A was measured by the dose-dependent and complete depletion of 1D1 1.31-free soluble TL1A. 1D1 1.31 depletes antibody-free soluble TL1A with a mean IC50 value of 1.06±1.68 pM (n=8; 5 unique donors). The presence of sTL1A was confirmed by the measure of total sTL1A (which could detect also antibody bound TL1A). Inhibition of IFNγ□ production started at concentrations of 1D1 1.31 at which depletion of antibody-free-soluble TL1A was ≥90%. The difference in IC50 values for antibody-free-sTL1A depletion and for IFNγ inhibition suggests that membrane bound TL1A activity might mediate IFNγ production by mediating cell to cell interactions. Indeed, early assay development experiments showed that addition of plasma containing similarly high concentrations of endogenous soluble TL1A to IL-12/IL-18 stimulated blood was not as effective on increasing IFNγ production as IC stimulation of TL1A up-regulation on monocytes.

The data disclosed herein demonstrate that 1D1 1.31 is a potent inhibitor of the activity of endogenous membrane and soluble form of TL1A in human peripheral blood. 1 D1 1.31 inhibits IFNγ secretion following human peripheral blood upregulation and activation of TL1A on monocytes and DR3 on effector cells by IC and IL-12 and IL-18 stimulation with a mean IC50 value of 277±125 pM.

Example 14: Inhibition of IFNγ Production and Depletion of Antibody-Free Soluble TL1A in Response to Immune Complex and IL-12/IL-18 Stimulation of Cynomolgus Monkey Whole Blood The purpose of this study was to evaluate the neutralizing activity and potency of the anti-TL1A antibody 1D1 1.31 in an assay in cynomolgus monkey peripheral blood that measures cytokine secretion under conditions of up-regulation and activation of membrane-expressed endogenous TL1A and DR3. In this assay, expression of the membrane-bound form of TL1A permits evaluation of the inhibition of both forms of TL1A, the cell associated and the soluble form, as well as soluble TL1A target coverage in a physiologically relevant ex vivo cynomolgus whole blood system.

The 1D1 1.31 antibody used for these experiments was produced in CHO cells. The isotype control antibody was an antibody which is also a human IgG1 antibody containing the same three effector function-null mutations as 1D1 1.31. Recombinant cynomolgus monkey soluble TL1A (cyno rsTL1A) (Leu72-Leu251, see SEQ ID NO:259) was produced using standard protocols known in the art.

For immune complex (IC) IC stimulation of cyno blood, IC plates were prepared the day of the experiment. Ninety-six well (96), flat bottom tissue culture plates were coated with 50 μL per well of 1 mg/mL of human immunoglobulin G (hlgG) in phosphate buffered saline (PBS), and incubated at 37° C. for 1 hour. Wells were then washed three times with 150 μL PBS per well. After removal of PBS, 50 μL per well of 0.04 mg/mL of mouse anti-human IgG in PBS were added and plates were incubated at 37° C. for 1 hour. Plates were then washed three times with 150 μL PBS per well prior to use.

For IC and IL-12 and IL-18 stimulation, cynomolgus monkey blood was collected in sodium heparin coated tubes and used within one hour after the blood draw. Human IL-12 (1 ng/mL final concentration) and human IL-18 (10 ng/mL final concentration) were mixed in with blood prior to addition of 95 μL of the blood/IL-12/IL-18 mixture to each well of the IC coated plates. To evaluate the inhibitory potency of 1D1 1.31, 12-concentration dose response curves were generated by adding 5 μL per well of a 20× final concentration of 1D1 1.31 (or isotype control antibody) in 0.1% bovine serum albumin (bovine serum albumin) in PBS. 1D1 1.31 (or isotype control antibody) concentrations were 100000, 33333, 11111, 3703.7, 1234.5, 411.5, 137.17, 13.717, 1.3717, 0.13717 and 0.0137 and 0.00137 pM for some sets of experiments, and 100000, 20000, 4000, 800, 160, 32, 6.4, 0.64, 0.064, 0.0064, 0.00064, and 0.000064 pM for other sets of experiments. All experiments were done in triplicate. Controls included stimulation without antibody as well as no, or single stimulation controls (only IC or only IL-12/IL-18) in triplicate. After 24 hours of culture at 37° C., 200 μL of 5% bovine serum albumin in PBS were added and mixed well with the 100 μL of blood cultures to dilute plasma (dilution factor: 3). One hundred and fifty(150) μL per well of diluted plasma were harvested after the plates were centrifuged at 930×g (2000 rpm) for 15 minutes and tested immediately for quantification of IFNγ and 1D1 1.31-free form of TL1A using MSD (Mesoscale Discovery, Rockville, MD)-based ligand-binding assays. IFNγ was measured using the MSD human IFNγ kit (Catalog No. K151AEB-1) following the manufacturer's instructions. Briefly, to measure 1D1 1.31-free sTL1A, MSD blank plates (MSD, Catalog No. L15XA-6) were coated with 30 μL per well of 4 μg/mL in PBS of anti-TL1A clone No. 26B11 at 4° C. overnight. The following day, plates were washed three times with 150 μL per well of 0.1% Tween 20 in PBS, followed with 150 μL per well of blocking solution (5% bovine serum albumin in PBS), then the plates were incubated at room temperature for 1 hour with orbital shaking (1500 rpm). After the plates were washed as mentioned above, 40 μL of plasma samples were added and incubated at 4° C. for 2 hours followed by the same washing three times and by addition of 1 μg/mL of Sulfo-tag labeled detection Ab (MSD anti-TL1A clone No. 1D1 1.31; 30 μL per well; labeled as per manufacturer's instructions).Plates were incubated at room temperature for 2 hours with orbital shaking (1500 rpm) followed by the same plate wash protocol mentioned above. TL1A standard curves were generated using recombinant cynomolgus monkey soluble TL1A. Plates were read following the manufacturer's procedure, standard curve and plasma concentration of the cytokine were calculated using the MSD software per manufacturer's instructions.

IC50 Determinations

The 1D1 1.31 inhibition dose response curves were generated by plotting the concentrations of either IFNγ or soluble TL1A in pg/mL of plasma against the log of antibody concentrations. 1D1 1.31 IC50 values were determined from these graphs using GraphPad Prism® (version 5.02, GraphPad Software, Inc, San Diego, CA) nonlinear regression curve fits and a sigmoidal log of antagonist dose response (variable slope, four parameters) model (Equation 1).

Equation 1

Log(inhibitor) vs. response-variable slope (four parameters)

$$Y=\text{Bottom}+(\text{Top}-\text{Bottom})/(1+10\hat{}((\text{Log IC50}-X)*\text{HillSlope}))$$

Where Y is the concentration of cytokine and X the antagonist 1D1 1.31 (Equation 1) concentration, Top is the maximum Y value corresponding to the upper plateau of the sigmoidal curve, Bottom is the minimum Y value corresponding to the lower plateau of the sigmoidal curve, and Log IC50 is the log of the concentration of the antagonist at the inflection point midway between the maximum and minimum. The IC50 values were summarized across experiments using means and standard deviations (STDEV).

1D1 1.31 Inhibition of IFN Gamma Production in Whole Blood Activated by Immune Complex and IL-2/IL-18

Figure 17A:
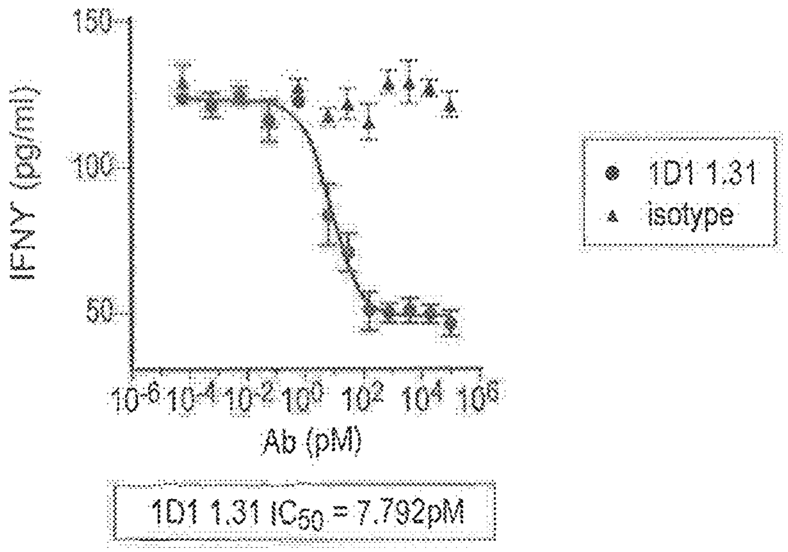
FIGS. 17A and 17B depict inhibition and depletion of cytokines by anti-TL1A antibodies in cynomolgus monkey whole blood. Specifically.

The ability of 1D1 1.31 to inhibit endogenous TL1A activation of DR3-expressing primary cells in cynomolgus monkey whole blood was evaluated in an assay that measures the release of IFNγ in response to stimulation by IC (which upregulates TL1A expression on monocytes) and IL-12 and IL-18 (which upregulate CD3 expression on NK and NKT cells). Experimental conditions were adapted from an assay developed in human whole blood and further optimized for cytokine production in cynomolgus blood. Mean IFNγ concentrations following IC and IL-12 and IL-18 stimulation were 222±220 pg/mL (range 99-667 pg/mL; mean 222 fold induction over un-stimulated blood; n=6 monkeys). This IFNγ production is lower than in human blood (4089±2908 pg/mL) possibly due to the fact that human (instead of cynomolgus monkey) IL-12 and IL-18 were used to activate the pathway. Nonetheless, the IC stimulation resulted in similar levels of sTL1A production as in human blood and the system was appropriate for evaluation of the pharmacologic activity of the test article. Dose-dependent inhibition by 1D1 1.31 of IFNγ production by monkey whole blood cells stimulated by IC and IL-12 and IL-18 is shown for a representative experiment in FIG. 17A. At the highest saturating 1D1 1.31 concentrations, inhibition reached a plateau of maximum inhibition without achieving complete inhibition,suggesting partial inhibition of the response. This is not surprising given that the stimulatory conditions used are not specific to the TL1A/DR3 pathway and are likely to also activate other pathways which may result in the production of inflammatory cytokines. Hence, the IFNγ response measured is likely contributed by TL1A-dependent and independent pathways. Nonetheless, under these conditions, the TL1A pathway seems to be a major contributor to the response as mean maximal inhibition of IFNγ secretion by 1D1 1.31 in this system was 71%±21% (n=6 different monkeys; range 50-99%) suggesting that the TL1A-dependent response accounts for approximately an average of two thirds of the response. These results were also similar in the human system (mean maximal inhibition was 62%±10%). The potency of 1D1 1.31 was determined by calculating the 1050 for the TL1A-mediated response. 1D1 1.31 inhibits IFNγ secretion by endogenous TL1A upregulated in monkey whole blood by IC with an IC50 of 36±42 pM (n=6 monkeys; range 6-119 pM). These results indicate that the inhibitory potency of 1D1 1.31 for the cynomolgus TL1A/DR3 pathway is similar or greater than its potency in the inhibition of the human pathway (1050 of 277±125 pM). In this assay, there was no dose-dependent inhibition by the isotype control antibody.

Soluble TL1A Levels in Whole Blood Activated by Immune Complex and IL-12/IL-18 and Treated by 1D1 1.31

Figure 17B:
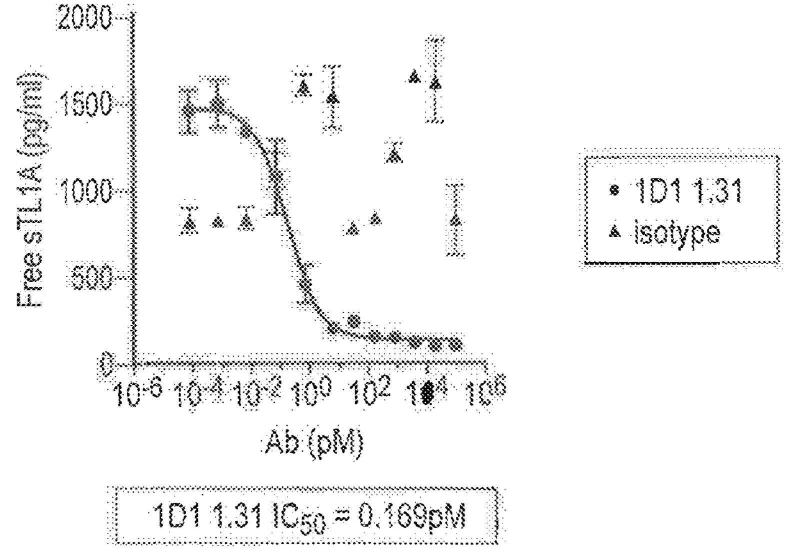

In the same human peripheral blood assay in which 1D1 1.31 was evaluated for its suppression on IFNγ levels in response to IC and IL-12 and IL-18 stimulation, 1D1 1.31 was also evaluated for its effect on sTL1A plasma levels. IC and IL-12/IL-18 stimulation of monkey whole blood resulted in endogenous soluble TL1A elevations to mean values of 1519±686 pg/mL (FIG. 17B; range 485-2597 pg/mL; mean 116 fold induction over unstimulated blood; n=6 monkeys). These values were similar to the ones measured in human whole blood (940±293 pg/mL; 50 fold induction) and also similar to the values 1430±211 pg/mL measured with IC stimulation alone (no IL-12/IL-18) of the cynomolgus monkey blood. These increases of sTL1A at 24 hours likely reflect proteolytic cleavage from monocyte membrane TL1A which was shown to be maximally and transiently expressed on human monocytes at earlier time points upon IC stimulation. 1D1 1.31 binding to soluble TL1A was measured by the dose-dependent decrease of 1D1 1.31-free soluble TL1A. 1D1 1.31 depletes antibody-free soluble TL1A with a mean IC50 value of 22±35 pM (range 0.114-90 pg/mL; n=6 monkeys). The corresponding human IC50 value was 1.06±1.68.

Anti-TL1A antibody 1D1 1.31 inhibits IFNγ secretion following activation of TL1A/DR3 pathway in cynomolgus monkey peripheral blood by stimulation with IC and IL-12 and IL-18 with a mean IC50 value of 36±45 pM. These values are indicative of pharmacological activity in cynomolgus monkey and are comparable to the potency of 1D1 1.31 in human peripheral blood.

Example 15: Biological Assays Using 1D1 Variant Antibodies

The above-described NFκB assay, Caspase assay, and human whole blood cytokine assay (Examples 11, 12, and 13) were also repeated with antibodies 1D1 1.27, 1D1 1.28, 1D1 1.29, 1D1 1.30, 1D1 1.31, 1D1 1.32, 1D1 1.33, and 1D1 1.34. The results of these experiments are summarized in Table 19. Each of the affinity matured antibodies demonstrated improved activity over 1D1 parental antibody.

TABLE 19

Average IC50 of antibody 1D1 and affinity matured variants in $NF_{K}B$ assay.

| | Average IC50 (pM) | | |
|---|---|---|---|
| Antibody | Caspase Assay | NFkB Assay | HWB Assay |
| 1D1 Parental | 216.6 | 742.0 | 247.8 |
| 1D1 1.27 | 70.2 | 139.6 | 0.968 |
| 1D1 1.28 | 96.2 | 189.3 | N/T |
| 1D1 1.29 | 85 | 281.1 | N/T |
| 1D1 1.30 | 102.6 | 370.4 | N/T |
| 1D1 1.31 | 106.5 | 150.1 | 1.667 |
| 1D1 1.32 | 61.5 | 180.4 | N/T |
| 1D1 1.33 | 145.6 | 200.3 | N/T |
| 1D1 1.34 | 62.7 | 181.9 | N/T |

N/T = Not Tested

Example 16: Epitope Mapping of TL1A Bound to Antibody 1D1 Parental

In the present disclosure, residues of the antigen and antibody are said to be hydrogen bonded if they include a hydrogen bond donor atom (bound to an electropositive hydrogen) in one molecule located within 3.2 Å of a hydrogen bond acceptor atom having a lone pair of electrons in the other molecule.

Residues of the antibody and antigen are said to form a salt bridge if they contain a positively charged atom in one molecule within 4 Å of a negatively charged atom in the other molecule.

The per-residue solvent exclusion was determined by calculating the solvent accessible surface area of each residue of the antibody and antigen in complex and subtracting this from the sum of the solvent accessible surface areas of the two components considered individually.

The solvent accessible surface area was calculated according to the method of Strake and Rupley (J Mol Biol 79 (2): 351-71, 1973). The pairwise buried surface area was used to estimate the individual contributions of pairs of residues from the antibody and antigen to the overall effect of buried surface area on binding energy. Since buried surface area is not pairwise decomposable, the buried surface area of each residue in the epitope was calculated in the presence of each individual antibody residue in the absence of the rest of the antibody. These individual contributions were then normalized so that the sum of all individual contributions of all antibody residues to the buried surface area of a given epitope residue would equal the total buried surface area of that epitope residue due to the binding of the entire antibody. This process was repeated in reverse for the individual contributions of epitope residues to the buried surface area of antibody residues. The value for each pair of residues shown in the tables is the sum of these two calculations for that pair of residues.

Analysis of the Co-Crystal Structure of TL1A with 1D1

Based on the co-crystal structures of homologous TNF family members with their receptors, TL1A is expected to interact with its receptor, DR3, at the intersections between monomers within the trimeric TL1A quaternary structure. The epitope of antibody 1D1 spans this intersection (FIG. 5) and would therefore be expected to block receptor activation by directly occluding the receptor binding interface on TL1A. The geometry of the interaction between the 1D1 variable domain and the epitope on TL1A is such that it is unlikely that a single dimeric 1D1 molecule could simultaneously bind two epitopes on a single trimeric TL1A molecule.

Mapping TL Epitope with 1D1

1D1 binding buries a surface area of approximately 1018 $Å^2$ on TL1A with 697 $Å^2$ contributed by one TL1A monomer (monomer A or chain A) and 321 $Å^2$ contributed by its neighbor (monomer B or chain B). Residues from each of the two monomers that participate in the interaction are labeled as chain A or chain B. The overall contribution of each residue to the binding energy of the interaction is a function of both the electrostatic interactions including hydrogen bonds and salt bridges, and the Van der Waals force which is related to the buried surface area (BSA).

FIG. 18 show the area on both TL1A and 1D1 buried by each pair of interacting residues. Tables 20, 21, 22 and 23 summarize the data from FIG. 18, separated into CDR regions of the heavy and light chains.

TABLE 20

Buried surface area in interactions between anti-TL1A antibody 1D1 Parental CDR-H1 (as defined by AbM) and TL1A. Numbers represent normalized buried surface area between the two residues.

| TL1A | TL1A | 1D1 Heavy Chain CHR-H1 Residues | | | | | |
|---|---|---|---|---|---|---|---|
| monomer | residue | S25 | G26 | Y27 | S28 | T30 | Y31 |
| A | K113 | | | | 18.8 | 42.1 | |
| A | T115 | | | | 28.6 | | |
| A | Y118 | 15.5 | 48.8 | 50.4 | 36.8 | | |
| A | P121 | | | | | | 14.6 |
| A | T122 | | | | 28 | | 59.2 |
| A | Q123 | | | | | | 43.5 |

TABLE 20-continued

Buried surface area in interactions between anti-TL1A antibody 1D1 Parental CDR-H1 (as defined by AbM) and TL1A. Numbers represent normalized buried surface area between the two residues.

| TL1A | TL1A | 1D1 Heavy Chain CHR-H1 Residues | | | | | |
|---|---|---|---|---|---|---|---|
| monomer | residue | S25 | G26 | Y27 | S28 | T30 | Y31 |
| B | L55 | | | | | 21.4 | 35.6 |
| B | E171 | | | | | | 22.4 |

TABLE 21

Buried surface area in interactions between antibody 1D1 Parental CDR-H2/Framework 3 and TL1A. Numbers represent normalized buried surface area between the two residues. Where the interactions involve electrostatic interactions, the buried surface area is annotated with the following coding: h = hydrogen bond, s = salt Bridge, w = water-mediated hydrogen bond.

| TL1A | TL1A | 1D1 Heavy Chain CHR-H2/Framework 3 Residues | | | | | | | | |
|---|---|---|---|---|---|---|---|---|---|---|
| monomer | residue | W50 | S52 | Y53 | N54 | N56 | T57 | N58 | T73 | R76 |
| A | Y118 | | | | | | | | | 50.5 h |
| A | M147 | | | 17.6 w | | | | | | |
| A | F148 | | | 28.3 | | | | | | |
| A | S149 | | | 71.6 h | | | | | | |
| A | Q151 | | | | | | | | 71.9 | |
| B | H51 | | | | 12.7 | 26.6 | | | | |
| B | E52 | 36.2 | 15.8 | | 22.4 h | 33.1 | 6.4 | 34.8 h | | |
| B | L53 | 33.4 | | | 5.9 | | | | | |
| B | G54 | | 9.5 | 21.9 | 4.5 | | | | | |
| B | L55 | | | 62.7 w | | | | | | |
| B | A56 | | | 18.7 | 18.8 h | | | | | |
| B | F57 | | | 30.7 | 30.2 | | | | | |
| B | T58 | | | | | 33.2 | | | | |

TABLE 22

Buried surface area in interactions between antibody 1D1 Parental CDR-H3 and TL1A. Numbers represent normalized buried surface area between the two residues. Where the interactions involve electrostatic interactions, the buried surface area is annotated with the following coding: h = Hydrogen bond, s = Salt Bridge, w = Water-mediated hydrogen bond.

| TL1A | TL1A | 1D1 Heavy Chain CHR-H3 Residues | | | | | | | |
|---|---|---|---|---|---|---|---|---|---|
| monomer | residue | Y97 | Y98 | G99 | S100 | G100A | SWOB | Y100C | R100D |
| B | V31 | | | | | 28.8 | | | |
| B | V32 | | | | | 24.9 | | | |
| B | R.33 | | | | | 22.5 w | 43.2 | | |
| B | E50 | | | | | | | | 50.5 S |
| B | L53 | 44.7 | | | 16.4 | | | | 55.8 |
| B | G54 | 42.6 | | | 19.6 | | | | |
| B | E91 | | | | | | 20.5 | | |
| B | Y168 | | | | | 14.7 | 33.6 h | | |
| B | T169 | | | 3.1 | 12.1 | 10.3 | 27.7 | 15 | |
| B | K170 | | 25.9 | 40.2 | 11.8 | 10 | 2.1 | 15.8 | |
| B | E171 | | | 34.3 | 36.5 | 13.8 | | | |

TABLE 23

Buried surface area in interactions between antibody 1D1 Parental light chain and TL1A. Numbers represent normalized buried surface area between the two residues. Where the interactions involve electrostatic interactions, the buried surface area is annotated with the following coding: h = Hydrogen bond, s = Salt Bridge, w = Water-mediated hydrogen bond.

| TL1A | TL1A | 1D1 Light Chain Residues | | | |
|---|---|---|---|---|---|
| monomer | residue | S31 | Y32 | W94 | W96 |
| B | V32 | | 7.4 | | |
| B | R33 | 34.7 h | 56.8 w | | |
| B | E52 | | | 42.7 h | |
| B | L53 | | | 21.2 | 27 |

There are 3 key residues in the epitope having buried surface area greater than 100 Å$^2$. These are tyrosine 118 (Y118) on TL1A chain A or monomer A, and glutamic Acid 52 (E52) and leucine 53 (L53) on TL1A chain B or monomer B. Arginine 33, on chain B, also has a high buried surface area, of 93.4 Å2. These residues define important interactions on both sides of the receptor binding cleft.

There are 9 direct hydrogen bonds (formed by the residues: Y118, S149, R33, E50, E52, A56, and Y168), 4 water mediated hydrogen bonds (M147, R33, and L55) and 1 salt bridge (E50) visible in the crystal structure of the TL1A-1D1 complex. These are listed in Table 24. The introduction of additional hydrogen bonding and salt-bridge interactions were responsible for most of the improvement seen in affinity optimized versions of 1D1.

TABLE 24

Residues involved in electrostatic interactions between TL1A and antibody 1D1 (Parental).

| TL1A Chain | Residue Number | 1D1 Chain | Residue Number |
|---|---|---|---|
| Salt Bridged Residue Pairs | | | |
| B | 50 | H | 100D |
| Hydrogen Bonded Residue Pairs | | | |
| A | 118 | H | 76 |
| A | 149 | H | 53 |
| B | 33 | L | 31 |
| B | 50 | H | 100D |
| B | 52 | H | 54 |
| B | 52 | H | 58 |
| B | 52 | L | 94 |
| B | 56 | H | 54 |
| B | 168 | H | 100B |
| Shared Water Residue Pairs | | | |
| A | 147 | H | 53 |
| B | 55 | H | 53 |
| B | 33 | H | 100A |
| B | 33 | L | 32 |

Table 25 summarizes the TL1A epitope residues that either have electrostatic interactions with 20 Å$^2$ or more of buried surface area when bound with antibody 1D1 parental.

TABLE 25

TL1A epitope residues having electrostatic interactions and/or more than 20 Å$^2$ of buried surface area (BSA) by interaction with 1D1. Electrostatic interaction codes: H = Hydrogen bond, S = Salt Bridge, W = Water-mediated hydrogen bond

| TL1A monomer | TL1A residue | Buried Surface Area | Electrostatic Interactions | |
|---|---|---|---|---|
| A | K113 | 25.0 | | |
| A | Y118 | 118.1 | H | |
| A | T122 | 43.7 | | |
| A | S149 | 39.1 | H | |
| A | Q151 | 38.8 | | |
| B | R33 | 93.4 | H | W |
| B | E50 | 20.4 | H | S |
| B | E52 | 110.5 | H | |
| B | L53 | 118.1 | | |
| B | G54 | 51.3 | | |
| B | L55 | 53.4 | W | |
| B | A56 | 11.9 | H | |
| B | F57 | 26.3 | | |
| B | T58 | 20.1 | | |
| B | Y168 | 15.6 | H | |
| B | T169 | 33.0 | | |
| B | K170 | 46.0 | | |
| B | E171 | 49.0 | | |

Table 26 below summarizes the TL1A residues having key interactions with antibody 1D1, namely buried surface area greater than 100 Å$^2$ or participating in buried salt bridge interactions.

TABLE 26

TL1A epitope residues having buried surface area (BSA) > 100 Å$^2$ or participating in buried salt bridge interactions

| TL1A monomer | TL1A residue | BSA | Electrostatic Interactions | |
|---|---|---|---|---|
| A | Y118 | 118.1 | H | |
| B | E50 | 20.4 | H | S |
| B | E52 | 110.5 | H | |
| B | L53 | 118.1 | | |

In addition, a number of TL1A residues are within 3.8 Å of the antibody, many of which overlap with the electrostatic interactions residues identified above; K113, Y118, T122, F148, S149, Q151, V31, V32, R33, E50, E52, L53, G54, L55, A56, F57, E91, Y168, T169, K170, and E171. These are presented in Table 27 with annotations regarding location of the epitope residues on TL1A monomers.

TABLE 27

TL1A residues within 3.8 Å of residues on antibody 1D1 Parental

| TL1A monomer | TL1A residue | Antibody Chain | Antibody Residue |
|---|---|---|---|
| A | 113 | H | 30 |
| A | 118 | H | 26 |
| A | 118 | H | 27 |
| A | 118 | H | 76 |
| A | 122 | H | 31 |
| A | 148 | H | 53 |
| A | 149 | H | 53 |
| A | 151 | H | 73 |
| B | 31 | H | 100A |
| B | 32 | H | 100A |
| B | 33 | H | 100A |
| B | 33 | H | 100B |
| B | 33 | L | 30 |

TABLE 27-continued

TL1A residues within 3.8 Å of residues on antibody 1D1 Parental

| TL1A monomer | TL1A residue | Antibody Chain | Antibody Residue |
|---|---|---|---|
| B | 33 | L | 31 |
| B | 33 | L | 32 |
| B | 50 | H | 100D |
| B | 52 | H | 50 |
| B | 52 | H | 54 |
| B | 52 | H | 56 |
| B | 52 | H | 58 |
| B | 52 | L | 94 |
| B | 53 | H | 50 |
| B | 53 | H | 100D |
| B | 54 | H | 53 |
| B | 54 | H | 97 |
| B | 54 | H | 100 |
| B | 55 | H | 53 |
| B | 56 | H | 53 |
| B | 56 | H | 54 |
| B | 57 | H | 54 |
| B | 91 | H | 100B |
| B | 168 | H | 100A |
| B | 168 | H | 100B |
| B | 169 | H | 100 |
| B | 169 | H | 100B |
| B | 170 | H | 99 |
| B | 171 | H | 99 |
| B | 171 | H | 100 |

The paratope on antibody 1D1 when bound to TL1A lies almost entirely in its heavy chain. Heavy chain CDR-H1 and CDR-H2 regions contact both TL1A chains. In particular, 1D1 heavy chain tyrosine 31 and tyrosine 53 make extensive contacts with both TL1A monomers. Heavy chain CDR-H3 makes extensive contacts with only one TL1A monomer. There are also two significant interactions between the Framework 3 loop of 1D1 and TL1A. Although it makes many fewer contacts than the heavy chain, the light chain of 1D1 does play a part in the interaction with TL1A. The paratope residues of antibody 1D1 are listed in Table 28.

TABLE 28

Antibody 1D1 Parental paratope residues having electrostatic interactions and/or more than 20 $Å^2$ of surface buried by interaction with TL1A. Electrostatic interaction codes: H = Hydrogen bond, S = Salt Bridge, W = Water-mediated hydrogen bond

| Antibody Chain | Kabat Position | Residue | Buried Surface Area | Electrostatic Interaction With TL1A | |
|---|---|---|---|---|---|
| H | 26 | GLY | 23.5 | | |
| H | 27 | TYR | 20.2 | | |
| H | 28 | SER | 57.7 | | |
| H | 30 | THR | 33.2 | | |
| H | 31 | TYR | 99.0 | | |
| H | 50 | TRP | 28.4 | | |
| H | 53 | TYR | 152.7 | H | W |
| H | 54 | ASN | 58.1 | H | |
| H | 56 | ASN | 48.2 | | |
| H | 58 | ASN | 13.1 | H | |
| H | 73 | THR | 33.0 | | |
| H | 76 | ARG | 22.6 | H | |
| H | 97 | TYR | 39.2 | | |
| H | 99 | GLY | 45.1 | | |
| H | 100 | SER | 50.1 | | |
| H | 100A | GLY | 72.2 | W | |
| H | 100B | SER | 79.4 | H | |
| H | 100D | ARG | 54.0 | H | S |

TABLE 28-continued

Antibody 1D1 Parental paratope residues having electrostatic interactions and/or more than 20 $Å^2$ of surface buried by interaction with TL1A. Electrostatic interaction codes: H = Hydrogen bond, S = Salt Bridge, W = Water-mediated hydrogen bond

| Antibody Chain | Kabat Position | Residue | Buried Surface Area | Electrostatic Interaction With TL1A |
|---|---|---|---|---|
| L | 32 | TYR | 29.7 | W |
| L | 94 | TRP | 26.1 | H |

Example 17: Mapping Binding Epitope of TL1A by Antibody 1D1 1.31

Analysis of the Co-Crystal Structure of TL1A with 1.31

Figure 11:
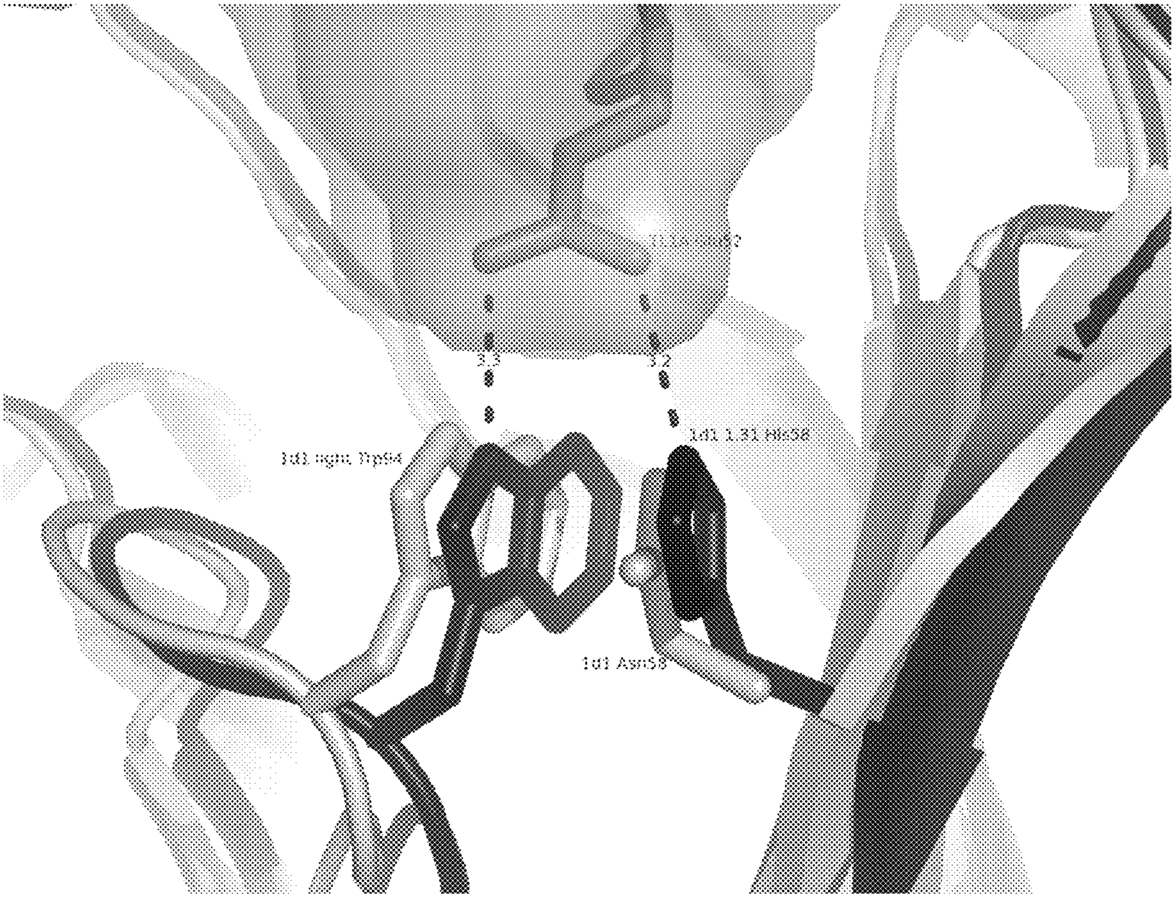
FIG. 11 depicts a comparison of the crystal structure of anti-TL1A antibodies 1D1 (parental) and affinity optimized 1D1 1.31 with human TL1A in the region surrounding residue 58 of the antibodies. 1D1 1.31 is shown in black (heavy chain on right) and dark gray (light chain on left). Parental 1D1 is shown in light gray. TL1A is shown as thin sticks.

The crystal structure of the complex of TL1A with the antibody 1D1 1.31, was also solved. The binding mode of 1D1 1.31 is essentially the same as that of its parental antibody. There are three sequence differences between 1D1 and 1D1 1.31. The change from serine to aspartic acid at heavy chain residue 28 was suggested by the above-described computational analysis of the 1D1:TL1A complex crystal structure. The serine hydroxyl in the 1D1 complex has no appropriate hydrogen bonding partners (FIG. 11). Replacement with aspartic acid allows hydrogen bonding to TL1A threonine 122 and formation of a salt bridge with TL1A lysine 113. There is an additional conformational change of some surrounding residues so that TL1A tyrosine 118, which faced outwards in the 1D1-TL1A complex, is pointed inwards toward the center of the epitope in the 1D1 1.31 complex.

Figure 12:
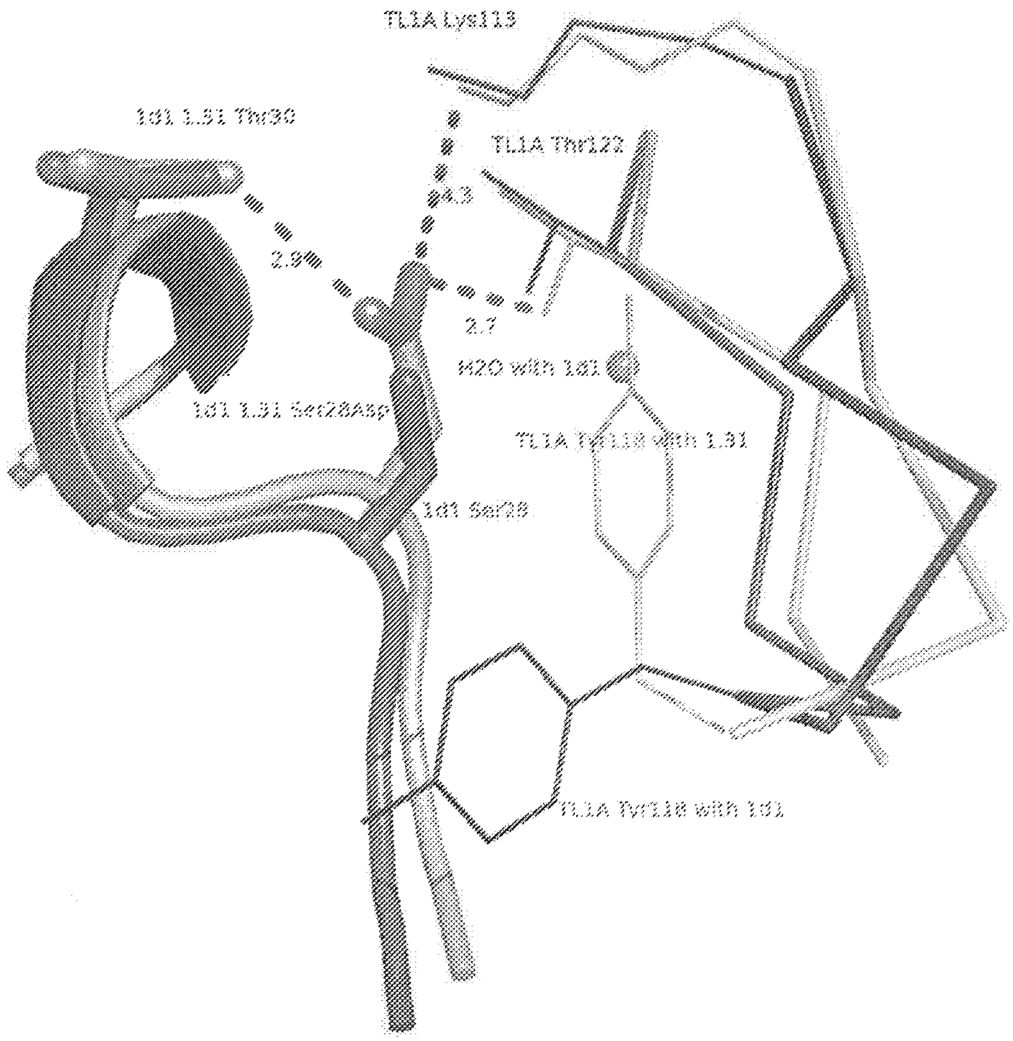
FIG. 12 depicts a comparison of the crystal structure of anti-TL1A antibodies 1D1 (parental) and 1D1 1.31 and human TL1A in the region surrounding residue 28 of the antibodies. Parental 1D1 is shown in light gray thick sticks. 1D1 1.31 is shown in black sticks. TL1A is shown in thin sticks with the conformation from the parental 1D1 costructure in light gray and the conformation from the 1D1 1.31 costructure in black.

The change from asparagine to histidine at heavy chain position 58 was found from a phage-display affinity optimization approach. Histidine 122 was postulated to make a stronger electrostatic interaction with TL1A glutamic acid 52 (FIG. 12).

The structural basis for any improvement in binding due to the substitution of alanine for serine at antibody heavy chain position 100B is less clear. The original serine does not have a clear hydrogen bonding partner. Without wishing to be bound by any particular theory, it may be that removal of the serine hydroxyl by substitution with alanine stabilizes the complex by eliminating a buried polar group with unsatisfied hydrogen bond donor and acceptor atoms.

The full list of interactions between 1D1 1.31 and TL1A are shown in FIG. 19 and Tables 29-38. The water-mediated hydrogen bonds seen in the structure with 1D1 are not visible in the structure with 1D1 1.31. This may be due to the lower resolution of the latter structure. Despite its tighter binding, the total buried surface area due to antibody binding is somewhat lower for 1D1 1.31 (877 $Å^2$) than 1D1 (1018 $Å^2$). Much of this difference is due to the conformational change involving TL1A tyrosine 118 described above. Without wishing to be bound to any particular theory, the enhanced binding of 1D1 1.31 may be due to the improved electrostatic interactions of heavy chain residues 28 and 58.

There are 11 direct hydrogen bonds (formed by the residues: T122, S149, E50, E52, A56, Y168, T169, and E171), and 3 salt bridges (K113, E50, E52) visible in the crystal structure of the TL1A-1D1 complex. These are listed in Table 29. The introduction of additional hydrogen bonding and salt-bridge interactions appear to be responsible for most of the affinity improvement seen over 1D1.

TABLE 29

Residues involved in electrostatic interactions between TL1A and antibody 1D1 1.31

| TL1A monomer | TL1A residue | 1D1 1.31 Chain | 1D1 1.31 Residue |
|---|---|---|---|
| Salt Bridged Residue Pairs | | | |
| B | E50 | H | 100D |
| B | E52 | H | 58 |
| A | K113 | H | 28 |
| Hydrogen Bonded Residue Pairs | | | |
| A | T122 | H | 28 |
| A | S149 | H | 53 |
| B | E50 | H | 100D |

TABLE 29-continued

Residues involved in electrostatic interactions between TL1A and antibody 1D1 1.31

| TL1A monomer | TL1A residue | 1D1 1.31 Chain | 1D1 1.31 Residue |
|---|---|---|---|
| B | E52 | H | 54 |
| B | E52 | H | 58 |
| B | E52 | L | 94 |
| B | A56 | H | 54 |
| B | Y168 | H | 100B |
| B | T169 | H | 100 |
| B | T169 | H | 100B |
| B | E171 | H | 99 |

TABLE 30

Buried surface area interactions between anti-TL1A antibody 1D1 1.31 CDRH1 (as defined by AbM) and TL1A. Numbers represent normalized buried surface area between the two residues. Where the interactions involve electrostatic interactions, the buried surface area is annotated with the following coding: h = hydrogen bond, s = salt Bridge, w = water-mediated hydrogen bond.

| TL1A | TL1A | 1D1 1.31 Heavy Chain CDR-H1 Residues | | | | |
|---|---|---|---|---|---|---|
| monomer | residue | G26 | Y27 | D28 | T30 | Y31 |
| A | K113 | | | 29.3 s | 18 | |
| A | S117 | 24.5 | 7.7 | | | |
| A | Y118 | 15.2 | 37.3 | 54.2 | | |
| A | P119 | 28.8 | | | | |
| A | T122 | | | 37.4 h | | 50.2 |
| A | Q123 | | | | | 42.2 |
| A | Q151 | | | 6.6 | 41.6 | |
| B | L55 | | | | 21.8 | 38.9 |
| B | E171 | | | | | 26.4 |

TABLE 31

Buried surface area in interactions between 1D1 1.31 CDRH2/Framework 3 and TL1A. Numbers represent normalized buried surface area between the two residues. Where the interactions involve electrostatic interactions, the buried surface area is annotated with the following coding: h = hydrogen bond, s = salt Bridge, w = water-mediated hydrogen bond.

| TL1A | TL1A | 1D1 1.31 Heavy Chain CDR-H2/FW3 Residues | | | | | | | |
|---|---|---|---|---|---|---|---|---|---|
| monomer | residue | W50 | S52 | Y53 | N54 | N56 | H58 | T73 | R76 |
| A | S117 | | | | | | | | 44.5 |
| A | M147 | | | 7.8 | | | | | |
| A | F148 | | | 32.7 | | | | | |
| A | S149 | | | 71.8 h | | | | | |
| A | Q151 | | | | | | | 47.2 | |
| B | H51 | | | | 14.1 | | | | |
| B | E52 | 33.3 | 16.2 | | 25.8 h | 56.3 | 33.3 S | | |
| B | L53 | 33.1 | | | | | | | |
| B | G54 | | 12 | 23.2 | 4.1 | | | | |
| B | L55 | | | 57.8 | | | | | |
| B | A56 | | | 20.2 | 17.3 h | | | | |
| B | F57 | | | 30.2 | 31 | | | | |

TABLE 32

Buried surface area in interactions between 1D1 1.31 CDR-H3 and TL1A. Numbers represent normalized buried surface area between the two residues. Where the interactions involve electrostatic interactions, the buried surface area is annotated with the following coding: h = hydrogen bond, s = salt Bridge, w = water-mediated hydrogen bond.

| TL1A | TL1A | 1D1 1.31 Heavy Chain CDR-H2/FW3 Residues | | | | | | |
|---|---|---|---|---|---|---|---|---|
| monomer | residue | Y97 | G99 | S100 | G100A | A100B | Y100C | R100D |
| B | V31 | | | | 32 | | | |
| B | V32 | | | | 27.6 | | | |
| B | R.33 | | | | 13.2 | | | |
| B | E50 | | | | | | | 42.0 S |
| B | L53 | 43 | | 16 | | | | 46.3 |
| B | G54 | 40.9 | | 19.8 | | | | |
| B | Y168 | | | 1.7 | 15.9 | 43.2 h | | |
| B | T169 | | 5 | 14.5 h | 10.6 | 28.8 h | 21.7 | |
| B | K170 | | 25.6 | 7.1 | 8.2 | 2.8 | | |
| B | E171 | | 30.9 h | 36.9 | 14.3 | | | |
| B | D172 | | 5.9 | | | | | |

TABLE 33

Buried surface area ininteractions between 1D1 1.31 Light Chain and TL1A. Numbers represent normalized buried surface area between the two residues. Where the interactions involve electrostatic interactions, the buried surface area is annotated with the following coding: h = hydrogen bond, s = salt Bridge, w = water-mediated hydrogen bond.

| TL1A | TL1A | 1D1 1.31 Light Chain Residues | | |
|---|---|---|---|---|
| monomer | residue | L Y32 | L W94 | L W96 |
| B | R33 | 45.5 | | |
| B | E52 | | 40.2 h | |
| B | L53 | | 22.5 | 30.2 |

TABLE 34

TL1A epitope residues having electrostatic interactions and/or more than 20 Å$^2$ of surface buried by interaction with 1D1 1.31. Electrostatic interaction codes: H = Hydrogen bond, S = Salt Bridge, W = Water-mediated hydrogen bond

| TL1A monomer | TL1A residue | Buried Surface Area | Electrostatic Interactions | |
|---|---|---|---|---|
| A | K113 | 17.7 | S | |
| A | S117 | 41.9 | | |
| A | Y118 | 48.9 | | |
| A | T122 | 43.9 | H | |
| A | S149 | 35.4 | H | |
| A | Q151 | 49.3 | | |
| B | R33 | 31.6 | | |
| B | E50 | 19.6 | H | S |
| B | E52 | 110.9 | H | S |
| B | L53 | 113.8 | | |
| B | G54 | 51.3 | | |
| B | L55 | 56.3 | | |
| B | A56 | 10.7 | H | |
| B | F57 | 26.4 | | |
| B | Y168 | 25.6 | H | |
| B | T169 | 43.6 | H | |
| B | E171 | 51.2 | H | |

TABLE 35

1D1 1.31 paratope residues having electrostatic interactions and/or more than 20 Å$^2$ of surface buried by interaction with TL1A. Electrostatic interaction codes: H = Hydrogen bond, S = Salt Bridge, W = Water-mediated hydrogen bond

| Chain | Residue | Kabat Position | BSA | Electrostatic Interactions | |
|---|---|---|---|---|---|
| H | GLY | 26 | 32.8 | | |
| H | ASP | 28 | 76.3 | H | S |
| H | THR | 30 | 34.1 | | |
| H | TYR | 31 | 88.1 | | |
| H | TRP | 50 | 25.2 | | |
| H | TYR | 53 | 151.1 | H | |
| H | ASN | 54 | 50.5 | H | |
| H | ASN | 56 | 35.1 | | |
| H | HIS | 58 | 11.1 | H | S |
| H | THR | 73 | 24.7 | | |
| H | ARG | 76 | 24.0 | | |
| H | TYR | 97 | 36.0 | | |
| H | GLY | 99 | 38.5 | H | |
| H | SER | 100 | 48.2 | H | |
| H | GLY | 100A | 68.0 | | |
| H | ALA | 100B | 46.9 | H | |
| H | ARG | 100D | 41.7 | H | S |
| L | TYR | 32 | 20.9 | | |
| L | TRP | 94 | 26.3 | H | |

TABLE 36

TL1A-1D1 1.31 binding epitope residues having buried surface area > 100 Å$^2$, participating in buried salt bridges, or participating in interactions with residues changed during affinity optimization of 1D1 parental antibody

| TL1A monomer | TL1A residue | Buried Surface Area | Electrostatic Interactions | |
|---|---|---|---|---|
| A | K113 | 17.7 | S | |
| A | Y118 | 48.9 | | |
| A | T122 | 43.9 | H | |
| B | E50 | 19.6 | H | S |
| B | E52 | 110.9 | H | S |
| B | L53 | 113.8 | | |

In addition, a number of TL1A residues are within 3.8 Å when bound to antibody 1D1 1.31; K113, Y118, P119, T122, Q123, F148, S149, V31, V32, E50, E52, L53, G54, L55, A56, Y168, T169, K170, and E171 (Table 37).

TABLE 37

| TL1A binding epitope residues having atoms within 3.8 Angstrom of 1D1 1.31 | | | |
|---|---|---|---|
| Antigen Chain | Antigen Residue | Antibody Chain | Antibody Residue |
| A | K113 | H | 28 |
| A | Y118 | H | 27 |
| A | Y118 | H | 28 |
| A | P119 | H | 26 |
| A | T122 | H | 28 |
| A | T122 | H | 31 |
| A | Q123 | H | 31 |
| A | F148 | H | 53 |
| A | S149 | H | 53 |
| B | V31 | H | 100A |
| B | V32 | H | 100A |
| B | E50 | H | 100D |
| B | E52 | H | 52 |
| B | E52 | H | 54 |
| B | E52 | H | 56 |
| B | E52 | H | 58 |
| B | E52 | L | 94 |
| B | L53 | H | 50 |
| B | L53 | H | 97 |
| B | L53 | H | 100D |
| B | G54 | H | 53 |
| B | G54 | H | 97 |
| B | L55 | H | 31 |
| B | L55 | H | 53 |
| B | A56 | H | 53 |
| B | A56 | H | 54 |
| B | Y168 | H | 100A |
| B | Y168 | H | 100B |
| B | T169 | H | 100 |
| B | T169 | H | 100A |
| B | T169 | H | 100B |
| B | K170 | H | 99 |
| B | E171 | H | 31 |
| B | E171 | H | 99 |
| B | E171 | H | 100 |

Example 18: Formulation of the TL1A Antibody 1D1 1.31

The antibody 1D1 1.31 will be provided as a powder for solution for injection in dosage strength of 100 mg/vial. The drug product is supplied in a 6 mL type 1 clear glass vial, sealed with a coated rubber stopper and flip-off aluminum seal. The drug product is designed to be reconstituted in either full volume with 2.2 mL of sterile Water for Injection (sWFI) to allow for intravenous administration (IV) or in approximately half volume with 1.0 mL of sWFI to allow for intravenous (IV) administration or subcutaneous (SC) administration. The formulation is 10 mM histidine, 5% sucrose, 0.01% polysorbate-80 pH 5.8 as a lyophilized powder and is 10 mM histidine, 5% sucrose, 0.01% polysorbate-80 pH5.8 when reconstituted in full volume and is 20 mM histidine, 10% sucrose, 0.02% polysorbate-80 pH 5.8 when reconstituted in half volume.

All components used in the manufacture of the drug product and their functions are provided in Table 38 below.

TABLE 38

| Composition of Antibody 1D1 1.31 Powder for Solution for Injection, 100 mg/vial | | | | |
|---|---|---|---|---|
| Name of Ingredients | Function | Unit Formula (mg/vial) | Unit Formula Reconstituted Full Volume (mg/mL) | Unit Formula Reconstituted Half Volume (mg/mL) |
| 1D1 1.31 | Active Ingredient | 100 | 50 | 100 |
| L-histidine | Buffer component[a] | 1.2 | 0.6 | 1.2 |
| L-histidine, hydrochloride, monohydrate | Buffer component[a] | 2.6 | 1.3 | 2.6 |
| Sucrose (low endotoxin) | Cryoprotectent, Tonicifier | 100 | 50 | 100 |
| Polysorbate-80 | Surfactant | 0.2 | 0.1 | 0.2 |
| Water for injection | Solvent (removed during lyophilization) | q.s. to 2.0 mL | q.s. to 1.0 mL | q.s. to 1.0 mL |
| Nitrogen | Vial headspace | As needed | N/A | N/A |

Overfill

To ensure that 2 mL volume can be withdrawn from the vial after full volume reconstitution and 1 mL volume can be withdrawn from the vial after half volume reconstitution, there is an overfill of 0.4 mL. There is no manufacturing overage.

Antibody 1D1 1.31 drug product is formulated at a concentration of 50 mg/mL and 2.4 mL is filled into each vial for lyophilization. Prior to dosing, the drug product is reconstituted to either full volume or half volume to accommodate different injection volumes and concentrations. For full volume reconstitution, 2.2 mL of sterile water for injection is added to the vial resulting in a reconstituted total volume of approximately 2.4 mL, of which 2.0 mL can be withdrawn for dosing. The full volume reconstitution is suitable for intravenous (IV) administration. For half volume reconstitution, 1.0 mL of sterile water for injection is added to the vial resulting in a reconstituted total volume of approximately 1.2 mL, of which 1.0 mL can be withdrawn for dosing. The half volume reconstitution is suitable for either intravenous (IV) administration or subcutaneous (SC) administration. Reconstitution volumes added to the vial for both full volume and half volume reconstitution take into account the volume of the lyophilized cake. Antibody 1D1 1.31 drug product release and stability testing are executed after full volume reconstitution with 2.2 mL of sterile water for injection.

The choice of the excipients for the lyophile formulation was made to achieve an appropriate solution, upon reconstitution, for IV infusion and SC injection with a stability profile that will allow an extended drug product shelf-life and robustness with respect to temperature excursions. In addition, the formulation is designed to be robust with respect to freeze and thaw cycles of the drug substance.

The choice of histidine with sucrose and polysorbate 80 at pH 5.8 was based on early phase formulation development work. Polysorbate 80 has been added to the 1D1 1.31 formulation to reduce the potential for aggregate formation. Sucrose was selected for its stabilizing effect for lyophilization and storage stability. The amount of sucrose chosen for the formulation targets an isotonic solution when reconstituted in half volume.

Development studies were performed to evaluate administration component compatibility and hold times that support proposed clinical study designs. The conclusion of these studies is that the dosage form is compatible with administration components to be used in the proposed clinical studies and is stable during dose preparation and administration.

Example 19: Binding Specificity of of anti-TL1A Antibody clone 1D1 1.31 to TL1A and Homologs The goal of these studies was to evaluate the binding specificity of 1D1 1.31 for human TL1A (TNFSF15) versus its closest human homologues: TNFSF6 (FAS Ligand); TNFSF10 (TRAIL); TNFSF14 (LIGHT); TNF-β; TNF-α; and lymphotoxin-β isoforms; which are 36%, 35%, 31%, 30%, 29% and 25% identical to TL1A respectively.

Materials and Methods

1D1 1.31 binding selectivity was evaluated in plate-based ELISA assays.

To test binding of 1D1 1.31 to each cytokine, each cytokine and TL1A were tested separately in a 96 well plate. All conditions were performed in duplicate. The first 6 rows of each plate were coated with the test article cytokine, and the last two rows were coated with TL1A as a positive control. Rows 1 and 2 were duplicate rows where the test article cytokine was tested for binding to increasing concentrations of its corresponding anti-cytokine positive control antibody. Rows 3 and 4 were duplicate rows tested against increasing concentrations of the anti-TL1A isotype control antibody 8.8; rows 5 through 8 were tested against increasing concentrations of the anti-TL1A antibody 1D1 1.31 (5 and 6 duplicate rows containing the cytokine test article and 7 and 8 duplicate rows containing TL1A as positive control for the anti-TL1A antibody). The experiment for each cytokine was repeated three times.

Briefly, plates were coated with cytokine by adding 50 μL of a 1 μg/mL solution of cytokine in PBS to each well (rows 1-6 were coated with test article cytokine and rows 7 and 8 were coated with TL1A) (TNFSF6, TNFSF10, TNFSF14, and TNF-α from R&D systems, Human Lymphotoxin α2-β1, and Lymphotoxin α1-β2 purchased from Sigma, Human TNF-β from Peprotech). Plates were incubated overnight at 4° C. After washing the plates three times (3X) with 300 μL PBST using a plate washer (model ELx405; BioTek), plates were blocked by incubating for 1 hour at room temperature with 300 μL of blocking buffer (PBST+0.5% BSA) in each well. Plates were washed 3× with PBST as above prior to addition of 50 μL of the corresponding antibody solution (as indicated above for the various rows) at a starting concentration of 25 μg/mL (followed by 1:5 subsequent dilutions in PBST+0.5% BSA for a total of 11 antibody concentrations ranging from 25 μg/mL to $2\times10^{-6}$ μg/mL) and the PBST only control. Plates were incubated for 1 hour at room temperature and then washed five times with 300 μL of PBST using the plate washer, followed by addition of 50 μL of 1:5000 anti-human IgG HRP (from Jackson Immunoresearch)(for detection of anti-TL1A; isotype control 8.8 or anti-TNF-α infliximab antibody); or 1:8000 Streptavidin HRP (from Pierce/Thermo Scientific) (for detection of biotinylated anti-human TNFSF6, TNFSF10, TNFSF14 or TNF-β, all from R&D systems); or 1:5000 anti-mouse IgG HRP (R&D systems)(for anti-lymphotoxin detection) and incubation for 1 hour at room temperature. Plates were then washed 5 times with PBST using the plate washer. 50 μL of the horse radish peroxidase substrate TMB1 were added to each well and plates incubated for 5 minutes at room temperature prior to addition of 50 μL of stop solution (0.18 M $H_2SO_4$) (TMB1 from Fisher). Plates were then read at 450 nm in a plate reader (Envision; Perkin Elmer)

Antibody binding curves were generated by plotting the Optical Density at 450 nm values against the log of antibody concentrations. $EC_{50}$ values (for 1D1 1.31 binding to TL1A or cytokine antibody binding to its corresponding cytokine) were determined from these graphs using GraphPad Prism® (version 5.02, GraphPad Software, Inc., San Diego, CA) and nonlinear regression curve fits and a sigmoidal log of agonist (three parameters) dose response model.

Results

Anti-TL1A 1D1 1.31 did not bind to any of the closest TL1A homologue-cytokines tested, but it bound to TL1A in the same plate in which the cytokine homologues of TL1A were tested. Each cytokine tested bound to its corresponding anti-cytokine specific antibody except for lymphotoxin for which binding was detected only at very high antibody concentrations of the anti-lymphotoxin antibody.

Figure 20:
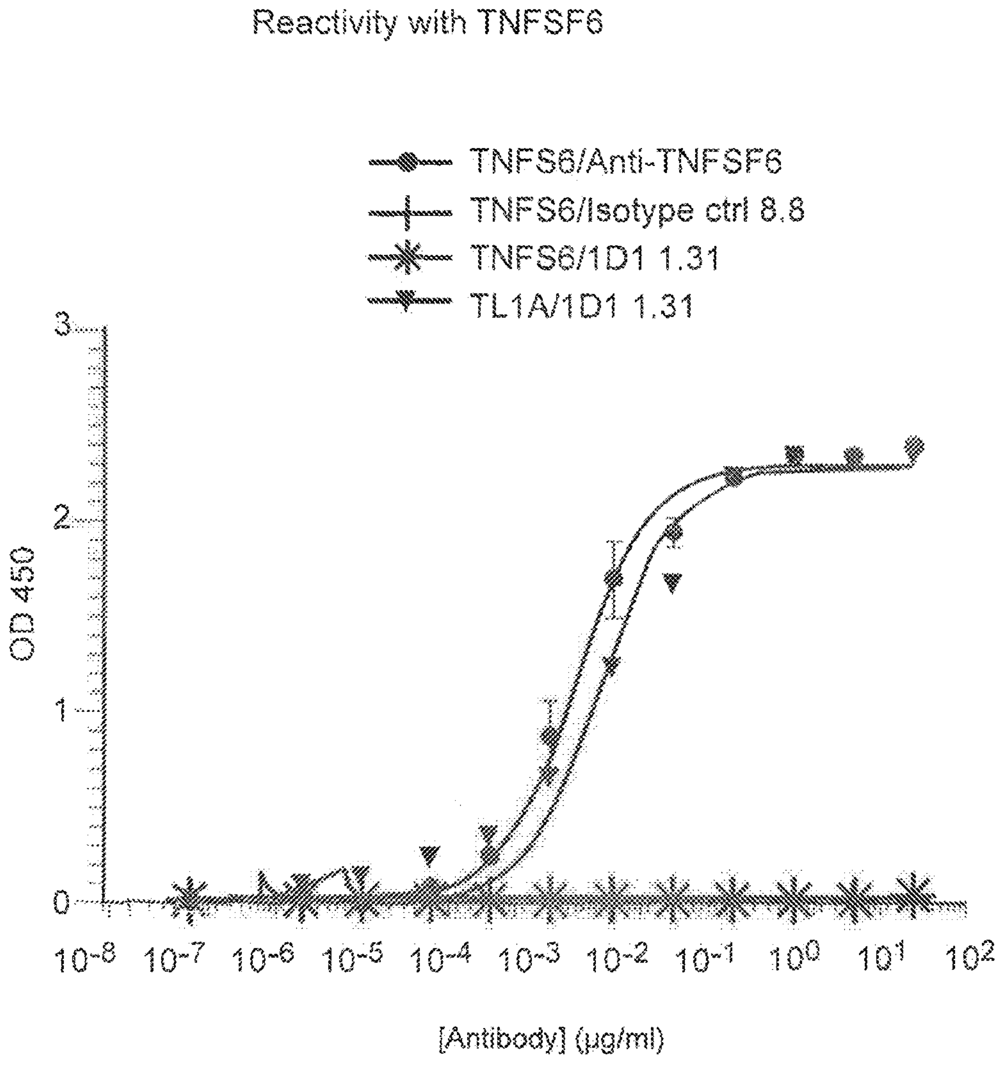
FIG. 20 shows a graph comparing the binding of 1D1 1.31 to TL1A and TNFSF6. Antibody binding was determined as described in materials and methods. This graph represents 3 independent experiments executed in duplicate (n=6). 1D1 1.31 bound TL1A with an $EC_{50}$ value of 8.4 pg/mL (bottom triangles) but did not bind TNFSF6 (stars). The anti-TNFSF6 antibody bound TNFSF6 (circles) with an $EC_{50}$ value of 3 pg/mL.

FIG. 20 shows the experimental results for testing selectivity of binding of 1D1 1.31 to the closest homologue of TL1A, TNFSF6 (n=6; 3 independent experiments in duplicate). TNFSF6 bound to the anti-TNFSF6 antibody (circle) but it did not bind to anti-TL1A 1D1 1.31 (upward triangle). TL1A bound to 1D1 1.31. This plot is a representative plot for all other cytokines tested except for lymphotoxin which binding to its specific anti-lymphotoxin antibody only occurred at high antibody concentrationsa.

Table 39 shows the $EC_{50}$ values obtained for each cytokine experiment (n=6; 3 independent experiments in duplicate) for binding of anti-TL1A 1D1 1.31 to TL1A and for the anti-cytokine antibody binding to each corresponding cytokine in each plate.

TABLE 39

Summarizes the $EC_{50}$ values obtained for binding of anti-TL1A 1D1 1.31 to TL1A and of the respective anti-cytokine antibody to its corresponding cytokine in the triplicate experiments performed for each cytokine.

| | $EC_{50}$ (pg/mL) | | | | | | | | | | | | | |
|---|---|---|---|---|---|---|---|---|---|---|---|---|---|---|
| | TNFS F6 | TL1 A | TNFSF 10 | TL1 A | TNFSF 14 | TL1 A | TNF β | TL1 A | TNF α | TL1 A | Lymp 1 | TL1 A | Lymp 2 | TL1 A |
| 1D1 1.31 | NB | 8.5 | NB | 8 | NB | 8.4 | NB | 2.3 | NB | 8.2 | NB | 6.3 | NB | 5.8 |
| Cytokine AB | 3 | Nd | 1.8 | Nd | 1.8 | Nd | 2 | Nd | 40 | Nd | NB | Nd | NB | Nd |

NB = no binding;

Nd—does not apply because it was not measured.

Data is n = 6 from 3 independent experiments performed in duplicate.

$EC_{50}$ is defined as the concentration of antibody yielding half of maximal optical density obtained at saturating antibody concentrations.

Conclusion

1D1 1.31 is selective for binding to human TL1A and does not detectably bind to any of the closest homologues of TL1A: TNFSF6, TNFSF10, TNFSF14, TNF-β, TNF-α, Lymphotoxin α2-β1, or Lymphotoxin α1-β2.

Example 20: Inhibition of TL1A:DR3 Interaction using Anti-TL1A Antibody 1D1 1.31

Aim

The purpose of this study was to evaluate the ability of the anti-TL1A antibody 1D1 1.31 to inhibit binding of TL1A to its receptor DR3 in DR3-expressing HEK293 cells.

Materials and Methods

DR3-transfected HEK293 cells were plated in a 96 round-well plate at cell density of 100,000 cells per well in PBS 4% FCS and incubated for 15 minutes at 4° C. with 10 μg/mL of biotinylated TL1A and increasing concentrations of the anti-TL1A antibody 1D1 1.31 or its isotype control (8.8 IgG1 3 m) in the concentration range from 0.5 μg/mL to 250 μg/mL in 2 fold dilutions for 10 concentrations. As a positive control, cells were incubated with biotinylated TL1A without any antibody. In a parallel experiment biotinylated TL1A was also incubated with untransfected parental HEK293 cells and demonstrated to have no binding (data not shown).

Following this 15 minute incubation, cells were centrifuged at 485 g, the supernatant was aspirated, and the cells were resuspended in a solution of Streptavidin-PE (BD Biosciences) (1:500 dilution in PBS/fetal calf serum (FCS)). The cells were then incubated for 15 minutes at 4° C. Following incubation, cells were washed 3 times with the same buffer, resuspended in 200 μL of the same buffer and binding of TL1A examined by flow cytometric analysis on an LSR Fortessa cytometer (BD Biosciences).

Data analysis

Data was analyzed with FlowJo software.

Following identification of singlet cells, the geometric mean of the cell population's fluorescent intensity for PE was measured. This is a measurement of how much Streptavidin-PE is on the cells, which should only bind TL1A-biotin. The geometric mean of unstained cells was subtracted from all values as a background. The streptavidin alone control background was similar to the background of the unstained cells.

These corrected geometric mean values were plotted against log of Ab concentration and $IC_{50}$ was calculated with Graph Pad Prism software.

Results

Figure 21:
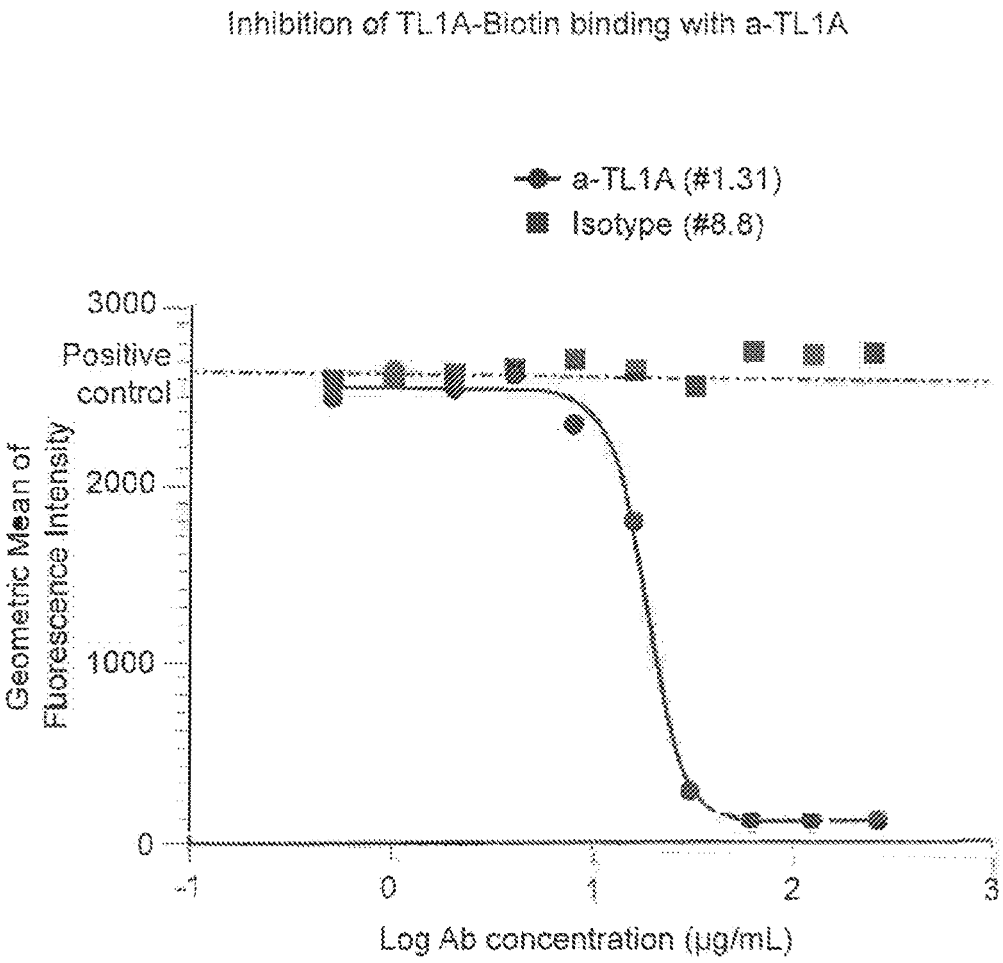
FIG. 21 shows a graph demonstrating the inhibition of binding of biotinylated-TL1A to DR3-expressing HEK293 cells by the anti-TL1A antibody 1D1 1.31. Anti-TL1A antibody 1D1 1.31 inhibited binding of 10 μg/mL of biotinylated-TL1A to DR3-expressing HEK293 cells with an $IC_{50}$ of 18.68 μg/mL.
Figure 22A:
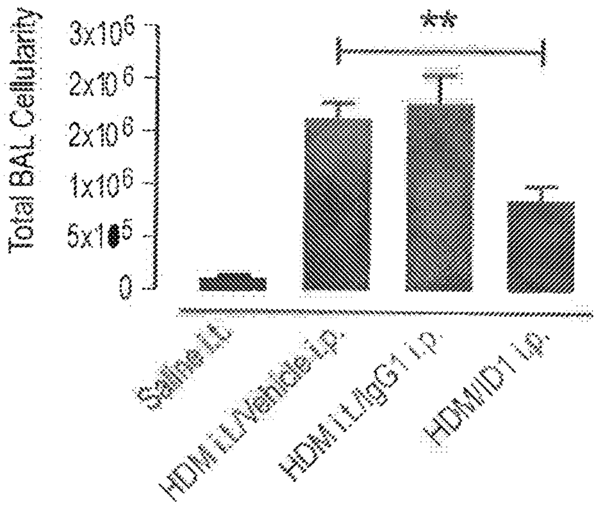
FIGS. 22A, 22B, 22C, 22D, and 22E show results of administration of an anti-TL1A antibody on airway inflammation in an HDM mouse model. Administration of the 1D1 antibody resulted in a significant reduction in total BAL cellularity FIG. 22A, the number of BAL Eosinophils FIG. 22B, BAL lymphocytes FIG. 22C, and BAL macrophages FIG. 22D. BAL neutrophil numbers did not appear to be significantly modulated by anti-TL1A treatment FIG. 22E, although it is worth noting that BAL neutrophils represent a small cell population in this model.
Figure 22B:
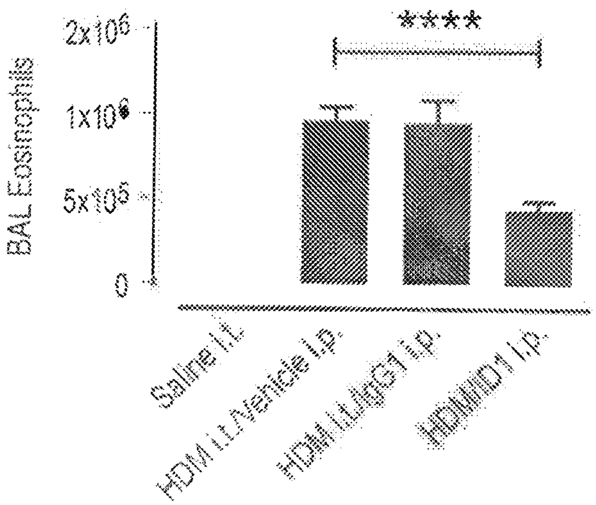
Figure 22C:
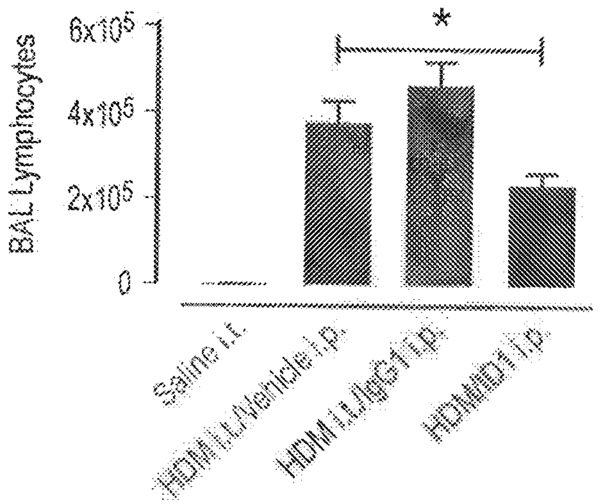
Figure 22D:
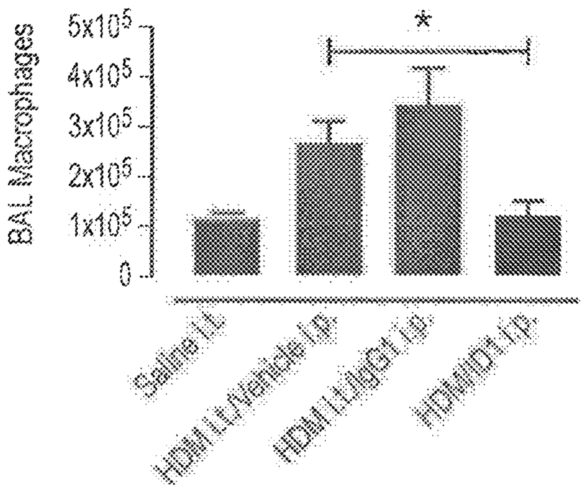
Figure 22E:
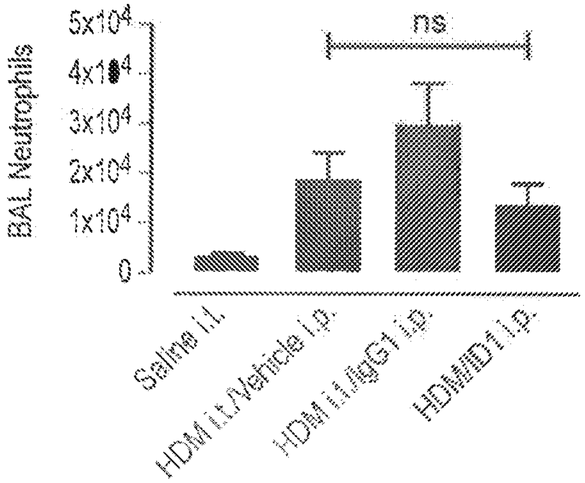

Biotinylated TL1A was shown to bind to DR3-HEK293 transfected cells (but not to untransfected cells) and this binding was completely inhibited by the anti-TL1A antibody 1D1 1.31 (FIG. 21). The isotype control antibody 8.8 IgG1 3 m did not show any inhibition. 1D1 1.31 inhibited binding of 10 μg/mL of TL1A with $IC_{50}$ value of 18.68 μg/mL.

Conclusion

Biotinylated TL1A was shown to bind to DR3-HEK293 transfected cells (but not to untransfected cells) and this binding was completely inhibited by the anti-TL1A antibody 1D1 1.31 but not by the isotype control antibody 8.8 IgG1 3 m. 1D1 1.31 inhibited binding of 10 μg/mL of biotinylated TL1A with $IC_{50}$ value of 18.68 μg/mL.

Example 21: Thermal Stability of Representative Antibodies

Aim

The aim was to characterize the anti-TL1A antibodies generated by affinity maturation and structure-based design with respect to thermal stability and to confirm that the stability of these antibodies was not affected by the mutations.

Methods

Differential Scanning calometry was performed essentially as described in King et al. (2011), Protein Sci., 20 (9): 1546-1557, which is incorporated herein by reference. Briefly, antibody samples were diluted to 0.1 mg/mL in PBS. Sypro Orange was diluted from its original 5000× concentration to a working concentration of 2.5×. The total volume of 210 μL was split into four wells in a PCR microwell plate and heated from 20 to 95° C. at 1C per minute. Fluorescence was collected using the SYBR filters. Following data fitting to three Gaussians, the Tm values of each unfolding transition could be determined, as well as the onset of unfolding.

Results

Table 43 shows the transition temperatures of various mutated antibodies, compared with the parental antibody (1D1).

| Construct | Tm1 | Tm2 | Tm3 | T1% |
|---|---|---|---|---|
| 1D1 | 70.98 ± 0.07 | 79.46 ± 0.12 | 86.04 ± 0.11 | 62.67 |
| VH 1.29 | 71.32 ± 0.06 | 80.90 ± 0.11 | 85.67 ± 0.37 | 61.64 |
| VH 1.28 | 71.20 ± 0.06 | 81.06 ± 0.04 | 86.25 ± 0.25 | 61.73 |
| VH 1.32 | 70.42 ± 0.03 | 78.72 ± 0.02 | 85.61 ± 0.35 | 61.77 |
| VH 1.34 | 70.72 ± 0.09 | 79.42 ± 0.05 | 86.26 ± 0.25 | 61.80 |
| VH 1.27 | 71.90 ± 0.04 | 82.38 ± 0.09 | 87.00 ± 0.19 | 61.85 |
| VH 1.30 | 71.84 ± 0.10 | 83.04 ± 0.12 | 87.35 ± 0.19 | 61.91 |
| VH 1.33 | 71.48 ± 0.16 | 81.14 ± 0.10 | 86.75 ± 0.07 | 62.06 |
| VH 1.31 | 72.24 ± 0.15 | 82.37 ± 0.08 | 87.60 ± 0.40 | 62.36 |

T1%, or the temperature at which the protein was 1% unfolded or the onset of unfolding, was calculated, also as described in King et al. (ibid). Each melting temperature refers to the melting of a different key interface. In a canonical antibody, TM3 is the temperature at which the interface of two CH3 domains melts, TM1 is the temperature at which the interface of the two CH2 domains melts and TM2 is the temperature at which the interface of the heavy and light chain melts.

Conclusion

All antibodies tested were stable, with a Tm1>65° C. and T1% of greater than 50° C. Variations in thermal stability could be seen in the Tm2, corresponding to the Fab domain.

Example 22: High Concentration Stability Test of anti-TL1A Antibodies

Aim

Stability of biological drugs is a very important characteristic to ensure that the therapeutic can be formulated to maintain its safety and potency for a defined period of time. The long-term stability of the anti-TL1A antibodies of the present invention were tested.

Methods

The samples of antibodies 1D1 1.27, 1D1 1.31, and 1D1 1.32 were were concentrated in Amicon Ultra 4 mL and Vivaspin 500 spin concentrators with 30 kDa cutoff membranes. When the final volumes had been reached, typically ~30 μL, the concentration of all samples was measured using a Nanodrop after 10-fold dilution. Samples were adjusted to ~150 mg/mL, then placed in SEC vials with 15 μL mineral oil overlays, and placed either at room temperature or at 4° C. Samples were measured weekly for formation of aggregates. SEC runs consisted of 1 μL injections onto a TOSOH GSK-300 column, with PBS running buffer, flow rate 0.5 mL/min. Recovery was calculated using the area under the curve.

Results and Discussion

Samples were concentrated to 150 mg/mL, and good agreement was seen between Nanodrop and SEC recovery numbers. After 12 weeks at room temperature or 4° C., less than 2% aggregation was seen in all samples except for Antibody 1D1 1.32, which had started to increase in aggregation at ~6 weeks and reached approximately 7.5% aggregation after 12 weeks. Overall, therefore, these antibodies appear as stable, with all except 1D1 1.32 antibody exhibiting less than 5% aggregation at high concentration after 12 weeks at room temperature.

Example 23: Efficacy of Anti-TL1A Antibodies in House Dust Mite (HDM)-Induced Allergic Airway Disease Model Background DR3, also known as TNFRSF25, is a death domain-containing tumor necrosis factor (TNF)-family receptor expressed on various subsets of lymphoid cells. TL1A, the TNF-family ligand for DR3, is expressed by myeloid cells, e.g. dendritic cells, and contributes to the accumulation of lymphocytes into inflamed tissues as well as the release of cytokines involved in type-17 and type-2 immune responses [Meylan, F. et al. (2008)The TNF-family receptor DR3 is essential for diverse T cell-mediated inflammatory diseases. Immunity 29, 79-89]

Materials and Methods

All in-vivo experiments were conducted in accordance to protocols approved by Pfizer's Institutional Animal Care and Use Committee. The murine model of house dust mite (HDM)-induced allergic airway disease was previously described in Fitz LJ et al. Vol. 46 (2012), pp. 71-79. Briefly, 8-12 week old BALB/c female mice were purchased from Taconic Farms (Hudson, NY). On Days 0, 7, and 14 of the study, mice were anesthetized with isoflurane and received 100 μg HDM extract instilled intratracheally (*Dermatophagoides pteronyssinus*, Greer Laboratories, Lenoir, NC). Anti-TL1A antibodies (20 mg/kg, clone 1D1 murine IgG1-4mut), anti-Eimeria tenella IgG1 isotype control antibodies, or vehicle (saline) were injected intraperitoneally on days 0, 2, 4, 7, 9, 11, 14 and 16 of the study. All animals were euthanized by CO2 asphyxiation on day 17 and bronchoalveolar lavage (BAL) fluid samples were collected to assess pulmonary inflammation. Statistical analysis was performed using a Mann-Whitney U test. Differences between groups were considered significant for p value<0.05.

Results

Modulation of HDM-induced allergic airway inflammation by anti-TL1A treatment. Total BAL cellularity was determined using a Cell-Dyn 3700 analyzer (Abbott Laboratories, Abbott Park, IL), while differential cell counts were obtained by manually evaluating cell populations on cytospin slides stained by the Diff-Quik method. Data represent mean±SEM for each group, 9-10 animals/group. When mice were treated 3 times per week by intraperitoneal injections of anti-TL1A antibodies, total BAL cellularity was significantly decreased compared to vehicle-treated animals (p=0.0021). FIG. 22 shows that, following 3 weekly intratracheal challenges with HDM, mice developed robust airway inflammation dominated by eosinophilia, although BAL lymphocyte, macrophage and neutrophil numbers were also increased. In contrast with control IgG1, administration of the 1D1 antibody resulted in a significant reduction in total BAL cellularity [FIG. 22(*a*)], the number of BAL Eosinophils [FIG. 22(*b*)] (p<0.0001, compared to vehicle-treated animals), BAL lymphocytes [FIG. 22(*c*)] (p=0.0285), and BAL macrophages [FIG. 22(*d*)] (p=0.0207). BAL neutrophil numbers did not appear to be significantly modulated by anti-TL1A treatment [FIG. 22(*e*)], although it is worth noting that BAL neutrophils represent a small cell population in this model.

Conclusion

Systemic anti-TL1A treatment used in a murine model of repeated airway challenges with HDM significantly alleviated allergic airway inflammation, including eosinophilia.

Example 24: A Phase 1, Randomized, Double-Blind, Third-Party Open Placebo-Controlled, Dose Escalating Study to Evaluate the Safety, Tolerability, Pharmacokinetics and Pharmacodynamics of Single Intravenous and Multiple Subcutaneous and Intravenous Doses of Anti-TL1A (1D1 1.31) in Healthy Volunteers Objectives The primary objectives of the study are to determine the safety and tolerability of administration of single (IV) and multiple infusions (SC and IV) of 1D1 1.31 in healthy subjects.

The secondary objectives are to characterize the PK profile of 1D1 1.31 following single IV infusions, as well as multiple SC and IV doses. In addition, it is a secondary objective to evaluate the immunogenicity of 1D1 1.31.

Finally, exploratory objectives of the study include the evaluation of exploratory biomarkers which may be informative in demonstrating the pharmacologic effect of 1D1 1.31.

Endpoints

The primary endopoints of the study are to determine the incidence of dose limiting or intolerability treatment related adverse events (AEs), the incidence, severity and causal relationship of treatment emergent AEs (TEAEs) and withdrawals due to treatment emergent adverse events; the incidence and magnitude of abnormal laboratory findings; and, identification of abnormal and clinically relevant changes in vital signs, blood pressure (BP) and electrocardiogram (ECG) parameters.

The secondary (pharmacokinetic) endopoints include the determination of serum 1D1 1.31 concentrations after single dose (SAD) or multiple doses (MAD), to be determined by a validated assay. PK parameters will be generated by noncompartmental methods and will include, but are not limited to:

- Single Ascending Dose Phase (IV infusions): $C_{max}$, $T_{max}$, $AUC_{14\ days}$, $AUC_{inf}$, $AUC_{last}$, $C_{max}$(dn), $AUC_{inf}$(dn), $AUC_{last}$(dn), t½, mean residence time (MRT), volume of distribution ($V_{ss}$), and clearance (CL).
- Multiple Dose Phase (SC dosing and IV infusion):
  - First Dose: $C_{max}$, $T_{max}$, $AUC_T$, $C_{max}$(dn), $AUC_T$ (dn), t½, MRT, apparent volume of distribution (Vz/F), Vss, apparent total body clearance (CL/F) and CL.
  - Multiple Dose: $C_{max}$, $T_{max}$, $AUC_T$, $C_{max}$(dn), $AUC_T$ (dn), t½, MRT, Vz/F, $V_{ss}$, CL/F, CL, minimum concentration over the dosing interval ($C_{min}$), average concentration at steady state ($C_{av}$), observed accumulation ratio ($R_{ac}$) and peak to trough fluctuation (PTF).

Additional Parameter: estimate of bioavailability (F) for SC administration at the corresponding IV dose (ratio of $AUC_T$ (SC, first dose)/$AUC_{14\ days}$ (IV, single dose).

Secondary (immunogenicity) endpoints include the incidence of the development of anti-drug antibody (ADA).

Exploratory endpoints include the evaluation of high sensitivity C-reactive protein (hsCRP) and IP-10 gene expression and protein concentration, total TL1A protein concentration in serum and leukocyte analysis.

Study Design

Approximately 92 healthy subjects have been enrolled at a single study site into the proposed cohorts listed below. To date, over 80 subjects have been administered with the anti-TL1A antibody at varying doses.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

TABLE 40

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 2 | NA sequence of 9B3 light chain V domain (9B3-VL) | GACATCCAGATGACCCAGTCTCCATCCTCACTGTCTGCATCTGTAGGA<br>GACAGAGTCACCATCACTTGTCGGGCGAGTCAGGGTATTAGCAGCTGG<br>TTAGCCTGGTATCAGCAGAAACCAGAGAAAGCCCCTAAGTCCCTGATC<br>TATGCTGCATCCAGTTTGCAGAGTGGGGTCCCATCAAGGTTCAGCGGC<br>AGTGGATCTGGGACAGATTTCACTCTCACCATCAGTAGCCTGCAGCCT<br>GAAGATTATGCAACTTATTACTGCCAACAGTATAATAGTTACCCGTAC<br>ACTTTTGGCCAGGGGACCAAGCTGGAGATCAAA |
| 4 | NA sequence of 9B3 heavy chain V domain 1 (9B3-VH1) | CAGGTGCAGCTGGTGGAGTCTGGGGGAGGCGTGGTCCAGCCTGGGAGG<br>TCCCTGAGACTCTCCTGTGCAGCCTCTGGATTCACCTTCAGTAACTAT<br>GCTCTGCACTGGGTCCGCCAGGCTCCAGGCAAGGGGCTGGAGTGGGTG<br>GCACTTATATCATATGATGGAAGCGATAAATACTACGCAGACTCCGTG<br>AAGGGCCGATTCGCCATCTCCAGAGACAATTCCAAGAACACGCTGTAT<br>CTGCAAATGAACAGCCTGAGAGCTGAGGACACGGCTGTGTATTACTGT<br>GCGAGAGATCGGGAATATTGTACTTATAGTAGCTGCTCCTATGATGCT<br>TTTGATATCTGGGGCCAAGGGACAATGGTCACCGTCTCTTCA |
| 6 | NA sequence of 9B3 heavy chain V domain 2 (9B3-VH2) | CAGGTTCAGCTGGTGGAGTCTGGGGGGGGCGTGGTCCAGCCTGGGAGG<br>TCCCTGAGACTCTCCTGTGCAGCCTCTGGATTCACCTTCAGTAGCTTT<br>GCTATGCACTGGGTCCGCCAGGCTCCAGGCAAGGGGCTGGAGTGGGTG<br>GCACTTATACCGTTTGATGGAAGCAGTAACTATTACGCAGACTCCGTG<br>AAGGGCCGATTCACCATCTCCAGAGACAATTCCAAGAACACGCTGTAT<br>CTGCAAATGAACAGCCTGAGAGCTGAGGACACGGCTGTGTATTACTGT<br>GCGAGAGATAGGAATTACTATGGTTCGGGGAGTTTTTCCTTTGATGCT<br>TTTGATATCTGGGGCCAAGGGACACTGGTCACCGTCTCCTCA |
| 7 | AA sequence of 9B3 full length light chain (9B3-LC) | DIQMTQSPSSLSASVGDRVTITCRASQGISSWLAWYQQKPEKAPKSLI<br>YAASSLQSGVPSRFSGSGSGTDFTLTISSLQPEDYATYYCQQYNSYPY<br>TFGQGTKLEIKRTVAAPSVFIFPPSDEQLKSGTASVVCLLNNFYPREA<br>KVQWKVDNALQSGNSQESVTEQDSKDSTYSLSSTLTLSKADYEKHKVY<br>ACEVTHQGLSSPVTKSFNRGEC |
| 8 | NA sequence of 9B3 full length light chain (9B3-LC) | GACATCCAGATGACCCAGTCTCCATCCTCACTGTCTGCATCTGTAGGA<br>GACAGAGTCACCATCACTTGTCGGGCGAGTCAGGGTATTAGCAGCTGG<br>TTAGCCTGGTATCAGCAGAAACCAGAGAAAGCCCCTAAGTCCCTGATC<br>TATGCTGCATCCAGTTTGCAGAGTGGGGTCCCATCAAGGTTCAGCGGC<br>AGTGGATCTGGGACAGATTTCACTCTCACCATCAGTAGCCTGCAGCCT<br>GAAGATTATGCAACTTATTACTGCCAACAGTATAATAGTTACCCGTAC<br>ACTTTTGGCCAGGGGACCAAGCTGGAGATCAAACGTACTGTGGCTGCA<br>CCATCTGTCTTCATCTTCCCGCCATCTGATGAGCAGTTGAAATCTGGA |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| | | ACTGCCTCTGTTGTGTGCCTGCTGAATAACTTCTATCCCAGAGAGGCC<br>AAAGTACAGTGGAAGGTGGATAACGCCCTCCAATCGGGTAACTCCCAG<br>GAGAGTGTCACAGAGCAGGACAGCAAGGACAGCACCTACAGCCTCAGC<br>AGCACCCTGACGCTGAGCAAAGCAGACTACGAGAAACACAAAGTCTAC<br>GCCTGCGAAGTCACCCATCAGGGCCTGAGCTCGCCCGTCACAAAGAGC<br>TTCAACAGGGGAGAGTGT |
| 9 | AA sequence of 9B3 full length heavy chain with VH1 and effector null mutation IgG1 constant domain (9B3-hIgG1-3m-HC1) | QVQLVESGGGVVQPGRSLRLSCAASGFTFSNYALHWVRQAPGKGLEWV<br>ALISYDGSDKYYADSVKGRFAISRDNSKNTLYLQMNSLRAEDTAVYYC<br>ARDREYCTYSSCSYDAFDIWGQGTMVTVSSASTKGPSVFPLAPSSKST<br>SGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPA<br>PEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKA<br>LPAPIEKTISKAKGQPREPQVYTLPPSREEMTKNQVSLTCLVKGFYPS<br>DIAVEWESNGQPENNYKTTPPVLDSDGSFFLYSKLTVDKSRWQQGNVF<br>SCSVMHEALHNHYTQKSLSLSPG |
| 10 | NA sequence of 9B3 full length heavy chain with VH1 and effector null mutation IgG1 constant domain (9B3-hIgG1-3m-HC1) | CAGGTGCAGCTGGTGGAGTCTGGGGGAGGCGTGGTCCAGCCTGGGAGG<br>TCCCTGAGACTCTCCTGTGCAGCCTCTGGATTCACCTTCAGTAACTAT<br>GCTCTGCACTGGGTCCGCCAGGCTCCAGGCAAGGGGCTGGAGTGGGTG<br>GCACTTATATCATATGATGGAAGCGATAAATACTACGCAGACTCCGTG<br>AAGGGCCGATTCGCCATCTCCAGAGACAATTCCAAGAACACGCTGTAT<br>CTGCAAATGAACAGCCTGAGAGCTGAGGACACGGCTGTGTATTACTGT<br>GCGAGAGATCGGGAATATTGTACTTATAGTAGCTGCTCCTATGATGCT<br>TTTGATATCTGGGGCCAAGGGACAATGGTCACCGTCTCTTCAGCGTCG<br>ACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCC<br>GAACCGGTGACGGTGTCGTGGAACTCAGGCGCCCTGACCAGCGGCGTG<br>CACACCTTCCCGGCTGTCCTACAGTCCTCAGGACTCTACTCCCTCAGC<br>AGCGTGGTGACCGTGCCCTCCAGCAGCTTGGGCACCCAGACCTACATC<br>TGCAACGTGAATCACAAGCCCAGCAACACCAAGGTGGACAAGAAAGTT<br>GAGCCCAAATCTTGTGACAAAACTCACACATGCCCACCGTGCCCAGCA<br>CCTGAAGCCGCTGGGGCACCGTCAGTCTTCCTCTTCCCCCCAAAACCC<br>AAGGACACCCTCATGATCTCCCGGACCCCTGAGGTCACATGCGTGGTG<br>GTGGACGTGAGCCACGAAGACCCTGAGGTCAAGTTCAACTGGTACGTG<br>GACGGCGTGGAGGTGCATAATGCCAAGACAAAGCCGCGGGAGGAGCAG<br>TACAACAGCACGTACCGTGTGGTCAGCGTCCTCACCGTCCTGCACCAG<br>GACTGGCTGAATGGCAAGGAGTACAAGTGCAAGGTCTCCAACAAAGCC<br>CTCCCAGCCCCCATCGAGAAAACCATCTCCAAAGCCAAAGGGCAGCCC<br>CGAGAACCACAGGTGTACACCCTGCCCCCATCCCGGGAGGAGATGACC<br>AAGAACCAGGTCAGCCTGACCTGCCTGGTCAAAGGCTTCTATCCCAGC<br>GACATCGCCGTGGAGTGGGAGAGCAATGGGCAGCCGGAGAACAACTAC<br>AAGACCACGCCTCCCGTGCTGGACTCCGACGGCTCCTTCTTCCTCTAT<br>AGCAAGCTCACCGTGGACAAGAGCAGGTGGCAGCAGGGGAACGTCTTC<br>TCATGCTCCGTGATGCATGAGGCTCTGCACAACCACTACACGCAGAAG<br>AGCCTCTCCCTGTCCCCGGGT |
| 11 | AA sequence of 9B3 full length heavy chain with VH2 and effector null mutation IgG1 constant domain (9B3-hIgG1-3m-HC2) | QVQLVESGGGVVQPGRSLRLSCAASGFTFSSFAMHWVRQAPGKGLEWV<br>ALIPFDGSSNYYADSVKGRFTISRDNSKNTLYLQMNSLRAEDTAVYYC<br>ARDRNYYGSGSFSFDAFDIWGQGTLVTVSSASTKGPSVFPLAPSSKST<br>SGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPA<br>PEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKA<br>LPAPIEKTISKAKGQPREPQVYTLPPSREEMTKNQVSLTCLVKGFYPS<br>DIAVEWESNGQPENNYKTTPPVLDSDGSFFLYSKLTVDKSRWQQGNVF<br>SCSVMHEALHNHYTQKSLSLSPG |
| 12 | NA sequence of 9B3 full length heavy chain with VH2 and effector null mutation IgG1 constant domain (9B3-hIgG1-3m-HC2) | CAGGTTCAGCTGGTGGAGTCTGGGGGGGGCGTGGTCCAGCCTGGGAGG<br>TCCCTGAGACTCTCCTGTGCAGCCTCTGGATTCACCTTCAGTAGCTTT<br>GCTATGCACTGGGTCCGCCAGGCTCCAGGCAAGGGGCTGGAGTGGGTG<br>GCACTTATACCGTTTGATGGAAGCAGTAACTATTACGCAGACTCCGTG<br>AAGGGCCGATTCACCATCTCCAGAGACAATTCCAAGAACACGCTGTAT<br>CTGCAAATGAACAGCCTGAGAGCTGAGGACACGGCTGTGTATTACTGT<br>GCGAGAGATAGGAATTACTATGGTTCGGGGAGTTTTTCCTTTGATGCT<br>TTTGATATCTGGGGCCAAGGGACACTGGTCACCGTCTCCTCAGCGTCG<br>ACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCC<br>GAACCGGTGACGGTGTCGTGGAACTCAGGCGCCCTGACCAGCGGCGTG<br>CACACCTTCCCGGCTGTCCTACAGTCCTCAGGACTCTACTCCCTCAGC |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| | | AGCGTGGTGACCGTGCCCTCCAGCAGCTTGGGCACCCAGACCTACATC<br>TGCAACGTGAATCACAAGCCCAGCAACACCAAGGTGGACAAGAAAGTT<br>GAGCCCAAATCTTGTGACAAAACTCACACATGCCCACCGTGCCCAGCA<br>CCTGAAGCCGCTGGGGCACCGTCAGTCTTCCTCTTCCCCCCAAAACCC<br>AAGGACACCCTCATGATCTCCCGGACCCCTGAGGTCACATGCGTGGTG<br>GTGGACGTGAGCCACGAAGACCCTGAGGTCAAGTTCAACTGGTACGTG<br>GACGGCGTGGAGGTGCATAATGCCAAGACAAAGCCGCGGGAGGAGCAG<br>TACAACAGCACGTACCGTGTGGTCAGCGTCCTCACCGTCCTGCACCAG<br>GACTGGCTGAATGGCAAGGAGTACAAGTGCAAGGTCTCCAACAAAGCC<br>CTCCCAGCCCCCATCGAGAAAACCATCTCCAAAGCCAAAGGGCAGCCC<br>CGAGAACCACAGGTGTACACCCTGCCCCCATCCCGGGAGGAGATGACC<br>AAGAACCAGGTCAGCCTGACCTGCCTGGTCAAAGGCTTCTATCCCAGC<br>GACATCGCCGTGGAGTGGGAGAGCAATGGGCAGCCGGAGAACAACTAC<br>AAGACCACGCCTCCCGTGCTGGACTCCGACGGCTCCTTCTTCCTCTAT<br>AGCAAGCTCACCGTGGACAAGAGCAGGTGGCAGCAGGGGAACGTCTTC<br>TCATGCTCCGTGATGCATGAGGCTCTGCACAACCACTACACGCAGAAG<br>AGCCTCTCCCTGTCCCCGGGT |
| 23 | NA sequence of 15A9 light chain V domain (15A9-VL) | GAAATTGTGTTGACACAGTCTCCAGCCACCCTGTCTTTGTCTCCAGGG<br>GAAAGAGCCACCCTCTCCTGCAGGGCCAGTCAGAGTGTTAGCAGCTAC<br>TTAGCCTGGTACCAACAGAAACCTGGCCAGGCTCCCAGGCTCCTCATC<br>TATGATGCATCCAACAGGGCCACTGGCATCCCAGCCAGGTTCAGTGGC<br>AGTGGGTCTGGGACAGACTTCACTCTCACCATCAGCAGCCTAGAGCCT<br>GAAGATTTTGCAGTTTATTACTGTCAGCAGCGTAGCAACTGGCCGTGG<br>ACGTTCGGCCAAGGGACCAAGGTGGAAATCAAA |
| 25 | NA sequence of 15A9 heavy chain V domain (15A9-VH) | CAGGTTCAGCTGGTGCAGTCTGGAGCTGAGGTGAAGAAGCCTGGGGCC<br>TCACTGAAGGTCTCCTGCAAGGCTTCTGGTTACCCCTTTACCAACTAT<br>GGTATCAGCTGGGTGCGACAGGCCCCTGGACAAGGGCTTGAGTGGATG<br>GGATGGATCAGCACTTACAATGGTAACACTCACTATGCACAGAAGCTC<br>CAGGGCAGAGTCACCATGACCACAGACACATCCACGACCACAGCCTAC<br>ATGGACCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 26 | AA sequence of 15A9 full length light chain (15A9-LC) | EIVLTQSPATLSLSPGERATLSCRASQSVSSYLAWYQQKPGQAPRLLI<br>YDASNRATGIPARFSGSGSGTDFTLTISSLEPEDFAVYYCQQRSNWPW<br>TFGQGTKVEIKRTVAAPSVFIFPPSDEQLKSGTASVVCLLNNFYPREA<br>KVQWKVDNALQSGNSQESVTEQDSKDSTYSLSSTLTLSKADYEKHKVY<br>ACEVTHQGLSSPVTKSFNRGEC |
| 27 | NA sequence of 15A9 full length light chain (15A9-LC) | GAAATTGTGTTGACACAGTCTCCAGCCACCCTGTCTTTGTCTCCAGGG<br>GAAAGAGCCACCCTCTCCTGCAGGGCCAGTCAGAGTGTTAGCAGCTAC<br>TTAGCCTGGTACCAACAGAAACCTGGCCAGGCTCCCAGGCTCCTCATC<br>TATGATGCATCCAACAGGGCCACTGGCATCCCAGCCAGGTTCAGTGGC<br>AGTGGGTCTGGGACAGACTTCACTCTCACCATCAGCAGCCTAGAGCCT<br>GAAGATTTTGCAGTTTATTACTGTCAGCAGCGTAGCAACTGGCCGTGG<br>ACGTTCGGCCAAGGGACCAAGGTGGAAATCAAACGTACTGTGGCTGCA<br>CCATCTGTCTTCATCTTCCCGCCATCTGATGAGCAGTTGAAATCTGGA<br>ACTGCCTCTGTTGTGTGCCTGCTGAATAACTTCTATCCCAGAGAGGCC<br>AAAGTACAGTGGAAGGTGGATAACGCCCTCCAATCGGGTAACTCCCAG<br>GAGAGTGTCACAGAGCAGGACAGCAAGGACAGCACCTACAGCCTCAGC<br>AGCACCCTGACGCTGAGCAAAGCAGACTACGAGAAACACAAAGTCTAC<br>GCCTGCGAAGTCACCCATCAGGGCCTGAGCTCGCCCGTCACAAAGAGC<br>TTCAACAGGGGAGAGTGT |
| 28 | AA sequence of 15A9 full length heavy chain with effector null mutation IgG1 constant domain (15A9-hIgG1-3m-HC) | QVQLVQSGAEVKKPGASLKVSCKASGYPFTNYGISWVRQAPGQGLEWM<br>GWISTYNGNTHYAQKLQGRVTMTTDTSTTTAYMDLRSLRSDDTAVYYC<br>ARENYYGSGSYRGGMDVWGQGTTVTVSSASTKGPSVFPLAPSSKSTSG<br>GTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPE<br>AAGAPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDI<br>AVEWESNGQPENNYKTTPPVLDSDGSFFLYSKLTVDKSRWQQGNVFSC<br>SVMHEALHNHYTQKSLSLSPG |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 29 | NA sequence of 15A9 full length heavy chain with effector null mutation IgG1 constant domain (15A9-hIgG1-3m-HC) | CAGGTTCAGCTGGTGCAGTCTGGAGCTGAGGTGAAGAAGCCTGGGGCC TCACTGAAGGTCTCCTGCAAGGCTTCTGGTTACCCCTTTACCAACTAT GGTATCAGCTGGGTGCGACAGGCCCCTGGACAAGGGCTTGAGTGGATG GGATGGATCAGCACTTACAATGGTAACACTCACTATGCACAGAAGCTC CAGGGCAGAGTCACCATGACCACAGACACATCCACGACCACAGCCTAC ATGGACCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCAGCGTCGACCAAG GGCCCATCGGTCTTCCCCCTGGCACCCTCCTCCAAGAGCACCTCTGGG GGCACAGCGGCCCTGGGCTGCCTGGTCAAGGACTACTTCCCCGAACCG GTGACGGTGTCGTGGAACTCAGGCGCCCTGACCAGCGGCGTGCACACC TTCCCGGCTGTCCTACAGTCCTCAGGACTCTACTCCCTCAGCAGCGTG GTGACCGTGCCCTCCAGCAGCTTGGGCACCCAGACCTACATCTGCAAC GTGAATCACAAGCCCAGCAACACCAAGGTGGACAAGAAAGTTGAGCCC AAATCTTGTGACAAAACTCACACATGCCCACCGTGCCCAGCACCTGAA GCCGCTGGGGCACCGTCAGTCTTCCTCTTCCCCCCAAAACCCAAGGAC ACCCTCATGATCTCCCGGACCCCTGAGGTCACATGCGTGGTGGTGGAC GTGAGCCACGAAGACCCTGAGGTCAAGTTCAACTGGTACGTGGACGGC GTGGAGGTGCATAATGCCAAGACAAAGCCGCGGGAGGAGCAGTACAAC AGCACGTACCGTGTGGTCAGCGTCCTCACCGTCCTGCACCAGGACTGG CTGAATGGCAAGGAGTACAAGTGCAAGGTCTCCAACAAAGCCCTCCCA GCCCCCATCGAGAAAACCATCTCCAAAGCCAAAGGGCAGCCCCGAGAA CCACAGGTGTACACCCTGCCCCCATCCCGGGAGGAGATGACCAAGAAC CAGGTCAGCCTGACCTGCCTGGTCAAAGGCTTCTATCCCAGCGACATC GCCGTGGAGTGGGAGAGCAATGGGCAGCCGGAGAACAACTACAAGACC ACGCCTCCCGTGCTGGACTCCGACGGCTCCTTCTTCCTCTATAGCAAG CTCACCGTGGACAAGAGCAGGTGGCAGCAGGGGAACGTCTTCTCATGC TCCGTGATGCATGAGGCTCTGCACAACCACTACACGCAGAAGAGCCTC TCCCTGTCCCCGGGT |
| 37 | NA sequence of 15C11 light chain V domain (15C11-VL) | GAAATTGTGTTGACACAGTCTCCAGCCACCCTGTCTTTGTCTCCAGGG GAAAGAGCCACCCTCTCCTGCAGGGCCAGTCAGAGTGTTAGCAGCTAC TTAGCCTGGTACCAACAGAAACCTGGCCAGGCTCCCAGGCTCCTCATC TATGATGCATCCAACAGGGCCACTGGCATCCCAGCCAGGTTCAGTGGC AGTGGGTCTGGGACAGACTTCACTCTCACCATCAGCAGCCTAGAGCCT GAAGATTTTGCAGTTTATTACTGTCAGCAGCGTAGCAACTGGCCGTGG ACGTTCGGCCAAGGGACCAAGGTGGAAATCAAA |
| 39 | NA sequence of 15C11 heavy chain V domain (15C11-VH) | CAGGTTCAGCTGGTGCAGTCTGGAGCTGAGGTGAAGAAGCCTGGGGCC TCAGTGAAGGTCTCCTGCAAGGCTTCTGGTTACTCCTTTACCACCTAT GGTATCAGCTGGGTGCGACAGGCCCCTGGACAAGGGCTTGAGTGGATG GGATGGATCAGCACTTACAATGGTAACACACACTATGCACAGAAGCTC CAGGGCAGAGTCACCATGACCACAGACACATCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 40 | AA sequence of 15C11 full length light chain (15C11-LC) | EIVLTQSPATLSLSPGERATLSCRASQSVSSYLAWYQQKPGQAPRLLI YDASNRATGIPARFSGSGSGTDFTLTISSLEPEDFAVYYCQQRSNWPW TFGQGTKVEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 41 | NA sequence of 15C11 full length light chain (15C11-LC) | GAAATTGTGTTGACACAGTCTCCAGCCACCCTGTCTTTGTCTCCAGGG GAAAGAGCCACCCTCTCCTGCAGGGCCAGTCAGAGTGTTAGCAGCTAC TTAGCCTGGTACCAACAGAAACCTGGCCAGGCTCCCAGGCTCCTCATC TATGATGCATCCAACAGGGCCACTGGCATCCCAGCCAGGTTCAGTGGC AGTGGGTCTGGGACAGACTTCACTCTCACCATCAGCAGCCTAGAGCCT GAAGATTTTGCAGTTTATTACTGTCAGCAGCGTAGCAACTGGCCGTGG ACGTTCGGCCAAGGGACCAAGGTGGAAATCAAACGTACTGTGGCTGCA CCATCTGTCTTCATCTTCCCGCCATCTGATGAGCAGTTGAAATCTGGA ACTGCCTCTGTTGTGTGCCTGCTGAATAACTTCTATCCCAGAGAGGCC AAAGTACAGTGGAAGGTGGATAACGCCCTCCAATCGGGTAACTCCCAG GAGAGTGTCACAGAGCAGGACAGCAAGGACAGCACCTACAGCCTCAGC AGCACCCTGACGCTGAGCAAAGCAGACTACGAGAAACACAAAGTCTAC GCCTGCGAAGTCACCCATCAGGGCCTGAGCTCGCCCGTCACAAAGAGC TTCAACAGGGGAGAGTGT |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 42 | AA sequence of 15C11 full length heavy chain with effector null mutation IgG1 constant domain (15C11-hIgG1-3m-HC) | QVQLVQSGAEVKKPGASVKVSCKASGYSFTTYGISWVRQAPGQGLEWM<br>GWISTYNGNTHYAQKLQGRVTMTTDTSTRTAYMELRSLRSDDTAVYYC<br>ARENYYGSGSYRGGMDVWGQGTTVTVSSASTKGPSVFPLAPSSKSTSG<br>GTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPE<br>AAGAPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDI<br>AVEWESNGQPENNYKTTPPVLDSDGSFFLYSKLTVDKSRWQQGNVFSC<br>SVMHEALHNHYTQKSLSLSPG |
| 43 | NA sequence of 15C11 full length heavy chain with effector null mutation IgG1 constant domain (15C11-hIgG1-3m-HC) | CAGGTTCAGCTGGTGCAGTCTGGAGCTGAGGTGAAGAAGCCTGGGGCC<br>TCAGTGAAGGTCTCCTGCAAGGCTTCTGGTTACTCCTTTACCACCTAT<br>GGTATCAGCTGGGTGCGACAGGCCCCTGGACAAGGGCTTGAGTGGATG<br>GGATGGATCAGCACTTACAATGGTAACACACACTATGCACAGAAGCTC<br>CAGGGCAGAGTCACCATGACCACAGACACATCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCAGCGTCGACCAAG<br>GGCCCATCGGTCTTCCCCCTGGCACCCTCCTCCAAGAGCACCTCTGGG<br>GGCACAGCGGCCCTGGGCTGCCTGGTCAAGGACTACTTCCCCGAACCG<br>GTGACGGTGTCGTGGAACTCAGGCGCCCTGACCAGCGGCGTGCACACC<br>TTCCCGGCTGTCCTACAGTCCTCAGGACTCTACTCCCTCAGCAGCGTG<br>GTGACCGTGCCCTCCAGCAGCTTGGGCACCCAGACCTACATCTGCAAC<br>GTGAATCACAAGCCCAGCAACACCAAGGTGGACAAGAAAGTTGAGCCC<br>AAATCTTGTGACAAAACTCACACATGCCCACCGTGCCCAGCACCTGAA<br>GCCGCTGGGGCACCGTCAGTCTTCCTCTTCCCCCCAAAACCCAAGGAC<br>ACCCTCATGATCTCCCGGACCCCTGAGGTCACATGCGTGGTGGTGGAC<br>GTGAGCCACGAAGACCCTGAGGTCAAGTTCAACTGGTACGTGGACGGC<br>GTGGAGGTGCATAATGCCAAGACAAAGCCGCGGGAGGAGCAGTACAAC<br>AGCACGTACCGTGTGGTCAGCGTCCTCACCGTCCTGCACCAGGACTGG<br>CTGAATGGCAAGGAGTACAAGTGCAAGGTCTCCAACAAAGCCCTCCCA<br>GCCCCCATCGAGAAAACCATCTCCAAAGCCAAAGGGCAGCCCCGAGAA<br>CCACAGGTGTACACCCTGCCCCCATCCCGGGAGGAGATGACCAAGAAC<br>CAGGTCAGCCTGACCTGCCTGGTCAAAGGCTTCTATCCCAGCGACATC<br>GCCGTGGAGTGGGAGAGCAATGGGCAGCCGGAGAACAACTACAAGACC<br>ACGCCTCCCGTGCTGGACTCCGACGGCTCCTTCTTCCTCTATAGCAAG<br>CTCACCGTGGACAAGAGCAGGTGGCAGCAGGGGAACGTCTTCTCATGC<br>TCCGTGATGCATGAGGCTCTGCACAACCACTACACGCAGAAGAGCCTC<br>TCCCTGTCCCCGGGT |
| 51 | NA sequence of 22F9 light chain V domain (22F9-VL) | GCCATCCAGTTGACCCAGTCTCCATCCTCCCTGTCTGCATCTGTAGGA<br>GACAGAGTCACCATCACTTGCCGGGCAAGTCAGGGCATTAGCAGTGCT<br>TTAGCCTGGTATCAGCAGAAACCAGGGAAAGCTCCTAAGCTCCTGATC<br>TATGATGCCTCCAGTTTGGAAAGTGGGGTCCCATCAAGGTTCAGCGGC<br>AGTGGATCTGGGACAGATTTCACTCTCACCATCAGCAGCCTGCAGCCT<br>GAAGATTTTGCAACTTATTACTGTCAACAGTTTAATAGTTACCCGCTC<br>ACTTTCGGCGGAGGGACCAAGGTGGAGATCAAA |
| 53 | NA sequence of 22F9 heavy chain V domain (22F9-VH) | CAGGTCCAGCTTGTGCAGTCTGGGGCTGAGGTGAAGAAGCCTGGGGCC<br>TCAGTGAAGGTTTCCTGCAAGGCTTCTGGATACACCTTCACTAGCTAT<br>GCTATGCATTGGGTGCGCCAGGCCCCCGGACAAAGGCTTGAGTGGATG<br>GGATGGATCAACGCTGGCAATGGTAACACAAAATATTCACAGAAGTTC<br>CAGGGCAGAGTCACCATTACCAGGGACACATCCGCGAGCACAGCCTAC<br>ATGGAGCTGAGCAGCCTGAGATCTGAAGACACGGCTGTGTATTACTGT<br>GCGAGAGGGTATAGCAGTGCCTGGTTCGATGCTTTTGATATCTGGGGC<br>CAAGGGACAATGGTCACCGTCTCTTCA |
| 54 | AA sequence of 22F9 full length light chain (22F9-LC) | AIQLTQSPSSLSASVGDRVTITCRASQGISSALAWYQQKPGKAPKLLI<br>YDASSLESGVPSRFSGSGSGTDFTLTISSLQPEDFATYYCQQFNSYPL<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHKVY<br>ACEVTHQGLSSPVTKSFNRGEC |
| 55 | NA sequence of 22F9 full length light chain (22F9-LC) | GCCATCCAGTTGACCCAGTCTCCATCCTCCCTGTCTGCATCTGTAGGA<br>GACAGAGTCACCATCACTTGCCGGGCAAGTCAGGGCATTAGCAGTGCT<br>TTAGCCTGGTATCAGCAGAAACCAGGGAAAGCTCCTAAGCTCCTGATC<br>TATGATGCCTCCAGTTTGGAAAGTGGGGTCCCATCAAGGTTCAGCGGC<br>AGTGGATCTGGGACAGATTTCACTCTCACCATCAGCAGCCTGCAGCCT<br>GAAGATTTTGCAACTTATTACTGTCAACAGTTTAATAGTTACCCGCTC |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| | | ACTTTCGGCGGAGGGACCAAGGTGGAGATCAAACGTACTGTGGCTGCA CCATCTGTCTTCATCTTCCCGCCATCTGATGAGCAGTTGAAATCTGGA ACTGCCTCTGTTGTGTGCCTGCTGAATAACTTCTATCCCAGAGAGGCC AAAGTACAGTGGAAGGTGGATAACGCCCTCCAATCGGGTAACTCCCAG GAGAGTGTCACAGAGCAGGACAGCAAGGACAGCACCTACAGCCTCAGC AGCACCCTGACGCTGAGCAAAGCAGACTACGAGAAACACAAAGTCTAC GCCTGCGAAGTCACCCATCAGGGCCTGAGCTCGCCCGTCACAAAGAGC TTCAACAGGGGAGAGTGT |
| 56 | AA sequence of 22F9 full length heavy chain with effector null mutation IgG1 constant domain (22F9-hIgG1-3m-HC) | QVQLVOSGAEVKKPGASVKVSCKASGYTFTSYAMHWVRQAPGQRLEWM GWINAGNGNTKYSQKFQGRVTITRDTSASTAYMELSSLRSEDTAVYYC ARGYSSAWFDAFDIWGQGTMVTVSSASTKGPSVFPLAPSSKSTSGGTA ALGCLVKDYFPEPVTVSWNSGALTSGVHTFPAVLQSSGLYSLSSVVTV PSSSLGTQTYICNVNHKPSNTKVDKKVEPKSCDKTHTCPPCPAPEAAG APSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPI EKTISKAKGQPREPQVYTLPPSREEMTKNQVSLTCLVKGFYPSDIAVE WESNGQPENNYKTTPPVLDSDGSFFLYSKLTVDKSRWQQGNVFSCSVM HEALHNHYTQKSLSLSPG |
| 57 | NA sequence of 22F9 full length heavy chain with effector null mutation IgG1 constant domain (22F9-hIgG1-3m-HC) | CAGGTCCAGCTTGTGCAGTCTGGGGCTGAGGTGAAGAAGCCTGGGGCC TCAGTGAAGGTTTCCTGCAAGGCTTCTGGATACACCTTCACTAGCTAT GCTATGCATTGGGTGCGCCAGGCCCCCGGACAAAGGCTTGAGTGGATG GGATGGATCAACGCTGGCAATGGTAACACAAAATATTCACAGAAGTTC CAGGGCAGAGTCACCATTACCAGGGACACATCCGCGAGCACAGCCTAC ATGGAGCTGAGCAGCCTGAGATCTGAAGACACGGCTGTGTATTACTGT GCGAGAGGGTATAGCAGTGCCTGGTTCGATGCTTTTGATATCTGGGGC CAAGGGACAATGGTCACCGTCTCTTCAGCGTCGACCAAGGGCCCATCG GTCTTCCCCCTGGCACCCTCCTCCAAGAGCACCTCTGGGGGCACAGCG GCCCTGGGCTGCCTGGTCAAGGACTACTTCCCCGAACCGGTGACGGTG TCGTGGAACTCAGGCGCCCTGACCAGCGGCGTGCACACCTTCCCGGCT GTCCTACAGTCCTCAGGACTCTACTCCCTCAGCAGCGTGGTGACCGTG CCCTCCAGCAGCTTGGGCACCCAGACCTACATCTGCAACGTGAATCAC AAGCCCAGCAACACCAAGGTGGACAAGAAAGTTGAGCCCAAATCTTGT GACAAAACTCACACATGCCCACCGTGCCCAGCACCTGAAGCCGCTGGG GCACCGTCAGTCTTCCTCTTCCCCCCAAAACCCAAGGACACCCTCATG ATCTCCCGGACCCCTGAGGTCACATGCGTGGTGGTGGACGTGAGCCAC GAAGACCCTGAGGTCAAGTTCAACTGGTACGTGGACGGCGTGGAGGTG CATAATGCCAAGACAAAGCCGCGGGAGGAGCAGTACAACAGCACGTAC CGTGTGGTCAGCGTCCTCACCGTCCTGCACCAGGACTGGCTGAATGGC AAGGAGTACAAGTGCAAGGTCTCCAACAAAGCCCTCCCAGCCCCCATC GAGAAAACCATCTCCAAAGCCAAAGGGCAGCCCCGAGAACCACAGGTG TACACCCTGCCCCCATCCCGGGAGGAGATGACCAAGAACCAGGTCAGC CTGACCTGCCTGGTCAAAGGCTTCTATCCCAGCGACATCGCCGTGGAG TGGGAGAGCAATGGGCAGCCGGAGAACAACTACAAGACCACGCCTCCC GTGCTGGACTCCGACGGCTCCTTCTTCCTCTATAGCAAGCTCACCGTG GACAAGAGCAGGTGGCAGCAGGGGAACGTCTTCTCATGCTCCGTGATG CATGAGGCTCTGCACAACCACTACACGCAGAAGAGCCTCTCCCTGTCC CCGGGT |
| 65 | NA sequence of 26B11 light chain V domain (26B11-VL) | GACATCCAGATGACCCAGTCTCCATCCTCACTGTCTGCATCTGTAGGA GACAGAGTCACCATCACTTGTCGGGCGAGTCAGGGTATTAGCAACTGG TTAGCCTGGTATCAGCAGAAACCAGAGAAAGCCCCTAAGTCCCTGATC TATGCTGCATCCAGTTTGCAAAGTGGGGTCCCATCAAGGTTCAGCGGC AGTGGATCTGGGACAGATTTCACTCTCACCATCAGCAGCCTGCAGCCT GAAGATTTTGCAACTTATTACTGCCAACAGTATAATAGTTACCCGTAC ACTTTTGGCCAGGGGACCAAGCTGGAGATCAAA |
| 67 | NA sequence of 26B11 heavy chain V domain 1 (26B11-VH1) | CAGGTGCAGCTGGTGGAGTCTGGGGGAGGCGTGGTCCAGCCTGGGAGG TCCCTGAGACTCTCCTGTGCAGCCTCTGGATTCACCTTCAGTAACTAT GCTCTGCACTGGGTCCGCCAGGCTCCAGGCAAGGGGCTGGAGTGGGTG GCACTTATATCATATGATGGAAGCGATAAATACTACGCAGACTCCGTG AAGGGCCGATTCGCCATCTCCAGAGACAATTCCAAGAACACGCTGTAT CTGCAAATGAACAGCCTGAGAGCTGAGGACACGGCTGTGTATTACTGT GCGAGAGATCGGGAATATTGTACTTATAGTAGCTGCTCCTATGATGCT TTTGATATCTGGGGCCAAGGGACAATGGTCACCGTCTCTTCA |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 69 | NA sequence of 26B11 heavy chain V domain 2 (26B11-VH2) | CAGGTTCAGCTGGTGGAGTCTGGGGGGGGCGTGGTCCAGCCTGGGAGG TCCCTGAGACTCTCCTGTGCAGCCTCTGGATTCACCTTCAGTAGCTTT GCTATGCACTGGGTCCGCCAGGCTCCAGGCAAGGGGCTGGAGTGGGTG GCACTTATACCGTTTGATGGAAGCAGTAACTATTACGCAGACTCCGTG AAGGGCCGATTCACCATCTCCAGAGACAATTCCAAGAACACGCTGTAT CTGCAAATGAACAGCCTGAGAGCTGAGGACACGGCTGTGTATTACTGT GCGAGAGATAGGAATTACTATGGTTCGGGGAGTTTTTCCTTTGATGCT TTTGATATCTGGGGCCAAGGGACACTGGTCACCGTCTCCTCA |
| 71 | NA sequence of 26B11 heavy chain V domain MDX (26B11-VH-MDX) | CAGGTTCAGCTGGTGGAGTCTGGGGGAGGCGTGGTCCAGCCTGGGAGG TCCCTGAGACTCTCCTGTGAAGCCTCTGGATTCACCTTCAGTAACTAT GCTATTCACTGGGTCCGCCAGGCTCCAGGCAAGGGGCTGGAATGGGTG GCACTTATACCATATGATGGAAGCAATAACTATTACGCAGCCTCCGTG AAGGGCCGATTCACCATCTCCAGAGACAATTCCAAGAACACGCTGTAT CTGCAAATGAACAGCCTGAGAGCTGAGGACACGGCTGTGTATTACTGT GCGAGAGATAGGAATTACTATGGTTCGGGGAGTTTTTCCTTTGATGCT TTTGATATCTGGGGCCAAGGCACAATGGTCACCGTCTCCTCA |
| 72 | AA sequence of 26B11 full length light chain (26B11-LC) | DIQMTQSPSSLSASVGDRVTITCRASQGISNWLAWYQQKPEKAPKSLI YAASSLQSGVPSRFSGSGSGTDFTLTISSLQPEDFATYYCQQYNSYPY TFGQGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 73 | NA sequence of 26B11 full length light chain (26B11-LC) | GACATCCAGATGACCCAGTCTCCATCCTCACTGTCTGCATCTGTAGGA GACAGAGTCACCATCACTTGTCGGGCGAGTCAGGGTATTAGCAACTGG TTAGCCTGGTATCAGCAGAAACCAGAGAAAGCCCCTAAGTCCCTGATC TATGCTGCATCCAGTTTGCAAAGTGGGGTCCCATCAAGGTTCAGCGGC AGTGGATCTGGGACAGATTTCACTCTCACCATCAGCAGCCTGCAGCCT GAAGATTTTGCAACTTATTACTGCCAACAGTATAATAGTTACCCGTAC ACTTTTGGCCAGGGGACCAAGCTGGAGATCAAACGTACTGTGGCTGCA CCATCTGTCTTCATCTTCCCGCCATCTGATGAGCAGTTGAAATCTGGA ACTGCCTCTGTTGTGTGCCTGCTGAATAACTTCTATCCCAGAGAGGCC AAAGTACAGTGGAAGGTGGATAACGCCCTCCAATCGGGTAACTCCCAG GAGAGTGTCACAGAGCAGGACAGCAAGGACAGCACCTACAGCCTCAGC AGCACCCTGACGCTGAGCAAAGCAGACTACGAGAAACACAAAGTCTAC GCCTGCGAAGTCACCCATCAGGGCCTGAGCTCGCCCGTCACAAAGAGC TTCAACAGGGGAGAGTGT |
| 74 | AA sequence of 26B11 full length heavy chain 2 with effector null mutation IgG1 constant domain (26B11-hIgG1-3m-HC) | QVQLVESGGGVVQPGRSLRLSCAASGFTFSSFAMHWVRQAPGKGLEWV ALIPFDGSSNYYADSVKGRFTISRDNSKNTLYLQMNSLRAEDTAVYYC ARDRNYYGSGSFSFDAFDIWGQGTLVTVSSASTKGPSVFPLAPSSKST SGGTAALGCLVKDYFPEPVTVSWNSGALTSGVHTFPAVLQSSGLYSLS SVVTVPSSSLGTQTYICNVNHKPSNTKVDKKVEPKSCDKTHTCPPCPA PEAAGAPSVFLFPPKPKDTLMISRTPEVTCVVVDVSHEDPEVKFNWYV DGVEVHNAKTKPREEQYNSTYRVVSVLTVLHQDWLNGKEYKCKVSNKA LPAPIEKTISKAKGQPREPQVYTLPPSREEMTKNQVSLTCLVKGFYPS DIAVEWESNGQPENNYKTTPPVLDSDGSFFLYSKLTVDKSRWQQGNVF SCSVMHEALHNHYTQKSLSLSPG |
| 75 | NA sequence of 26B11 full length heavy chain 2 with effector null mutation IgG1 constant domain (26B11-hIgG1-3m-HC) | CAGGTTCAGCTGGTGGAGTCTGGGGGGGGCGTGGTCCAGCCTGGGAGG TCCCTGAGACTCTCCTGTGCAGCCTCTGGATTCACCTTCAGTAGCTTT GCTATGCACTGGGTCCGCCAGGCTCCAGGCAAGGGGCTGGAGTGGGTG GCACTTATACCGTTTGATGGAAGCAGTAACTATTACGCAGACTCCGTG AAGGGCCGATTCACCATCTCCAGAGACAATTCCAAGAACACGCTGTAT CTGCAAATGAACAGCCTGAGAGCTGAGGACACGGCTGTGTATTACTGT GCGAGAGATAGGAATTACTATGGTTCGGGGAGTTTTTCCTTTGATGCT TTTGATATCTGGGGCCAAGGGACACTGGTCACCGTCTCCTCAGCGTCG ACCAAGGGCCCATCGGTCTTCCCCCTGGCACCCTCCTCCAAGAGCACC TCTGGGGGCACAGCGGCCCTGGGCTGCCTGGTCAAGGACTACTTCCCC GAACCGGTGACGGTGTCGTGGAACTCAGGCGCCCTGACCAGCGGCGTG CACACCTTCCCGGCTGTCCTACAGTCCTCAGGACTCTACTCCCTCAGC AGCGTGGTGACCGTGCCCTCCAGCAGCTTGGGCACCCAGACCTACATC TGCAACGTGAATCACAAGCCCAGCAACACCAAGGTGGACAAGAAAGTT GAGCCCAAATCTTGTGACAAAACTCACACATGCCCACCGTGCCCAGCA CCTGAAGCCGCTGGGGCACCGTCAGTCTTCCTCTTCCCCCCAAAACCC AAGGACACCCTCATGATCTCCCGGACCCCTGAGGTCACATGCGTGGTG GTGGACGTGAGCCACGAAGACCCTGAGGTCAAGTTCAACTGGTACGTG GACGGCGTGGAGGTGCATAATGCCAAGACAAAGCCGCGGGAGGAGCAG TACAACAGCACGTACCGTGTGGTCAGCGTCCTCACCGTCCTGCACCAG |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| | | GACTGGCTGAATGGCAAGGAGTACAAGTGCAAGGTCTCCAACAAAGCC CTCCCAGCCCCCATCGAGAAAACCATCTCCAAAGCCAAAGGGCAGCCC CGAGAACCACAGGTGTACACCCTGCCCCCATCCCGGGAGGAGATGACC AAGAACCAGGTCAGCCTGACCTGCCTGGTCAAAGGCTTCTATCCCAGC GACATCGCCGTGGAGTGGGAGAGCAATGGGCAGCCGGAGAACAACTAC AAGACCACGCCTCCCGTGCTGGACTCCGACGGCTCCTTCTTCCTCTAT AGCAAGCTCACCGTGGACAAGAGCAGGTGGCAGCAGGGGAACGTCTTC TCATGCTCCGTGATGCATGAGGCTCTGCACAACCACTACACGCAGAAG AGCCTCTCCCTGTCCCCGGGT |
| 89 | NA sequence of 7D4 light chain V domain (7D4-VL) | GCCATCCAGTTGACCCAGTCTCCATCCTCCCTGTCTGCATCTGTAGGA GACAGAGTCACCATCACTTGCCGGGCAAGTCAGGGCATTAGCAGTGCT TTAGCCTGGTATCAGCAGAAACCAGGGAAAGCTCCTAAGCTCCTGATC TATGATGCCTCCAGTTTGGAAAGTGGGGTCCCATCAAGGTTCAGCGGC AGTGGATCTGGGACAGATTTCACTCTCACCATCAGCAGCCTGCAGCCT GAAGATTTTGCAACTTATTACTGTCAACAGTTTAATAGTTACCCGCTC ACTTTCGGCGGAGGGACCAAGGTGGAGATCAAA |
| 91 | NA sequence of 7D4 heavy chain V domain (7D4-VH) | CAGGTGCAGCTGGTGCAGTCTGGAGCTGAGGTGAAGAAGCCTGGGGCC TCAGTGAAGGTCTCCTGCAAGGCTTCTGGTTACACCTTTACCAGCTAT GGTATCAACTGGGTGCGACAGGCCCCTGGACAAGGGCTTGAGTGGATG GGGTGGATCAGCACTTACAATGGTAACACAAACTCTGCACAGAAGCTC CAGGGCAGAGTCACCATGACCACAGACACATCCACGAGCACAGCCTAC ATGGAGCTGAGGAGCCTGAGATCTGACGACACGGCCGTGTATTACTGT GCGAGAGCGCATAGCAGCAGCTGGTTTGATGCTTTTGATATCTGGGGC CAAGGGACAATGGTCACCGTCTCCTCA |
| 92 | AA sequence of 7D4 full length light chain (7D4-LC) | AIQLTQSPSSLSASVGDRVTITCRASQGISSALAWYQQKPGKAPKLLI YDASSLESGVPSRFSGSGSGTDFTLTISSLQPEDFATYYCQQFNSYPL TFGGGTKVEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 93 | NA sequence of 7D4 full length light chain (7D4-LC) | GCCATCCAGTTGACCCAGTCTCCATCCTCCCTGTCTGCATCTGTAGGA GACAGAGTCACCATCACTTGCCGGGCAAGTCAGGGCATTAGCAGTGCT TTAGCCTGGTATCAGCAGAAACCAGGGAAAGCTCCTAAGCTCCTGATC TATGATGCCTCCAGTTTGGAAAGTGGGGTCCCATCAAGGTTCAGCGGC AGTGGATCTGGGACAGATTTCACTCTCACCATCAGCAGCCTGCAGCCT GAAGATTTTGCAACTTATTACTGTCAACAGTTTAATAGTTACCCGCTC ACTTTCGGCGGAGGGACCAAGGTGGAGATCAAACGTACTGTGGCTGCA CCATCTGTCTTCATCTTCCCGCCATCTGATGAGCAGTTGAAATCTGGA ACTGCCTCTGTTGTGTGCCTGCTGAATAACTTCTATCCCAGAGAGGCC AAAGTACAGTGGAAGGTGGATAACGCCCTCCAATCGGGTAACTCCCAG GAGAGTGTCACAGAGCAGGACAGCAAGGACAGCACCTACAGCCTCAGC AGCACCCTGACGCTGAGCAAAGCAGACTACGAGAAACACAAAGTCTAC GCCTGCGAAGTCACCCATCAGGGCCTGAGCTCGCCCGTCACAAAGAGC TTCAACAGGGGAGAGTGT |
| 94 | AA sequence of 7D4 full length heavy chain with effector null mutation IgG1 constant domain (7D4-hIgG1-3m-HC) | QVQLVQSGAEVKKPGASVKVSCKASGYTFTSYGINWVRQAPGQGLEWM GWISTYNGNTNSAQKLQGRVTMTTDTSTSTAYMELRSLRSDDTAVYYC ARAHSSSWFDAFDIWGQGTMVTVSSASTKGPSVFPLAPSSKSTSGGTA ALGCLVKDYFPEPVTVSWNSGALTSGVHTFPAVLQSSGLYSLSSVVTV PSSSLGTQTYICNVNHKPSNTKVDKKVEPKSCDKTHTCPPCPAPEAAG APSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPI EKTISKAKGQPREPQVYTLPPSREEMTKNQVSLTCLVKGFYPSDIAVE WESNGQPENNYKTTPPVLDSDGSFFLYSKLTVDKSRWQQGNVFSCSVM HEALHNHYTQKSLSLSPG |
| 95 | NA sequence of 7D4 full length heavy chain with effector null mutation IgG1 constant domain (7D4-hIgG1-3m-HC) | CAGGTGCAGCTGGTGCAGTCTGGAGCTGAGGTGAAGAAGCCTGGGGCC TCAGTGAAGGTCTCCTGCAAGGCTTCTGGTTACACCTTTACCAGCTAT GGTATCAACTGGGTGCGACAGGCCCCTGGACAAGGGCTTGAGTGGATG GGGTGGATCAGCACTTACAATGGTAACACAAACTCTGCACAGAAGCTC CAGGGCAGAGTCACCATGACCACAGACACATCCACGAGCACAGCCTAC ATGGAGCTGAGGAGCCTGAGATCTGACGACACGGCCGTGTATTACTGT GCGAGAGCGCATAGCAGCAGCTGGTTTGATGCTTTTGATATCTGGGGC CAAGGGACAATGGTCACCGTCTCCTCAGCGTCGACCAAGGGCCCATCG GTCTTCCCCCTGGCACCCTCCTCCAAGAGCACCTCTGGGGGCACAGCG GCCCTGGGCTGCCTGGTCAAGGACTACTTCCCCGAACCGGTGACGGTG TCGTGGAACTCAGGCGCCCTGACCAGCGGCGTGCACACCTTCCCGGCT GTCCTACAGTCCTCAGGACTCTACTCCCTCAGCAGCGTGGTGACCGTG |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| | | CCCTCCAGCAGCTTGGGCACCCAGACCTACATCTGCAACGTGAATCAC AAGCCCAGCAACACCAAGGTGGACAAGAAAGTTGAGCCCAAATCTTGT GACAAAACTCACACATGCCCACCGTGCCCAGCACCTGAAGCCGCTGGG GCACCGTCAGTCTTCCTCTTCCCCCCAAAACCCAAGGACACCCTCATG ATCTCCCGGACCCCTGAGGTCACATGCGTGGTGGTGGACGTGAGCCAC GAAGACCCTGAGGTCAAGTTCAACTGGTACGTGGACGGCGTGGAGGTG CATAATGCCAAGACAAAGCCGCGGGAGGAGCAGTACAACAGCACGTAC CGTGTGGTCAGCGTCCTCACCGTCCTGCACCAGGACTGGCTGAATGGC AAGGAGTACAAGTGCAAGGTCTCCAACAAAGCCCTCCCAGCCCCCATC GAGAAAACCATCTCCAAAGCCAAAGGGCAGCCCCGAGAACCACAGGTG TACACCCTGCCCCCATCCCGGGAGGAGATGACCAAGAACCAGGTCAGC CTGACCTGCCTGGTCAAAGGCTTCTATCCCAGCGACATCGCCGTGGAG TGGGAGAGCAATGGGCAGCCGGAGAACAACTACAAGACCACGCCTCCC GTGCTGGACTCCGACGGCTCCTTCTTCCTCTATAGCAAGCTCACCGTG GACAAGAGCAGGTGGCAGCAGGGGAACGTCTTCTCATGCTCCGTGATG CATGAGGCTCTGCACAACCACTACACGCAGAAGAGCCTCTCCCTGTCC CCGGGT |
| 103 | NA sequence of 1D1 light chain V domain (1D1-VL) | GAAATTGTGTTGACACAGTCTCCAGCCACCCTGTCTTTGTCTCCAGGG GAAAGAGCCACCCTCTCCTGCAGGGCCAGTCAGAGTGTTAGCAGCTAC TTAGCCTGGTACCAACAGAAACCTGGCCAGGCTCCCAGGCTCCTCATC TATGATGCATCCAACAGGGCCACTGGCATCCCAGCCAGGTTCAGTGGC AGTGGGTCTGGGACAGACTTCACTCTCACCATCAGCAGCCTAGAGCCT GAAGATTTTGCAGTTTATTACTGTCAGCAGCGTAGCAACTGGCCGTGG ACGTTCGGCCAAGGGACCAAGGTGGAAATCAAA |
| 105 | NA sequence of 1D1 heavy chain V domain (1D1-VH) | CAGGTTCAGCTGGTGCAGTCTGGAGCTGAGGTGAAGAAGCCTGGGGCC TCAGTGAAGGTCTCCTGCAAGGCCTCTGGTTACTCCTTTACCTACTAT GGTATCAGCTGGGTGCGACAGGCCCCTGGACAAGGGCTTGAGTGGATG GGATGGATCAGCACTTACAATGGTAACACAAACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 106 | AA sequence of 1D1 full length light chain (1D1-LC) | EIVLTQSPATLSLSPGERATLSCRASQSVSSYLAWYQQKPGQAPRLLI YDASNRATGIPARFSGSGSGTDFTLTISSLEPEDFAVYYCQQRSNWPW TFGQGTKVEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 107 | NA sequence of 1D1 full length light chain (1D1-LC) | GAAATTGTGTTGACACAGTCTCCAGCCACCCTGTCTTTGTCTCCAGGG GAAAGAGCCACCCTCTCCTGCAGGGCCAGTCAGAGTGTTAGCAGCTAC TTAGCCTGGTACCAACAGAAACCTGGCCAGGCTCCCAGGCTCCTCATC TATGATGCATCCAACAGGGCCACTGGCATCCCAGCCAGGTTCAGTGGC AGTGGGTCTGGGACAGACTTCACTCTCACCATCAGCAGCCTAGAGCCT GAAGATTTTGCAGTTTATTACTGTCAGCAGCGTAGCAACTGGCCGTGG ACGTTCGGCCAAGGGACCAAGGTGGAAATCAAACGTACTGTGGCTGCA CCATCTGTCTTCATCTTCCCGCCATCTGATGAGCAGTTGAAATCTGGA ACTGCCTCTGTTGTGTGCCTGCTGAATAACTTCTATCCCAGAGAGGCC AAAGTACAGTGGAAGGTGGATAACGCCCTCCAATCGGGTAACTCCCAG GAGAGTGTCACAGAGCAGGACAGCAAGGACAGCACCTACAGCCTCAGC AGCACCCTGACGCTGAGCAAAGCAGACTACGAGAAACACAAAGTCTAC GCCTGCGAAGTCACCCATCAGGGCCTGAGCTCGCCCGTCACAAAGAGC TTCAACAGGGGAGAGTGT |
| 108 | AA sequence of 1D1 full length heavy chain with effector null mutation IgG1 constant domain (1D1-hIgG1-3m-HC) | QVQLVQSGAEVKKPGASVKVSCKASGYSFTYYGISWVRQAPGQGLEWM GWISTYNGNTNYARMLQGRVTMTTDTSTRTAYMELRSLRSDDTAVYYC ARENYYGSGSYRGGMDVWGQGTTVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPE AAGAPSVFLFPPKPKDTLMISRTPEVTCVVVDVSHEDPEVKFNWYVDG VEVHNAKTKPREEQYNSTYRVVSVLTVLHQDWLNGKEYKCKVSNKALP APIEKTISKAKGQPREPQVYTLPPSREEMTKNQVSLTCLVKGFYPSDI AVEWESNGQPENNYKTTPPVLDSDGSFFLYSKLTVDKSRWQQGNVFSC SVMHEALHNHYTQKSLSLSPG |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 109 | NA sequence of 1D1 full length heavy chain with effector null mutation IgG1 constant domain (1D1-hIgG1-3m-HC) | CAGGTTCAGCTGGTGCAGTCTGGAGCTGAGGTGAAGAAGCCTGGGGCC TCAGTGAAGGTCTCCTGCAAGGCCTCTGGTTACTCCTTTACCTACTAT GGTATCAGCTGGGTGCGACAGGCCCCTGGACAAGGGCTTGAGTGGATG GGATGGATCAGCACTTACAATGGTAACACAAACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCAGCGTCGACCAAG GGCCCATCGGTCTTCCCCCTGGCACCCTCCTCCAAGAGCACCTCTGGG GGCACAGCGGCCCTGGGCTGCCTGGTCAAGGACTACTTCCCCGAACCG GTGACGGTGTCGTGGAACTCAGGCGCCCTGACCAGCGGCGTGCACACC TTCCCGGCTGTCCTACAGTCCTCAGGACTCTACTCCCTCAGCAGCGTG GTGACCGTGCCCTCCAGCAGCTTGGGCACCCAGACCTACATCTGCAAC GTGAATCACAAGCCCAGCAACACCAAGGTGGACAAGAAAGTTGAGCCC AAATCTTGTGACAAAACTCACACATGCCCACCGTGCCCAGCACCTGAA GCCGCTGGGGCACCGTCAGTCTTCCTCTTCCCCCCAAAACCCAAGGAC ACCCTCATGATCTCCCGGACCCCTGAGGTCACATGCGTGGTGGTGGAC GTGAGCCACGAAGACCCTGAGGTCAAGTTCAACTGGTACGTGGACGGC GTGGAGGTGCATAATGCCAAGACAAAGCCGCGGGAGGAGCAGTACAAC AGCACGTACCGTGTGGTCAGCGTCCTCACCGTCCTGCACCAGGACTGG CTGAATGGCAAGGAGTACAAGTGCAAGGTCTCCAACAAAGCCCTCCCA GCCCCCATCGAGAAAACCATCTCCAAAGCCAAAGGGCAGCCCCGAGAA CCACAGGTGTACACCCTGCCCCCATCCCGGGAGGAGATGACCAAGAAC CAGGTCAGCCTGACCTGCCTGGTCAAAGGCTTCTATCCCAGCGACATC GCCGTGGAGTGGGAGAGCAATGGGCAGCCGGAGAACAACTACAAGACC ACGCCTCCCGTGCTGGACTCCGACGGCTCCTTCTTCCTCTATAGCAAG CTCACCGTGGACAAGAGCAGGTGGCAGCAGGGGAACGTCTTCTCATGC TCCGTGATGCATGAGGCTCTGCACAACCACTACACGCAGAAGAGCCTC TCCCTGTCCCCGGGT |
| 117 | NA sequence of 1D1 D5 VH | CAGGTTCAGCTGGTGCAGTCTGGAGCTGAGGTGAAGAAGCCTGGGGCC TCAGTGAAGGTCTCCTGCAAGGCCTCTGGTTACTCCTTTACCTACTAT GGTATCAGCTGGGTGCGACAGGCCCCTGGACAAGGGCTTGAGTGGATG GGATGGATCAGCACTTACAATGGTAACACAAACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCTGGCGCCTTCAGAGGGGGTATGGAC GGTTGGGGCCAAGGGACCACGGTCACCGTCTCCTCA |
| 119 | NA sequence of 1D1 D18 VH | CAGGTTCAGCTGGTGCAGTCTGGAGCTGAGGTGAAGAAGCCTGGGGCC TCAGTGAAGGTCTCCTGCAAGGCCTCTGGTTACTCCTTTACCTACTAT GGTATCAGCTGGGTGCGACAGGCCCCTGGACAAGGGCTTGAGTGGATG GGATGGATCTCTACTTACAATGGTAATACACATTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 121 | NA sequence of 1D1 D21 VH | CAGGTTCAGCTGGTGCAGTCTGGAGCTGAGGTGAAGAAGCCTGGGGCC TCAGTGAAGGTCTCCTGCAAGGCCTCTGGTTACTCCTTTACCTACTAT GGTATCAGCTGGGTGCGACAGGCCCCTGGACAAGGGCTTGAGTGGATG GGATGGATCTCGACCTACAATGGTAAAACACACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 123 | NA sequence of 1D1 D24 VH | CAGGTTCAGCTGGTGCAGTCTGGAGCTGAGGTGAAGAAGCCTGGGGCC TCAGTGAAGGTCTCCTGCAAGGCCTCTGGTTACTCCTTTACCTACTAT GGTATCAGCTGGGTGCGACAGGCCCCTGGACAAGGGCTTGAGTGGATG GGATGGATCTCTCCCTACAATGGTAATACACATTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 125 | NA sequence of 1D1 D25 VH | CAGGTTCAGCTGGTGCAGTCTGGAGCTGAGGTGAAGAAGCCTGGGGCC TCAGTGAAGGTCTCCTGCAAGGCCTCTGGTTACTCCTTTACCTACTAT GGTATCAGCTGGGTGCGACAGGCCCCTGGACAAGGGCTTGAGTGGATG GGATGGATCTCCACCTACAATGGTGCTACACATTATGCACGGATGCTC |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| | | CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 127 | NA sequence of 1D1 D28 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCTCTACCTACAATGGTAAAACACATTATGCACGGATGCAC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 129 | NA sequence of 1D1 D29 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCTCTTCCTACAATGGTAATACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 131 | NA sequence of 1D1 D31 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCTCTACCTACAATGGTAATAAACATTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 133 | NA sequence of 1D1 D37 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCTCTACCTACAATGGTGGAACACATTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 135 | NA sequence of 1D1 D38 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCTCTACCTACAATGGTGTTACACATTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 137 | NA sequence of 1D1 D39 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCACTTACAATGGTAACACAAACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCTGGCGCCTACAGAGGTGGCATGGAC<br>GCTTGGGGCCAAGGGACCACGGTCACCGTCTCCTCA |
| 139 | NA sequence of 1D1 DH3 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCTCTACCTACAATGGTAATACACATTATGCACAGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 141 | NA sequence of 1D1 DH8 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| | | GGATGGATCTCCGCCTACAATGGTAATACACATTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 143 | NA sequence of 1D1 DH9 VH | CAGGTTCAGCTGGTGCAGTCTGGAGCTGAGGTGAAGAAGCCTGGGGCC TCAGTGAAGGTCTCCTGCAAGGCCTCTGGTTACTCCTTTACCTACTAT GGTATCAGCTGGGTGCGACAGGCCCCTGGACAAGGGCTTGAGTGGATG GGATGGATCTCTCCATACAATGGTAAGACACATTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 145 | NA sequence of 1D1 DH10 VH | CAGGTTCAGCTGGTGCAGTCTGGAGCTGAGGTGAAGAAGCCTGGGGCC TCAGTGAAGGTCTCCTGCAAGGCCTCTGGTTACTCCTTTACCTACTAT GGTATCAGCTGGGTGCGACAGGCCCCTGGACAAGGGCTTGAGTGGATG GGATGGATCAGCACTTACAATGGTAACACAAACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCTGGTGCTTACAGAGGTGGTATGGAC GTTTGGGGCCAAGGGACCACGGTCACCGTCTCCTCA |
| 147 | NA sequence of 1D1 1.1 VH | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCAGCACTTACAATGGTAACACAAACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 149 | NA sequence of 1D1 1.2 VH | CAGGTTCAGCTGGTGCAGTCTGGAGCTGAGGTGAAGAAGCCTGGGGCC TCAGTGAAGGTCTCCTGCAAGGCCTCTGGTTACAACTTTACCTACTAT GGTATCAGCTGGGTGCGACAGGCCCCTGGACAAGGGCTTGAGTGGATG GGATGGATCAGCACTTACAATGGTAACACAAACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 151 | NA sequence of 1D1 1.3 VH | CAGGTTCAGCTGGTGCAGTCTGGAGCTGAGGTGAAGAAGCCTGGGGCC TCAGTGAAGGTCTCCTGCAAGGCCTCTGGTTACCAATTTACCTACTAT GGTATCAGCTGGGTGCGACAGGCCCCTGGACAAGGGCTTGAGTGGATG GGATGGATCAGCACTTACAATGGTAACACAAACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 153 | NA sequence of 1D1 1.4VH | CAGGTTCAGCTGGTGCAGTCTGGAGCTGAGGTGAAGAAGCCTGGGGCC TCAGTGAAGGTCTCCTGCAAGGCCTCTGGTTACTCCTTTACCCACTAT GGTATCAGCTGGGTGCGACAGGCCCCTGGACAAGGGCTTGAGTGGATG GGATGGATCAGCACTTACAATGGTAACACAAACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 155 | NA sequence of 1D1 1.5 VH | CAGGTTCAGCTGGTGCAGTCTGGAGCTGAGGTGAAGAAGCCTGGGGCC TCAGTGAAGGTCTCCTGCAAGGCCTCTGGTTACAACTTTCGCTACTAT GGTATCAGCTGGGTGCGACAGGCCCCTGGACAAGGGCTTGAGTGGATG GGATGGATCAGCACTTACAATGGTAACACAAACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 157 | NA sequence of 1D1 1.6 VH | CAGGTTCAGCTGGTGCAGTCTGGAGCTGAGGTGAAGAAGCCTGGGGCC<br>TCAGTGAAGGTCTCCTGCAAGGCCTCTGGTTACAACTTTACCCACTAT<br>GGTATCAGCTGGGTGCGACAGGCCCCTGGACAAGGGCTTGAGTGGATG<br>GGATGGATCAGCACTTACAATGGTAACACAAACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 159 | NA sequence of 1D1 1.7VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCACTTACAATGGTAAGACAAACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 161 | NA sequence of 1D1 1.8 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTCGCTACTAT<br>GGTATCAGCTGGGTGCGACAGGCCCCTGGACAAGGGCTTGAGTGGATG<br>GGATGGATCAGCACTTACAATGGTAACACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 163 | NA sequence of 1D1 1.9 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCACTTACAATGGTAACACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GTCTGGGGCCAAGGGACCACGGTCACCGTCTCCTCA |
| 165 | NA sequence of 1D1 1.10 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCCCTTACAATGGTAAAACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GTCTGGGGCCAAGGGACCACGGTCACCGTCTCCTCA |
| 167 | NA sequence of 1D1 1.11 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTCGCTACTAT<br>GGTATCAGCTGGGTGCGACAGGCCCCTGGACAAGGGCTTGAGTGGATG<br>GGATGGATCAGCACTTACAATGGTAACACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GTCTGGGGCCAAGGGACCACGGTCACCGTCTCCTCA |
| 169 | NA sequence of 1D1 1.12 VH | CAGGTTCAGCTGGTGCAGTCTGGAGCTGAGGTGAAGAAGCCTGGGGCC<br>TCAGTGAAGGTCTCCTGCAAGGCCTCTGGTTACAACTTTACCTACTAT<br>GGTATCAGCTGGGTGCGACAGGCCCCTGGACAAGGGCTTGAGTGGATG<br>GGATGGATCAGCCCTTACAATGGTAAAACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GTCTGGGGCCAAGGGACCACGGTCACCGTCTCCTCA |
| 171 | NA sequence of 1D1 1.13VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCCACTAT<br>GGTATCAGCTGGGTGCGACAGGCCCCTGGACAAGGGCTTGAGTGGATG<br>GGATGGATCAGCCCTTACAATGGTAAAACACACTATGCACGGATGCTC<br>CAGGGCAGAGTCACCATGACCACAGACACGTCCACGCGCACAGCCTAC |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| | | ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GTCTGGGGCCAAGGGACCACGGTCACCGTCTCCTCA |
| 173 | NA sequence of 1D1 1.14 VH | CAGGTTCAGCTGGTGCAGTCTGGAGCTGAGGTGAAGAAGCCTGGGGCC<br>TCAGTGAAGGTCTCCTGCAAGGCCTCTGGTTACAACTTTACCCACTAT<br>GGTATCAGCTGGGTGCGACAGGCCCCTGGACAAGGGCTTGAGTGGATG<br>GGATGGATCAGCCCTTACAATGGTAAAACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GTCTGGGGCCAAGGGACCACGGTCACCGTCTCCTCA |
| 175 | NA sequence of 1D1 1.15 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCCCTTACAATGGTGGCACACACTATGCACAGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 177 | NA sequence of 1D1 1.16 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCCCTTACAATGGTGTCACACACTATGCACAGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 179 | NA sequence of 1D1 1.17 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCCCTTACAATGGTGCCACACACTATGCACAGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 181 | NA sequence of 1D1 1.18 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCCCTTACAATGGTAACAAGCACTATGCACAGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 183 | NA sequence of 1D1 1.19 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCACTTACAATGGTGGCACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 185 | NA sequence of 1D1 1.20 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCCCTTACAATGGTAACACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 187 | NA sequence of 1D1 1.21 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCACTTACAATGGTAACACACACTATGCACAGATGCTC |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| | | CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 189 | NA sequence of 1D1 1 22 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCACTTACAATGGTGTCACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 191 | NA sequence of 1D1 1.23 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCACTTACAATGGTGCCACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 193 | NA sequence of 1D1 1.24 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCACTTACAATGGTAACAAACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 195 | NA sequence of 1D1 1.25 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCACTTACAATGGTAAGACACACTATGCACGGATGCAC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 197 | NA sequence of 1D1 1.26 VH | CAGGTTCAGCTGGTGCAGTCTGGAGCTGAGGTGAAGAAGCCTGGGGCC<br>TCAGTGAAGGTCTCCTGCAAGGCCTCTGGTTACTCCTTTACCTACTAT<br>GGTATCAGCTGGGTGCGACAGGCCCCTGGACAAGGGCTTGAGTGGATG<br>GGATGGATCAGCACTTACAATGGTAACACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCA |
| 199 | NA sequence of 1D1 1.27 VH | CAGGTTCAGCTGGTGCAGTCTGGAGCTGAGGTGAAGAAGCCTGGGGCC<br>TCAGTGAAGGTCTCCTGCAAGGCCTCTGGTTACGACTTTACCTACTAT<br>GGTATCAGCTGGGTGCGACAGGCCCCTGGACAAGGGCTTGAGTGGATG<br>GGATGGATCTCTACTTACAATGGTAATACACATTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCA |
| 200 | AA sequence of 1D1 1.27 full length heavy chain with effector null mutation IgG1 constant domain (1D1 1.27-hIgG1-3m-HC) | QVQLVQSGAEVKKPGASVKVSCKASGYDFTYYGISWVRQAPGQGLEWM<br>GWISTYNGNTHYARMLQGRVTMTTDTSTRTAYMELRSLRSDDTAVYYC<br>ARENYYGSGSYRGGMDVWGQGTTVTVSSASTKGPSVFPLAPSSKSTSG<br>GTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPE<br>AAGAPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDI<br>AVEWESNGQPENNYKTTPPVLDSDGSFFLYSKLTVDKSRWQQGNVFSC<br>SVMHEALHNHYTQKSLSLSPG |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 201 | NA sequence of 1D1 1.27 full length heavy chain with effector null mutation IgG1 constant domain (1D1 1.27-hIgG1-3m-HC) | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCTCTACTTACAATGGTAATACACATTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCAGCGTCGACCAAG GGCCCATCGGTCTTCCCCCTGGCACCCTCCTCCAAGAGCACCTCTGGG GGCACAGCGGCCCTGGGCTGCCTGGTCAAGGACTACTTCCCCGAACCG GTGACGGTGTCGTGGAACTCAGGCGCCCTGACCAGCGGCGTGCACACC TTCCCGGCTGTCCTACAGTCCTCAGGACTCTACTCCCTCAGCAGCGTG GTGACCGTGCCCTCCAGCAGCTTGGGCACCCAGACCTACATCTGCAAC GTGAATCACAAGCCCAGCAACACCAAGGTGGACAAGAAAGTTGAGCCC AAATCTTGTGACAAAACTCACACATGCCCACCGTGCCCAGCACCTGAA GCCGCTGGGGCACCGTCAGTCTTCCTCTTCCCCCCAAAACCCAAGGAC ACCCTCATGATCTCCCGGACCCCTGAGGTCACATGCGTGGTGGTGGAC GTGAGCCACGAAGACCCTGAGGTCAAGTTCAACTGGTACGTGGACGGC GTGGAGGTGCATAATGCCAAGACAAAGCCGCGGGAGGAGCAGTACAAC AGCACGTACCGTGTGGTCAGCGTCCTCACCGTCCTGCACCAGGACTGG CTGAATGGCAAGGAGTACAAGTGCAAGGTCTCCAACAAAGCCCTCCCA GCCCCCATCGAGAAAACCATCTCCAAAGCCAAAGGGCAGCCCCGAGAA CCACAGGTGTACACCCTGCCCCCATCCCGGGAGGAGATGACCAAGAAC CAGGTCAGCCTGACCTGCCTGGTCAAAGGCTTCTATCCCAGCGACATC GCCGTGGAGTGGGAGAGCAATGGGCAGCCGGAGAACAACTACAAGACC ACGCCTCCCGTGCTGGACTCCGACGGCTCCTTCTTCCTCTATAGCAAG CTCACCGTGGACAAGAGCAGGTGGCAGCAGGGGAACGTCTTCTCATGC TCCGTGATGCATGAGGCTCTGCACAACCACTACACGCAGAAGAGCCTC TCCCTGTCCCCGGGT |
| 206 | NA sequence of 1D1 1.28 VH | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCTCTACCTACAATGGTAATAAACATTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 207 | AA sequence of 1D1 1.28 full length heavy chain with effector null mutation IgG1 constant domain (1D1 1.28-hIgG1-3m-HC) | QVQLVQSGAEVKKPGASVKVSCKASGYDFTYYGISWVRQAPGQGLEWM GWISTYNGNKHYARMLQGRVTMTTDTSTRTAYMELRSLRSDDTAVYYC ARENYYGSGSYRGGMDVWGQGTTVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPE AAGAPSVFLFPPKPKDTLMISRTPEVTCVVVDVSHEDPEVKFNWYVDG VEVHNAKTKPREEQYNSTYRVVSVLTVLHQDWLNGKEYKCKVSNKALP APIEKTISKAKGQPREPQVYTLPPSREEMTKNQVSLTCLVKGFYPSDI AVEWESNGQPENNYKTTPPVLDSDGSFFLYSKLTVDKSRWQQGNVFSC SVMHEALHNHYTQKSLSLSPG |
| 208 | NA sequence of 1D1 1.28 full length heavy chain with effector null mutation IgG1 constant domain (1D1 1.28-hIgG1-3m-HC) | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCTCTACCTACAATGGTAATAAACATTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCAGCGTCGACCAAG GGCCCATCGGTCTTCCCCCTGGCACCCTCCTCCAAGAGCACCTCTGGG GGCACAGCGGCCCTGGGCTGCCTGGTCAAGGACTACTTCCCCGAACCG GTGACGGTGTCGTGGAACTCAGGCGCCCTGACCAGCGGCGTGCACACC TTCCCGGCTGTCCTACAGTCCTCAGGACTCTACTCCCTCAGCAGCGTG GTGACCGTGCCCTCCAGCAGCTTGGGCACCCAGACCTACATCTGCAAC GTGAATCACAAGCCCAGCAACACCAAGGTGGACAAGAAAGTTGAGCCC AAATCTTGTGACAAAACTCACACATGCCCACCGTGCCCAGCACCTGAA GCCGCTGGGGCACCGTCAGTCTTCCTCTTCCCCCCAAAACCCAAGGAC ACCCTCATGATCTCCCGGACCCCTGAGGTCACATGCGTGGTGGTGGAC GTGAGCCACGAAGACCCTGAGGTCAAGTTCAACTGGTACGTGGACGGC GTGGAGGTGCATAATGCCAAGACAAAGCCGCGGGAGGAGCAGTACAAC AGCACGTACCGTGTGGTCAGCGTCCTCACCGTCCTGCACCAGGACTGG |

TABLE 40-continued

| SEQ ID NO: | DESCRIPTION | SEQUENCE |
| --- | --- | --- |
| | Sequence Listing Table CDR amino acid sequences, as defined by Kabat are underlined, CDR H1 amino acid sequences are shown in italics. In the heavy chain sequences, effector null mutations are also underlined. | |
| | | CTGAATGGCAAGGAGTACAAGTGCAAGGTCTCCAACAAAGCCCTCCCA GCCCCCATCGAGAAAACCATCTCCAAAGCCAAAGGGCAGCCCCGAGAA CCACAGGTGTACACCCTGCCCCCATCCCGGGAGGAGATGACCAAGAAC CAGGTCAGCCTGACCTGCCTGGTCAAAGGCTTCTATCCCAGCGACATC GCCGTGGAGTGGGAGAGCAATGGGCAGCCGGAGAACAACTACAAGACC ACGCCTCCCGTGCTGGACTCCGACGGCTCCTTCTTCCTCTATAGCAAG CTCACCGTGGACAAGAGCAGGTGGCAGCAGGGGAACGTCTTCTCATGC TCCGTGATGCATGAGGCTCTGCACAACCACTACACGCAGAAGAGCCTC TCCCTGTCCCCGGGT |
| 213 | NA sequence of 1D1 1.29 VH | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCTCTACCTACAATGGTGGAACACATTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |
| 214 | AA sequence of 1D1 1.29 full length heavy chain with effector null mutation IgG1 constant domain (1D1 1.29-hIgG1-3m-HC) | QVQLVQSGAEVKKPGASVKVSCKASGYDFTYYGISWVRQAPGQGLEWM GWISTYNGGTHYARMLQGRVTMTTDTSTRTAYMELRSLRSDDTAVYYC ARENYYGSGSYRGGMDVWGQGTTVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPE AAGAPSVFLFPPKPKDTLMISRTPEVTCVVVDVSHEDPEVKFNWYVDG VEVHNAKTKPREEQYNSTYRVVSVLTVLHQDWLNGKEYKCKVSNKALP APIEKTISKAKGQPREPQVYTLPPSREEMTKNQVSLTCLVKGFYPSDI AVEWESNGQPENNYKTTPPVLDSDGSFFLYSKLTVDKSRWQQGNVFSC SVMHEALHNHYTQKSLSLSPG |
| 215 | NA sequence of 1D1 1.29 full length heavy chain with effector null mutation IgG1 constant domain (1D1 1.29-hIgG1-3m-HC) | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCTCTACCTACAATGGTGGAACACATTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCAGCGTCGACCAAG GGCCCATCGGTCTTCCCCCTGGCACCCTCCTCCAAGAGCACCTCTGGG GGCACAGCGGCCCTGGGCTGCCTGGTCAAGGACTACTTCCCCGAACCG GTGACGGTGTCGTGGAACTCAGGCGCCCTGACCAGCGGCGTGCACACC TTCCCGGCTGTCCTACAGTCCTCAGGACTCTACTCCCTCAGCAGCGTG GTGACCGTGCCCTCCAGCAGCTTGGGCACCCAGACCTACATCTGCAAC GTGAATCACAAGCCCAGCAACACCAAGGTGGACAAGAAAGTTGAGCCC AAATCTTGTGACAAAACTCACACATGCCCACCGTGCCCAGCACCTGAA GCCGCTGGGGCACCGTCAGTCTTCCTCTTCCCCCCAAAACCCAAGGAC ACCCTCATGATCTCCCGGACCCCTGAGGTCACATGCGTGGTGGTGGAC GTGAGCCACGAAGACCCTGAGGTCAAGTTCAACTGGTACGTGGACGGC GTGGAGGTGCATAATGCCAAGACAAAGCCGCGGGAGGAGCAGTACAAC AGCACGTACCGTGTGGTCAGCGTCCTCACCGTCCTGCACCAGGACTGG CTGAATGGCAAGGAGTACAAGTGCAAGGTCTCCAACAAAGCCCTCCCA GCCCCCATCGAGAAAACCATCTCCAAAGCCAAAGGGCAGCCCCGAGAA CCACAGGTGTACACCCTGCCCCCATCCCGGGAGGAGATGACCAAGAAC CAGGTCAGCCTGACCTGCCTGGTCAAAGGCTTCTATCCCAGCGACATC GCCGTGGAGTGGGAGAGCAATGGGCAGCCGGAGAACAACTACAAGACC ACGCCTCCCGTGCTGGACTCCGACGGCTCCTTCTTCCTCTATAGCAAG CTCACCGTGGACAAGAGCAGGTGGCAGCAGGGGAACGTCTTCTCATGC TCCGTGATGCATGAGGCTCTGCACAACCACTACACGCAGAAGAGCCTC TCCCTGTCCCCGGGT |
| 220 | NA sequence of 1D1 1.30 VH | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCTCTACCTACAATGGTGTTACACATTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGAGTTATAGAGGGGGTATGGAC GTCTGGGGCCAAGGGACCACGGTCACCGTCTCCTCA |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 221 | AA sequence of 1D1 1.30 full length heavy chain with effector null mutation IgG1 constant domain (1D1 1.30-hIgG1-3m-HC) | QVQLVQSGAEVKKPGASVKVSCKASGYDFTYYGISWVRQAPGQGLEWM<br>GWISTYNGVTHYARMLQGRVTMTTDTSTRTAYMELRSLRSDDTAVYYC<br>ARENYYGSGSYRGGMDVWGQGTTVTVSSASTKGPSVFPLAPSSKSTSG<br>GTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPE<br>AAGAPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDI<br>AVEWESNGQPENNYKTTPPVLDSDGSFFLYSKLTVDKSRWQQGNVFSC<br>SVMHEALHNHYTQKSLSLSPG |
| 222 | NA sequence of 1D1 1.30 full length heavy chain with effector null mutation IgG1 constant domain (1D1 1.30-hIgG1-3m-HC) | CAGGTTCAGCTGGTGCAGTCTGGAGCTGAGGTGAAGAAGCCTGGGGCC<br>TCAGTGAAGGTCTCCTGCAAGGCCTCTGGTTACGACTTTACCTACTAT<br>GGTATCAGCTGGGTGCGACAGGCCCCTGGACAAGGGCTTGAGTGGATG<br>GGATGGATCTCTACCTACAATGGTGTTACACATTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGAGTTATAGAGGGGGTATGGAC<br>GTCTGGGGCCAAGGGACCACGGTCACCGTCTCCTCAGCGTCGACCAAG<br>GGCCCATCGGTCTTCCCCCTGGCACCCTCCTCCAAGAGCACCTCTGGG<br>GGCACAGCGGCCCTGGGCTGCCTGGTCAAGGACTACTTCCCCGAACCG<br>GTGACGGTGTCGTGGAACTCAGGCGCCCTGACCAGCGGCGTGCACACC<br>TTCCCGGCTGTCCTACAGTCCTCAGGACTCTACTCCCTCAGCAGCGTG<br>GTGACCGTGCCCTCCAGCAGCTTGGGCACCCAGACCTACATCTGCAAC<br>GTGAATCACAAGCCCAGCAACACCAAGGTGGACAAGAAAGTTGAGCCC<br>AAATCTTGTGACAAAACTCACACATGCCCACCGTGCCCAGCACCTGAA<br>GCCGCTGGGGCACCGTCAGTCTTCCTCTTCCCCCCAAAACCCAAGGAC<br>ACCCTCATGATCTCCCGGACCCCTGAGGTCACATGCGTGGTGGTGGAC<br>GTGAGCCACGAAGACCCTGAGGTCAAGTTCAACTGGTACGTGGACGGC<br>GTGGAGGTGCATAATGCCAAGACAAAGCCGCGGGAGGAGCAGTACAAC<br>AGCACGTACCGTGTGGTCAGCGTCCTCACCGTCCTGCACCAGGACTGG<br>CTGAATGGCAAGGAGTACAAGTGCAAGGTCTCCAACAAAGCCCTCCCA<br>GCCCCCATCGAGAAAACCATCTCCAAAGCCAAAGGGCAGCCCCGAGAA<br>CCACAGGTGTACACCCTGCCCCCATCCCGGGAGGAGATGACCAAGAAC<br>CAGGTCAGCCTGACCTGCCTGGTCAAAGGCTTCTATCCCAGCGACATC<br>GCCGTGGAGTGGGAGAGCAATGGGCAGCCGGAGAACAACTACAAGACC<br>ACGCCTCCCGTGCTGGACTCCGACGGCTCCTTCTTCCTCTATAGCAAG<br>CTCACCGTGGACAAGAGCAGGTGGCAGCAGGGGAACGTCTTCTCATGC<br>TCCGTGATGCATGAGGCTCTGCACAACCACTACACGCAGAAGAGCCTC<br>TCCCTGTCCCCGGGT |
| 227 | NA sequence of 1D1 1.31 VH | CAGGTTCAGCTGGTGCAGTCTGGAGCTGAGGTGAAGAAGCCTGGGGCC<br>TCAGTGAAGGTCTCCTGCAAGGCCTCTGGTTACGACTTTACCTACTAT<br>GGTATCAGCTGGGTGCGACAGGCCCCTGGACAAGGGCTTGAGTGGATG<br>GGATGGATCAGCACTTACAATGGTAACACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GTCTGGGGCCAAGGGACCACGGTCACCGTCTCCTCA |
| 228 | AA sequence of 1D1 1.31 full length heavy chain with effector null mutation IgG1 constant domain (1D1 1.31-hIgG1-3m-HC) | QVQLVQSGAEVKKPGASVKVSCKASGYDFTYYGISWVRQAPGQGLEWM<br>GWISTYNGNTHYARMLQGRVTMTTDTSTRTAYMELRSLRSDDTAVYYC<br>ARENYYGSGAYRGGMDVWGQGTTVTVSSASTKGPSVFPLAPSSKSTSG<br>GTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPE<br>AAGAPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDI<br>AVEWESNGQPENNYKTTPPVLDSDGSFFLYSKLTVDKSRWQQGNVFSC<br>SVMHEALHNHYTQKSLSLSPG |
| 229 | NA sequence of 1D1 1.31 full length heavy chain with effector null mutation IgG1 constant domain (1D1 1.31-hIgG1-3m-HC) | CAGGTTCAGCTGGTGCAGTCTGGAGCTGAGGTGAAGAAGCCTGGGGCC<br>TCAGTGAAGGTCTCCTGCAAGGCCTCTGGTTACGACTTTACCTACTAT<br>GGTATCAGCTGGGTGCGACAGGCCCCTGGACAAGGGCTTGAGTGGATG<br>GGATGGATCAGCACTTACAATGGTAACACACACTATGCACGGATGCTC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GTCTGGGGCCAAGGGACCACGGTCACCGTCTCCTCAGCGTCGACCAAG<br>GGCCCATCGGTCTTCCCCCTGGCACCCTCCTCCAAGAGCACCTCTGGG |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| | | GGCACAGCGGCCCTGGGCTGCCTGGTCAAGGACTACTTCCCCGAACCG GTGACGGTGTCGTGGAACTCAGGCGCCCTGACCAGCGGCGTGCACACC TTCCCGGCTGTCCTACAGTCCTCAGGACTCTACTCCCTCAGCAGCGTG GTGACCGTGCCCTCCAGCAGCTTGGGCACCCAGACCTACATCTGCAAC GTGAATCACAAGCCCAGCAACACCAAGGTGGACAAGAAAGTTGAGCCC AAATCTTGTGACAAAACTCACACATGCCCACCGTGCCCAGCACCTGAA GCCGCTGGGGCACCGTCAGTCTTCCTCTTCCCCCCAAAACCCAAGGAC ACCCTCATGATCTCCCGGACCCCTGAGGTCACATGCGTGGTGGTGGAC GTGAGCCACGAAGACCCTGAGGTCAAGTTCAACTGGTACGTGGACGGC GTGGAGGTGCATAATGCCAAGACAAAGCCGCGGGAGGAGCAGTACAAC AGCACGTACCGTGTGGTCAGCGTCCTCACCGTCCTGCACCAGGACTGG CTGAATGGCAAGGAGTACAAGTGCAAGGTCTCCAACAAAGCCCTCCCA GCCCCCATCGAGAAAACCATCTCCAAAGCCAAAGGGCAGCCCCGAGAA CCACAGGTGTACACCCTGCCCCCATCCCGGGAGGAGATGACCAAGAAC CAGGTCAGCCTGACCTGCCTGGTCAAAGGCTTCTATCCCAGCGACATC GCCGTGGAGTGGGAGAGCAATGGGCAGCCGGAGAACAACTACAAGACC ACGCCTCCCGTGCTGGACTCCGACGGCTCCTTCTTCCTCTATAGCAAG CTCACCGTGGACAAGAGCAGGTGGCAGCAGGGGAACGTCTTCTCATGC TCCGTGATGCATGAGGCTCTGCACAACCACTACACGCAGAAGAGCCTC TCCCTGTCCCCGGGT |
| 234 | NA sequence of 1D1 1.32 VH | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCAGCACTTACAATGGTGGCACACACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGGCTTATAGAGGGGGTATGGAC GCCTGGGGCCAAGGGACCACGGTCACCGTCTCCTCA |
| 235 | AA sequence of 1D1 1.32 full length heavy chain with effector null mutation IgG1 constant domain (1D1 1.32-hIgG1-3m-HC) | QVQLVQSGAEVKKPGASVKVSCKASGYDFTYYGISWVRQAPGQGLEWM GWISTYNGGTHYARMLQGRVTMTTDTSTRTAYMELRSLRSDDTAVYYC ARENYYGSGAYRGGMDAWGQGTTVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPE AAGAPSVFLFPPKPKDTLMISRTPEVTCVVVDVSHEDPEVKFNWYVDG VEVHNAKTKPREEQYNSTYRVVSVLTVLHQDWLNGKEYKCKVSNKALP APIEKTISKAKGQPREPQVYTLPPSREEMTKNQVSLTCLVKGFYPSDI AVEWESNGQPENNYKTTPPVLDSDGSFFLYSKLTVDKSRWQQGNVFSC SVMHEALHNHYTQKSLSLSPG |
| 236 | NA sequence of 1D1 1.32 full length heavy chain with effector null mutation IgG1 constant domain (1D1 1.32-hIgG1-3m-HC) | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCAGCACTTACAATGGTGGCACACACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGGCTTATAGAGGGGGTATGGAC GCCTGGGGCCAAGGGACCACGGTCACCGTCTCCTCAGCGTCGACCAAG GGCCCATCGGTCTTCCCCCTGGCACCCTCCTCCAAGAGCACCTCTGGG GGCACAGCGGCCCTGGGCTGCCTGGTCAAGGACTACTTCCCCGAACCG GTGACGGTGTCGTGGAACTCAGGCGCCCTGACCAGCGGCGTGCACACC TTCCCGGCTGTCCTACAGTCCTCAGGACTCTACTCCCTCAGCAGCGTG GTGACCGTGCCCTCCAGCAGCTTGGGCACCCAGACCTACATCTGCAAC GTGAATCACAAGCCCAGCAACACCAAGGTGGACAAGAAAGTTGAGCCC AAATCTTGTGACAAAACTCACACATGCCCACCGTGCCCAGCACCTGAA GCCGCTGGGGCACCGTCAGTCTTCCTCTTCCCCCCAAAACCCAAGGAC ACCCTCATGATCTCCCGGACCCCTGAGGTCACATGCGTGGTGGTGGAC GTGAGCCACGAAGACCCTGAGGTCAAGTTCAACTGGTACGTGGACGGC GTGGAGGTGCATAATGCCAAGACAAAGCCGCGGGAGGAGCAGTACAAC AGCACGTACCGTGTGGTCAGCGTCCTCACCGTCCTGCACCAGGACTGG CTGAATGGCAAGGAGTACAAGTGCAAGGTCTCCAACAAAGCCCTCCCA GCCCCCATCGAGAAAACCATCTCCAAAGCCAAAGGGCAGCCCCGAGAA CCACAGGTGTACACCCTGCCCCCATCCCGGGAGGAGATGACCAAGAAC CAGGTCAGCCTGACCTGCCTGGTCAAAGGCTTCTATCCCAGCGACATC GCCGTGGAGTGGGAGAGCAATGGGCAGCCGGAGAACAACTACAAGACC ACGCCTCCCGTGCTGGACTCCGACGGCTCCTTCTTCCTCTATAGCAAG CTCACCGTGGACAAGAGCAGGTGGCAGCAGGGGAACGTCTTCTCATGC TCCGTGATGCATGAGGCTCTGCACAACCACTACACGCAGAAGAGCCTC TCCCTGTCCCCGGGT |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 241 | NA sequence of 1D1 1.33 VH | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCAGCACTTACAATGGTGTCACACACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGGCTTATAGAGGGGGTATGGAC GCCTGGGGCCAAGGGACCACGGTCACCGTCTCCTCA |
| 242 | AA sequence of 1D1 1.33 full length heavy chain with effector null mutation IgG1 constant domain (1D1 1.33-hIgG1-3m-HC) | QVQLVQSGAEVKKPGASVKVSCKASGYDFTYYGISWVRQAPGQGLEWM GWISTYNGVTHYARMLQGRVTMTTDTSTRTAYMELRSLRSDDTAVYYC ARENYYGSGAYRGGMDAWGQGTTVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPE AAGAPSVFLFPPKPKDTLMISRTPEVTCVVVDVSHEDPEVKFNWYVDG VEVHNAKTKPREEQYNSTYRVVSVLTVLHQDWLNGKEYKCKVSNKALP APIEKTISKAKGQPREPQVYTLPPSREEMTKNQVSLTCLVKGFYPSDI AVEWESNGQPENNYKTTPPVLDSDGSFFLYSKLTVDKSRWQQGNVFSC SVMHEALHNHYTQKSLSLSPG |
| 243 | NA sequence of 1D1 1.33 full length heavy chain with effector null mutation IgG1 constant domain (1D1 1.33-hIgG1-3m-HC) | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCAGCACTTACAATGGTGTCACACACTATGCACGGATGCTC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGGCTTATAGAGGGGGTATGGAC GCCTGGGGCCAAGGGACCACGGTCACCGTCTCCTCAGCGTCGACCAAG GGCCCATCGGTCTTCCCCCTGGCACCCTCCTCCAAGAGCACCTCTGGG GGCACAGCGGCCCTGGGCTGCCTGGTCAAGGACTACTTCCCCGAACCG GTGACGGTGTCGTGGAACTCAGGCGCCCTGACCAGCGGCGTGCACACC TTCCCGGCTGTCCTACAGTCCTCAGGACTCTACTCCCTCAGCAGCGTG GTGACCGTGCCCTCCAGCAGCTTGGGCACCCAGACCTACATCTGCAAC GTGAATCACAAGCCCAGCAACACCAAGGTGGACAAGAAAGTTGAGCCC AAATCTTGTGACAAAACTCACACATGCCCACCGTGCCCAGCACCTGAA GCCGCTGGGGCACCGTCAGTCTTCCTCTTCCCCCCAAAACCCAAGGAC ACCCTCATGATCTCCCGGACCCCTGAGGTCACATGCGTGGTGGTGGAC GTGAGCCACGAAGACCCTGAGGTCAAGTTCAACTGGTACGTGGACGGC GTGGAGGTGCATAATGCCAAGACAAAGCCGCGGGAGGAGCAGTACAAC AGCACGTACCGTGTGGTCAGCGTCCTCACCGTCCTGCACCAGGACTGG CTGAATGGCAAGGAGTACAAGTGCAAGGTCTCCAACAAAGCCCTCCCA GCCCCCATCGAGAAAACCATCTCCAAAGCCAAAGGGCAGCCCCGAGAA CCACAGGTGTACACCCTGCCCCCATCCCGGGAGGAGATGACCAAGAAC CAGGTCAGCCTGACCTGCCTGGTCAAAGGCTTCTATCCCAGCGACATC GCCGTGGAGTGGGAGAGCAATGGGCAGCCGGAGAACAACTACAAGACC ACGCCTCCCGTGCTGGACTCCGACGGCTCCTTCTTCCTCTATAGCAAG CTCACCGTGGACAAGAGCAGGTGGCAGCAGGGGAACGTCTTCTCATGC TCCGTGATGCATGAGGCTCTGCACAACCACTACACGCAGAAGAGCCTC TCCCTGTCCCCGGGT |
| 248 | NA sequence of 1D1 1.34 VH | CAGGTTCAGCTGGTGCAGTCTGGAGCTGAGGTGAAGAAGCCTGGGGCC TCAGTGAAGGTCTCCTGCAAGGCCTCTGGTTACGACTTTACCTACTAT GGTATCAGCTGGGTGCGACAGGCCCCTGGACAAGGGCTTGAGTGGATG GGATGGATCAGCACTTACAATGGTAAGACACACTATGCACGGATGCAC CAGGGCAGAGTCACCATGACCACAGACACGTCCACGCGCACAGCCTAC ATGGAGCTGAGGAGCCTGAGATCTGACGACACGGCCGTGTATTACTGT GCGAGAGAGAATTACTATGGTTCGGGGGCTTATAGAGGGGGTATGGAC GCCTGGGGCCAAGGGACCACGGTCACCGTCTCCTCA |
| 249 | AA sequence of 1D1 1.34 full length heavy chain with effector null mutation IgG1 constant domain (1D1 1.34-hIgG1-3m-HC) | QVQLVQSGAEVKKPGASVKVSCKASGYDFTYYGISWVRQAPGQGLEWM GWISTYNGKTHYARMHQGRVTMTTDTSTRTAYMELRSLRSDDTAVYYC ARENYYGSGAYRGGMDAWGQGTTVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPE AAGAPSVFLFPPKPKDTLMISRTPEVTCVVVDVSHEDPEVKFNWYVDG VEVHNAKTKPREEQYNSTYRVVSVLTVLHQDWLNGKEYKCKVSNKALP APIEKTISKAKGQPREPQVYTLPPSREEMTKNQVSLTCLVKGFYPSDI AVEWESNGQPENNYKTTPPVLDSDGSFFLYSKLTVDKSRWQQGNVFSC SVMHEALHNHYTQKSLSLSPG |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 250 | NA sequence of 1D1 1.34 full length heavy chain with effector null mutation IgG1 constant domain (1D1 1.34-hIgG1-3m-HC) | CAGGTTCAGCTGGTGCAGTCTGGAGCTGAGGTGAAGAAGCCTGGGGCC<br>TCAGTGAAGGTCTCCTGCAAGGCCTCTGGTTACGACTTTACCTACTAT<br>GGTATCAGCTGGGTGCGACAGGCCCCTGGACAAGGGCTTGAGTGGATG<br>GGATGGATCAGCACTTACAATGGTAAGACACACTATGCACGGATGCAC<br>CAGGGCAGAGTCACCATGACCACAGACACGTCCACGCGCACAGCCTAC<br>ATGGAGCTGAGGAGCCTGAGATCTGACGACACGGCCGTGTATTACTGT<br>GCGAGAGAGAATTACTATGGTTCGGGGGCTTATAGAGGGGGTATGGAC<br>GCCTGGGGCCAAGGGACCACGGTCACCGTCTCCTCAGCGTCGACCAAG<br>GGCCCATCGGTCTTCCCCCTGGCACCCTCCTCCAAGAGCACCTCTGGG<br>GGCACAGCGGCCCTGGGCTGCCTGGTCAAGGACTACTTCCCCGAACCG<br>GTGACGGTGTCGTGGAACTCAGGCGCCCTGACCAGCGGCGTGCACACC<br>TTCCCGGCTGTCCTACAGTCCTCAGGACTCTACTCCCTCAGCAGCGTG<br>GTGACCGTGCCCTCCAGCAGCTTGGGCACCCAGACCTACATCTGCAAC<br>GTGAATCACAAGCCCAGCAACACCAAGGTGGACAAGAAAGTTGAGCCC<br>AAATCTTGTGACAAAACTCACACATGCCCACCGTGCCCAGCACCTGAA<br>GCCGCTGGGGCACCGTCAGTCTTCCTCTTCCCCCCAAAACCCAAGGAC<br>ACCCTCATGATCTCCCGGACCCCTGAGGTCACATGCGTGGTGGTGGAC<br>GTGAGCCACGAAGACCCTGAGGTCAAGTTCAACTGGTACGTGGACGGC<br>GTGGAGGTGCATAATGCCAAGACAAAGCCGCGGGAGGAGCAGTACAAC<br>AGCACGTACCGTGTGGTCAGCGTCCTCACCGTCCTGCACCAGGACTGG<br>CTGAATGGCAAGGAGTACAAGTGCAAGGTCTCCAACAAAGCCCTCCCA<br>GCCCCCATCGAGAAAACCATCTCCAAAGCCAAAGGGCAGCCCCGAGAA<br>CCACAGGTGTACACCCTGCCCCCATCCCGGGAGGAGATGACCAAGAAC<br>CAGGTCAGCCTGACCTGCCTGGTCAAAGGCTTCTATCCCAGCGACATC<br>GCCGTGGAGTGGGAGAGCAATGGGCAGCCGGAGAACAACTACAAGACC<br>ACGCCTCCCGTGCTGGACTCCGACGGCTCCTTCTTCCTCTATAGCAAG<br>CTCACCGTGGACAAGAGCAGGTGGCAGCAGGGGAACGTCTTCTCATGC<br>TCCGTGATGCATGAGGCTCTGCACAACCACTACACGCAGAAGAGCCTC<br>TCCCTGTCCCCGGGT |
| 254 | AA sequence of recombinant soluble human TL1A (rsTL1A) | ALKGQEFAPSHQQVYAPLRADGDKPRAHLTVVRQTPTQHFKNQFPALH<br>WEHELGLAFTKNRMNYTNKFLLIPESGDYFIYSQVTFRGMTSECSEIR<br>QAGRPNKPDSITVVITKVTDSYPEPTQLLMGTKSVCEVGSNWFQPIYL<br>GAMFSLQEGDKLMVNVSDISLVDYTKEDKTFFGAFLL |
| 255 | AA sequence of human wild type kappa constant domain (Cκ) | RTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSS<br>PVTKSFNRGEC |
| 256 | AA sequence of human wild type IgG1 constant region (hIgG1) | ASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEVTC<br>VVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFF<br>LYSKLTVDKSRWQQGNVFSCSVMHEALHNHYTQKSLSLSPGK |
| 257 | AA sequence of human IgG1 triple mutant (3m) effector null mutant constant region (hIgG1-3m) | ASTKGPSVFPLAPSSKSTSGGTAALGCLVKDYFPEPVTVSWNSGALTS<br>GVHTFPAVLQSSGLYSLSSWTVPSSSLGTQTYICNVNHKPSNTKVDK<br>KVEPKSCDKTHTCPPCPAPEAAGAPSVFLFPPKPKDTLMISRTPEVTC<br>VVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFF<br>LYSKLTVDKSRWQQGNVFSCSVMHEALHNHYTQKSLSLSPG |
| 258 | AA Sequence of human TL1A (human TL1A) | MAEDLGLSFGETASVEMLPEHGSCRPKARSSSARWALTCCLVLLPFLA<br>GLTTYLLVSQLRAQGEACVQFQALKGQEFAPSHQQVYAPLRADGDKPR<br>AHLTVVRQTPTQHFKNQFPALHWEHELGLAFTKNRMNYTNKFLLIPES<br>GDYFIYSQVTFRGMTSECSEIRQAGRPNKPDSITVVITKVTDSYPEPT<br>QLLMGTKSVCEVGSNWFQPIYLGAMFSLQEGDKLMVNVSDISLVDYTK<br>EDKTFFGAFL(L) |
| 259 | AA Sequence of recombinant soluble cynomolgus monkey TL1A (cyno rsTLIA) | TGLKGQEFAPSHQQVYAPLRADGDKPRAHLTVVRQTPTQHLKNQFPAL<br>HWEHELGLAFTKNRMNYTNKFLLIPESGDYFVYSQVTFRGMTSECSEI<br>RQAGRPNKPDSITVVITKVTDSYPEPTQLLMGTKSVCEVGSNWFQPIY<br>LGAMFSLQEGDKLMVNVSDISLVDYTKEDKTFFGAFLL |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 260 | AA Sequence of recombinant soluble murine TL1A (murine rsTLIA) | AITEERSEPSPQQVYSPPRGKPRAHLTIKKQTPAPHLKNQLSALHWEH<br>DLGMAFTKNGMKYINKSLVIPESGDYFIYSQITFRGTTSVCGDISRGR<br>RPNKPDSITVVITKVADSYPEPARLLTGSKSVCEISNNWFQSLYLGAM<br>FSLEEGDRLMVNVSDISLVDYTKEDKTFFGAFLL |
| 261 | AA Sequence of rat recombinant soluble TL1A (rat rsTLIA) | TGVTEERSAPSAQPVYTPSRDKPKAHLTIMRQTPVPHLKNELAALHWE<br>NNLGMAFTKNRMNYTNKFLVIPESGDYFIYSQITFRGTTSECGDISRV<br>RRPKKPDSITVVITKVADSYPEPAHLLTGTKSVCEISSNWFQPIYLGA<br>MFSLEEGDRLMVNVSDISLVDYTKEDKTFFGAFLI |
| 262 | AA Sequence of recombinant soluble rabbit TL1A (rabbit rsTLIA) | TGLKGREFGPSQQRAYMPLRADGNKPRAHLTAVKQTPTQPLRNHFPAL<br>HWEHELGLAFTKNRMNYTNKFLVIPESGDYFVYSQVTFRGTTSECGVI<br>NQRRRQTKPDSIVVVITKVTDNYPEPAQLLTGTKSVCEMGNWFQPIYL<br>GAMFSLEEGDKLMVNVSDVSLVDYTKEDKTFFGAFLL |
| 374 | Consensus CH1 sequence of antibodies across epitope bins 1, 2A and 2B | G   F   T   F   S   N   Y   A   L   H<br>    Y   P       T   S   F   G   M   S<br>        S       R   T           I   N<br>        D           Y<br>        Q           H<br>        N |
| 375 | Consensus CH1 sequence of antibodies across epitope bins 2A and 2B | G   Y   P   F   T   N   Y   A   I   S<br>        S       R   T       G   M   H<br>        T           S               N<br>        D           Y<br>        Q           H<br>        N |
| 376 | Consensus CH1 sequence of antibodies in epitope bin 2B | G   Y   P   F   T   N   Y   G   I   S<br>        S       R   T<br>        D           Y<br>        Q           H<br>        N |
| 377 | Consensus CH2 sequence of antibodies across epitope bins 1, 2A and 2B | L   I   S   Y   D   G   S   D   K   Y   Y   A   D   S   V   K   G<br>W       P   F   G   N   G   S   N   K   S   S   A   K   F   Q<br>        N   A   Y           N   T   N           Q   M   L<br>            T               G       H           R       H<br>            P               V<br>            S               K<br>                            A |
| 378 | Consensus CH2 sequence of antibodies across epitope bins 2A and 2B | W   I   N   A   G   N   G   N   T   K   Y   S   Q   K   F   Q   G<br>        S   T   Y           G   K   N   S   A   R   M   L<br>            P               V       H                   H<br>            S               K<br>                            A |
| 379 | Consensus CH2 sequence of antibodies in epitope bin 2B | W   I   S   T   Y   N   G   N   T   H   Y   A   Q   K   L   Q   G<br>            P               G   K   N           R   M   H<br>            S               V<br>            A               K<br>                            A |
| 380 | Consensus CH3 sequence of antibodies across epitope bins 1, 2A and 2B | .   .   .   Y   C   T   Y   S   S   C   S   Y   D   A   F   .   .<br>D   R   E   G   Y   G   S   G   Y   F   G   F   M   D   V   D   I<br>E   N   N   A   G   S   G   A   W   R   D   G   F       I<br>        Y       H               F           A           A<br>                                                        G |
| 381 | Consensus CH3 sequence of antibodies across epitope bins 2A and 2B | .   .   .   Y   G   S   G   S   Y   R   G   G   M   D   V   .   .<br>E   N   Y   G   Y       S   A   W   F   D   A   F       I<br>            A   H               F                       A<br>                                                        G |

TABLE 40-continued

Sequence Listing Table
CDR amino acid sequences, as defined by Kabat are underlined, CDR H1 amino acid sequences are shown in italics. In the heavy chain sequences, effector null mutations are also underlined.

| SEQ ID NO: | DESCRIPTION | SEQUENCE |
|---|---|---|
| 382 | Consensus CH3 sequence of antibodies in epitope bin 2B | E N Y Y G S G S Y R G G M D V . .<br>A F A<br>G |
| 383 | Linker sequence | GGGGSGGGGSGGGGS |
| 384 | Consensus CH1 sequence | G Y S F T Y Y G I S<br>D R H<br>Q<br>N<br>P |
| 385 | Consensus CH2 sequence | W I S T Y N G K T N Y A Q M L Q G<br>P A K H R H<br>S G<br>A N<br>V |
| 386 | Consensus CH1 sequence | G Y T F T S Y G I N<br>A M H |
| 387 | Consensus CH2 sequence | W I S T Y N G N T N S A Q K L Q G<br>N A G K Y S F |
| 388 | Consensus CH3 sequence | A H S S S W F D A F D I<br>G Y A |
| 389 | Consensus CH1 sequence | G F T F S N Y A L H<br>S F M<br>I |
| 390 | Consensus CH2 sequence | L I S Y D G S D K Y Y A D S V K G<br>P F S N<br>N |
| 391 | Consensus CH3 sequence | D R E Y C T Y S S C S Y D A F D I<br>N Y G S G F F |
| 392 | 6X Histidine Tag | HHHHHH |
| 393 | Forward PCR primer | 5'CAACAGCTACAGGCGCGCACTCCCAGGTTCAGCTGGTG3' |
| 394 | Reverse PCR primer | 5'GACCGATGGGCCCTTGGTCGACGCTGAGGAGACGGTGAC3' |
| 395 | Recognition sequence | DEVD |

TABLE 41

Sequence Listing Table of the structural features of antibodies
CDR amino acid sequences, as defined by Kabat are underlined, CDR H1 amino acid sequences are shown in italics. In the heavy chain sequences, effector null mutations are also underlined.

| Antibody | VL PROT | VL DNA | VH PROT | VH DNA | FL Light Prot | FL Light DNA | FL Heavy Prot | FL Heavy DNA | FL Heavy Prot | FL Heavy DNA |
|---|---|---|---|---|---|---|---|---|---|---|
| 9B3 | 1 | 2 | 3 (VH1)<br>5 (VH2) | 4 (VH1)<br>6 (VH2) | 7 | 8 | 9 | 10 | 11 | 12 |
| 15A9 | 22 | 23 | 24 | 25 | 26 | 27 | 28 | 29 | | |
| 15C1 | 36 | 37 | 38 | 39 | 40 | 41 | 42 | 43 | | |
| 22F9 | 50 | 51 | 52 | 53 | 54 | 55 | 56 | 57 | | |
| 26B1 | 64 | 65 | 66 (VH1)<br>68 (VH2)<br>70 (VH MDX) | 67 (VH1)<br>69 (VH2)<br>71 (VH MDX) | 72 | 73 | 74 | 75 | | |

TABLE 41-continued

Sequence Listing Table of the structural features of antibodies
CDR amino acid sequences, as defined by Kabat are underlined, CDR H1 amino acid sequences are shown in italics. In the heavy chain sequences, effector null mutations are also underlined.

| | | | | | | | | |
|---|---|---|---|---|---|---|---|---|
| 7D4 | 88 | 89 | 90 | 91 | 92 | 93 | 94 | 95 |
| 1D1 | 102 | 103 | 104 | 105 | 106 | 107 | 108 | 109 |
| 1D1 D5 | 102 | 103 | 116 | 117 | 106 | 107 | | |
| 1D1 D18 | 102 | 103 | 118 | 119 | 106 | 107 | | |
| 1D1 D21 | 102 | 103 | 120 | 121 | 106 | 107 | | |
| 1D1 D24 | 102 | 103 | 122 | 123 | 106 | 107 | | |
| 1D1 D25 | 102 | 103 | 124 | 125 | 106 | 107 | | |
| 1D1 D28 | 102 | 103 | 126 | 127 | 106 | 107 | | |
| 1D1 D29 | 102 | 103 | 128 | 129 | 106 | 107 | | |
| 1D1 D31 | 102 | 103 | 130 | 131 | 106 | 107 | | |
| 1D1 D37 | 102 | 103 | 132 | 133 | 106 | 107 | | |
| 1D1 D38 | 102 | 103 | 134 | 135 | 106 | 107 | | |
| 1D1 D39 | 102 | 103 | 136 | 137 | 106 | 107 | | |
| 1D1 DH3 | 102 | 103 | 138 | 139 | 106 | 107 | | |
| 1D1 DH8 | 102 | 103 | 140 | 141 | 106 | 107 | | |
| 1D1 DH9 | 102 | 103 | 142 | 143 | 106 | 107 | | |
| 1D1 DH10 | 102 | 103 | 144 | 145 | 106 | 107 | | |
| 1D1 1.1 | 102 | 103 | 146 | 147 | 106 | 107 | | |
| 1D1 1.2 | 102 | 103 | 148 | 149 | 106 | 107 | | |
| 1D1 1.3 | 102 | 103 | 150 | 151 | 106 | 107 | | |
| 1D1 1.4 | 102 | 103 | 152 | 153 | 106 | 107 | | |
| 1D1 1.5 | 102 | 103 | 154 | 155 | 106 | 107 | | |
| 1D1 1.6 | 102 | 103 | 156 | 157 | 106 | 107 | | |
| 1D1 1.7 | 102 | 103 | 158 | 159 | 106 | 107 | | |
| 1D1 1.8 | 102 | 103 | 160 | 161 | 106 | 107 | | |
| 1D1 1.9 | 102 | 103 | 162 | 163 | 106 | 107 | | |
| 1D1 1.10 | 102 | 103 | 164 | 165 | 106 | 107 | | |
| 1D1 1.11 | 102 | 103 | 166 | 167 | 106 | 107 | | |
| 1D1 1.12 | 102 | 103 | 168 | 169 | 106 | 107 | | |
| 1D1 1.13 | 102 | 103 | 170 | 171 | 106 | 107 | | |
| 1D1 1.14 | 102 | 103 | 172 | 173 | 106 | 107 | | |
| 1D1 1.15 | 102 | 103 | 174 | 175 | 106 | 107 | | |
| 1D1 1.16 | 102 | 103 | 176 | 177 | 106 | 107 | | |
| 1D1 1.17 | 102 | 103 | 178 | 179 | 106 | 107 | | |
| 1D1 1.18 | 102 | 103 | 180 | 181 | 106 | 107 | | |
| 1D1 1.19 | 102 | 103 | 182 | 183 | 106 | 107 | | |
| 1D1 1.20 | 102 | 103 | 184 | 185 | 106 | 107 | | |
| 1D1 1.21 | 102 | 103 | 186 | 187 | 106 | 107 | | |
| 1D1 1.22 | 102 | 103 | 188 | 189 | 106 | 107 | | |
| 1D1 1.23 | 102 | 103 | 190 | 191 | 106 | 107 | | |
| 1D1 1.24 | 102 | 103 | 192 | 193 | 106 | 107 | | |
| 1D1 1.25 | 102 | 103 | 194 | 195 | 106 | 107 | | |
| 1D1 1.26 | 102 | 103 | 196 | 197 | 106 | 107 | | |
| 1D1 1.27 | 102 | 103 | 198 | 199 | 106 | 107 | 200 | 201 |
| 1D1 1.28 | 102 | 103 | 205 | 206 | 106 | 107 | 207 | 208 |
| 1D1 1.29 | 102 | 103 | 212 | 213 | 106 | 107 | 214 | 215 |
| 1D1 1.30 | 102 | 103 | 219 | 220 | 106 | 107 | 221 | 222 |
| 1D1 1.31 | 102 | 103 | 226 | 227 | 106 | 107 | 228 | 229 |
| 1D1 1.32 | 102 | 103 | 233 | 234 | 106 | 107 | 235 | 236 |
| 1D1 1.33 | 102 | 103 | 240 | 241 | 106 | 107 | 242 | 243 |
| 1D1 1.34 | 102 | 103 | 247 | 248 | 106 | 107 | 249 | 250 |

| Antibody | CDR-L1 | CDR-L2 | CDR-L3 | CDR-H1 | CDR-H2 | CDR-H3 |
|---|---|---|---|---|---|---|
| 9B3 | 13 | 14 | 15 | 16 (VH1)<br>19 (VH2) | 17 (VH1)<br>20 (VH2) | 18 (VH1)<br>21 (VH2) |
| 15A9 | 30 | 31 | 32 | 33 | 34 | 35 |
| 15C1 | 44 | 45 | 46 | 47 | 48 | 49 |
| 22F9 | 58 | 59 | 60 | 61 | 62 | 63 |
| 26B1 | 76 | 77 | 78 | 79 (VH1)<br>82 (VH2)<br>85 (VH MDX) | 80 (VH1)<br>83 (VH2)<br>86 (VH MDX) | 81 (VH1)<br>84 (VH2)<br>87 (VH MDX) |
| 7D4 | 96 | 97 | 98 | 99 | 100 | 101 |
| 1D1 | 110 | 111 | 112 | 113 | 114 | 115 |
| 1D1 D5 | 110 | 111 | 112 | 263 | 264 | 265 |
| 1D1 D18 | 110 | 111 | 112 | 266 | 267 | 268 |
| 1D1 D21 | 110 | 111 | 112 | 269 | 270 | 271 |
| 1D1 D24 | 110 | 111 | 112 | 272 | 273 | 274 |
| 1D1 D25 | 110 | 111 | 112 | 275 | 276 | 277 |
| 1D1 D28 | 110 | 111 | 112 | 278 | 279 | 280 |
| 1D1 D29 | 110 | 111 | 112 | 281 | 282 | 283 |
| 1D1 D31 | 110 | 111 | 112 | 284 | 285 | 286 |
| 1D1 D37 | 110 | 111 | 112 | 287 | 288 | 289 |
| 1D1 D38 | 110 | 111 | 112 | 290 | 291 | 292 |

TABLE 41-continued

Sequence Listing Table of the structural features of antibodies
CDR amino acid sequences, as defined by Kabat are underlined, CDR H1 amino acid sequences are shown in italics. In the heavy chain sequences, effector null mutations are also underlined.

| | | | | | | |
|---|---|---|---|---|---|---|
| 1D1 D39 | 110 | 111 | 112 | 293 | 294 | 295 |
| 1D1 DH3 | 110 | 111 | 112 | 296 | 297 | 298 |
| 1D1 DH8 | 110 | 111 | 112 | 299 | 300 | 301 |
| 1D1 DH9 | 110 | 111 | 112 | 302 | 303 | 304 |
| 1D1 DH10 | 110 | 111 | 112 | 305 | 306 | 307 |
| 1D1 1.1 | 110 | 111 | 112 | 308 | 309 | 310 |
| 1D1 1.2 | 110 | 111 | 112 | | | |
| 1D1 1.3 | 110 | 111 | 112 | 311 | 312 | 313 |
| 1D1 1.4 | 110 | 111 | 112 | 314 | 315 | 316 |
| 1D1 1.5 | 110 | 111 | 112 | 317 | 318 | 319 |
| 1D1 1.6 | 110 | 111 | 112 | | | |
| 1D1 1.7 | 110 | 111 | 112 | 320 | 321 | 322 |
| 1D1 1.8 | 110 | 111 | 112 | 323 | 324 | 325 |
| 1D1 1.9 | 110 | 111 | 112 | 326 | 327 | 328 |
| 1D1 1.10 | 110 | 111 | 112 | 329 | 330 | 331 |
| 1D1 1.11 | 110 | 111 | 112 | 332 | 333 | 334 |
| 1D1 1.12 | 110 | 111 | 112 | | | |
| 1D1 1.13 | 110 | 111 | 112 | 335 | 336 | 337 |
| 1D1 1.14 | 110 | 111 | 112 | | | |
| 1D1 1.15 | 110 | 111 | 112 | 338 | 339 | 340 |
| 1D1 1.16 | 110 | 111 | 112 | 341 | 342 | 343 |
| 1D1 1.17 | 110 | 111 | 112 | 344 | 345 | 346 |
| 1D1 1.18 | 110 | 111 | 112 | 347 | 348 | 349 |
| 1D1 1.19 | 110 | 111 | 112 | 350 | 351 | 352 |
| 1D1 1.20 | 110 | 111 | 112 | 353 | 354 | 355 |
| 1D1 1.21 | 110 | 111 | 112 | 356 | 357 | 358 |
| 1D1 1.22 | 110 | 111 | 112 | 359 | 360 | 361 |
| 1D1 1.23 | 110 | 111 | 112 | 362 | 363 | 364 |
| 1D1 1.24 | 110 | 111 | 112 | 365 | 366 | 367 |
| 1D1 1.25 | 110 | 111 | 112 | 368 | 369 | 370 |
| 1D1 1.26 | 110 | 111 | 112 | 371 | 372 | 373 |
| 1D1 1.27 | 110 | 111 | 112 | 202 | 203 | 204 |
| 1D1 1.28 | 110 | 111 | 112 | 209 | 210 | 211 |
| 1D1 1.29 | 110 | 111 | 112 | 216 | 217 | 218 |
| 1D1 1.30 | 110 | 111 | 112 | 223 | 224 | 225 |
| 1D1 1.31 | 110 | 111 | 112 | 230 | 231 | 232 |
| 1D1 1.32 | 110 | 111 | 112 | 237 | 238 | 239 |
| 1D1 1.33 | 110 | 111 | 112 | 244 | 245 | 246 |
| 1D1 1.34 | 110 | 111 | 112 | 251 | 252 | 253 |

Shown are amino acid residues of TL1A that interact with the ligand DR3 or antibodies 1D1, 1D1 1.31 (1.31), 26B11, or 7D4. Shown are amino acid positions (either based on the full-length or mature sequence) of TL1A. Interactions in the form of residues with normalized surface area (Å$^2$) buried due to interactions between pairs of 1D1 antibody residues and TL1A residues, formation of hydrogen bonds, salt bridges and water-mediated hydrogen bonds formed through the TL1A amino acid residues, are shown.

TABLE 42

Interaction of TL1A and DR3 and various antibodies described herein

| Sub- | Position | Position | | Interacting Residues | | | | | Buried Surface Area (Å$^2$) | | | | Hydrogen Bond | | | |
|---|---|---|---|---|---|---|---|---|---|---|---|---|---|---|---|---|
| unit | (FL) | (mature) | AA | DR3 | 1.31 | 1D1 | 26B11 | 7D4 | 1.31 | 1D1 | 26B11 | 7D4 | 1.31 | 1D1 | 26B11 | 7D4 |
| 0 | 100 | 30 | T | + | | | | | | | | | | | | |
| 0 | 101 | 31 | V | + | + | + | | | | | | | | | | |
| 0 | 102 | 32 | V | + | + | + | | | | | | | | | | |
| 0 | 103 | 33 | R | + | + | + | | + | 31.6 | 93.4 | | 108.4 | | 1 | | |
| 0 | 104 | 34 | Q | | | | | + | | | | 35.6 | | | | 1 |
| 0 | 105 | 35 | T | | | | + | + | | | 23.2 | 51.3 | | | | |
| 0 | 106 | 36 | P | | | | + | + | | | 40.9 | 63.5 | | | | 1 |
| 0 | 107 | 37 | T | | | | + | + | | | 31.6 | 18.7 | | | | |
| 0 | 108 | 38 | Q | | | | + | + | | | 172.9 | 25 | | | 3 | |
| 0 | 109 | 39 | H | | | | + | + | | | 61.3 | 93 | | | 1 | |
| 0 | 110 | 40 | F | | | | + | + | | | 150.9 | 6.5 | | | | |
| 0 | 111 | 41 | K | | | | + | | | | 126.4 | | | | 1 | |
| 0 | 112 | 42 | N | | | | + | | | | 54.3 | | | | 1 | |
| 0 | 113 | 43 | Q | | | | + | + | | | 15.8 | 13.1 | | | | |
| 0 | 114 | 44 | F | | | | | + | | | | 0.2 | | | | |
| 0 | 115 | 45 | P | | | | | + | | | | 24.2 | | | | |
| 0 | 120 | 50 | E | + | + | + | | | 19.6 | 20.4 | | | | | | |
| 0 | 121 | 51 | H | | + | + | | | | | | | | | | |
| 0 | 122 | 52 | E | | + | + | | | 110.9 | 110.5 | | | 2 | 3 | | |

TABLE 42-continued

Interaction of TL1A and DR3 and various antibodies described herein

| | | | | | | | | | | | | | | | | |
|---|---|---|---|---|---|---|---|---|---|---|---|---|---|---|---|---|
| 0 | 123 | 53 | L | + | + | + | | | 113.8 | 118.1 | | | | | | |
| 0 | 124 | 54 | G | + | + | + | | | 51.3 | 51.3 | | | | | | |
| 0 | 125 | 55 | L | | + | + | | | 56.3 | 53.4 | | | | | | |
| 0 | 126 | 56 | A | | + | + | | | 10.7 | 11.9 | | | 1 | 1 | | |
| 0 | 127 | 57 | F | | + | + | | | 26.4 | 26.3 | | | | | | |
| 0 | 128 | 58 | T | | | + | | | | 20.1 | | | | | | |
| 0 | 156 | 86 | R | + | | | | + | | | | 100.9 | | | | 2 |
| 0 | 157 | 87 | G | + | | | | + | | | | 6.3 | | | | |
| 0 | 158 | 88 | M | + | | | | + | | | | 144.5 | | | | |
| 0 | 159 | 89 | T | | | | | + | | | | 47.6 | | | | |
| 0 | 161 | 91 | E | | | + | | | | | | | | | | |
| 0 | 169 | 99 | G | | | | + | | | | 6.7 | | | | | |
| 0 | 170 | 100 | R | | | | + | | | | 0 | | | | | |
| 0 | 171 | 101 | P | | | | + | | | | 77.3 | | | | 1 | |
| 0 | 172 | 102 | N | | | | + | | | | 66.5 | | | | 3 | |
| 0 | 173 | 103 | K | | | | + | | | | 68.8 | | | | 2 | |
| 0 | 174 | 104 | P | | | | + | | | | 20.8 | | | | | |
| 0 | 175 | 105 | D | | | | + | | | | 80 | | | | | |
| 0 | 176 | 106 | S | | | | + | | | | 13.3 | | | | | |
| 0 | 206 | 136 | S | + | | | | + | | | | 26.6 | | | | |
| 0 | 207 | 137 | N | + | | | | + | | | | 58.9 | | | | 1 |
| 0 | 209 | 139 | F | + | | | | | | | | | | | | |
| 0 | 231 | 161 | S | | | | | + | | | | 10.5 | | | | |
| 0 | 232 | 162 | D | | | | | + | | | | 42.5 | | | | 1 |
| 0 | 233 | 163 | I | | | | | + | | | | 22.9 | | | | |
| 0 | 234 | 164 | S | + | | | + | + | | | 29.4 | 91.2 | | | | |
| 0 | 235 | 165 | L | + | | | | + | | | | 8.6 | | | | |
| 0 | 236 | 166 | V | | | | | + | | | | 8.7 | | | | |
| 0 | 237 | 167 | D | | | | | + | | | | 3.9 | | | | |
| 0 | 238 | 168 | Y | + | + | + | | + | 25.6 | 15.6 | | 71 | 1 | 1 | | 1 |
| 0 | 239 | 169 | T | + | + | + | | + | 43.6 | 33 | | 4.4 | 2 | | | |
| 0 | 240 | 170 | K | + | + | + | | | | 46 | | | | | | |
| 0 | 241 | 171 | E | + | + | + | | | 51.2 | 49 | | | 1 | | | |
| 0 | 242 | 172 | D | | + | | | | | | | | | | | |
| 1 | 112 | 42 | N | + | | | | | | | 54.3 | | | | | |
| 1 | 114 | 44 | F | + | | | | | | | | 0.2 | | | | |
| 1 | 173 | 103 | K | + | | | | | | | 68.8 | | | | | |
| 1 | 174 | 104 | P | + | | | | | | | 20.8 | | | | | |
| 1 | 175 | 105 | D | + | | | | | | | 80 | | | | | |
| 1 | 176 | 106 | S | + | | | | | | | 13.3 | | | | | |
| 1 | 183 | 113 | K | | + | + | | | 17.7 | 25 | | | | | | |
| 1 | 185 | 115 | T | | | + | | | | | | | | | | |
| 1 | 187 | 117 | S | + | + | | | | 41.9 | | | | | | | |
| 1 | 188 | 118 | Y | + | + | + | | | 48.9 | 118.1 | | | | 1 | | |
| 1 | 189 | 119 | P | + | + | | | | | | | | | | | |
| 1 | 190 | 120 | E | + | | | | | | | | | | | | |
| 1 | 191 | 121 | P | | | + | | | | | | | | | | |
| 1 | 192 | 122 | T | | + | + | | | 43.9 | 43.7 | | | 1 | | | |
| 1 | 193 | 123 | Q | | + | + | | | | | | | | | | |
| 1 | 217 | 147 | M | | + | + | | | | | | | | | | |
| 1 | 218 | 148 | F | | + | + | | | | | | | | | | |
| 1 | 219 | 149 | S | | + | + | | | 35.4 | 39.1 | | | 1 | 1 | | |
| 1 | 221 | 151 | Q | + | + | + | | | 49.3 | 38.8 | | | | | | |

| Sub-unit | Position (FL) | Position (mature) | AA | Salt Bridge 1.31 | Salt Bridge 1D1 | Salt Bridge 26B11 | Salt Bridge 7D4 | $H_2O$-mediated H Bond 1.31 | $H_2O$-mediated H Bond 1D1 | $H_2O$-mediated H Bond 26B11 | $H_2O$-mediated H Bond 7D4 |
|---|---|---|---|---|---|---|---|---|---|---|---|
| 0 | 100 | 30 | T | | | | | | | | |
| 0 | 101 | 31 | V | | | | | | | | |
| 0 | 102 | 32 | V | | | | | | | | |
| 0 | 103 | 33 | R | | | | + | | + | | |
| 0 | 104 | 34 | Q | | | | | | | | |
| 0 | 105 | 35 | T | | | | | | | | |
| 0 | 106 | 36 | P | | | | | | | | |
| 0 | 107 | 37 | T | | | | | | | | |
| 0 | 108 | 38 | Q | | | | | | | + | |
| 0 | 109 | 39 | H | | | | | | | | |
| 0 | 110 | 40 | F | | | | | | | | |
| 0 | 111 | 41 | K | | | + | | | | + | |
| 0 | 112 | 42 | N | | | | | | | + | |
| 0 | 113 | 43 | Q | | | | | | | | |
| 0 | 114 | 44 | F | | | | | | | | |
| 0 | 115 | 45 | P | | | | | | | | |
| 0 | 120 | 50 | E | + | + | | | | | | |
| 0 | 121 | 51 | H | | | | | | | | |
| 0 | 122 | 52 | E | + | | | | | | | |
| 0 | 123 | 53 | L | | | | | | | | |

TABLE 42-continued

Interaction of TL1A and DR3 and various antibodies described herein

| | | | | | | |
|---|---|---|---|---|---|---|
| 0 | 124 | 54 | G | | | |
| 0 | 125 | 55 | L | | + | |
| 0 | 126 | 56 | A | | | |
| 0 | 127 | 57 | F | | | |
| 0 | 128 | 58 | T | | | |
| 0 | 156 | 86 | R | | | |
| 0 | 157 | 87 | G | | | |
| 0 | 158 | 88 | M | | | |
| 0 | 159 | 89 | T | | | |
| 0 | 161 | 91 | E | | | |
| 0 | 169 | 99 | G | | | |
| 0 | 170 | 100 | R | | | |
| 0 | 171 | 101 | P | | | |
| 0 | 172 | 102 | N | | | + |
| 0 | 173 | 103 | K | | | |
| 0 | 174 | 104 | P | | | |
| 0 | 175 | 105 | D | | | + |
| 0 | 176 | 106 | S | | | |
| 0 | 206 | 136 | S | | | |
| 0 | 207 | 137 | N | | | |
| 0 | 209 | 139 | F | | | |
| 0 | 231 | 161 | S | | | |
| 0 | 232 | 162 | D | | | |
| 0 | 233 | 163 | I | | | |
| 0 | 234 | 164 | S | | | |
| 0 | 235 | 165 | L | | | |
| 0 | 236 | 166 | V | | | |
| 0 | 237 | 167 | D | | | |
| 0 | 238 | 168 | Y | | | |
| 0 | 239 | 169 | T | | | |
| 0 | 240 | 170 | K | | | |
| 0 | 241 | 171 | E | | | |
| 0 | 242 | 172 | D | | | |
| 1 | 112 | 42 | N | | | |
| 1 | 114 | 44 | F | | | |
| 1 | 173 | 103 | K | | | |
| 1 | 174 | 104 | P | | | |
| 1 | 175 | 105 | D | | | |
| 1 | 176 | 106 | S | | | |
| 1 | 183 | 113 | K | + | | |
| 1 | 185 | 115 | T | | | |
| 1 | 187 | 117 | S | | | |
| 1 | 188 | 118 | Y | | | |
| 1 | 189 | 119 | P | | | |
| 1 | 190 | 120 | E | | | |
| 1 | 191 | 121 | P | | | |
| 1 | 192 | 122 | T | | | |
| 1 | 193 | 123 | Q | | | |
| 1 | 217 | 147 | M | | + | |
| 1 | 218 | 148 | F | | | |
| 1 | 219 | 149 | S | | | |
| 1 | 221 | 151 | Q | | | |

SEQUENCE LISTING

```
Sequence total quantity: 395
SEQ ID NO: 1           moltype = AA  length = 107
FEATURE                Location/Qualifiers
REGION                 1..107
                       note = source = /note="Description of Artificial Sequence:
                        Syntheticpolypeptide"
source                 1..107
                       mol_type = protein
                       organism = synthetic construct
SEQUENCE: 1
DIQMTQSPSS LSASVGDRVT ITCRASQGIS SWLAWYQQKP EKAPKSLIYA ASSLQSGVPS  60
RFSGSGSGTD FTLTISSLQP EDYATYYCQQ YNSYPYTFGQ GTKLEIK                107

SEQ ID NO: 2           moltype = DNA  length = 321
FEATURE                Location/Qualifiers
misc_feature           1..321
                       note = source = /note="Description of Artificial Sequence:
                        Syntheticpolynucleotide"
```

```
source                 1..321
                       mol_type = other DNA
                       organism = synthetic construct
SEQUENCE: 2
gacatccaga tgacccagtc tccatcctca ctgtctgcat ctgtaggaga cagagtcacc  60
atcacttgtc gggcgagtca gggtattagc agctggttag cctggtatca gcagaaacca  120
gagaaagccc ctaagtccct gatctatgct gcatccagtt tgcagagtgg ggtcccatca  180
aggttcagcg gcagtggatc tgggacagat ttcactctca ccatcagtag cctgcagcct  240
gaagattatg caacttatta ctgccaacag tataatagtt acccgtacac ttttggccag  300
gggaccaagc tggagatcaa a                                            321

SEQ ID NO: 3           moltype = AA  length = 126
FEATURE                Location/Qualifiers
REGION                 1..126
                       note = source = /note="Description of Artificial Sequence:
                        Syntheticpolypeptide"
source                 1..126
                       mol_type = protein
                       organism = synthetic construct
SEQUENCE: 3
QVQLVESGGG VVQPGRSLRL SCAASGFTFS NYALHWVRQA PGKGLEWVAL ISYDGSDKYY  60
ADSVKGRFAI SRDNSKNTLY LQMNSLRAED TAVYYCARDR EYCTYSSCSY DAFDIWGQGT  120
MVTVSS                                                             126

SEQ ID NO: 4           moltype = DNA  length = 378
FEATURE                Location/Qualifiers
misc_feature           1..378
                       note = source = /note="Description of Artificial Sequence:
                        Syntheticpolynucleotide"
source                 1..378
                       mol_type = other DNA
                       organism = synthetic construct
SEQUENCE: 4
caggtgcagc tggtggagtc tgggggaggc gtggtccagc ctgggaggtc cctgagactc  60
tcctgtgcag cctctggatt caccttcagt aactatgctc tgcactgggt ccgccaggct  120
ccaggcaagg ggctggagtg ggtggcactt atatcatatg atggaagcga taaatactac  180
gcagactccg tgaagggccg attcgccatc tccagagaca attccaagaa cacgctgtat  240
ctgcaaatga acagcctgag agctgaggac acggctgtgt attactgtgc gagagatcgg  300
gaatattgta cttatagtag ctgctcctat gatgcttttg atatctgggg ccaagggaca  360
atggtcaccg tctcttca                                                378

SEQ ID NO: 5           moltype = AA  length = 126
FEATURE                Location/Qualifiers
REGION                 1..126
                       note = source = /note="Description of Artificial Sequence:
                        Syntheticpolypeptide"
source                 1..126
                       mol_type = protein
                       organism = synthetic construct
SEQUENCE: 5
QVQLVESGGG VVQPGRSLRL SCAASGFTFS SFAMHWVRQA PGKGLEWVAL IPFDGSSNYY  60
ADSVKGRFTI SRDNSKNTLY LQMNSLRAED TAVYYCARDR NYYGSGSFSF DAFDIWGQGT  120
LVTVSS                                                             126

SEQ ID NO: 6           moltype = DNA  length = 378
FEATURE                Location/Qualifiers
misc_feature           1..378
                       note = source = /note="Description of Artificial Sequence:
                        Syntheticpolynucleotide"
source                 1..378
                       mol_type = other DNA
                       organism = synthetic construct
SEQUENCE: 6
caggttcagc tggtggagtc tgggggggc gtggtccagc ctgggaggtc cctgagactc  60
tcctgtgcag cctctggatt caccttcagt agctttgcta tgcactgggt ccgccaggct  120
ccaggcaagg ggctggagtg ggtggcactt ataccgtttg atggaagcag taactattac  180
gcagactccg tgaagggccg attcaccatc tccagagaca attccaagaa cacgctgtat  240
ctgcaaatga acagcctgag agctgaggac acggctgtgt attactgtgc gagagatagg  300
aattactatg gttcggggag tttttccttt gatgcttttg atatctgggg ccaagggaca  360
ctggtcaccg tctcctca                                                378

SEQ ID NO: 7           moltype = AA  length = 214
FEATURE                Location/Qualifiers
REGION                 1..214
                       note = source = /note="Description of Artificial Sequence:
                        Syntheticpolypeptide"
source                 1..214
                       mol_type = protein
                       organism = synthetic construct
```

```
SEQUENCE: 7
DIQMTQSPSS LSASVGDRVT ITCRASQGIS SWLAWYQQKP EKAPKSLIYA ASSLQSGVPS  60
RFSGSGSGTD FTLTISSLQP EDYATYYCQQ YNSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 8           moltype = DNA  length = 642
FEATURE                Location/Qualifiers
misc_feature           1..642
                       note = source = /note="Description of Artificial Sequence:
                        Syntheticpolynucleotide"
source                 1..642
                       mol_type = other DNA
                       organism = synthetic construct
SEQUENCE: 8
gacatccaga tgacccagtc tccatcctca ctgtctgcat ctgtaggaga cagagtcacc  60
atcacttgtc gggcgagtca gggtattagc agctggttag cctggtatca gcagaaacca  120
gagaaagccc ctaagtccct gatctatgct gcatccagtt tgcagagtgg ggtcccatca  180
aggttcagcg gcagtggatc tgggacagat ttcactctca ccatcagtag cctgcagcct  240
gaagattatg caacttatta ctgccaacag tataatagtt acccgtacac ttttggccag  300
gggaccaagc tggagatcaa acgtactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 9           moltype = AA  length = 455
FEATURE                Location/Qualifiers
REGION                 1..455
                       note = source = /note="Description of Artificial Sequence:
                        Syntheticpolypeptide"
source                 1..455
                       mol_type = protein
                       organism = synthetic construct
SEQUENCE: 9
QVQLVESGGG VVQPGRSLRL SCAASGFTFS NYALHWVRQA PGKGLEWVAL ISYDGSDKYY  60
ADSVKGRFAI SRDNSKNTLY LQMNSLRAED TAVYYCARDR EYCTYSSCSY DAFDIWGQGT  120
MVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGAPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPG                             455

SEQ ID NO: 10          moltype = DNA  length = 1365
FEATURE                Location/Qualifiers
misc_feature           1..1365
                       note = source = /note="Description of Artificial Sequence:
                        Syntheticpolynucleotide"
source                 1..1365
                       mol_type = other DNA
                       organism = synthetic construct
SEQUENCE: 10
caggtgcagc tggtggagtc tgggggaggc gtggtccagc ctgggaggtc cctgagactc  60
tcctgtgcag cctctggatt caccttcagt aactatgctc tgcactgggt ccgccaggct  120
ccaggcaagg ggctggagtg ggtggcactt atatcatatg atggaagcga taaatactac  180
gcagactccg tgaagggccg attcgccatc tccagagaca attccaagaa cacgctgtat  240
ctgcaaatga acagcctgag agctgaggac acggctgtgt attactgtgc gagagatcgg  300
gaatattgta cttatagtag ctgctcctat gatgcttttg atatctgggg ccaagggaca  360
atggtcaccg tctcttcagc gtcgaccaag ggcccatcgg tcttccccct ggcaccctcc  420
tccaagagca cctctggggg cacagcggcc ctgggctgcc tggtcaagga ctacttcccc  480
gaaccggtga cggtgtcgtg gaactcaggc gccctgacca gcggcgtgca caccttcccg  540
gctgtcctac agtcctcagg actctactcc ctcagcagcg tggtgaccgt gccctccagc  600
agcttgggca cccagaccta catctgcaac gtgaatcaca agcccagcaa caccaaggtg  660
gacaagaaag ttgagcccaa atcttgtgac aaaactcaca catgcccacc gtgcccagca  720
cctgaagccg ctggggcacc gtcagtcttc ctcttccccc caaaacccaa ggacaccctc  780
atgatctccc ggacccctga ggtcacatgc gtggtggtgg acgtgagcca cgaagaccct  840
gaggtcaagt tcaactggta cgtggacggc gtggaggtgc ataatgccaa gacaaagccg  900
cgggaggagc agtacaacag cacgtaccgt gtggtcagcg tcctcaccgt cctgcaccag  960
gactggctga atggcaagga gtacaagtgc aaggtctcca acaaagccct cccagccccc  1020
atcgagaaaa ccatctccaa agccaaaggg cagccccgag aaccacaggt gtacaccctg  1080
cccccatccc gggaggagat gaccaagaac caggtcagcc tgacctgcct ggtcaaaggc  1140
ttctatccca gcgacatcgc cgtggagtgg gagagcaatg ggcagccgga gaacaactac  1200
aagaccacgc ctcccgtgct ggactccgac ggctccttct tcctctatag caagctcacc  1260
gtggacaaga gcaggtggca gcaggggaac gtcttctcat gctccgtgat gcatgaggct  1320
ctgcacaacc actacacgca gaagagcctc tccctgtccc cgggt                  1365

SEQ ID NO: 11          moltype = AA  length = 455
```

-continued

```
FEATURE                Location/Qualifiers
REGION                 1..455
                       note = source = /note="Description of Artificial Sequence:
                        Syntheticpolypeptide"
source                 1..455
                       mol_type = protein
                       organism = synthetic construct
SEQUENCE: 11
QVQLVESGGG VVQPGRSLRL SCAASGFTFS SFAMHWVRQA PGKGLEWVAL IPFDGSSNYY  60
ADSVKGRFTI SRDNSKNTLY LQMNSLRAED TAVYYCARDR NYYGSGSFSF DAFDIWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGAPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPG                            455

SEQ ID NO: 12          moltype = DNA  length = 1365
FEATURE                Location/Qualifiers
misc_feature           1..1365
                       note = source = /note="Description of Artificial Sequence:
                        Syntheticpolynucleotide"
source                 1..1365
                       mol_type = other DNA
                       organism = synthetic construct
SEQUENCE: 12
caggttcagc tggtggagtc tgggggggc gtggtccagc ctgggaggtc cctgagactc  60
tcctgtgcag cctctggatt caccttcagt agctttgcta tgcactgggt ccgccaggct  120
ccaggcaagg ggctggagtg ggtggcactt ataccgtttg atggaagcag taactattac  180
gcagactccg tgaagggccg attcaccatc tccagagaca attccaagaa cacgctgtat  240
ctgcaaatga acagcctgag agctgaggac acggctgtgt attactgtgc gagagatagg  300
aattactatg gttcggggag tttttccttt gatgcttttg atatctgggg ccaagggaca  360
ctggtcaccg tctcctcagc gtcgaccaag ggcccatcgg tcttccccct ggcaccctcc  420
tccaagagca cctctggggg cacagcggcc ctgggctgcc tggtcaagga ctacttcccc  480
gaaccggtga cggtgtcgtg gaactcaggc gccctgacca gcggcgtgca caccttcccg  540
gctgtcctac agtcctcagg actctactcc ctcagcagcg tggtgaccgt gccctccagc  600
agcttgggca cccagaccta catctgcaac gtgaatcaca agcccagcaa caccaaggtg  660
gacaagaaag ttgagcccaa atcttgtgac aaaactcaca catgcccacc gtgcccagca  720
cctgaagccg ctggggcacc gtcagtcttc ctcttccccc caaaacccaa ggacaccctc  780
atgatctccc ggacccctga ggtcacatgc gtggtggtgg acgtgagcca cgaagaccct  840
gaggtcaagt tcaactggta cgtggacggc gtggaggtgc ataatgccaa gacaaagccg  900
cgggaggagc agtacaacag cacgtaccgt gtggtcagcg tcctcaccgt cctgcaccag  960
gactggctga atggcaagga gtacaagtgc aaggtctcca acaaagccct cccagccccc  1020
atcgagaaaa ccatctccaa agccaaaggg cagccccgag aaccacaggt gtacaccctg  1080
cccccatccc gggaggagat gaccaagaac caggtcagcc tgacctgcct ggtcaaaggc  1140
ttctatccca gcgacatcgc cgtggagtgg gagagcaatg ggcagccgga gaacaactac  1200
aagaccacgc ctcccgtgct ggactccgac ggctccttct tcctctatag caagctcacc  1260
gtggacaaga gcaggtggca gcaggggaac gtcttctcat gctccgtgat gcatgaggct  1320
ctgcacaacc actacacgca gaagagcctc tccctgtccc cgggt                 1365

SEQ ID NO: 13          moltype = AA  length = 11
FEATURE                Location/Qualifiers
REGION                 1..11
                       note = source = /note="Description of Artificial Sequence:
                        Syntheticpeptide"
source                 1..11
                       mol_type = protein
                       organism = synthetic construct
SEQUENCE: 13
RASQGISSWL A                                                      11

SEQ ID NO: 14          moltype = AA  length = 7
FEATURE                Location/Qualifiers
REGION                 1..7
                       note = source = /note="Description of Artificial Sequence:
                        Syntheticpeptide"
source                 1..7
                       mol_type = protein
                       organism = synthetic construct
SEQUENCE: 14
AASSLQS                                                           7

SEQ ID NO: 15          moltype = AA  length = 9
FEATURE                Location/Qualifiers
REGION                 1..9
                       note = source = /note="Description of Artificial Sequence:
                        Syntheticpeptide"
source                 1..9
                       mol_type = protein
```

```
                        organism = synthetic construct
SEQUENCE: 15
QQYNSYPYT                                                                9

SEQ ID NO: 16           moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 16
GFTFSNYALH                                                               10

SEQ ID NO: 17           moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 17
LISYDGSDKY YADSVKG                                                       17

SEQ ID NO: 18           moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 18
DREYCTYSSC SYDAFDI                                                       17

SEQ ID NO: 19           moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 19
GFTFSSFAMH                                                               10

SEQ ID NO: 20           moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 20
LIPFDGSSNY YADSVKG                                                       17

SEQ ID NO: 21           moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 21
DRNYYGSGSF SFDAFDI                                                       17

SEQ ID NO: 22           moltype = AA  length = 107
FEATURE                 Location/Qualifiers
REGION                  1..107
                        note = source = /note="Description of Artificial Sequence:
                         Syntheticpolypeptide"
source                  1..107
                        mol_type = protein
                        organism = synthetic construct
SEQUENCE: 22
```

-continued

```
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPWTFGQ GTKVEIK                107

SEQ ID NO: 23          moltype = DNA  length = 321
FEATURE                Location/Qualifiers
misc_feature           1..321
                       note = source = /note="Description of Artificial Sequence:
                        Syntheticpolynucleotide"
source                 1..321
                       mol_type = other DNA
                       organism = synthetic construct
SEQUENCE: 23
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgtggac gttcggccaa  300
gggaccaagg tggaaatcaa a                                            321

SEQ ID NO: 24          moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 24
QVQLVQSGAE VKKPGASLKV SCKASGYPFT NYGISWVRQA PGQGLEWMGW ISTYNGNTHY  60
AQKLQGRVTM TTDTSTTTAY MDLRSLRSDD TAVYYCAREN YYGSGSYRGG MDVWGQGTTV  120
TVSS                                                               124

SEQ ID NO: 25          moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 25
caggttcagc tggtgcagtc tggagctgag gtgaagaagc ctggggcctc actgaaggtc  60
tcctgcaagg cttctggtta cccctttacc aactatggta tcagctgggt gcgacaggcc  120
cctggacaag ggcttgagtg gatgggatgg atcagcactt acaatggtaa cactcactat  180
gcacagaagc tccagggcag agtcaccatg accacagaca catccacgac cacagcctac  240
atggacctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 26          moltype = AA  length = 214
FEATURE                Location/Qualifiers
REGION                 1..214
                       note = source = /note="Description of Artificial Sequence:
                        Syntheticpolypeptide"
source                 1..214
                       mol_type = protein
                       organism = synthetic construct
SEQUENCE: 26
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 27          moltype = DNA  length = 642
FEATURE                Location/Qualifiers
misc_feature           1..642
                       note = source = /note="Description of Artificial Sequence:
                        Syntheticpolynucleotide"
source                 1..642
                       mol_type = other DNA
                       organism = synthetic construct
SEQUENCE: 27
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgtggac gttcggccaa  300
gggaccaagg tggaaatcaa acgtactgtg gctgcaccat ctgtcttcat cttcccgcca  360
tctgatgagc agttgaaatc tggaactgcc tctgttgtgt gcctgctgaa taacttctat  420
```

```
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 28          moltype = AA  length = 453
FEATURE                Location/Qualifiers
REGION                 1..453
                       note = source = /note="Description of Artificial Sequence:
                        Syntheticpolypeptide"
source                 1..453
                       mol_type = protein
                       organism = synthetic construct
SEQUENCE: 28
QVQLVQSGAE VKKPGASLKV SCKASGYPFT NYGISWVRQA PGQGLEWMGW ISTYNGNTHY  60
AQKLQGRVTM TTDTSTTTAY MDLRSLRSDD TAVYYCAREN YYGSGSYRGG MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 29          moltype = DNA  length = 1359
FEATURE                Location/Qualifiers
misc_feature           1..1359
                       note = source = /note="Description of Artificial Sequence:
                        Syntheticpolynucleotide"
source                 1..1359
                       mol_type = other DNA
                       organism = synthetic construct
SEQUENCE: 29
caggttcagc tggtgcagtc tggagctgag gtgaagaagc ctggggcctc actgaaggtc  60
tcctgcaagg cttctggtta cccctttacc aactatggta tcagctgggt gcgacaggcc  120
cctggacaag ggcttgagtg gatgggatgg atcagcactt acaatggtaa cactcactat  180
gcacagaagc tccagggcag agtcaccatg accacagaca catccacgac cacagcctac  240
atggacctga ggagcctgag atctgacgac acggccgtgt attactgtgc gagagagaat  300
tactatggtt cggggagtta tagagggggt atggacgtct ggggccaagg gaccacggtc  360
accgtctcct cagcgtcgac caagggccca tcggtcttcc ccctggcacc ctcctccaag  420
agcacctctg gggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
aaccactaca cgcagaagag cctctccctg tccccgggt                       1359

SEQ ID NO: 30          moltype = AA  length = 11
FEATURE                Location/Qualifiers
REGION                 1..11
                       note = source = /note="Description of Artificial Sequence:
                        Syntheticpeptide"
source                 1..11
                       mol_type = protein
                       organism = synthetic construct
SEQUENCE: 30
RASQSVSSYL A                                                      11

SEQ ID NO: 31          moltype = AA  length = 7
FEATURE                Location/Qualifiers
REGION                 1..7
                       note = source = /note="Description of Artificial Sequence:
                        Syntheticpeptide"
source                 1..7
                       mol_type = protein
                       organism = synthetic construct
SEQUENCE: 31
DASNRAT                                                           7

SEQ ID NO: 32          moltype = AA  length = 9
```

```
FEATURE                Location/Qualifiers
REGION                 1..9
                       note = source = /note="Description of Artificial Sequence:
                        Syntheticpeptide"
source                 1..9
                       mol_type = protein
                       organism = synthetic construct
SEQUENCE: 32
QQRSNWPWT                                                        9

SEQ ID NO: 33          moltype = AA  length = 10
FEATURE                Location/Qualifiers
REGION                 1..10
                       note = source = /note="Description of Artificial Sequence:
                        Syntheticpeptide"
source                 1..10
                       mol_type = protein
                       organism = synthetic construct
SEQUENCE: 33
GYPFTNYGIS                                                       10

SEQ ID NO: 34          moltype = AA  length = 17
FEATURE                Location/Qualifiers
REGION                 1..17
                       note = source = /note="Description of Artificial Sequence:
                        Syntheticpeptide"
source                 1..17
                       mol_type = protein
                       organism = synthetic construct
SEQUENCE: 34
WISTYNGNTH YAQKLQG                                               17

SEQ ID NO: 35          moltype = AA  length = 15
FEATURE                Location/Qualifiers
REGION                 1..15
                       note = source = /note="Description of Artificial Sequence:
                        Syntheticpeptide"
source                 1..15
                       mol_type = protein
                       organism = synthetic construct
SEQUENCE: 35
ENYYGSGSYR GGMDV                                                 15

SEQ ID NO: 36          moltype = AA  length = 107
FEATURE                Location/Qualifiers
REGION                 1..107
                       note = source = /note="Description of Artificial Sequence:
                        Syntheticpolypeptide"
source                 1..107
                       mol_type = protein
                       organism = synthetic construct
SEQUENCE: 36
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPWTFGQ GTKVEIK                107

SEQ ID NO: 37          moltype = DNA  length = 321
FEATURE                Location/Qualifiers
misc_feature           1..321
                       note = source = /note="Description of Artificial Sequence:
                        Syntheticpolynucleotide"
source                 1..321
                       mol_type = other DNA
                       organism = synthetic construct
SEQUENCE: 37
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgtggac gttcggccaa  300
gggaccaagg tggaaatcaa a                                             321

SEQ ID NO: 38          moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
```

```
SEQUENCE: 38
QVQLVQSGAE VKKPGASVKV SCKASGYSFT TYGISWVRQA PGQGLEWMGW ISTYNGNTHY  60
AQKLQGRVTM TTDTSTRTAY MELRSLRSDD TAVYYCAREN YYGSGSYRGG MDVWGQGTTV  120
TVSS                                                               124

SEQ ID NO: 39          moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 39
caggttcagc tggtgcagtc tggagctgag gtgaagaagc ctggggcctc agtgaaggtc  60
tcctgcaagg cttctggtta ctcctttacc acctatggta tcagctgggt gcgacaggcc  120
cctggacaag ggcttgagtg gatgggatgg atcagcactt acaatggtaa cacacactat  180
gcacagaagc tccagggcag agtcaccatg accacagaca catccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 40          moltype = AA  length = 214
FEATURE                Location/Qualifiers
REGION                 1..214
                       note = source = /note="Description of Artificial Sequence:
                        Syntheticpolypeptide"
source                 1..214
                       mol_type = protein
                       organism = synthetic construct
SEQUENCE: 40
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 41          moltype = DNA  length = 642
FEATURE                Location/Qualifiers
misc_feature           1..642
                       note = source = /note="Description of Artificial Sequence:
                        Syntheticpolynucleotide"
source                 1..642
                       mol_type = other DNA
                       organism = synthetic construct
SEQUENCE: 41
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgtggac gttcggccaa  300
gggaccaagg tggaaatcaa acgtactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 42          moltype = AA  length = 453
FEATURE                Location/Qualifiers
REGION                 1..453
                       note = source = /note="Description of Artificial Sequence:
                        Syntheticpolypeptide"
source                 1..453
                       mol_type = protein
                       organism = synthetic construct
SEQUENCE: 42
QVQLVQSGAE VKKPGASVKV SCKASGYSFT TYGISWVRQA PGQGLEWMGW ISTYNGNTHY  60
AQKLQGRVTM TTDTSTRTAY MELRSLRSDD TAVYYCAREN YYGSGSYRGG MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                               453

SEQ ID NO: 43          moltype = DNA  length = 1359
FEATURE                Location/Qualifiers
misc_feature           1..1359
                       note = source = /note="Description of Artificial Sequence:
```

```
                         Syntheticpolynucleotide"
source                  1..1359
                        mol_type = other DNA
                        organism = synthetic construct
SEQUENCE: 43
caggttcagc tggtgcagtc tggagctgag gtgaagaagc ctggggcctc agtgaaggtc  60
tcctgcaagg cttctggtta ctcctttacc acctatggta tcagctgggt gcgacaggcc  120
cctggacaag ggcttgagtg gatgggatgg atcagcactt acaatggtaa cacacactat  180
gcacagaagc tccagggcag agtcaccatg accacagaca catccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct cagcgtcgac caagggccca tcggtcttcc ccctggcacc ctcctccaag  420
agcacctctg ggggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
aaccactaca cgcagaagag cctctccctg tccccgggt                        1359

SEQ ID NO: 44           moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 44
RASQSVSSYL A                                                      11

SEQ ID NO: 45           moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 45
DASNRAT                                                           7

SEQ ID NO: 46           moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 46
QQRSNWPWT                                                         9

SEQ ID NO: 47           moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 47
GYSFTTYGIS                                                        10

SEQ ID NO: 48           moltype = AA  length = 17
FEATURE                 Location/Qualifiers
REGION                  1..17
                        note = source = /note="Description of Artificial Sequence:
                         Syntheticpeptide"
source                  1..17
```

```
                        mol_type = protein
                        organism = synthetic construct
SEQUENCE: 48
WISTYNGNTH YAQKLQG                                                  17

SEQ ID NO: 49           moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 49
ENYYGSGSYR GGMDV                                                    15

SEQ ID NO: 50           moltype = AA  length = 107
FEATURE                 Location/Qualifiers
REGION                  1..107
                        note = source = /note="Description of Artificial Sequence:
                         Syntheticpolypeptide"
source                  1..107
                        mol_type = protein
                        organism = synthetic construct
SEQUENCE: 50
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPLTFGG GTKVEIK                107

SEQ ID NO: 51           moltype = DNA  length = 321
FEATURE                 Location/Qualifiers
misc_feature            1..321
                        note = source = /note="Description of Artificial Sequence:
                         Syntheticpolynucleotide"
source                  1..321
                        mol_type = other DNA
                        organism = synthetic construct
SEQUENCE: 51
gccatccagt tgacccagtc tccatcctcc ctgtctgcat ctgtaggaga cagagtcacc  60
atcacttgcc gggcaagtca gggcattagc agtgctttag cctggtatca gcagaaacca  120
gggaaagctc ctaagctcct gatctatgat gcctccagtt tggaaagtgg ggtcccatca  180
aggttcagcg gcagtggatc tgggacagat ttcactctca ccatcagcag cctgcagcct  240
gaagattttg caacttatta ctgtcaacag tttaatagtt acccgctcac tttcggcgga  300
gggaccaagg tggagatcaa a                                             321

SEQ ID NO: 52           moltype = AA  length = 121
FEATURE                 Location/Qualifiers
REGION                  1..121
                        note = source = /note="Description of Artificial Sequence:
                         Syntheticpolypeptide"
source                  1..121
                        mol_type = protein
                        organism = synthetic construct
SEQUENCE: 52
QVQLVQSGAE VKKPGASVKV SCKASGYTFT SYAMHWVRQA PGQRLEWMGW INAGNGNTKY  60
SQKFQGRVTI TRDTSASTAY MELSSLRSED TAVYYCARGY SSAWFDAFDI WGQGTMVTVS  120
S                                                                   121

SEQ ID NO: 53           moltype = DNA  length = 363
FEATURE                 Location/Qualifiers
misc_feature            1..363
                        note = source = /note="Description of Artificial Sequence:
                         Syntheticpolynucleotide"
source                  1..363
                        mol_type = other DNA
                        organism = synthetic construct
SEQUENCE: 53
caggtccagc ttgtgcagtc tggggctgag gtgaagaagc ctggggcctc agtgaaggtt  60
tcctgcaagg cttctggata caccttcact agctatgcta tgcattgggt gcgccaggcc  120
cccggacaaa ggcttgagtg gatgggatgg atcaacgctg gcaatggtaa cacaaaatat  180
tcacagaagt tccagggcag agtcaccatt accagggaca catccgcgag cacagcctac  240
atggagctga gcagcctgag atctgaagac acggctgtgt attactgtgc gagagggtat  300
agcagtgcct ggttcgatgc ttttgatatc tggggccaag ggacaatggt caccgtctct  360
tca                                                                 363

SEQ ID NO: 54           moltype = AA  length = 214
FEATURE                 Location/Qualifiers
REGION                  1..214
                        note = source = /note="Description of Artificial Sequence:
                         Syntheticpolypeptide"
```

```
source                  1..214
                        mol_type = protein
                        organism = synthetic construct
SEQUENCE: 54
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 55           moltype = DNA  length = 642
FEATURE                 Location/Qualifiers
misc_feature            1..642
                        note = source = /note="Description of Artificial Sequence:
                         Syntheticpolynucleotide"
source                  1..642
                        mol_type = other DNA
                        organism = synthetic construct
SEQUENCE: 55
gccatccagt tgacccagtc tccatcctcc ctgtctgcat ctgtaggaga cagagtcacc  60
atcacttgcc gggcaagtca gggcattagc agtgctttag cctggtatca gcagaaacca  120
gggaaagctc ctaagctcct gatctatgat gcctccagtt tggaaagtgg ggtcccatca  180
aggttcagcg gcagtggatc tgggacagat ttcactctca ccatcagcag cctgcagcct  240
gaagattttg caacttatta ctgtcaacag tttaatagtt acccgctcac tttcggcgga  300
gggaccaagg tggagatcaa acgtactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 56           moltype = AA  length = 450
FEATURE                 Location/Qualifiers
REGION                  1..450
                        note = source = /note="Description of Artificial Sequence:
                         Syntheticpolypeptide"
source                  1..450
                        mol_type = protein
                        organism = synthetic construct
SEQUENCE: 56
QVQLVQSGAE VKKPGASVKV SCKASGYTFT SYAMHWVRQA PGQRLEWMGW INAGNGNTKY  60
SQKFQGRVTI TRDTSASTAY MELSSLRSED TAVYYCARGY SSAWFDAFDI WGQGTMVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 57           moltype = DNA  length = 1350
FEATURE                 Location/Qualifiers
misc_feature            1..1350
                        note = source = /note="Description of Artificial Sequence:
                         Syntheticpolynucleotide"
source                  1..1350
                        mol_type = other DNA
                        organism = synthetic construct
SEQUENCE: 57
caggtccagc ttgtgcagtc tggggctgag gtgaagaagc ctggggcctc agtgaaggtt  60
tcctgcaagg cttctggata caccttcact agctatgcta tgcattgggt gcgccaggcc  120
cccggacaaa ggcttgagtg gatgggatgg atcaacgctg gcaatggtaa cacaaaatat  180
tcacagaagt tccagggcag agtcaccatt accagggaca catccgcgag cacagcctac  240
atggagctga gcagcctgag atctgaagac acggctgtgt attactgtgc gagagggtat  300
agcagtgcct ggttcgatgc ttttgatatc tggggccaag ggacaatggt caccgtctct  360
tcagcgtcga ccaagggccc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga agccgctggg  720
gcaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tatagcaagc tcaccgtgga caagagcagg  1260
tggcagcagg ggaacgtctt ctcatgctcc gtgatgcatg aggctctgca caaccactac  1320
```

-continued

```
acgcagaaga gcctctccct gtccccgggt                                1350

SEQ ID NO: 58           moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 58
RASQGISSAL A                                                    11

SEQ ID NO: 59           moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 59
DASSLES                                                         7

SEQ ID NO: 60           moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 60
QQFNSYPLT                                                       9

SEQ ID NO: 61           moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 61
GYTFTSYAMH                                                      10

SEQ ID NO: 62           moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 62
WINAGNGNTK YSQKFQG                                              17

SEQ ID NO: 63           moltype = AA  length = 12
FEATURE                 Location/Qualifiers
REGION                  1..12
                        note = source = /note="Description of Artificial Sequence:
                         Syntheticpeptide"
source                  1..12
                        mol_type = protein
                        organism = synthetic construct
SEQUENCE: 63
GYSSAWFDAF DI                                                   12

SEQ ID NO: 64           moltype = AA  length = 107
FEATURE                 Location/Qualifiers
REGION                  1..107
                        note = source = /note="Description of Artificial Sequence:
                         Syntheticpolypeptide"
source                  1..107
                        mol_type = protein
                        organism = synthetic construct
SEQUENCE: 64
DIQMTQSPSS LSASVGDRVT ITCRASQGIS NWLAWYQQKP EKAPKSLIYA ASSLQSGVPS  60
RFSGSGSGTD FTLTISSLQP EDFATYYCQQ YNSYPYTFGQ GTKLEIK             107
```

```
SEQ ID NO: 65          moltype = DNA  length = 321
FEATURE                Location/Qualifiers
misc_feature           1..321
                       note = source = /note="Description of Artificial Sequence:
                       Syntheticpolynucleotide"
source                 1..321
                       mol_type = other DNA
                       organism = synthetic construct
SEQUENCE: 65
gacatccaga tgacccagtc tccatcctca ctgtctgcat ctgtaggaga cagagtcacc   60
atcacttgtc gggcgagtca gggtattagc aactggttag cctggtatca gcagaaacca  120
gagaaagccc ctaagtccct gatctatgct gcatccagtt tgcaaagtgg ggtcccatca  180
aggttcagcg gcagtggatc tgggacagat ttcactctca ccatcagcag cctgcagcct  240
gaagattttg caacttatta ctgccaacag tataatagtt acccgtacac ttttggccag  300
gggaccaagc tggagatcaa a                                            321

SEQ ID NO: 66          moltype = AA  length = 126
FEATURE                Location/Qualifiers
REGION                 1..126
                       note = source = /note="Description of Artificial Sequence:
                       Syntheticpolypeptide"
source                 1..126
                       mol_type = protein
                       organism = synthetic construct
SEQUENCE: 66
QVQLVESGGG VVQPGRSLRL SCAASGFTFS NYALHWVRQA PGKGLEWVAL ISYDGSDKYY   60
ADSVKGRFAI SRDNSKNTLY LQMNSLRAED TAVYYCARDR EYCTYSSCSY DAFDIWGQGT  120
MVTVSS                                                             126

SEQ ID NO: 67          moltype = DNA  length = 378
FEATURE                Location/Qualifiers
misc_feature           1..378
                       note = source = /note="Description of Artificial Sequence:
                       Syntheticpolynucleotide"
source                 1..378
                       mol_type = other DNA
                       organism = synthetic construct
SEQUENCE: 67
caggtgcagc tggtggagtc tgggggaggc gtggtccagc ctgggaggtc cctgagactc   60
tcctgtgcag cctctggatt caccttcagt aactatgctc tgcactgggt ccgccaggct  120
ccaggcaagg ggctggagtg ggtggcactt atatcatatg atggaagcga taaatactac  180
gcagactccg tgaagggccg attcgccatc tccagagaca attccaagaa cacgctgtat  240
ctgcaaatga acagcctgag agctgaggac acggctgtgt attactgtgc gagagatcgg  300
gaatattgta cttatagtag ctgctcctat gatgcttttg atatctgggg ccaagggaca  360
atggtcaccg tctcttca                                                378

SEQ ID NO: 68          moltype = AA  length = 126
FEATURE                Location/Qualifiers
REGION                 1..126
                       note = source = /note="Description of Artificial Sequence:
                       Syntheticpolypeptide"
source                 1..126
                       mol_type = protein
                       organism = synthetic construct
SEQUENCE: 68
QVQLVESGGG VVQPGRSLRL SCAASGFTFS SFAMHWVRQA PGKGLEWVAL IPFDGSSNYY   60
ADSVKGRFTI SRDNSKNTLY LQMNSLRAED TAVYYCARDR NYYGSGSFSF DAFDIWGQGT  120
LVTVSS                                                             126

SEQ ID NO: 69          moltype = DNA  length = 378
FEATURE                Location/Qualifiers
misc_feature           1..378
                       note = source = /note="Description of Artificial Sequence:
                       Syntheticpolynucleotide"
source                 1..378
                       mol_type = other DNA
                       organism = synthetic construct
SEQUENCE: 69
caggttcagc tggtggagtc tggggggggc gtggtccagc ctgggaggtc cctgagactc   60
tcctgtgcag cctctggatt caccttcagt agctttgcta tgcactgggt ccgccaggct  120
ccaggcaagg ggctggagtg ggtggcactt ataccgtttg atggaagcag taactattac  180
gcagactccg tgaagggccg attcaccatc tccagagaca attccaagaa cacgctgtat  240
ctgcaaatga acagcctgag agctgaggac acggctgtgt attactgtgc gagagatagg  300
aattactatg gttcggggag tttttccttt gatgcttttg atatctgggg ccaagggaca  360
ctggtcaccg tctcctca                                                378

SEQ ID NO: 70          moltype = AA  length = 126
FEATURE                Location/Qualifiers
```

-continued

```
REGION                 1..126
                       note = source = /note="Description of Artificial Sequence:
                        Syntheticpolypeptide"
source                 1..126
                       mol_type = protein
                       organism = synthetic construct
SEQUENCE: 70
QVQLVESGGG VVQPGRSLRL SCEASGFTFS NYAIHWVRQA PGKGLEWVAL IPYDGSNNYY  60
AASVKGRFTI SRDNSKNTLY LQMNSLRAED TAVYYCARDR NYYGSGSFSF DAFDIWGQGT  120
MVTVSS                                                            126

SEQ ID NO: 71          moltype = DNA  length = 378
FEATURE                Location/Qualifiers
misc_feature           1..378
                       note = source = /note="Description of Artificial Sequence:
                        Syntheticpolynucleotide"
source                 1..378
                       mol_type = other DNA
                       organism = synthetic construct
SEQUENCE: 71
caggttcagc tggtggagtc tgggggaggc gtggtccagc ctgggaggtc cctgagactc  60
tcctgtgaag cctctggatt caccttcagt aactatgcta ttcactgggt ccgccaggct  120
ccaggcaagg ggctggaatg ggtggcactt ataccatatg atggaagcaa taactattac  180
gcagcctccg tgaagggccg attcaccatc tccagagaca attccaagaa cacgctgtat  240
ctgcaaatga acagcctgag agctgaggac acggctgtgt attactgtgc gagagatagg  300
aattactatg gttcggggag tttttccttt gatgcttttg atatctgggg ccaaggcaca  360
atggtcaccg tctcctca                                               378

SEQ ID NO: 72          moltype = AA  length = 214
FEATURE                Location/Qualifiers
REGION                 1..214
                       note = source = /note="Description of Artificial Sequence:
                        Syntheticpolypeptide"
source                 1..214
                       mol_type = protein
                       organism = synthetic construct
SEQUENCE: 72
DIQMTQSPSS LSASVGDRVT ITCRASQGIS NWLAWYQQKP EKAPKSLIYA ASSLQSGVPS  60
RFSGSGSGTD FTLTISSLQP EDFATYYCQQ YNSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 73          moltype = DNA  length = 642
FEATURE                Location/Qualifiers
misc_feature           1..642
                       note = source = /note="Description of Artificial Sequence:
                        Syntheticpolynucleotide"
source                 1..642
                       mol_type = other DNA
                       organism = synthetic construct
SEQUENCE: 73
gacatccaga tgacccagtc tccatcctca ctgtctgcat ctgtaggaga cagagtcacc  60
atcacttgtc gggcgagtca gggtattagc aactggttag cctggtatca gcagaaacca  120
gagaaagccc ctaagtccct gatctatgct gcatccagtt tgcaaagtgg ggtcccatca  180
aggttcagcg gcagtggatc tgggacagat ttcactctca ccatcagcag cctgcagcct  240
gaagattttg caacttatta ctgccaacag tataatagtt acccgtacac ttttggccag  300
gggaccaagc tggagatcaa acgtactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 74          moltype = AA  length = 455
FEATURE                Location/Qualifiers
REGION                 1..455
                       note = source = /note="Description of Artificial Sequence:
                        Syntheticpolypeptide"
source                 1..455
                       mol_type = protein
                       organism = synthetic construct
SEQUENCE: 74
QVQLVESGGG VVQPGRSLRL SCAASGFTFS SFAMHWVRQA PGKGLEWVAL IPFDGSSNYY  60
ADSVKGRFTI SRDNSKNTLY LQMNSLRAED TAVYYCARDR NYYGSGSFSF DAFDIWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGAPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSREEMTKN QVSLTCLVKG FYPSDIAVEW ESNGQPENNY KTTPPVLDSD GSFFLYSKLT  420
```

```
VDKSRWQQGN VFSCSVMHEA LHNHYTQKSL SLSPG                        455

SEQ ID NO: 75           moltype = DNA  length = 1365
FEATURE                 Location/Qualifiers
misc_feature            1..1365
                        note = source = /note="Description of Artificial Sequence:
                         Syntheticpolynucleotide"
source                  1..1365
                        mol_type = other DNA
                        organism = synthetic construct
SEQUENCE: 75
caggttcagc tggtggagtc tggggggggc gtggtccagc ctgggaggtc cctgagactc  60
tcctgtgcag cctctggatt caccttcagt agctttgcta tgcactgggt ccgccaggct  120
ccaggcaagg ggctggagtg ggtggcactt ataccgtttg atggaagcag taactattac  180
gcagactccg tgaagggccg attcaccatc tccagagaca attccaagaa cacgctgtat  240
ctgcaaatga acagcctgag agctgaggac acggctgtgt attactgtgc gagagatagg  300
aattactatg gttcggggag tttttccttt gatgcttttg atatctgggg ccaagggaca  360
ctggtcaccg tctcctcagc gtcgaccaag ggcccatcgg tcttccccct ggcaccctcc  420
tccaagagca cctctggggg cacagcggcc ctgggctgcc tggtcaagga ctacttcccc  480
gaaccggtga cggtgtcgtg gaactcaggc gccctgacca gcggcgtgca caccttcccg  540
gctgtcctac agtcctcagg actctactcc ctcagcagcg tggtgaccgt gccctccagc  600
agcttgggca cccagaccta catctgcaac gtgaatcaca agcccagcaa caccaaggtg  660
gacaagaaag ttgagcccaa atcttgtgac aaaactcaca catgcccacc gtgcccagca  720
cctgaagccg ctggggcacc gtcagtcttc ctcttccccc caaaacccaa ggacaccctc  780
atgatctccc ggacccctga ggtcacatgc gtggtggtgg acgtgagcca cgaagaccct  840
gaggtcaagt tcaactggta cgtggacggc gtggaggtgc ataatgccaa gacaaagccg  900
cgggaggagc agtacaacag cacgtaccgt gtggtcagcg tcctcaccgt cctgcaccag  960
gactggctga atggcaagga gtacaagtgc aaggtctcca acaaagccct cccagccccc  1020
atcgagaaaa ccatctccaa agccaaaggg cagccccgag aaccacaggt gtacaccctg  1080
cccccatccc gggaggagat gaccaagaac caggtcagcc tgacctgcct ggtcaaaggc  1140
ttctatccca gcgacatcgc cgtggagtgg gagagcaatg ggcagccgga gaacaactac  1200
aagaccacgc ctcccgtgct ggactccgac ggctccttct tcctctatag caagctcacc  1260
gtggacaaga gcaggtggca gcaggggaac gtcttctcat gctccgtgat gcatgaggct  1320
ctgcacaacc actacacgca gaagagcctc tccctgtccc cgggt              1365

SEQ ID NO: 76           moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 76
RASQGISNWL A                                                  11

SEQ ID NO: 77           moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 77
AASSLQS                                                       7

SEQ ID NO: 78           moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 78
QQYNSYPYT                                                     9

SEQ ID NO: 79           moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 79
GFTFSNYALH                                                    10
```

```
SEQ ID NO: 80           moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 80
LISYDGSDKY YADSVKG                                                   17

SEQ ID NO: 81           moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 81
DREYCTYSSC SYDAFDI                                                   17

SEQ ID NO: 82           moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 82
GFTFSSFAMH                                                           10

SEQ ID NO: 83           moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 83
LIPFDGSSNY YADSVKG                                                   17

SEQ ID NO: 84           moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 84
DRNYYGSGSF SFDAFDI                                                   17

SEQ ID NO: 85           moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 85
GFTFSNYAIH                                                           10

SEQ ID NO: 86           moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 86
LIPYDGSNNY YAASVKG                                                   17

SEQ ID NO: 87           moltype = AA  length = 17
FEATURE                 Location/Qualifiers
```

```
REGION                 1..17
                       note = source = /note="Description of Artificial Sequence:
                        Syntheticpeptide"
source                 1..17
                       mol_type = protein
                       organism = synthetic construct
SEQUENCE: 87
DRNYYGSGSF SFDAFDI                                                 17

SEQ ID NO: 88          moltype = AA  length = 107
FEATURE                Location/Qualifiers
REGION                 1..107
                       note = source = /note="Description of Artificial Sequence:
                        Syntheticpolypeptide"
source                 1..107
                       mol_type = protein
                       organism = synthetic construct
SEQUENCE: 88
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPLTFGG GTKVEIK                107

SEQ ID NO: 89          moltype = DNA  length = 321
FEATURE                Location/Qualifiers
misc_feature           1..321
                       note = source = /note="Description of Artificial Sequence:
                        Syntheticpolynucleotide"
source                 1..321
                       mol_type = other DNA
                       organism = synthetic construct
SEQUENCE: 89
gccatccagt tgacccagtc tccatcctcc ctgtctgcat ctgtaggaga cagagtcacc  60
atcacttgcc gggcaagtca gggcattagc agtgctttag cctggtatca gcagaaacca  120
gggaaagctc ctaagctcct gatctatgat gcctccagtt tggaaagtgg ggtcccatca  180
aggttcagcg gcagtggatc tgggacagat ttcactctca ccatcagcag cctgcagcct  240
gaagattttg caacttatta ctgtcaacag tttaatagtt acccgctcac tttcggcgga  300
gggaccaagg tggagatcaa a                                            321

SEQ ID NO: 90          moltype = AA  length = 121
FEATURE                Location/Qualifiers
REGION                 1..121
                       note = source = /note="Description of Artificial Sequence:
                        Syntheticpolypeptide"
source                 1..121
                       mol_type = protein
                       organism = synthetic construct
SEQUENCE: 90
QVQLVQSGAE VKKPGASVKV SCKASGYTFT SYGINWVRQA PGQGLEWMGW ISTYNGNTNS  60
AQKLQGRVTM TTDTSTSTAY MELRSLRSDD TAVYYCARAH SSSWFDAFDI WGQGTMVTVS  120
S                                                                  121

SEQ ID NO: 91          moltype = DNA  length = 363
FEATURE                Location/Qualifiers
misc_feature           1..363
                       note = source = /note="Description of Artificial Sequence:
                        Syntheticpolynucleotide"
source                 1..363
                       mol_type = other DNA
                       organism = synthetic construct
SEQUENCE: 91
caggtgcagc tggtgcagtc tggagctgag gtgaagaagc ctggggcctc agtgaaggtc  60
tcctgcaagg cttctggtta cacctttacc agctatggta tcaactgggt gcgacaggcc  120
cctggacaag ggcttgagtg gatggggtgg atcagcactt acaatggtaa cacaaactct  180
gcacagaagc tccagggcag agtcaccatg accacagaca catccacgag cacagcctac  240
atggagctga ggagcctgag atctgacgac acggccgtgt attactgtgc gagagcgcat  300
agcagcagct ggtttgatgc ttttgatatc tggggccaag ggacaatggt caccgtctcc  360
tca                                                                363

SEQ ID NO: 92          moltype = AA  length = 214
FEATURE                Location/Qualifiers
REGION                 1..214
                       note = source = /note="Description of Artificial Sequence:
                        Syntheticpolypeptide"
source                 1..214
                       mol_type = protein
                       organism = synthetic construct
SEQUENCE: 92
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
```

```
LSKADYEKHK VYACEVTHQG LSSPVTKSFN RGEC                          214

SEQ ID NO: 93          moltype = DNA  length = 642
FEATURE                Location/Qualifiers
misc_feature           1..642
                       note = source = /note="Description of Artificial Sequence:
                        Syntheticpolynucleotide"
source                 1..642
                       mol_type = other DNA
                       organism = synthetic construct
SEQUENCE: 93
gccatccagt tgacccagtc tccatcctcc ctgtctgcat ctgtaggaga cagagtcacc  60
atcacttgcc gggcaagtca gggcattagc agtgctttag cctggtatca gcagaaacca  120
gggaaagctc ctaagctcct gatctatgat gcctccagtt tggaaagtgg ggtcccatca  180
aggttcagcg gcagtggatc tgggacagat ttcactctca ccatcagcag cctgcagcct  240
gaagattttg caacttatta ctgtcaacag tttaatagtt acccgctcac tttcggcgga  300
gggaccaagg tggagatcaa acgtactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                 642

SEQ ID NO: 94          moltype = AA  length = 450
FEATURE                Location/Qualifiers
REGION                 1..450
                       note = source = /note="Description of Artificial Sequence:
                        Syntheticpolypeptide"
source                 1..450
                       mol_type = protein
                       organism = synthetic construct
SEQUENCE: 94
QVQLVQSGAE VKKPGASVKV SCKASGYTFT SYGINWVRQA PGQGLEWMGW ISTYNGNTNS  60
AQKLQGRVTM TTDTSTSTAY MELRSLRSDD TAVYYCARAH SSSWFDAFDI WGQGTMVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                               450

SEQ ID NO: 95          moltype = DNA  length = 1350
FEATURE                Location/Qualifiers
misc_feature           1..1350
                       note = source = /note="Description of Artificial Sequence:
                        Syntheticpolynucleotide"
source                 1..1350
                       mol_type = other DNA
                       organism = synthetic construct
SEQUENCE: 95
caggtgcagc tggtgcagtc tggagctgag gtgaagaagc ctggggcctc agtgaaggtc  60
tcctgcaagg cttctggtta cacctttacc agctatggta tcaactgggt gcgacaggcc  120
cctggacaag ggcttgagtg gatggggtgg atcagcactt acaatggtaa cacaaactct  180
gcacagaagc tccagggcag agtcaccatg accacagaca catccacgag cacagcctac  240
atggagctga ggagcctgag atctgacgac acggccgtgt attactgtgc gagagcgcat  300
agcagcagct ggtttgatgc ttttgatatc tggggccaag ggacaatggt caccgtctcc  360
tcagcgtcga ccaagggccc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga agccgctggg  720
gcaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tatagcaagc tcaccgtgga caagagcagg  1260
tggcagcagg ggaacgtctt ctcatgctcc gtgatgcatg aggctctgca caaccactac  1320
acgcagaaga gcctctccct gtccccgggt                               1350

SEQ ID NO: 96          moltype = AA  length = 11
FEATURE                Location/Qualifiers
REGION                 1..11
                       note = source = /note="Description of Artificial Sequence:
                        Syntheticpeptide"
```

```
source                1..11
                      mol_type = protein
                      organism = synthetic construct
SEQUENCE: 96
RASQGISSAL A                                                 11

SEQ ID NO: 97         moltype = AA  length = 7
FEATURE               Location/Qualifiers
REGION                1..7
                      note = source = /note="Description of Artificial Sequence:
                       Syntheticpeptide"
source                1..7
                      mol_type = protein
                      organism = synthetic construct
SEQUENCE: 97
DASSLES                                                      7

SEQ ID NO: 98         moltype = AA  length = 9
FEATURE               Location/Qualifiers
REGION                1..9
                      note = source = /note="Description of Artificial Sequence:
                       Syntheticpeptide"
source                1..9
                      mol_type = protein
                      organism = synthetic construct
SEQUENCE: 98
QQFNSYPLT                                                    9

SEQ ID NO: 99         moltype = AA  length = 10
FEATURE               Location/Qualifiers
REGION                1..10
                      note = source = /note="Description of Artificial Sequence:
                       Syntheticpeptide"
source                1..10
                      mol_type = protein
                      organism = synthetic construct
SEQUENCE: 99
GYTFTSYGIN                                                   10

SEQ ID NO: 100        moltype = AA  length = 17
FEATURE               Location/Qualifiers
REGION                1..17
                      note = source = /note="Description of Artificial Sequence:
                       Syntheticpeptide"
source                1..17
                      mol_type = protein
                      organism = synthetic construct
SEQUENCE: 100
WISTYNGNTN SAQKLQG                                           17

SEQ ID NO: 101        moltype = AA  length = 12
FEATURE               Location/Qualifiers
REGION                1..12
                      note = source = /note="Description of Artificial Sequence:
                       Syntheticpeptide"
source                1..12
                      mol_type = protein
                      organism = synthetic construct
SEQUENCE: 101
AHSSSWFDAF DI                                                12

SEQ ID NO: 102        moltype = AA  length = 107
FEATURE               Location/Qualifiers
REGION                1..107
                      note = source = /note="Description of Artificial Sequence:
                       Syntheticpolypeptide"
source                1..107
                      mol_type = protein
                      organism = synthetic construct
SEQUENCE: 102
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPWTFGQ GTKVEIK              107

SEQ ID NO: 103        moltype = DNA  length = 321
FEATURE               Location/Qualifiers
misc_feature          1..321
                      note = source = /note="Description of Artificial Sequence:
                       Syntheticpolynucleotide"
source                1..321
```

```
                        mol_type = other DNA
                        organism = synthetic construct
SEQUENCE: 103
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgtggac gttcggccaa  300
gggaccaagg tggaaatcaa a                                           321

SEQ ID NO: 104          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 104
QVQLVQSGAE VKKPGASVKV SCKASGYSFT YYGISWVRQA PGQGLEWMGW ISTYNGNTNY  60
ARMLQGRVTM TTDTSTRTAY MELRSLRSDD TAVYYCAREN YYGSGSYRGG MDVWGQGTTV  120
TVSS                                                              124

SEQ ID NO: 105          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 105
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                     372

SEQ ID NO: 106          moltype = AA  length = 214
FEATURE                 Location/Qualifiers
REGION                  1..214
                        note = source = /note="Description of Artificial Sequence:
                         Syntheticpolypeptide"
source                  1..214
                        mol_type = protein
                        organism = synthetic construct
SEQUENCE: 106
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 107          moltype = DNA  length = 642
FEATURE                 Location/Qualifiers
misc_feature            1..642
                        note = source = /note="Description of Artificial Sequence:
                         Syntheticpolynucleotide"
source                  1..642
                        mol_type = other DNA
                        organism = synthetic construct
SEQUENCE: 107
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgtggac gttcggccaa  300
gggaccaagg tggaaatcaa acgtactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 108          moltype = AA  length = 453
FEATURE                 Location/Qualifiers
REGION                  1..453
                        note = source = /note="Description of Artificial Sequence:
```

```
                         Syntheticpolypeptide"
source                  1..453
                        mol_type = protein
                        organism = synthetic construct
SEQUENCE: 108
QVQLVQSGAE VKKPGASVKV SCKASGYSFT YYGISWVRQA PGQGLEWMGW ISTYNGNTNY  60
ARMLQGRVTM TTDTSTRTAY MELRSLRSDD TAVYYCAREN YYGSGSYRGG MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 109          moltype = DNA  length = 1359
FEATURE                 Location/Qualifiers
misc_feature            1..1359
                        note = source = /note="Description of Artificial Sequence:
                         Syntheticpolynucleotide"
source                  1..1359
                        mol_type = other DNA
                        organism = synthetic construct
SEQUENCE: 109
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct cagcgtcgac caagggccca tcggtcttcc ccctggcacc ctcctccaag  420
agcacctctg ggggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
aaccactaca cgcagaagag cctctccctg tccccgggt                       1359

SEQ ID NO: 110          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 110
RASQSVSSYL A                                                      11

SEQ ID NO: 111          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 111
DASNRAT                                                           7

SEQ ID NO: 112          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 112
QQRSNWPWT                                                         9
```

```
SEQ ID NO: 113          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 113
GYSFTYYGIS                                                            10

SEQ ID NO: 114          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 114
WISTYNGNTN YARMLQG                                                    17

SEQ ID NO: 115          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 115
ENYYGSGSYR GGMDV                                                      15

SEQ ID NO: 116          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 116
QVQLVQSGAE VKKPGASVKV SCKASGYSFT YYGISWVRQA PGQGLEWMGW ISTYNGNTNY  60
ARMLQGRVTM TTDTSTRTAY MELRSLRSDD TAVYYCAREN YYGSGAFRGG MDGWGQGTTV  120
TVSS                                                                  124

SEQ ID NO: 117          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 117
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt ctggcgcctt cagagggggt atggacggtt ggggccaagg gaccacggtc  360
accgtctcct ca                                                         372

SEQ ID NO: 118          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 118
QVQLVQSGAE VKKPGASVKV SCKASGYSFT YYGISWVRQA PGQGLEWMGW ISTYNGNTHY  60
ARMLQGRVTM TTDTSTRTAY MELRSLRSDD TAVYYCAREN YYGSGSYRGG MDVWGQGTTV  120
TVSS                                                                  124

SEQ ID NO: 119          moltype = DNA  length = 372
FEATURE                 Location/Qualifiers
```

-continued

```
misc_feature           1..372
                       note = source = /note="Description of Artificial Sequence:
                        Syntheticpolynucleotide"
source                 1..372
                       mol_type = other DNA
                       organism = synthetic construct
SEQUENCE: 119
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctctactt acaatggtaa tacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 120         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 120
QVQLVQSGAE VKKPGASVKV SCKASGYSFT YYGISWVRQA PGQGLEWMGW ISTYNGKTHY  60
ARMLQGRVTM TTDTSTRTAY MELRSLRSDD TAVYYCAREN YYGSGSYRGG MDVWGQGTTV  120
TVSS                                                               124

SEQ ID NO: 121         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 121
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctcgacct acaatggtaa aacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 122         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 122
QVQLVQSGAE VKKPGASVKV SCKASGYSFT YYGISWVRQA PGQGLEWMGW ISPYNGNTHY  60
ARMLQGRVTM TTDTSTRTAY MELRSLRSDD TAVYYCAREN YYGSGSYRGG MDVWGQGTTV  120
TVSS                                                               124

SEQ ID NO: 123         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 123
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctctccct acaatggtaa tacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 124         moltype = AA  length = 124
FEATURE                Location/Qualifiers
REGION                 1..124
                       note = source = /note="Description of Artificial Sequence:
```

```
                        Syntheticpolypeptide"
source                  1..124
                        mol_type = protein
                        organism = synthetic construct
SEQUENCE: 124
QVQLVQSGAE VKKPGASVKV SCKASGYSFT YYGISWVRQA PGQGLEWMGW ISTYNGATHY  60
ARMLQGRVTM TTDTSTRTAY MELRSLRSDD TAVYYCAREN YYGSGSYRGG MDVWGQGTTV  120
TVSS                                                              124

SEQ ID NO: 125          moltype = DNA  length = 372
FEATURE                 Location/Qualifiers
misc_feature            1..372
                        note = source = /note="Description of Artificial Sequence:
                        Syntheticpolynucleotide"
source                  1..372
                        mol_type = other DNA
                        organism = synthetic construct
SEQUENCE: 125
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctccacct acaatggtgc tacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                     372

SEQ ID NO: 126          moltype = AA  length = 124
FEATURE                 Location/Qualifiers
REGION                  1..124
                        note = source = /note="Description of Artificial Sequence:
                        Syntheticpolypeptide"
source                  1..124
                        mol_type = protein
                        organism = synthetic construct
SEQUENCE: 126
QVQLVQSGAE VKKPGASVKV SCKASGYSFT YYGISWVRQA PGQGLEWMGW ISTYNGKTHY  60
ARMHQGRVTM TTDTSTRTAY MELRSLRSDD TAVYYCAREN YYGSGSYRGG MDVWGQGTTV  120
TVSS                                                              124

SEQ ID NO: 127          moltype = DNA  length = 372
FEATURE                 Location/Qualifiers
misc_feature            1..372
                        note = source = /note="Description of Artificial Sequence:
                        Syntheticpolynucleotide"
source                  1..372
                        mol_type = other DNA
                        organism = synthetic construct
SEQUENCE: 127
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctctacct acaatggtaa aacacattat  180
gcacggatgc accagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                     372

SEQ ID NO: 128          moltype = AA  length = 124
FEATURE                 Location/Qualifiers
REGION                  1..124
                        note = source = /note="Description of Artificial Sequence:
                        Syntheticpolypeptide"
source                  1..124
                        mol_type = protein
                        organism = synthetic construct
SEQUENCE: 128
QVQLVQSGAE VKKPGASVKV SCKASGYSFT YYGISWVRQA PGQGLEWMGW ISSYNGNTHY  60
ARMLQGRVTM TTDTSTRTAY MELRSLRSDD TAVYYCAREN YYGSGSYRGG MDVWGQGTTV  120
TVSS                                                              124

SEQ ID NO: 129          moltype = DNA  length = 372
FEATURE                 Location/Qualifiers
misc_feature            1..372
                        note = source = /note="Description of Artificial Sequence:
                        Syntheticpolynucleotide"
source                  1..372
                        mol_type = other DNA
                        organism = synthetic construct
SEQUENCE: 129
caggttcagc tggtgcagtc tggagctgag gtgaagaagc ctggggcctc agtgaaggtc  60
```

```
tcctgcaagg cctctggtta ctcctttacc tactatggta tcagctgggt gcgacaggcc  120
cctggacaag ggcttgagtg gatgggatgg atctcttcct acaatggtaa tacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 130         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 130
QVQLVQSGAE VKKPGASVKV SCKASGYSFT YYGISWVRQA PGQGLEWMGW ISTYNGNKHY  60
ARMLQGRVTM TTDTSTRTAY MELRSLRSDD TAVYYCAREN YYGSGSYRGG MDVWGQGTTV  120
TVSS                                                               124

SEQ ID NO: 131         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 131
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctctacct acaatggtaa taaacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 132         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 132
QVQLVQSGAE VKKPGASVKV SCKASGYSFT YYGISWVRQA PGQGLEWMGW ISTYNGGTHY  60
ARMLQGRVTM TTDTSTRTAY MELRSLRSDD TAVYYCAREN YYGSGSYRGG MDVWGQGTTV  120
TVSS                                                               124

SEQ ID NO: 133         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 133
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctctacct acaatggtgg aacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 134         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 134
QVQLVQSGAE VKKPGASVKV SCKASGYSFT YYGISWVRQA PGQGLEWMGW ISTYNGVTHY  60
ARMLQGRVTM TTDTSTRTAY MELRSLRSDD TAVYYCAREN YYGSGSYRGG MDVWGQGTTV  120
TVSS                                                               124
```

```
SEQ ID NO: 135          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 135
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctctacct acaatggtgt tacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                     372

SEQ ID NO: 136          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 136
QVQLVQSGAE VKKPGASVKV SCKASGYSFT YYGISWVRQA PGQGLEWMGW ISTYNGNTNY  60
ARMLQGRVTM TTDTSTRTAY MELRSLRSDD TAVYYCAREN YYGSGAYRGG MDAWGQGTTV  120
TVSS                                                              124

SEQ ID NO: 137          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 137
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt ctggcgccta cagaggtggc atggacgctt ggggccaagg gaccacggtc  360
accgtctcct ca                                                     372

SEQ ID NO: 138          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 138
QVQLVQSGAE VKKPGASVKV SCKASGYSFT YYGISWVRQA PGQGLEWMGW ISTYNGNTHY  60
AQMLQGRVTM TTDTSTRTAY MELRSLRSDD TAVYYCAREN YYGSGSYRGG MDVWGQGTTV  120
TVSS                                                              124

SEQ ID NO: 139          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 139
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctctacct acaatggtaa tacacattat  180
gcacagatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                     372

SEQ ID NO: 140          moltype = AA  length = 124
```

-continued

```
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 140
QVQLVQSGAE VKKPGASVKV SCKASGYSFT YYGISWVRQA PGQGLEWMGW ISAYNGNTHY  60
ARMLQGRVTM TTDTSTRTAY MELRSLRSDD TAVYYCAREN YYGSGSYRGG MDVWGQGTTV  120
TVSS                                                              124

SEQ ID NO: 141         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 141
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctccgcct acaatggtaa tacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                     372

SEQ ID NO: 142         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 142
QVQLVQSGAE VKKPGASVKV SCKASGYSFT YYGISWVRQA PGQGLEWMGW ISPYNGKTHY  60
ARMLQGRVTM TTDTSTRTAY MELRSLRSDD TAVYYCAREN YYGSGSYRGG MDVWGQGTTV  120
TVSS                                                              124

SEQ ID NO: 143         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 143
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atctctccat acaatggtaa gacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                     372

SEQ ID NO: 144         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 144
QVQLVQSGAE VKKPGASVKV SCKASGYSFT YYGISWVRQA PGQGLEWMGW ISTYNGNTNY  60
ARMLQGRVTM TTDTSTRTAY MELRSLRSDD TAVYYCAREN YYGSGAYRGG MDVWGQGTTV  120
TVSS                                                              124

SEQ ID NO: 145         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
```

-continued

```
                         organism = synthetic construct
SEQUENCE: 145
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt ctggtgctta cagaggtggt atggacgttt ggggccaagg gaccacggtc  360
accgtctcct ca                                                      372

SEQ ID NO: 146           moltype = AA  length = 124
FEATURE                  Location/Qualifiers
REGION                   1..124
                         note = source = /note="Description of Artificial Sequence:
                          Syntheticpolypeptide"
source                   1..124
                         mol_type = protein
                         organism = synthetic construct
SEQUENCE: 146
QVQLVQSGAE VKKPGASVKV SCKASGYDFT YYGISWVRQA PGQGLEWMGW ISTYNGNTNY  60
ARMLQGRVTM TTDTSTRTAY MELRSLRSDD TAVYYCAREN YYGSGSYRGG MDVWGQGTTV  120
TVSS                                                               124

SEQ ID NO: 147           moltype = DNA  length = 372
FEATURE                  Location/Qualifiers
misc_feature             1..372
                         note = source = /note="Description of Artificial Sequence:
                          Syntheticpolynucleotide"
source                   1..372
                         mol_type = other DNA
                         organism = synthetic construct
SEQUENCE: 147
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 148           moltype = AA  length = 124
FEATURE                  Location/Qualifiers
REGION                   1..124
                         note = source = /note="Description of Artificial Sequence:
                          Syntheticpolypeptide"
source                   1..124
                         mol_type = protein
                         organism = synthetic construct
SEQUENCE: 148
QVQLVQSGAE VKKPGASVKV SCKASGYNFT YYGISWVRQA PGQGLEWMGW ISTYNGNTNY  60
ARMLQGRVTM TTDTSTRTAY MELRSLRSDD TAVYYCAREN YYGSGSYRGG MDVWGQGTTV  120
TVSS                                                               124

SEQ ID NO: 149           moltype = DNA  length = 372
FEATURE                  Location/Qualifiers
misc_feature             1..372
                         note = source = /note="Description of Artificial Sequence:
                          Syntheticpolynucleotide"
source                   1..372
                         mol_type = other DNA
                         organism = synthetic construct
SEQUENCE: 149
caggttcagc tggtgcagtc tggagctgag gtgaagaagc ctggggcctc agtgaaggtc  60
tcctgcaagg cctctggtta caactttacc tactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 150           moltype = AA  length = 124
FEATURE                  Location/Qualifiers
REGION                   1..124
                         note = source = /note="Description of Artificial Sequence:
                          Syntheticpolypeptide"
source                   1..124
                         mol_type = protein
                         organism = synthetic construct
SEQUENCE: 150
```

-continued

```
QVQLVQSGAE VKKPGASVKV SCKASGYQFT YYGISWVRQA PGQGLEWMGW ISTYNGNTNY  60
ARMLQGRVTM TTDTSTRTAY MELRSLRSDD TAVYYCAREN YYGSGSYRGG MDVWGQGTTV  120
TVSS                                                              124

SEQ ID NO: 151          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 151
caggttcagc tggtgcagtc tggagctgag gtgaagaagc ctggggcctc agtgaaggtc  60
tcctgcaagg cctctggtta ccaatttacc tactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 152          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 152
QVQLVQSGAE VKKPGASVKV SCKASGYSFT HYGISWVRQA PGQGLEWMGW ISTYNGNTNY  60
ARMLQGRVTM TTDTSTRTAY MELRSLRSDD TAVYYCAREN YYGSGSYRGG MDVWGQGTTV  120
TVSS                                                              124

SEQ ID NO: 153          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 153
caggttcagc tggtgcagtc tggagctgag gtgaagaagc ctggggcctc agtgaaggtc  60
tcctgcaagg cctctggtta ctcctttacc cactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 154          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 154
QVQLVQSGAE VKKPGASVKV SCKASGYNFR YYGISWVRQA PGQGLEWMGW ISTYNGNTNY  60
ARMLQGRVTM TTDTSTRTAY MELRSLRSDD TAVYYCAREN YYGSGSYRGG MDVWGQGTTV  120
TVSS                                                              124

SEQ ID NO: 155          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 155
caggttcagc tggtgcagtc tggagctgag gtgaagaagc ctggggcctc agtgaaggtc  60
tcctgcaagg cctctggtta caactttcgc tactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
```

```
accgtctcct ca                                                372

SEQ ID NO: 156         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 156
QVQLVQSGAE VKKPGASVKV SCKASGYNFT HYGISWVRQA PGQGLEWMGW ISTYNGNTNY  60
ARMLQGRVTM TTDTSTRTAY MELRSLRSDD TAVYYCAREN YYGSGSYRGG MDVWGQGTTV  120
TVSS                                                         124

SEQ ID NO: 157         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 157
caggttcagc tggtgcagtc tggagctgag gtgaagaagc ctggggcctc agtgaaggtc  60
tcctgcaagg cctctggtta caactttacc cactatggta tcagctgggt gcgacaggcc  120
cctggacaag ggcttgagtg gatgggatgg atcagcactt acaatggtaa cacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                372

SEQ ID NO: 158         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 158
QVQLVQSGAE VKKPGASVKV SCKASGYSFT YYGISWVRQA PGQGLEWMGW ISTYNGKTNY  60
ARMLQGRVTM TTDTSTRTAY MELRSLRSDD TAVYYCAREN YYGSGSYRGG MDVWGQGTTV  120
TVSS                                                         124

SEQ ID NO: 159         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 159
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa gacaaactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                372

SEQ ID NO: 160         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 160
QVQLVQSGAE VKKPGASVKV SCKASGYSFR YYGISWVRQA PGQGLEWMGW ISTYNGNTHY  60
ARMLQGRVTM TTDTSTRTAY MELRSLRSDD TAVYYCAREN YYGSGSYRGG MDVWGQGTTV  120
TVSS                                                         124

SEQ ID NO: 161         moltype = DNA  length = 372
FEATURE                Location/Qualifiers
misc_feature           1..372
                       note = source = /note="Description of Artificial Sequence:
```

```
                          Syntheticpolynucleotide"
source                   1..372
                         mol_type = other DNA
                         organism = synthetic construct
SEQUENCE: 161
caggttcagc tggtgcagtc tggagctgag gtgaagaagc ctggggcctc agtgaaggtc  60
tcctgcaagg cctctggtta ctcctttcgc tactatggta tcagctgggt gcgacaggcc  120
cctggacaag ggcttgagtg gatgggatgg atcagcactt acaatggtaa cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                      372

SEQ ID NO: 162           moltype = AA  length = 124
FEATURE                  Location/Qualifiers
REGION                   1..124
                         note = source = /note="Description of Artificial Sequence:
                          Syntheticpolypeptide"
source                   1..124
                         mol_type = protein
                         organism = synthetic construct
SEQUENCE: 162
QVQLVQSGAE VKKPGASVKV SCKASGYSFT YYGISWVRQA PGQGLEWMGW ISTYNGNTHY  60
ARMLQGRVTM TTDTSTRTAY MELRSLRSDD TAVYYCAREN YYGSGAYRGG MDVWGQGTTV  120
TVSS                                                               124

SEQ ID NO: 163           moltype = DNA  length = 372
FEATURE                  Location/Qualifiers
misc_feature             1..372
                         note = source = /note="Description of Artificial Sequence:
                          Syntheticpolynucleotide"
source                   1..372
                         mol_type = other DNA
                         organism = synthetic construct
SEQUENCE: 163
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgtct ggggccaagg gaccacggtc  360
accgtctcct ca                                                      372

SEQ ID NO: 164           moltype = AA  length = 124
FEATURE                  Location/Qualifiers
REGION                   1..124
                         note = source = /note="Description of Artificial Sequence:
                          Syntheticpolypeptide"
source                   1..124
                         mol_type = protein
                         organism = synthetic construct
SEQUENCE: 164
QVQLVQSGAE VKKPGASVKV SCKASGYSFT YYGISWVRQA PGQGLEWMGW ISPYNGKTHY  60
ARMLQGRVTM TTDTSTRTAY MELRSLRSDD TAVYYCAREN YYGSGAYRGG MDVWGQGTTV  120
TVSS                                                               124

SEQ ID NO: 165           moltype = DNA  length = 372
FEATURE                  Location/Qualifiers
misc_feature             1..372
                         note = source = /note="Description of Artificial Sequence:
                          Syntheticpolynucleotide"
source                   1..372
                         mol_type = other DNA
                         organism = synthetic construct
SEQUENCE: 165
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagccctt acaatggtaa aacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgtct ggggccaagg gaccacggtc  360
accgtctcct ca                                                      372

SEQ ID NO: 166           moltype = AA  length = 124
FEATURE                  Location/Qualifiers
REGION                   1..124
                         note = source = /note="Description of Artificial Sequence:
                          Syntheticpolypeptide"
source                   1..124
```

```
                        mol_type = protein
                        organism = synthetic construct
SEQUENCE: 166
QVQLVQSGAE VKKPGASVKV SCKASGYSFR YYGISWVRQA PGQGLEWMGW ISTYNGNTHY  60
ARMLQGRVTM TTDTSTRTAY MELRSLRSDD TAVYYCAREN YYGSGAYRGG MDVWGQGTTV  120
TVSS                                                              124

SEQ ID NO: 167          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 167
caggttcagc tggtgcagtc tggagctgag gtgaagaagc ctggggcctc agtgaaggtc  60
tcctgcaagg cctctggtta ctcctttcgc tactatggta tcagctgggt gcgacaggcc  120
cctggacaag ggcttgagtg gatgggatgg atcagcactt acaatggtaa cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgtct ggggccaagg gaccacggtc  360
accgtctcct ca                                                     372

SEQ ID NO: 168          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 168
QVQLVQSGAE VKKPGASVKV SCKASGYNFT YYGISWVRQA PGQGLEWMGW ISPYNGKTHY  60
ARMLQGRVTM TTDTSTRTAY MELRSLRSDD TAVYYCAREN YYGSGAYRGG MDVWGQGTTV  120
TVSS                                                              124

SEQ ID NO: 169          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 169
caggttcagc tggtgcagtc tggagctgag gtgaagaagc ctggggcctc agtgaaggtc  60
tcctgcaagg cctctggtta caactttacc tactatggta tcagctgggt gcgacaggcc  120
cctggacaag ggcttgagtg gatgggatgg atcagccctt acaatggtaa aacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgtct ggggccaagg gaccacggtc  360
accgtctcct ca                                                     372

SEQ ID NO: 170          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 170
QVQLVQSGAE VKKPGASVKV SCKASGYSFT HYGISWVRQA PGQGLEWMGW ISPYNGKTHY  60
ARMLQGRVTM TTDTSTRTAY MELRSLRSDD TAVYYCAREN YYGSGAYRGG MDVWGQGTTV  120
TVSS                                                              124

SEQ ID NO: 171          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 171
caggttcagc tggtgcagtc tggagctgag gtgaagaagc ctggggcctc agtgaaggtc  60
tcctgcaagg cctctggtta ctcctttacc cactatggta tcagctgggt gcgacaggcc  120
cctggacaag ggcttgagtg gatgggatgg atcagccctt acaatggtaa aacacactat  180
```

-continued

```
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgtct ggggccaagg gaccacggtc  360
accgtctcct ca                                                      372

SEQ ID NO: 172         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 172
QVQLVQSGAE VKKPGASVKV SCKASGYNFT HYGISWVRQA PGQGLEWMGW ISPYNGKTHY  60
ARMLQGRVTM TTDTSTRTAY MELRSLRSDD TAVYYCAREN YYGSGAYRGG MDVWGQGTTV  120
TVSS                                                               124

SEQ ID NO: 173         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 173
caggttcagc tggtgcagtc tggagctgag gtgaagaagc ctggggcctc agtgaaggtc  60
tcctgcaagg cctctggtta caactttacc cactatggta tcagctgggt gcgacaggcc  120
cctggacaag ggcttgagtg gatgggatgg atcagccctt acaatggtaa aacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgtct ggggccaagg gaccacggtc  360
accgtctcct ca                                                      372

SEQ ID NO: 174         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 174
QVQLVQSGAE VKKPGASVKV SCKASGYSFT YYGISWVRQA PGQGLEWMGW ISPYNGGTHY  60
AQMLQGRVTM TTDTSTRTAY MELRSLRSDD TAVYYCAREN YYGSGAYRGG MDAWGQGTTV  120
TVSS                                                               124

SEQ ID NO: 175         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 175
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagccctt acaatggtgg cacacactat  180
gcacagatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgcct ggggccaagg gaccacggtc  360
accgtctcct ca                                                      372

SEQ ID NO: 176         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 176
QVQLVQSGAE VKKPGASVKV SCKASGYSFT YYGISWVRQA PGQGLEWMGW ISPYNGVTHY  60
AQMLQGRVTM TTDTSTRTAY MELRSLRSDD TAVYYCAREN YYGSGAYRGG MDAWGQGTTV  120
TVSS                                                               124

SEQ ID NO: 177         moltype = DNA  length = 372
```

```
FEATURE                     Location/Qualifiers
misc_feature                1..372
                            note = source = /note="Description of Artificial Sequence:
                              Syntheticpolynucleotide"
source                      1..372
                            mol_type = other DNA
                            organism = synthetic construct
SEQUENCE: 177
caggttcagc tggtgcagtc tggagctgag gtgaagaagc ctggggcctc agtgaaggtc    60
tcctgcaagg cctctggtta ctcctttacc tactatggta tcagctgggt gcgacaggcc   120
cctggacaag ggcttgagtg gatgggatgg atcagccctt acaatggtgt cacacactat   180
gcacagatgc tccagggcag agtcaccatg accacagaca cgtccacgcg cacagcctac   240
atggagctga ggagcctgag atctgacgac acggccgtgt attactgtgc gagagagaat   300
tactatggtt cgggggctta tagagggggt atggacgcct ggggccaagg gaccacggtc   360
accgtctcct ca                                                       372

SEQ ID NO: 178              moltype = AA  length = 124
FEATURE                     Location/Qualifiers
REGION                      1..124
                            note = source = /note="Description of Artificial Sequence:
                              Syntheticpolypeptide"
source                      1..124
                            mol_type = protein
                            organism = synthetic construct
SEQUENCE: 178
QVQLVQSGAE VKKPGASVKV SCKASGYSFT YYGISWVRQA PGQGLEWMGW ISPYNGATHY    60
AQMLQGRVTM TTDTSTRTAY MELRSLRSDD TAVYYCAREN YYGSGAYRGG MDAWGQGTTV   120
TVSS                                                                124

SEQ ID NO: 179              moltype = DNA  length = 372
FEATURE                     Location/Qualifiers
misc_feature                1..372
                            note = source = /note="Description of Artificial Sequence:
                              Syntheticpolynucleotide"
source                      1..372
                            mol_type = other DNA
                            organism = synthetic construct
SEQUENCE: 179
caggttcagc tggtgcagtc tggagctgag gtgaagaagc ctggggcctc agtgaaggtc    60
tcctgcaagg cctctggtta ctcctttacc tactatggta tcagctgggt gcgacaggcc   120
cctggacaag ggcttgagtg gatgggatgg atcagccctt acaatggtgc cacacactat   180
gcacagatgc tccagggcag agtcaccatg accacagaca cgtccacgcg cacagcctac   240
atggagctga ggagcctgag atctgacgac acggccgtgt attactgtgc gagagagaat   300
tactatggtt cgggggctta tagagggggt atggacgcct ggggccaagg gaccacggtc   360
accgtctcct ca                                                       372

SEQ ID NO: 180              moltype = AA  length = 124
FEATURE                     Location/Qualifiers
REGION                      1..124
                            note = source = /note="Description of Artificial Sequence:
                              Syntheticpolypeptide"
source                      1..124
                            mol_type = protein
                            organism = synthetic construct
SEQUENCE: 180
QVQLVQSGAE VKKPGASVKV SCKASGYSFT YYGISWVRQA PGQGLEWMGW ISPYNGNKHY    60
AQMLQGRVTM TTDTSTRTAY MELRSLRSDD TAVYYCAREN YYGSGAYRGG MDAWGQGTTV   120
TVSS                                                                124

SEQ ID NO: 181              moltype = DNA  length = 372
FEATURE                     Location/Qualifiers
misc_feature                1..372
                            note = source = /note="Description of Artificial Sequence:
                              Syntheticpolynucleotide"
source                      1..372
                            mol_type = other DNA
                            organism = synthetic construct
SEQUENCE: 181
caggttcagc tggtgcagtc tggagctgag gtgaagaagc ctggggcctc agtgaaggtc    60
tcctgcaagg cctctggtta ctcctttacc tactatggta tcagctgggt gcgacaggcc   120
cctggacaag ggcttgagtg gatgggatgg atcagccctt acaatggtaa caagcactat   180
gcacagatgc tccagggcag agtcaccatg accacagaca cgtccacgcg cacagcctac   240
atggagctga ggagcctgag atctgacgac acggccgtgt attactgtgc gagagagaat   300
tactatggtt cgggggctta tagagggggt atggacgcct ggggccaagg gaccacggtc   360
accgtctcct ca                                                       372

SEQ ID NO: 182              moltype = AA  length = 124
FEATURE                     Location/Qualifiers
REGION                      1..124
```

```
                         note = source = /note="Description of Artificial Sequence:
                          Syntheticpolypeptide"
source                   1..124
                         mol_type = protein
                         organism = synthetic construct
SEQUENCE: 182
QVQLVQSGAE VKKPGASVKV SCKASGYSFT YYGISWVRQA PGQGLEWMGW ISTYNGGTHY  60
ARMLQGRVTM TTDTSTRTAY MELRSLRSDD TAVYYCAREN YYGSGAYRGG MDAWGQGTTV  120
TVSS                                                               124

SEQ ID NO: 183           moltype = DNA  length = 372
FEATURE                  Location/Qualifiers
misc_feature             1..372
                         note = source = /note="Description of Artificial Sequence:
                          Syntheticpolynucleotide"
source                   1..372
                         mol_type = other DNA
                         organism = synthetic construct
SEQUENCE: 183
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtgg cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgcct ggggccaagg gaccacggtc  360
accgtctcct ca                                                      372

SEQ ID NO: 184           moltype = AA  length = 124
FEATURE                  Location/Qualifiers
REGION                   1..124
                         note = source = /note="Description of Artificial Sequence:
                          Syntheticpolypeptide"
source                   1..124
                         mol_type = protein
                         organism = synthetic construct
SEQUENCE: 184
QVQLVQSGAE VKKPGASVKV SCKASGYSFT YYGISWVRQA PGQGLEWMGW ISPYNGNTHY  60
ARMLQGRVTM TTDTSTRTAY MELRSLRSDD TAVYYCAREN YYGSGAYRGG MDAWGQGTTV  120
TVSS                                                               124

SEQ ID NO: 185           moltype = DNA  length = 372
FEATURE                  Location/Qualifiers
misc_feature             1..372
                         note = source = /note="Description of Artificial Sequence:
                          Syntheticpolynucleotide"
source                   1..372
                         mol_type = other DNA
                         organism = synthetic construct
SEQUENCE: 185
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagccctt acaatggtaa cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgcct ggggccaagg gaccacggtc  360
accgtctcct ca                                                      372

SEQ ID NO: 186           moltype = AA  length = 124
FEATURE                  Location/Qualifiers
REGION                   1..124
                         note = source = /note="Description of Artificial Sequence:
                          Syntheticpolypeptide"
source                   1..124
                         mol_type = protein
                         organism = synthetic construct
SEQUENCE: 186
QVQLVQSGAE VKKPGASVKV SCKASGYSFT YYGISWVRQA PGQGLEWMGW ISTYNGNTHY  60
AQMLQGRVTM TTDTSTRTAY MELRSLRSDD TAVYYCAREN YYGSGAYRGG MDAWGQGTTV  120
TVSS                                                               124

SEQ ID NO: 187           moltype = DNA  length = 372
FEATURE                  Location/Qualifiers
misc_feature             1..372
                         note = source = /note="Description of Artificial Sequence:
                          Syntheticpolynucleotide"
source                   1..372
                         mol_type = other DNA
                         organism = synthetic construct
SEQUENCE: 187
```

```
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa cacacactat  180
gcacagatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgcct ggggccaagg gaccacggtc  360
accgtctcct ca                                                      372

SEQ ID NO: 188         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 188
QVQLVQSGAE VKKPGASVKV SCKASGYSFT YYGISWVRQA PGQGLEWMGW ISTYNGVTHY  60
ARMLQGRVTM TTDTSTRTAY MELRSLRSDD TAVYYCAREN YYGSGAYRGG MDAWGQGTTV  120
TVSS                                                               124

SEQ ID NO: 189         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 189
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtgt cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgcct ggggccaagg gaccacggtc  360
accgtctcct ca                                                      372

SEQ ID NO: 190         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 190
QVQLVQSGAE VKKPGASVKV SCKASGYSFT YYGISWVRQA PGQGLEWMGW ISTYNGATHY  60
ARMLQGRVTM TTDTSTRTAY MELRSLRSDD TAVYYCAREN YYGSGAYRGG MDAWGQGTTV  120
TVSS                                                               124

SEQ ID NO: 191         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 191
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtgc cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgcct ggggccaagg gaccacggtc  360
accgtctcct ca                                                      372

SEQ ID NO: 192         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 192
QVQLVQSGAE VKKPGASVKV SCKASGYSFT YYGISWVRQA PGQGLEWMGW ISTYNGNKHY  60
ARMLQGRVTM TTDTSTRTAY MELRSLRSDD TAVYYCAREN YYGSGAYRGG MDAWGQGTTV  120
```

```
TVSS                                                                  124

SEQ ID NO: 193          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 193
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa caaacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgcct ggggccaagg gaccacggtc  360
accgtctcct ca                                                         372

SEQ ID NO: 194          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 194
QVQLVQSGAE VKKPGASVKV SCKASGYSFT YYGISWVRQA PGQGLEWMGW ISTYNGKTHY  60
ARMHQGRVTM TTDTSTRTAY MELRSLRSDD TAVYYCAREN YYGSGAYRGG MDAWGQGTTV  120
TVSS                                                                  124

SEQ ID NO: 195          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 195
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa gacacactat  180
gcacggatgc accagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgcct ggggccaagg gaccacggtc  360
accgtctcct ca                                                         372

SEQ ID NO: 196          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 196
QVQLVQSGAE VKKPGASVKV SCKASGYSFT YYGISWVRQA PGQGLEWMGW ISTYNGNTHY  60
ARMLQGRVTM TTDTSTRTAY MELRSLRSDD TAVYYCAREN YYGSGAYRGG MDAWGQGTTV  120
TVSS                                                                  124

SEQ ID NO: 197          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 197
caggttcagc tggtgcagtc tggagctgag gtgaagaagc ctggggcctc agtgaaggtc  60
tcctgcaagg cctctggtta ctcctttacc tactatggta tcagctgggt gcgacaggcc  120
cctggacaag ggcttgagtg gatgggatgg atcagcactt acaatggtaa cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgcct ggggccaagg gaccacggtc  360
accgtctcct ca                                                         372
```

```
SEQ ID NO: 198         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 198
QVQLVQSGAE VKKPGASVKV SCKASGYDFT YYGISWVRQA PGQGLEWMGW ISTYNGNTHY  60
ARMLQGRVTM TTDTSTRTAY MELRSLRSDD TAVYYCAREN YYGSGSYRGG MDVWGQGTTV  120
TVSS                                                              124

SEQ ID NO: 199         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 199
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atctctactt acaatggtaa tacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                     372

SEQ ID NO: 200         moltype = AA  length = 453
FEATURE                Location/Qualifiers
REGION                 1..453
                       note = source = /note="Description of Artificial Sequence:
                        Syntheticpolypeptide"
source                 1..453
                       mol_type = protein
                       organism = synthetic construct
SEQUENCE: 200
QVQLVQSGAE VKKPGASVKV SCKASGYDFT YYGISWVRQA PGQGLEWMGW ISTYNGNTHY  60
ARMLQGRVTM TTDTSTRTAY MELRSLRSDD TAVYYCAREN YYGSGSYRGG MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 201         moltype = DNA  length = 1359
FEATURE                Location/Qualifiers
misc_feature           1..1359
                       note = source = /note="Description of Artificial Sequence:
                        Syntheticpolynucleotide"
source                 1..1359
                       mol_type = other DNA
                       organism = synthetic construct
SEQUENCE: 201
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atctctactt acaatggtaa tacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct cagcgtcgac caagggccca tcggtcttcc ccctggcacc ctcctccaag  420
agcacctctg ggggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
```

-continued aaccactaca cgcagaagag cctctccctg tccccgggt 1359

SEQ ID NO: 202 moltype = AA length = 10
FEATURE Location/Qualifiers
REGION 1..10
note = source = /note="Description of Artificial Sequence: Syntheticpeptide"
source 1..10
mol_type = protein
organism = synthetic construct
SEQUENCE: 202
GYDFTYYGIS 10

SEQ ID NO: 203 moltype = AA length = 17
FEATURE Location/Qualifiers
REGION 1..17
note = source = /note="Description of Artificial Sequence: Syntheticpeptide"
source 1..17
mol_type = protein
organism = synthetic construct
SEQUENCE: 203
WISTYNGNTH YARMLQG 17

SEQ ID NO: 204 moltype = AA length = 15
FEATURE Location/Qualifiers
REGION 1..15
note = source = /note="Description of Artificial Sequence: Syntheticpeptide"
source 1..15
mol_type = protein
organism = synthetic construct
SEQUENCE: 204
ENYYGSGSYR GGMDV 15

SEQ ID NO: 205 moltype = AA length = 124
FEATURE Location/Qualifiers
REGION 1..124
note = source = /note="Description of Artificial Sequence: Syntheticpolypeptide"
source 1..124
mol_type = protein
organism = synthetic construct
SEQUENCE: 205
QVQLVQSGAE VKKPGASVKV SCKASGYDFT YYGISWVRQA PGQGLEWMGW ISTYNGNKHY 60
ARMLQGRVTM TTDTSTRTAY MELRSLRSDD TAVYYCAREN YYGSGSYRGG MDVWGQGTTV 120
TVSS 124

SEQ ID NO: 206 moltype = DNA length = 372
FEATURE Location/Qualifiers
misc_feature 1..372
note = source = /note="Description of Artificial Sequence: Syntheticpolynucleotide"
source 1..372
mol_type = other DNA
organism = synthetic construct
SEQUENCE: 206
caggttcagc tggtgcagtc tggagctgag gtgaagaagc ctggggcctc agtgaaggtc 60
tcctgcaagg cctctggtta cgactttacc tactatggta tcagctgggt gcgacaggcc 120
cctggacaag ggcttgagtg gatgggatgg atctctacct acaatggtaa taaacattat 180
gcacggatgc tccagggcag agtcaccatg accacagaca cgtccacgcg cacagcctac 240
atggagctga ggagcctgag atctgacgac acggccgtgt attactgtgc gagagagaat 300
tactatggtt cggggagtta tagagggggt atggacgtct ggggccaagg gaccacggtc 360
accgtctcct ca 372

SEQ ID NO: 207 moltype = AA length = 453
FEATURE Location/Qualifiers
REGION 1..453
note = source = /note="Description of Artificial Sequence: Syntheticpolypeptide"
source 1..453
mol_type = protein
organism = synthetic construct
SEQUENCE: 207
QVQLVQSGAE VKKPGASVKV SCKASGYDFT YYGISWVRQA PGQGLEWMGW ISTYNGNKHY 60
ARMLQGRVTM TTDTSTRTAY MELRSLRSDD TAVYYCAREN YYGSGSYRGG MDVWGQGTTV 120
TVSSASTKGP SVFPLAPSSK STSGGTAALG CLVKDYFPEP VTVSWNSGAL TSGVHTFPAV 180
LQSSGLYSLS SVVTVPSSSL GTQTYICNVN HKPSNTKVDK KVEPKSCDKT HTCPPCPAPE 240
AAGAPSVFLF PPKPKDTLMI SRTPEVTCVV VDVSHEDPEV KFNWYVDGVE VHNAKTKPRE 300

-continued

```
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 208         moltype = DNA  length = 1359
FEATURE                Location/Qualifiers
misc_feature           1..1359
                       note = source = /note="Description of Artificial Sequence:
                        Syntheticpolynucleotide"
source                 1..1359
                       mol_type = other DNA
                       organism = synthetic construct
SEQUENCE: 208
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atctctacct acaatggtaa taaacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct cagcgtcgac caagggccca tcggtcttcc ccctggcacc ctcctccaag  420
agcacctctg gggggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
aaccactaca cgcagaagag cctctccctg tccccgggt                        1359

SEQ ID NO: 209         moltype = AA  length = 10
FEATURE                Location/Qualifiers
REGION                 1..10
                       note = source = /note="Description of Artificial Sequence:
                        Syntheticpeptide"
source                 1..10
                       mol_type = protein
                       organism = synthetic construct
SEQUENCE: 209
GYDFTYYGIS                                                        10

SEQ ID NO: 210         moltype = AA  length = 17
FEATURE                Location/Qualifiers
REGION                 1..17
                       note = source = /note="Description of Artificial Sequence:
                        Syntheticpeptide"
source                 1..17
                       mol_type = protein
                       organism = synthetic construct
SEQUENCE: 210
WISTYNGNKH YARMLQG                                                17

SEQ ID NO: 211         moltype = AA  length = 15
FEATURE                Location/Qualifiers
REGION                 1..15
                       note = source = /note="Description of Artificial Sequence:
                        Syntheticpeptide"
source                 1..15
                       mol_type = protein
                       organism = synthetic construct
SEQUENCE: 211
ENYYGSGSYR GGMDV                                                  15

SEQ ID NO: 212         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 212
```

```
QVQLVQSGAE VKKPGASVKV SCKASGYDFT YYGISWVRQA PGQGLEWMGW ISTYNGGTHY  60
ARMLQGRVTM TTDTSTRTAY MELRSLRSDD TAVYYCAREN YYGSGSYRGG MDVWGQGTTV  120
TVSS                                                              124

SEQ ID NO: 213         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 213
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atctctacct acaatggtgg aacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                     372

SEQ ID NO: 214         moltype = AA  length = 453
FEATURE                Location/Qualifiers
REGION                 1..453
                       note = source = /note="Description of Artificial Sequence:
                        Syntheticpolypeptide"
source                 1..453
                       mol_type = protein
                       organism = synthetic construct
SEQUENCE: 214
QVQLVQSGAE VKKPGASVKV SCKASGYDFT YYGISWVRQA PGQGLEWMGW ISTYNGGTHY  60
ARMLQGRVTM TTDTSTRTAY MELRSLRSDD TAVYYCAREN YYGSGSYRGG MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 215         moltype = DNA  length = 1359
FEATURE                Location/Qualifiers
misc_feature           1..1359
                       note = source = /note="Description of Artificial Sequence:
                        Syntheticpolynucleotide"
source                 1..1359
                       mol_type = other DNA
                       organism = synthetic construct
SEQUENCE: 215
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atctctacct acaatggtgg aacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct cagcgtcgac caagggccca tcggtcttcc ccctggcacc ctcctccaag  420
agcacctctg ggggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
aaccactaca cgcagaagag cctctccctg tccccgggt                        1359

SEQ ID NO: 216         moltype = AA  length = 10
FEATURE                Location/Qualifiers
REGION                 1..10
                       note = source = /note="Description of Artificial Sequence:
                        Syntheticpeptide"
source                 1..10
                       mol_type = protein
```

```
                        organism = synthetic construct
SEQUENCE: 216
GYDFTYYGIS                                                    10

SEQ ID NO: 217          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 217
WISTYNGGTH YARMLQG                                            17

SEQ ID NO: 218          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 218
ENYYGSGSYR GGMDV                                              15

SEQ ID NO: 219          moltype = AA  length = 124
FEATURE                 Location/Qualifiers
REGION                  1..124
                        note = source = /note="Description of Artificial Sequence:
                         Syntheticpolypeptide"
source                  1..124
                        mol_type = protein
                        organism = synthetic construct
SEQUENCE: 219
QVQLVQSGAE VKKPGASVKV SCKASGYDFT YYGISWVRQA PGQGLEWMGW ISTYNGVTHY  60
ARMLQGRVTM TTDTSTRTAY MELRSLRSDD TAVYYCAREN YYGSGSYRGG MDVWGQGTTV  120
TVSS                                                          124

SEQ ID NO: 220          moltype = DNA  length = 372
FEATURE                 Location/Qualifiers
misc_feature            1..372
                        note = source = /note="Description of Artificial Sequence:
                         Syntheticpolynucleotide"
source                  1..372
                        mol_type = other DNA
                        organism = synthetic construct
SEQUENCE: 220
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atctctacct acaatggtgt tacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct ca                                                 372

SEQ ID NO: 221          moltype = AA  length = 453
FEATURE                 Location/Qualifiers
REGION                  1..453
                        note = source = /note="Description of Artificial Sequence:
                         Syntheticpolypeptide"
source                  1..453
                        mol_type = protein
                        organism = synthetic construct
SEQUENCE: 221
QVQLVQSGAE VKKPGASVKV SCKASGYDFT YYGISWVRQA PGQGLEWMGW ISTYNGVTHY  60
ARMLQGRVTM TTDTSTRTAY MELRSLRSDD TAVYYCAREN YYGSGSYRGG MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                          453

SEQ ID NO: 222          moltype = DNA  length = 1359
FEATURE                 Location/Qualifiers
misc_feature            1..1359
                        note = source = /note="Description of Artificial Sequence:
                         Syntheticpolynucleotide"
```

-continued

```
source                 1..1359
                       mol_type = other DNA
                       organism = synthetic construct
SEQUENCE: 222
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atctctacct acaatggtgt tacacattat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggagtta tagagggggt atggacgtct ggggccaagg gaccacggtc  360
accgtctcct cagcgtcgac caagggccca tcggtcttcc ccctggcacc ctcctccaag  420
agcacctctg ggggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
aaccactaca cgcagaagag cctctccctg tccccgggt                         1359

SEQ ID NO: 223         moltype = AA  length = 10
FEATURE                Location/Qualifiers
REGION                 1..10
                       note = source = /note="Description of Artificial Sequence:
                        Syntheticpeptide"
source                 1..10
                       mol_type = protein
                       organism = synthetic construct
SEQUENCE: 223
GYDFTYYGIS                                                         10

SEQ ID NO: 224         moltype = AA  length = 17
FEATURE                Location/Qualifiers
REGION                 1..17
                       note = source = /note="Description of Artificial Sequence:
                        Syntheticpeptide"
source                 1..17
                       mol_type = protein
                       organism = synthetic construct
SEQUENCE: 224
WISTYNGVTH YARMLQG                                                 17

SEQ ID NO: 225         moltype = AA  length = 15
FEATURE                Location/Qualifiers
REGION                 1..15
                       note = source = /note="Description of Artificial Sequence:
                        Syntheticpeptide"
source                 1..15
                       mol_type = protein
                       organism = synthetic construct
SEQUENCE: 225
ENYYGSGSYR GGMDV                                                   15

SEQ ID NO: 226         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 226
QVQLVQSGAE VKKPGASVKV SCKASGYDFT YYGISWVRQA PGQGLEWMGW ISTYNGNTHY  60
ARMLQGRVTM TTDTSTRTAY MELRSLRSDD TAVYYCAREN YYGSGAYRGG MDVWGQGTTV  120
TVSS                                                               124

SEQ ID NO: 227         moltype = DNA  length = 372
FEATURE                Location/Qualifiers
misc_feature           1..372
                       note = source = /note="Description of Artificial Sequence:
                        Syntheticpolynucleotide"
```

```
source                  1..372
                        mol_type = other DNA
                        organism = synthetic construct
SEQUENCE: 227
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atcagcactt acaatggtaa cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggggctta tagagggggt atggacgtct ggggccaagg gaccacggtc  360
accgtctcct ca                                                      372

SEQ ID NO: 228          moltype = AA  length = 453
FEATURE                 Location/Qualifiers
REGION                  1..453
                        note = source = /note="Description of Artificial Sequence:
                         Syntheticpolypeptide"
source                  1..453
                        mol_type = protein
                        organism = synthetic construct
SEQUENCE: 228
QVQLVQSGAE VKKPGASVKV SCKASGYDFT YYGISWVRQA PGQGLEWMGW ISTYNGNTHY  60
ARMLQGRVTM TTDTSTRTAY MELRSLRSDD TAVYYCAREN YYGSGAYRGG MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                                453

SEQ ID NO: 229          moltype = DNA  length = 1359
FEATURE                 Location/Qualifiers
misc_feature            1..1359
                        note = source = /note="Description of Artificial Sequence:
                         Syntheticpolynucleotide"
source                  1..1359
                        mol_type = other DNA
                        organism = synthetic construct
SEQUENCE: 229
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atcagcactt acaatggtaa cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggggctta tagagggggt atggacgtct ggggccaagg gaccacggtc  360
accgtctcct cagcgtcgac caagggccca tcggtcttcc ccctggcacc ctcctccaag  420
agcacctctg ggggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
aaccactaca cgcagaagag cctctccctg tccccgggt                          1359

SEQ ID NO: 230          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 230
GYDFTYYGIS                                                          10

SEQ ID NO: 231          moltype = AA  length = 17
FEATURE                 Location/Qualifiers
REGION                  1..17
                        note = source = /note="Description of Artificial Sequence:
                         Syntheticpeptide"
```

```
source                1..17
                      mol_type = protein
                      organism = synthetic construct
SEQUENCE: 231
WISTYNGNTH YARMLQG                                             17

SEQ ID NO: 232        moltype = AA  length = 15
FEATURE               Location/Qualifiers
REGION                1..15
                      note = source = /note="Description of Artificial Sequence:
                       Syntheticpeptide"
source                1..15
                      mol_type = protein
                      organism = synthetic construct
SEQUENCE: 232
ENYYGSGAYR GGMDV                                               15

SEQ ID NO: 233        moltype = AA  length = 124
FEATURE               Location/Qualifiers
REGION                1..124
                      note = source = /note="Description of Artificial Sequence:
                       Syntheticpolypeptide"
source                1..124
                      mol_type = protein
                      organism = synthetic construct
SEQUENCE: 233
QVQLVQSGAE VKKPGASVKV SCKASGYDFT YYGISWVRQA PGQGLEWMGW ISTYNGGTHY  60
ARMLQGRVTM TTDTSTRTAY MELRSLRSDD TAVYYCAREN YYGSGAYRGG MDAWGQGTTV  120
TVSS                                                           124

SEQ ID NO: 234        moltype = DNA  length = 372
FEATURE               Location/Qualifiers
misc_feature          1..372
                      note = source = /note="Description of Artificial Sequence:
                       Syntheticpolynucleotide"
source                1..372
                      mol_type = other DNA
                      organism = synthetic construct
SEQUENCE: 234
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atcagcactt acaatggtgg cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cggggcctta tagagggggt atggacgcct ggggccaagg gaccacggtc  360
accgtctcct ca                                                  372

SEQ ID NO: 235        moltype = AA  length = 453
FEATURE               Location/Qualifiers
REGION                1..453
                      note = source = /note="Description of Artificial Sequence:
                       Syntheticpolypeptide"
source                1..453
                      mol_type = protein
                      organism = synthetic construct
SEQUENCE: 235
QVQLVQSGAE VKKPGASVKV SCKASGYDFT YYGISWVRQA PGQGLEWMGW ISTYNGGTHY  60
ARMLQGRVTM TTDTSTRTAY MELRSLRSDD TAVYYCAREN YYGSGAYRGG MDAWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                           453

SEQ ID NO: 236        moltype = DNA  length = 1359
FEATURE               Location/Qualifiers
misc_feature          1..1359
                      note = source = /note="Description of Artificial Sequence:
                       Syntheticpolynucleotide"
source                1..1359
                      mol_type = other DNA
                      organism = synthetic construct
SEQUENCE: 236
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atcagcactt acaatggtgg cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
```

-continued

```
tactatggtt cgggggctta tagagggggt atggacgcct ggggccaagg gaccacggtc  360
accgtctcct cagcgtcgac caagggccca tcggtcttcc ccctggcacc ctcctccaag  420
agcacctctg ggggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
aaccactaca cgcagaagag cctctccctg tccccgggt                         1359

SEQ ID NO: 237         moltype = AA  length = 10
FEATURE                Location/Qualifiers
REGION                 1..10
                       note = source = /note="Description of Artificial Sequence:
                        Syntheticpeptide"
source                 1..10
                       mol_type = protein
                       organism = synthetic construct
SEQUENCE: 237
GYDFTYYGIS                                                        10

SEQ ID NO: 238         moltype = AA  length = 17
FEATURE                Location/Qualifiers
REGION                 1..17
                       note = source = /note="Description of Artificial Sequence:
                        Syntheticpeptide"
source                 1..17
                       mol_type = protein
                       organism = synthetic construct
SEQUENCE: 238
WISTYNGGTH YARMLQG                                                17

SEQ ID NO: 239         moltype = AA  length = 15
FEATURE                Location/Qualifiers
REGION                 1..15
                       note = source = /note="Description of Artificial Sequence:
                        Syntheticpeptide"
source                 1..15
                       mol_type = protein
                       organism = synthetic construct
SEQUENCE: 239
ENYYGSGAYR GGMDA                                                  15

SEQ ID NO: 240         moltype = AA  length = 124
FEATURE                Location/Qualifiers
REGION                 1..124
                       note = source = /note="Description of Artificial Sequence:
                        Syntheticpolypeptide"
source                 1..124
                       mol_type = protein
                       organism = synthetic construct
SEQUENCE: 240
QVQLVQSGAE VKKPGASVKV SCKASGYDFT YYGISWVRQA PGQGLEWMGW ISTYNGVTHY  60
ARMLQGRVTM TTDTSTRTAY MELRSLRSDD TAVYYCAREN YYGSGAYRGG MDAWGQGTTV  120
TVSS                                                               124

SEQ ID NO: 241         moltype = DNA  length = 372
FEATURE                Location/Qualifiers
misc_feature           1..372
                       note = source = /note="Description of Artificial Sequence:
                        Syntheticpolynucleotide"
source                 1..372
                       mol_type = other DNA
                       organism = synthetic construct
SEQUENCE: 241
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atcagcactt acaatggtgt cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
```

```
tactatggtt cgggggctta tagagggggt atggacgcct ggggccaagg gaccacggtc  360
accgtctcct ca                                                      372

SEQ ID NO: 242         moltype = AA  length = 453
FEATURE                Location/Qualifiers
REGION                 1..453
                       note = source = /note="Description of Artificial Sequence:
                        Syntheticpolypeptide"
source                 1..453
                       mol_type = protein
                       organism = synthetic construct
SEQUENCE: 242
QVQLVQSGAE VKKPGASVKV SCKASGYDFT YYGISWVRQA PGQGLEWMGW ISTYNGVTHY  60
ARMLQGRVTM TTDTSTRTAY MELRSLRSDD TAVYYCAREN YYGSGAYRGG MDAWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                               453

SEQ ID NO: 243         moltype = DNA  length = 1359
FEATURE                Location/Qualifiers
misc_feature           1..1359
                       note = source = /note="Description of Artificial Sequence:
                        Syntheticpolynucleotide"
source                 1..1359
                       mol_type = other DNA
                       organism = synthetic construct
SEQUENCE: 243
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atcagcactt acaatggtgt cacacactat  180
gcacggatgc tccagggcag agtcaccatg accacagaca cgtccacgcg cacagcctac  240
atggagctga ggagcctgag atctgacgac acggccgtgt attactgtgc gagagagaat  300
tactatggtt cgggggctta tagagggggt atggacgcct ggggccaagg gaccacggtc  360
accgtctcct cagcgtcgac caagggccca tcggtcttcc ccctggcacc ctcctccaag  420
agcacctctg ggggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
aaccactaca cgcagaagag cctctccctg tccccgggt                         1359

SEQ ID NO: 244         moltype = AA  length = 10
FEATURE                Location/Qualifiers
REGION                 1..10
                       note = source = /note="Description of Artificial Sequence:
                        Syntheticpeptide"
source                 1..10
                       mol_type = protein
                       organism = synthetic construct
SEQUENCE: 244
GYDFTYYGIS                                                         10

SEQ ID NO: 245         moltype = AA  length = 17
FEATURE                Location/Qualifiers
REGION                 1..17
                       note = source = /note="Description of Artificial Sequence:
                        Syntheticpeptide"
source                 1..17
                       mol_type = protein
                       organism = synthetic construct
SEQUENCE: 245
WISTYNGVTH YARMLQG                                                 17

SEQ ID NO: 246         moltype = AA  length = 15
FEATURE                Location/Qualifiers
REGION                 1..15
```

```
                         note = source = /note="Description of Artificial Sequence:
                          Syntheticpeptide"
source                   1..15
                         mol_type = protein
                         organism = synthetic construct
SEQUENCE: 246
ENYYGSGAYR GGMDA                                                    15

SEQ ID NO: 247           moltype = AA  length = 124
FEATURE                  Location/Qualifiers
REGION                   1..124
                         note = source = /note="Description of Artificial Sequence:
                          Syntheticpolypeptide"
source                   1..124
                         mol_type = protein
                         organism = synthetic construct
SEQUENCE: 247
QVQLVQSGAE VKKPGASVKV SCKASGYDFT YYGISWVRQA PGQGLEWMGW ISTYNGKTHY  60
ARMHQGRVTM TTDTSTRTAY MELRSLRSDD TAVYYCAREN YYGSGAYRGG MDAWGQGTTV  120
TVSS                                                                124

SEQ ID NO: 248           moltype = DNA  length = 372
FEATURE                  Location/Qualifiers
misc_feature             1..372
                         note = source = /note="Description of Artificial Sequence:
                          Syntheticpolynucleotide"
source                   1..372
                         mol_type = other DNA
                         organism = synthetic construct
SEQUENCE: 248
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atcagcactt acaatggtaa gacacactat  180
gcacggatgc accagggcag agtcaccatg accacagaca cgtccacgcg cacagcctac  240
atggagctga ggagcctgag atctgacgac acggccgtgt attactgtgc gagagagaat  300
tactatggtt cggggggctta tagaggggggt atggacgcct ggggccaagg gaccacggtc  360
accgtctcct ca                                                       372

SEQ ID NO: 249           moltype = AA  length = 453
FEATURE                  Location/Qualifiers
REGION                   1..453
                         note = source = /note="Description of Artificial Sequence:
                          Syntheticpolypeptide"
source                   1..453
                         mol_type = protein
                         organism = synthetic construct
SEQUENCE: 249
QVQLVQSGAE VKKPGASVKV SCKASGYDFT YYGISWVRQA PGQGLEWMGW ISTYNGKTHY  60
ARMHQGRVTM TTDTSTRTAY MELRSLRSDD TAVYYCAREN YYGSGAYRGG MDAWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                                453

SEQ ID NO: 250           moltype = DNA  length = 1359
FEATURE                  Location/Qualifiers
misc_feature             1..1359
                         note = source = /note="Description of Artificial Sequence:
                          Syntheticpolynucleotide"
source                   1..1359
                         mol_type = other DNA
                         organism = synthetic construct
SEQUENCE: 250
caggttcagc tggtgcagtc tggagctgag gtgaagaagc ctggggcctc agtgaaggtc  60
tcctgcaagg cctctggtta cgactttacc tactatggta tcagctgggt gcgacaggcc  120
cctggacaag ggcttgagtg gatgggatgg atcagcactt acaatggtaa gacacactat  180
gcacggatgc accagggcag agtcaccatg accacagaca cgtccacgcg cacagcctac  240
atggagctga ggagcctgag atctgacgac acggccgtgt attactgtgc gagagagaat  300
tactatggtt cggggggctta tagaggggggt atggacgcct ggggccaagg gaccacggtc  360
accgtctcct cagcgtcgac caagggccca tcggtcttcc ccctggcacc ctcctccaag  420
agcacctctg ggggcacagc ggccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
gccgctgggg caccgtcagt cttcctcttc cccccaaaac ccaaggacac cctcatgatc  780
tcccggaccc ctgaggtcac atgcgtggtg gtggacgtga gccacgaaga ccctgaggtc  840
```

-continued

```
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggagg agatgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct atagcaagct caccgtggac  1260
aagagcaggt ggcagcaggg gaacgtcttc tcatgctccg tgatgcatga ggctctgcac  1320
aaccactaca cgcagaagag cctctccctg tccccgggt                        1359
```

```
SEQ ID NO: 251         moltype = AA  length = 10
FEATURE                Location/Qualifiers
REGION                 1..10
                       note = source = /note="Description of Artificial Sequence:
                        Syntheticpeptide"
source                 1..10
                       mol_type = protein
                       organism = synthetic construct
SEQUENCE: 251
GYDFTYYGIS                                                        10
```

```
SEQ ID NO: 252         moltype = AA  length = 17
FEATURE                Location/Qualifiers
REGION                 1..17
                       note = source = /note="Description of Artificial Sequence:
                        Syntheticpeptide"
source                 1..17
                       mol_type = protein
                       organism = synthetic construct
SEQUENCE: 252
WISTYNGKTH YARMHQG                                                17
```

```
SEQ ID NO: 253         moltype = AA  length = 15
FEATURE                Location/Qualifiers
REGION                 1..15
                       note = source = /note="Description of Artificial Sequence:
                        Syntheticpeptide"
source                 1..15
                       mol_type = protein
                       organism = synthetic construct
SEQUENCE: 253
ENYYGSGAYR GGMDA                                                  15
```

```
SEQ ID NO: 254         moltype = AA  length = 181
FEATURE                Location/Qualifiers
REGION                 1..181
                       note = source = /note="Description of Artificial Sequence:
                        Syntheticpolypeptide"
source                 1..181
                       mol_type = protein
                       organism = synthetic construct
SEQUENCE: 254
ALKGQEFAPS HQQVYAPLRA DGDKPRAHLT VVRQTPTQHF KNQFPALHWE HELGLAFTKN  60
RMNYTNKFLL IPESGDYFIY SQVTFRGMTS ECSEIRQAGR PNKPDSITVV ITKVTDSYPE  120
PTQLLMGTKS VCEVGSNWFQ PIYLGAMFSL QEGDKLMVNV SDISLVDYTK EDKTFFGAFL  180
L                                                                 181
```

```
SEQ ID NO: 255         moltype = AA  length = 107
FEATURE                Location/Qualifiers
source                 1..107
                       mol_type = protein
                       organism = Homo sapiens
SEQUENCE: 255
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107
```

```
SEQ ID NO: 256         moltype = AA  length = 330
FEATURE                Location/Qualifiers
source                 1..330
                       mol_type = protein
                       organism = Homo sapiens
SEQUENCE: 256
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330
```

-continued

```
SEQ ID NO: 257         moltype = AA  length = 329
FEATURE                Location/Qualifiers
REGION                 1..329
                       note = source = /note="Description of Artificial Sequence:
                        Syntheticpolypeptide"
source                 1..329
                       mol_type = protein
                       organism = synthetic construct
SEQUENCE: 257
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 258         moltype = AA  length = 251
FEATURE                Location/Qualifiers
source                 1..251
                       mol_type = protein
                       organism = Homo sapiens
SEQUENCE: 258
MAEDLGLSFG ETASVEMLPE HGSCRPKARS SSARWALTCC LVLLPFLAGL TTYLLVSQLR  60
AQGEACVQFQ ALKGQEFAPS HQQVYAPLRA DGDKPRAHLT VVRQTPTQHF KNQFPALHWE  120
HELGLAFTKN RMNYTNKFLL IPESGDYFIY SQVTFRGMTS ECSEIRQAGR PNKPDSITVV  180
ITKVTDSYPE PTQLLMGTKS VCEVGSNWFQ PIYLGAMFSL QEGDKLMVNV SDISLVDYTK  240
EDKTFFGAFL L                                                      251

SEQ ID NO: 259         moltype = AA  length = 182
FEATURE                Location/Qualifiers
REGION                 1..182
                       note = source = /note="Description of Artificial Sequence:
                        Syntheticpolypeptide"
source                 1..182
                       mol_type = protein
                       organism = synthetic construct
SEQUENCE: 259
TGLKGQEFAP SHQQVYAPLR ADGDKPRAHL TVVRQTPTQH LKNQFPALHW EHELGLAFTK  60
NRMNYTNKFL LIPESGDYFV YSQVTFRGMT SECSEIRQAG RPNKPDSITV VITKVTDSYP  120
EPTQLLMGTK SVCEVGSNWF QPIYLGAMFS LQEGDKLMVN VSDISLVDYT KEDKTFFGAF  180
LL                                                                182

SEQ ID NO: 260         moltype = AA  length = 178
FEATURE                Location/Qualifiers
REGION                 1..178
                       note = source = /note="Description of Artificial Sequence:
                        Syntheticpolypeptide"
source                 1..178
                       mol_type = protein
                       organism = synthetic construct
SEQUENCE: 260
AITEERSEPS PQQVYSPPRG KPRAHLTIKK QTPAPHLKNQ LSALHWEHDL GMAFTKNGMK  60
YINKSLVIPE SGDYFIYSQI TFRGTTSVCG DISRGRRPNK PDSITVVITK VADSYPEPAR  120
LLTGSKSVCE ISNNWFQSLY LGAMFSLEEG DRLMVNVSDI SLVDYTKEDK TFFGAFLL    178

SEQ ID NO: 261         moltype = AA  length = 179
FEATURE                Location/Qualifiers
REGION                 1..179
                       note = source = /note="Description of Artificial Sequence:
                        Syntheticpolypeptide"
source                 1..179
                       mol_type = protein
                       organism = synthetic construct
SEQUENCE: 261
TGVTEERSAP SAQPVYTPSR DKPKAHLTIM RQTPVPHLKN ELAALHWENN LGMAFTKNRM  60
NYTNKFLVIP ESGDYFIYSQ ITFRGTTSEC GDISRVRRPK KPDSITVVIT KVADSYPEPA  120
HLLTGTKSVC EISSNWFQPI YLGAMFSLEE GDRLMVNVSD ISLVDYTKED KTFFGAFLI   179

SEQ ID NO: 262         moltype = AA  length = 181
FEATURE                Location/Qualifiers
REGION                 1..181
                       note = source = /note="Description of Artificial Sequence:
                        Syntheticpolypeptide"
source                 1..181
                       mol_type = protein
                       organism = synthetic construct
SEQUENCE: 262
TGLKGREFGP SQQRAYMPLR ADGNKPRAHL TAVKQTPTQP LRNHFPALHW EHELGLAFTK  60
NRMNYTNKFL VIPESGDYFV YSQVTFRGTT SECGVINQRR RQTKPDSIVV VITKVTDNYP  120
```

```
EPAQLLTGTK SVCEMGNWFQ PIYLGAMFSL EEGDKLMVNV SDVSLVDYTK EDKTFFGAFL  180
L                                                                  181

SEQ ID NO: 263          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 263
GYSFTYYGIS                                                         10

SEQ ID NO: 264          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 264
WISTYNGNTN YARMLQG                                                 17

SEQ ID NO: 265          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 265
ENYYGSGAFR GGMDG                                                   15

SEQ ID NO: 266          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 266
GYSFTYYGIS                                                         10

SEQ ID NO: 267          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 267
WISTYNGNTH YARMLQG                                                 17

SEQ ID NO: 268          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 268
ENYYGSGSYR GGMDV                                                   15

SEQ ID NO: 269          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 269
GYSFTYYGIS                                                         10
```

```
SEQ ID NO: 270          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 270
WISTYNGKTH YARMLQG                                                 17

SEQ ID NO: 271          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 271
ENYYGSGSYR GGMDV                                                   15

SEQ ID NO: 272          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 272
GYSFTYYGIS                                                         10

SEQ ID NO: 273          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 273
WISPYNGNTH YARMLQG                                                 17

SEQ ID NO: 274          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 274
ENYYGSGSYR GGMDV                                                   15

SEQ ID NO: 275          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 275
GYSFTYYGIS                                                         10

SEQ ID NO: 276          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 276
WISTYNGATH YARMLQG                                                 17

SEQ ID NO: 277          moltype = AA  length = 15
```

-continued

```
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 277
ENYYGSGSYR GGMDV                                                    15

SEQ ID NO: 278          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 278
GYSFTYYGIS                                                          10

SEQ ID NO: 279          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 279
WISTYNGKTH YARMHQG                                                  17

SEQ ID NO: 280          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 280
ENYYGSGSYR GGMDV                                                    15

SEQ ID NO: 281          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 281
GYSFTYYGIS                                                          10

SEQ ID NO: 282          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 282
WISSYNGNTH YARMLQG                                                  17

SEQ ID NO: 283          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 283
ENYYGSGSYR GGMDV                                                    15

SEQ ID NO: 284          moltype = AA  length = 10
FEATURE                 Location/Qualifiers
REGION                  1..10
```

```
                      note = source = /note="Description of Artificial Sequence:
                       Syntheticpeptide"
source                1..10
                      mol_type = protein
                      organism = synthetic construct
SEQUENCE: 284
GYSFTYYGIS                                                                10

SEQ ID NO: 285        moltype = AA  length = 17
FEATURE               Location/Qualifiers
REGION                1..17
                      note = source = /note="Description of Artificial Sequence:
                       Syntheticpeptide"
source                1..17
                      mol_type = protein
                      organism = synthetic construct
SEQUENCE: 285
WISTYNGNKH YARMLQG                                                        17

SEQ ID NO: 286        moltype = AA  length = 15
FEATURE               Location/Qualifiers
REGION                1..15
                      note = source = /note="Description of Artificial Sequence:
                       Syntheticpeptide"
source                1..15
                      mol_type = protein
                      organism = synthetic construct
SEQUENCE: 286
ENYYGSGSYR GGMDV                                                          15

SEQ ID NO: 287        moltype = AA  length = 10
FEATURE               Location/Qualifiers
REGION                1..10
                      note = source = /note="Description of Artificial Sequence:
                       Syntheticpeptide"
source                1..10
                      mol_type = protein
                      organism = synthetic construct
SEQUENCE: 287
GYSFTYYGIS                                                                10

SEQ ID NO: 288        moltype = AA  length = 17
FEATURE               Location/Qualifiers
REGION                1..17
                      note = source = /note="Description of Artificial Sequence:
                       Syntheticpeptide"
source                1..17
                      mol_type = protein
                      organism = synthetic construct
SEQUENCE: 288
WISTYNGGTH YARMLQG                                                        17

SEQ ID NO: 289        moltype = AA  length = 15
FEATURE               Location/Qualifiers
REGION                1..15
                      note = source = /note="Description of Artificial Sequence:
                       Syntheticpeptide"
source                1..15
                      mol_type = protein
                      organism = synthetic construct
SEQUENCE: 289
ENYYGSGSYR GGMDV                                                          15

SEQ ID NO: 290        moltype = AA  length = 10
FEATURE               Location/Qualifiers
REGION                1..10
                      note = source = /note="Description of Artificial Sequence:
                       Syntheticpeptide"
source                1..10
                      mol_type = protein
                      organism = synthetic construct
SEQUENCE: 290
GYSFTYYGIS                                                                10

SEQ ID NO: 291        moltype = AA  length = 17
FEATURE               Location/Qualifiers
REGION                1..17
                      note = source = /note="Description of Artificial Sequence:
                       Syntheticpeptide"
```

```
source                  1..17
                        mol_type = protein
                        organism = synthetic construct
SEQUENCE: 291
WISTYNGVTH YARMLQG                                                  17

SEQ ID NO: 292          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 292
ENYYGSGSYR GGMDV                                                    15

SEQ ID NO: 293          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 293
GYSFTYYGIS                                                          10

SEQ ID NO: 294          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 294
WISTYNGNTN YARMLQG                                                  17

SEQ ID NO: 295          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 295
ENYYGSGAYR GGMDA                                                    15

SEQ ID NO: 296          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 296
GYSFTYYGIS                                                          10

SEQ ID NO: 297          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 297
WISTYNGNTH YAQMLQG                                                  17

SEQ ID NO: 298          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
```

```
                        organism = synthetic construct
SEQUENCE: 298
ENYYGSGSYR GGMDV                                                15

SEQ ID NO: 299          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 299
GYSFTYYGIS                                                      10

SEQ ID NO: 300          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 300
WISAYNGNTH YARMLQG                                              17

SEQ ID NO: 301          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 301
ENYYGSGSYR GGMDV                                                15

SEQ ID NO: 302          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 302
GYSFTYYGIS                                                      10

SEQ ID NO: 303          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 303
WISPYNGKTH YARMLQG                                              17

SEQ ID NO: 304          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 304
ENYYGSGSYR GGMDV                                                15

SEQ ID NO: 305          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 305
```

```
GYSFTYYGIS                                                        10

SEQ ID NO: 306          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 306
WISTYNGNTN YARMLQG                                                17

SEQ ID NO: 307          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 307
ENYYGSGAYR GGMDV                                                  15

SEQ ID NO: 308          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 308
GYDFTYYGIS                                                        10

SEQ ID NO: 309          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 309
WISTYNGNTN YARMLQG                                                17

SEQ ID NO: 310          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 310
ENYYGSGSYR GGMDV                                                  15

SEQ ID NO: 311          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 311
GYQFTYYGIS                                                        10

SEQ ID NO: 312          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 312
WISTYNGNTN YARMLQG                                                17
```

```
SEQ ID NO: 313          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 313
ENYYGSGSYR GGMDV                                                          15

SEQ ID NO: 314          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 314
GYSFTHYGIS                                                                10

SEQ ID NO: 315          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 315
WISTYNGNTN YARMLQG                                                        17

SEQ ID NO: 316          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 316
ENYYGSGSYR GGMDV                                                          15

SEQ ID NO: 317          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 317
GYNFRYYGIS                                                                10

SEQ ID NO: 318          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 318
WISTYNGNTN YARMLQG                                                        17

SEQ ID NO: 319          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 319
ENYYGSGSYR GGMDV                                                          15

SEQ ID NO: 320          moltype = AA  length = 10
FEATURE                 Location/Qualifiers
```

```
REGION                  1..10
                        note = source = /note="Description of Artificial Sequence:
                         Syntheticpeptide"
source                  1..10
                        mol_type = protein
                        organism = synthetic construct
SEQUENCE: 320
GYSFTYYGIS                                                                   10

SEQ ID NO: 321          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 321
WISTYNGKTN YARMLQG                                                           17

SEQ ID NO: 322          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 322
ENYYGSGSYR GGMDV                                                             15

SEQ ID NO: 323          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 323
GYSFRYYGIS                                                                   10

SEQ ID NO: 324          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 324
WISTYNGNTH YARMLQG                                                           17

SEQ ID NO: 325          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 325
ENYYGSGSYR GGMDV                                                             15

SEQ ID NO: 326          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 326
GYSFTYYGIS                                                                   10

SEQ ID NO: 327          moltype = AA  length = 17
FEATURE                 Location/Qualifiers
REGION                  1..17
                        note = source = /note="Description of Artificial Sequence:
```

-continued

```
                         Syntheticpeptide"
source                  1..17
                        mol_type = protein
                        organism = synthetic construct
SEQUENCE: 327
WISTYNGNTH YARMLQG                                                    17

SEQ ID NO: 328          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 328
ENYYGSGAYR GGMDV                                                      15

SEQ ID NO: 329          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 329
GYSFTYYGIS                                                            10

SEQ ID NO: 330          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 330
WISPYNGKTH YARMLQG                                                    17

SEQ ID NO: 331          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 331
ENYYGSGAYR GGMDV                                                      15

SEQ ID NO: 332          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 332
GYSFRYYGIS                                                            10

SEQ ID NO: 333          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 333
WISTYNGNTH YARMLQG                                                    17

SEQ ID NO: 334          moltype = AA  length = 15
FEATURE                 Location/Qualifiers
REGION                  1..15
                        note = source = /note="Description of Artificial Sequence:
                         Syntheticpeptide"
source                  1..15
```

```
                        mol_type = protein
                        organism = synthetic construct
SEQUENCE: 334
ENYYGSGAYR GGMDV                                              15

SEQ ID NO: 335          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 335
GYSFTHYGIS                                                    10

SEQ ID NO: 336          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 336
WISPYNGKTH YARMLQG                                            17

SEQ ID NO: 337          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 337
ENYYGSGAYR GGMDV                                              15

SEQ ID NO: 338          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 338
GYSFTYYGIS                                                    10

SEQ ID NO: 339          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 339
WISPYNGGTH YAQMLQG                                            17

SEQ ID NO: 340          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 340
ENYYGSGAYR GGMDA                                              15

SEQ ID NO: 341          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
```

```
SEQUENCE: 341
GYSFTYYGIS                                                    10

SEQ ID NO: 342          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 342
WISPYNGVTH YAQMLQG                                            17

SEQ ID NO: 343          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 343
ENYYGSGAYR GGMDA                                              15

SEQ ID NO: 344          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 344
GYSFTYYGIS                                                    10

SEQ ID NO: 345          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 345
WISPYNGATH YAQMLQG                                            17

SEQ ID NO: 346          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 346
ENYYGSGAYR GGMDA                                              15

SEQ ID NO: 347          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 347
GYSFTYYGIS                                                    10

SEQ ID NO: 348          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 348
WISPYNGNKH YAQMLQG                                            17
```

SEQ ID NO: 349 moltype = AA length = 15
FEATURE Location/Qualifiers
REGION 1..15
note = source = /note="Description of Artificial Sequence: Syntheticpeptide"
source 1..15
mol_type = protein
organism = synthetic construct
SEQUENCE: 349
ENYYGSGAYR GGMDA 15

SEQ ID NO: 350 moltype = AA length = 10
FEATURE Location/Qualifiers
REGION 1..10
note = source = /note="Description of Artificial Sequence: Syntheticpeptide"
source 1..10
mol_type = protein
organism = synthetic construct
SEQUENCE: 350
GYSFTYYGIS 10

SEQ ID NO: 351 moltype = AA length = 17
FEATURE Location/Qualifiers
REGION 1..17
note = source = /note="Description of Artificial Sequence: Syntheticpeptide"
source 1..17
mol_type = protein
organism = synthetic construct
SEQUENCE: 351
WISTYNGGTH YARMLQG 17

SEQ ID NO: 352 moltype = AA length = 15
FEATURE Location/Qualifiers
REGION 1..15
note = source = /note="Description of Artificial Sequence: Syntheticpeptide"
source 1..15
mol_type = protein
organism = synthetic construct
SEQUENCE: 352
ENYYGSGAYR GGMDA 15

SEQ ID NO: 353 moltype = AA length = 10
FEATURE Location/Qualifiers
REGION 1..10
note = source = /note="Description of Artificial Sequence: Syntheticpeptide"
source 1..10
mol_type = protein
organism = synthetic construct
SEQUENCE: 353
GYSFTYYGIS 10

SEQ ID NO: 354 moltype = AA length = 17
FEATURE Location/Qualifiers
REGION 1..17
note = source = /note="Description of Artificial Sequence: Syntheticpeptide"
source 1..17
mol_type = protein
organism = synthetic construct
SEQUENCE: 354
WISPYNGNTH YARMLQG 17

SEQ ID NO: 355 moltype = AA length = 15
FEATURE Location/Qualifiers
REGION 1..15
note = source = /note="Description of Artificial Sequence: Syntheticpeptide"
source 1..15
mol_type = protein
organism = synthetic construct
SEQUENCE: 355
ENYYGSGAYR GGMDA 15

SEQ ID NO: 356 moltype = AA length = 10

-continued

```
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 356
GYSFTYYGIS                                                                   10

SEQ ID NO: 357          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 357
WISTYNGNTH YAQMLQG                                                           17

SEQ ID NO: 358          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 358
ENYYGSGAYR GGMDA                                                             15

SEQ ID NO: 359          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 359
GYSFTYYGIS                                                                   10

SEQ ID NO: 360          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 360
WISTYNGVTH YARMLQG                                                           17

SEQ ID NO: 361          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 361
ENYYGSGAYR GGMDA                                                             15

SEQ ID NO: 362          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 362
GYSFTYYGIS                                                                   10

SEQ ID NO: 363          moltype = AA  length = 17
FEATURE                 Location/Qualifiers
REGION                  1..17
```

```
                        note = source = /note="Description of Artificial Sequence:
                         Syntheticpeptide"
source                  1..17
                        mol_type = protein
                        organism = synthetic construct
SEQUENCE: 363
WISTYNGATH YARMLQG                                                  17

SEQ ID NO: 364          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 364
ENYYGSGAYR GGMDA                                                    15

SEQ ID NO: 365          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 365
GYSFTYYGIS                                                          10

SEQ ID NO: 366          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 366
WISTYNGNKH YARMLQG                                                  17

SEQ ID NO: 367          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 367
ENYYGSGAYR GGMDA                                                    15

SEQ ID NO: 368          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 368
GYSFTYYGIS                                                          10

SEQ ID NO: 369          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 369
WISTYNGKTH YARMHQG                                                  17

SEQ ID NO: 370          moltype = AA  length = 15
FEATURE                 Location/Qualifiers
REGION                  1..15
                        note = source = /note="Description of Artificial Sequence:
                         Syntheticpeptide"
```

```
source                  1..15
                        mol_type = protein
                        organism = synthetic construct
SEQUENCE: 370
ENYYGSGAYR GGMDA                                                    15

SEQ ID NO: 371          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 371
GYSFTYYGIS                                                          10

SEQ ID NO: 372          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 372
WISTYNGNTH YARMLQG                                                  17

SEQ ID NO: 373          moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 373
ENYYGSGAYR GGMDA                                                    15

SEQ ID NO: 374          moltype = AA  length = 10
FEATURE                 Location/Qualifiers
VARIANT                 2
                        note = /replace="Tyr"
VARIANT                 3
                        note = /replace="Pro" or "Ser" or "Asp" or "Gln" or "Asn"
VARIANT                 5
                        note = /replace="Thr" or "Arg"
VARIANT                 6
                        note = /replace="Ser" or "Thr" or "Tyr" or "His"
VARIANT                 7
                        note = /replace="Phe"
VARIANT                 8
                        note = /replace="Gly"
VARIANT                 9
                        note = /replace="Met" or "Ile"
VARIANT                 10
                        note = /replace="Ser" or "Asn
REGION                  1..10
                        note = misc_feature - /note="Variant residues given in the
                         sequence have nopreference with respect to those in the
                         annotationsfor variant positions"
REGION                  1..10
                        note = source = /note="Description of Artificial Sequence:
                         Syntheticpeptide"
source                  1..10
                        mol_type = protein
                        organism = synthetic construct
SEQUENCE: 374
GFTFSNYALH                                                          10

SEQ ID NO: 375          moltype = AA  length = 10
FEATURE                 Location/Qualifiers
VARIANT                 3
                        note = /replace="Ser" or "Thr" or "Asp" or "Gln" or "Asn"
VARIANT                 5
                        note = /replace="Arg"
VARIANT                 6
                        note = /replace="Thr" or "Ser" or "Tyr" or "His"
VARIANT                 8
```

```
                        note = /replace="Gly"
VARIANT                 9
                        note = /replace="Met"
VARIANT                 10
                        note = /replace="His" or "Asn"
REGION                  1..10
                        note = misc_feature - /note="Variant residues given in the
                         sequence have nopreference with respect to those in the
                         annotationsfor variant positions"
REGION                  1..10
                        note = source = /note="Description of Artificial Sequence:
                         Syntheticpeptide"
source                  1..10
                        mol_type = protein
                        organism = synthetic construct
SEQUENCE: 375
GYPFTNYAIS                                                                  10

SEQ ID NO: 376          moltype = AA  length = 10
FEATURE                 Location/Qualifiers
VARIANT                 3
                        note = /replace="Ser" or "Asp" or "Gln" or "Asn"
VARIANT                 5
                        note = /replace="Arg"
VARIANT                 6
                        note = /replace="Thr" or "Tyr" or "His"
REGION                  1..10
                        note = misc_feature - /note="Variant residues given in the
                         sequence have nopreference with respect to those in the
                         annotationsfor variant positions"
REGION                  1..10
                        note = source = /note="Description of Artificial Sequence:
                         Syntheticpeptide"
source                  1..10
                        mol_type = protein
                        organism = synthetic construct
SEQUENCE: 376
GYPFTNYGIS                                                                  10

SEQ ID NO: 377          moltype = AA  length = 17
FEATURE                 Location/Qualifiers
VARIANT                 1
                        note = /replace="Trp"
VARIANT                 3
                        note = /replace="Pro" or "Asn"
VARIANT                 4
                        note = /replace="Phe" or "Ala" or "Thr" or "Pro" or "Ser"
VARIANT                 5
                        note = /replace="Gly" or "Tyr"
VARIANT                 6
                        note = /replace="Asn"
VARIANT                 7
                        note = /replace="Gly"
VARIANT                 8
                        note = /replace="Ser" or "Asn" or "Gly" or "Val" or "Lys"
                         or "Ala"
VARIANT                 9
                        note = /replace="Asn" or "Thr"
VARIANT                 10
                        note = /replace="Lys" or "Asn" or "His"
VARIANT                 11..12
                        note = /replace="Ser"
VARIANT                 13
                        note = /replace="Ala" or "Gln" or "Arg"
VARIANT                 14
                        note = /replace="Lys" or "Met"
VARIANT                 15
                        note = /replace="Phe" or "Leu" or "His"
VARIANT                 16
                        note = /replace="Gln"
REGION                  1..17
                        note = misc_feature - /note="Variant residues given in the
                         sequence have nopreference with respect to those in the
                         annotationsfor variant positions"
REGION                  1..17
                        note = source = /note="Description of Artificial Sequence:
                         Syntheticpeptide"
source                  1..17
                        mol_type = protein
```

```
                        organism = synthetic construct
SEQUENCE: 377
LISYDGSDKY YADSVKG                                                  17

SEQ ID NO: 378          moltype = AA  length = 17
FEATURE                 Location/Qualifiers
VARIANT                 3
                        note = /replace="Ser"
VARIANT                 4
                        note = /replace="Thr" or "Pro" or "Ser"
VARIANT                 5
                        note = /replace="Tyr"
VARIANT                 8
                        note = /replace="Gly" or "Val" or "Lys" or "Ala"
VARIANT                 9
                        note = /replace="Lys"
VARIANT                 10
                        note = /replace="Asn" or "His"
VARIANT                 11
                        note = /replace="Ser"
VARIANT                 12
                        note = /replace="Ala"
VARIANT                 13
                        note = /replace="Arg"
VARIANT                 14
                        note = /replace="Met"
VARIANT                 15
                        note = /replace="Leu" or "His"
REGION                  1..17
                        note = misc_feature - /note="Variant residues given in the
                         sequence have nopreference with respect to those in the
                         annotationsfor variant positions"
REGION                  1..17
                        note = source = /note="Description of Artificial Sequence:
                         Syntheticpeptide"
source                  1..17
                        mol_type = protein
                        organism = synthetic construct
SEQUENCE: 378
WINAGNGNTK YSQKFQG                                                  17

SEQ ID NO: 379          moltype = AA  length = 17
FEATURE                 Location/Qualifiers
VARIANT                 4
                        note = /replace="Pro" or "Ser" or "Ala"
VARIANT                 8
                        note = /replace="Gly" or "Val" or "Lys" or "Ala"
VARIANT                 9
                        note = /replace="Lys"
VARIANT                 10
                        note = /replace="Asn"
VARIANT                 13
                        note = /replace="Arg"
VARIANT                 14
                        note = /replace="Met"
VARIANT                 15
                        note = /replace="His"
REGION                  1..17
                        note = misc_feature - /note="Variant residues given in the
                         sequence have nopreference with respect to those in the
                         annotationsfor variant positions"
REGION                  1..17
                        note = source = /note="Description of Artificial Sequence:
                         Syntheticpeptide"
source                  1..17
                        mol_type = protein
                        organism = synthetic construct
SEQUENCE: 379
WISTYNGNTH YAQKLQG                                                  17

SEQ ID NO: 380          moltype = AA  length = 17
FEATURE                 Location/Qualifiers
VARIANT                 1
                        note = /replace="Glu" or " "
VARIANT                 2
                        note = /replace="Asn" or " "
VARIANT                 3
                        note = /replace="Asn" or "Tyr" or " "
VARIANT                 4
```

```
                        note = /replace="Gly" or "Ala"
VARIANT                 5
                        note = /replace="Tyr" or "Gly" or "His"
VARIANT                 6
                        note = /replace="Gly" or "Ser"
VARIANT                 7
                        note = /replace="Ser" or "Gly"
VARIANT                 8
                        note = /replace="Gly" or "Ala"
VARIANT                 9
                        note = /replace="Tyr" or "Trp" or "Phe"
VARIANT                 10
                        note = /replace="Phe" or "Arg"
VARIANT                 11
                        note = /replace="Gly" or "Asp"
VARIANT                 12
                        note = /replace="Phe" or "Gly" or "Ala"
VARIANT                 13
                        note = /replace="Met" or "Phe"
VARIANT                 14
                        note = /replace="Asp"
VARIANT                 15
                        note = /replace="Val" or "Ile" or "Ala" or "Gly"
VARIANT                 16..17
                        note = /replace=" "
REGION                  1..17
                        note = misc_feature - /note="Variant residues given in the
                         sequence have nopreference with respect to those in the
                         annotationsfor variant positions"
REGION                  1..17
                        note = source = /note="Description of Artificial Sequence:
                         Syntheticpeptide"
source                  1..17
                        mol_type = protein
                        organism = synthetic construct
SEQUENCE: 380
DREYCTYSSC SYDAFDI                                                  17

SEQ ID NO: 381          moltype = AA  length = 15
FEATURE                 Location/Qualifiers
VARIANT                 1..3
                        note = /replace=" "
VARIANT                 4
                        note = /replace="Gly" or "Ala"
VARIANT                 5
                        note = /replace="Tyr" or "His"
VARIANT                 7
                        note = /replace="Ser"
VARIANT                 8
                        note = /replace="Ala"
VARIANT                 9
                        note = /replace="Trp" or "Phe"
VARIANT                 10
                        note = /replace="Phe"
VARIANT                 11
                        note = /replace="Asp"
VARIANT                 12
                        note = /replace="Ala"
VARIANT                 13
                        note = /replace="Phe"
VARIANT                 15
                        note = /replace="Ile" or "Ala" or "Gly"
REGION                  1..15
                        note = misc_feature - /note="Variant residues given in the
                         sequence have nopreference with respect to those in the
                         annotationsfor variant positions"
REGION                  1..15
                        note = source = /note="Description of Artificial Sequence:
                         Syntheticpeptide"
source                  1..15
                        mol_type = protein
                        organism = synthetic construct
SEQUENCE: 381
ENYYGSGSYR GGMDV                                                    15

SEQ ID NO: 382          moltype = AA  length = 15
FEATURE                 Location/Qualifiers
VARIANT                 8
                        note = /replace="Ala"
```

-continued

```
VARIANT              9
                     note = /replace="Phe"
VARIANT              15
                     note = /replace="Ala" or "Gly"
REGION               1..15
                     note = misc_feature - /note="Variant residues given in the
                      sequence have nopreference with respect to those in the
                      annotationsfor variant positions"
REGION               1..15
                     note = source = /note="Description of Artificial Sequence:
                      Syntheticpeptide"
source               1..15
                     mol_type = protein
                     organism = synthetic construct
SEQUENCE: 382
ENYYGSGSYR GGMDV                                                  15

SEQ ID NO: 383       moltype = AA  length = 15
FEATURE              Location/Qualifiers
REGION               1..15
                     note = source = /note="Description of Artificial Sequence:
                      Syntheticpeptide"
source               1..15
                     mol_type = protein
                     organism = synthetic construct
SEQUENCE: 383
GGGGSGGGGS GGGGS                                                  15

SEQ ID NO: 384       moltype = AA  length = 10
FEATURE              Location/Qualifiers
VARIANT              3
                     note = /replace="Asp" or "Gln" or "Asn" or "Pro"
VARIANT              5
                     note = /replace="Arg"
VARIANT              6
                     note = /replace="His"
REGION               1..10
                     note = misc_feature - /note="Variant residues given in the
                      sequence have nopreference with respect to those in the
                      annotationsfor variant positions"
REGION               1..10
                     note = source = /note="Description of Artificial Sequence:
                      Syntheticpeptide"
source               1..10
                     mol_type = protein
                     organism = synthetic construct
SEQUENCE: 384
GYSFTYYGIS                                                        10

SEQ ID NO: 385       moltype = AA  length = 17
FEATURE              Location/Qualifiers
VARIANT              4
                     note = /replace="Pro" or "Ser" or "Ala"
VARIANT              8
                     note = /replace="Ala" or "Gly" or "Asn" or "Val"
VARIANT              9
                     note = /replace="Lys"
VARIANT              10
                     note = /replace="His"
VARIANT              13
                     note = /replace="Gln"
VARIANT              15
                     note = /replace="His"
REGION               1..17
                     note = misc_feature - /note="Variant residues given in the
                      sequence have nopreference with respect to those in the
                      annotationsfor variant positions"
REGION               1..17
                     note = source = /note="Description of Artificial Sequence:
                      Syntheticpeptide"
source               1..17
                     mol_type = protein
                     organism = synthetic construct
SEQUENCE: 385
WISTYNGKTN YARMLQG                                                17

SEQ ID NO: 386       moltype = AA  length = 10
FEATURE              Location/Qualifiers
VARIANT              8
```

```
                        note = /replace="Ala"
VARIANT                 9
                        note = /replace="Met"
VARIANT                 10
                        note = /replace="His"
REGION                  1..10
                        note = misc_feature - /note="Variant residues given in the
                         sequence have nopreference with respect to those in the
                         annotationsfor variant positions"
REGION                  1..10
                        note = source = /note="Description of Artificial Sequence:
                         Syntheticpeptide"
source                  1..10
                        mol_type = protein
                        organism = synthetic construct
SEQUENCE: 386
GYTFTSYGIN                                                                  10

SEQ ID NO: 387          moltype = AA  length = 17
FEATURE                 Location/Qualifiers
VARIANT                 3
                        note = /replace="Asn"
VARIANT                 4
                        note = /replace="Ala"
VARIANT                 5
                        note = /replace="Gly"
VARIANT                 10
                        note = /replace="Lys"
VARIANT                 11
                        note = /replace="Tyr"
VARIANT                 12
                        note = /replace="Ser"
VARIANT                 15
                        note = /replace="Phe"
REGION                  1..17
                        note = misc_feature - /note="Variant residues given in the
                         sequence have nopreference with respect to those in the
                         annotationsfor variant positions"
REGION                  1..17
                        note = source = /note="Description of Artificial Sequence:
                         Syntheticpeptide"
source                  1..17
                        mol_type = protein
                        organism = synthetic construct
SEQUENCE: 387
WISTYNGNTN SAQKLQG                                                          17

SEQ ID NO: 388          moltype = AA  length = 12
FEATURE                 Location/Qualifiers
VARIANT                 1
                        note = /replace="Gly"
VARIANT                 2
                        note = /replace="Tyr"
VARIANT                 5
                        note = /replace="Ala"
REGION                  1..12
                        note = misc_feature - /note="Variant residues given in the
                         sequence have nopreference with respect to those in the
                         annotationsfor variant positions"
REGION                  1..12
                        note = source = /note="Description of Artificial Sequence:
                         Syntheticpeptide"
source                  1..12
                        mol_type = protein
                        organism = synthetic construct
SEQUENCE: 388
AHSSSWFDAF DI                                                               12

SEQ ID NO: 389          moltype = AA  length = 10
FEATURE                 Location/Qualifiers
VARIANT                 6
                        note = /replace="Ser"
VARIANT                 7
                        note = /replace="Phe"
VARIANT                 9
                        note = /replace="Met" or "Ile"
REGION                  1..10
                        note = misc_feature - /note="Variant residues given in the
                         sequence have nopreference with respect to those in the
```

```
                          annotationsfor variant positions"
REGION                   1..10
                         note = source = /note="Description of Artificial Sequence:
                          Syntheticpeptide"
source                   1..10
                         mol_type = protein
                         organism = synthetic construct
SEQUENCE: 389
GFTFSNYALH                                                                    10

SEQ ID NO: 390           moltype = AA  length = 17
FEATURE                  Location/Qualifiers
VARIANT                  3
                         note = /replace="Pro"
VARIANT                  4
                         note = /replace="Phe"
VARIANT                  8
                         note = /replace="Ser" or "Asn"
VARIANT                  9
                         note = /replace="Asn"
REGION                   1..17
                         note = misc_feature - /note="Variant residues given in the
                          sequence have nopreference with respect to those in the
                          annotationsfor variant positions"
REGION                   1..17
                         note = source = /note="Description of Artificial Sequence:
                          Syntheticpeptide"
source                   1..17
                         mol_type = protein
                         organism = synthetic construct
SEQUENCE: 390
LISYDGSDKY YADSVKG                                                            17

SEQ ID NO: 391           moltype = AA  length = 17
FEATURE                  Location/Qualifiers
VARIANT                  3
                         note = /replace="Asn"
VARIANT                  5
                         note = /replace="Tyr"
VARIANT                  6
                         note = /replace="Gly"
VARIANT                  7
                         note = /replace="Ser"
VARIANT                  8
                         note = /replace="Gly"
VARIANT                  10
                         note = /replace="Phe"
VARIANT                  12
                         note = /replace="Phe"
REGION                   1..17
                         note = misc_feature - /note="Variant residues given in the
                          sequence have nopreference with respect to those in the
                          annotationsfor variant positions"
REGION                   1..17
                         note = source = /note="Description of Artificial Sequence:
                          Syntheticpeptide"
source                   1..17
                         mol_type = protein
                         organism = synthetic construct
SEQUENCE: 391
DREYCTYSSC SYDAFDI                                                            17

SEQ ID NO: 392           moltype = AA  length = 6
FEATURE                  Location/Qualifiers
REGION                   1..6
                         note = source = /note="Description of Artificial Sequence:
                          Synthetic6xHis tag"
source                   1..6
                         mol_type = protein
                         organism = synthetic construct
SEQUENCE: 392
HHHHHH                                                                        6

SEQ ID NO: 393           moltype = DNA  length = 38
FEATURE                  Location/Qualifiers
misc_feature             1..38
                         note = source = /note="Description of Artificial Sequence:
                          Syntheticprimer"
source                   1..38
```

-continued

```
                       mol_type = other DNA
                       organism = synthetic construct
SEQUENCE: 393
caacagctac aggcgcgcac tcccaggttc agctggtg                          38

SEQ ID NO: 394         moltype = DNA  length = 39
FEATURE                Location/Qualifiers
misc_feature           1..39
                       note = source = /note="Description of Artificial Sequence:
                        Syntheticprimer"
source                 1..39
                       mol_type = other DNA
                       organism = synthetic construct
SEQUENCE: 394
gaccgatggg cccttggtcg acgctgagga gacggtgac                         39

SEQ ID NO: 395         moltype = AA  length = 4
FEATURE                Location/Qualifiers
REGION                 1..4
                       note = source = /note="Description of Artificial Sequence:
                        Syntheticpeptide"
source                 1..4
                       mol_type = protein
                       organism = synthetic construct
SEQUENCE: 395
DEVD                                                               4
```

What is claimed is:

1. A method of treating a disease, disorder, or condition in a subject in need thereof, comprising administering to the subject an effective amount of a pharmaceutical composition comprising:

an antibody or antigen-binding fragment thereof that specifically binds tumor necrosis factor-like ligand 1A (TL1A), wherein the antibody or antigen-binding fragment thereof comprises:

a VH comprising a CDR-H1 comprising the amino acid sequence of SEQ ID NO:230, a CDR-H2 comprising the amino acid sequence of SEQ NO: 231, a CDR-H3 comprising the amino acid sequence of SEQ ID NO:232, and a VL comprising a CDR-L1 comprising the amino acid sequence of SEQ ID NO:110, a CDR-L2 comprising the amino acid sequence of SEQ ID NO:111, and a CDR-L3 comprising the amino acid sequence of SEQ ID NO:112;

and a pharmaceutically acceptable carrier or excipient; and wherein the disease, disorder, or condition is asthma or inflammatory bowel disease (IBD).

2. The method of claim 1, wherein the antibody or antigen-binding fragment thereof comprises a VH comprising the amino acid sequence of SEQ ID NO:226 and a VL comprising the amino acid sequence of SEQ ID NO:102.

3. The method of claim 1, wherein the antibody or antigen-binding fragment thereof comprises a heavy chain comprising the amino acid sequence of SEQ ID NO: 228 and a light chain comprising the amino acid sequence of SEQ ID NO: 106.

4. The method of claim 1, wherein the antibody or antigen-binding fragment thereof comprises a human IgG1 CH2 domain having the following amino acids at the indicated positions: 234A, 235A, and 237A, wherein the positions are numbered by the EU numbering system.

5. The method of claim 1, wherein the antibody or antigen-binding fragment thereof comprises a VH encoded by the nucleic acid sequence of the insert of the vector deposited as 1D1 1.31 VH having ATCC accession number PTA-120639 and a VL encoded by the nucleic acid sequence of the insert of the vector deposited as ID1 1.31 VL having ATCC accession number PTA-120640.

6. The method of claim 1, wherein the antibody binds to an epitope comprising the TL1A amino acids: Y118 and Q151 of a first TL1A monomer and R33, E50, L53, and K170 of a second TL1A monomer, according to the numbering of the amino acid sequence of TL1A as set forth in SEQ ID NO:254.

7. The method of claim 6, wherein the epitope further comprises the TL1A amino acids: S117 of the first monomer and V31, V32 and T169 of the second monomer, according to the numbering of the amino acid sequence of TL1A as set forth in SEQ ID NO:254.

8. The method of claim 6, wherein the epitope further comprises the TL1A amino acids: G54, Y168 and E171 of the second monomer, according to the numbering of the amino acid sequence of TL1A as set forth in SEQ ID NO:254.

9. A method of treating inflammatory bowel disease (IBD) in a subject in need thereof, comprising administering to the subject an effective amount of a pharmaceutical composition comprising:

an antibody or antigen-binding fragment thereof that specifically binds TL1A, wherein the antibody or antigen-binding fragment thereof comprises a VH comprising the CDR-H1 amino acid sequence of SEQ ID NO:230, the CDR-H2 amino acid sequence of SEQ NO: 231, the CDR-H3 amino acid sequence of SEQ ID NO:232, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

and a pharmaceutically acceptable carrier or excipient.

10. The method of claim 9, wherein the antibody or antigen-binding fragment thereof comprises a VH comprising the amino acid sequence of SEQ ID NO:226 and a VL comprising the amino acid sequence of SEQ ID NO:102.

11. The method of claim 9, wherein the antibody or antigen-binding fragment thereof comprises a heavy chain comprising the amino acid sequence of SEQ ID NO: 228 and a light chain comprising the amino acid sequence of SEQ ID NO: 106.

12. The method of claim 9, wherein the antibody or antigen-binding fragment thereof comprises a human IgG1 CH2 domain having the following amino acids at the indicated positions: 234A, 235A, and 237A, wherein the positions are numbered by the EU numbering system.

13. The method of claim 9, wherein the antibody or antigen-binding fragment thereof comprises a VH encoded by the nucleic acid sequence of the insert of the vector deposited as 1D1 1.31 VH having ATCC accession number PTA-120639 and a VL encoded by the nucleic acid sequence of the insert of the vector deposited as ID1 1.31 VL having ATCC accession number PTA-120640.

14. The method of claim 9, wherein the IBD is ulcerative colitis (UC).

15. The method of claim 9, wherein the IBD is Crohn's disease (CD).

16. The method of claim 10, wherein the IBD is UC.

17. The method of claim 10, wherein the IBD is CD.

18. The method of claim 11, wherein the IBD is UC.

19. The method of claim 11, wherein the IBD is CD.

20. A method of treating asthma in a subject in need thereof, comprising administering to the subject an effective amount of a pharmaceutical composition comprising: an antibody or antigen-binding fragment thereof that specifically binds TL1A, wherein the antibody or antigen-binding fragment thereof comprises a VH comprising the CDR-H1 amino acid sequence of SEQ ID NO:230, the CDR-H2 amino acid sequence of SEQ NO: 231, the CDR-H3 amino acid sequence of SEQ ID NO:232, and a VL comprising the CDR-L1 amino acid sequence of SEQ ID NO:110, the CDR-L2 amino acid sequence of SEQ ID NO:111, and the CDR-L3 amino acid sequence of SEQ ID NO:112;

and a pharmaceutically acceptable carrier or excipient.

21. The method of claim 20, wherein the antibody or antigen-binding fragment thereof comprises a VH comprising the amino acid sequence of SEQ ID NO:226 and a VL comprising the amino acid sequence of SEQ ID NO:102.

22. The method of claim 20, wherein the antibody or antigen-binding fragment thereof comprises a heavy chain comprising the amino acid sequence of SEQ ID NO:228 and a light chain comprising the amino acid sequence of SEQ ID NO: 106.

23. The method of claim 20, wherein the antibody or antigen-binding fragment thereof comprises a human IgG1 CH2 domain having the following amino acids at the indicated positions: 234A, 235A, and 237A, wherein the positions are numbered by the EU numbering system.

24. The method of claim 20, wherein the antibody or antigen-binding fragment thereof comprises a VH encoded by the nucleic acid sequence of the insert of the vector deposited as 1D1 1.31 VH having ATCC accession number PTA-120639 and a VL encoded by the nucleic acid sequence of the insert of the vector deposited as ID1 1.31 VL having ATCC accession number PTA-120640.

25. The method of claim 20, wherein the asthma is intrinsic asthma.

26. The method of claim 20, wherein the asthma is allergic asthma.

27. The method of claim 21, wherein the asthma is intrinsic asthma.

28. The method of claim 21, wherein the asthma is allergic asthma.

29. The method of claim 22, wherein the asthma is intrinsic asthma.

30. The method of claim 22, wherein the asthma is allergic asthma.

* * * * *